US007162371B1

(12) United States Patent
Cairney et al.

(10) Patent No.: US 7,162,371 B1
(45) Date of Patent: Jan. 9, 2007

(54) DIFFERENTIALLY-EXPRESSED CONIFER CDNAS, AND THEIR USE IN IMPROVING SOMATIC EMBRYOGENESIS

(75) Inventors: John Cairney, Decatur, GA (US); Nanfei Xu, Wildwood, MO (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 09/973,994

(22) Filed: Oct. 11, 2001

Related U.S. Application Data

(60) Provisional application No. 60/260,882, filed on Jan. 12, 2001, provisional application No. 60/239,250, filed on Oct. 11, 2000.

(51) Int. Cl.
*G06F 19/00* (2006.01)
*C12Q 1/68* (2006.01)
*C12N 15/29* (2006.01)

(52) U.S. Cl. ............................ 702/19; 435/6; 536/24.3

(58) Field of Classification Search ............... 536/23.1; 435/6

See application file for complete search history.

(56) References Cited

U.S. PATENT DOCUMENTS 5,882,874 A * 3/1999 Fisher ........................... 435/6

OTHER PUBLICATIONS

Attwood, Science, 290:471-473, 2000.*

Gerhold et al. BioEssays, 18(12):973-981, 1996.*

Lopez et al. Molecular Biology, 32:881-891,1999.*

Russell et al. Journal of Molecular Biology, 244:332-350, 1994.*

Wells et al. Journal of Leukocyte Biology, 61(5):545-550, 1997.*

Dong et al., Plant Mol Biol., vol. 39(4), pp. 859-864, Mar. 1999.*

Dong et al., Planta vol. 199, pp. 459-466, 1996.*

Cairney et al., Stress-Related Genes in Woody Plants: Transciptional and Post-Transcriptional Regulation, *Somatic Cell Genetics and Molecular Genetics of Trees*, 1996, pp. 277-283.

Cairney et al., "Conifer Embryogenesis: Gene Expression Studies in Loblolly Pine Using Differential Display, Mass Gene Cloning and High-Density cDNA Array," Abstract Barcelona EPEN Meeting, 1997.

Cairney et al., "Large-Scale Gene Discovery and Expression Analysis—Embryo Development," Abstract, IEG Meeting Gene Discovery Tools, 1997.

Cairney et al., "Differential Display: A Tool to Follow Natural and Somatic Embryo Development in Loblolly Pine," *1997 Biologically Sciences Symposium, TAPPI Proceedings*, pp. 85-91.

Cairney, et al., "Mass Gene Cloning, High-Density cDNA Array and Somatic Embryogenesis in Loblolly Pine: Tools for Monitoring Embryogenesis," SE Abstract Rutgers Conifer Biotech Meeting, 1998.

Cairney et al., "Natural and Somatic Embryo Development in Loblolly Pine," *Applied Biochemistry and Biotechnology*, vol. 77-79, 1999, pp. 5-17.

Cairney et al., "Gene Expression During Conifer Embryogenesis: DNA Arrays as a Means of Following Somatic and Zygotic Embryo Development," Abstract P5 Plant Symposia, *In Vitro* (*Cellular & Development Biology*), vol. 35, No. 3, Part II, Mar. 1999.

Cairney et al., "Special Symposium: *In Vitro* Plant Recalcitrance Transcript Profiling: A Tool to Assess the Development of Conifer Embryos," *In Vitro Cell. Dev. Biol.*, 36:155-162, May-Jun. 2002.

Dong, et al., "Molecular biology of somatic embryogenesis in conifers," *Molecular Biology of Woody Plants*, vol. 1, 2000, pp. 51-87.

Pedroso et al., "Factors controlling somatic embryogenesis," *Plant Cell, Tissue and Organ Culture*, vol. 43, 1995, pp. 147-154.

Pullman et al., "Gene Expression Differences Between Zygotic and Somatic Embryos Monitored by Differential Display and cDNA Array: A Potential Tool to Improve Loblolly Pine Somatic Embryo Quality," *Plant Biotechonolgy and In Vitro Biology in the 21st Century*, 1999, A. Altman et al. (eds.), pp. 81-84.

Xu et al., "Rapid and Reliable Differential Display from Minute Amounts of Tissue: Mass Cloning and Characterization of Differentially Expressed Genes from Loblolly Pine Embryos", *Plant Molecular Biology Reporter*, vol. 15, 1997, pp. 377-391.

Xu et al., "Differential Display as a Tool to Monitor Embryo Development in Loblolly Pine," Supplemental to *Plant Physiology*, Abstract 1516, vol. 114, No. 3, Jul. 1997.

Xu et al., "Contrasting zygotic and somatic embryo development," W-1 Abstract, *In Vitro* (*Cellular & Development Biology*), vol. 36, No. 3, Part II, Mar. 1999.

* cited by examiner

*Primary Examiner*—John S. Brusca

(74) *Attorney, Agent, or Firm*—Troutman Sanders LLP; Ryan A. Schneider

(57) ABSTRACT

The invention relates to a method for staging embryos of plants. In particular, this invention relates to a method for creating a relational database by determining transcript levels of sets of genes expressed at predetermined stages in embryo development. This approach creates a method by which embryos of unknown stage development can be determined by comparisons between expression levels of those embryos to the expression levels found in the database. This approach further allows rapid identification of transcripts in an embryo to be staged by the utilization of probes corresponding to cDNAs comprising the database. Additionally, this invention relates to a method for selecting advantageous plant clones for future propagation. Specifically, this method relates to an approach to link the biochemical condition of an embryo to current culture conditions and thus provides a method for enhancing conditions to produce embryos with a desired biochemical state.

7 Claims, 14 Drawing Sheets

FiGURE 1

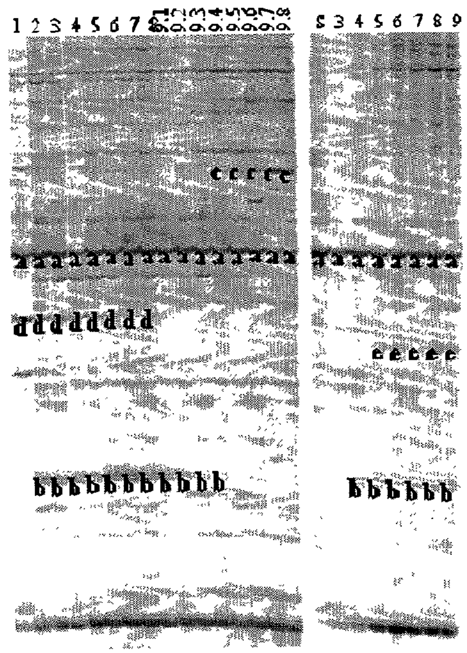

Figure 1. Differential display of loblolly pine zygotic and somatic embryos at different stages of development. The zygotic embryos (left panel) used were from tree BC-1 and the somatic embryos (right panel) are of genotype 260. Primer pair T12VC-AP3 (GenHunter, Nashville, TN) were used in the PCR reactions. The numbers on the top of the lanes indicate the stages of the embryos used. The letters superimposed on the images mark different types of banding patterns: (a), the band appeared in both embryos at all the stages; (b), early to middle stages in ZE and middle to late stages in SE; (c), late stages in ZE and absent in SE; (d), early stages in ZE and absent in SE; (e), present in SE but not in ZE.

FIGURE 2

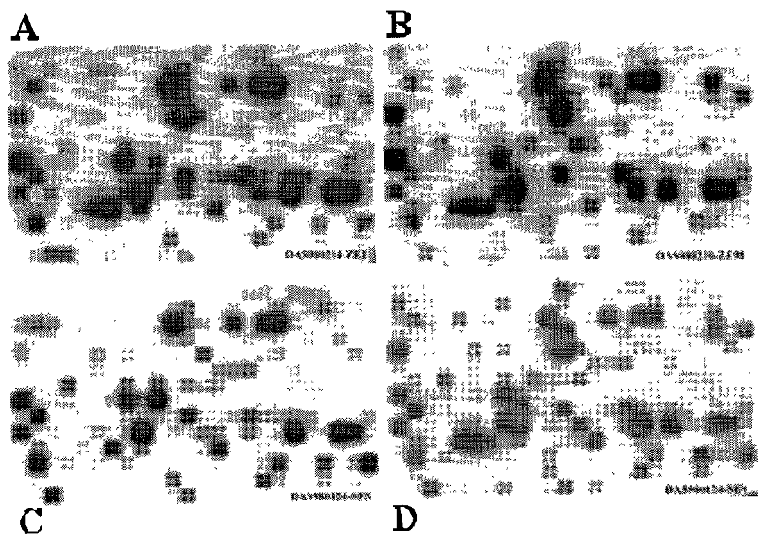

Figure 2. Detection of gene expression by high-density array Southern hybridization. Cloned cDNAs (327) were blotted on a membrane as high-density arrays. Each cDNA was blotted four times as a quadrate. The membranes were hybridized to the total cDNAs derived from total mRNA isolated from zygotic embryos at stage 1 (A), stage 9.8 (B), somatic embryos at suspension stage (C), and stage 9 (D). Dark spots indicate high level of gene expression and light spots indicate low level of gene expression.

Figure 3. Gene regulation studies arising from the cDNA cloning of genes expressed in embryos. See text for their applicability to process improvement.

FIGURE 4

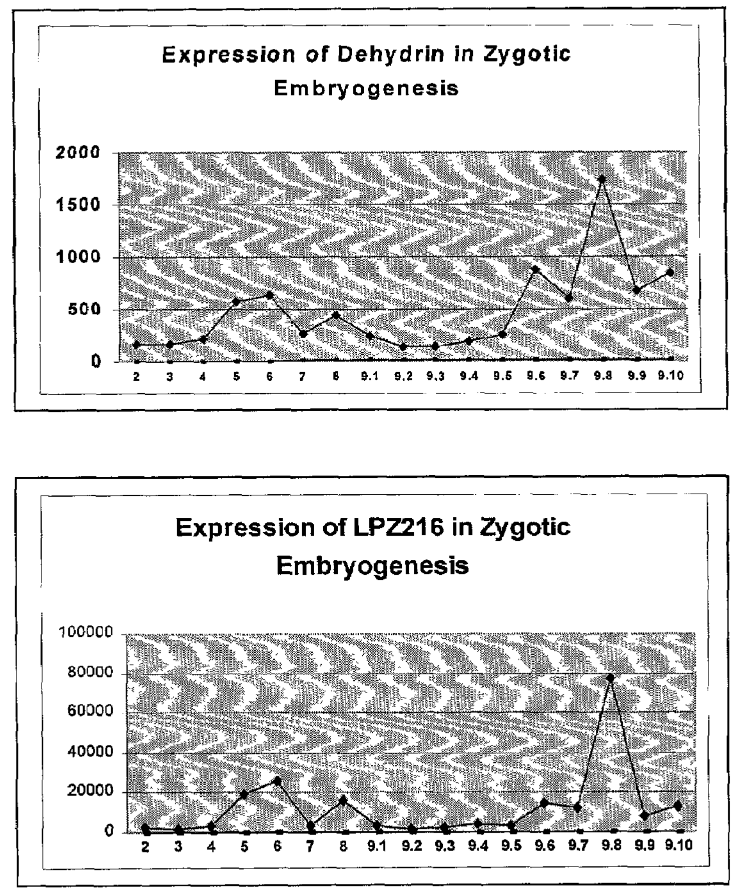

Figure 4. Graphical representation of hybridization of 'dehydrin' and LPZ-216 cDNA probes to total RNA isolated from zygotic embryos of loblolly pine. Five micrograms of RNA was loaded on a slot blot and hybridized with one of the cDNA probes. The hybridization signals were measured by a Fuji BAS-1000 Imaging system and signals were quantified using the associated software. The membrane was then stripped of probe and re-probed with labeled 26S rDNA to determine the equivalence of loading. These signals from this hybridization were captured and used to normalize the signals from dehydrin and LPZ-216.

**Figure 5. Determination of ABA concentration of loblolly pine embryos as described more fully by Kapik et al., *Tree Physiology* 15:485-490 (1995)**

Figure 6. Scheme showing use of gene studies to improve somatic embryogenesis.
TC = Tissue Culture, DAS = DNA Array Southern (an expression monitoring technique), ZE = Zygotic (Natural) Embryo

FIGURE 7

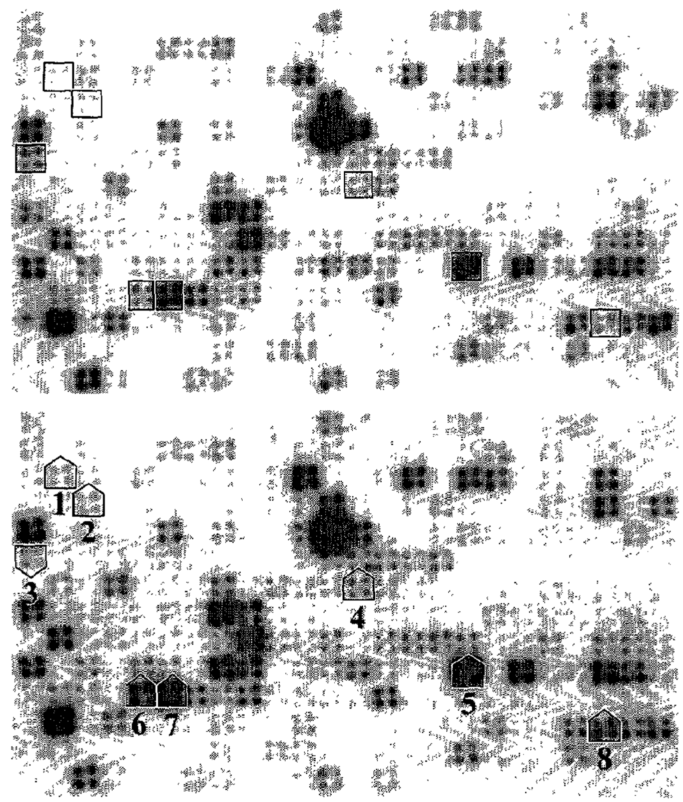

Figure 7. Detection of gene expression by high density array Southern hybridization for loblolly pine genotype 333 after 12 weeks on two maturation media. Top, 5.2 mg/L ABA; bottom 10 mg/L ABA. Arrows up indicate increased gene expression in the 10 mg ABA treatment; arrow down, expression lower in 10 mg ABA treatment. Squares in top panel mark the corresponding spots marked in the bottom panel. Gene 1 (LPS-064), expression is usually higher in ZE than in SE; 2 (LPS-092) expressed in late ZE; 3 (LPZ-049) is starch synthase, higher level in ZE; 4 (LPZ-091) LMW heat shock protein, found in late stage ZE; 5 (LPZ-202) lea gene (late embryo abundant); 6 (LPZ-215) higher level in late ZE; 7 (LPZ-216) lea gene; 8 (LPZ-270) 70S heat shock protein, found in late ZE. A lower level of #3 means a decreased synthesis of starch in 10 mg ABA treatment. All the others bring the expression closer to ZE.

Figure 8. Application of results.

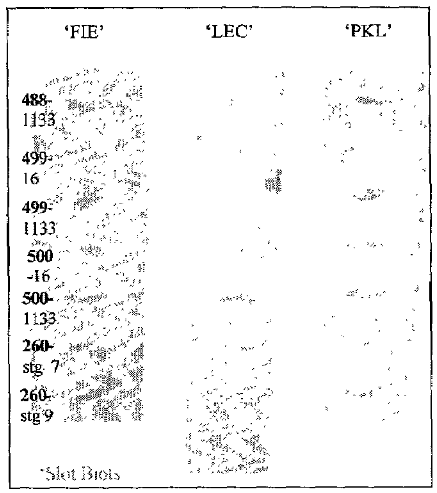

B.

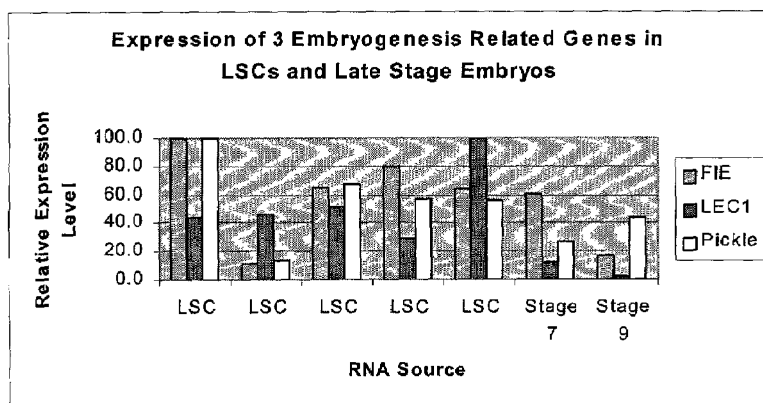

Figure 9. a. Image of RNA slot blot probed with pine cDNA clones bearing similarity to the 'fie' 'lec' or 'pkl' genes from Arabidopsis thaliana. Two micrograms of Loblolly Pine RNA, extracted from either liquid suspension culture (somatic embryos, stage1 &2) or from somatic embryos stage 7 or stage 9, were blotted using a slot blot manifold (Hoeffer ScientificInsturments, San Francisco) according to manufacturers instructions onto Hybond™ N+ (Amersham Pharmacia Biotech, Piscataway, NJ, USA) and UV crosslinked. Each of the three membranes contains identical amounts of the same RNA. The numbers in bold on the left hand side of the images refer to the genotype of the cell line, the numbers below the genotype refer to the media in which embryos were cultured. B. Quantification of the signals shown in panel 9a. Blots were exposed to a phosphorimaging plate for 10 minutes. Screens were read with a BAS1800 (software v1.0) and images were manipulated with ImageGauge (v2.54) (Fuji Photo Film Co., Ltd., Kanagawa, Japan).

FIGURE 10

GGGCACAAAGCTCCGCAGCCTGAGCGAGCGTCATTAGCTTGTCAGTCGGAACCAT

TACCCCTTTCCTCTTCGCTGGCTAGCGAATGATAGGGAATGCTAGCCAGCGAACAA

GATTAGAGCACAGAAAGTATAGCCAGCGAATCAACAGCATAACAACTTAGAGATTTCTTGCAT

TCCCCAGACGGTATCAAGTCATAGTGGAGAATAATCATAATAAGATTTGTGAAAATG

TTTGTGTAGATTAATGTGTAAAATTCAATCCATCAACCATGAAGTGAAGTGCATTCCGTTTTTAA

ATGTTTATTGTATTTGAATGAATAAACAGTTTACACGCGAAAATCCCTACTTTATGTG

CGTACAAACTATGATTTTTTTGCAGTATATAAAAGTTTCCACTATCGTAATTATTTTC

CAGATCCGTCTTCTTAACAACCCGATTTCCTAGCATCCATCTGCGTGGAATAAATCT

ATTGAATTATTAACCCTTGTGATTGGCTAAAAAAAAAA

Figure 10. Sequence of LP2-3 differential display fragment, 507 nucleotides, clone LPS-097.

Figure 11. Expression of LP2-3 Gene: Northern Blot of total RNA isolated from Liquid Suspension Culture (Stages 1-3) and Late Stage (Stage 9) Loblolly Pine Somatic Embryos (Pullman & Webb 1994).

FIGURE 12

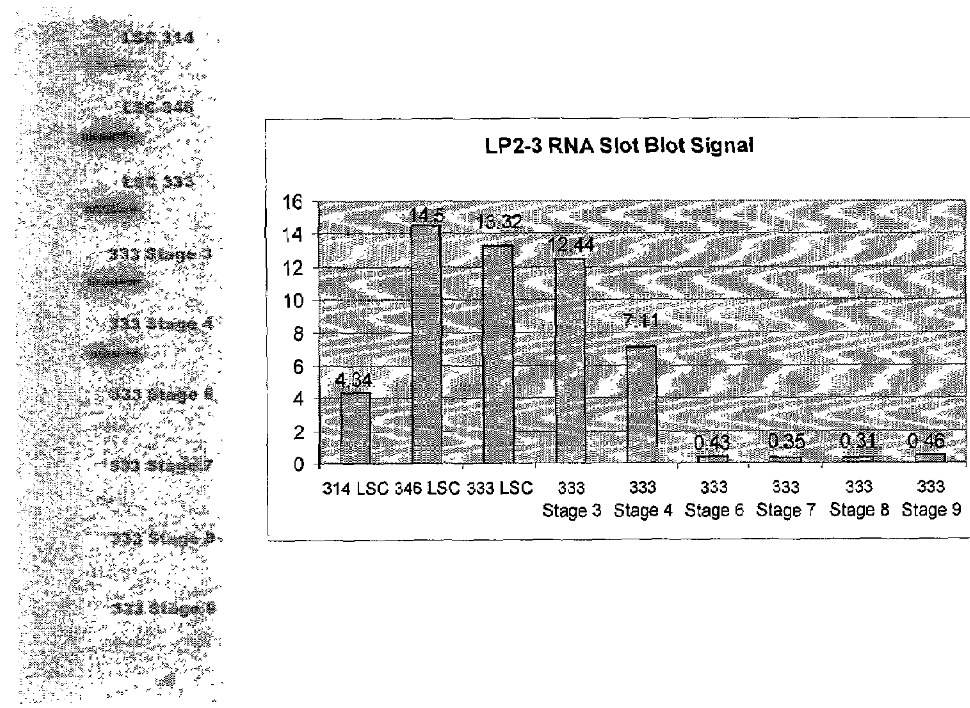

Figures 12A & 12B. Image (1A) and quantification (1B) of a total RNA slot blot probed with an LP2-3-specific probe. For each somatic embryo tissue (liquid suspension culture (LSC) genotypes 314, 346, and 333, and genotype 333 stages 3, 4, 6, 7, 8, and 9) two micrograms of total RNA was attached at each position on the membrane. This blot shows that LP2-3 mRNA is most abundant in early stage somatic embryos, especially when they are in the liquid multiplication medium, and decreases rapidly as embryos begin to mature on maturation medium. It is also apparent that when comparing genotypes, there is variability in LP2-3 abundance in LSC.

FIGURE 13

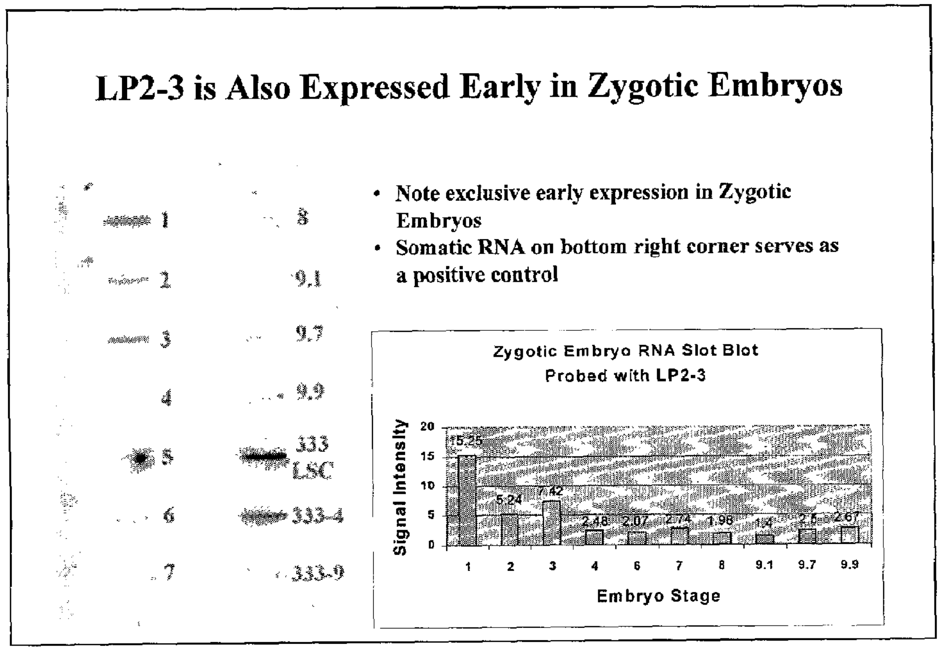

A

B

Figures 13A & 13B. Image (A) and quantification (B) of a total RNA slot blot probed with an LP2-3-specific probe. Isolation of zygotic embryos used in this experiment. From June to September 1996, open-pollinated cones were collected from Union Camp mother tree UC5-1036 were packed on ice and shipped overnight to IPST. Seeds were removed from cones, cracked with a hemostat, and dissected with scalpel and forceps. From each seed the intact ovule was extracted and the megametophyte was sliced open. Embryos were removed, visually judged for stage of development (Pullman & Webb 1994), plunged into liquid nitrogen and stored (20 embryos per 2 mL cryogenic vial (Nalgene Cat. No. 5000)) at -70°C. For somatic embryos, liquid suspension tissue (LSC) was collected, dried by squeezing gently in miracloth (Behring Diagnostics), plunged into liquid nitrogen, and stored at -70°C. Similarly, later stage somatic embryos were plucked from culture, assessed for stage of development, plunged into liquid nitrogen, and stored in vials of 20 to 25 embryos at -70°C.

A

B

Figures 14A & 14B. Image (A) is as shown in Fig. 13A. The quantified expression of early stage zygotic embryos compared to early stage somatic embryos shown in Fig. B

SEQUENCE LISTING

<160> NUMBER OF SEQ ID NOS: 339

<210> SEQ ID NO 1
<211> LENGTH: 567
<212> TYPE: DNA
<213> ORGANISM: Pinus taeda

<400> SEQUENCE: 1
ggtactccac cgtaataacc cttgggaaat agcctatgat ccaggggagg caaccaccta 60
tatcattgac aacagcgaaa aatgtggcgc aagaagtttc acatacaatt catggttaca 120
aagatcacat accaggtgtt ggagcagatt cgatagatat tgaagatatg aagccaagga 180
gtggagcagt tattgaaaag ggcacaaaaa aatttgccat ttacaaagat gaaaatgggc 240
tgattcacaa atactcggca atatgcccac acatgaactg tattgtgaaa tggaatccta 300
tagactcaac tttcgattgc ccctgccatg gttcaatgtt tgataatctg ggtcgatgca 360
tcaatggacc tgccaaggcg gacctatttc ccgaagatta acgatagttg tttgtacatg 420
taattatctt gatattgtat atatatgtat ttaaattata cagtacaata aatccatgtt 480
tgcaggctat ttctgcttga taatttagct ccagatttat acataaccag tttatttggc 540
tgtttttccc ctggcaaaaa aaaaaaa 567

<210> SEQ ID NO 2
<211> LENGTH: 276
<212> TYPE: DNA
<213> ORGANISM: Pinus taeda

<400> SEQUENCE: 2
ggtactccac agaaagaaat gatttgacag aaaaagagag ctgtaggatt gggtaaaccc 60
tgcagtggat atatacaatg tatatgtact ctgtctgttt ttctgttatt tgacggaaat 120
aaaaacgcca tagcgacgga tgactgtaaa tccttaggga cggatgactg taaatcctta 180
ggttggaaga ttacaaacga catatgggtc tttcaatttt cagatttctg taagacttac 240
atttcaaaga ctgtttggat gggcaaaaaa aaaaaa 276

<210> SEQ ID NO 3
<211> LENGTH: 267
<212> TYPE: DNA
<213> ORGANISM: Pinus taeda

<400> SEQUENCE: 3
ggtactccac cagaatgccg cagtttagtt ctctaaagca agcagtaaat taattttgtc 60
aaaatctaaa gagtgtatag tatcagtggg tttgtatttc ctagtttgcc tacaataacg 120
atggggattc accagttttt gtagaatttg caatcatcgg atgacaattt caaagttttc 180
tctaagtcac ccgcattgat atcgagaagc cttccatttt caattattta atatcagaaa 240
atcttttcag ttggcaaaaa aaaaaaa 267

<210> SEQ ID NO 4
<211> LENGTH: 589
<212> TYPE: DNA
<213> ORGANISM: Pinus taeda

<400> SEQUENCE: 4
agcccagctg cgaaggggat gtgctgcaag cgataagtgg taacgccagg tttccagtca 60
gacgtgtaaa cgacgccagt gatgtatacg aatcactata ggcgatggcc ttctagatgc 120

```
atgctcgagc gccgcagtgt gatgaattgc agaatcggct ggtactcacg ggctagagaa    180

aggcacaagc actttttgtc attttaggat cagaggcatt caggtatagg aagggtggct    240

cagataggca gatggatcgg cattttgccc agtcatgaaa cattttatgc atgttattgc    300

ctcccaagga cgaaatcagt tctttgtgcc ttctggtgat atcacttcaa acaaaaggca    360

acagttctgt gatttcatat ggtttgtcac tgaatatttt gttgcagatg ttctctacta    420

tttttatct  gctttcaagt gattatttgt tgattcccca tggatagtta tgctaatcag    480

ttgcatttct cttgtaccag tcaacaaaca aaaatgcttg taggaatcca ttactattta    540

ttttcagaca ggtaaacgtg tagctaattg ttctggcaaa aaaaaaaaa                589
```

<210> SEQ ID NO 5
<211> LENGTH: 431
<212> TYPE: DNA
<213> ORGANISM: Pinus taeda

<400> SEQUENCE: 5

```
tccaaaatac aaaggcttta tttgcatcat gatataatac aaagtaagaa atttacccaa     60

ctgtttaacc taataataat acaaaggaag cattttaccc aactctttaa cgtaataata    120

ccaaagagtg gaatgcttta ttgaccagca agaccttgaa atttttataa ccaatgccca    180

tcaacagagc ctttcttaaa aaacgcaaag cccagctctg tcaccttatt agttagtata    240

aactgacatt cttccaagct tgtgtgcgca gaaacaataa agaacttcac cttggtttaa    300

agaacgtgcc atgaagaaaa cgtcccaaga aaaatgaaat ggctccttcg accattcagt    360

cctccctaga aaaatcaaaa gactccttcg accattaggt cctccaattg ggcatctaac    420

tacaagcggt c                                                         431
```

<210> SEQ ID NO 6
<211> LENGTH: 434
<212> TYPE: DNA
<213> ORGANISM: Pinus taeda

<400> SEQUENCE: 6

```
ggtactccac gggctagaga aaaggcacaa gcacttcttc gtcattttag ggatcagagg     60

cattcaggta taggaagggg tggctcagat aggcagatgg atcggcattt tgcccagtca    120

tgaaacattt tatgcatgtt attgcctccc aaggacgaaa tcagttcttt gtgccttctg    180

gtgatatcac ttcaaacaaa aggcaacagt tctgtgattt catatggttt gtcactgaat    240

attttgttgc agatgttctc tactattttt tatctgcttt caagtgatta tttgttgatt    300

ccccatggat agttatgcta atcagttgca tttctcttgt accagtcaac aaacaaaaat    360

gcttgtagga atccattact atttattttc agacaggtaa acgtgtagct aattgttctg    420

gcaaaaaaaa aaaa                                                      434
```

<210> SEQ ID NO 7
<211> LENGTH: 540
<212> TYPE: DNA
<213> ORGANISM: Pinus taeda

<400> SEQUENCE: 7

```
acgacgtgta aacgacggcc agtgattgta tacgactcac tatagggcga ttggccttct     60

agatgcatgc tcgagcggcc gcaggtgatg gatatctgca gaattcgctt ggtactccac    120

ggctagagaa aaggcacaag cacttcttcg tcattttagg atcagaggca ttcaggtata    180
```

-continued

```
ggaagggtgg tcagataggc agatggatcg gcattttgcc cagtcatgaa acattttatg    240

catgttattg cctcccaagg acgaaatcag ttctttgtgc cttctggtga tatcacttca    300

aacaaaaggc aacagttctg tgatttcata tggtttgtca ctgaatattt tgttgcagat    360

gttctctact attttttatc tgctttcaag tgattatttg ttgattcccc atggatagtt    420

atgctaatca gttgcatttc tcttgtacca gtcaacaaac aaaaatgctt gtaggaatcc    480

attactattt attttcagac aggtaaacgt gtagctaatt gttctggcaa aaaaaaaaaa    540


<210> SEQ ID NO 8
<211> LENGTH: 794
<212> TYPE: DNA
<213> ORGANISM: Pinus taeda

<400> SEQUENCE: 8

ggtactccac gaagcaaaaa gagtcagggg aatgaagatg gggggctccg acaagaagcg     60

gatcagagaa gagcaggaaa tgagtccacc tgaggaatcc tggagacaga aacaggggcg    120

tttaatggag tttgaggcag ggatggccta tgataaacct gaaaatgccg gtgcaggtaa    180

tgagaatttg ccagagtttt gctctctttc aaatgagtac tcgatgttat tgaaagatcc    240

atggagttgg gaggatagca ctggtttcgg aatccgaagc ttagctgctg tcaggaagca    300

gtcttgtata ttggactatc tccatgattc tgctgtagat aatcgctgtg aaaaggattt    360

tgccgagcag cacaaggtac aggaagagga ggattgtttg agaaggtctc tttttgaagc    420

cacagatgat cagctctgga ggcttcagag tctttgcagg atacagaagg tctgtttcct    480

ctggattccg tgggtagcca tgattgcacg accttgttgc aggatgagag cattgttcag    540

ggcgctgctt cttacttcag aatttgggaa caggatgatg gtcacaagga tgccaaaatt    600

catgaagatg gcattggttt tgtgtatggg agtgggatct cggattggat tcggagggct    660

ccctcgaatc aatctgagtt ttctgaatct gttgaatttg aaagctctat gttttcactg    720

taatttgggt ctttttaatt tcttcctatg taatttgggt gtttctaatt tcttccttca    780

gcaaaaaaaa aaaa                                                      794


<210> SEQ ID NO 9
<211> LENGTH: 330
<212> TYPE: DNA
<213> ORGANISM: Pinus taeda

<400> SEQUENCE: 9

ggtactccac catatccagg taaacaaggg aaaacagagt cagcttctag tatgttgtat     60

gccttgctct gtctgttttc tttgatcttt gatgccaagc aagttgaatg tgatcactaa    120

atgttgctgg cagtagagct ggagatgtgc tgtctctttg gtgtcattag cacagaagct    180

attggagaaa tgattattat ctgtttgata acttctagag catttttctg cttccaattc    240

cacaaggtgg aaagtgcaag gatgtttact ttcttaaact gtacttgcct tgtatttgat    300

gatgtaaggt tgtgtggcaa aaaaaaaaaa                                     330


<210> SEQ ID NO 10
<211> LENGTH: 515
<212> TYPE: DNA
<213> ORGANISM: Pinus taeda

<400> SEQUENCE: 10

ggtactcacc atatccggta acaagggaac aagtcagttt tagaaagtgg acccccggtt     60

ccgtcgtttt cttgatctcg gagccaagca agtggatgtg atcactaaat gttgctggca    120
```

```
gtagagctgg agatgtgctg tctctttggg tcattagcac agaagctatt ggagaaatga    180

ttatggtatt ccaccatatc caggtaaaca agggaaaaca gagctcagct tctagtatgt    240

tgtatgccct gctctgtctg ttttctttga tctttgatgc caagcaagtt gaatgtgatc    300

actaaatgtt gctggcagta gagctggaga tgtgctgtct ctttggtgtc attagcacag    360

aagctattgg agaaatgatt attatctgtt tgataacttc tagagcattt ttctgcttcc    420

aattccacaa ggtggaaagt gcaaggatgt ttactttctt aaactgtact tgccttgtat    480

ttgatgatgt aaggttgtgt ggcaaaaaaa aaaaa                               515


<210> SEQ ID NO 11
<211> LENGTH: 331
<212> TYPE: DNA
<213> ORGANISM: Pinus taeda

<400> SEQUENCE: 11

ggtactccac catatccatg taaacaaggg aaaacagagc tcagcttcta gtatgtagta     60

tgccctgctc tgtctgtttt ctttgatctt tgatgccaag caagttgaat gtgatcacta    120

aatgttgctg gcagtagagc tggagatgtg ctgtctcttt ggtgtcatta gcacagaagc    180

tattggagaa atgattatta tctgttacat aacttataga gcatttttct gcttccaatt    240

ccacaaggtg gaaagtgcaa ggatgtttac tttcttaaac tgtacttgcc ttgtatttga    300

tgatgtaagg ttgtgtggca aaaaaaaaaa a                                   331


<210> SEQ ID NO 12
<211> LENGTH: 241
<212> TYPE: DNA
<213> ORGANISM: Pinus taeda

<400> SEQUENCE: 12

ggtactccac tagaccgggt agggtctctc catggttttg cgacttaggt taggtgtcct     60

gttctgttaa tgattttgag gttttgtaat tgtgagtatg tttccagggt tttgaacctg    120

ggtactcggc ctttgttgga atgtagtctg gttaatttat atgtatatgt aaccttgggg    180

tttcgagccc agttctctgt tcttcttgaa atgaaatgcg atttgttcta aaaaaaaaaa    240

a                                                                    241


<210> SEQ ID NO 13
<211> LENGTH: 247
<212> TYPE: DNA
<213> ORGANISM: Pinus taeda

<400> SEQUENCE: 13

atatatacgt atggtattcc acagcatgaa ctcttcgaca ttatatgctt gttatagttt     60

ttaagagagg agacttacct cacacatgta cagcttttta ttgtcgtgct ttcagttgat    120

ggatgattgt tgtagtcctg tcattggttg gacaattttc atcatcctaa agatccaaga    180

attcatgtgg caagaaactt taataaagtc aaatataatc cgatgacgta accctaaaaa    240

aaaaaaa                                                              247


<210> SEQ ID NO 14
<211> LENGTH: 197
<212> TYPE: DNA
<213> ORGANISM: Pinus taeda

<400> SEQUENCE: 14
```

-continued

```
ggtactccac tagtgatcga ttctctgtat gtgacgctgc gcggcggctt atagcgcttc     60

actgagaatg tacggtatat tatgattgat gtgatggatt tgctccgcag cttcggctgt    120

tgtatctgct cacttcggcg tatatatgta atatgttgct tcttcagaga gatgaacttc    180

cccctaaaaa aaaaaaa                                                   197


<210> SEQ ID NO 15
<211> LENGTH: 177
<212> TYPE: DNA
<213> ORGANISM: Pinus taeda

<400> SEQUENCE: 15

atagatcatt ttaaagtttc agtgatttga atctaattcc actgcatttc ctcgcaaact     60

ggcagtcaaa tagtattccc tctttcagtg acaggctggc aggtgtttca ttcttataca    120

aacatgatta tcataattcc attaattcat ggcgttttct ttgccaaaaa aaaaaaa       177


<210> SEQ ID NO 16
<211> LENGTH: 475
<212> TYPE: DNA
<213> ORGANISM: Pinus taeda

<400> SEQUENCE: 16

ttttttttt ttagggagaa aggtaacttc agccagcttt caaaggcaac acctacaaaa      60

ggggtgactg agaactcaga cacagacgac aagtgatcat tcgggccaga tttttgttga    120

gagagttgta gtgtgtaatt gattcatttc atacatttga tatgcaagcc tgtacaatag    180

cctgtgactg ttaagggcat tcttttgtct ccctgttgct atttgggttt ccggtgtgtt    240

cattttcact tatttttgtg ttttagctgg aagaatttga gagggtagaa ttgtgtcatc    300

gctatggctt gtgcatgact catgagccag cagttgaaac ttttatttat taagttataa    360

tactatgtct tgtcaattct caataaaaga tattttatgc tgttgggcag catctaaaat    420

gttttgtatg ttagcataaa atcccatttt ctataagttt ttgccaaaaa aaaaa         475


<210> SEQ ID NO 17
<211> LENGTH: 592
<212> TYPE: DNA
<213> ORGANISM: Pinus taeda

<400> SEQUENCE: 17

agcaggttca gtcagacgtg taaacgacgc catgatgtat acgaactcat atagggcgat     60

tggcctttag atgcatgttg acggcccgca gtgtgatatt cgcagatcgc ttttttttt     120

ttttaggcat ggtgcgcgat gagctgatag cgatgatgaa gaccaagacc accaaaggaa    180

gattcttcag agcaaaagct acggagacag aaccagagga ctcaaagccg gaatccattg    240

gtgaggtacc tgcaaatgtg tgatggacta actaagaagg ctccttgaga ggacccatta    300

agcacagtgt ttttaagtcc caaattctgt tgcaattccg ttgaaaatca tttttacgat    360

tttaggtatg atgtgtgcaa ttttaaagtt ggaattattg tgggcaaagg ctataagtga    420

ttgtctaatc catttaattt attatctttt gactaagagc atatctaggc tggaagaaat    480

tagggcacat taatgtaagt tttgaatttg aacattctgg gttttgcaat gcaaaacacc    540

acaaatattt tataatgtta gaggtgtact ttttctggcc aaaaaaaaaa aa            592


<210> SEQ ID NO 18
<211> LENGTH: 204
<212> TYPE: DNA
<213> ORGANISM: Pinus taeda
```

<400> SEQUENCE: 18
ggtactccac caataatact tgtctgttct tgcttccctg ctgatccact aagcagatta 60
tttctgtcca ccccacttta gagtctcagt ttgtaaagca ctccctagga gctaaactca 120
tttccaatgg attaaagcac tccataggag ctaaactcat ttccaaggga tttttgtcca 180
tttctctgtg ctaaaaaaaa aaaa 204

<210> SEQ ID NO 19
<211> LENGTH: 347
<212> TYPE: DNA
<213> ORGANISM: Pinus taeda

<400> SEQUENCE: 19
atgtatacat atatgtggta ctccacacac tcaaataaca gcatcacaat caaaacaaga 60
aggcggccag aaagctttaa aatgctaagc ctacaggtaa tattcacaac tgcattaagc 120
accccgcttc ctagttctga agaagccaga aagctttaaa atgctaagcc tacaggtaat 180
attcacaact gcattaagca ccccgcttcc tagtaggcta gtactaggac taggaccgca 240
ttaccagttc ccttatcttc tactcatcct ctacaggaaa aactatgact aaaactgcat 300
taccagttcc cttatcttct caactcgtcc tctacaaaaa aaaaaaa 347

<210> SEQ ID NO 20
<211> LENGTH: 376
<212> TYPE: DNA
<213> ORGANISM: Pinus taeda

<400> SEQUENCE: 20
ggtaatttcc acccaccacg ggctttttca attaacccat ttctaccact ccacattagg 60
gttctaagtt ttgtgactca cccccaattt cgctgatatt ttgcattgca gcttgtttat 120
ctacaggaaa tggctaatca gtactttcag aatttggttg cttctgtaca ggaaatggat 180
aatcaatcag tacttctata cttaagttgc ttacgcgggg atcagagcct tacttcagaa 240
aattgaatac attttcttct ttgtgtatgt atcaggcatg gaattatatg tagcatgcca 300
tggaatgcgt atttactaga ttatctttta atttaataca tatgttgctt actaatttgt 360
ccacaaaaaa aaaaaa 376

<210> SEQ ID NO 21
<211> LENGTH: 332
<212> TYPE: DNA
<213> ORGANISM: Pinus taeda

<400> SEQUENCE: 21
ggtactccac acactcaaac aacagcatca caatcaaaac aagaaggcgg ccagaaagct 60
ttaaaatgct aagcctacag gtaatattca caactgcatt aagcaccccg cttcctagtt 120
ctgaagaagg ccagaaagct ttaaaatgct aagcctacag gtaatattca caactgcatt 180
aagcaccccg cttcctagta ggctagtact aggactagga ccgcattacc agttccctta 240
tcttctactc atcctctaca ggaaaaacta ggactaaaac tgcattacca gttcccttat 300
cttctcaact cgtcctctac aaaaaaaaaa aa 332

<210> SEQ ID NO 22
<211> LENGTH: 238
<212> TYPE: DNA
<213> ORGANISM: Pinus taeda

<400> SEQUENCE: 22

```
ggtactccac tattagattg atgcaagacc aactgatcat ggctagggtg tattcaagca     60

tttcccaggc taggaataat cttgatttat accatgaatt gatgcttcgt attaaagaat    120

gtcaacgtac attgggtgag actaatgccg attctgatct acctcaaagg taataatttt    180

tgcattagct gcttctaaat caagagtagt aagtgcttcc atttgcaaaa aaaaaaaa      238
```

<210> SEQ ID NO 23
<211> LENGTH: 170
<212> TYPE: DNA
<213> ORGANISM: Pinus taeda

<400> SEQUENCE: 23

```
ggtactccac aaggcatata tgggcaattg attttgccta gcccaaattc ctattcaagc     60

ttgcgtattt ctaaaagatg cactattttt tgtccgagtg taggttttga attcattgta    120

acattcagca atattaattc aggggtagca tttctggcaa aaaaaaaaaa               170
```

<210> SEQ ID NO 24
<211> LENGTH: 152
<212> TYPE: DNA
<213> ORGANISM: Pinus taeda

<400> SEQUENCE: 24

```
tttttttttt ttagggtaga aaaccatgct tcactaacaa ggtataaaat tacaatataa     60

ttctgggtgt aaacgacctg atagatgatc tgcaagtgcc aggaggcaat atctagcaga    120

atacgtacaa attaaattgc caaaaaaaaa aa                                  152
```

<210> SEQ ID NO 25
<211> LENGTH: 197
<212> TYPE: DNA
<213> ORGANISM: Pinus taeda

<400> SEQUENCE: 25

```
ggtactccac caatgatcac ccatgtccat ttggttaatt caatgtcaag atttagtagt     60

tccgtattcc cttgggtaag ctgtaatggt ccatttggga acagtccatg tttgggacac    120

aagttcaata gagatgtcat ccataaatat gggtatgaat ctcttccttc cctctccgcc    180

caataataaa aaaaaaa                                                   197
```

<210> SEQ ID NO 26
<211> LENGTH: 199
<212> TYPE: DNA
<213> ORGANISM: Pinus taeda

<400> SEQUENCE: 26

```
tttttttttt ttagtagcaa tagcaatcca ttttagggat ctgcagatca gtgactaagt     60

gacccctacc cccaaaggat taattgtact ttggcttaac cacaaaacct gattcaaaaa    120

atgtgaagtt tttacccatt aaattaattc ccaaaagtaa ctacaaattc cagagtacat    180

ttttacccaa aaaaaaaaa                                                 199
```

<210> SEQ ID NO 27
<211> LENGTH: 455
<212> TYPE: DNA
<213> ORGANISM: Pinus taeda

<400> SEQUENCE: 27

```
ggtactccac tatacaatat caaggcatat ctgccggttg ttgaatcatt cggattctca     60
```

agcactctcc gtgccgcaac ttctggccag gctttccctc aatgtgtgtt tgaccactgg 120
gatatgatgg gatctgatcc attggaacct ggttcccaag ctgggcagct tgtgactgat 180
atccgtaaga ggaagggtct taaggagagt atgactccct tgtcagagtt cgaagacaag 240
ctgtagagct ttgctatgtt tgcatgtcgg atgctgtcaa gattgaggaa cctccgagta 300
ttaaaacaca gttttgtgtg ctaggactat ttaaatttat gctattcacg tatttttgtg 360
atctgttatt tatgttattc acgtattttt gattggaaaa tactttttac aagtcatcca 420
ttaatctttt aaatgttaca taattctctc ttgtc 455

<210> SEQ ID NO 28
<211> LENGTH: 93
<212> TYPE: DNA
<213> ORGANISM: Pinus taeda

<400> SEQUENCE: 28
aagcttggta ccgagctcgg atccactagt aacggccgcc agtgtgctgg aattcggctt 60
ggtactccac tatacaacat caaggcatat ctg 93

<210> SEQ ID NO 29
<211> LENGTH: 28
<212> TYPE: DNA
<213> ORGANISM: Pinus taeda

<400> SEQUENCE: 29
cttttcttcg tgcttttcgt ggagtacc 28

<210> SEQ ID NO 30
<211> LENGTH: 156
<212> TYPE: DNA
<213> ORGANISM: Pinus taeda

<400> SEQUENCE: 30
ggtactccac aaagtgagat gagtgatatg aggtcaaaca cgtaaatgac aatagctatt 60
atttccccac ttgtttgtgg ctgtgtatat tatacttcat tgtcaggact tttgtatggt 120
tgaagttgca aggttttggc aaaaaaaaaa aaaaaa 156

<210> SEQ ID NO 31
<211> LENGTH: 421
<212> TYPE: DNA
<213> ORGANISM: Pinus taeda

<400> SEQUENCE: 31
ggtactccac ctccagctgc ttatccaagt actacggata gttcatactc ctattatgct 60
tctgccaagt gaaccagaag gcttctgttt ctacactagc aaactgatag ctcgagcatt 120
ctcatttact aaggatgata attcaaaatt gtaacattgc aaacatcagc aaacatcagc 180
atcaactctg ttactattac aagcaatgga tgcgtcgctg atgctgcggg agagtaaatt 240
tttagtttac tgcggttggt aattgagtag gttgacttac atttctgttg taaagccgtt 300
gtcgggcatt gtttatctgg ccgagttagc gccaggaagc taaatgtacc aaatatttat 360
ttttatttta ttaagaatat aaaatttagt cgtcttctgc tgcccaaaaa aaaaaaaaaa 420
a 421

<210> SEQ ID NO 32
<211> LENGTH: 163
<212> TYPE: DNA

-continued

<213> ORGANISM: Pinus taeda

<400> SEQUENCE: 32
atggccatgg acttatgact ttcaaaaccc taaaacctat ctacaacttt ccacgctgag 60
attttccgag gaaggcattc taagccattc ccaccgtact ttaataaaat aaaaacaaga 120
agatagtaaa gctaagctac aaccttccgc caaaaaaaaa aaa 163

<210> SEQ ID NO 33
<211> LENGTH: 554
<212> TYPE: DNA
<213> ORGANISM: Pinus taeda

<400> SEQUENCE: 33
gaccgcttgt aggaacacta gcagattccg gaacataggt actttgaaca tctttcactc 60
ctcaccatat gaatagtgag tcgatggcgg ccttaacagt cgagcatgct ttgatttcgt 120
ctctctctct agtgaccgaa atcaatctca ttatatatgt cattatgcat tcattcccac 180
ttcctaactt tcattattgt tcaaaacttc gccttcctga aaatgctata atagtagggg 240
aatattgaaa aacttccgcc aagctaaaaa ggcacttaaa gcacctggat ttgaaccagg 300
atttcccacc ccgatgaggg ggggtgtctt tccattgaga cgatgcctta ctcggcagac 360
cctgtggggg tctttatagg tgacttaata cttaagtata ggacttaaga gagaggaagc 420
gaccgcctct ctgatcaagc ctttacgtgc gacgtgccca ggtaaaggct gatctcacca 480
aataattcag agaaagaaga tgactccaca gtagcgaaac tcctacattg tcttacatat 540
cgtaacaagc ggtc 554

<210> SEQ ID NO 34
<211> LENGTH: 557
<212> TYPE: DNA
<213> ORGANISM: Pinus taeda

<400> SEQUENCE: 34
gaccgcttgt gcctggtgtc caaactagga cgccttagtt ttcctaagaa ggaaacccag 60
gcgttgactt gaggcagact tgtgcttctg ggtactctca ttcactgcgt gaccttgaga 120
aagggacttt acctccagga tcctcaaact tcttctctgt aaaatgagca ttgtaataat 180
tatatcccag gcttatgttg ggaatattca ataaatgctc ccttcattct ttaaaaaata 240
agtaaagaca gcctgaatgg gagccacgtt ctcattcttc tttctctatg caaaatgtat 300
tgtgtaatgt ttgtgtacta gtagttcaag agcaaataag tagttggtta atggctaaca 360
tatttcttaa atttgtaact gttaagataa acattgaaca aggaaaaaga ttcgtaactg 420
aaatgtaaag tcatttgacc ctggatagtc aatgacaatc ttattcacag tgtaataagt 480
aattcataac gagatgatta ttatgaaatt atcaatagcc tgctatatca ctttatgttt 540
atgatccaca agcggtc 557

<210> SEQ ID NO 35
<211> LENGTH: 373
<212> TYPE: DNA
<213> ORGANISM: Pinus taeda

<400> SEQUENCE: 35
gaccgcttgt ggaagaaaag aaagaatctc tttcggattc aataggcggt atgggagagt 60
ctgctactgc ctcttggatt ccaggaatcc tagagctggg agtatgagtt ggagatgatg 120
aaggtgtctc ttacctattt cttgaagtgg atggagttgt gaaaatcgaa cttctagctt 180

```
cagctaaaaa ccttccccta gaatctcttg ctctatgcat atcattttta tttttttcttt    240

caagataggg taataattct ctttctgatc ttccaggtca ctctaggtgc aagaagagag    300

catagtcaag gaactattaa accaataact ttctcttttc tgatcctcca gttcactcta    360

ggtacaagcg gtc                                                        373


<210> SEQ ID NO 36
<211> LENGTH: 485
<212> TYPE: DNA
<213> ORGANISM: Pinus taeda

<400> SEQUENCE: 36

gaccgcttgt gcaaagtaga taccgtcctg ttccggtgaa ttgaagtaca ttttcaaaat     60

gcgctactat gacattttat aggatgtctg agtgtaaaat aatggtactg gttgttgcaa    120

agaatctgat gtttggatgt atggaactat aaatagatgt tattttctga tccagaaggc    180

tttccttacc aactgatttc atcttcagaa actaaaagct cttgaacttg tgtagatggg    240

gcttggtcat tgtagtttaa atgcattatg tagtggcaaa aaaaaaaagt tatagcctac    300

gtttcaaatg gatttgctcg acaatcaaat gaattacaat tgaatattca tgtataccca    360

aattttaaat gtagaatgac atcatcaatg tagacaaaca ccactgtgct tgtccttgat    420

atcctctttc accatataat tggtggctta ctcaaagtca ctatctgatg caactacaag    480

cggtc                                                                 485


<210> SEQ ID NO 37
<211> LENGTH: 500
<212> TYPE: DNA
<213> ORGANISM: Pinus taeda

<400> SEQUENCE: 37

gaccgcttgt tcaatgcaga atctcgaaga gatgtcttgg acaaatactg aactggcacg     60

attggtgtag tgcggttcaa aaggcgctcc agattcgtct ggaacgaatc ttcatacgct    120

gaacaattag acatcttgta cgcaagagaa ttacgatcgg ccatataaaa accccaaaga    180

gaagaaagtg tttcgaaatt ctcccagaaa acagtcttat gccaccgatt tgtcttttca    240

acatgcattt gcaatgaagt ctttggattc ttactgtgag tgctgatcag caacggattt    300

tcgatctgta tagctctgcc gattcctggt taaagcagct aagagttagg catccagatt    360

ttgagttttt tgcatctcac aatgtttgaa tacatttcaa atccattgtt ggagtaacct    420

aacaacaact gtactcttct tcctatttct gaagccctct gccagtttaa ggcagagaac    480

tgagttatct acaagcggtc                                                 500


<210> SEQ ID NO 38
<211> LENGTH: 398
<212> TYPE: DNA
<213> ORGANISM: Pinus taeda

<400> SEQUENCE: 38

gaccgcttgt ataataaagt ggtaccgcgt cctgcaaaca gggttctctt gccatcctgc     60

tacaaccctg cagtggtcgc agtagagaga atcggagcaa cgaacgtttt cccgaatata    120

tggagcggga ggaagagttt tcttgctgat gatccaatcg gagtcgaact gccaccgctg    180

gatgaagggc ggcgaggaaa tcttgggggg cagaggcccg tcggcgtagg aaataagaaa    240

cgatttgata tggaacgaaa gggcccgtcc agggttcgat ccccggcagg gcagccagcc    300
```

-continued

```
ccgaactaaa caaaacaata agaacaaaca gcaaagtaaa agaaagcacc agaagaaaca    360

gcagcagacg aagagtaagg agctgcccac aagcggtc                            398


<210> SEQ ID NO 39
<211> LENGTH: 179
<212> TYPE: DNA
<213> ORGANISM: Pinus taeda

<400> SEQUENCE: 39

gaccgcttgt aatccacagc attttcaata acttcctgag gtgacatcca cctccactca     60

gaaaactcgg ctgcatctgt cccatcacca gctagattga tctcactctc gtctcctcta    120

aattttagga ggaaccattt ctgtgcttga cctttccatt cgcctcccca caagcggtc     179


<210> SEQ ID NO 40
<211> LENGTH: 221
<212> TYPE: DNA
<213> ORGANISM: Pinus taeda

<400> SEQUENCE: 40

gaccgcttgt atataatgtg aagacacaat aaaattttgt ccaacaaagc aaccaaacga     60

ccaaaaattt agctgtgaca tcaaaaagct caacccctac aatgaatgta accttaatct    120

agaaaattga tccatgatct ccactgaatt ttctcgttca tcctgaagaa tgagaaactt    180

aaatgtaccc gattccctca accaagcccc cacaagcggt c                        221


<210> SEQ ID NO 41
<211> LENGTH: 473
<212> TYPE: DNA
<213> ORGANISM: Pinus taeda

<400> SEQUENCE: 41

gaccgcttgt aatccacagc attttcaata acttcctgag gtgacatcca cctccactca     60

gaaaactcgg ctgcatctgt cccatcacca gctagattga tctcactctc gtctcctcta    120

aattttagga ggaacctgta attggtaggg gcttgtcata aatgatcaag acgacccgca    180

tcgtgatgcc aagcttagtc tttctactta ctgtctatgt aatggtcacg ggcccttctt    240

atgtttatgt ctctttgaaa tggacgattt ttttgtttta ggtattcagt ttctgaagct    300

gttttggtag taaactgggc tcaatcattt ctgttgcttg aactttccat tcgcctcccc    360

cacaagcgtc agccgaattc tgcagatatc catcacctgg gggggccgct cgaacatgca    420

tctagaaggc caatcccta tatgaattct attaaatccc tggcctcgtt tta            473


<210> SEQ ID NO 42
<211> LENGTH: 339
<212> TYPE: DNA
<213> ORGANISM: Pinus taeda

<400> SEQUENCE: 42

ggtgcgatcc agaaaactat catctctcac tgctcgtgaa caaaatgctg gttcatagcc     60

atcactaagg ctaaggtact atccagccaa actgatctca aataataatt tcataagctt    120

aaataaatag tccagccagt agatggagcc aaaaagccat agaagcttca aatacttgtg    180

gtatcaatct ctcctctgtt aagggaggta tcagatcaga agcactaatc aaatgcatac    240

ataaatgcag tagactgcaa taaaacaaaa tctgcagata gcaacagagc gcttaacgaa    300

cggaaaagag tttaacttga tctatcacag gatcgcacc                           339
```

-continued

<210> SEQ ID NO 43
<211> LENGTH: 303
<212> TYPE: DNA
<213> ORGANISM: Pinus taeda

<400> SEQUENCE: 43
ggtgcgatcc acaatagttc gtacgagcga cgtctatctg gttaatcaga acacatatct 60
aatttggaaa tttgtgggca taaagctcca cagtgtaggt gggctaatcc catgaaacat 120
tactcttcaa aacatcatac aactgaggtg gaaattgcaa aagattatta ctggatgctg 180
atctgggact aaggtggtgg ccattggtaa tgttgtgttt cagaaatata tcttcatgat 240
gatcagtagt tgcatctggt tggaagaatg ataaattctg gtaatttgtc ttgggatcgc 300
acc 303

<210> SEQ ID NO 44
<211> LENGTH: 274
<212> TYPE: DNA
<213> ORGANISM: Pinus taeda

<400> SEQUENCE: 44
ggtgcgatcc aactagaaga atataaagaa aaattacgga ctaccagaaa acatcacatc 60
acagtgtatt gcattctcaa taatcagaac tgtactggct aatatcgctg tgcctgtcgt 120
ttcattttcc tgtcatccgc atagggcccc tcattttccc tatcttgcag aaatccaaga 180
aatgcaagaa aaccaaaaag gaagaaaccc ccagaggaag agtccgaaga ggatatgggt 240
gtcagtcttt ttgactagat tggaggatcg cacc 274

<210> SEQ ID NO 45
<211> LENGTH: 269
<212> TYPE: DNA
<213> ORGANISM: Pinus taeda

<400> SEQUENCE: 45
ggtgcgatcc cagaacattt cagacagatt aaaacaagat ctagtcaatt cctacaaggg 60
aaacttttgt caagatccgg atccagattt tcctcaagta aaactaatct cattaaatcc 120
aagccaatct ctagcaaaat tcaaacactt tttattaaat ccaagccata tatctggcaa 180
attcaccgaa atatgtacaa tcgcagcgca ttgcttggct tgcgacagaa accatattcg 240
cacgtcttca taaggctttg gatcgcacc 269

<210> SEQ ID NO 46
<211> LENGTH: 240
<212> TYPE: DNA
<213> ORGANISM: Pinus taeda

<400> SEQUENCE: 46
ggtgcgatcc aacaacacag cttcacactt actccatcct ctggaactct catcagattg 60
tgttcttcgt agaccaagtt cctgtgagag tccacaggca cactgaggct acaagcgatg 120
tgttccctaa agaacagggg atgtacatgt tttccagcat ttggaatgca gacgactggg 180
caaccagggg tgggcttggg aagacaaact ggactgccgc tccattcagc ggatcgcacc 240

<210> SEQ ID NO 47
<211> LENGTH: 242
<212> TYPE: DNA
<213> ORGANISM: Pinus taeda

<400> SEQUENCE: 47

-continued

```
ggtgcgatcc caacaccaag tgagaatgaa gcaatataaa tcagcagact cactaaagcc     60

aaaacagtga aaaatgtttc atattgggaa tctgctccag aatgagcctt caagtaaaat    120

gacaaactaa cgaggaagag acatacggcc atgcccccag atgagaccat gaggaggaga    180

cgtcgtccgg ctttatccat gagccataca gcaactgcag tcatgatgac ctggatcgca    240

cc                                                                   242
```

```
<210> SEQ ID NO 48
<211> LENGTH: 213
<212> TYPE: DNA
<213> ORGANISM: Pinus taeda

<400> SEQUENCE: 48

ggtgcgatcc aggaaatcat caaaggggag cacatccaat gtgcaaaata agatcatcat     60

gcagcaagat ctctgaaata taagctctgt aagaccaatc tgaagtgctg atgatcaata    120

tgaactgaaa catcatgcca caatgggctg gtacttgtgc aaaattctct ggcatgtgat    180

gagaatcaca tggttacctc tttggatcgc acc                                 213
```

```
<210> SEQ ID NO 49
<211> LENGTH: 235
<212> TYPE: DNA
<213> ORGANISM: Pinus taeda

<400> SEQUENCE: 49

ggtgcgatcc aaagagcctt cttgcagaca atccgtgaaa acatggctat acaataaatt     60

cccagtttgg aattctaaat aaaactgttc aatatttgaa ggcctctgat atcacagaga    120

ctgatattag aatggaagca tgtagcaacc ctagaagctt tcgcataaag ataccagatt    180

aattcataag aaggatctct cgttcaccag tcacatatca cagtcggatc gcacc         235
```

```
<210> SEQ ID NO 50
<211> LENGTH: 216
<212> TYPE: DNA
<213> ORGANISM: Pinus taeda

<400> SEQUENCE: 50

ggtgcgatcc gttagatgag ctgccaagta tggaattatt gacatttttg gacgggttat     60

gggcagaggg atgtgccaag ctgaagaaga taccggggtt ggagcaagcc acaaaacttc    120

gagagttaga tgttagtggg tgccctcagt tagatgagct gccaagtatg gaattattga    180

catctttgga cggcttgtgg gcaaagggat cgcacc                              216
```

```
<210> SEQ ID NO 51
<211> LENGTH: 462
<212> TYPE: DNA
<213> ORGANISM: Pinus taeda

<400> SEQUENCE: 51

ggtgcgatcc acatagtttg aatgcaagga aattgcacat acttcgtggg gaatttcgat     60

ggcaaatcag tccaggtaaa tgacttctca acataggtcc aaaactcttt catagaccag    120

atcttgaccg tgttgtccat gccacagctt gcaatacgat atacatctga aggatgaaaa    180

tctacactga gaacttcatt gcgatgtccc ccagctccag caaatatcaa aatgcatatt    240

ccagtttgaa cattccagag tcgtacagat tcatctttgc tagcagataa aataagggaa    300

ggtttcagtt gcttgggtcc ttatttcatt cacagaactc catggccaac gaaactctta    360

tggacttttc atttgcacat ccattctcga attatacatt gtgaccgcag ccactaataa    420
```

```
tggggaacat cactcgcctg cccacttatg tgttaaagaa tc                          462


<210> SEQ ID NO 52
<211> LENGTH: 246
<212> TYPE: DNA
<213> ORGANISM: Pinus taeda

<400> SEQUENCE: 52

ggtgcgatcc cctccattta ccatggtata ctgttccaaa ggttccagag cctagctctt      60

tcaattcttc aaggtcagca ttctttatta tctggaaact tcgctagctg tgtctataat     120

cacgaaaccc agacggggaa ctaataggcg atgaagtttc tcttatccat aaccgttgca     180

aagatcttac acggagtttt ctcttcttct gcgtggcttt tctttcccgt attctcggat     240

cgcacc                                                                246


<210> SEQ ID NO 53
<211> LENGTH: 527
<212> TYPE: DNA
<213> ORGANISM: Pinus taeda

<400> SEQUENCE: 53

ggtgcgatcc atacatgcga gggcgcatga gagactacca caaatcctac atacctccat      60

tcacccctgg atcggttata caaggatttg gggtggctaa agtgatactc tcaaatcacc     120

cagacttcag agagggtgac tttgtatctg gtactatagg atgggaagag tacagcataa     180

taccaaaagg gagtaactta agaaagatca aatatacgga cgtaccactt tcatattttg     240

tgggtgtttt aagaatgccc gggtttactg cttatgctgg attctttgaa gtttgctctc     300

ctaaaaaggg ggagcatgtt tttgtctctg ccgcttcagg agctgttggc cagcttgttg     360

ggcactttgc aaagttgatg ggttgctatg ttgttaggga gcgcgggtaa caaacagaag     420

gctgatctgc tgaaacataa aatgggcttt gatgatgatc tccaccataa cgaggagcat     480

gacttcgatg tggctttaaa aaggcatttt ccagatggga ttgcacc                   527


<210> SEQ ID NO 54
<211> LENGTH: 273
<212> TYPE: DNA
<213> ORGANISM: Pinus taeda

<400> SEQUENCE: 54

ggtgcgatcg aactgaatga atgacgttgc caagctatgt ttgggaatta aaacttgaat      60

gccgttattc tctccttttt ccaaaagggc cttttctgcc agaaaacctt aaatttctga     120

ctggtttcca agtccaattt ttaaaatatg gattggttta ccattgaagg caccaccatg     180

ctctgaaagt tatggactgc acttgcccca gtgctatatt tagtccagat agcgcttgtg     240

tctctaaatg catctccctg ctcggatatc acc                                  273


<210> SEQ ID NO 55
<211> LENGTH: 220
<212> TYPE: DNA
<213> ORGANISM: Pinus taeda

<400> SEQUENCE: 55

ggtgcgatcc gaacagaggg agcagatttt gcccttgcaa gtattcacaa cattagagaa      60

gccctgccag agatatggga ggaagaagat gcagagaaca ccaaaaatgt tgtgggatca     120

agaggagcgg atgcaactat agaaactgtt gtcacggcat aagccatcgc ctcattgaat     180
```

```
gagggaatgg aggactagac aaatcccttt ggatcgcacc                      220


<210> SEQ ID NO 56
<211> LENGTH: 483
<212> TYPE: DNA
<213> ORGANISM: Pinus taeda

<400> SEQUENCE: 56

ggtgcgatcc gattgggcag ctgcagcctt gggaagcttt agaatcaaat tgcactcatc     60

ctccaggagg tattgagaag tcaatttctc aaggtctaca gtgacagaag gaaccatctt    120

gacaatctta tcaggtttcc tgctctggtt aaacacttca actttgacag gacgagagaa    180

tgtgactaat tcatcttctt catcagactc tacatcttcc tgtttcaaga aacaaagata    240

ctgatcatca ctagggcaag aattgatgat tttgatatct ctggagaagc cagtgtttac    300

attggtttgc ttcatggcca ccagtctatg gcataaagct ttcccgaaag ggtacttggc    360

agatttaaca gagcccaacg ttatatttaa ggcccatctc tttgctctca aaatttttct    420

tgcatcctct ggagaatata aaaccccttg gtgtctcttt ccacaaacac cttctcattg    480

atc                                                                  483


<210> SEQ ID NO 57
<211> LENGTH: 472
<212> TYPE: DNA
<213> ORGANISM: Pinus taeda

<400> SEQUENCE: 57

ggtgcgatcc aactgagaag ggtgtttggt ggaaagatga caccaagtgg gttctatatt     60

ctccagagga tgcaagaaaa attttgagag aaagaagatg ggcccttaaa tataacgtgg    120

ggttctgtta aatctgccaa gtacccttca ggaaagttta tgccatagac ttggtggcca    180

tgaagcaaac caatgtaaac actggttctc cagagatatc aaaatcatca attcttgccc    240

tagtgatgat caggaagatg tagagtctga tgaagaagat gaattagtca cattctctcg    300

tcctgtcaaa gttgaagtgc ttaaccagag caggaaacct gataagattg tcaagatggt    360

tccttctgtc actgtagacc ttgagaaatt gacttctcaa tacctcctgg aggatgagtg    420

caatttgatt ctaaagcttc ccaaggctgc agctgcccaa tcggatcgca cc            472


<210> SEQ ID NO 58
<211> LENGTH: 246
<212> TYPE: DNA
<213> ORGANISM: Pinus taeda

<400> SEQUENCE: 58

ggtgcgatcc atgtagtgcc aacttacgag atcactaact ttaaaactat catgcaattg     60

gccaatagaa gcgacacttg ctgtgccaaa gtatcgatag gctactcccg atggctcaat    120

catatatagt tggggcccat ctctatcata acctccaagg ataactccag atccaaaagg    180

ccttaaccac caatatagtg tgcacaaatg cacataactg gcaacacgtt cacaaagttc    240

cttaat                                                               246


<210> SEQ ID NO 59
<211> LENGTH: 255
<212> TYPE: DNA
<213> ORGANISM: Pinus taeda

<400> SEQUENCE: 59

ggtgcgatcc catgggatag ttgcaagaca cacaaatttg ttgtgaaaga agagagacac     60
```

```
gcacagacaa ccatatgatc tttttttttt tttttttttt tttttttttt ttttttttag    120

caaaattcaa acacttttta ttaaatccaa gccatatatc tggcaaattc accgaaatat    180

gtacaatcgc agcgcattgc ttggcttgcg acagaaacca tattcgcacg tcttcataag    240

gctttggatc gcacc                                                     255
```

<210> SEQ ID NO 60
<211> LENGTH: 368
<212> TYPE: DNA
<213> ORGANISM: Pinus taeda

<400> SEQUENCE: 60

```
ggtgcgatcc cactgtagtt gtccttgttg agcatagttc aagctgttct gattccacca     60

gttagtggcc caacactgcg aggtgctgcc atttccattc cattcacaga cgtcagtgtt    120

gaaattcata taggaagcca caaagggtga ggaagaccaa tctattttca ctcgcccccc    180

ttgagttgcc cactggtctc cgctccatat gctagagaat actctcattg cctgctcatt    240

cggataggga acgcctatgt tttcattgtt tgcaaatact ctgattggca aaccatcaac    300

gaaaatcgca atttgctggg ggttccagag aatagagtaa ttgtggaaat ctgctgtagg    360

atcgcacc                                                             368
```

<210> SEQ ID NO 61
<211> LENGTH: 354
<212> TYPE: DNA
<213> ORGANISM: Pinus taeda

<400> SEQUENCE: 61

```
ggtgcgatcc cacactccta accctattat atgtctcccg tccatggagt catagaagga     60

gtacgataat atgcccttca gccaagcgaa gtatgacttt agtatggcca ggcagcagta    120

tgaaagcaca tcttgtttct tccaggtcgg catgtatagt ctccggaggc taacaatgtc    180

acccaaagct aattgcgcaa acggaactcc tctgctgatc tcccgggaac ttaggcggaa    240

ccaccctgaa tccactattc tcaccgcgca tttcatccct ttggtgaacg ccgctgcctc    300

tggtagatac agagctggct tgtctccact ggaacccccct ttccggatcg cacc         354
```

<210> SEQ ID NO 62
<211> LENGTH: 364
<212> TYPE: DNA
<213> ORGANISM: Pinus taeda

<400> SEQUENCE: 62

```
ggtgcgatcc aaactgtggt tatcggtgga gagattaagc aatttattgg agtagcaagt     60

acgctgaatt aagggggtcc atcttcaagc aaaggttcct ttggatgact atgtgttctg    120

gaagtgttta tggatcaatc atctcataaa ttttggtaat atataacaga agattatggc    180

atccagttag gatggtagtt tcattgaggt atagtaaaaa ctacactagt cttgtgttgc    240

cacccacttt tcagagaagt caggaggtct ctttgtgaat cattgataac tttatgagtg    300

ggtacctaaa tgaaatattt gcatcttgag tatatactca attgatctta cttgtggatc    360

gcac                                                                 364
```

<210> SEQ ID NO 63
<211> LENGTH: 381
<212> TYPE: DNA
<213> ORGANISM: Pinus taeda

<400> SEQUENCE: 63

```
cttggtaccg agctcggatc cactagtaac ggccgccagt gtgctggaat ttacggctgc     60
gagaagacga cagaacacct atcataactt gaattctgat gcaaatcgga atttgccaaa    120
aacttggacg gaaatataat aggcaatatc atccccgcaa gtaacaaaaa aattgcatga    180
aagctcaaat cctatgtgct ttacaccttg actgcatact ttctcattgg aaaatacatc    240
tctttctttt tctgtctctc agtcttcaat gacgcctgat gcttggtaag gcgtcgcctg    300
atagcacgag tcttcttggg acgcaaatca agaggcaggt acttcttttt tttgtatgct    360
tctcttaatg cggatcgcac c                                              381
```

<210> SEQ ID NO 64
<211> LENGTH: 382
<212> TYPE: DNA
<213> ORGANISM: Pinus taeda

<400> SEQUENCE: 64

```
ggtgcgatcc aagattgtac ggcacaggca aatgctgttc tttttcttaa tcacgatgtg     60
cttgaagaat atgagcgccg atgtgaacag atccacaacc tggagttaaa attggaggaa    120
gacagagcag tgctgaatag gagcttggca gaaataaata gtcttaagga atcctggctt    180
cccacattga ggagtttggt taccagaatt aatgaaactt tcagccacaa ctttcaaggg    240
atggctgttg ctggagaagt tacactagat gaacatggca tggattttga caagttatgg    300
tattctaata aaagtcaagt tcaggcaaac tggacagttg caggtattga attgctcatc    360
atcagtctgg agggatcgca cc                                             382
```

<210> SEQ ID NO 65
<211> LENGTH: 367
<212> TYPE: DNA
<213> ORGANISM: Pinus taeda

<400> SEQUENCE: 65

```
ggtgcgatcc gagggaagcg atgtagtctt gccccaagcg acgaccatga tcccttattc     60
ttgggcaata tgtgcaagac gtggacaaat gaagcggtta aagggaagct tatggactat    120
ggaatagagg gtcttgaaga gctaactcta gtgggtgata ctcaaaatga aggaataagc    180
cgtggttttg catttatagc attttctacg cacatggatg cgatgaatgc atacaaacgc    240
cttcagaggc cagatgttat ttttggtgct gatcgaactg cgaatgtggc atttgcagag    300
ccactgcgtg agcctgacga agagatcatg gcccaggtta agtcagtgtt gttgatggga    360
tcgcacc                                                              367
```

<210> SEQ ID NO 66
<211> LENGTH: 298
<212> TYPE: DNA
<213> ORGANISM: Pinus taeda

<400> SEQUENCE: 66

```
ggtgcgatcc agtcctgaaa atgtacttta ccatttgtat aatgatgtaa aaatcttggc     60
catagtctgg tcaaaccaga ctgtattgtt gctaaagtta tggaaattct ggccatattt    120
ttgtctaacc agactgtatt gttgccaaag ttatgggaat tccggctata tttttgtctt    180
cgaaaaaaaa aaaaaaaaaa aaaaaaaaaa aaaaaaaaga tcatagggtt gtctgtgcgt    240
gtctctcttc ttacacaaca aatttgtgtg ttttgcaact atcccatggg atcgcacc      298
```

<210> SEQ ID NO 67
<211> LENGTH: 425
<212> TYPE: DNA
<213> ORGANISM: Pinus taeda

<400> SEQUENCE: 67

```
ggtgcgatcc gctggaaggt gggcagctgg acatctggga attataagtc gaatgtcaat     60
tgctgggcca tctgggggat gagcaatagc atcggaggcc aagttcttct gcagccgggc    120
accaaatgcc atgtggaggt ctgaatctta gtttggaggt cgaagtttca atccccttgt    180
gtttactctg tttctggttt tatttgaata atttgagcaa tttaatgtgg gtccttagtg    240
cttctgtgga tcagattcta gggaacgcca tcctgataag taaagatccg agttttaatg    300
gagattcaat tctatcagaa ttccatggtg gtttaaattc ccttgtactg ttgatctacg    360
tcgctttgta tatcagtgtg tgttaagatt ttctcagaat ccacagcttt gttatggatc    420
gcacc                                                                425
```

<210> SEQ ID NO 68
<211> LENGTH: 335
<212> TYPE: DNA
<213> ORGANISM: Pinus taeda

<400> SEQUENCE: 68

```
ggtgcgatcc aagcacttac gactcccaac aaggacggga aactctaaaa tcggaaaaat     60
atcatatact gaggcatcaa ctttgttgat aaaactttaa acaagaacaa tatttgcagc    120
atattagccc acatgccata atgacaaaca aatatgagaa cactgcctac aggtttgcca    180
aaagcatggc cctcactttt gccctgaggt catcaggagc ttctgaggct cgagaaggag    240
aaaaagattg tgtcacttca ggagctgagg cctccacatc ttttaatgat ttcgcagcag    300
gcctctcttt aatgttttct ttagaggatc gcacc                               335
```

<210> SEQ ID NO 69
<211> LENGTH: 711
<212> TYPE: DNA
<213> ORGANISM: Pinus taeda

<400> SEQUENCE: 69

```
ggtgcgatcc aaggtacgag cgaacaagtt tcttcagcaa gccacctgga actttccatg     60
agtccaaaac aagttgaaga aggcttcttt ggctactttt aagatgctga agtgattgtg    120
ctcgcctctt gcacagttca accgcaataa cattgggttt tacaaaaccg attacctgtt    180
taacctgctg tgcactcttt ttcgaaacat gacaagttcc aacaagataa acttcggccc    240
cattctcgcc attccgcaaa taaaccacgc tctcatcttc tgttatcgaa ctcgagtgca    300
tgccacgacg ctcaattgca ggattccaac cccggacttg cgaatggtgc aaagcgatgc    360
ccgttcgtct cagcgatact gctaaagatc ggcagacccg aaccagtttg atgcttccat    420
tgccttaaac atccagagtt ttccttcgac cttaaaccct aacaagatta ctgatttctg    480
gtccggatgt tcactgtctg ttatacttct cacaaatctg tcacactcct gataatcttc    540
ggtattgaac ttcattgaat tgaattttcc ttctcattgg aattcaattg taccttgtaa    600
atgtctggat cctacactat accaatattt acaggtctga gtattttgcc tgtagtataa    660
ttatctttcc ttcggtctcg tgtttccgta ttattcgtgt aggatcgcac c             711
```

<210> SEQ ID NO 70
<211> LENGTH: 622
<212> TYPE: DNA

<213> ORGANISM: Pinus taeda

<400> SEQUENCE: 70

```
ggtgcgatcc cggggggagg ttgatgttct gagagaatca atgaagggat ttcagctgag     60
cttgcctttt tgaagacgga atgcgaacaa ccagtcattt gcaatagcga gaattctctt    120
aagccactgc ctgctgggga ggcgagttct gattccggtg attgcatcac tcaacggcag    180
cagcagcggc agaaccttta gtttcccatg acaggtctct ctgtacaagt atcttcctgt    240
tatgatctaa ttccgggttg ttcgattatc gtgatgtctc ctgtattgac atattagcag    300
aatattacca tgatacgatg ttaagtggca tggtttatgc cctgcatgtt atgttatgga    360
ggaggtgagg catgtggcgc tcatgggagg gcccacatgg tccatggacg tcttattaaa    420
cgcatagtcg tgaatgaaaa tagttcaata cattcaaaat tccaacacaa tttcattaca    480
atggaagtga cttcgacttg aatgttcatt gaagcatttg catgcacaaa caaagtatac    540
tagattagaa gaaaattgca aaaaaggaca ttgtgccctt cttagtgaat atataaagat    600
gttcttcatg ctggatcgca cc                                             622
```

<210> SEQ ID NO 71
<211> LENGTH: 471
<212> TYPE: DNA
<213> ORGANISM: Pinus taeda

<400> SEQUENCE: 71

```
ggtgcgatcc caatagccaa tattgcctcc aagatagcct agactgcctt ttgcatagtt     60
ctagaagcca gtcacccaac ctcccaaaag aaattgcgca atctttccca tcagtttccc    120
gggtatgtgt tctgtcattc cccgaatttt ctttggtttt cactaataga tttctttcca    180
tgcacattgc ttgtctccag atcttttagg tgttcatcca tctcttagta gtactagatc    240
gatggcttcc aagagaacag gatcatatga cactgttgga aatgtagctg gagcagcagt    300
tgagcaagtg tcctctagtc tatctatcta tgaaagatac acattgtttc tagacatgga    360
tatcaaattg aaattgccag aagtccatga aacatttgcc gcctttttgaa gaaaggctcc    420
aaactgtcag ggttcgttga acatcacatg ttctcgctgt ctgatccccc c             471
```

<210> SEQ ID NO 72
<211> LENGTH: 418
<212> TYPE: DNA
<213> ORGANISM: Pinus taeda

<400> SEQUENCE: 72

```
ggtgcgatcc tcagggtaat ggcctggctg aatcaagtaa caagaatctt ataaccatta     60
tctaagaaga tagtaggaga taacaagcgg tcttgggaca acaaaatcaa gtgcgctttg    120
tgggcagata ggataactaa aaagaaagcc actggtaaaa gtccctttga acttgtctat    180
ggcatggatt tgacattaca tgcccatctt aaattactag cttaccaact ccttcaacat    240
ttttctagtg ataaaggtgt tgtccaaaac atggttgatc aaattgtgca gttggatgaa    300
atccgcagga aagattttga tagtgcaaaa atcagtctac cattaagaaa atctttgaca    360
aatcttctcg gtctagatat ttacaggttg gagatatggt tttactatgg attccacc      418
```

<210> SEQ ID NO 73
<211> LENGTH: 416
<212> TYPE: DNA
<213> ORGANISM: Pinus taeda

<400> SEQUENCE: 73

```
ggtgcgatcc tgcaggctta gatagtttcg gcgctcctct gaaagaagca cgagtaggtg     60
tctccacatt aggttggcct gatcccttgc ctgcacttgc agcttgtctt acaacatctc    120
ctatgctttg atccaggctt ttcactgaca taacttcagg ggcttccttc tcccagggcc    180
gtgctgccat ccagcgttct agccagctcc atccccaatt tggcttgttt gggtcaattt    240
ccatcagcat aggatgagct gctcctcgtg tgcttttcaa tgactgatga gaatatgcgt    300
tatgccaatg ccctttctcg cttcatggct gcttcttgct tgctttgcaa actagcctca    360
atttcctctt tggattgcaa ctgtcatcca atcctttgct tccatactgg atccac        416
```

<210> SEQ ID NO 74
<211> LENGTH: 346
<212> TYPE: DNA
<213> ORGANISM: Pinus taeda

<400> SEQUENCE: 74

```
ggtgcgatcc caaatgaaca ttcaacattc gatcatgtca agcgctaaat gccttggcag     60
cttaaaagct agactccgca agtgaccctt ctgacttagt acacatatta agactcatca    120
agggtccaat tccatgaaaa gaaattttaa aacggttaca tattcacaag aacagcacga    180
gatttcccag atagtcaacc accaacttgc cctatcagcc caaatattac tcattccatg    240
ttaaaaatag caaatttcca gatagaatgt cgaaagagat cttcatgcac catatatgga    300
ctcttaaaac cagccaaaat ctatactgcc atgcttggat cgcacc                   346
```

<210> SEQ ID NO 75
<211> LENGTH: 346
<212> TYPE: DNA
<213> ORGANISM: Pinus taeda

<400> SEQUENCE: 75

```
ggtgcgatcc tggagagaga agcaaaaagc ctaccatcta aatctacatt ctaaatcaga     60
tatctttact gtgaaaggaa ttgaatgctg cttcagatat cctacaagaa ttaagaagaa    120
aagaatgatc aactccaaat caggcagatg gctcagaatt tcccgcagct tcattttcga    180
cggcctccac aacaccaacc tcggcaggac gtattactct gccatgaagt gtatagccag    240
gcttcaaaac cacagccaca ctgccaggct gcttactagc atcttgaact tgagatactg    300
ccatgttgca tatgaggatc aaactcttca tttattggat cgcacc                   346
```

<210> SEQ ID NO 76
<211> LENGTH: 286
<212> TYPE: DNA
<213> ORGANISM: Pinus taeda

<400> SEQUENCE: 76

```
ggtgcgatcc ccagaggtta ttttgggttc aaagtattct acaccagttg acatgtggtc     60
atttgcttgc ataatttttg aactggctac aggtgatatg ttatttgatc ctcagagtgc    120
agaaggttat gaccgcgatg aggaccacct tgccctgatg atggagcttc ttggaaaaat    180
acctcgtaag atcgccttag gtgggagcta ttcacgggaa ctttttgaca ggcatgggga    240
tttaaagcac attagacggc ttcggtattg gcccttggat cgcacc                   286
```

<210> SEQ ID NO 77
<211> LENGTH: 395
<212> TYPE: DNA
<213> ORGANISM: Pinus taeda

<400> SEQUENCE: 77

```
ggtgcgatcc taaactgtat gtctccacaa ttgtcttcaa tatagaagca gctacgcccc     60

tcctaagtca tcataagtta aaaacttcat ctttccaata caattaaact atctagctta    120

tcagtttgga atagagatac aaaattacag atagattagc gaaactgtgc cacaaaacct    180

cttcaaaatt agaagcatga ttgtctacaa ctccacttca aaaaggagct gaaccagtcc    240

ttcgaagggt gtgctttggt tgtggtggag gtacagaagg cagcaatttc tccaagaact    300

gctgtttttt tagcctctca ttctcctctt taagctgcat cacttcattc tctagctcat    360

ttgtgtatgc ctgctttctt gccctggatc gcacc                               395
```

<210> SEQ ID NO 78
<211> LENGTH: 308
<212> TYPE: DNA
<213> ORGANISM: Pinus taeda

<400> SEQUENCE: 78

```
ggtgcgatcc gagtgatggc acaaagaaaa gcaatgatag aaaacaaaga acaggtagct     60

cagaaggttc agcaacttag agagtcaact tcgagttaag gagggcggga gcaattggca    120

gattcttcca aatttgtcaa gatctcttgg catgagatga ccttatagga tgttaaggag    180

caagaggatt ctaggaataa tgccaaggat aataagacta aaaggatgct tcaagaccag    240

gtggcaagga aggcttctaa ttcaaaggga gttagcaacg gcaacagatg caattctagg    300

atcgcacc                                                             308
```

<210> SEQ ID NO 79
<211> LENGTH: 307
<212> TYPE: DNA
<213> ORGANISM: Pinus taeda

<400> SEQUENCE: 79

```
ggtgcgatcc tagaattgca tctgttgccg ttgctactcc ctttgaatta gaagccttcc     60

ttgccacctg gtcttgaagc atccttttag tcttattatc cttggcatta ttcctagaat    120

cctcttgctc cttaacatcc tataaggtca tctcatgcca agagatcttg acaaatttgg    180

aagaatctgc caattgctcc cgccctcctt aactcgaagt tgactctcta agttgctgaa    240

ccttctgagc tacctgttct ttgttttcta tcattgcttt tctttgtgcc atcactcgga    300

tcgcacc                                                              307
```

<210> SEQ ID NO 80
<211> LENGTH: 521
<212> TYPE: DNA
<213> ORGANISM: Pinus taeda
<220> FEATURE:
<221> NAME/KEY: modified_base
<222> LOCATION: (391)
<223> OTHER INFORMATION: a, t, c, g, other or unknown
<221> NAME/KEY: modified_base
<222> LOCATION: (428)
<223> OTHER INFORMATION: a, t, c, g, other or unknown
<221> NAME/KEY: modified_base
<222> LOCATION: (433)
<223> OTHER INFORMATION: a, t, c, g, other or unknown
<221> NAME/KEY: modified_base
<222> LOCATION: (443)
<223> OTHER INFORMATION: a, t, c, g, other or unknown
<221> NAME/KEY: modified_base
<222> LOCATION: (471)
<223> OTHER INFORMATION: a, t, c, g, other or unknown
<221> NAME/KEY: modified_base
<222> LOCATION: (494)

```
<223> OTHER INFORMATION: a, t, c, g, other or unknown
<221> NAME/KEY: modified_base
<222> LOCATION: (497)
<223> OTHER INFORMATION: a, t, c, g, other or unknown
<221> NAME/KEY: modified_base
<222> LOCATION: (512)
<223> OTHER INFORMATION: a, t, c, g, other or unknown

<400> SEQUENCE: 80

atctagatca tcgatcttgt ccaaatttta actagtgaat agttttaaaa aaaagcaact     60

agcagaagag aacctaacca ctgacaaatt gcaaatactc tagaacacta ttcatcattt    120

tttgcgattc acgctggacc cacaagaacc ccttgagctg aactttcttt tcgttctccc    180

tccttttgga tcgcaccatc tagaccatcg atcttgtcca aattttaact agtgaatagt    240

tttaaaaaaa agcaactagc agaagagaac taaccactga caaattgcaa atactctaga    300

acactattca tcatttttg cgattcacgc tggaccacaa gaactcttga gctgaatttc    360

ttttcgtctc ctccttttgg attggacatc naatcctgca gccggggatt catattctta    420

acggcgcncg cgngactcc atnccccata tgatcttttc atcctggcgc ntttaactct    480

gaagggaaac cggnttnccc ttatccctgg anatcccttc c                        521


<210> SEQ ID NO 81
<211> LENGTH: 163
<212> TYPE: DNA
<213> ORGANISM: Pinus taeda

<400> SEQUENCE: 81

gtggagtgta aaggtcaacg tgccatccgg gtacaaacta ttgtagaaaa aatggcaaag     60

ttaggtctga aaatatccat ttggcctgct ctagttgtac agtacatgat tttgcactcg    120

cacaacaatg gactataatt attttcctgg caaaaaaaaa aaa                      163


<210> SEQ ID NO 82
<211> LENGTH: 486
<212> TYPE: DNA
<213> ORGANISM: Pinus taeda
<220> FEATURE:
<221> NAME/KEY: modified_base
<222> LOCATION: (330)
<223> OTHER INFORMATION: a, t, c, g, other or unknown
<221> NAME/KEY: modified_base
<222> LOCATION: (349)
<223> OTHER INFORMATION: a, t, c, g, other or unknown
<221> NAME/KEY: modified_base
<222> LOCATION: (364)
<223> OTHER INFORMATION: a, t, c, g, other or unknown
<221> NAME/KEY: modified_base
<222> LOCATION: (368)
<223> OTHER INFORMATION: a, t, c, g, other or unknown
<221> NAME/KEY: modified_base
<222> LOCATION: (411)
<223> OTHER INFORMATION: a, t, c, g, other or unknown
<221> NAME/KEY: modified_base
<222> LOCATION: (431)
<223> OTHER INFORMATION: a, t, c, g, other or unknown
<221> NAME/KEY: modified_base
<222> LOCATION: (447)
<223> OTHER INFORMATION: a, t, c, g, other or unknown
<221> NAME/KEY: modified_base
<222> LOCATION: (461)
<223> OTHER INFORMATION: a, t, c, g, other or unknown
<221> NAME/KEY: modified_base
<222> LOCATION: (476)
<223> OTHER INFORMATION: a, t, c, g, other or unknown
<221> NAME/KEY: modified_base
<222> LOCATION: (478)
<223> OTHER INFORMATION: a, t, c, g, other or unknown
<221> NAME/KEY: modified_base
```

<222> LOCATION: (480)
<223> OTHER INFORMATION: a, t, c, g, other or unknown

<400> SEQUENCE: 82
ggtgcgatcc aggacatgag gccgagtttg ccattgtgat atgattgagg aagtccagtc 60
ctaaaattag gtttatcttg atgtttgaca agagatatag aggggcatga tgattcattg 120
atctgtttgc agatctgtaa ctgcaaccat tctaatgaca taatagcgct attgtttggg 180
ttcgtgtgat gacataataa attgatttaa tttaataaca tctgttaatg caatggctgt 240
agctgcatca tcaccgtatc catcgaatgt tccatttttc caaatgtttg tttccaaaac 300
cagaacacca aaatgtcccc tgcgtttgtn ttgaaaaata ttgggcccnt actatactat 360
aatntttngg catactatac tataatgttt ctcccattcc ccccaaatga ntcctataca 420
atcctggccg nctttacact cctgacngga aacccggctt nccactaatc cctggncnan 480
cccttc 486

<210> SEQ ID NO 83
<211> LENGTH: 144
<212> TYPE: DNA
<213> ORGANISM: Pinus taeda

<400> SEQUENCE: 83
ggtgcgatcc gactgtgata tgtgactggt gaacgagaga tccttcttat gaattaatct 60
ggtatcttta tgcgaaagct tttagggttg ctacatgctc tcctcttttg tatgaatttc 120
cattctaata tcagtctctg tgat 144

<210> SEQ ID NO 84
<211> LENGTH: 525
<212> TYPE: DNA
<213> ORGANISM: Pinus taeda

<400> SEQUENCE: 84
ggggagtgtc aagggataag tggtaagcca ggtttccagt cagaagtgta aaggcggcca 60
gtgatgtaat agattcatat aggggaatgg agtcaccggg gtgcgccgtt ttagaatagt 120
ggatccccgg ctgcaggatt tgatggtgcg atcctgcccc tgataatttg gttgcaatgg 180
aaaatgcagt attaggtgcg agatgtaaag cccgcccgga gcggtgcatg aagtactgca 240
atatttgttg tagtaaatgt gctggttgtg ttcccagcgg tcactatggc aacaaggacg 300
agtgcccctg ctacagagat atgaagtccg cagccggcaa gcccaagtgt ccctgatctt 360
agcacttcag tccagtcgct cacttctttt attctttttt tttataaaag tgacgaggcc 420
gtttttcttg tacttggtgg ccatatgtag agcggtggct acttctcctg tgttaggaaa 480
tgttgcagta ctaataataa gaacttcttt ggcaaaaaaa aaaaa 525

<210> SEQ ID NO 85
<211> LENGTH: 543
<212> TYPE: DNA
<213> ORGANISM: Pinus taeda

<400> SEQUENCE: 85
gggtttcctt aagagttaaa ggcgcatgat gtatagaatc atatagggga tggattcccc 60
ccggggggcc tttcagaata gggattcccg gctgcaggat tgatagtgcg atccaagaca 120
cagtggagta ccacaatggg gatctggcca gtgctttgtg gctattcact gcagctgtat 180
taaaacagga agccgcaaat ggccagaagg ccattgaact tgctgagagc agactatcta 240
aggatggctg gcctgaatat tatgatggga agcttggacg atatattgga aagcagtctc 300
gaaagtggca aacctggtca gttgctggat atcttgtagc caagatgatg cttgaagatc 360
catcccattt aggtatgata gcattggaag aggacaaaaa gatgaagccg tccctcactc 420
gatcagcttc ttggataatg taaaatgggg aaatcctaaa ctttcaggcc actcttgaat 480
gttttgtcac ttctgtatga caaatgaggc aattcatagt acatgttgtg caaaaaaaaa 540
aaa 543

<210> SEQ ID NO 86
<211> LENGTH: 370
<212> TYPE: DNA
<213> ORGANISM: Pinus taeda

<400> SEQUENCE: 86
ggtgcgatcc cagagaatat tagttcatgt gttgctctca ttttcttcaa tatgcagggc 60
aaccatttga atgaaattat tcctttcgaa tttcaaaaac ttaataggct aacttatcta 120
tctggagccg attttcattg acgagtaacc tgtaagctgg ccagcaaaag ccaacagatg 180
ttcagctcgt tggaaccagt tgaagattgt aatagagatg gtgaataatc gcggacggct 240
cggccaatgg aatatttgtt gcatcatcat caagggggta tgaattccaa agaacttgtt 300
gattgaaatt cccaagcaaa attctgtgaa atgaaaaatt tattgagacc attgggcaaa 360
aaaaaaaaaa 370

<210> SEQ ID NO 87
<211> LENGTH: 237
<212> TYPE: DNA
<213> ORGANISM: Pinus taeda

<400> SEQUENCE: 87
ggtgcgatcc aaagaacaca agatggagtt accacaatgg aggatcttgg ccagtgcttt 60
tgtggctatt cactgcagcc tgtattaaaa caggaaggcc gcaaatggcc agaagggcca 120
ttgaacttgc tgagagcaga ctatctaagg atggctggcc tgaatattat gatgggaagc 180
ttggacgata tattggaaag cagtctcgaa agtggcaaac ctggtcagtt gctggat 237

<210> SEQ ID NO 88
<211> LENGTH: 476
<212> TYPE: DNA
<213> ORGANISM: Pinus taeda
<220> FEATURE:
<221> NAME/KEY: modified_base
<222> LOCATION: (379)
<223> OTHER INFORMATION: a, t, c, g, other or unknown
<221> NAME/KEY: modified_base
<222> LOCATION: (394)
<223> OTHER INFORMATION: a, t, c, g, other or unknown
<221> NAME/KEY: modified_base
<222> LOCATION: (400)
<223> OTHER INFORMATION: a, t, c, g, other or unknown
<221> NAME/KEY: modified_base
<222> LOCATION: (403)..(404)
<223> OTHER INFORMATION: a, t, c, g, other or unknown
<221> NAME/KEY: modified_base
<222> LOCATION: (406)
<223> OTHER INFORMATION: a, t, c, g, other or unknown
<221> NAME/KEY: modified_base
<222> LOCATION: (414)
<223> OTHER INFORMATION: a, t, c, g, other or unknown
<221> NAME/KEY: modified_base
<222> LOCATION: (421)
<223> OTHER INFORMATION: a, t, c, g, other or unknown
<221> NAME/KEY: modified_base
<222> LOCATION: (430)

<223> OTHER INFORMATION: a, t, c, g, other or unknown
<221> NAME/KEY: modified_base
<222> LOCATION: (433)..(434)
<223> OTHER INFORMATION: a, t, c, g, other or unknown
<221> NAME/KEY: modified_base
<222> LOCATION: (444)
<223> OTHER INFORMATION: a, t, c, g, other or unknown
<221> NAME/KEY: modified_base
<222> LOCATION: (450)
<223> OTHER INFORMATION: a, t, c, g, other or unknown
<221> NAME/KEY: modified_base
<222> LOCATION: (454)
<223> OTHER INFORMATION: a, t, c, g, other or unknown
<221> NAME/KEY: modified_base
<222> LOCATION: (463)
<223> OTHER INFORMATION: a, t, c, g, other or unknown
<221> NAME/KEY: modified_base
<222> LOCATION: (470)
<223> OTHER INFORMATION: a, t, c, g, other or unknown
<221> NAME/KEY: modified_base
<222> LOCATION: (476)
<223> OTHER INFORMATION: a, t, c, g, other or unknown

<400> SEQUENCE: 88
ggtgcgatct gtgtggctct gaaacatccc ggctcccctc tgcactataa taatcccaaa 60
attaagtgaa cccaacagaa tttgctcata tctctacagt tattgcagac tgagcaaaac 120
cctcaaactc atgtgacctc tcaataggag cccacgccca agatttgtcc agcatgtaac 180
acacctgatc gccgccactg caagcacaac cgctcacaaa tatcttgtca caccacactg 240
ttgcgcaagt taacaatatt catgtctcca ggaaagaaat gccacacttc ccaacattct 300
ctttactatt atagaacttc cttgttgcta tggaaaaaat acattcccaa cgcagaaccc 360
caacgggggt tcccaatanc ccatttcccc cctntccaan ccnntntgaa tgcnccccat 420
nccctattgn atnntttaaa tccnggcgcn ttanctggaa ggnaacccgn ttcccn 476

<210> SEQ ID NO 89
<211> LENGTH: 364
<212> TYPE: DNA
<213> ORGANISM: Pinus taeda

<400> SEQUENCE: 89
gttttcccag tcaggacgtg taaaacgacg gccagggatt gtaatacgat tcactatagg 60
cgaattggag gtcgatccgt ataggtagtt ggatgatgaa cgggcaaaga aggcaaagga 120
gtacagtgat ggatcctgta attcctgttt cagaaaacag aaaatctgca atataaggat 180
ggctaagctt ttcagctatg aaaatatatg gtgcagtggc actcatatca gttgcagagt 240
tgtcaatata acttttgtga ataggaaagt tgtcctcttt tagagtgcag aaatcctgca 300
atataaggat ggctaagttt ttcagctata tgaaaatata tggtgcagtg gcaaaaaaaa 360
aaaa 364

<210> SEQ ID NO 90
<211> LENGTH: 170
<212> TYPE: DNA
<213> ORGANISM: Pinus taeda

<400> SEQUENCE: 90
ggtgcgatcc tacagagagc agcttgacga gggccaaaag gttaaggatg aagaatgacc 60
tcagctagta aggtttacag aagcagcaga ggcatcttaa ctgtttttat gttttggcaa 120
aagttgttgc gtcggttgtt taatccagga tttcagatgt attttgtaga 170

<210> SEQ ID NO 91

-continued

<211> LENGTH: 210
<212> TYPE: DNA
<213> ORGANISM: Pinus taeda

<400> SEQUENCE: 91
attgtaatac gactcactat agggcgaatt ggagggtccg atcctgcgag accgagggtt 60
cattttcctt tagacaacga cgttcagtgg cgaccagagt ttcccaatca cttcagcgat 120
tctattcctt cgttgtaata aagcttaagg aatccatgct ttattccttg gaaggtttga 180
atatttatat ttattggcaa aaaaaaaaaa 210

<210> SEQ ID NO 92
<211> LENGTH: 237
<212> TYPE: DNA
<213> ORGANISM: Pinus taeda

<400> SEQUENCE: 92
aggtgaccgt caaaatgatt gcagaggact tagagaggga aaaccgttcc gatctggtga 60
agcaattgga tgaagcagct ctggaattga ttcccgtttc tgatgatatc gtacggctaa 120
gctcagctct tcaggcaatt ggcagagaat acgattcttc aaatgagatg acagatttta 180
agaaacttat agatgaacat atttccaagc ttgaagcgga ttcccctacg gtcacct 237

<210> SEQ ID NO 93
<211> LENGTH: 525
<212> TYPE: DNA
<213> ORGANISM: Pinus taeda

<400> SEQUENCE: 93
aggtgaccgt aaaatactat gagaaatgct ttcatcaggc accgctggta ggttttcttc 60
aagcttttca ttaggcaaaa gaggctccgt gagttgatcg ttaattctct ccttgaatgg 120
ccatattgac cagacactct gattagaaac tggaatacaa ctgcacatat agtcattctt 180
atatgattca tccttctgca cttcagcatc ctgcggcaac tcttcatccc gccatactgc 240
agaaaaatta tttgactctt gatcatgttg tagatgaatc ttcatgaatc ttctcatctt 300
gcattcttgt ctttatatct ttaggaaatt gcatctggta aaagtataaa tgcatcttca 360
ctggttgctt cagtttttgc atgctcctgt tcttcttgtt tacatgtgat ctaccaaatc 420
atctaatgta ttctctcaat gtcttgtgga cattctcctt cattccgaga ttaccaatca 480
tctacccgaa taaatgttgc cccgtcagca atgccgtttt ggtcc 525

<210> SEQ ID NO 94
<211> LENGTH: 437
<212> TYPE: DNA
<213> ORGANISM: Pinus taeda

<400> SEQUENCE: 94
aggtgaccgt agtaggcgtc cagaggctga caaaatccca ggcctgtgca aatctggaag 60
ccgcatgcag ggccgtggca ccttacactt gcggccttaa caaagtggcc cgcggcaccc 120
acttctacca gtgtgtttat attcttgtgc agccaacacc agaggttatg caggcgaatg 180
tgctggccaa gcgttgtttc ggcttgtccg caaaccctct cgagtcttac atgccgcata 240
tgagtcttgt gtatggcgat ttgcctgacg acgagaaaga gaaggccaag gttaaggcgc 300
agctaaattc gatgaactta tccgcaacac ggaattccaa gtctccagct tgtgcttgta 360
ctcgacagat ctgaaaataa tcctcactca tgcataagtg caaaatgtga tcttaacctg 420
ctctgaaaat tacataa 437

<210> SEQ ID NO 95
<211> LENGTH: 372
<212> TYPE: DNA
<213> ORGANISM: Pinus taeda

<400> SEQUENCE: 95
aggtgaccgt ccacgagaat ttggcttcaa aaccctagga gagggatatg aacttgccaa 60
ggcacaactg acgcatgaac aagacgtaaa atgactcatt agacactgac atgataatga 120
aaaacctatg aatgatgata gactcagcta cttgatgaca tcgcccgcca tttggacatc 180
tttataagga gtttaagcaa accctagacc tactgcctag tgaccaactt ttgcttgacg 240
actcactgaa atgacaatat ttgaccttga cacttcaaaa tcactttgta ggaactcatt 300
tgatcactgg aggacggctg gaaagactga cactaacagg actttatata tgcacctcgt 360
ctatccgaac tt 372

<210> SEQ ID NO 96
<211> LENGTH: 442
<212> TYPE: DNA
<213> ORGANISM: Pinus taeda

<400> SEQUENCE: 96
aggtgaccgt aagcacaagt cgtcaaaatt atctctattc cggcagtaaa aacctatagc 60
taatgatgga tcaatagcac taagtggcag ctggcgtaca tcactgcaat gataagaacc 120
agtatcaacc cccatattat caggagatat ctccaccacc tgctgcacta catgtggatc 180
taagtacaga gcctgatcat cctgaacacc aacaatatac gttgaagctc caggctttcc 240
accagcaata ccaagacttt ggggaaatgt gaacgtttca cgaagtgatg gtacatacct 300
tgggttgatc ttctctacac caagaacaag cggcaccaaa atcaggatag gcacttggtc 360
ttccccttct ccattggacc actctgaaca cagcctcgca gcatcatcaa tgcagataac 420
tggagtccct ccacggtcac ct 442

<210> SEQ ID NO 97
<211> LENGTH: 381
<212> TYPE: DNA
<213> ORGANISM: Pinus taeda

<400> SEQUENCE: 97
aggtgaccgt gaatatggtg ggtatttgca gggcaagatt caggatgctg ctcccggagc 60
ttaagtaagg tcttggaccc taataaattc agggtatatg cattatgtat atgctctcat 120
ttagctgctc atctgatttc cattgggtga atcagttgtt ttgcagtacg tgggggtctg 180
tttattttgt gagtttatgg tggagttcat tttgttgttg ttgtttttttc ttatctaggg 240 tttagggttt tgccctgtaa tcggtcttcc cctctctcct gcgcttgaat ttgacctgaa 300
acctcttgaa gtaggccctg gttttctggg ctttgacgaa aaccatggtt gtggatctcc 360
tctctcctgc tacggtcacc t 381

<210> SEQ ID NO 98
<211> LENGTH: 364
<212> TYPE: DNA
<213> ORGANISM: Pinus taeda

<400> SEQUENCE: 98
aggtgaccgt cctacttcac cgcagtgact tccatctggt tttaggaaac tatccctaaa 60

-continued

```
tccttcacta gttgacgaat tgattgactc aaatcaactg tcggtcaaac ccactctctc    120

tgaaagtgaa ttctatgagt ctatacccaa cccaaatcaa taggttgagg taacagttga    180

cccgatttca ccttcaacaa atcatacctt tcccgaagag agtgaacatg attcaacaca    240

agttcttttt ggttcaccag attcaaatga gcttgggggt aatcctcctg ttccatcaag    300

acaagaagaa aatcctccca ctctcgtaac tcaagggtta atcctcccat ttctacggtc    360

acct                                                                 364
```

```
<210> SEQ ID NO 99
<211> LENGTH: 274
<212> TYPE: DNA
<213> ORGANISM: Pinus taeda
<220> FEATURE:
<221> NAME/KEY: modified_base
<222> LOCATION: (12)
<223> OTHER INFORMATION: a, t, c, g, other or unknown
<221> NAME/KEY: modified_base
<222> LOCATION: (21)
<223> OTHER INFORMATION: a, t, c, g, other or unknown
<221> NAME/KEY: modified_base
<222> LOCATION: (29)
<223> OTHER INFORMATION: a, t, c, g, other or unknown
<221> NAME/KEY: modified_base
<222> LOCATION: (40)
<223> OTHER INFORMATION: a, t, c, g, other or unknown
<221> NAME/KEY: modified_base
<222> LOCATION: (44)
<223> OTHER INFORMATION: a, t, c, g, other or unknown
<221> NAME/KEY: modified_base
<222> LOCATION: (48)
<223> OTHER INFORMATION: a, t, c, g, other or unknown
<221> NAME/KEY: modified_base
<222> LOCATION: (53)
<223> OTHER INFORMATION: a, t, c, g, other or unknown
<221> NAME/KEY: modified_base
<222> LOCATION: (56)
<223> OTHER INFORMATION: a, t, c, g, other or unknown
<221> NAME/KEY: modified_base
<222> LOCATION: (68)
<223> OTHER INFORMATION: a, t, c, g, other or unknown
<221> NAME/KEY: modified_base
<222> LOCATION: (71)
<223> OTHER INFORMATION: a, t, c, g, other or unknown
<221> NAME/KEY: modified_base
<222> LOCATION: (75)..(76)
<223> OTHER INFORMATION: a, t, c, g, other or unknown
<221> NAME/KEY: modified_base
<222> LOCATION: (81)
<223> OTHER INFORMATION: a, t, c, g, other or unknown
<221> NAME/KEY: modified_base
<222> LOCATION: (84)
<223> OTHER INFORMATION: a, t, c, g, other or unknown
<221> NAME/KEY: modified_base
<222> LOCATION: (87)
<223> OTHER INFORMATION: a, t, c, g, other or unknown
<221> NAME/KEY: modified_base
<222> LOCATION: (94)
<223> OTHER INFORMATION: a, t, c, g, other or unknown
<221> NAME/KEY: modified_base
<222> LOCATION: (96)
<223> OTHER INFORMATION: a, t, c, g, other or unknown
<221> NAME/KEY: modified_base
<222> LOCATION: (113)
<223> OTHER INFORMATION: a, t, c, g, other or unknown
<221> NAME/KEY: modified_base
<222> LOCATION: (123)
<223> OTHER INFORMATION: a, t, c, g, other or unknown
<221> NAME/KEY: modified_base
<222> LOCATION: (125)
<223> OTHER INFORMATION: a, t, c, g, other or unknown
<221> NAME/KEY: modified_base
<222> LOCATION: (132)
<223> OTHER INFORMATION: a, t, c, g, other or unknown
<221> NAME/KEY: modified_base
```

-continued

<222> LOCATION: (135)..(137)
<223> OTHER INFORMATION: a, t, c, g, other or unknown
<221> NAME/KEY: modified_base
<222> LOCATION: (139)
<223> OTHER INFORMATION: a, t, c, g, other or unknown
<221> NAME/KEY: modified_base
<222> LOCATION: (143)
<223> OTHER INFORMATION: a, t, c, g, other or unknown
<221> NAME/KEY: modified_base
<222> LOCATION: (159)
<223> OTHER INFORMATION: a, t, c, g, other or unknown
<221> NAME/KEY: modified_base
<222> LOCATION: (161)
<223> OTHER INFORMATION: a, t, c, g, other or unknown
<221> NAME/KEY: modified_base
<222> LOCATION: (166)
<223> OTHER INFORMATION: a, t, c, g, other or unknown
<221> NAME/KEY: modified_base
<222> LOCATION: (170)
<223> OTHER INFORMATION: a, t, c, g, other or unknown
<221> NAME/KEY: modified_base
<222> LOCATION: (174)
<223> OTHER INFORMATION: a, t, c, g, other or unknown
<221> NAME/KEY: modified_base
<222> LOCATION: (193)
<223> OTHER INFORMATION: a, t, c, g, other or unknown
<221> NAME/KEY: modified_base
<222> LOCATION: (195)..(197)
<223> OTHER INFORMATION: a, t, c, g, other or unknown
<221> NAME/KEY: modified_base
<222> LOCATION: (225)
<223> OTHER INFORMATION: a, t, c, g, other or unknown
<221> NAME/KEY: modified_base
<222> LOCATION: (228)
<223> OTHER INFORMATION: a, t, c, g, other or unknown
<221> NAME/KEY: modified_base
<222> LOCATION: (233)
<223> OTHER INFORMATION: a, t, c, g, other or unknown
<221> NAME/KEY: modified_base
<222> LOCATION: (235)
<223> OTHER INFORMATION: a, t, c, g, other or unknown
<221> NAME/KEY: modified_base
<222> LOCATION: (239)
<223> OTHER INFORMATION: a, t, c, g, other or unknown
<221> NAME/KEY: modified_base
<222> LOCATION: (241)..(242)
<223> OTHER INFORMATION: a, t, c, g, other or unknown
<221> NAME/KEY: modified_base
<222> LOCATION: (244)
<223> OTHER INFORMATION: a, t, c, g, other or unknown
<221> NAME/KEY: modified_base
<222> LOCATION: (254)..(256)
<223> OTHER INFORMATION: a, t, c, g, other or unknown
<221> NAME/KEY: modified_base
<222> LOCATION: (262)
<223> OTHER INFORMATION: a, t, c, g, other or unknown
<221> NAME/KEY: modified_base
<222> LOCATION: (267)
<223> OTHER INFORMATION: a, t, c, g, other or unknown
<221> NAME/KEY: modified_base
<222> LOCATION: (271)
<223> OTHER INFORMATION: a, t, c, g, other or unknown

<400> SEQUENCE: 99
aggtgaccgt cncgggatag ntggagccna acaaagtacn gaanaaantg aancgcnctg 60
ggaagcgngc ngaaanntgg ncanacntgc cctncnactc ggttacccag ccnttctcta 120
ccnanaatta tnacnnnana gcnccatgct gggtttgtna naaaanaacn gctnttgata 180
aaattacata gantnnngaa cacgttaaga ggaatatggt tccanatnca ttntnaatna 240
nnanttaaaa actnnntatg tnctagngtc ncct 274

<210> SEQ ID NO 100
<211> LENGTH: 271
<212> TYPE: DNA

<213> ORGANISM: Pinus taeda

<400> SEQUENCE: 100
aggtgaccgt acagcacagg tatacaaatc atagaaatgg gcttctgtcc aactgtcagc 60
agaagcgata tgaaacccag aagcatcaac tctgctttca atttttcaag cgcttcatat 120
agagcctttt tatttcttct ggagagccaa ttgctagcat aatgaatacc atgttcaaga 180
agtaaagaga tgaccacaaa tgccaaacaa acaactgcta ctgcccaagt taggagtttg 240
ctctagagaa cggtcattgc cacggtcacc t 271

<210> SEQ ID NO 101
<211> LENGTH: 474
<212> TYPE: DNA
<213> ORGANISM: Pinus taeda

<400> SEQUENCE: 101
aggtgaccgt ggatatggga gcagagccgt ccgcagtgga tgctgcaatt caacttgaag 60
tggcagaagc tgtgaagact ctccaaatgg acaaggcacg aagacaaaac caagacaagg 120
atgagggcaa gagtggcaac gctgattcag atgacttgaa tgaaatggaa gtcaaagcta 180
aagcagccga acaactgctt gctgtgcatg gggcagcatt actacagaat gctctgaaag 240
aaaatttgtc gagtcatgaa atgcgggttg gttcaaatac aagggaggaa ggtgaagtta 300
gaaagaacag aaagggcatc aacgcagacc cctcactgat atcggcaaca ctacggtcac 360
ctaagccaat tctgcaaatt tccatcactg gcggggcccg ctccaacttc ctctaaaagg 420
ccaattcccc tatatgattc ttattacaat ccctggccct ccttttccac ttct 474

<210> SEQ ID NO 102
<211> LENGTH: 197
<212> TYPE: DNA
<213> ORGANISM: Pinus taeda

<400> SEQUENCE: 102
aggtgaccgt agcaggagag aggagatcca caaccatggt tttcgtcaaa gcccagaaaa 60
ccagggccta cttcaagagg tttcaggtca aattcaagcg caggagagag gggaagaccg 120
attacagggc aaggatccgc ctgattaacc aagataagaa caagtacaac acacccttgc 180
caaaaaaaaa aaaaaaa 197

<210> SEQ ID NO 103
<211> LENGTH: 208
<212> TYPE: DNA
<213> ORGANISM: Pinus taeda

<400> SEQUENCE: 103
aggtgaccgt atgagcaagg agggaacagt atgacaggca gtcaaagccc acgaggggtg 60
ccccactgcc tgcagcagcg cacttacttg gactaacaaa cttgtatcgt gattaaaacg 120
atgaacatcg tattgtggag tggagccact cgtgacctga ttctgtccta agtacttggt 180
cctggaatac aatattgcac ggtcacct 208

<210> SEQ ID NO 104
<211> LENGTH: 511
<212> TYPE: DNA
<213> ORGANISM: Pinus taeda

<400> SEQUENCE: 104
aggtgaccgt caaagtacaa tggagtcata tatccacttg aattgaaacc tctaatttaa 60
aagttctcaa aaaatatttt atttacaaaa cagggaaaat aaaaaatgac tctatcaact 120
atacaatcct aacatccatc tcccgacaga cctccagtat atgtacaagg cgctgaaaga 180
aggctgatta ttttctattc cagctcgcat aacgtggttc ttctgaggct ttgcctattc 240
ctttctttaa aatctttcgc acgaaagatt ggcattgacc ttcggctaaa tctcagactc 300
cagggaacct tggactccct ttaaaaccta gagctacttt ttacgaaccc ctgcttctct 360
tgaacactta gggaacttat acttacaaaa cttcgggaac tccaccccct agctttgcag 420
gactccagca gattccccaa actgccagaa ggcatatttc catgcactgt taggggtgaa 480
ttcctactat caaaaccccc aaaacatcat a 511

<210> SEQ ID NO 105
<211> LENGTH: 430
<212> TYPE: DNA
<213> ORGANISM: Pinus taeda

<400> SEQUENCE: 105
aggtgaccgt atgggaacaa gtatgggaac aagaacgtta ttacataaaa gatggagatg 60
caacacagca taaattgatg ctaagtttgt tacaatgatg catacagctt aaccaagctt 120
ggaaatgaca tcattaagtg cggtcacagc ctctgcatag tatttctctg ccttgggtgt 180
atccttgctc cttgcagcgt agtccaggtt gtcaagggtt gtcaaaaagc ttggtggtga 240
aggttttgag ggcttcttc tggtccttgg gctttgagga gataacggtg tttgaagtcc 300
ttagcgaaag taagaaacct ttggaaccga agtccgttct tgacgttacc gcacgccttc 360
cttatctatc actttttcac ctccagaaat tgcttcccga atcccttgct ctcccacccc 420
ctgttccccc 430

<210> SEQ ID NO 106
<211> LENGTH: 362
<212> TYPE: DNA
<213> ORGANISM: Pinus taeda

<400> SEQUENCE: 106
aggtgaccgt agtgttgccg atatcagtga ggggtctgcg ttgatgccct ttctgttctt 60
ctacttcacc ctcctctctt gtatttgaac caacccgcat ttcatgactc gacaaatttt 120
ctttcagagc attctgtagt aatgctgccc catgcacagc aagcagttgt tcggctgctt 180
tagctttgac ttccatttca ttcaagtcat ctgaatcagc gttgccactc ttgccctcat 240
ccttgtcttg gttttgtctt ccgtgccttg tccatttgga gagtcttcac agcttctgcc 300
acttcaattt gaattgcagc atccacttgc ggaacggtct gctccccata tcacggcacc 360
tt 362

<210> SEQ ID NO 107
<211> LENGTH: 360
<212> TYPE: DNA
<213> ORGANISM: Pinus taeda

<400> SEQUENCE: 107
aggtgaccgt agtgttgccg atatcagtga ggggtctgcg ttgatgccct ttctgttctt 60
ctacttcacc ctcctctctt gtatttgaac caacccgcat ttcatgactc gacaaatttt 120
ctttcagagc attctgtagt aatgctgccc catgcacagc aagcagttgt tcggctgctt 180
tagctttgac ttccatttca ttcaagtcat ctgaatcagt gttgccactc ttgccctcat 240

-continued

```
ccttgtcttg gttttgtctt cgtgccttgt ccatttggag agtcttcaca gcttctgcca    300

cttcaatttg aattgcagca tccactgcgg acggctctgc tcccatatcc acggtcacct    360


<210> SEQ ID NO 108
<211> LENGTH: 370
<212> TYPE: DNA
<213> ORGANISM: Pinus taeda

<400> SEQUENCE: 108

aggtgaccgt cgtgaaatag cgagaacggc gtggaacatc gcaacggcgg ggaggctggc     60

ggacgttgca cgtttctgga aggtatgcgg ctctctcctc cgcctcagtt tccatgaaga    120

ggtcctccct ggttgaatca tacgattgcg attgatcgag tacttgctgt atggctcggc    180

atcggcattg tggagacatt ctttcctatt cctcgcagca tctctccgat ggttgctctc    240

tccggagctc catgttatcc ccggcactga gacagtcgct gccgaatcgc aagagcttct    300

ttgtttttg caggcttctc caaacataat gcctccgggc ccctcaaccg aattctgcca     360

aatccacccc                                                           370


<210> SEQ ID NO 109
<211> LENGTH: 578
<212> TYPE: DNA
<213> ORGANISM: Pinus taeda

<400> SEQUENCE: 109

aggtgaccgt ggacgacagt gagtgcagtc atcatgctct ccagtggact ttaagcaatc     60

tgcatcttta tggaagtgat gtatctcttg tggtttttca tgctcaacca ttggcagtct    120

tcaacagtgc tgcaacaatg ggcataacgt ctcccgaatt aattgaaact attgtgaatc    180

aacagatagg tttctggtca catctagcaa tacaaacaca aataactgtg gaacagagcc    240

acaaaactat gcttcagagc atctaattac acatatcttc tctaaaaccc ttgcataaaa    300

aataaactga atctcgacct tagcactatt gccaccatca tctcaagcaa acattctcta    360

gaataccatc ttcacaatgc actaaagtta cataagcact gaacttaaaa catttctgtg    420

acgaatgaag gaccaattca tcatactcag cctttgcatc caatctgttg aatgtgctga    480

aaaatgccca ataaacctcc atccaacact gtcttcctct ctgaggtgca cactgatttc    540

tgctgctgaa ccagtcggga ttccctgctc aacgtccc                            578


<210> SEQ ID NO 110
<211> LENGTH: 297
<212> TYPE: DNA
<213> ORGANISM: Pinus taeda

<400> SEQUENCE: 110

aggtgcccgt ggaactactg ttaaatctgg aatcccttgt ctagctgtaa aaactcgaca     60

agtgcatgtt ggtattagta gggttaacag aagggttctt acccagattt accccttttgg   120

cggagatatt taaaaaaaaa gaattgtcat tatggtaaat aggtgtgaca ggttatcaat    180

agaataactg acgagagtaa actgataatt attaaggtta aagtgttcgt aaaggagact    240

tggactctag gttggatgcc tacacttaga gccgttcccg cacttggacg gtcacct      297


<210> SEQ ID NO 111
<211> LENGTH: 295
<212> TYPE: DNA
<213> ORGANISM: Pinus taeda

<400> SEQUENCE: 111
```

```
aggtgaccgt ccagtgcggg aacggctcta agtgtaggca tccacctaga gtccaagtct     60

cctttacgaa cactttaacc ttaataatta tcagtttact ctcgtcagtt attctattga    120

taacctgtca cacctattta ccataatgac aattcttttt ttttaaatat ctccgccaaa    180

ggggtaaatc tgggtaagaa cccttctgtt aaccctacta ataccaacat gcacttgtcg    240

agtttttaca gctagacaag ggattccaga tttaacagta gttccacggt cacct         295
```

<210> SEQ ID NO 112
<211> LENGTH: 576
<212> TYPE: DNA
<213> ORGANISM: Pinus taeda

<400> SEQUENCE: 112

```
aggtgaccgt atgggaacaa gaacgttatt acataaaaga tggagatgca acacagcata     60

aattgatgct aagtttgtta caatgatgca tacagcttaa ccaagcttgg aaatgacatc    120

attaagtgcg gtcacagcct ctgcatagta tttctctgcc ttgggtgtat ccttgctcct    180

tgcagcgtag tccaagttgt caagggtgtc aaaaaacttg gtggtgaagg ttttgaaggg    240

cttcttctgg tccttgggct ttgaagaaat aacggtgttg aagtccttac caaaggttaa    300

taaacctttg gagccgaagt cgttctggac gtacggccac cccttcctta tctatcagct    360

ttttcacctc caagaatttg cttccccgaa ttcctttgct ctcccagccg cctggtcccc    420

cgaaaagggc tgaatataaa accgtcctca acggcattcc attcctccct cgtctgaaac    480

acttccccgc tgcccccgag gtgaagggcc atcaacttga tgaacggctt ttgcaaggct    540

ctgaccccgg ccccgtcact aaccaattct gcaatc                              576
```

<210> SEQ ID NO 113
<211> LENGTH: 363
<212> TYPE: DNA
<213> ORGANISM: Pinus taeda

<400> SEQUENCE: 113

```
aggtgaccgt ggggaacaac tacatgacaa atcatttctt tgtggtggat gtactggaca     60

ccaaataagt gttgagagtc cactggctct gtacgcgtgg cagaatcaca acggacttga    120

gaaagttgaa gatggaattt gtatcgctag atggccagac catgttgctt caagggatgc    180

actcgtaacc cccacagtct gtctctaccc actagatgga ggctgacatg agacatggag    240

acattaattg ggttgtggag ttaaagatct ctcacgttcg ggaaaaatcc aagccatcat    300

acttatatat ccgtcccgtg catgtaacct cctccactct gtcccttagg cccgttgttg    360

cct                                                                  363
```

<210> SEQ ID NO 114
<211> LENGTH: 583
<212> TYPE: DNA
<213> ORGANISM: Pinus taeda
<220> FEATURE:
<221> NAME/KEY: modified_base
<222> LOCATION: (24)..(25)
<223> OTHER INFORMATION: a, t, c, g, other or unknown
<221> NAME/KEY: modified_base
<222> LOCATION: (54)
<223> OTHER INFORMATION: a, t, c, g, other or unknown
<221> NAME/KEY: modified_base
<222> LOCATION: (71)
<223> OTHER INFORMATION: a, t, c, g, other or unknown
<221> NAME/KEY: modified_base
<222> LOCATION: (75)
<223> OTHER INFORMATION: a, t, c, g, other or unknown
<221> NAME/KEY: modified_base
<222> LOCATION: (77)
<223> OTHER INFORMATION: a, t, c, g, other or unknown
<221> NAME/KEY: modified_base
<222> LOCATION: (85)
<223> OTHER INFORMATION: a, t, c, g, other or unknown
<221> NAME/KEY: modified_base
<222> LOCATION: (111)
<223> OTHER INFORMATION: a, t, c, g, other or unknown
<221> NAME/KEY: modified_base
<222> LOCATION: (119)
<223> OTHER INFORMATION: a, t, c, g, other or unknown
<221> NAME/KEY: modified_base
<222> LOCATION: (124)
<223> OTHER INFORMATION: a, t, c, g, other or unknown
<221> NAME/KEY: modified_base
<222> LOCATION: (153)
<223> OTHER INFORMATION: a, t, c, g, other or unknown
<221> NAME/KEY: modified_base
<222> LOCATION: (177)
<223> OTHER INFORMATION: a, t, c, g, other or unknown
<221> NAME/KEY: modified_base
<222> LOCATION: (187)
<223> OTHER INFORMATION: a, t, c, g, other or unknown
<221> NAME/KEY: modified_base
<222> LOCATION: (194)
<223> OTHER INFORMATION: a, t, c, g, other or unknown
<221> NAME/KEY: modified_base
<222> LOCATION: (213)
<223> OTHER INFORMATION: a, t, c, g, other or unknown
<221> NAME/KEY: modified_base
<222> LOCATION: (242)
<223> OTHER INFORMATION: a, t, c, g, other or unknown
<221> NAME/KEY: modified_base
<222> LOCATION: (258)
<223> OTHER INFORMATION: a, t, c, g, other or unknown
<221> NAME/KEY: modified_base
<222> LOCATION: (270)
<223> OTHER INFORMATION: a, t, c, g, other or unknown
<221> NAME/KEY: modified_base
<222> LOCATION: (279)
<223> OTHER INFORMATION: a, t, c, g, other or unknown
<221> NAME/KEY: modified_base
<222> LOCATION: (281)
<223> OTHER INFORMATION: a, t, c, g, other or unknown
<221> NAME/KEY: modified_base
<222> LOCATION: (299)
<223> OTHER INFORMATION: a, t, c, g, other or unknown
<221> NAME/KEY: modified_base
<222> LOCATION: (312)
<223> OTHER INFORMATION: a, t, c, g, other or unknown
<221> NAME/KEY: modified_base
<222> LOCATION: (316)
<223> OTHER INFORMATION: a, t, c, g, other or unknown
<221> NAME/KEY: modified_base
<222> LOCATION: (322)..(323)
<223> OTHER INFORMATION: a, t, c, g, other or unknown
<221> NAME/KEY: modified_base
<222> LOCATION: (361)
<223> OTHER INFORMATION: a, t, c, g, other or unknown
<221> NAME/KEY: modified_base
<222> LOCATION: (409)
<223> OTHER INFORMATION: a, t, c, g, other or unknown
<221> NAME/KEY: modified_base
<222> LOCATION: (414)..(415)
<223> OTHER INFORMATION: a, t, c, g, other or unknown
<221> NAME/KEY: modified_base
<222> LOCATION: (457)..(458)
<223> OTHER INFORMATION: a, t, c, g, other or unknown
<221> NAME/KEY: modified_base
<222> LOCATION: (468)
<223> OTHER INFORMATION: a, t, c, g, other or unknown
<221> NAME/KEY: modified_base
<222> LOCATION: (480)..(481)
<223> OTHER INFORMATION: a, t, c, g, other or unknown
<221> NAME/KEY: modified_base
<222> LOCATION: (487)
<223> OTHER INFORMATION: a, t, c, g, other or unknown
<221> NAME/KEY: modified_base
<222> LOCATION: (489)
<223> OTHER INFORMATION: a, t, c, g, other or unknown
<221> NAME/KEY: modified_base
<222> LOCATION: (493)
<223> OTHER INFORMATION: a, t, c, g, other or unknown
<221> NAME/KEY: modified_base
<222> LOCATION: (511)
<223> OTHER INFORMATION: a, t, c, g, other or unknown
<221> NAME/KEY: modified_base
<222> LOCATION: (515)
<223> OTHER INFORMATION: a, t, c, g, other or unknown
<221> NAME/KEY: modified_base
<222> LOCATION: (558)
<223> OTHER INFORMATION: a, t, c, g, other or unknown
<221> NAME/KEY: modified_base
<222> LOCATION: (565)
<223> OTHER INFORMATION: a, t, c, g, other or unknown
<221> NAME/KEY: modified_base
<222> LOCATION: (575)
<223> OTHER INFORMATION: a, t, c, g, other or unknown

<400> SEQUENCE: 114
aggtgaccgt atgagcaagg aaannaccgc actggctccc agcagcatga acanccaggt 60
cccaaccata naccncntgg agaangtgat caagatatta gcgacagtgt nattgtacnt 120
ctcnccaaac acattataca cgataagaga gcntaaacta ctctattcct ttgacgnagt 180
gactacntga gtanaagcga tcattatctt gcnaactttg catgaaaaac aacaaaccca 240
cntccagttt ctctatantc tggccccacn atgaataana ntcctgccat aataatgant 300
ctttgtcccc anaganaaat tnnataagac aggagcccac tgttgcttgc atgactacca 360
ntcactttaa ggcgttgcga atcccggtcc taaccatctc cataccatng gcanncttta 420
ctttccaact gcccaagact gtgaacaggg cggttcnnac cctataantt ttagcctctn 480
ntcgaancnc ttnttttcgt tccccggaaa nccgnttccc accctttgga accttttttt 540
tttgccgggc cccaggcnaa ttctncaatt ccccnctggg ggg 583

<210> SEQ ID NO 115
<211> LENGTH: 443
<212> TYPE: DNA
<213> ORGANISM: Pinus taeda

<400> SEQUENCE: 115
aggtgaccgt ggcggaggtt agggaagttt gacttctcat tttctcacgc actcctctcc 60
ctcgtaacct cggtcgagtc gatggcggct ttttagtcga gtgtgctaac gcaccctccg 120
ggcctcaaaa tttccagcta ctcgtatttg atcaatgctg aaatcgcgta atcacgtaga 180
taataaagcg taatgaattc tataatgaag catgtttctc tatagttcat gttgccgaga 240
aggaataatg aaaatgaagc cttatatatt atctggggct caaggagatg ttatcttttc 300
tcttccttgg ttagagaccg tcaccttcac tttgaattgg ataaagcttc atttgtttaa 360
gacctcccac ccgtaaatac atacggtagc cttcttatgt tagaaacata cgtcacctac 420
gcagaattgt tagaatgaaa tga 443

<210> SEQ ID NO 116
<211> LENGTH: 483
<212> TYPE: DNA
<213> ORGANISM: Pinus taeda

<400> SEQUENCE: 116
aggtgaccgt ggaacaagat gattagttct catgcgggcc aggatgatta gttctcctat 60
ggcaactgtt ggacaggatg attcgttctc ctgtggacag gatgattagt tctcctatcg 120

-continued

```
aggcatccta cccaagcagt ttgggactca tgggaagtac ctctcatctg atcaatgagt    180

aggaaatggg gttagggacc attaagtagt attatcgatg gatgcattgt tgtatctatt    240

gtactcccta tgctagaatg aactccattg atctgggatc aatgaatact gtttctggga    300

atcattgaaa atttgtatga acacactctg aacactgaat ttccggttca ttggaagaga    360

tggttttaaa cactctcctc atctcatttc ttccccttcc ttattccaac caaatttggg    420

ccaccctgcc aggaaattca tttgatggtt ggaaaatacc acgggcccta accaattctg    480

caa                                                                  483


<210> SEQ ID NO 117
<211> LENGTH: 593
<212> TYPE: DNA
<213> ORGANISM: Pinus taeda
<220> FEATURE:
<221> NAME/KEY: modified_base
<222> LOCATION: (11)
<223> OTHER INFORMATION: a, t, c, g, other or unknown
<221> NAME/KEY: modified_base
<222> LOCATION: (24)
<223> OTHER INFORMATION: a, t, c, g, other or unknown
<221> NAME/KEY: modified_base
<222> LOCATION: (27)
<223> OTHER INFORMATION: a, t, c, g, other or unknown
<221> NAME/KEY: modified_base
<222> LOCATION: (39)
<223> OTHER INFORMATION: a, t, c, g, other or unknown
<221> NAME/KEY: modified_base
<222> LOCATION: (48)
<223> OTHER INFORMATION: a, t, c, g, other or unknown
<221> NAME/KEY: modified_base
<222> LOCATION: (50)
<223> OTHER INFORMATION: a, t, c, g, other or unknown
<221> NAME/KEY: modified_base
<222> LOCATION: (54)
<223> OTHER INFORMATION: a, t, c, g, other or unknown
<221> NAME/KEY: modified_base
<222> LOCATION: (56)..(57)
<223> OTHER INFORMATION: a, t, c, g, other or unknown
<221> NAME/KEY: modified_base
<222> LOCATION: (59)
<223> OTHER INFORMATION: a, t, c, g, other or unknown
<221> NAME/KEY: modified_base
<222> LOCATION: (63)
<223> OTHER INFORMATION: a, t, c, g, other or unknown
<221> NAME/KEY: modified_base
<222> LOCATION: (66)..(67)
<223> OTHER INFORMATION: a, t, c, g, other or unknown
<221> NAME/KEY: modified_base
<222> LOCATION: (71)..(74)
<223> OTHER INFORMATION: a, t, c, g, other or unknown
<221> NAME/KEY: modified_base
<222> LOCATION: (78)
<223> OTHER INFORMATION: a, t, c, g, other or unknown
<221> NAME/KEY: modified_base
<222> LOCATION: (92)
<223> OTHER INFORMATION: a, t, c, g, other or unknown
<221> NAME/KEY: modified_base
<222> LOCATION: (96)
<223> OTHER INFORMATION: a, t, c, g, other or unknown
<221> NAME/KEY: modified_base
<222> LOCATION: (112)..(113)
<223> OTHER INFORMATION: a, t, c, g, other or unknown
<221> NAME/KEY: modified_base
<222> LOCATION: (126)
<223> OTHER INFORMATION: a, t, c, g, other or unknown
<221> NAME/KEY: modified_base
<222> LOCATION: (146)
<223> OTHER INFORMATION: a, t, c, g, other or unknown
<221> NAME/KEY: modified_base
<222> LOCATION: (167)
<223> OTHER INFORMATION: a, t, c, g, other or unknown
<221> NAME/KEY: modified_base
<222> LOCATION: (173)
```

<223> OTHER INFORMATION: a, t, c, g, other or unknown
<221> NAME/KEY: modified_base
<222> LOCATION: (184)
<223> OTHER INFORMATION: a, t, c, g, other or unknown
<221> NAME/KEY: modified_base
<222> LOCATION: (186)
<223> OTHER INFORMATION: a, t, c, g, other or unknown
<221> NAME/KEY: modified_base
<222> LOCATION: (197)
<223> OTHER INFORMATION: a, t, c, g, other or unknown
<221> NAME/KEY: modified_base
<222> LOCATION: (203)
<223> OTHER INFORMATION: a, t, c, g, other or unknown
<221> NAME/KEY: modified_base
<222> LOCATION: (206)
<223> OTHER INFORMATION: a, t, c, g, other or unknown
<221> NAME/KEY: modified_base
<222> LOCATION: (252)
<223> OTHER INFORMATION: a, t, c, g, other or unknown
<221> NAME/KEY: modified_base
<222> LOCATION: (254)
<223> OTHER INFORMATION: a, t, c, g, other or unknown
<221> NAME/KEY: modified_base
<222> LOCATION: (258)
<223> OTHER INFORMATION: a, t, c, g, other or unknown
<221> NAME/KEY: modified_base
<222> LOCATION: (268)
<223> OTHER INFORMATION: a, t, c, g, other or unknown
<221> NAME/KEY: modified_base
<222> LOCATION: (276)..(277)
<223> OTHER INFORMATION: a, t, c, g, other or unknown
<221> NAME/KEY: modified_base
<222> LOCATION: (291)
<223> OTHER INFORMATION: a, t, c, g, other or unknown
<221> NAME/KEY: modified_base
<222> LOCATION: (300)
<223> OTHER INFORMATION: a, t, c, g, other or unknown
<221> NAME/KEY: modified_base
<222> LOCATION: (304)..(305)
<223> OTHER INFORMATION: a, t, c, g, other or unknown
<221> NAME/KEY: modified_base
<222> LOCATION: (324)
<223> OTHER INFORMATION: a, t, c, g, other or unknown
<221> NAME/KEY: modified_base
<222> LOCATION: (331)
<223> OTHER INFORMATION: a, t, c, g, other or unknown
<221> NAME/KEY: modified_base
<222> LOCATION: (339)
<223> OTHER INFORMATION: a, t, c, g, other or unknown
<221> NAME/KEY: modified_base
<222> LOCATION: (344)
<223> OTHER INFORMATION: a, t, c, g, other or unknown
<221> NAME/KEY: modified_base
<222> LOCATION: (348)
<223> OTHER INFORMATION: a, t, c, g, other or unknown
<221> NAME/KEY: modified_base
<222> LOCATION: (353)
<223> OTHER INFORMATION: a, t, c, g, other or unknown
<221> NAME/KEY: modified_base
<222> LOCATION: (373)
<223> OTHER INFORMATION: a, t, c, g, other or unknown
<221> NAME/KEY: modified_base
<222> LOCATION: (380)
<223> OTHER INFORMATION: a, t, c, g, other or unknown
<221> NAME/KEY: modified_base
<222> LOCATION: (401)
<223> OTHER INFORMATION: a, t, c, g, other or unknown
<221> NAME/KEY: modified_base
<222> LOCATION: (416)
<223> OTHER INFORMATION: a, t, c, g, other or unknown
<221> NAME/KEY: modified_base
<222> LOCATION: (430)
<223> OTHER INFORMATION: a, t, c, g, other or unknown
<221> NAME/KEY: modified_base
<222> LOCATION: (433)
<223> OTHER INFORMATION: a, t, c, g, other or unknown
<221> NAME/KEY: modified_base
<222> LOCATION: (444)
<223> OTHER INFORMATION: a, t, c, g, other or unknown
<221> NAME/KEY: modified_base
<222> LOCATION: (472)
<223> OTHER INFORMATION: a, t, c, g, other or unknown
<221> NAME/KEY: modified_base
<222> LOCATION: (475)
<223> OTHER INFORMATION: a, t, c, g, other or unknown
<221> NAME/KEY: modified_base
<222> LOCATION: (481)
<223> OTHER INFORMATION: a, t, c, g, other or unknown
<221> NAME/KEY: modified_base
<222> LOCATION: (484)..(485)
<223> OTHER INFORMATION: a, t, c, g, other or unknown
<221> NAME/KEY: modified_base
<222> LOCATION: (497)
<223> OTHER INFORMATION: a, t, c, g, other or unknown
<221> NAME/KEY: modified_base
<222> LOCATION: (502)
<223> OTHER INFORMATION: a, t, c, g, other or unknown
<221> NAME/KEY: modified_base
<222> LOCATION: (506)
<223> OTHER INFORMATION: a, t, c, g, other or unknown
<221> NAME/KEY: modified_base
<222> LOCATION: (508)..(510)
<223> OTHER INFORMATION: a, t, c, g, other or unknown
<221> NAME/KEY: modified_base
<222> LOCATION: (520)
<223> OTHER INFORMATION: a, t, c, g, other or unknown
<221> NAME/KEY: modified_base
<222> LOCATION: (529)
<223> OTHER INFORMATION: a, t, c, g, other or unknown
<221> NAME/KEY: modified_base
<222> LOCATION: (533)
<223> OTHER INFORMATION: a, t, c, g, other or unknown
<221> NAME/KEY: modified_base
<222> LOCATION: (561)
<223> OTHER INFORMATION: a, t, c, g, other or unknown
<221> NAME/KEY: modified_base
<222> LOCATION: (568)
<223> OTHER INFORMATION: a, t, c, g, other or unknown
<221> NAME/KEY: modified_base
<222> LOCATION: (579)..(580)
<223> OTHER INFORMATION: a, t, c, g, other or unknown

<400> SEQUENCE: 117
aggtgaccgt ncatctctac catnatncct ccctcccgnc tgtatcancn ggcntnnang 60
tcnttnncta nnnnaagntt aatcctatcc cnttanagtt gacggtctct anncctagaa 120
gagaanccat aacatctcct tgagcnacac atgggatata ccgccanctt atntaatact 180
ttcncngcac ggtaacngac canaancatt cttcactata gaattcatgt cgcttcatta 240
tctacctcat tncnccanat cccccttnat ctcatnnatt tatctagaaa nttctgaagn 300
tccnnaaggg ttcgttttgc accnccccaa ntaaaaaanc cctnccgntt acntcgaacg 360
aaggttttca aangaacagn aattccttta caaaaatcaa naattttaac ttcccnaatc 420
cggccccccn gtncccgaaa cccnatttct acgattgcat caccccgggg gnccnctcaa 480
nccnncttct taaaggncca tncccntnnn tgatcctctn ccatccaang gcncctttcc 540
acttttattg gaaaaccccc nttccccntt ttacccttnn aaggcccctt ccc 593

<210> SEQ ID NO 118
<211> LENGTH: 298
<212> TYPE: DNA
<213> ORGANISM: Pinus taeda
<220> FEATURE:
<221> NAME/KEY: modified_base
<222> LOCATION: (237)
<223> OTHER INFORMATION: a, t, c, g, other or unknown

<400> SEQUENCE: 118
aggtgaccgt ggaactactg ttaaatctgg aatcccttgt ctagctgtaa aaactcgaca 60

```
agtgcatgtt ggtattagta gggttaacag aagggttctt acccagattt accccctttgg    120

cggagatatt taaaaaaaaa gaattgtcat tatggtaaat aggtgtgaca ggttatcaat    180

agaataactg acgagagtaa actgataatt attaaggtta aagtgttcgt aaaggancat    240

tggactctag gttggatgcc tacacttaga gcccgttccc gcacttggac ggtcacct      298
```

<210> SEQ ID NO 119
<211> LENGTH: 631
<212> TYPE: DNA
<213> ORGANISM: Pinus taeda
<220> FEATURE:
<221> NAME/KEY: modified_base
<222> LOCATION: (591)
<223> OTHER INFORMATION: a, t, c, g, other or unknown
<221> NAME/KEY: modified_base
<222> LOCATION: (607)
<223> OTHER INFORMATION: a, t, c, g, other or unknown
<221> NAME/KEY: modified_base
<222> LOCATION: (609)
<223> OTHER INFORMATION: a, t, c, g, other or unknown
<221> NAME/KEY: modified_base
<222> LOCATION: (616)
<223> OTHER INFORMATION: a, t, c, g, other or unknown

<400> SEQUENCE: 119

```
aggtgaccgt gggggatggg gccgtgggga agacttgtat gctcatctcc tacacaagca     60

acacgtttcc aacggattac gtgccgactg tttttgacaa ttttagtgca aatgtggttg    120

ttgatggcaa tacagtaaac cttggcttgt gggacactgc agggcaagaa gattacaaca    180

gactgaggcc attgagttat agaggtgcag atgcttttct gcttgccttt tctctgatca    240

gcaaggctag ttatgaaaat atatcaaaga agtggattcc agaacttaga cattatgcac    300

caaatgtgcc aatcattctt gtgggaacta aattagattt gcgtgatgac aagcagttct    360

ttgctgatca tcctggagca gcccctataa caacagctca aggtgaagag ttgaagaagc    420

agattggagc agcagcatat attgagtgca gttccaaaac ccagcagaat gtcaaggctg    480

tttttgatgc tgcaattaaa gtggttcttc agccaccaaa gcagaaaaag cggagaaaaa    540

agcagaaaaa ttgttctatt ctctaagaaa aatgtggatg ttctgaacgc ncttcactga    600

caataangnt gacgtnggaa tatcttcctc c                                   631
```

<210> SEQ ID NO 120
<211> LENGTH: 443
<212> TYPE: DNA
<213> ORGANISM: Pinus taeda

<400> SEQUENCE: 120

```
aggtgaccgt aagcacaagt cgtcaaaatt atctctattc cggcagtaaa aacctatagc     60

taatgatgga tcaataccac taagtggcag ctggcgtaca tctctgcaat gataagaacc    120

agtatcagtc cccatataat caggagatat ctccagcacc tgctgcacta catgtggatc    180

ttagtacaga gcctgatcat cctgaacacc aacaatatac gttgaagctc cgggctttcc    240

accagcaata ccaagacttt ggggaaatgt gaacgtttca cgaagtgatg gtacatacct    300

tgggttgatc ttctctacac caagaacaag cggcaccaaa atcaggatag gcacttggtc    360

ttccccttct ccattggacc actctgaaca caagcctcgc agcatcatca atgcagataa    420

ctgggcgccc tccacggtca ctt                                            443
```

<210> SEQ ID NO 121
<211> LENGTH: 327
<212> TYPE: DNA

<213> ORGANISM: Pinus taeda

<400> SEQUENCE: 121
aggtgaccgt gccatagcgc atggcgtgta actggatgag accgcatggc tcaaatctgc 60
taggaatcaa catgaaatca gctccagctg ttatcatatg agcaagtggc acgttaaact 120
ttgctactcc cctgacgttg tctggatatt tctcttcaag ctcttcaagc tgcttctcca 180
agtacttttt accggtgcct aggataatta actgcacgtt ttcatctgca attagaggga 240
cagcttcagc aagaatatct ggacctttct gctcttcaag tcttccaata aatcctataa 300
caggaatatc tggatccacg gtcacct 327

<210> SEQ ID NO 122
<211> LENGTH: 284
<212> TYPE: DNA
<213> ORGANISM: Pinus taeda

<400> SEQUENCE: 122
atgtgaccgt caaaagggca tataaatcgg ggagctcaat ggcaagaatg tacgatttct 60
ggcctcaagt cgccctgaat ttggtcaaca acatcttgat agagcgagag gacgctccca 120
attaagatct ggaaactgtc gagagtgatt gaggtcattt ttaatctaaa ctgaattgtg 180
gggacaattt ttcaattcag atccttctag caaagcaaag caaagcttaa cagtattgta 240
tccatgagaa tggattctgc acaggtcagg ctccacggtc acct 284

<210> SEQ ID NO 123
<211> LENGTH: 412
<212> TYPE: DNA
<213> ORGANISM: Pinus taeda

<400> SEQUENCE: 123
aggtgaccgt ggagaagaga acgctttgcc gactctctgg gatgcccttc cctccatagc 60
cgtcgtggga ggacagagct ccgggaaatc ctctgtgctg gagagcatcg ttggaaggga 120
ttttttaccg cgtggatcag gtattgttac tagacggccg cttgtccttc aacttcacaa 180
gactgatgaa ggcagcaggg attacgccga attccttcac caacccagaa agaaatacac 240
cgactttgca ctggtaagga aggaaattgc ggatgagact gatcgaatta cagggcgttc 300
caagcaagtc tcaagtgtcc caattcacct tagtatttat tcacccaatg tttgtaaatt 360
tgactctaat tgatctccct gggttgacaa aagtggctat tgacggtcac ct 412

<210> SEQ ID NO 124
<211> LENGTH: 235
<212> TYPE: DNA
<213> ORGANISM: Pinus taeda

<400> SEQUENCE: 124
aggtgaccgt gcaatattgt attccaggac caagtactta ggacagaatc aggttacgag 60
tggctccact ccacaatacg atgttcatcg ttttgatcac aatacaggtt tgttagtcca 120
agtaggtgcg ctgctgcaga cagtggggca gccctcgtgg gcttggactg cctgtcatac 180
tgttctctcc ttgcttcagg ctctactgct gttgctgctg ctgatacggt cacct 235

<210> SEQ ID NO 125
<211> LENGTH: 353
<212> TYPE: DNA
<213> ORGANISM: Pinus taeda

<400> SEQUENCE: 125

```
aggtgaccgt acatacaagg tcttatcacc agcagcaaga ataatcagtt ggccatcttc     60

tgcaggcttc ttgctgcctg agacaggagc ctcaagaaat cttccccccct tttcaatgat    120

tgcctcattg atctttgttg aagtgatagt atcaactgtt gacatgtcaa tgtatccttt    180

tcctgtacac atttgctcta ggacaccatc cgagagggca gcaggaggat cagacaggat    240

ggctatggta tagttgcact tctttacaac ttcggcagga gtgcttccta tggaagcacc    300

ttgctgaaca agttcttcac acctagacat tgtcctattc cacacggtca cct           353
```

<210> SEQ ID NO 126
<211> LENGTH: 355
<212> TYPE: DNA
<213> ORGANISM: Pinus taeda

<400> SEQUENCE: 126

```
ggtgaccgta catacaaggt cttatcacca gcagcaagaa taatcagttg gccatcttct     60

gcaggcttct ggctgcctga gacaggagcc tcatgaaatc ttccccccctt ttcaatgatt    120

gcctcattga tctttgttga aatgataata tcaactgttg acatgtcaat gtatcctttg    180

tcctgtacac atttgctcta ggacaccatc cgagagggca gcaggaggat cagacaggat    240

ggctatggta tagtcgcact tctttacaac ttcggcagga gtgcttccta tggaagcacc    300

ttgctgaaca aagttcttca cacctagaca tttgtcctat tccgcacggt cacct         355
```

<210> SEQ ID NO 127
<211> LENGTH: 441
<212> TYPE: DNA
<213> ORGANISM: Pinus taeda

<400> SEQUENCE: 127

```
aggtgaccgt ggaggggctc cagttatctg cattgatgat gctgcgaggc tgtgttcaga     60

gtggtccaat ggagaagggg aagaccaagt gcctatcctg attttggtgc cgcttgttct    120

tggtgtagag aagatcaacc caaggtatgt accatcactt cgtgaaacgt tcacatttcc    180

ccaaagtctt ggtattgctg gtggaaagcc tggagcttca acgtatattg ttggtgttca    240

ggatgatcag gctctgtact tagatccaca tgtagtgcag caggtggtgg agatatctcc    300

tgataatatg gggttgata ctggttctta tcattgcagt gatgttcgcc actgccactt    360

aatgctattg atccatcatt agctataggt ttttactgcc cggaatagaa ataattttga    420

caacttgtgc ttacggcacc t                                              441
```

<210> SEQ ID NO 128
<211> LENGTH: 437
<212> TYPE: DNA
<213> ORGANISM: Pinus taeda

<400> SEQUENCE: 128

```
aggtgaccgt ggaggggctc cagttatctg cattgatgat gctgcgaggc tgtgttcaga     60

gtggtccaat ggagaagggg aagaccaagt gcctatcctg attttggtgc cgcttgttct    120

tggtgtagag aagatcaacc caaggtatgt accatcactt cgtgaaacgt tcacatttcc    180

ccaaagtctt ggtattgctg gtggaaagcc tggagcttca acgtatattg ttggtgttca    240

ggatgatcag gctctgtact tagatccaca tgtagtgcag caggtggtgg agatatctcc    300

tgataatatg gggttgata ctggttctta tcattgcagt gatgtaccca ctgccactta    360

gtgctattga tccatcatta gctataggtt ttactgccgg aatagaaaaa ttttgacaac    420
```

-continued

```
ttgtgcttac ggtccct                                                  437

<210> SEQ ID NO 129
<211> LENGTH: 434
<212> TYPE: DNA
<213> ORGANISM: Pinus taeda

<400> SEQUENCE: 129

aggtgaccgt gctaggacac acaatttctc agcaaggatt acaggtggat cctaacaaaa    60

ttgctataat tcaaaaggtt ccacctcctt aaaaggtaag agatgtttgg agttttctag   120

gcttggcagg atattataga agattcatca aagatttcat taagctagcc tcgccattgt   180

ctagcctctt agggaaagat gttgagtttc aatggactga tgactgccaa ggggctctgg   240

atgagttgag agataagctg gtatccgccc cgatcttgag aggtctaaac tgggccctac   300

ctttccacat ccacattgat gcctcgaaca aagccatagg ggcagcctta ggacaagttg   360

aagagaaaat accatatgcc atatactttg tcagcaaaaa tctgtctaag gcagaactga   420

actatacggt cact                                                     434

<210> SEQ ID NO 130
<211> LENGTH: 427
<212> TYPE: DNA
<213> ORGANISM: Pinus taeda

<400> SEQUENCE: 130

aggtgaccgt catattcccc tctatagcag cactaacaat ccattttctg agtgcatcag    60

aaaatcaaca cacggtaaat gtcttgagac taacgagaaa ttaataatca cgttgtacaa   120

agaacagtat gtcccgtcac gtcacgagtg ccctgagaga tcatccaact ttctctgaac   180

cctcgtgtta cacgcacgca aaatcaagga tcagttgtag ttattgctgg cgtgacagac   240

gtgacaccta ctgttccgct acaaacgata taattgaatc catgatcgga ttatgtatta   300

tgatcttagc gcagtggtta tgaaattatg atgaatttgc ttatgatttt ctcagcgttt   360

gtggaagaat ctcgctattg aaaacttccc cgtatatttc caaacttatt atcatcccac   420

ggtccct                                                             427

<210> SEQ ID NO 131
<211> LENGTH: 261
<212> TYPE: DNA
<213> ORGANISM: Pinus taeda

<400> SEQUENCE: 131

aggtgaccgt acagcattta ttgatgttct attttgttgt ttgcaagttt ttccgattcg    60

ctgtgaggca cggaaaacga gataagttgt aaaagtttgc tcgctgattt gaggcacgga   120

aaacgagata agttgtaaaa ttttgctcgc tgattttttg ctgaatattt ctctcactat   180

aaaaagcatt ttccagaaat aagaaggagc tttcgaactg gttttcccca agagttgtag   240

ggggtttttc cacggtcacc t                                             261

<210> SEQ ID NO 132
<211> LENGTH: 262
<212> TYPE: DNA
<213> ORGANISM: Pinus taeda

<400> SEQUENCE: 132

aggtgaccgt atttatggtc gcaggcacaa attctgctac tgtagaaggg ttcttaccaa    60

ctttaggtag aaggcgagga gggctttatt agtacagttc tgtgtaatct taatgatatt   120
```

ttttgcacta ttattttatg gtaaaaggat tgatttgtct tttgcaaagg ccttaggatt 180
gtttatttac ctttgggcta agggaggagg taaatttttc acattgggaa aaaaaatgcc 240
tcggtcgttg tcacggtcac ct 262

<210> SEQ ID NO 133
<211> LENGTH: 126
<212> TYPE: DNA
<213> ORGANISM: Pinus taeda

<400> SEQUENCE: 133
aggtgaccgt gccagtatga cagatggaac catgcagcta gccaccaaat tgtaaacatc 60
aaattttgtc ttcaatataa gttgcaaatt cttaattaat tatgatcacc atttcaacgg 120
tcacct 126

<210> SEQ ID NO 134
<211> LENGTH: 238
<212> TYPE: DNA
<213> ORGANISM: Pinus taeda

<400> SEQUENCE: 134
aggtgaccgt gaatagaagc gaacacatcc ttgttgctga atctaacgac caatcggtat 60
ttgggtgtgt tgtacttgtt cttatcttgg ttaatcaggc ggatccttgc cctgtaatcg 120
gtcttcccct ctctcctgcg cttgaatttg acctgaaacc tcttgaagta ggccctggtt 180
ttctgggctt tgacgaaaac catggttgtg gatctcctct ctcctgctac ggtcacct 238

<210> SEQ ID NO 135
<211> LENGTH: 245
<212> TYPE: DNA
<213> ORGANISM: Pinus taeda

<400> SEQUENCE: 135
aggtgaccgt ggtagaggag gcaggcactc atctaacagt cgaaagccct ttacaaaggg 60
gaatggtacc agcatagaga agaaacacag acggtttgaa gaggatgatg gatctgccat 120
agatgaacga tcaaataagg ttcaaaagct ggaaaatgat ggtgaattcc atgcatccca 180
cttggctctg tccctcaagt tgaatatacc tggacgagag gtattgcatt tcccaacggt 240
cacct 245

<210> SEQ ID NO 136
<211> LENGTH: 239
<212> TYPE: DNA
<213> ORGANISM: Pinus taeda

<400> SEQUENCE: 136
aggtgaccgt actgataata gaagaggcag ggaaagagaa atcaatgata atagaagagg 60
cagggaaagg gagatcaatg gcatcatgct acttcttgta gctgtttaac cttagtgatg 120
taatcttcca tggcagactc gggggtttta tctttaagtt gaatttccat gcatcccctt 180
gggctctgtc ctccagttga atatcctgga acaagaggtt ttgctttcca cggtcccct 239

<210> SEQ ID NO 137
<211> LENGTH: 276
<212> TYPE: DNA
<213> ORGANISM: Pinus taeda

<400> SEQUENCE: 137

-continued

```
aggtgaccgt gagaaggcaa ctttatcccc tgctaaacca agtccagaaa tgaggaaaat     60

atgtgaaaac tgaattgcta tatatgatgc ctagtcttgg cctctcaatt acaagttcaa    120

cgtcttcaaa tgattgaaat atggaccttc ttaaccgttc tggaaatcta tcaatcttca    180

aaattttgaa actttgcctc gatcttggag tgatcagact tgatttctaa tcctagaaat    240

accctatcac tggctacctg gtctgtacgg tcacct                              276
```

<210> SEQ ID NO 138
<211> LENGTH: 274
<212> TYPE: DNA
<213> ORGANISM: Pinus taeda

<400> SEQUENCE: 138

```
ggtgaccgtg ggataggcag aagcaagaaa cacagaagtt cttccgggaa tgtaagcgct     60

gacagtgggg gagaaagtag tgaacaagga catggtcggt atgaaataca tggcaggcga    120

tggatttcaa gggattaagc atctcaatgg atatttacta ttggactgta gtaactttcg    180

ccatcgcttt ttgaacacat ctgtggctta actgtcatct gtaatggtaa gcgaaccagg    240

ttttgttctg aaccacttgt atgtacggtc acct                                274
```

<210> SEQ ID NO 139
<211> LENGTH: 526
<212> TYPE: DNA
<213> ORGANISM: Pinus taeda

<400> SEQUENCE: 139

```
aggtgaccgt ggtggagcga ttagtgattg tgataaaggg agcatcaata tctatgtaga     60

cgccgtataa aggtggaaaa ggtatgtttt gcaggtattt ctttgtaaat ggtttataat    120

gggttaagct cggatatatg aggtttatat ataagtcctg ttagtgtcag tcttaccagc    180

cttcctccag tgatcaaatg tgctctaaca aagtgatttt gaagtgtcaa ggtcaaatta    240

tgtcatttca gtgagtcttc aaacaaaatt tggtcactag gcattaggtc taagggtttg    300

cttgaactcc ctctagagtt gtccaaatgg gcgggctatg tcatcattta agctgaatct    360

atcatccaat caataaggtt tttcattatc atgtcagtgt ctaaatgagt cattttaccg    420

tcttgttcac ggcttcactt gtgcctttgg caaattcaat tccctcctcc aagggtttga    480

aaccaattct cttggacggc ccctaaacca aatctgcaaa atccac                   526
```

<210> SEQ ID NO 140
<211> LENGTH: 538
<212> TYPE: DNA
<213> ORGANISM: Pinus taeda

<400> SEQUENCE: 140

```
aggtgaccgt ggtggagcga ttagtgattg tgataaaggg agcatcaata tctatgtaga     60

cgccgtataa aggtggaaaa ggtatgtttt gcaggtattt ctttgtaaat ggtttataat    120

gggttaagct cggatatatg aggtttatat ataagtcctg ttagtgtcag tctttccagc    180

cttcctccag tgatcaaatg tgctcttaca aagtgatttt gaagtgtcaa ggtcaaattt    240

tgtcatttca gtgagtcttc aagcaaaatt tggtcactag gcattaggtc taaggtttgc    300

tttaactcct tctaaaagtt gtccaaatgg cgggctatgt catcatttag ctgagtctat    360

catcatcata ggttttcatt atcatgtcag tgtctaatga gtcatttacg tcttgttcag    420

ctcagtgtgc ctggcaattc attcctctct aaggtttgaa ccattctctt gacggcacta    480

agccaatcca cactggggcc gtctattgaa tcaacccgga cactgggtta caggcaac      538
```

<210> SEQ ID NO 141
<211> LENGTH: 498
<212> TYPE: DNA
<213> ORGANISM: Pinus taeda

<400> SEQUENCE: 141
aggtgaccgt ccaagaagaa attggcttca aaaccctagg agagggaaat gaacttgcca 60
aggcacaact gaagcatgaa caagacgtaa aatgactcat tagacactga catgataatg 120
aaaaacctat gaatgatgat agactcagct aaatgatgac atagcccgcc atttggacaa 180
attttagaag gagttaaagc aaaccttaga cttaatgctt agtgaccaaa ttttgtttga 240
agactcactg aaatgacaaa atttgacctt gacacttcaa aatcactttg taagagcaca 300
tttgatcact ggaggaaggc tggaaagact gacactaaca ggacttatat ataaacctca 360
tatatccgag cttaacccat tataaaccat ttacaaagaa atacctgcaa aacatacctt 420
ttccaccttt atacggcgtc tacatagata ttgatgctcc ctttatcaca atcactaatc 480
gctccaccac ggtcacct 498

<210> SEQ ID NO 142
<211> LENGTH: 350
<212> TYPE: DNA
<213> ORGANISM: Pinus taeda

<400> SEQUENCE: 142
aggtgaccgt gatagacccc aagaaaaata gatccaaccc tcagagggac aaagacttat 60
aaagactaga agagtgaatc aacctattct atttagaata tatatttttg gggtgcttgc 120
ttatcgtttt gggggttaat gtatgtcgta ctacggtctt atgccctaat ttgcccattg 180
aaatcaacta aattgacagt aaccgactaa aagttggtcc acactaagat atcgatgacc 240
aacgatcata aaggtgtcca tgatcctaat agtatatgtg tcaattaatg taactttggt 300
gctacaacat aaaaccattc gtggggatcc tcctttttat gcggtcacct 350

<210> SEQ ID NO 143
<211> LENGTH: 346
<212> TYPE: DNA
<213> ORGANISM: Pinus taeda

<400> SEQUENCE: 143
aggtgaccgt gggaccgacc ttgactacag gccaaaattt tgactgttga ccagcgttca 60
cttctgtatt tttggttggt atgagcaaca ttgacttgct ggaaattgac caggtttgac 120
tggtatttgg acttggattt tggcacagat ttctagacaa tttgtatttg taaaccttac 180
agaagaataa tttatcgaag aagaaaaatg ctaggtttcc cctcaagttt gggtttccca 240
agggaaaaat tgttgtccca atggttgaat tttccaaagg tctcctaacc cgacaatacc 300
tcctaagaat tccttaattt aacctttctt gttttcacgg tcacct 346

<210> SEQ ID NO 144
<211> LENGTH: 335
<212> TYPE: DNA
<213> ORGANISM: Pinus taeda

<400> SEQUENCE: 144
aggtgaccgt gaaggagcag caacaatttg attttgtttg ggtagatcgg ggattttctc 60
gtggaacata cctgattgag tataaactaa gtcaaggtac tgtgcttgag aaattacttg 120
ctcctcagta actactctgg ccttagctac atcctcagtg atcttgggta gtaaagattt 180
tacaaaccat tcagctaaga tctgatccgg gatataaact ttcactaaac gtcgtcgacg 240
tctccattca tggatatgat ctgaaatgta agtggacgtt gactgcttta acgaagttaa 300
taattctgtg ccattttcat atctgacggt cacct 335

<210> SEQ ID NO 145
<211> LENGTH: 344
<212> TYPE: DNA
<213> ORGANISM: Pinus taeda

<400> SEQUENCE: 145
aggtgaccgt acctaatggg aagacacttc aaggtaaaaa caaatcatga tagtcttaaa 60
taccttttag aacaaagatt atattcagaa caacttgctg gaagtgtacc aagtatgact 120
ggtattgaga cttagatctt cgcacagatt tcaagacaat ttgttgttgt aagactcact 180
cacgaaaagt gatgtggata tgaagaactt ccctgtcgcc tcttggttag gagtctccca 240
ctcataggaa ttgtgtaact tataacttgg tccactaaag aagttaggta cagtgtgttc 300
ctttaccagg ttccctgttg taacttacaa atctacggct acct 344

<210> SEQ ID NO 146
<211> LENGTH: 288
<212> TYPE: DNA
<213> ORGANISM: Pinus taeda

<400> SEQUENCE: 146
aggtgaccgt cactggaggt ttgagatgct tgatcggtac tgaaatgaga catgatcaga 60
ataggacctt gttgaggccg tgtctcaccc cccatccaca atcttttgta attttgagtt 120
tcgtttagaa catacttgta ggataaaact taccttactc atggatcatg gctgtatatg 180
tttatcgacc agagacagat atgccgaatg aaagcgagtc tagtattcta atgcaatata 240
ttggtagtat gggacatagt actgaacact tgtatagtac ggtcacct 288

<210> SEQ ID NO 147
<211> LENGTH: 288
<212> TYPE: DNA
<213> ORGANISM: Pinus taeda

<400> SEQUENCE: 147
aggtgaccgt ggtctcagtt atgccatatg tccgcccctc catatgatgc tccgcctcta 60
tgggggtctt tgcgatgttg atatctagta gtacttcttg tcctattgca gcaacctgta 120
ctggtgttgg tgttggttat gggtctccta cgcgatggag atatgagaca cccataggtc 180
gaacaggtct aatatctgga atccaacgct atttgttgta gaagaaacgt tgctcccgtc 240
ctttagcttt ggctggtcac tatccttacg ctccacgtac ggtcacct 288

<210> SEQ ID NO 148
<211> LENGTH: 208
<212> TYPE: DNA
<213> ORGANISM: Pinus taeda

<400> SEQUENCE: 148
aggtgaccgt tgggaaatgc aatacctctc gtccaggtat attcaacttg agggacagag 60
ccaagtggga tgcatggaat tcacttaaag ataaaacccc cgagtctgcc atggaagatt 120
acatcactaa ggttaaacag ctacaagaag tagcatgatg ccattgatct ccctttccct 180
gcctcttcta ttatcagtac ggtcacct 208

<210> SEQ ID NO 149
<211> LENGTH: 197
<212> TYPE: DNA
<213> ORGANISM: Pinus taeda

<400> SEQUENCE: 149

```
aggtgaccgt caaggcaaag tgtcatgcca ctcattggaa ttagttaata tagctaattt     60

gagatattac agtcaactgt gggtatatgt atgtgagatc aaggtgcagt ttagatatta    120

tcagtggtgc agtttagata ttatcagtgt ttgtgaatct gcatactgct tttggttggt    180

tctaactacg gtcacct                                                   197
```

<210> SEQ ID NO 150
<211> LENGTH: 527
<212> TYPE: DNA
<213> ORGANISM: Pinus taeda

<400> SEQUENCE: 150

```
aggtgaccgt agacatatat catggaaaac ccaagtaaca tacaaacaca aaacacatgg     60

aaacttcata aaacctccac tcgtcataag ctttattgct atgttattgt ggtgttgcat    120

cgtacttagt ggaggttatt gttatgttat gtgttctatt ttcctcccga acgcccttcg    180

gaattgagct aaccgtggtt aacaacatgt gggctttttt tctcgacagt atatatataa    240

taaatcttta tttttttaaa aactaatgct attgcattta tatactggaa aaaatgattt    300

ttcttgtatt atcgaaaata ataatttagt ttcttgataa tcacttggaa ttaagaaatt    360

acaaacccta acaacatcaa gaaattttaa aacacataag ctagaaattt taaaacacat    420

aagcgtgaca acaagaagat caaatctaat acttgcttgg gccggagatt atggattcat    480

gaagcgattt gacagcgtcc attgatcttc ctctcccacg gtcacct                  527
```

<210> SEQ ID NO 151
<211> LENGTH: 171
<212> TYPE: DNA
<213> ORGANISM: Pinus taeda

<400> SEQUENCE: 151

```
gggggtaggg gtgtttatac tgagcatact tcgaaagtgg ttcaccacca ccatgatgac     60

taattgttcc tgactttggt agacctataa taaattccat agaaacctcc gtccatattg    120

atgccggaat gggcaacggt tgtaatgtgc ctggtacttt gacggtcacc t             171
```

<210> SEQ ID NO 152
<211> LENGTH: 412
<212> TYPE: DNA
<213> ORGANISM: Pinus taeda

<400> SEQUENCE: 152

```
aggtgaccgt tgggaaatgc aatacctctc gtccaggtat attcaacttg agggacagag     60

ccaagtggga tgcatggaat tcacttaaag ataaaacccc cgagtctgcc atggaagatt    120

acatcactaa ggttaaacag ctacaagaag tagcatgatg cctagacaaa tagctttgct    180

caacacatcc tgatagtgta cactaaatcg cacaacttta ctactacaaa gaaagatcgt    240

tgacaccttg acaaatagct ttgctcaaca catcccaaca atttggattg cgaataccga    300

ctccaatttg tacttgatcc atatgtcgtt gcgatgtact agttcctcta tacatatgtt    360

tctgcaagaa tcggagttgg acctcttctt ccctgttatc agcacggtca ct            412
```

<210> SEQ ID NO 153
<211> LENGTH: 409
<212> TYPE: DNA
<213> ORGANISM: Pinus taeda
<220> FEATURE:
<221> NAME/KEY: modified_base
<222> LOCATION: (307)
<223> OTHER INFORMATION: a, t, c, g, other or unknown

<400> SEQUENCE: 153

```
aggtgaccgt ggataagaga acgctttgcc gactctctgg gatgcccttc cctccatagc     60

cgtcgtggga ggacagagct ccgggaaatc ctctgtgctg gagagcatcg ttggaaggga    120

ttttttaccg cgtggatcag gtattgttac tagacggccg cttgtccttc aacttcacaa    180

gactgatgaa ggcagcaggg attacgccga attccttcac caacccagaa agacatacac    240

cgactttgca ctggtaagga acgaaattgc ggatgagact gatcgaatta catggcgtgc    300

caagcanagt ctcaagtgtc ccaattcacc ttaatattta ttcacccaat gttgttaatt    360

tgactctaat tgatctcctg ggttgacaaa attgctattg acggtcact                409
```

<210> SEQ ID NO 154
<211> LENGTH: 241
<212> TYPE: DNA
<213> ORGANISM: Pinus taeda

<400> SEQUENCE: 154

```
aggtgaccgt tgggaaatgc aatacctctc gtccaggtat attcaacttg agggacagag     60

ccaagtggga tgcatggaat tcacttaaag ataaaacccc cgagtctgcc atggaagatt    120

acatcactaa ggttaaacag ctacaagaag tagcatgatg ccattgatct ccctttccct    180

gcctcttcta ttatcattga tctctctttc cctgcctctt ctattatcag tacggtcacc    240

t                                                                    241
```

<210> SEQ ID NO 155
<211> LENGTH: 289
<212> TYPE: DNA
<213> ORGANISM: Pinus taeda

<400> SEQUENCE: 155

```
aggtgaccgt acatacaagt gctcagtaca atgtcatata ctaccaatac atttgattag     60

aatacgagac tcgctttcat tcggcatatc tgtctctgga tgataaacat ataaagcctt    120

gatccatgag taaggtaagt ttgaagctac aagtattttc taaacgaagt tcaaaattac    180

ataagattgt ggctggggcg tgagaaacgg cctcaacaat gtcctgttct gatcatgtat    240

catttcagta ccgatcatgc ctatcatacc cgcctggtga cggtcacct                289
```

<210> SEQ ID NO 156
<211> LENGTH: 209
<212> TYPE: DNA
<213> ORGANISM: Pinus taeda

<400> SEQUENCE: 156

```
aggtgaccgt actgataata gaagaggcag ggaaagggag atcaatggca tcatgctact     60

tcttgtagct gtttaacctt agtgatgtaa tcttccatgg cagactcggg ggttttatct    120

ttaagtgaat tgccatgcat cccacttggc tctgtccctc aagttgaata tacctggacg    180

agaggtattg catttcccaa cggtcacct                                      209
```

<210> SEQ ID NO 157
<211> LENGTH: 191
<212> TYPE: DNA
<213> ORGANISM: Pinus taeda

<400> SEQUENCE: 157

```
aggtgaccgt atagtgtcaa gcttttctgg attggataat ggacggcggc ttgcgacata     60
catctacaca ttctgtaaca agtacactct actgcaacag cagacccaat ttcacctctt    120
cagtcagcca gagatctcga tggatttggg ttgaggaggt tggggttctg cctgcttcgg    180
cacggtcacc t                                                         191
```

<210> SEQ ID NO 158
<211> LENGTH: 415
<212> TYPE: DNA
<213> ORGANISM: Pinus taeda

<400> SEQUENCE: 158

```
aggtgaccgt gctaagtaat tatcatctgt acctgtgctt gctgcaggaa gtaaaccaac     60
ccgactagtc tttttaataa tacagggagc cttgccacca atttcctctt gaagcaccca    120
tattggacgg gtttgtgtca tcctctgtat tatccttttt catcccaagc aggctgtctg    180
tttttgtagt agaaggatca caacacagat caggccctcc atagtacaaa gaagaaccga    240
ggaaagtatc attaacgttc tgactcctgc catgaaggct tccactatga ccttgaccct    300
tttgtgaatt actgccattt agaccttgac tggctcttgc aaccaaatgc cccagaatgg    360
aacttctttg tgctccagtt ccattgtggt tagttgaatc cctaccacgg tcact         415
```

<210> SEQ ID NO 159
<211> LENGTH: 414
<212> TYPE: DNA
<213> ORGANISM: Pinus taeda

<400> SEQUENCE: 159

```
aggtgaccgt gcaatattgt attccaggac caagtactta ggacagaatc aggtcacgag     60
tggctccact ccacaatacg atgttcatcg ttttaatcac aatacaagtt tgttagtcca    120
agtaagtgcg ctgctgcaga cagtggggca ccccccgtgg gctttgactg cctgtcatac    180
tgttccctcc ttgctcctgc tcttgctctc gctgggctgt ggtgagttac taacctggtt    240
cgacccacaa gggcttctca ctagggcgtt aggctgcatg gatctgccag atattgtggt    300
tgcaagggac agaggcatga gacacaggcc tttgctttgc agaaactgca ttgctgaccc    360
catgttttca tccatcagtt ttgctacctc tccttctgtt atggacggtc acct          414
```

<210> SEQ ID NO 160
<211> LENGTH: 225
<212> TYPE: DNA
<213> ORGANISM: Pinus taeda

<400> SEQUENCE: 160

```
aggtgaccgt atccgcagca gcaacagcag tagagcctga agcaggggac ctaattacag     60
tcaaaagtcc agggctacca atgcctgcta acagcgcact tacttggact aacaaacttg    120
tattgtgatt aagacgatga acatcgtatt gtggagtgga agccactcgt gacctgattc    180
tgtcataagt acttggtcct ggaatacaat attgcacggt cacct                    225
```

<210> SEQ ID NO 161
<211> LENGTH: 234
<212> TYPE: DNA

<213> ORGANISM: Pinus taeda

<400> SEQUENCE: 161
aggtgaccgt atccgcagca gcaacagcag tagagcctga agcaggggac ctaattacag 60
tcaaaagtcc agggctacca atgcctgcta acagcgcact tacttggaac taacaaaatt 120
tttattgtta attaaaaacg aataacatcg tttttgtggg agtggaacca ctcgtgaact 180
gaatcctgtc ctaagttctg ggtcctggga ataacatatt gcacgggtca cctt 234

<210> SEQ ID NO 162
<211> LENGTH: 548
<212> TYPE: DNA
<213> ORGANISM: Pinus taeda

<400> SEQUENCE: 162
aggtgaccgt tacagctagg gaagacttta aaagtttgta aaactaagca tagctcttaa 60
acactgaagt taaaagacat gattggaatg tgcaagtggt tcagtatcca aatattgaag 120
gttgcagaat atggagctac tgtgcaaacg agtaacttta tctatatttt cacaagatca 180
tacaatggga aacgttgaga taacaactgc atcggtgaac cagaatagtt ataaaagttc 240
ttgcaagtaa agggatgaat aattgcatgg ttggaattaa gaatgaccat gtagagctgc 300
tatacagatt ctccaaggtt ttatatttga ggagtgcgcg ctattgatgt tgtgcaaaaa 360
tttcagaaat taagttctgc ggcatttatc aaggttgttt gagccattta aatagcaagt 420
ttttgtttct ccaagtactt tcaggaaagc agatagctct agttataatg ctccagtgac 480
aaacacatct agttggggca gtgaatgacg cttttgtcat tctcttttgg tttcaggcac 540
ggtcacct 548

<210> SEQ ID NO 163
<211> LENGTH: 176
<212> TYPE: DNA
<213> ORGANISM: Pinus taeda

<400> SEQUENCE: 163
aggtgaccgt ggacaaactc tagaacaggc atagctttca tgttcagttg tttttaaaga 60
gcagtcctcg cagcagatcg tgcagcttcc tgcttcactt ccgttgattt tcctgatctg 120
aaatacccgt aaacttgctg aagaacccaa atacttaata gcgtctctaa acaaaa 176

<210> SEQ ID NO 164
<211> LENGTH: 699
<212> TYPE: DNA
<213> ORGANISM: Pinus taeda

<400> SEQUENCE: 164
aggtgaccgt gcctgaaacc aaaagagaat gacaaaagcg tcattcactg ccccaactaa 60
tgtgtttgtc actggagcat tataactaga gctatctaca agccaaaaca gtgtttggga 120
gagattccat aacgtcattg cctctgctac acatcattca ttggttccaa taatgaagcc 180
acgtgctaag gacattgaga gaatcttata aaacaagaaa tatagtaaat tgggaaatgc 240
attttatcgt ctaacctgct ttcctgaaag tacttggaga aacaaaaact tgctattaaa 300
tggctcaaac aaccttgata aatgccgcag aacttaattt ctgaaatttt tgcaaacatc 360
aatagcgcgc actcttcaaa tataaaacct tggagaagtc tgtatagcag ctcacatggt 420
cattcttaat tcacaccatg caattattca tccctttact tgcaagaact ttataactat 480
tctggttcac cgatgcagtt gttatctcaa cgtttcccat tgtatgatct ttgaaaatat 540

-continued

```
agataaagtt actcgtttgc acagtagctc catattctgc aaccttcaat tttggatact    600

gaaccacttg cacattccaa tcatgtcttt taacttcagt gtttaagagt atgcttagtt    660

ttacaaactt ttaaagtctt ccctagctgt aacggtcac                           699
```

<210> SEQ ID NO 165
<211> LENGTH: 620
<212> TYPE: DNA
<213> ORGANISM: Pinus taeda

<400> SEQUENCE: 165

```
aggtgaccgt aaaataccat gagaaatgct ttcatcaggc accgctggta ggttttctta     60

agcttttcat taggcaaaag aggctccgtg agttgatcgt taattctctc cttgaatgcc    120

atattgacca gacactctga ttagaaactg gaatacaact gcacatatag tcattctata    180

tgattcatcc ttctgcactt cagcatcctg cggcaactct tcatcccgcc atactgagaa    240

aaattatttg actcttgatc atgtgtagat gaatcttcat gaatcttctc atcttcattc    300

ttgtctttat atctttagga agtgcatctg gtaaaagtat aaatgcatct tcacgggtgc    360

ttcagttttt gcatgctccc ggttcttctt gtttagcatg tggatctagc aaatcactaa    420

atgtagttct ctcaattggt ctggtggaaa ttctcctcaa ttcgagaatt acgaatcatc    480

atacctgagt aatatatgtt gccctgtaca tgcatatgct ggtttttggc tccaccattc    540

tccaaagggc tcaaaaacta tgcgacccct ggttgccgta gtggaaggtt atacattgcg    600

ttcccagtag ccacggtcac                                                620
```

<210> SEQ ID NO 166
<211> LENGTH: 439
<212> TYPE: DNA
<213> ORGANISM: Pinus taeda

<400> SEQUENCE: 166

```
aggtgaccgt ggaggggctc cacttatatg catagatgat gctgcgaggc tgtgttcatc     60

tggtccaatg gagaagggga agaccaagtg cctatcctga ttttggtgcc gcttgttctg    120

gtgtacagaa tatcaaccca gggtatgtac catcacttcg tgagacgttc acatttcccc    180

acttcttggt ggagctggtg gaaagcctgg aacttcatca atctatcgtt ggtgtgagga    240

tgatcaggct ctgtacttat atccacatgt agtgcagcag gtggtggaga tgtctctgat    300

aagttggggg ttgatactgg ttcgtatcat ttgcagtgat gttccccccgc tgcccttaat    360

tgctattgat ccatcattaa ctataggttt ttactcgccc ggaataagac aatcttttga    420

cacttgttgc ttgggtcac                                                 439
```

<210> SEQ ID NO 167
<211> LENGTH: 289
<212> TYPE: DNA
<213> ORGANISM: Pinus taeda

<400> SEQUENCE: 167

```
aggtgaccgt ggcgcctgac ctgtgcagaa tccattctca tggatacaat actgttaagt     60

ttgctttgct ttgcttgaag gatctgaatt gaaaaattgt ccccacaatt ctgtttcgtt    120

aaaaatgacc tcaatcactc tcgacagttt ccagatcttg attgggagcg tcctctcctc    180

tctcaagatg ttgttgacca aattcagggc gacttgtggc cagaaatcgt acattctgcc    240

atctacctgt tattgagctc cccgatttat atgcgctttt gacggtcac                289
```

<210> SEQ ID NO 168
<211> LENGTH: 314
<212> TYPE: DNA
<213> ORGANISM: Pinus taeda

<400> SEQUENCE: 168

```
aggtgaccgt caataccatt aaactgggga ttcgtctcaa caagtcaaca tgctaacctc     60

acagctccaa tcaaacaacg tccgtcgaag ggcgctcaca ctcatccaaa ttacttccct    120

ctgcaagact cacaaaatca gattcttcat gaattgctca aacgaggctg ttatggatga    180

tgcagctgat tactcaagtg acagcactct gaatccccgt cccatatata gcgacgcggc    240

gtttcagccg tgactggtcg caacagcctc agtgggacaa aaggccagaa gccccccaag    300

gttctcacgg tcag                                                      314
```

<210> SEQ ID NO 169
<211> LENGTH: 242
<212> TYPE: DNA
<213> ORGANISM: Pinus taeda

<400> SEQUENCE: 169

```
aggtgaccgt gtcgatgttg ttagatgtga ttagggtttt atttcttgat acagatgcac     60

tgtttctctg tttattcttt tatttcttca atgtatgttg tcaaattata cttagtcaga    120

tctcctttta tcgttcgtca aaaaaaaaaa aaaaaaaaaa aaaaaaaaaa aagtttaaca    180

attaaaaggg gaaattaggc catatcagct tgtcgtatgg acccacatgc actgtaggtc    240

ac                                                                   242
```

<210> SEQ ID NO 170
<211> LENGTH: 195
<212> TYPE: DNA
<213> ORGANISM: Pinus taeda

<400> SEQUENCE: 170

```
aggtgaccgt atgcagagtc aaggtttagt tccttcagag cctgcccgag tagcactgag     60

gcagctcaag ccatttcacg taggaagccc acaacaaaat agaaatcaga gtgagtcttt    120

gatcgagtaa cccataagtt cttagctccc gttccatctt aacataagca tttttcttcg    180

tcttctcgca gccgt                                                     195
```

<210> SEQ ID NO 171
<211> LENGTH: 217
<212> TYPE: DNA
<213> ORGANISM: Pinus taeda

<400> SEQUENCE: 171

```
attgcagagg acttagagag ggaaaaccgt tccgatctgg tgaagcaatt ggatgaagcg     60

ctctggaatt gattcccgtt tctgatgata tcgtacggct aagctcagct cttcaggcat    120

tggcagacaa tacgattctt caaatgagat gacagatttt aagaaactta taggatgaca    180

tatttcctag cttgaagcgg attcccccta cggtcac                             217
```

<210> SEQ ID NO 172
<211> LENGTH: 381
<212> TYPE: DNA
<213> ORGANISM: Pinus taeda

<400> SEQUENCE: 172

```
aggtgaccgt ccgataaagg atgagaatat aggtagatca acccaaaaac actctcagaa     60
```

```
aacgattaaa gcctaacccc aagatcgttg agtaaattta acccggtaac ctccacataa    120

aatatactta gcaacaataa actcaacaac taaactatcc ctttaaaatt aaattatcct    180

tatttattta aaaaaacaaa tcctttatat actaaggtcc cctgcacatc tattactaag    240

gtaaaggaag ggaattatat gctatcattg taaactttga cttccgtatt tatgatcaga    300

ccatgagttt gataattaat tttacgctct ttactcccca ttcaaggcac gtgcctggtg    360

atatatgaac gccaaattat t                                               381
```

<210> SEQ ID NO 173
<211> LENGTH: 498
<212> TYPE: DNA
<213> ORGANISM: Pinus taeda

<400> SEQUENCE: 173

```
aggtgaccgt agaatacaat ctatgtatca aaatgctaac aaagagaatt tgttgtctag     60

cttgtaaata tacaaaagaa actctcacaa ggagtgagaa gcactaaggc ccttggaaag    120

aatacgtttc tattcagcgg agtgtatttt gagctacggc ttggcacaac tcatcctata    180

aaacaagact ctgtgagagg gcagagacct tgatcctggg cgtggcaagc cgggtgccta    240

ttgcggtaaa atcgagaagg gggaccctgg aaaagagagg ctgaaatttg tttcattctg    300

caactgaaac ctaaccggag gccgaatctg atcatttcta agacctttgg ggtcctgggc    360

atcccattaa aagaacgctg ctaactctcc cctccacaaa gggccaatgc gctcaggtcg    420

ggcttctcat cttcacattt cttgccgaaa tctatctgaa tttgttgtat tgaataacac    480

tgcctcctac acggtcac                                                  498
```

<210> SEQ ID NO 174
<211> LENGTH: 604
<212> TYPE: DNA
<213> ORGANISM: Pinus taeda

<400> SEQUENCE: 174

```
aggtgaccgt gggcgccgtg gctcaaaagg ccctcgcaga cgcccgctcc atcaagctca     60

tgggcccccct ccaccctcgg ggggcaagcc gggaacgttg ctgtcagacg aggcgaggac    120

ctggaactgc cgttgaagga acggttctat attcagcccc tctcggcgga ccaggcgctg    180

cgagagccaa ggaatccgcg gaagcaaatc ctggaggtga aaaagctgat agataaaagg    240

cgtggccgta cgtccagaac gacctccgct ccaaggcttc ttaccttcgc tacgactcaa    300

caccgttatc tcctcaaagc ccaaggaaca gaaaaaaccc ctcaaaacct caccccaaag    360

ctttttgac accettgaca aacctggact acgctgcaag gagccaagga taccccaagg    420

gcagaaaaaa tactttgcag aagctggtga accgccctta atgatgttca ttccaagctt    480

ggttaagctg tattgcactc attgttaacc acacttaacg ccaatccaat ctatgctgtg    540

ttgcatctcc acttcttagt taataacgtt ctgtgttccc aaactctgtg ccacacacgg    600

tcac                                                                 604
```

<210> SEQ ID NO 175
<211> LENGTH: 561
<212> TYPE: DNA
<213> ORGANISM: Pinus taeda

<400> SEQUENCE: 175

```
aggtgaccgt acaatacaaa taggtagttt atcacattgt agcttataga atgtacaatt     60
```

-continued gaaatcaaat aaattcaacc aaactcaaat aatatgatca tgtgctcctc accttctcag 120
caaactcgta gagcagaaaa aaggattatg ttaaatcaca gttcacacat tagggtaaat 180
cccactaaat gacctctctt cattatccaa gtatctgaca ccaacatatt tcaaacaaat 240
agtgcaaaaa ggaatggtga agtaaaatag tcaaaactaa aaaataagct taaaatttct 300
cacatgtttg aatatgtgca ccacaaattt tgttagtgtc atcaaaatgc atgtaatcaa 360
cttgccgtgt atataatttc acacaatatc cgtaaaattt tgcaattcct tatgagcatt 420
tcatgtctag agattgcaat gacttggcta caaacatgtt tctctacaca agatcacaat 480
atttagtcag gacacgaatt gcaatgggga ttctcacaag catcacaagt catctcccat 540
gtactaaaaa attgtttaaa t 561

<210> SEQ ID NO 176
<211> LENGTH: 382
<212> TYPE: DNA
<213> ORGANISM: Pinus taeda

<400> SEQUENCE: 176
aggtgaccgt atagtgcata ttcagattgc aattacagac gtattagaac cagattttcg 60
cttcgataca gctcatcgag agcaacagag atccagatca aaaaccagac acagtttaag 120
aacatcgaaa taccaagccc agggacagtt accagcatat agctctacca ccaacagatt 180
attacagaac caaaacataa gaccacttgc agacaaaaat aaaccctaac gcagaacgtg 240
gcaactatct cctccagcta ccaccatcgg aaccaccacc accatagcga gaaccccacc 300
accaccatag ccgccaccgc caccaccata accaccacca ccaccaccac tgtaccgcca 360
ctaccgccat aaccacggtc ac 382

<210> SEQ ID NO 177
<211> LENGTH: 196
<212> TYPE: DNA
<213> ORGANISM: Pinus taeda

<400> SEQUENCE: 177
aggtgaccgt ccttggagat accagcttca aaacctccag tggtggagtc gatgatcaaa 60
ctgcacagtc agcctgagat gttccagtaa tcatgttctt gataaaatca cgatggccgg 120
ggcatcaatc acagtgcagt agtatttagt tgtctcaaac ttccagagtg caatatcatt 180
gtgataccac ggtcac 196

<210> SEQ ID NO 178
<211> LENGTH: 141
<212> TYPE: DNA
<213> ORGANISM: Pinus taeda

<400> SEQUENCE: 178
aggtgaccgt atagtaggaa ctttaggtgc tttggtggca ctctccaatt ttcatgtcct 60
tacatacccc actacggaga agggtagccc aagatttgaa cccaagactt ccggttcgtg 120
agacttcatt tccacggtca c 141

<210> SEQ ID NO 179
<211> LENGTH: 478
<212> TYPE: DNA
<213> ORGANISM: Pinus taeda

<400> SEQUENCE: 179
aggtgaccgt aagatcaaga gcacagaaag cagccatagc cccgcccatt gaatgcccat 60

```
aacaataatc tgtaacccat ctctctgttt ctgagctttc tgaactgctt ctacaacagt    120

ggtcgtaagg ttgtgttgtg ataagcagag taaaatccat aatgtaccat tgcaccagca    180

tattaggata gttgagatca agtgtcttac agaataaatc ctccacccaa ttctgtagct    240

cctttcttga gtacccctga atgcaattac aattgcattg atatcttctg ccacaccaca    300

aaagcctgaa ggcagtgttg tacatcaact ataagctcta ccacctgaaa accccagtca    360

aaccattgca cctagaacaa gtccaagaca ttagagcact caaatcatcc ataagaccgc    420

agaagcatat tgcacaagta tctcagcaag tgttcgatta tagacatggc caggtcac      478
```

<210> SEQ ID NO 180
<211> LENGTH: 381
<212> TYPE: DNA
<213> ORGANISM: Pinus taeda
<220> FEATURE:
<221> NAME/KEY: modified_base
<222> LOCATION: (58)
<223> OTHER INFORMATION: a, t, c, g, other or unknown

<400> SEQUENCE: 180

```
aggtgaccgt gggaggggag atttttgatt tatatttcca atataaaaga aaatctangt     60

tgtaaggaca tggcaagagc tcttatttcc ggggttttag ccgtggcccg gagcggatga    120

aagcaaatgt aagtcactcc gtgctttctc ggcatttgga cgcttctact ctaccgcact    180

acagacggga ttgaacctcg catctctgag tgtttggtcg tttacatggc ggacttgttc    240

cgcacctctg cggacgtcaa atgccgcgac gataatccct ttgagaacag cgatacggca    300

gaaagatcgc cgttgacgaa gcgagaaaac tattgagact tgcagatgtg gagctgaaga    360

agagcttgag tcgacggtca c                                              381
```

<210> SEQ ID NO 181
<211> LENGTH: 521
<212> TYPE: DNA
<213> ORGANISM: Pinus taeda

<400> SEQUENCE: 181

```
aggtgaccgt ccgttcgggg tgtattgtcg aacacgtagg atggtgctac gttgaaacca     60

ccgttacctt cttcgatatg ttatagttcg agttcatacg gagggaatac cgtttgtagt    120

gttattcagc acaaccccgt cctgattaaa cacccccgca accaaggacg tattcgacgt    180

tcggtattgt ttgacacact caagttataa ccctgaatag gcgctacccg aagtaagcat    240

tgtaccagtc gttatttttg ccttcgtatt gcgaaggatt ttgaaatata tccggacagg    300

ctgcaaccga tcttcataaa actctttctt aaactgagca aactgaacag cattagcatt    360

ttgacccgac ctttcatcgg cacctgctgc acacccgcat acgtattaaa gctatgttcg    420

tctggccagg tttgcctttt ttggttgtaa tcaggacaac gccgttagcc gcccgcgatc    480

cgtagagcga cgtagaaagc cgcatctttc agcacggtca c                        521
```

<210> SEQ ID NO 182
<211> LENGTH: 307
<212> TYPE: DNA
<213> ORGANISM: Pinus taeda

<400> SEQUENCE: 182

```
aggtgaccgt gaaatatgtg ggagatgata tgtggtttcc tgaatattca cctcttgtgt     60

agaaaagtga gatccttaag atgttttgct aataagactc ttaggaatgt tggacccctt    120
```

-continued

```
tcagaatgcc atttgaatag attcaaggtg gtagctgttg cctggggctg ttttagggtt    180

ttaggccatg ctctgtaatt tcattgagtc aaaattggat taactggtgt cttttacctc    240

ataatagcta ctgcagtatt tgtcgatata gcttccctat ttattgactc tccttaggta    300

cggtcac                                                              307
```

<210> SEQ ID NO 183
<211> LENGTH: 519
<212> TYPE: DNA
<213> ORGANISM: Pinus taeda

<400> SEQUENCE: 183

```
aggtgaccgt ccgttcgggg tgtattgtcg aacacgtagg atggtgctac gttgaaacca     60

ccgttacctt cttcgatatg ttatagttcg agttcatacg gagggaatac cgtttgtagt    120

gttattcagc acaaccccgt cctgattaaa cacccccgca accaaggacg tattcgacgt    180

tcggtattgt ttgacacact caagttataa ctctgaatag gcgctacccg aagtaagcat    240

tgtaccaagt cgttattttt gccttcgtac tgcgaaggat tttgaaatat atccgcacag    300

gctgcaactg atcttcgtaa aactctttct taaactgagc aaactgaaca gcatcagcat    360

tttgacccga cctttcatcg gcacctgctg cacacccgca tacgtattaa agcaatgttc    420

gtctggccag gtttgccttt tttggttgta acaggacaac gccgttagcc gccgcgatcc    480

gtagagcgac gtagaagccg catctttcag cacggtcac                           519
```

<210> SEQ ID NO 184
<211> LENGTH: 629
<212> TYPE: DNA
<213> ORGANISM: Pinus taeda

<400> SEQUENCE: 184

```
aggtgaccgt cgtcagaaaa aacgtgattt ccgcaaactt tggatcactc gtatcaatgg     60

gcagctcgtt tgaacggact ttcatactca caattgatgc atggtttgaa gttggctgaa    120

tcgaagtgaa ccgtaaaatg ttggctgact tggctgttaa cgatgcagca gctttcaaac    180

tcttgcagac gcagctaaag ctaagcttgg gtaaataatt aaaaaaagaa ccgaggtttc    240

cttggttctt ttttataact tttaatgaaa agtatgaaga gagaaacagc ctgtcttcta    300

cttatagtat aagataaaag cttgttactg ataagacagc tttcatggta aagcagttaa    360

aaatagggat ttgcgatata atagaaaaaa cagacgttta tgtaaataaa aaacagtaga    420

atggagaaat tatgtcagag aatcgtttgg cttgggatca gtattttgcg gccaggctct    480

cttaatcgct aatcgctcaa cctgtaagcg agccaaaggt ggctccgtat tgtcaaggat    540

aataagggtt atttcaactg ggtacaatgg ctcagtttca gggactggag actgtattga    600

ccaaggagtg cctggtcatt gacggtcac                                      629
```

<210> SEQ ID NO 185
<211> LENGTH: 413
<212> TYPE: DNA
<213> ORGANISM: Pinus taeda

<400> SEQUENCE: 185

```
aggtgaccgt ggcggaggtt agggaagttt gacttctcat tttctcacgc actcctctcc     60

tcgtaacctc ggtcgagtcg atggcggctt tttagtcgag tgtgctaacg caccctccgg    120

cctcaaaatt tccagctact cgtatttgat caatgctgaa atcgcgtaat tacgtagtaa    180

taaagcgtaa tgaattctat aatgaagcat gtttctctat agttcatgtg ccgagaggaa    240
```

```
taatgaaaat gaggccttat atattatctg gggctcaagg agatgttatc ttttccttcc    300

ttggttagag accgtcaacc ttcacttgat tggataaagc ttcattttgt taaaacctcc    360

aagccagtag atacatacgg taggcacgta ttatggtaga gacatacggt cac           413
```

<210> SEQ ID NO 186
<211> LENGTH: 397
<212> TYPE: DNA
<213> ORGANISM: Pinus taeda

<400> SEQUENCE: 186

```
aggtgaccgt cctgttgcct aaccgcgaat ccaaatcgac ttgggctgct tcctttcgtg     60

cagatatttc tggtttggac tctagttctt gctcctggaa atcatgcttg agtgctgggt    120

agctgcctcc aagtttggtt gacaggccca ttccttacag cttctctctt ccgcttatga    180

cagagtaatg acaggaattc aacctgacgg atccgtctag ctctcacaag gttgggaccc    240

tgtcttcgag agggttattt cttgagactg ttgactatat tttggatgag ccctcagctc    300

tgtgtactat tgttcatgta ctggatactt tgtaaatgat tttattctgg ttttaccccg    360

gggggggcat tttgactcct gggtttaata cggtcac                             397
```

<210> SEQ ID NO 187
<211> LENGTH: 467
<212> TYPE: DNA
<213> ORGANISM: Pinus taeda

<400> SEQUENCE: 187

```
aggtgaccgt ggaacatgat gattagttct tctgtgggcc aggatgatta gttctctgtg     60

tgactgtggg ccaggatgat tagttctcct gtgacgactg ttggatagga tgattcgtct    120

cctgtggaca ggatgattag ttctcctgtc gaggcaccct acccatgcaa tttgggatca    180

tgggaagtac ctctcatctg atcaatgagt agggaaatgg ggttagggac cattagagta    240

ctatcgatgg acacatcgtt gtatctaccg tcctatgcta ggacgacctc cattgtttgg    300

gattagtgag agtggtatga cactctgaga ctgactttgg gtcagtggag gatgtatgat    360

acatcctcga tcatttcttc ttcttcatag ttcgagcaga gcagagcaca acaggccaag    420

tagtgcaggg tagtgcattt gatggctggg atagtagcga cggtcac                   467
```

<210> SEQ ID NO 188
<211> LENGTH: 555
<212> TYPE: DNA
<213> ORGANISM: Pinus taeda

<400> SEQUENCE: 188

```
aggtgaccgt aaataagatg acccacatgg agtttggccc tagtttccaa ttttaacacc     60

gctctcaact agggagaact ccattcgctg atccatttgt ccgactatac tatctctgca    120

tcagtgccct acactactct gcactgctct gctctactaa accatgaaga agaagaatga    180

ccgagaatgt ctcatgccat tctctattga cctgaagtta gtcctatatg aagagatgtg    240

tcatatcact cttattgacc caaagtcagt tttattgatc ccagatcaat atcacagaga    300

gtgtctcaaa ccactcatac tgatcccaga tcagtttcat tgatcccata tcaaggagat    360

catcctagaa tagggagtac agtagataca atgatgcatc catcaatagt actctatggt    420

ccctaacccc atttccctgc tcattgatca gatgagaggt acttccgatg agcccacact    480

gcatgggtag gatgcctcga catgagaaat aatcatccta tccacaggag acgaatcctc    540
```

ctgtcccacg gtcac 555

<210> SEQ ID NO 189
<211> LENGTH: 695
<212> TYPE: DNA
<213> ORGANISM: Pinus taeda

<400> SEQUENCE: 189
ctagggaaga ctttaaaagt ttgtaaaact aagcatagct cttaaacact gaagttaaag 60
acatgattgg aatgtgcaag tggttcagta tccaaatatt gaaggttgca gaatatgggc 120
tactgtgcaa acgagtaact ttatctatat tttcacaaga tcatacaatg ggaaacgtga 180
gataacaact gcatcggtga accagaatag ttataaaagt tcttgcaagt aaagggtgaa 240
taattgcatg gtgtgaatta agaatgacca tgtagagctg ctatacagac ttctcaaggt 300
tttatatttg aggagtgcgc gctattgatg ttgtgcaaaa atttcagaaa ttaattctgc 360
ggcatttatc aaggttgttt gagccattta aatagcaagt ttttgtttct ccagtacttt 420
caggaaagca ggttagacga taaaatgcat cttcccaatt tactatattt ctgttttaaa 480
agattctctc aatgtcctta gcacgtggct ttcattattg ggaccaatga agatgtgtag 540
cagaggcatt acgttatgga atctctcacc aagaacactg ttttgggctt tagatagctc 600
ctagttataa atgctccagt gacaaacaca tcctaagttt ggggcaatta atgacgcctt 660
ttggtcattc tcctttgggt ttcaggcacg gtcac 695

<210> SEQ ID NO 190
<211> LENGTH: 144
<212> TYPE: DNA
<213> ORGANISM: Pinus taeda

<400> SEQUENCE: 190
tccctttagt gagggttaat agatctatag tgtcacctaa atcgcggccg ctctagaaca 60
gtggatccgc aagcaggata gacggcatat gcattggatg ctgagaattc gatatcaact 120
tatcgatacc gtcgacctcg aggg 144

<210> SEQ ID NO 191
<211> LENGTH: 185
<212> TYPE: DNA
<213> ORGANISM: Pinus taeda

<400> SEQUENCE: 191
ggtgcgatcc taaacatgca agctttgagt ttgtaacttt gtagaagtgg acatttctaa 60
gttggatgta caaatctact gttggttgta ttgtcatccc ataaacaact gtttgatgag 120
atgttttttt aaaaaccaca tcataatatt tttaggcctt gtaaaaaaaa aaaaaaaaaa 180
aaaaa 185

<210> SEQ ID NO 192
<211> LENGTH: 167
<212> TYPE: DNA
<213> ORGANISM: Pinus taeda

<400> SEQUENCE: 192
attccaaact tttctttcaa gatgtacacc aacatcattg tccccaactt agtagacttg 60
acttttcacc aggtccaaag agaggggtgg tggaagcaga tttcaggctt tcgaataagt 120
atcaatgata taagcatcat ccccttgcca attgttctgg atcgcac 167

<210> SEQ ID NO 193
<211> LENGTH: 167
<212> TYPE: DNA
<213> ORGANISM: Pinus taeda

<400> SEQUENCE: 193

```
ggtgcgatcc catcaggggt tgtgtttcta agaatcactt ccatgtttca aattcagcac      60

ttgatcttgt acatacccaa tttgttgcct gctactagct agtattgtct ttcagtttga     120

accatttttt tgagtaaatc gtgtttagtc tttggcaaaa aaaaaaa                   167
```

<210> SEQ ID NO 194
<211> LENGTH: 470
<212> TYPE: DNA
<213> ORGANISM: Pinus taeda

<400> SEQUENCE: 194

```
ggtgcgatcc gcattagaga agcatacagg aaaaagaagt acctgcctct tgatttgcgc      60

ccaagaagac tcgtgctatc aggcgacgcc ttaccaagca tcaggcatca ttgaagacga     120

gagacagaaa aagaaagaga tgtattttcc aatgagaaag tatgcagtca aggtgtaagc     180

cacaggattt gagctttcat gcaatttttt tgttacttgc gggatgatat tgcctatata     240

tttccgtcca cgtttttggc aaattccgat ttgcatcaga attcaagtta tgatagtgtt     300

ctttcgcttt tgagcagttg atattgttta tcttttattt ctcttgaatt gcaacatatt     360

ctaatgcaat gagtggatta ttatattgtg gtatttccat gttgaactca tataaatgag     420

cgtaatttga gtggtagcgc taggatattt acacttggca aaaaaaaaaa                470
```

<210> SEQ ID NO 195
<211> LENGTH: 289
<212> TYPE: DNA
<213> ORGANISM: Pinus taeda

<400> SEQUENCE: 195

```
ggtgcgatcc gtataggtag tttggatgat gaacgggcaa agaaggcaaa ggagtacagg      60

atggatcctg taattcctgt ttcagaaaac agaaaatctg caatataagg atggctaact     120

tttcagctat gaaaatatat ggtgcagtgg cactcatatc agttgcagag ttgtcaaata     180

acttttgtga ataggaaagt tgtcctcttt tagagtgcag aaatcctgca atataagatg     240

gctaagtttt tcagctatat gaaaatatat ggtgcagcaa aaaaaaaaa                 289
```

<210> SEQ ID NO 196
<211> LENGTH: 321
<212> TYPE: DNA
<213> ORGANISM: Pinus taeda

<400> SEQUENCE: 196

```
ggtgcgatcc catatacaat tacatatatt ttcaacaatt cttttgttgt tatgaaaatc      60

tattgaaata aattgaaata gtttgcatca tttatttatc ggaattcgta tttatatatt     120

aaatttctga tgtctcaaat ccttcgttac tgtaacgata tcattaatat aatgtgtctg     180

caagtttatt gggcaaaaca aaatttattt ttcggtcaca tcataagttt atttttggtc     240

acatcatatg caccatcaca ttaagcataa gcatatacag tagcgtaaaa atacaattat     300

tgttgttgac taggatcgca c                                               321
```

<210> SEQ ID NO 197
<211> LENGTH: 188
<212> TYPE: DNA

<213> ORGANISM: Pinus taeda

<400> SEQUENCE: 197
ggtgcgatcc tagtcaacaa caataatatg tatttttacg ctactgtata tgcttatgct 60
aatgtgatgg tgcatatgat gtgaccaaaa aataaactta tgatgtgacc gaaaaataat 120
tttgttttgt ccaattagac ttgctgtata tgtctggagt cctacccttg aaaattgact 180
tgtttccc 188

<210> SEQ ID NO 198
<211> LENGTH: 145
<212> TYPE: DNA
<213> ORGANISM: Pinus taeda

<400> SEQUENCE: 198
ggtgcgatcc catatacaat tacttatatt ttcaacaatt cttttgttgt tatgaaaatc 60
tattgaaata aattgaaata gtttgcatca tttatttatc ggaattcgta tttatatatt 120
aaatttctga tgtctcaaat ccttc 145

<210> SEQ ID NO 199
<211> LENGTH: 151
<212> TYPE: DNA
<213> ORGANISM: Pinus taeda

<400> SEQUENCE: 199
ccactgcacc atatattttc atatagctga aaaacttagc catccttata ttgcagattt 60
ctgttttctg aaacaggaat tacaggatcc atcactgtac tcctttgcct tctttgccgt 120
tcatcatcca aactacctat acggatcgca c 151

<210> SEQ ID NO 200
<211> LENGTH: 254
<212> TYPE: DNA
<213> ORGANISM: Pinus taeda

<400> SEQUENCE: 200
agagccttct tgcagacaat ccgtgaaaac atggctatac aataaaaatt cccagtttga 60
attctaaaga aaactgttca atatttgaag gcctctgata tcacagagac tgatattaaa 120
tggaaattca tacaaatgag gagagcatgt agcaacacta gaagctttgg cataaagcac 180
cagataaatt cataagaact aaatccataa gaaggatctc tcgttcacca gtcacaatca 240
cactcggatc gcac 254

<210> SEQ ID NO 201
<211> LENGTH: 363
<212> TYPE: DNA
<213> ORGANISM: Pinus taeda

<400> SEQUENCE: 201
ggtgcgatcc ctggccctga taactttggt tgcaatggaa aatgcagtac taggtgcgaa 60
atgctaaagc ccgcccggag cggtgcatga agtactgcaa tatttgttgt agtaaatggc 120
tggttgtgtt cccagtggtc actatggcaa caaggacgag tgcccctgct acagagaatg 180
aagtccgcag ccggcaagcc caagtgtccc tgatcttagc acttcagtcc agtcgccact 240
tcttttattc tcttttttta taaaagtgac gaggccgttt ttcttgtgct tggtgccata 300
tgtagagcgg tggctacttc tcctgtgtta ggaaatgttg cagtactaat aatagaactt 360
ctt 363

<210> SEQ ID NO 202
<211> LENGTH: 162
<212> TYPE: DNA
<213> ORGANISM: Pinus taeda

<400> SEQUENCE: 202
ggtgcgatcc aataaagata tactttgcaa caataatcaa aatatcatta tgcaaagttt 60
aagatcaaaa tagaatgcaa caaaaaaatg gttgtaacat aggaaccaac aatgttgcat 120
tcaagtaaga ctctttgcaa aaaaaaaaaa taaaaaaaaa aa 162

<210> SEQ ID NO 203
<211> LENGTH: 355
<212> TYPE: DNA
<213> ORGANISM: Pinus taeda

<400> SEQUENCE: 203
ggtgcgatcc acaagtaaga taattgagta tatattcaag atgcaaatat ttcattagga 60
ccactcataa agttatcaat gattcacaaa gagacctcct gacctctctc aaaagtggtg 120
gcaacacaag actagtgtag tttttactat acctcaatga aactaccatc ctaactgatg 180
ccataatctt ctgttatata ttaccaaaat ttatgagatg attgatccat aaacactcca 240
gaacacatag tcatccaaag gaacctttgc ttgaatatgg acccccttaa ttcaggtact 300
tgctactcca ataaattgct taatctctcc accgataacc acagtttgga tcgcc 355

<210> SEQ ID NO 204
<211> LENGTH: 297
<212> TYPE: DNA
<213> ORGANISM: Pinus taeda

<400> SEQUENCE: 204
ggtgcgatcc aggacatgag gccgagtttg ccattgtgat atgattgagg aagtccagtc 60
tcaaaattag gtttatcttg atgtttgaca agaaatatag aagggcatga tgaatcaaga 120
accttttcca aatctgttac tgcaaccaat ccaatgacat aataacgcca atggttggtt 180
cctgtgatga cataataaat tggattaaat taataacatc cctaatgcca tgtggttagc 240
tgcatcatca ccgtatccat cgagtgttca atttttggga tgtatgtatc aaaaaaa 297

<210> SEQ ID NO 205
<211> LENGTH: 337
<212> TYPE: DNA
<213> ORGANISM: Pinus taeda

<400> SEQUENCE: 205
aaatattttt caatacaacg ccatgtgaca tttttgtgct tcttgttttt gatacatact 60
tccaaaaact gaacactcga tggatacggt gatgatgcag ctacagccat tgcattacga 120
tgttactaaa ttaaatcaat ttattatgtc atcacacgaa cccaaacaat agcgctatat 180
gtcattagaa tggttgcagt tacagatctg gaaacagatc aatgaatcat catgccctct 240
atatctcttg tcaaacatca agataaacct aattttgagg actggacttc ctcaacatat 300
cacaatggca aactcggcct catgtcctgg atcgcac 337

<210> SEQ ID NO 206
<211> LENGTH: 344
<212> TYPE: DNA
<213> ORGANISM: Pinus taeda

<400> SEQUENCE: 206
ggtgcgatcc gtataggtag tttggatgat gaacgggcaa agaaggcaaa ggagtacagg 60
atggatcctg taattcctgt ttcagaaaac agaaaatctg caatataagg atggctaact 120
tttcagctat gaaaatatat ggtgcagtgg cactcatatc agttgcagag ttgtgaaata 180
acttttgtga ataggaaagt ttcctgtttt tagaatgcag aaatcctgca atataagatg 240
gctaagtttt tcagctatat gaaaatatat ggtgcagcag agttgtcaat ataaacttgt 300
gaatagggaa gttttggcaa aaaaaaaaaa aagaaaaaaa aaaa 344

<210> SEQ ID NO 207
<211> LENGTH: 349
<212> TYPE: DNA
<213> ORGANISM: Pinus taeda

<400> SEQUENCE: 207
ggtgcgatcc tcgttgtgaa gacgtagtga tggaaaggtc atgtttgtag gagacataat 60
tataggagtt tctttattat aataaccaag aagtccgatc ctgggggcgt tgagtatata 120
gtcagtcttt ggtaatttgg tgtggtgctg tttgacctgc ctttcctttg gagcaatgat 180
ccttgaggat ggaagaggtt atgttgaggc tcaagagatg attgtttgag ttgtggaaag 240
caaaaggttt ccagatgtag tcagatagta acttctatgc ttttaataaa atttagtctg 300
tggggcatgc cccttttttgc tggcaaaaaa aaaaaagaaa aaaaaaaaa 349

<210> SEQ ID NO 208
<211> LENGTH: 317
<212> TYPE: DNA
<213> ORGANISM: Pinus taeda

<400> SEQUENCE: 208
ggtgcgatcc gtataggtag tttggatgat gaacgggcaa agaaggcaaa ggagtacagt 60
gatggatcct gtaattcctg tttcagaaaa cagaaaatct gcaatataag gatggctaag 120
cttttcagct atgaaaatat atggtgcagt ggcactcata tcagttgcag agttgtgaat 180
ataacttttg tgaataggaa agttttcctg ttttagaatg cagaaatcct gcaatataag 240
gatggctaag tttttcagct atatgaaaat atatggtgca gcagagttgg aaaaaaaaaa 300
aaaaaaaaaa aaaaaaa 317

<210> SEQ ID NO 209
<211> LENGTH: 389
<212> TYPE: DNA
<213> ORGANISM: Pinus taeda

<400> SEQUENCE: 209
ggtgcgatcc caggagaata ttagtttcat gtgttgctat cattttcttc aatatgcagg 60
gcaaccattt gaatgaaact attcctttcg aatttcaaaa acttaatagg ctaacttatc 120
tatctggagc cgattttcat tgacgagtaa cctgtaagct ggccagcaaa agccaacaga 180
tgttcagctt gttggaacca gttgaagatt gtaatagaga tggtgaataa tcgcggacgg 240
ctcggccaat ggaatatttg ttgcatcatc atcaaggggg tatgaattcc aaagaacttg 300
ttgattgaaa ttcccaagca aaattctgtg aaatgaaaaa tttattgaga ccattgggca 360
aaaaaaaaaa aaaataaaaa aaaaaaaaa 389

<210> SEQ ID NO 210
<211> LENGTH: 242

<212> TYPE: DNA
<213> ORGANISM: Pinus taeda

<400> SEQUENCE: 210
ggtgcgatcc gactgtgata tgtgactggt gaacgagaga tccttcttat gaattaatct 60
ggtatcttta tgcgaaagct tctagggttg ctacatgctt ccattctaat atcagtctct 120
gtgatatcag aggccttcaa atattgaaca gttttcttta gaattccaaa ctgggaattt 180
ttattgtata gccatgtttt cacggattgt ctgcaagaag gctctttggc aaaaaaaaaa 240
aa 242

<210> SEQ ID NO 211
<211> LENGTH: 319
<212> TYPE: DNA
<213> ORGANISM: Pinus taeda

<400> SEQUENCE: 211 ttttttatt ttttttttt ccaacgagat cactgtcatt gttcaataac tatatgccaa 60
agagccttct tgcagacaat ccgtgaaaac atggctatac aataaaaatt cccagtttgg 120
aattctaaag aaaactgttc aatatttgaa ggcctctgat atcccagaga ctgatattag 180
aatggaaatt catacaaatg aggagagcat gtagcaacac tagaagcttt ggcataaaga 240
caccagataa attcataaga actaaatcca taagaaggat ctctcgttca ccagtcacat 300
atcatactcg gatcgcacc 319

<210> SEQ ID NO 212
<211> LENGTH: 271
<212> TYPE: DNA
<213> ORGANISM: Pinus taeda

<400> SEQUENCE: 212
ggtgcgatcc gactgtgata tgtggctggt gaacgagaga tccttcttat gaattaatct 60
ggtatcttta tgcgaaagct tttagggttg ctacatgctc tcctcttttg tatgaatttc 120
cattctaata tcagtctctg tgatatcaga ggccttcaaa tattgaacag ttttatttag 180
aattccaaac tgggaattta ttgtatagca atgttttcac ggattgtctg caagaaggct 240
ctttggaaaa aaaaaaaata aaaaaaaaaa a 271

<210> SEQ ID NO 213
<211> LENGTH: 30
<212> TYPE: DNA
<213> ORGANISM: Pinus taeda

<400> SEQUENCE: 213
tcccaaaggc aattatacat ggatcgcacc 30

<210> SEQ ID NO 214
<211> LENGTH: 517
<212> TYPE: DNA
<213> ORGANISM: Pinus taeda

<400> SEQUENCE: 214
ggtgcgatcc ccactgcaga aagatgagcc agtaccctga aattttgctg ttgtccatgc 60
ctgggtcacg gaggaaagaa cggcacggtg caatatgatt ttgctacata caagttccaa 120
gagtggatgc agacagtgct ggccatggct gattatttgc aggtgactaa tgctcttttg 180
gttatcctta ccatcatcat cttcctgcca ttcttttgta cctcggtatg gagacgaaca 240

-continued cccacttttc aaagtttgca gaggaagcat gtattcataa caggaggatc aagcggcatt 300
ggccttgaga ttgccaaaga ggctctttca cagggttctt acgtgacact ggcgtcaaga 360
aatctttcta aacttcgtag ggctgttgaa gaaatcatcc aagaagtgga gtgcgacgga 420
gacaagatta atatcaaggt aatataccct gcaaaatgtt gtctggaata caatccaaaa 480
ccaatttagc aattaaccca ttggcaaaaa aaaaaaa 517

<210> SEQ ID NO 215
<211> LENGTH: 734
<212> TYPE: DNA
<213> ORGANISM: Pinus taeda

<400> SEQUENCE: 215
ggtgcgatcc aagtgcggta ttcttccttt ggcagttctc tgaactgttg agagaatttg 60
agtaggataa cgacaataat tactatgctc acaagcccag acaacacgaa tagactccct 120
tccgtgcgtc gccttccaga ggacgcagca gctaaaatct cggcctgact caccacatat 180
atatttaata gcttgtatat gccatatgaa ctgttagcat gatctccctc taactgcgaa 240
ttgtgttgct gtaaactaat cccaaaggat gtttactctg ttgcttttcc aactgctgat 300
ggatttcgct catacaatga cccgagagca ccataaacct acccagcgtt gtggcctatg 360
acccatagct tttgttcgc acagcaattg aagaccggct acaggagatg actaatgcac 420
ttccgagaag gtttcaccgc gaatgacagg gaaggacaag gcagagcagc aggccaagac 480
agctttagtc gcagaagttc aagcagatct agattcatag taaatggaag ttctacacta 540
gttacaaatt taaaaacgta cctgcatgga ctacacggtt tatttacgag tgccacttgt 600
ctcattgttt tccatcagat gtctgctgga ttgtggtagt gtgttctacc gtatcggtgc 660
gggttttgta tattgtgcgt cgacagagtg acaggtggtg attttactgg caaaaaaaaa 720
aaacaaaaaa aaaa 734

<210> SEQ ID NO 216
<211> LENGTH: 664
<212> TYPE: DNA
<213> ORGANISM: Pinus taeda

<400> SEQUENCE: 216
ggtgcgatcc tagtacaggc gtttggaaca gagtggagaa tatgtggagt attgggggat 60
gcccccggtc gtgtgttgct gcgtttggga atttgtattt cttccatagg caacaagtga 120
tgtcttataa tagtaaagag aatgtttggg aagtggtggc atctcttcct ggagacatga 180
atattgttac tttgcgcaac agtgtggtgt gacaagatat ttgtgagcgg ttgtgcttgc 240
agtggcggcg atcaggtgtg ttacatgctg gacaaatctt gggcgtgggc tcctattgag 300
aggtcacatg agtttgaggg ttttgctcag tctgcaataa ctgtagagat atgagcaaat 360
tctgttgggt tcacttaatt ttgggattat tatagtgcag aggggagccg ggaagtttca 420
gtgtacagtg atgggcacca catgttgcca gcattggggg tgccctgtga atatgatttc 480
tataagtccg gattttaaat atctaggcca tctatctcat ccagcctctg attgtgtctg 540
tactaaatat atcctgtata ttcgtgatcc ctggttttga agtgagcaag ttttagtgga 600
agaggatttt tattaaatat atataaagtt tctgtattca gggttttggc aaaaaaaaaa 660
aaaa 664

<210> SEQ ID NO 217
<211> LENGTH: 422

-continued

<212> TYPE: DNA
<213> ORGANISM: Pinus taeda

<400> SEQUENCE: 217
ggtgcaatcc gccataagag aggcatacag gaaaaagaag tacctgcctc ttgatttgcg 60
tcccaagaag actcgtgcta tcaggtgacg ccttaccaag catcaggcat cattgaagac 120
tgagagacag aaaaagaaag agatgtattt tccaatgaga aagtatgcag tcaaggtgta 180
aagccatagg atttgagctt tcatgcaatt tttttgttac ttgcgggatg atattgccta 240
ttatatttcc gtccacgttt ttggcaaatt ccgatttgca tcagaattca agttatgata 300
ggtgttcttt cgcttttgag cagttgatat tgtttatctt tatttctctt gaattgcgaa 360
catattctaa tgcaatgagt ggattattat attgtggcaa aaaaaaaaaa aaaaaaaaaa 420
aa 422

<210> SEQ ID NO 218
<211> LENGTH: 239
<212> TYPE: DNA
<213> ORGANISM: Pinus taeda

<400> SEQUENCE: 218
gcggacgcct caggatagcg ttagggttgc cttaggatag cgttagctct gccttctaag 60
gttgccgtct tatcctccag cgtctagggc ttccactcct aggatttctc ttccactaaa 120
acccaagaca agtggagaga aatcaagata gaagtgtgtg tgaaatgact cttaagtcat 180
ctccttttag actaaaacat tgagcacatg tggggtttat ttggttgctg gccgtcgtt 239

<210> SEQ ID NO 219
<211> LENGTH: 303
<212> TYPE: DNA
<213> ORGANISM: Pinus taeda

<400> SEQUENCE: 219
ggtgcgatcc tgaaacaaca tattcccgat ggctcttccg aaggaaccat tgctctactg 60
tgtggccctc cccccatgat ccaagatgcc tgcctaccta acctggccaa aatgaattat 120
gacattcaga attcgtgttt tcagttctaa ttacaccctt ctggttaatc aaattgggac 180
atcccctccc acatcctgtt attaattaag ccatagtcta gtgtataaaa tctgttgatg 240
tgtacagcat caagttaatt tcctcctttt ctgtcaaaaa aaaaaaaaaa taaaaaaaaa 300
aaa 303

<210> SEQ ID NO 220
<211> LENGTH: 273
<212> TYPE: DNA
<213> ORGANISM: Pinus taeda

<400> SEQUENCE: 220
ggtgcgatcc gatcctaagc gggtgcatat atataatgac aagctgtagt aactaactct 60
tgtcatgagg ccattgctaa catagcctgt ccaatgcaca tagcagtcaa aaaaagcaaa 120
tagccgccat gttcccatac acgaagtaag taccctccct attgagtcac cttacccgcc 180
gagagagatc ccaattccat gtattcggtt aagtaagccc tgccagctat gtcccaccca 240
tgaaagaaag tactgatccg agtggatcgc acc 273

<210> SEQ ID NO 221
<211> LENGTH: 364
<212> TYPE: DNA

<213> ORGANISM: Pinus taeda

<400> SEQUENCE: 221
ggtgcgatcc aaactgtggt tatcggtgga gagattaagc aatttattgg agtagcaagt 60
acgctgaatt aagggggtcc atattcaagc aaaggttcct ttggatgact atgtgttctg 120
gaagtgttta tggatcaatc atctcataaa ttttggtaat atataacaga agattatggc 180
atccagttag gatggtagtt tcattgaggt atagtaaaaa ctacactaag tcttgtgttg 240
ccacccactt ttgagagagg tcaggaggtc tctttgtgaa tcattgataa ctttatgagt 300
ggtacctaat gaaatatttg catcttgaat atatactcaa ttgatcttac ttgtggatcg 360
cacc 364

<210> SEQ ID NO 222
<211> LENGTH: 357
<212> TYPE: DNA
<213> ORGANISM: Pinus taeda

<400> SEQUENCE: 222
caatctgtct gcaattgata ttattgcatc cagtaaacca gatacacatt caccacaaca 60
ttagagactc tagaagttcc tttggcgaca ggcaaaactc atgattacag ataattggag 120
tttcctctaa ccagagtcaa acgatctaaa gggatttgtc tagtcctcca ttccctcatt 180
caatgaggcg atggcttatg ccgtgacaac agtttctata gttgcatccg ctcctcttga 240
tcccacaaca tttttggtgt tctctgcatc ttcttcctcc catatctctg gcagggcttc 300
tctaatgttg tgaatacttg caagggcaaa atctgctccc tctgttcgga tcgcacc 357

<210> SEQ ID NO 223
<211> LENGTH: 222
<212> TYPE: DNA
<213> ORGANISM: Pinus taeda

<400> SEQUENCE: 223
ggtgcgatcc tctcagttac gagctcaatt tcgaccaggg gtctcggcaa attgaggatc 60
atgagaagca gggtatgccc ttgaatgccc tgaagccagg ggagtctcag ggcaatcacg 120
aatgaaacct gacaaaccct aagaaaaccc ctagagcgtg ccctgcagaa agggaattct 180
ttttgaggcc ggcggtcttt ctgtcgtctt ctcgcagccg ta 222

<210> SEQ ID NO 224
<211> LENGTH: 225
<212> TYPE: DNA
<213> ORGANISM: Pinus taeda

<400> SEQUENCE: 224
ggtgcgatcc agcaagagaa cgaaaaaggt atgagaatct atgaaatatt tgtacatcac 60
tgtattcata tgagggcctt tttttacaat gcggtagggt tgtttggaga attagaacct 120
gattaaaatg tagatggatt caagctttta gtgaaatgag gctcggaacg caagtatgct 180
gtccactttg agactcattc ttctatagta tctgaagcca aagcc 225

<210> SEQ ID NO 225
<211> LENGTH: 415
<212> TYPE: DNA
<213> ORGANISM: Pinus taeda

<400> SEQUENCE: 225
ggtgcgatcc catgggatag ttgcaaaaca cacaaatttg ttgtgaaaga agagagacac 60
gcacagacaa ccatatgatc tttttttttt tttttttttt tttttttttt tttttttttt 120
ttttcacaac tctgctgcac catatatttt catatagctg aaaaacttag ccatccttat 180
attgcaggat ttccgcattc taaaacagga aaactttcct attcacaaaa gttatattca 240
caactctgca actgatatga gtgccactgc accatatatt ttcatagctg aaaagcttag 300
ccagccttat attgcagatt ttctgttttc tgaaacagga attacaggat ccatcactgt 360
actcctttgc cttccttgcc cgttcatcat ccaaactact atacggatcg cacca 415

<210> SEQ ID NO 226
<211> LENGTH: 229
<212> TYPE: DNA
<213> ORGANISM: Pinus taeda

<400> SEQUENCE: 226
ggtgcgatcc tgcgagagcc gagggttcat tttcctttcg acaacgacgt tcagtggcga 60
ccagagtttc ccaatcactt cagcgattct attccttcgt tgtaataaag cttaaggaat 120
ccatgcttta ttccttggaa ggtttgaata tttatatttg ttggcattaa tgctatatac 180
atctatacta attttgggtt gttctaaact tgttttgaat aacttaaat 229

<210> SEQ ID NO 227
<211> LENGTH: 219
<212> TYPE: DNA
<213> ORGANISM: Pinus taeda

<400> SEQUENCE: 227
ggtgcgatcc atggcaaaga gctcgttcaa gcacgatcat cctccagaga gaagacaagc 60
tgaagcttct cggattcgag aaaagtatcc ggacaggatt ccggttattg tggagaaggc 120
tgagagaagt gagatacctg atattgataa aaagaaatat ttagtcccag cagatttgac 180
tgttgggcaa tttgtttatg ttgtccgaaa aaaaaaaaa 219

<210> SEQ ID NO 228
<211> LENGTH: 405
<212> TYPE: DNA
<213> ORGANISM: Pinus taeda

<400> SEQUENCE: 228
ggtgcgatcc cctgtattct tgaaagggtt ataacggaag atagcatttt gctcagattg 60
tagacagtct gcatgatttg tcaatactac tatttcgcat tatttgttaa tactactaat 120
ccttgtactc atctagacta tttaattatt aaattctaca gtttctttct cctagatggc 180
aaacaatatg aataaaatgc caatagtttt ggaactactc cattaagagc tttagatgat 240
tatcattcat catttgcctg ttttgaatcg taaatgaatg tgtcacggtc ttcttttctg 300
ttagtctcta tgctttcatc agaagagtct aagccagtta ctggaagcta tttgtcatct 360
ctttaaacat tgtttccgtg ccaaaaaaaa aaaaaaaaaa aaaaa 405

<210> SEQ ID NO 229
<211> LENGTH: 329
<212> TYPE: DNA
<213> ORGANISM: Pinus taeda

<400> SEQUENCE: 229
ggcagaactt ccaaagtcta gtatttgatt aactaatatg atgaagacac tcagtctata 60
acatgacgcc agaaatcaga ccatatgcat gataactagc acgattaaaa tacaattcgc 120

```
aacctttaat acactaaaaa cgtttactgt atagtccact cagaacattt cgatagtatt    180

gtcagatcga cttatttagc tcatattcag caatctgaac tgtacgatgc ggctcattca    240

agggcatttg ggtttgccct tggcattctt catatcccga tagcaaggac acgcgttctt    300

gttgccatat gtccctgggg gatcgcacc                                       329
```

<210> SEQ ID NO 230
<211> LENGTH: 354
<212> TYPE: DNA
<213> ORGANISM: Pinus taeda

<400> SEQUENCE: 230

```
ggtgcgatcc acattggcca ggccggtatt caggtcggca atgcctgttg ggagctttac     60

tgtctcgagc acgacattca gcctgatgga caaatgccaa gtgacaagac cgttggcggt    120

ggagatgatg cattcaacac atttttcagt gagacaggtg ccggtaagca tgttcctcgt    180

gccgtgtttc tggatctgga gccaactgtc attgatgaag ttcgaaccgg cacatatcgg    240

cagctttttc acccagagca gctgatcagt ggcaaagaag atgccgccaa caactttgct    300

cgtggccatt ataccattgg taaggaaatt gtggatctgt gcttggatcg cacc          354
```

<210> SEQ ID NO 231
<211> LENGTH: 271
<212> TYPE: DNA
<213> ORGANISM: Pinus taeda

<400> SEQUENCE: 231

```
ggtgcgatcc cagcattgga tgcatttcta gcacaaagcc atcttgacta aaatagcact     60

gcgggcaact gcagtccata actttcagag cattgttgct gcctcaattg tataccaatc    120

catattctaa aaattagacc tggaaaccag tcagaaattt aatgttttct tgcagaaaat    180

gcccttttag aaaaaggaga gaataactgc attcaagttc taactcccag acatagcctg    240

gcaacgtcat tcattcagtt cggatcgcac c                                    271
```

<210> SEQ ID NO 232
<211> LENGTH: 370
<212> TYPE: DNA
<213> ORGANISM: Pinus taeda

<400> SEQUENCE: 232

```
ggtgcgatcc agaaaacagc acaagcaatc tgtaagacca atattattat catctctcac     60

tgctcgtgaa caaaatgctg gttcatagcc atcacgaagg ctaaggctac tatccagcca    120

aactgatctc caacaataat ttcataagct taaataaata gtccatccag tggatggagc    180

cagaaagcca tagaaacttc aaatacttgt ggtatcaatc tctcctctgt taagggaggt    240

atcagatcag aagcactaat caaatgcata cataaatgca gtagactgca ataaaacaaa    300

atctgcagat agcaactgag cgcttaacga acggaaaaga gtttaacttg atctatcaca    360

ggatcgcacc                                                            370
```

<210> SEQ ID NO 233
<211> LENGTH: 328
<212> TYPE: DNA
<213> ORGANISM: Pinus taeda

<400> SEQUENCE: 233

```
gaaaatggga gcctcaaata ttcaaagcct catctcaaga gtctcagatt cggattcatt     60

tcatttggtt cgtaataaaa taatgcatca aatagttatt atccacaaaa atgggagaat    120
```

```
tattacaatc tgtcttctca acataaagtc atagcatagc atagaaccac accacagtcg    180

tcatcatttg ttttgttcac caccgaaggg gctctttaca gcgtccatga agccctgtgt    240

agcacccttc gccttgtccc ccgcctgttg gaagaaagag ccagtttgtt ctttcccctc    300

ttgggctttt cccgtgatgg atcgcacc                                       328


<210> SEQ ID NO 234
<211> LENGTH: 157
<212> TYPE: DNA
<213> ORGANISM: Pinus taeda

<400> SEQUENCE: 234

ggtgcgatcc tattatagaa ccatgactct tgtcgatggg gcataaactt ctcattctta     60

ggcgtgccta ctgtgactct tgccgatgtg gcataaactg cttattctta gttgtgcctt    120

ctgtgcagaa cttgttgagt cggtggatta cactgac                             157


<210> SEQ ID NO 235
<211> LENGTH: 334
<212> TYPE: DNA
<213> ORGANISM: Pinus taeda

<400> SEQUENCE: 235

ggtgcgatcc attaactaga ttaacgataa cattcctctg catccaatcc aatgctcatc     60

taaatctact tctacttaga tctctgcctc atctttctcc acctcctcat ccattctgaa    120

atattaattt ctgcatagat tttgttaggg tctagtaatc attttcatga atttaaatct    180

gttctagtct cttattatta tgctgcttat gctagcatca gaacctgtgt ataattcatt    240

catgtatata ttggattaca caaattatac ggatgccaga aaaaaaaaaa aaaaaaaaaa    300

aaaaaaaaaa aaaaaaaaaa aaaaaaaaaa aaaa                                334


<210> SEQ ID NO 236
<211> LENGTH: 199
<212> TYPE: DNA
<213> ORGANISM: Pinus taeda

<400> SEQUENCE: 236

cttgaagctg atatgtttga acccgaaatt ttgttaccca actccagtgt acattgtgtc     60

actgtcaaag agaacatgag agctgcatgc aagcttttgc atgatagata gattactgat    120

caccgaacat ttcttactct actttcctct cctatcccca gtgatttttg ggcattttct    180

atacccttcg gatcgcacc                                                 199


<210> SEQ ID NO 237
<211> LENGTH: 220
<212> TYPE: DNA
<213> ORGANISM: Pinus taeda

<400> SEQUENCE: 237

ctcatgaaca gcaatatgat gcattcctct tatacacatt tcatatatgt tcacccttgc     60

cgtcatggct actctaagaa gagcaaaaca gacccattga atctttacac gcgcttgttt    120

atatgaatac aaataattta ggcgtttctt tacacgccct tgtttacatt aatacaagtg    180

atttaggcgt tgttaccaga atagtgccac ggatcgcacc                          220


<210> SEQ ID NO 238
<211> LENGTH: 555
<212> TYPE: DNA
```

<213> ORGANISM: Pinus taeda

<400> SEQUENCE: 238

```
ggtgcgatcc caagatagaa aagggaacta tggtctcgag gagtgtcagg tgctacagat     60
cacaatatac ataagggtct gatagtagta ctcggcccaa tgtttgaggg ctctaactaa    120
ggaggatcaa ccgtaccctt agccgtaaaa cccgactacc ctatcgtacg ggcgagtaat    180
ctctctgagt gttgttctcg gtgtatcgta gcagcaacac ggctgacggt ttatctatgg    240
tgaggtttca aaggagctag gggcttcca atatacccag agggtacttg gaagacagtt    300
tatacgcggt tctgtctaat gcgctactac tcgaaggggt acccacaggg gttacaagag    360
agtgcaacaa gcatgaccac cccttgtatt tcttgcatgt atgcctcccc aaatccgcag    420
gtttatgcgc tcattgacag attccgtggt ttaaagatgc cggaacatgt ctctagccaa    480
aaaaaaaaaa aaaaaaaaaa aaaaaaaaaa aaaaaaaaaa aaaaaaaaaa aaaaaaaaaa    540
aaaaaaaaaa aaaaa                                                     555
```

<210> SEQ ID NO 239
<211> LENGTH: 419
<212> TYPE: DNA
<213> ORGANISM: Pinus taeda

<400> SEQUENCE: 239

```
ggtgcgatcc tcctaacctg caatgtcctt cctgcaacct gcaattattc aacagaaatt     60
aggtttattt ttctttttgt cttttcttct tttttttttt tttttttttt tttttttttt    120
tttttaagt aaacgaccat ttcaaacgcc atttcaaatg ctatgaatta atgttgaatt    180
aatgttagca ttaagtctta aacattttat gttaaggcat atatatcgtt ccaactactc    240
ttacaataca cctgcggtgt actcctgcca ccgcatgtac caccgttaca tgtacgcctg    300
ccagcacatc taacaggtgc caactccttt gaactcatcg tcgccatttt tgtatgcata    360
tttgaactca tcgtcgccat ttttggtatc ttcacatatg gccagtccag gatcgcacc     419
```

<210> SEQ ID NO 240
<211> LENGTH: 129
<212> TYPE: DNA
<213> ORGANISM: Pinus taeda

<400> SEQUENCE: 240

```
ggtgcgatcc aaggagtggg cgtgcaatgc gtcgaagata gccaccactg caggggcgtg     60
gcatgctgcc gtgcttccca cagggagatc aacacctgca cctccgcctc cttccgcggt    120
taccacgag                                                            129
```

<210> SEQ ID NO 241
<211> LENGTH: 349
<212> TYPE: DNA
<213> ORGANISM: Pinus taeda

<400> SEQUENCE: 241

```
ggtgcgatcc agccacagaa agattggttt actcgataat tgaacggtag actttgtgca     60
ggtttagatt gtgtacatgc tgatcagtat tgtctacacc attttcaatc ttgtttagtt    120
ctatggtaat ttatgtaaca aattcagcga tgttggggaa attggtcaca tcagctttgt    180
gcctatatat ttcaagtaaa tcaggggatc cattaatact gcttttaaaa taattggggc    240
aaagttgtgg gatgactgct tcagcggaat acgtgctttt catagtgctg tatgacattt    300
tgttgaatat gaattttctt tgtgatacag ttgcgcgaaa aaaaaaaaa                349
```

<210> SEQ ID NO 242
<211> LENGTH: 316
<212> TYPE: DNA
<213> ORGANISM: Pinus taeda

<400> SEQUENCE: 242
ggtgcgatcc atgccaagag ggtgaccatc atgcccaagg acattcagct cgctcgccgc 60
atccgtggag agagggcata aacagtcagt cagatccaat ggtgtgtttt cacaccacca 120
tatgtttctt ttactaaatt tgttaggtcc cttcggtggg tcttttcttt cccccgattt 180
tagtattttg ttgttcttct gagtttcatc attgcaagta caagatgcag aattgatggt 240
tattgggact tggagactgg ttattgctat gtagagtatt tatattagac aggtttcact 300
tgaagatata aaattg 316

<210> SEQ ID NO 243
<211> LENGTH: 188
<212> TYPE: DNA
<213> ORGANISM: Pinus taeda

<400> SEQUENCE: 243
ggtgcgatcc tcatgtgtta taaccgaagt ttgcgggatt cagatggtca gtatcttaaa 60
tgtccaactt tcggtacgaa tggggtgcgt tctgaaacgt gccacgaaag aggtgttcag 120
gatctgtctg aggcatcttt ccggtatttt ccacttccat ggtatgagaa actttcgtct 180
tgttgcag 188

<210> SEQ ID NO 244
<211> LENGTH: 170
<212> TYPE: DNA
<213> ORGANISM: Pinus taeda

<400> SEQUENCE: 244
aggagacaca actttacgaa aaagttcaat ctggagtctt ctaagttttt cagactctct 60
aaatatgaaa agcgccgagt ttctcctata ctggactcgt taaaatttta cagtaaagga 120
cctgttctat tacaaacagg aacggaccgc tcctccttag ggatcgcacc 170

<210> SEQ ID NO 245
<211> LENGTH: 164
<212> TYPE: DNA
<213> ORGANISM: Pinus taeda

<400> SEQUENCE: 245
ggtgcgatcc agcaagagaa cgaaaaagat atgaagaatc tatgaaatat ttgtacatca 60
ctgtattcat atgagggcct ttttttacaa tgcggtaggg ttgtttggag aattagaacc 120
tgattaaaat gtagatggat tcaagctttt agtgaaatga ggct 164

<210> SEQ ID NO 246
<211> LENGTH: 187
<212> TYPE: DNA
<213> ORGANISM: Pinus taeda

<400> SEQUENCE: 246
ctcaacataa agtcatagca tagcaccaca ccacagtcgt catcatttgt tttgttcacc 60
accgaagggg ctctttacag cgtccttgaa gccctgtata gcacccttcg ccttgtcccc 120
cgcctgttgg aagaaagagc cagtttgttc tttcccctct tgggcttttc ccgtgatgga 180
tcgcacc 187

<210> SEQ ID NO 247
<211> LENGTH: 471
<212> TYPE: DNA
<213> ORGANISM: Pinus taeda

<400> SEQUENCE: 247
ggtgcgatcc catgggatag ttgcaaaaca cacaaatttg ttgtgaaaga agagagacac 60
gcacagacaa ccatatgatc tttttttttt tttttttttt tttttttttt tttttttttt 120
tcgggaccaa atatttttca atacaacgcc atgtgacatt tttgtgcttc ttgtttttga 180
tacatacatt ccaaaaactg aacactcgat ggatacggtg atgatgcagc tacagccatt 240
gcattacaga tgttattaaa ttaaatcaat ttattatgtc atcacaccaa cccaaacaat 300
agcgctatta tgtcattaga atggttgcag ttacaagatc tgcaaacaga tcaatgaatc 360
atcatgcccc tctatatctc ttgtcaaaca tcaagataaa cctaatttta ggactggact 420
tcctcaatca tatcacaatg gcaaactcag cctcatgtcc tggatcgcac c 471

<210> SEQ ID NO 248
<211> LENGTH: 265
<212> TYPE: DNA
<213> ORGANISM: Pinus taeda

<400> SEQUENCE: 248
ggtgcgatcc tggactggcc atatgtgaag ataacaaaaa tggcgacgat gagttcaaat 60
atgcatagaa taagcgttct gtaattggaa cggccatagg agttggcacc tgttagatgt 120
gctggcaggc gtacatgtaa cggtggtaca tgcggtggca ggagtacacc gcaggtgtat 180
tgtaagagta gttggaacga tatatatgcc ttaacataaa atgtttaaga cttaatgcta 240
acattaattc aacattaatt catag 265

<210> SEQ ID NO 249
<211> LENGTH: 417
<212> TYPE: DNA
<213> ORGANISM: Pinus taeda

<400> SEQUENCE: 249
ggtgcgatcc catgggatag ttgcaaaaca cacaaatttg ttgtgaaaga agagagacac 60
gcacagacaa ccatatgatc tttttttttt tttttttttt tttttttttt tttttttttt 120
tttttttttt tttttttttt tttttgtttt tttttttttg tgaagtgaca aaatctaaac 180
caaagattaa aaggctttgg cttcagatac tatagaagaa tgagtctcaa agtggacagc 240
atacttgcgt tccgagcctc atttcactaa aagcttgaat ccatctacat tttaatcagg 300
ttctaattct ccaaacaacc ctaccgcatt gtaaaaaaag gccctcatat gaatacagtg 360
atgtacaaat atttcataga ttctcatatc tttttcgttc tcttgctgga tcgcacc 417

<210> SEQ ID NO 250
<211> LENGTH: 167
<212> TYPE: DNA
<213> ORGANISM: Pinus taeda

<400> SEQUENCE: 250
ggtgcgatcc caaccaggtg tccatgcaat atatggtgag catcaagttt gaggtggttg 60
attgaaagtt acaaattggt gacatctgaa gtctcattca gttatgtttt tgtatataaa 120
aaccataacc aattttgtat ataagatcca taatcaattt tggccaa 167

<210> SEQ ID NO 251
<211> LENGTH: 236
<212> TYPE: DNA
<213> ORGANISM: Pinus taeda

<400> SEQUENCE: 251
gttttcaaga agagcctgac ggtttcctcg gcgggatgac ggaaacagga agcggccggc 60
cggttccgga ccctccgcag gcggagcata gcattttgcc ggaaccaccg catgtcctgc 120
acccaacatc cgcgtctgac cagcggaggc acatgcaccc aaccctcccg gttccattgc 180
acctcgggca gcgcggccac ccgccggcca tcggcttatc catcatggat cgcacc 236

<210> SEQ ID NO 252
<211> LENGTH: 409
<212> TYPE: DNA
<213> ORGANISM: Pinus taeda

<400> SEQUENCE: 252
tgggcgaatc atatggcttg cattttcatt gtaacatgta tacgttaagg attatcataa 60
tgcctccaaa accttgtatc ttcgtccttg ccacaataca tccaggataa ctaatggaag 120
cttgacatgt cttcaccagt aataatatat caactataat acatgccatt cttttatcag 180
ttttgaacaa aataatcgat ttgcattctt gacaaagaac ctcgcgcata aaaacaaata 240
aattctcata atgcctccca aaccttgtag tctgggccct cagtcgccac aatccattta 300
agaggaattt gggggttgat agtgcccagg tccaatcttc atgaaaattc gttcatcaat 360
ctttgctgca tacacatctc tctctgcttt cactatctgg gatcgcacc 409

<210> SEQ ID NO 253
<211> LENGTH: 356
<212> TYPE: DNA
<213> ORGANISM: Pinus taeda

<400> SEQUENCE: 253
ccactataat gaacattgat attacaaata taatatacat taatattaca attcaaatca 60
ttgacaatga gcaggcacta cttgcagtgc tttggaattc agacttctga tttgcaatta 120
attcttgtag acgcttttct gggagggcag gttttccgct tcagagaaaa ccacgtacaa 180
aacgatatta aataaaaata gacacataca aaaaatactt cattttttgc tctttccatt 240
tggtttcttc ctctatctcc attttggagg gcttaaatga cttcaaattt aaaagtcaac 300
aacagagtgc agcacattct attagctttg ctgtaaatat ctgattggat cgcacc 356

<210> SEQ ID NO 254
<211> LENGTH: 375
<212> TYPE: DNA
<213> ORGANISM: Pinus taeda

<400> SEQUENCE: 254
ggtgcgatcc gcattaagag aagcatacaa gaaaaagaag tacctgcctc ttgatttgcg 60
tcccaagaag actcgtgcta tcaggcgacg ccttaccaag catcaggcat cattgaagac 120
tgagagacag aaaaagaaag agatgtattt tccaatgaga aagtatgcag ccaaggtgta 180
aagcacagga tttgagcttt catgcaattt ttttgttact cgcgggatga tattgcctat 240
tatatttccg tccaagtttt tggcaaattc ctatttgcat cagaattcaa gttatgatag 300
gtgttctttc gtttttgagc agttgatatt gtttatcttt tatttctatt attaatcttc 360

-continued

```
taagttggat cgcac                                                   375


<210> SEQ ID NO 255
<211> LENGTH: 189
<212> TYPE: DNA
<213> ORGANISM: Pinus taeda

<400> SEQUENCE: 255

aaacagacaa atatagaaat atgcatacat aagtccctgc agaattgttt tccgcaatga    60

attctggttt atggcaacat tacctactta gtactaaccc taagattatt ttcagctctg   120

ataagtggca tacgtgtatc aatcttgcat gagtctatcc ctgttttaat cttttgttgg   180

gatcgcacc                                                           189


<210> SEQ ID NO 256
<211> LENGTH: 105
<212> TYPE: DNA
<213> ORGANISM: Pinus taeda

<400> SEQUENCE: 256

gtggaagctt cattgtaaaa cactactggt tttgagagaa caaaatatat acgctagccg    60

agtggattat aacaaaatat aggctttatt ctattggatc gcacc                   105


<210> SEQ ID NO 257
<211> LENGTH: 348
<212> TYPE: DNA
<213> ORGANISM: Pinus taeda

<400> SEQUENCE: 257

ggtgcgatcc catacattaa catagccatc acagccccca gtggcaaaag taccatagct    60

gcaaaaacat tataaaacta acattcctac aaggaaataa aatacaacta aaaaagcaag   120

caataggcat taggggaggg agaagctaaa actattaagc aacttacatg ggatgaaagg   180

caattgcgtt tactggataa acagtatctc tgccagcctc tgacttgcga tgacatttaa   240

aggcatattt tttaagcttg accagcttca gatacatcat aatactccat agccatgcga   300

gcttccacag aactaagggg caaaacctgt tccatttgga tcgcatca                348


<210> SEQ ID NO 258
<211> LENGTH: 476
<212> TYPE: DNA
<213> ORGANISM: Pinus taeda

<400> SEQUENCE: 258

ggtgcgatcc aactgagaag ggtgtttggt ggaaagatga caccaagtgg gttctctatt    60

ctccagagga tgcaagaaaa attctgagag caaagaagaa tggggactca aatattacgt   120

tgggttctgt taaatctgcc aagtaccctt caggaaagct ttatgccata gacctggtgg   180

ccatgaagca aaccaatgta aacactggct tctccagaga tatcaaaatc atcaattctt   240

gccctactga tgatcaggaa gatgtagagt ctgatgaaga agatgaatta ttcacattct   300

ctcgtcctgt caaagttgaa gtgattaacc agagcaggaa acctgataag attgtcaaga   360

tggttccttc tgtcactgta gaccttgaga aattgacttc tcaatacctc ctggaggatg   420

agtgcaattt ggttctaaag cttcccaggg ctgcagctgc ccaatcggat cgcacc       476


<210> SEQ ID NO 259
<211> LENGTH: 317
<212> TYPE: DNA
<213> ORGANISM: Pinus taeda
```

<400> SEQUENCE: 259

```
ggtgcgatcc agctaatcaa acttaatgga gagcccttcc caggaagagt aaatggtagt     60
cacttgaagc cctacacggg tgggctggcg gtctgactaa ctgaccaaaa catagtcttc    120
gcgacccaac aagccagaca gaggtgtggg actataagca caagtactag aagctagcat    180
caaagtagag aattaagtta gatacagatg attcagaagc agaaatggag cagatccaga    240
ccacggtagc atggtgagtt acgaaccttc acgccacacc aacgcaattg gttaagactt    300
cgcactagga tcgcacc                                                   317
```

<210> SEQ ID NO 260
<211> LENGTH: 283
<212> TYPE: DNA
<213> ORGANISM: Pinus taeda

<400> SEQUENCE: 260

```
ggtgcatcca tagttccttt tgctaagcga ctactctatc tcttttgaca tttctccaaa     60
tattgggtct ttcagttcct tcaaatgcta gaatcatatc aacatgggat ttagtgaggc    120
cgcaatacta accagggcat taaaataata catttcattg atcctattcc caaaacattt    180
cccgctatcg tacgttgact cagcatattt agagcaattc ttcttacaaa ccttaagaag    240
gttgttcatg atagtctttc cgtctgcaat attggatcgc acc                      283
```

<210> SEQ ID NO 261
<211> LENGTH: 299
<212> TYPE: DNA
<213> ORGANISM: Pinus taeda

<400> SEQUENCE: 261

```
ggtgcgatcc cacccaagag ttaaattcac ttctccgcct ttctgaggaa gagcactctt     60
tggatgatat gaaaagtggt ccactcttaa aaaccgtatt cggaaccctg ttccgcggac    120
ggtcgtatgg cgtaaccggc gcagacattt tatctcctca cacaatatca acattcaagt    180
ccccgctgtt ccccgttgcc tttctctgct cccgaccgtt aaacaagaac gaccacaaga    240
atgaacaaca ccgcaaccga aacctgaccc tccacgttgt cttcggttcg gatcgcacc     299
```

<210> SEQ ID NO 262
<211> LENGTH: 352
<212> TYPE: DNA
<213> ORGANISM: Pinus taeda

<400> SEQUENCE: 262

```
gcggacgcct ggcaaaaaca gagggtatgc tcaagcctta cagaaattga aaaataagag     60
aacgtatgac catcaatctc aatctcaaga aaagaagttg caatacgact ccaacacttt    120
tgaaagttgg aggtttgctc tttctagcgt tgcagacatg gttggttttg agctggaagc    180
gtgtaacggg cactttacag ttgcgggaat tggagattga ggaccccctc tcaaacgtcg    240
atagggaggc taagcatcta tagaggattg tgattggtcc ttttccgcta catggaaaga    300
aagtcaaact cagaaaatta ccagaagaat tctgtcgtct tctcgcagcc gt            352
```

<210> SEQ ID NO 263
<211> LENGTH: 221
<212> TYPE: DNA
<213> ORGANISM: Pinus taeda

<400> SEQUENCE: 263

```
gacgttgtaa aacgacggcc agtgtaaaga gcagccccga tgcgccgaag ctcgcgaggg     60

aaaagctgca gaagatggga ccgatgacca agaatgagat catcatgagc ggcacgctac    120

tggtcacggt gggtctttgg atatttgggg gaatgctgaa cgtggatgct gttactgcag    180

cgatccttgg tttgtctgtc ctactctgca caggcgtccg c                        221
```

<210> SEQ ID NO 264
<211> LENGTH: 365
<212> TYPE: DNA
<213> ORGANISM: Pinus taeda

<400> SEQUENCE: 264

```
tacggctgcg agaagacgac agaagcagaa cctgccaata taggatcaat tgaatgttgt     60

gggattgctg catgcccacc tttcccagtt attactgcct tgaagaaccc acagccagcg    120

agtaagggcc cgggtttcga accaatcaca gatgtaggat aatcgcttga aacatgcata    180

gcgaatatgc cttccacatt ttccagtgct ccctcctcta tcattctttt tgatcctgca    240

cctgattcct ctgcaggctg gaagagtaat atgacagttc cctgtaacaa atgctgacgt    300

tgttgcaaaa tctttgcacc accaagaagc atggtaacat gtgcatcatg tccacaggcg    360

tccgc                                                                365
```

<210> SEQ ID NO 265
<211> LENGTH: 491
<212> TYPE: DNA
<213> ORGANISM: Pinus taeda

<400> SEQUENCE: 265

```
tacggctgcg agaagacgac agaaaagagg caaaccgagc tcgacacctc cactcagagc     60

atttgcaaaa atccacaaca aatctggagc caaggtcttt ccctcattga aaacatttat    120

cggacacatc aatgtctgta gtctttccca tggtccatcc agagtaatca cgggaagaac    180

aatgcacttc agttcagaat tttgatgac agctatcagc tcctgatcct ttgaaccagg    240

tatataataa tcttgacctg actcctgttt caacagtgta gaggttctgt caacctcaag    300

caatgaatcg gcagaacttc catttgctgt tttgtcaata caggcattgt ttttaccaag    360

actgtgacgc atcttctgtc cttgtctata cagtgcagtt tgttcaagca tagacttatg    420

tgctagaaca tgtcttcctt ttaaattgta agagaaatgt aggggttgac tgcttttact    480

gaggcgtccg c                                                         491
```

<210> SEQ ID NO 266
<211> LENGTH: 485
<212> TYPE: DNA
<213> ORGANISM: Pinus taeda

<400> SEQUENCE: 266

```
acggctgcag aagacgacag aaccctggct gactacaaca ttcaaaagga gtctaccctg     60

catctggtgc tccgtctaag aggaggcatg cagatttttg ttaaaaccct tacaggcaaa    120

acaattactc tggaagtgga aagctcggac actattgaca atgtaaaagc taagatccag    180

gacaaggagg gaatcccacc tgaccagcag aggttgatct ttgccggaaa gcagctagaa    240

gatggtcgta ctctggccga ttacaacatt cagaaggagt cgacccttca cctggtgctc    300

cgtctccgtg gtggctttta ggttggctgt tgtgtgtcaa tgtagtctgg tgatgttcag    360

tggttttcct gcttaatcct ttttatgtat gcatgtgttt gttgtgtttg tgttttgtct    420

ctatgttttt tctacttggt ttgtcggtcg gttgaagccc ggctggtgtc ctggtaggcg    480
```

tccgc 485

<210> SEQ ID NO 267
<211> LENGTH: 494
<212> TYPE: DNA
<213> ORGANISM: Pinus taeda

<400> SEQUENCE: 267
gcggacgcct ggacaaacac agaaggcgaa gtaaaagcca gtcttacttt tcatgtaaat 60
actatcaaac tgcatggccg ttccgctggt tggcaatacc acacctgcgc cggtagtgcc 120
aatgaacact gcaccggcag ctctttcaga agttgcagag gacttaccat tttaattttc 180
acggcatccc gtcaaacggc gggatgcttt taattttta atcaaaaaa atattaatta 240 tggcacacaa tattgttttc aacgaacaga caggcaaaca cagtttcttt agtgtaaaag 300
aaaaagcatg gcatggtttg ggcaaattg tacaggacta tcccaacagt aaagaagcat 360
tgcaatttgc agggcttgat tttgaagttt gcaaaaggcc caatattcac aggcttgata 420
atggtaatga gattatttct accagttcat tctatactta ccgtcctgat accaacgcca 480
tattaggcgt ccgc 494

<210> SEQ ID NO 268
<211> LENGTH: 469
<212> TYPE: DNA
<213> ORGANISM: Pinus taeda

<400> SEQUENCE: 268
gcggacgcct gaacatagga gcattcttaa gcatatcagg tataaccata aacctgactt 60
tgctgccccg aataaagaca tgctccaatt gggatacttt tccatccttg gcagtgtaag 120
tgatgccctc gagctggcaa ttccagttat cttcgcattc gatcatgcta cccctgtaca 180
gctcgccact tttgagttca actgtcacaa catgcccggc tgcttcatgg agcaacttca 240
caggaatccc caaacttctg ctcatttttt tgtcactgct caaaaaccct aaaccccaga 300
taaaaccctc ggttctgtgc cttttatccc cgggtggctt attgttgcag tagttggcaa 360
cggctagact tactcacatt ttgatttcaa tctttctaag tttgcccttt tgggttttcc 420
tcacagtaga tcctatttta tgtattttct cgtcttctcg gcagccgta 469

<210> SEQ ID NO 269
<211> LENGTH: 345
<212> TYPE: DNA
<213> ORGANISM: Pinus taeda

<400> SEQUENCE: 269
gcggacgcct gcaggaatcg gccgatttgc agttcgaggc ataagcgcat cgaggtcgcg 60
ttcgatgtag caattaagcg cgcatgaacc gccgctaagc aagccagtcc caatcaaagc 120
acatgcaaag cggatgcaat caaatcttcc gttgtaagca agcacaaatc caactgcaca 180
tgagatcacc accatgaatg caattcgagt gcgagctaaa tcccaaaacg ctgcgagtgt 240
cccctgaagg cgattcgtat gtaatatttg accgctgctc aacacaagca gtactccaaa 300
caccagtgct tccgccgtca attctgtcgt cttctcgcag ccgta 345

<210> SEQ ID NO 270
<211> LENGTH: 342
<212> TYPE: DNA
<213> ORGANISM: Pinus taeda -continued

<400> SEQUENCE: 270
ctgcgagaag acgacagaac acagacacaa aatttggaaa ctacagaaaa gaccatgtca 60
tgaaatcttc ataattgggc ttcagatgca gagggggtcg gttttggatt aagcaatggc 120
tgaagtgctt tgacaacaat actcatgtta ggacgaaaat ctgcttcata ctgcacacac 180
aatgccgcaa cagcagccat ctttgcaaca gcctttggag gatattcact cttcaacttg 240
ggatcaacac actgctttac tttgtcttca ctcaatcttg gagttgccca agtaacaagg 300
ctttgttgtc ccctaggcat tgtatggtcc acaggcgtcc gc 342

<210> SEQ ID NO 271
<211> LENGTH: 313
<212> TYPE: DNA
<213> ORGANISM: Pinus taeda

<400> SEQUENCE: 271
tacggctgcg agaagacgac agaaagagac aggcttggac ttcgtggcct tcttccacca 60
cgcattattt cttttcagca gcaatgtgat cgtttcatgg tttcttttag atccctggag 120
cataacactc gagatggttc agctgactta acagctctgg caaaatggcg tattcttaac 180
agattgcatg acagaaatga aacactatac tacaaggttc ttatagatca cattgaagag 240
tttgctccaa taatctacac tccaactgta ggattggttt gtcagaatta tggtgggctg 300
ttcaggcgtc cgc 313

<210> SEQ ID NO 272
<211> LENGTH: 277
<212> TYPE: DNA
<213> ORGANISM: Pinus taeda

<400> SEQUENCE: 272
gcggacgcct caatagttat ggaagggcag ctgcactact tcagcatgag tggaggccta 60
aaagttttgt taatctttct ggtgaggtgg acaccaaagc ccttcacaac agtgcaaagg 120
tggggctatc tctggttttg aagccttgaa ggatatgcac tatttggtac agatttaagc 180
gaaggtctgt gccaaatttt tattggaatt tttgagtttt tcctttcaga ataattattt 240
caatgcctgt gttttctgtc gtcttctcgc agccgta 277

<210> SEQ ID NO 273
<211> LENGTH: 278
<212> TYPE: DNA
<213> ORGANISM: Pinus taeda

<400> SEQUENCE: 273
gcggacgcct tttgcccaat taacatccct gcatctgcgc attaaaaatt gattgcagac 60
ctgaggttta agtggaagct tcttccacca tctctcccct gtttaaggaa gacccgaaac 120
cctagccact gtctcctctg tgacttaaaa ttccagttca ccaaccttaa ctctgcgtcc 180
gttaaaattc tgggcaaact gcactgccaa ttggtcatca tatcctctga atttggcaaa 240
gaaaacatag gtcattctgt cgtcttctcg cagccgta 278

<210> SEQ ID NO 274
<211> LENGTH: 180
<212> TYPE: DNA
<213> ORGANISM: Pinus taeda

<400> SEQUENCE: 274
gcggacgcct cgtcaatcca tggttgtaaa catgccttca aaactgtttc cttatgtcgc 60
acaatgtcta catgttcctt gagcgatttt tcctgctgca ttgcgagcct ctgtgtaagt 120
cccactatct gcgctgtccc ttttacttca taatacttct gtcgtcttct cgcagccgta 180

<210> SEQ ID NO 275
<211> LENGTH: 446
<212> TYPE: DNA
<213> ORGANISM: Pinus taeda

<400> SEQUENCE: 275
tacggctgcg agaagacgac agaaaaaact gtatacgagt aggcagcgag tcctggcagt 60
atgggagatt gaactccaat tacatttagt tacaagtagc atcaacagtg actgagccaa 120
gagctctaca cagaaaaata aaataaaaac tgtatatatt tacaggagaa accccaatgg 180
cctcagggcc tgaataaatc aatcgcagcg gtggtcgatg tggccttttc agggctgcaa 240
atcttgcaag gggaagccat catccttgtt ccgtatcctt tttgagggat agcgagccac 300
gcagccaaga tttgaagcga ttgaatactt tggggtgtcg agaacgcacc agaacaatgc 360
cactcgagaa atactactgt gattactgtg acaaacaatt ccaggatact ccctccgcta 420
gaaagcgaca tctacaaggc gtccgc 446

<210> SEQ ID NO 276
<211> LENGTH: 425
<212> TYPE: DNA
<213> ORGANISM: Pinus taeda

<400> SEQUENCE: 276
gcggacgcct gtaccgtatt ggaattctaa acccttcctt ggtatagggt tttcgccacc 60
cttgcgttca tttggttttg tattacgtcc gattcctccg tctgcgagct ctctgcaact 120
tggcaatttc attgtgattt tatcctatga tgcttcgtat ttgtttgaag ctcgtcctcc 180
tagttctctg tgataccagt tggtagtctg caagtttcga tgtgggttct tttagctggt 240
ctggggtttt gttgctctga gtatgttgag ctgcatgctc gtggcggtct tcacggctcc 300
atttgttcgg aatctgttgt ggaagtgtct cggtcatctg tggaactgtg gaaacctggt 360
aagatttgtt tatctgcttg tgtctaaact gttcttgagt tttctgtcgt cttctcgcag 420
ccgta 425

<210> SEQ ID NO 277
<211> LENGTH: 295
<212> TYPE: DNA
<213> ORGANISM: Pinus taeda

<400> SEQUENCE: 277
gcggacgcct gctgttgaag aaggatgaag tcattgtctg cggccctgtt cagcatgatt 60
tcggcattct taatctggtc aaccagtcag aaggtggcgc tgaaggtgac gaagaggcaa 120
cctgggtagc tgcactggaa actcaagctg caaggggcac cgaccctcag acttcgcgcg 180
attaacttct ccctctggct aagtcgatgc caaggtcctt gttctgggtt cttctctctg 240
tttcgcatgt tgttcttctc tctgtttcat ttgtttttct tctgtcgtct ctcgc 295

<210> SEQ ID NO 278
<211> LENGTH: 196
<212> TYPE: DNA
<213> ORGANISM: Pinus taeda

<400> SEQUENCE: 278

-continued

```
gcggacgcct gcacatacaa agaacgacaa aaacaaaagc ataaaatcca atagatgcaa     60

ctatatatca agtcagaaat gatataactc atcattatta caaagaacaa taagagtgga    120

accataataa tagtcgtcta ttattgataa ataaagaaga atacaaccat agttctgtcg    180

tcttctcgca gccgta                                                    196
```

<210> SEQ ID NO 279
<211> LENGTH: 172
<212> TYPE: DNA
<213> ORGANISM: Pinus taeda

<400> SEQUENCE: 279

```
gcggacgcct gtataacatg caccaagaga cccaatcaaa gcacatgcaa tctgtatata     60

tagcagaata acagccaggg attgcactct atcgtaatcg cgaaaccacg cactaatatg    120

tgcccatgct gatgatgcac acagcatgtt ctgtcgtctt ctcgcagccg ta            172
```

<210> SEQ ID NO 280
<211> LENGTH: 405
<212> TYPE: DNA
<213> ORGANISM: Pinus taeda

<400> SEQUENCE: 280

```
gcggacgcct gaactgtata gagttgaaac ttgagggaag gcttgctgcc accaaagcct     60

ccctcctctt tccttggcgg ttcgtcacct cctttcgcgt cagagcccca attcccctcc    120

tgcgcacacc agcaaactgc atcgaatgtt ttttccacca ttctgtaaat tccctcggag    180

ttaccttggg gcagaagccg cattgaagag cattgaatgc tattcattat cccaccgtaa    240

actaccattg caacctgcct gtgtatcgac ccgctgtcct ctacgcgtgg ctggcacatg    300

gcgtcgttaa ttgcatgttg acacccgtat ccgggtgtgc ttgtgtgctc gtctgcatat    360

catgttttag gatctcatag aaggtggacc attctgtcgt cttct                    405
```

<210> SEQ ID NO 281
<211> LENGTH: 412
<212> TYPE: DNA
<213> ORGANISM: Pinus taeda

<400> SEQUENCE: 281

```
gcggacgcct cttacaatgt ctcttaaaga ttggaaagat tgtcttgtct gcaaccataa     60

cttccgcgtg ctttcttatt aatgcaaccc actgtgatcc tttccgccat ttatcctttc    120

gaatggttgg agccattttt gggttgtacc gactagcttt tgggtctaca aagctgtcta    180

caaaactctt tggagatgac attacataat catatgtata gctgaagttg tacaaaggta    240

cacaactatc tgaaaccaaa atgaatctct cgttagctgg atcctcgagt gctttcctaa    300

gtagaatacg ctccgcttct atcatactgg cttctcccca aagtacctgt atgctatcac    360

taagctgcca gccgtaacaa aatgtacatt ctgtcgtctt ctcgcagccg ta            412
```

<210> SEQ ID NO 282
<211> LENGTH: 345
<212> TYPE: DNA
<213> ORGANISM: Pinus taeda

<400> SEQUENCE: 282

```
gcggacgcct tgctaggaga gctctacgcc attatttgaa cgattgagcc gaagtttcac     60

cgtttaaggc atttgtgtcc cagaggttat tggagattag cagcttggat ttggctgctt    120

cgctcagcgc cgtgattcag cttttgattg attctctcca gtttcataac ctgtaacgac    180
```

```
aatggcaatg aagacctaca catttgcagt ggcagctgcg tacgctgtag tcctgatgtt    240

cgctctcttt ggcatcgcaa aggctgctga tgcaccgtct cccagccccg ttactggcgc    300

gggttccatg gacttcgttc cttctgtcgt cttctcgcag ccgta                    345
```

<210> SEQ ID NO 283
<211> LENGTH: 218
<212> TYPE: DNA
<213> ORGANISM: Pinus taeda

<400> SEQUENCE: 283

```
gcggacgcct tatcagctgg gggcattcat aggtatggaa attcagatca acttcagtgg     60

acagtatgtg gatttaggcg acctgtgaca gttcacgata tctattcatt tctatccaga    120

gacagattcc catactcacc tccgtccttc ccatatattt tctggaaggc atcatgtcct    180

cccaaattta ctcattttgc ctggccgtcg ttttacaa                            218
```

<210> SEQ ID NO 284
<211> LENGTH: 219
<212> TYPE: DNA
<213> ORGANISM: Pinus taeda

<400> SEQUENCE: 284

```
gcggacgcct gttgccacag aagaatgaat aatgcttcaa attttgagac ctcttcggag     60

gaaaatcctt gttcttactg cctaaccact catgatgatc tgcgtcacgc tgattatgag    120

ctgcaattta aattatttca gatgaaacat tcccatattg agcttgcaga caagttgcag    180

acccttcaat ttcagttctg tcgtcttctc gcagccgta                           219
```

<210> SEQ ID NO 285
<211> LENGTH: 60
<212> TYPE: DNA
<213> ORGANISM: Pinus taeda

<400> SEQUENCE: 285

```
gacgttgtaa aacgacggcc aggattaagg ttcatgagct ccgcaacaag agcaaatcag     60
```

<210> SEQ ID NO 286
<211> LENGTH: 732
<212> TYPE: DNA
<213> ORGANISM: Pinus taeda

<400> SEQUENCE: 286

```
gcggacgcct ctaggagccg gcggaattcc tgtgagctcg aatttgccga gcaggttatt     60

gtccttcgtc cgcgctcgct caccttcata tacttgaatt agaaccccag gctgattatc    120

tgagtaagtt gagaaaatct gctccttctt ggttggaatg gtggtgttcc tcggtattaa    180

tactgtcatt acacctcccg ctgtctccaa ccccagactt aatggcgtga catctagcaa    240

cagcaggtcc tgcaccttct cgttgccttc gccgctgaga atggcagcct gcacagctgc    300

accatatgcc acggcttcgt ctgggttaat gctcttacaa agctctttgc cattgaagaa    360

atcttggagc aattgttgta ctttggggat acgagtcgaa cccccgacca agacgacatc    420

atctatttgg ctcttgtcca tcttagcatc ttcgcataca tttctccaca ggctccatac    480

ttctcctgaa aagatccatg ttgagttcct cgaagcgagc tcgcgtaatt gtggcgtaaa    540

aatcaattcc ttcatataga gaatcaatct caatcgttgt ctgtgtagta gaagacagcg    600

ttctttttgc cctctcacat gctgttctca gcctgcgaag agctctggca ttcccgctga    660
```

tgtcttttct gtgctttctt ttgaattcct gcacaaagtg attcaccatt ctgtcgtctt 720
ctcgcagccg ta 732

<210> SEQ ID NO 287
<211> LENGTH: 100
<212> TYPE: DNA
<213> ORGANISM: Pinus taeda

<400> SEQUENCE: 287
tagccatcgc catttctata atcttaggat ccttgctgaa cgataagccc ataaaattga 60
tgcactgcct cgctatccct ggccgtcgtt ttacaacgtc 100

<210> SEQ ID NO 288
<211> LENGTH: 347
<212> TYPE: DNA
<213> ORGANISM: Pinus taeda

<400> SEQUENCE: 288
gacgttgtaa aacgacggcc aggaaattac agctacctct aactggtttg acggcgttgc 60
atcttatgag ccgcaagggt tcgaatcctc tgcgggccag atctgcgatg gaaccctggg 120
cgagtgcaat gatgatgaag aagagtttgc gatggattct gaagcgcacg ggaggcttct 180
gaggaggatc cgttactata tcagctacgg agcattggct gctaatcgcg ttccttgccg 240
acctcggtct gggaggtctt attacactcg gaattgttac ggcgcaacag gccccgtcag 300
accttaccac agaagctgca ctgctatcac tcgttgcagg cgtccgc 347

<210> SEQ ID NO 289
<211> LENGTH: 106
<212> TYPE: DNA
<213> ORGANISM: Pinus taeda

<400> SEQUENCE: 289
gcggacgcct gggaagcaat ggatgggtgg ctagacgcca tccgtcttgt gtatactatt 60
tttgcacgcg gaaagagtga tgtcctggcc gtcgttttac aacgtc 106

<210> SEQ ID NO 290
<211> LENGTH: 307
<212> TYPE: DNA
<213> ORGANISM: Pinus taeda

<400> SEQUENCE: 290
gacgttgtaa aacgacggcc agattcaaaa gaaaaaatcc tcacttcttg gctccgtttg 60
cgctcccgcc gaagctcctc tgcaacccct ctgcagcgta cactgcatcc cgctcgcggt 120
gctggctcac ctcgcaggtc cgctgacggt aaatggtttc caataaagct atttgtcctc 180
tacccaaaat ccatctagca ttcgttgtgg attgacattc tgccatttct ctgcttttct 240
ggttgatatg caaagattga aagcccaatt gcaagcagtg gtcgtggatt cactataagg 300
cgtccgc 307

<210> SEQ ID NO 291
<211> LENGTH: 286
<212> TYPE: DNA
<213> ORGANISM: Pinus taeda

<400> SEQUENCE: 291
gacgttgtaa aacgacggcc aggaataaaa caaagcatca ctgcaaaatt tcaaacgtgg 60
taataacggc tagccagctc gacgtgaagg cagtgggggc cttgaggttg ccttttggcg 120

```
ttcaaaattg gctagactac cataacataa atattgattt ctcagtgaca tcactggttt    180

ggagtcatcc acagcctgtg caccagtacg gcaattgcct tttacatgaa gccatccttt    240

cacttttact tttgagattc tcagaactga ggggctaggc gtccgc                   286


<210> SEQ ID NO 292
<211> LENGTH: 290
<212> TYPE: DNA
<213> ORGANISM: Pinus taeda

<400> SEQUENCE: 292

gacgttgtaa aacgacggcc agcaccttcc tagtcccctg ttccattctc ctgaaatagg     60

agcagtttga cccagtccag ttttcagaat tgagaatatg aaacaaagaa cctaagcata    120

tgagagaaca tacaaagact ttgtataaac tacttttcac aggatctcaa cagccctctg    180

ctgagatcca tttgatacaa ggccccttgc atctccaccc tctcccttat cacctccact    240

agaaagatga tggaaagcag acacatggaa atgttgctgc aggcgtccgc               290


<210> SEQ ID NO 293
<211> LENGTH: 497
<212> TYPE: DNA
<213> ORGANISM: Pinus taeda

<400> SEQUENCE: 293

gacgttgtaa aacgacggcc agttaggttg tatattgatt gatgactctt tgactccatt     60

tatgaaaaca tctttgttct cgagatttaa tcagtattaa gctttcagag tgaagttcag    120

tttgatctgc ataaacctga tccaccatat ctacatcaca tctaaaatta ctaaaatgtg    180

aggagatgga atttgtttct tgagaatccc tattcctcat cgacactgtt tactggatca    240

gatccaatca aactcttgag aagtaatctc tggaaagaaa ttaaaaagtc tttacctgaa    300

ttatctcgat atcagaagca gaaattatga tacatagact tcttaataat gaagagtcat    360

tttgccaacg ttgtctttgc caccccacca atccccatga tcccaaagat ctgaggtttc    420

catctctatg tggctgtgat aacactggat ttttcaaaaa tcttctactt tcgcatccaa    480

acctttttgg gatattt                                                   497


<210> SEQ ID NO 294
<211> LENGTH: 238
<212> TYPE: DNA
<213> ORGANISM: Pinus taeda

<400> SEQUENCE: 294

gacgttgtaa aacgacggcc aggggggatgg gagatacaga aagattccgg ataaaaggga     60

gcaatgaacg gctggttaaa gcgtagtcca ccacactagc cccacctcca tgaggcctac    120

acgtgaagaa gcaggattct gggaagcgcg agaggccgtt caagattatc agctcatgtg    180

attcgcccaa ctgcaaaaga tgtctaccgt aggctgtgat ggggcccaag gcgtccgc      238


<210> SEQ ID NO 295
<211> LENGTH: 311
<212> TYPE: DNA
<213> ORGANISM: Pinus taeda

<400> SEQUENCE: 295

gcggacgcct atcagatggg tgagttgacc gacatttatc gtccgataaa tgtttgaggc     60

tgatgtcatg gcaatccacg tgtctgcacc atatttcatc ggagcccctc gtcggaatat    120
```

```
tccatcgccg gagagctggc gcgataggtt tcaggcggcc ggtttctggt ttgcagctgt    180

ggcttcccgc gcgccttaac tgttggcccg cgcgcacagg ggaaattaca aatttcaaca    240

tatccaatac catcatataa cccaacaaca ctagcaacag atcctgttct gtgccatcgt    300

ccaactcttg a                                                         311
```

<210> SEQ ID NO 296
<211> LENGTH: 202
<212> TYPE: DNA
<213> ORGANISM: Pinus taeda

<400> SEQUENCE: 296

```
gcggacgcct taattcgact acaaagatac tgaagccaat gatgacaggt tgtgccactt     60

tcccagctga taaagacagc tctgaaattg atagagccag aactccagct gcaatgctcc    120

ccagagcctg gttgaagcgc ttgctaaagg tggcacttta tagaccgacc caaaacctcc    180

ctggccgtcg ttttacaacg tc                                             202
```

<210> SEQ ID NO 297
<211> LENGTH: 507
<212> TYPE: DNA
<213> ORGANISM: Pinus taeda

<400> SEQUENCE: 297

```
gcggacgcct actggaaacc cggtccaccg aaggctgaaa ttgtcctgct ttgtataccg     60

aatggcagga aggttgtcga gcatcaggtt cacctggtaa agattatcga tcctatgctt    120

caataccttc agctgctctg ccccaaggac agtagtattg cacaggtaaa tttcagattc    180

attgacattc atccggaagc gatatggtga gttctcgatc ctgtccccca tgaggagctc    240

cccaagattt tctgccatgt ccttcacacc atccaagggc ttgcagaagg gcaggctgta    300

atagctgtag ggaagctctg tctcgactga ggtaagggaa ttgacgttca cccataaatc    360

tgacccctgg gagaatatga tgtgaggaat acagtgccca gtaaatataa ctccgcatta    420

tacgtttgtg tgtgccttcc ccaatattgc cccaacataa tcaaaaccca caatcccaaa    480

tcctggaccg tcgtttttac aactgtc                                        507
```

<210> SEQ ID NO 298
<211> LENGTH: 522
<212> TYPE: DNA
<213> ORGANISM: Pinus taeda

<400> SEQUENCE: 298

```
gcggacgcct tgtcaggacc aaatgtgtaa gaaacacctc tgtcattcga gccccatcct     60

tgaattgcat tgcaggggtc tgaccaaaga agatcacata acaaccctgt atctggcaca    120

tctgtaggtc gaggtatatt ctttatttgt tccaaattgg tcagttcagg cgaaagacca    180

ccatgcatgc ataggatctt ttcatctata agtgcagcaa caggcaggca gttgaaacag    240

tctgtaaaaa gtttccatag tcttacattg aatctgcgct tgcactcatc atagaaacca    300

tatatgcgat ttattgaggc acattcatga tttcccctca gaaggaaaaa gttctctggg    360

tatttaattt tgtaagcaag gaggaggcat attgtctcta ggctttgttt gccccggtcc    420

acataatctc ccaagaaata agtaatttga ttctggtggg aagccaccat attcaaaaag    480

ccttagacag atcagaatac cggcctgtcg ttttacaacg tc                       522
```

<210> SEQ ID NO 299
<211> LENGTH: 410

<212> TYPE: DNA
<213> ORGANISM: Pinus taeda

<400> SEQUENCE: 299
gacgttgtaa aacgacggcc aggagacggg aatacctatt tttgggagga ttattgggct 60
cgggaatcag catattgatg tggctgcaac tcgcatcctc gatctttggt ggttcttcgg 120
cgatttacac atttgagatc tacttcggtc tgctagtttt ccttgggtat attatatttg 180
acacacagat gatcatcgag aaagcggacc atggagacta tgattattta aaacattcac 240
tggacctctt tattgacttc gttgctgtat ttgttcgcct gatggtcata atggcaaaga 300
atgcagacag taaatccagg gaagggaaaa agaagagaag ggcttgaact atgtgagata 360
caaaaatatc gagaatagaa gggcttgaac tagggcttga aagcgtccgc 410

<210> SEQ ID NO 300
<211> LENGTH: 237
<212> TYPE: DNA
<213> ORGANISM: Pinus taeda

<400> SEQUENCE: 300
gcggacgcct atcagacaag ggttgttgac cgaactttat cctctgaaaa gtgcttgaag 60
ctgatgtcat ggcaatccac gtgtctgcac catatttcat cggagcccct cacacggaaa 120
caaccttaag ccaaaaggtg gtgcgatgac ttaccggccg tttatggttt gcttcggtgg 180
ttttctgttg ggtggtttcc cgcgcgcgtt aactgctggc cgtcgtttta caacgtc 237

<210> SEQ ID NO 301
<211> LENGTH: 625
<212> TYPE: DNA
<213> ORGANISM: Pinus taeda

<400> SEQUENCE: 301
gacgttgtaa aacgacggcc aagaggggga aactcccaaa acacttttcc atttttcttc 60
ttttattaaa cttcaaagta ttttccaaca gagttacaag gggccaacca tgtccaaatc 120
catgcattta ccaagtacaa agaatggtag tccttggctt gacctatcgc actagccaaa 180
agtgccaagt ccacaactag ggtgtgccca acctaaggtt gacaccttgc ctagaaaaaa 240
ccccaaactt ggcaccacaa ataacacaga aacacaactc ttgacctctg ccagaaacca 300
ggctctcttg ggaaagccac acctctctct gtgatatgtc ttatctccaa tttccctttt 360
tgtgatgcac tcccttgctt gtggttctgc gatatcacac aaacttacat ttctgcgatt 420
tttgtttctt gcttctccaa atcatgcgat cttattttta acccttgaga cccttcacac 480
tttccatcca tgacgtcact tcatcgtttt agccaattcg tcatttgggc atgttgggcg 540
ttgggtctac ccgtattccg gtcgtacagg ccaaattgac cattttggtc caggtgggtg 600
cacccattcc tggagggcgt tcggc 625

<210> SEQ ID NO 302
<211> LENGTH: 629
<212> TYPE: DNA
<213> ORGANISM: Pinus taeda

<400> SEQUENCE: 302
gcggacgcct ccacagagct cacacataca atatactatg atgcctccag aactatggca 60
ctctgtatgc cgcttcaata tggattagcc cacactgcgc catccaatta ggcgaatcaa 120
ccttatagca ccatccacaa cctccagcgc tctctttttc acgctagatt ggccaactac 180

-continued

```
aggctttaca acactactca tatacaactc aactcggctc ctctgctcac cactaaatca    240

cacaggctcc aatcgctaga cagagccact acacaggcac taatagccac tacacaggca    300

ctaatcttgg cgtcctccac caggttccaa caacaacccc aaattgcata tgcactccac    360

agtgagcacc aactaggtcc acacaatagg ccacaccaac aacactccaa ggaccctaga    420

tcctgcctca cccagacacc actaggcctt cctcacagct cacctaagtg agccaacaac    480

tggctgggca cacagctccc aactatatga gcacacagcc caactacagc tccaccacac    540

gcacagctac acgcacaatg ccttctcaag ttcacagcca caccataacg cagcacagtt    600

cttacaaaca tatctctcca ggcgtccgc                                      629
```

<210> SEQ ID NO 303
<211> LENGTH: 324
<212> TYPE: DNA
<213> ORGANISM: Pinus taeda

<400> SEQUENCE: 303

```
gacgttgtaa aacgacggcc aggataatgg acacgagaaa cctttggatg tgcctctaaa     60

gtgcgggcaa tccttaaagc tgttgaattt tgttgctgta cacgaaggtg cagggtcttt    120

atgccacgaa gaatcaagta cgctgcattt ggacttaata cacctcccaa gacattgtgc    180

aaagcacgta ctgtgccaat aaccttgttt gaaccactca aactgcctgc aagaacatca    240

ttatgacctg caatatattt agttaccgaa tgcaatacaa tatctgcgcc gagtgctaac    300

gctttctggt taacaggcgt ccgc                                           324
```

<210> SEQ ID NO 304
<211> LENGTH: 331
<212> TYPE: DNA
<213> ORGANISM: Pinus taeda

<400> SEQUENCE: 304

```
gacgttgtaa aacgacggcc agtcattatt gacaataatc ctttcagctt tttactgcaa     60

cctttaaacg gtataccttg cgtttctttc actggagcac actcagatga taatcagctt    120

ttacaggtgc tcttacctct gttgaagcat cttgccactc aggaggacgt gcgccctgtg    180

ttgtatgaaa gattttacat gcccgcatgg tttgaaaagc gtggcattcc agcatctgag    240

tggcccttgt gacttggttt tgattttgga tactctttgt cattttgggt caaggtaaag    300

gtgtacgtat ccaagtgatg caagcgtccg c                                   331
```

<210> SEQ ID NO 305
<211> LENGTH: 286
<212> TYPE: DNA
<213> ORGANISM: Pinus taeda

<400> SEQUENCE: 305

```
gcggacgcct gatagcacga gtcttcttgg gacgcaaatc aagaggcagg tacttctttt     60

tcttgtatgc ttctcttaat gcggatcgct ggctctgaga aatcacagtc agaacctgag    120

ctattgatag cctcacgacc ttgattttag agagtttgtt gggcgctcct ccagtgacct    180

ttgcaactct gagcaaggca agctcagcct tgagctcctt gacctggctt aacagctcgg    240

atttgccctt gtggcggact caaggacctt taacctgggc gttcgt                   286
```

<210> SEQ ID NO 306
<211> LENGTH: 271
<212> TYPE: DNA
<213> ORGANISM: Pinus taeda

<400> SEQUENCE: 306
gcggacgcct ggtgtcgctg ggccagttca agtattttag caacagtgtt cacacttatt 60
ccctgtgata ttcttgactc acacaaccac cttaactgac gcagaccata tcgatctgct 120
gctgtaagca aatgttcgat cattgtctca ggtgtcaaaa agcaagggga tggatcagaa 180
agctcttcta aatctgcatg ctcctctaaa tctggaaggg tatctttgta aataaagtgt 240
aacatagcct taaacacctc tggccgtcgt t 271

<210> SEQ ID NO 307
<211> LENGTH: 283
<212> TYPE: DNA
<213> ORGANISM: Pinus taeda

<400> SEQUENCE: 307
gacgttgtaa aacgacggcc agaggtgttt aaggctatgt tacactttat ttacaaagat 60
acccttccag atttaaagga gcatgcaaat ttaagaaaaa ctttcctgat tcaacccccct 120
gccttttggc accctgaaga tggttcaaca atttgctaac ggaaccaatt caaaagggcc 180
gcctccattt aaggtgttgt gttagtccag aatatcacaa ggaataagtg ttaacaccgg 240
tgccaaaata cctgaactgg accaacgaca ccaagcgttc gcc 283

<210> SEQ ID NO 308
<211> LENGTH: 259
<212> TYPE: DNA
<213> ORGANISM: Pinus taeda

<400> SEQUENCE: 308
gcggacgcct tgtaatccag ggccttgaat attgtaagag aagatcgaga aataatagtt 60
ttcttattat caggaatcac agcttgaaga aggcagacca tggactccca ctggcttcgt 120
gatattgagt ccccaacaaa cattagtcgt tttcccctca atctccacag caagtctctg 180
gcattgaatc tgcgaaagga acacccgagt ggcttccacc tccatttctc gtaatcagaa 240
tctggccgtc gtttaacaa 259

<210> SEQ ID NO 309
<211> LENGTH: 237
<212> TYPE: DNA
<213> ORGANISM: Pinus taeda

<400> SEQUENCE: 309
gacgttgtaa aacgacggcc agcagaagac cagtgcagta tgctgcagca tagtttgtaa 60
gccctacttc gagtccataa cgaggcaact ccctagaata agcagccgac ataacaacat 120
ctcccgcaag agttgcataa atgatctgtg ccaccacatc cttgttgctg aatctaacga 180
ccaatcggta tttgggtgtg ttgtacttgt tcttatcttg gttaatcagg cgtccgc 237

<210> SEQ ID NO 310
<211> LENGTH: 417
<212> TYPE: DNA
<213> ORGANISM: Pinus taeda

<400> SEQUENCE: 310
gacgttgtaa aacgacggcc agcatccatt gcagaaattt tgggggctat atttagcaac 60
agatatcaca gctgtaagtt caaagttgga cccttcttct tcgacatctt ttccagctgt 120
gcaataaact gaacactgtc cttttggata agcttcctca acatatttag aaagttcaac 180

-continued

```
atccaagaca ttgcggtact cctcaacata tatggatgca agttcatcat ctgcagctgg    240

tctcaccgct gtacaaactt gtttaacatg gttgacagtt gcaacttgag cagtccgtgg    300

atccaaataa tgagttccgt caagctcact gaactcagtc acaatcacct ggccactttg    360

attgggcatc tcgagggata tcatgtgaga cttgttgtgg atggggaaag cgtccgc       417


<210> SEQ ID NO 311
<211> LENGTH: 308
<212> TYPE: DNA
<213> ORGANISM: Pinus taeda

<400> SEQUENCE: 311

gcggacgcct gcataaacat cgctaccctg gggatgatta ataatagtac cagggttagg     60

attttcttca tcttgagcga tatcatcata cataaagacc acaatgtttt cctctttcaa    120

accgcctttc ctcagaattt ggtaggcatg gcagatatca gcctgatgcc tgtagttcca    180

ataaccggaa gaaccagcca acagaatagc ccactgagta ccgatcgtat cactatcatc    240

aacgatatga tcggtgggca ttttcagtac tgaatcccaa ccccttctgg ccgtcgtttt    300

acaacgtc                                                             308


<210> SEQ ID NO 312
<211> LENGTH: 183
<212> TYPE: DNA
<213> ORGANISM: Pinus taeda

<400> SEQUENCE: 312

gcggacgcct agactgggca taccaactac cttcctcatg ccaggccatg ggccacctac     60

ctggtactta ggcataacac cttacttacg agcatgccag gctcagtcag ataggcatgc    120

atcccaccca cctagctatg acccaatcct tataaacact agatattctc cctggccgtc    180

gtt                                                                  183


<210> SEQ ID NO 313
<211> LENGTH: 255
<212> TYPE: DNA
<213> ORGANISM: Pinus taeda

<400> SEQUENCE: 313

gcggacgcct agacaatcat taactgaaga tctgtaagcc atgacaagac gaataaaacg     60

aagcacggcg caaccagcgt gaatattgac gccttaattt cattcaactg ggttgcggat    120

tctttattcc tcaacaagtg ttcgatagct tcacatacgc aaggcccctt ttactctcac    180

cttcatggtt taatgctgta accgtcgaag gttgatgaaa ggacttggat gatgatgttg    240

ccaaaaaaaa aaaaa                                                     255


<210> SEQ ID NO 314
<211> LENGTH: 184
<212> TYPE: DNA
<213> ORGANISM: Pinus taeda

<400> SEQUENCE: 314

gcggacgcct gctcaacacc tgttatagtc atttcttgtt tccttttctc aattttctct     60

ttcgaatgac cgcattgaaa ttcaggctgc ccaacgcgtt tttgttttca caattaattt    120

ttgaatcata cgcgaagatc atgatgagaa tggttgtgga aaaaaactgt ttgtaaatat    180

ttag                                                                 184
```

-continued

<210> SEQ ID NO 315
<211> LENGTH: 345
<212> TYPE: DNA
<213> ORGANISM: Pinus taeda

<400> SEQUENCE: 315
atatcacatt accattcaaa aaataaacat tttacaaaat acaattccat aacaattttc 60
ttccctgttc caacctccac aaaagtaaat gatcgtataa gaaattaact accaacaaaa 120
atcccaaagt taaaggaaga catccccaaa aaagatgtaa ctttcaaaac cggatgactt 180
cactcctgcc attgcaccta gtcatttact tctcagagga gtttggccct ttcttctttc 240
caaaagtaac cactgcggta acaaaccggc ggttgtattg cattcgcttg taggcgcggc 300
ctctaggctt cttcttctgt cttgtttggc caccttaggg tccgc 345

<210> SEQ ID NO 316
<211> LENGTH: 292
<212> TYPE: DNA
<213> ORGANISM: Pinus taeda

<400> SEQUENCE: 316
gcggacgcct tggtacaatg gacttgcaaa aataaaatga gttctcattt gtgggtgaga 60
tgcggatatt ttatgcatag gcacttcatg gagatgtggt ttataaacgc catcttaata 120
tctgtaccta ttactttcaa aatatgaagg caagatggaa agctactcat ctgttgtgaa 180
gtcagaatgt tggtagcggt tgggctctga aagtaagaaa ctttttgatt ggtttaatta 240
aatgagggaa tttgcctggt ttccctcttc cttccgaaaa aaaaaaaaaa aa 292

<210> SEQ ID NO 317
<211> LENGTH: 298
<212> TYPE: DNA
<213> ORGANISM: Pinus taeda

<400> SEQUENCE: 317
gacgttgtaa aacgacggcc agacaatatt ggaagggaga aaggcgccag cagggttgag 60
gggaagaaat gcataatgac atatataatg agatctattt gtatacgata ttacgggtac 120
gatcgatgat tcgagctacg atcccatacg acgctaaagc gtaattacat atataataga 180
tgcatttcag aatgacttat ctatttcatt acgcgatatt atatacgtaa ttacgtatat 240
aattgcagag atctcaccga ccaaccaaat agtctttcat ttcatcccag gcgtccgc 298

<210> SEQ ID NO 318
<211> LENGTH: 337
<212> TYPE: DNA
<213> ORGANISM: Pinus taeda

<400> SEQUENCE: 318
gcggacgcct gtatcactag aggtgaatac tcagcaagca aaactgaagg atattattga 60
aaaagctgtc aaggctaaat tgggtgtcaa ttccccattg atcatgcatg gttctacact 120
tttgtttgag tccggtgatg acattgagga agatgttgct gcacattatg cacaaaactt 180
agagaagacg ttagcagaat ttccagttcc aatcacaaat ggtgttattc ttacagtaga 240
ggactaccag caagagttct tatgcagtat taatattaag cacagagatg actttgatga 300
ggagtcaggt ggcattgtac tgtctggagg cgtccgc 337

<210> SEQ ID NO 319
<211> LENGTH: 237
<212> TYPE: DNA

<213> ORGANISM: Pinus taeda

<400> SEQUENCE: 319
gcggacgcct ccttgtagat accatacatg agtctaagat caaaatcata caagaagagc 60
ttcattccgg gcctcacctt ttctacaagc tcctttttgg ctggtggaaa gccaaacact 120
ctgtatcgga aacactcctg cctagtttca gaattacaca taaaaatcaa gccggcaaac 180
ctatctttgc cactgccatc ttcattgttt gcgtcctggc cgtcgtttta caacgtc 237

<210> SEQ ID NO 320
<211> LENGTH: 484
<212> TYPE: DNA
<213> ORGANISM: Pinus taeda

<400> SEQUENCE: 320
gcggacgcct tactaaaacg acggccagat gtgtaatggg gaaaatgtgt catgatagtt 60
gggtacaaat aacgagccac ctgctctatg ttttcgaagt tttctgttgg atttgtccgg 120
gtgagagagc gttcgttcgt tgcgcgagag gggcaaaatg ctgagcgtgg ggaattgcca 180
ttgccgcccc tggaagtgcc gcacgaacgc gatcacattt aaatcaccat ttacttcatc 240
atcaccatgg ttaaatgcag tccctgctcc ttcaaacagg aacttcagat ccttcaagct 300
cgaaatctcc gcctctgctt cctcgaagac aagactctgt gaggaggaag cgcagcagct 360
gagcttagcg gatctgctga agcccggtgg cctcgccccc gatgggttct cgtacaagga 420
gaactttacc atacgctgct atgaagtccg agttaaaccg cactgccacc attgaggcgt 480
ccgc 484

<210> SEQ ID NO 321
<211> LENGTH: 248
<212> TYPE: DNA
<213> ORGANISM: Pinus taeda

<400> SEQUENCE: 321
gacgttgtaa aacgacggcc agcaaccaaa taaaccccac atgtgctcaa tgttttagta 60
taaaaggaga tgacttaaga gtcatttcac acacacttct atcttgattt ctctccactt 120
gtcttgggtt ttagtggaag agaaatctag gagtggaagc cctagacgtt ggaggataag 180
aaggcaaccc tagaaggcag agctaacgct atcctaaggc aaccctaacg ctatcctaag 240
gcgtccgc 248

<210> SEQ ID NO 322
<211> LENGTH: 401
<212> TYPE: DNA
<213> ORGANISM: Pinus taeda

<400> SEQUENCE: 322
gcggacgcct gctcagcacc tgttatagtc atttcttttt tcctttttct catttttctc 60
tttcgaatga ccgcaatgaa attcaggctg cccaacgcgt ttttgttttc acaattaatt 120
tttgaatcat acgcgaagat catgatgaga atggttgtgg aaaaaaactg tttgtaaata 180
tttaggtgac caacaatttt catgattgca atctaaagtt gataattgat ttatcgggtc 240
gacatttgta attattaaca cggaaaatct gaggcttaca atttttggat tgtaaatatt 300
taggtgacga acaattttca tgattgcaat ctaaagttga caattgagtt atcgtgtcga 360
catttgtaat tattaacaca caaaatctat gaggcgtccg c 401

<210> SEQ ID NO 323
<211> LENGTH: 493
<212> TYPE: DNA
<213> ORGANISM: Pinus taeda

<400> SEQUENCE: 323
gcggacgcct catcaatcca tggttgtaca cgcgccttca aagcggcttc cttatgtcgc 60
gcagcgtcta cttgttcctt gagcgctttt ccctgctaca tccgcgcgag cctctgtgca 120
agggccactg tctgcgcggt ccctttaact tcgtcgtact tctgctgcag ctcacgtgtc 180
tctatttcta agtgctatat atttgggtcc tcctgcatag tagtgaactt cgaacgactc 240
ctcaaatagc caggtgtagt ctttcattgc actattgatc tccactattc ctgctataat 300
ggcgctaaca tgctgttcct tcacctttgg cggagttgaa ggctgcgcct tcttggagct 360
cggttatttg aagctgaacc ttgggcatat cttccttcac ctcgtgcatc ccctgcttcg 420
agtttctgga tgcacgcctc cactgggtct tctgctggga tgggcaactc taagaccaac 480
tggtatgcgt cgc 493

<210> SEQ ID NO 324
<211> LENGTH: 143
<212> TYPE: DNA
<213> ORGANISM: Pinus taeda

<400> SEQUENCE: 324
gcggacgcct tcttcaatcc atcaggcctg attaatgtat tgaccttctt tgtctgaatg 60
tcatacattt ttttcactgc atccttgatc ttcttcttgt cttgctttct atcctttctc 120
ttgctttcta tcctttctct ggc 143

<210> SEQ ID NO 325
<211> LENGTH: 314
<212> TYPE: DNA
<213> ORGANISM: Pinus taeda

<400> SEQUENCE: 325
gacgttgtaa aacgacggcc agcaaaattg atataaagaa tagacacatc gactcaaatg 60
aagtgactca acagttcatt aattcatgtc agcttgaatg catggacata cacccataaa 120
taggcagttg gggtcaccca aaagaacata gaaacatctc gcatctctct gaagaaactc 180
ggatgggtac aggtctgtga cttcgcatat tttgaaggag cactctcttg gataagtaca 240
atataggtac catctcggac tcgcctgaaa tctcgcaaag aagtctcatt ctcctccttg 300
ttacaggcgt ccgc 314

<210> SEQ ID NO 326
<211> LENGTH: 332
<212> TYPE: DNA
<213> ORGANISM: Pinus taeda

<400> SEQUENCE: 326
gacgttgtaa aacgacggcc agaagcatca ataaacaaaa tgacagatta acaagttctc 60
tcttaatctt aagagaatac atcaacatcc aagtaaagtc ataacacatt tacaaaatgg 120
tgccacggta tccattctct gtaacaaggt tttctgaaa atagttttcc tcttatctat 180
gtaactcttc atagggatgc ctgtgtcaac gtgccatatt cccaaatttg gccacaatca 240
aaccttcctc attagaagaa acaatctctg gtctagctca aaattggcaa aatttccagc 300
atctcccttt aacatcatta gaaggcgtcc gc 332

<210> SEQ ID NO 327
<211> LENGTH: 1098
<212> TYPE: DNA
<213> ORGANISM: Pinus taeda
<220> FEATURE:
<221> NAME/KEY: modified_base
<222> LOCATION: (879)
<223> OTHER INFORMATION: a, t, c, g, other or unknown

<400> SEQUENCE: 327

```
gggagatgct aatttgaagc ccttctctga aggtggacaa ttccagcagc agtggtctaa     60

agccccaata tggctataga aattcttctg ggggttgcac ctatggaaga gggtcggaga    120

ggacgaagct gtggatcgct cttaccatct gtgcggaagg tggtagcaga attcattgga    180

acgttcttcc tcatatttgt aggatgcgga tctgtcgttg ttgataagat aagcaacggt    240

tccataactc atcttggtgt gtcgcttgta tggggaatgg cggccatgat tgtaatttat    300

tccataggcc atatttctgg agctcatttg aatcctgcag tgacgttggc ccttgcggct    360

gtgaagagat ttccatgggt tcaggttcca ggctacatag tagctcaagt atttggatcg    420

atatctgctg ggtttctcct acgtttcatg tttggagaag tggcattcat gggagccaca    480

gttccttcag gctcagaaat gcagtctttc gctttggaaa ttattactac gtcattgttg    540

gtgtttgtgg tttctgcagt cgccactgat acaaaagcgg tgggtgaatt gggaggttca    600

gcaattggag cgaccatcgc aatgaatgta gccatatccg gaccaatctc aggagcttca    660

atgaatccag caaggacaat aggatccgca gtggctggca acaaatatac aagcatttgg    720

gtttacatgg ttgggcctgt aatcggtgcg ctaatgggtg caatgagtta taacatgatt    780

agagagacaa aaatgtccga aagggagatt atgaagagtg ggtcatttgt taaggacatg    840

ggctccagcg aatcaacagc ataacaactt agagatttnt tgcattcccg agacggtatc    900

cagtgatagt ggagagtagt cataataaga tttgtgaaaa tgtttgtgta gattaatgtg    960

taaaattcaa tccatcaacc atgaagcgaa ctgcattccg tttttaaatg tttattggat   1020

ttgaattaat aaacagctta tacgtgaaaa tccctacttt atgtacggaa aaaaaaaaaa   1080

aaaaaaaaaa aaaaaaa                                                  1098
```

<210> SEQ ID NO 328
<211> LENGTH: 992
<212> TYPE: DNA
<213> ORGANISM: Pinus taeda
<220> FEATURE:
<221> NAME/KEY: modified_base
<222> LOCATION: (762)
<223> OTHER INFORMATION: a, t, c, g, other or unknown
<221> NAME/KEY: modified_base
<222> LOCATION: (774)
<223> OTHER INFORMATION: a, t, c, g, other or unknown
<221> NAME/KEY: modified_base
<222> LOCATION: (778)
<223> OTHER INFORMATION: a, t, c, g, other or unknown
<221> NAME/KEY: modified_base
<222> LOCATION: (808)
<223> OTHER INFORMATION: a, t, c, g, other or unknown
<221> NAME/KEY: modified_base
<222> LOCATION: (828)
<223> OTHER INFORMATION: a, t, c, g, other or unknown
<221> NAME/KEY: modified_base
<222> LOCATION: (849)
<223> OTHER INFORMATION: a, t, c, g, other or unknown
<221> NAME/KEY: modified_base
<222> LOCATION: (881)
<223> OTHER INFORMATION: a, t, c, g, other or unknown
<221> NAME/KEY: modified_base
<222> LOCATION: (898)

<223> OTHER INFORMATION: a, t, c, g, other or unknown
<221> NAME/KEY: modified_base
<222> LOCATION: (936)
<223> OTHER INFORMATION: a, t, c, g, other or unknown
<221> NAME/KEY: modified_base
<222> LOCATION: (945)
<223> OTHER INFORMATION: a, t, c, g, other or unknown
<221> NAME/KEY: modified_base
<222> LOCATION: (953)
<223> OTHER INFORMATION: a, t, c, g, other or unknown
<221> NAME/KEY: modified_base
<222> LOCATION: (967)
<223> OTHER INFORMATION: a, t, c, g, other or unknown
<221> NAME/KEY: modified_base
<222> LOCATION: (977)
<223> OTHER INFORMATION: a, t, c, g, other or unknown
<221> NAME/KEY: modified_base
<222> LOCATION: (984)..(985)
<223> OTHER INFORMATION: a, t, c, g, other or unknown

<400> SEQUENCE: 328

```
actatagggc acgcgtggtc gacggcccga gctggtatcc gatgaagcta gattcaatgg     60

ttcaagtcct atgaaagcta gattggagaa ttgcaaagaa atctaatctc cgttagttgt    120

cccaaccact gactcgcacc caatcagagt atattaaagt taaagattat ataaaggtaa    180

attgaacatt tataaaatct taaatgtatt tttagagtta aacattatat agaatattta    240

atgtagtata gatataataa aatattaaaa attaatttct ctttactatc aagtgaataa    300

aaataaaaaa taaatgtaag acaatataat aaaagacttg tttttagtgc attttttgga    360

ctcttcgtta ttgtgtggta ttgtgttatt taaactgatc tttttactgt atatatggat    420

gggttaccca tcaaacttgt gatttcaata aattcctccc ggattttaga gaaattagac    480

cataaaaact cacgaaaaaa attttagacc ataaaaactc acgaaaaaaa cttccccaaa    540

atcacgctaa aaacaactag ataaaaaaat acccatcttt gatgatgtgg atagtgacag    600

cctattccaa actatcacct aaattgtaag ttacatgcat aacacgatga cctcatctat    660

acgttgtgcc aaataaaggt atgaccgttc aaactaaaga atcaacgagc tccaacgcat    720

cttttgctgt ggggggattc tcacggctta acattcatgg anccgattac cttnctancc    780

aaccaagggt tttaacctgg aacaaatncc aaaccaatta ccagcttnac aaatcaaccg    840

agccgcccna ccgggatcat tttggtcaag tctcgaaaac nggcattggg tatatggnat    900

atggaattgg aattggatca atggtaacct tggganaagc ttaanttgga aanccctttt    960

ttttganggg ggccaanttc ccgnnccccc gg                                  992
```

<210> SEQ ID NO 329
<211> LENGTH: 996
<212> TYPE: DNA
<213> ORGANISM: Pinus taeda
<220> FEATURE:
<221> NAME/KEY: modified_base
<222> LOCATION: (933)
<223> OTHER INFORMATION: a, t, c, g, other or unknown
<221> NAME/KEY: modified_base
<222> LOCATION: (952)
<223> OTHER INFORMATION: a, t, c, g, other or unknown
<221> NAME/KEY: modified_base
<222> LOCATION: (982)
<223> OTHER INFORMATION: a, t, c, g, other or unknown

<400> SEQUENCE: 329

```
atactcaagc tatgcatcca acgcgttggg agctctccct atggtcgacc tgcaggcggc     60

cgcgaattca ctagtgatta gatggtaaga gcgatccaca gcttcgtcct ctccgaccct    120

cttccatagg tgcaaccccc agaagaattt ctatagccat attgaggctt tagaccactg    180
```

```
gtgctggaat tgtccacctt cagagaaggg cttcaaatta gcatctccaa gttacattga    240

tctattctat tcatatacat ataacaatgc tgcttcgaga ctgacaaaat gatccgttgg    300

cgctcgttga ttgttagctg taattgtttg gattgttcag ttaaagcctt gttggtagga    360

ggtaatcggt catgaatgtt agccgtgaga atcctcacag caaaagatgc gttggagctc    420

gttgattctt tagtttgaac ggtcatacct ttatttggca caacgtatag atgaggtcat    480

cgtgttatgc atgtaactta caatttaggt gatagtttgg aataggctgt cactatccac    540

atcatcaaag atgggtattt tttatctagt tgtttttagc gtgattttgg ggaagttttt    600

ttcgtgagtt tttatggtct aaaatttttt tcgtgagttt ttatggtcta atttctctaa    660

aatccgggag gaatttattg aaatcacaag tttgatgggt aacccatcca tatatacagt    720

aaaaagatca gtttaccagc ccgggccgtc gaccacgcgt gccctatagt aatcgaattc    780

ccgcggccgc catggcggcc gggagcatgc gacgtcgggc ccaattcgcc ctatagtgag    840

tcgtattaca attcactggc cgcgtttaca cgtcgtgact gggaaaccct gcgttaccac    900

ttaatcgctt gagcacatcc ccttttccag tgngtaaaac gaaaaggccc cnccatcgcc    960

tttcaaaaat tggcaactga angggaagga cccccct                              996
```

<210> SEQ ID NO 330
<211> LENGTH: 1041
<212> TYPE: DNA
<213> ORGANISM: Pinus taeda
<220> FEATURE:
<221> NAME/KEY: modified_base
<222> LOCATION: (918)
<223> OTHER INFORMATION: a, t, c, g, other or unknown
<221> NAME/KEY: modified_base
<222> LOCATION: (934)
<223> OTHER INFORMATION: a, t, c, g, other or unknown
<221> NAME/KEY: modified_base
<222> LOCATION: (943)
<223> OTHER INFORMATION: a, t, c, g, other or unknown
<221> NAME/KEY: modified_base
<222> LOCATION: (991)
<223> OTHER INFORMATION: a, t, c, g, other or unknown
<221> NAME/KEY: modified_base
<222> LOCATION: (1009)
<223> OTHER INFORMATION: a, t, c, g, other or unknown
<221> NAME/KEY: modified_base
<222> LOCATION: (1025)..(1026)
<223> OTHER INFORMATION: a, t, c, g, other or unknown
<221> NAME/KEY: modified_base
<222> LOCATION: (1030)
<223> OTHER INFORMATION: a, t, c, g, other or unknown

<400> SEQUENCE: 330

```
atactcaagc tatgcatcca acgcgttggg agctctccca tatggtcgac ctgcaggcgg     60

ccgcgaattc actagtgatt agatggtaag agcgatccac agcttcgtcc cctccgaccc    120

tcttccatag gtataaaacc cagaatttgg tgagcaggaa gaatttccat agccatattg    180

aggctttaca ccactgctgc tcgaattgtc caccttcaga gaagggcttc aaattagcat    240

ctccaagtta catggatcta ttctattcat atatttataa caatgctgct tcgagactga    300

caaaattatt tgttggcgct tgttcatcgt tagctgtaat ggtttggatt gttcagtgta    360

ggaccagccc gggccgtcga ccacgcgtgc cctatagtaa tcgaattccc gcggccgcca    420

tggcggccgg gagcatgcga cgtcgggccc aattcgccct atagtgagtc gtattacaat    480

tcactggccg tcgttttaca acgtcgtgac tgggaaaacc ctggcgttac ccaacttaat    540

cgccttgcag cacatccccc tttcgccagc tggcgtaata gcgaagaggc ccgcaccgat    600
```

```
cgcccttccc aacagttgcg cagcctgaat ggcgaatgga cgcgccctgt agcggcgcat    660

taagcgcggc gggtgtggtg gttacgcgca gcgtgaccgc tacacttgcc agcgccctag    720

cgcccgctcc tttcgctttc ttccttcctt tctcgccacg ttcgccggct ttccccgtca    780

agctctaaat cgggggcttc ctttagggtt ccgatttaat gctttacggc acctcgacc     840

ccaaaaaaac ttgattaggg gtgatgggtc acgtagtggg ccatcgccct tgatagacgg    900

tttttcgccc tttgacgntg gaagtccacg tttntttaat agngggactc ttggttcaaa    960

atgggacaac acttcaaacc ttttttgggg ntattttttt tgatttatna agggattttt   1020

gccgnntttn gggccttttg g                                             1041
```

```
<210> SEQ ID NO 331
<211> LENGTH: 993
<212> TYPE: DNA
<213> ORGANISM: Pinus taeda
<220> FEATURE:
<221> NAME/KEY: modified_base
<222> LOCATION: (939)
<223> OTHER INFORMATION: a, t, c, g, other or unknown
<221> NAME/KEY: modified_base
<222> LOCATION: (952)
<223> OTHER INFORMATION: a, t, c, g, other or unknown
<221> NAME/KEY: modified_base
<222> LOCATION: (965)
<223> OTHER INFORMATION: a, t, c, g, other or unknown
<221> NAME/KEY: modified_base
<222> LOCATION: (973)
<223> OTHER INFORMATION: a, t, c, g, other or unknown
<221> NAME/KEY: modified_base
<222> LOCATION: (993)
<223> OTHER INFORMATION: a, t, c, g, other or unknown

<400> SEQUENCE: 331

atactcaagc tatgcatcca acgcgttggg agctctccct atggtcgacc tgcaggcggc     60

cgcgaattca ctagtgatta ctatagggca cgcgtggtcg acggccccgg ctggtttcaa    120

taaattcctc ccggatttta gagaaattag accataaaaa ctcacgaaaa aaattttaga    180

ccataaaaac tcacgaaaaa aacttcccca aaatcacgct aaaaacaact agataaaaaa    240

atacccatct ttgatgatgt ggatagtgac agcctattcc aaactatcac ctaaattgta    300

agttacatgc ataacacgat gacctcatct atacgttgtg ccaaataaag gtatgaccgt    360

tcaaactaaa gaatcaacga gctccaacgc atcttttgct gtgaggattc tcacggctaa    420

cattcatgac cgattacctc ctaccaacaa ggctttaact gaacaatcca aacaattaca    480

gctaacaatc aacgagcgcc aacggatcat tttgtcagtc tcgaagcagc attgttatat    540

gtatatgaat agaatagatc aatgtaactt ggagatgcta atttgaagcc cttctctgaa    600

ggtggacaat tccagcacca gtggtctaaa gcctcaatat ggctatagaa attcttctgg    660

gggttgcacc tatggaagag ggtcggagag gacgaagctg tggatgctct taccatctaa    720

tcgaattccc gcggccgcca tggcggccgg gagcatgcga cgtcgggccc aattcgccct    780

atagtgagtc gtattacaat tcactggccg tcgttttaca acgtcgtgac tgggaaaacc    840

ctggcgtacc caacttaatc gccttgcagc acatcccctt tcgcagctgg gtaatagcga    900

aaaggccgca cgatgccttc cacagtgcca actgatggng aaggaccccc tntcgggcat    960

taacncgggg ggnggggttc cccccggcct ccn                                 993
```

```
<210> SEQ ID NO 332
<211> LENGTH: 1014
<212> TYPE: DNA
<213> ORGANISM: Pinus taeda
```

<220> FEATURE:
<221> NAME/KEY: modified_base
<222> LOCATION: (994)
<223> OTHER INFORMATION: a, t, c, g, other or unknown
<221> NAME/KEY: modified_base
<222> LOCATION: (998)
<223> OTHER INFORMATION: a, t, c, g, other or unknown
<221> NAME/KEY: modified_base
<222> LOCATION: (1014)
<223> OTHER INFORMATION: a, t, c, g, other or unknown

<400> SEQUENCE: 332

```
atactcaagc tatgcatcca acgcgttggg agctctccca tatggtcgac ctgcaggcgg     60
ccgcgaattc actagtgatt agatggtaag agcgatccac agcttcgtcc tctccgaccc    120
tcttccatag gtgcaacccc cagaagaatt tctatagcca tattgaggct ttagaccact    180
ggtgctggaa ttgtccacct tcagagaagg gcttcaaatt agcatctcca agttacattg    240
atctattcta ttcatataca tataacaatg ctgcttcgag actgacaaaa tgatccgttg    300
gcgctcgttg attgttagct gtaattgttt ggattgttca gttaaggcct tgttggtagg    360
aggtaatcgg tcatgaatgt tagccgtgag aatcctcaca gcaaaagatg cgtcggagct    420
cgttgattct ttagtttgaa cggtcatacc tttatttggc acaacgtata gatgaggtca    480
tcgtgttatg catgtaactt acaatttagg tgatagtttg gaataggctg tcactatcca    540
catcatcaaa gatgggtatt tttttatcta gttgttttta gcgtgatttt ggggaagttt    600
ttttcgtgag tttttatggt ctaaaatttt tttcgtgagt ttttatggtc taatttctct    660
aaaatccggg aggaatttat tgaaatcaca agtttgatgg gtaacccatc catatataca    720
gtaaaaagat cagtttaaat aacacaatac cacacaataa cgaagagtcc aaaaaatgca    780
ctaaaaacaa gtcttttatt atattggctt acatttattt tttactttta ttcacttgga    840
tagtaaaaga gaaattaatt tttaatattt tattatatct atactacatt aaatattcta    900
tataatgtta actctaaaaa acatttaaga tttatatatg gtcaattacc cttatataat    960
ctttaacttt aaatccctga tgggggccaa taanggtngg gaaactaacg gaan         1014
```

<210> SEQ ID NO 333
<211> LENGTH: 640
<212> TYPE: DNA
<213> ORGANISM: Pinus taeda

<400> SEQUENCE: 333

```
actatagggc acgcgtggtc gacggcccgg gctggtttca ataaattcct cccggatttt     60
agagaaatta gaccataaaa actcacgaaa aaaattttag accataaaaa ctcacgaaaa    120
aaacttcccc aaaatcacgc taaaaacaac tagataaaaa aatacccatc tttgatgatg    180
tggatagtga cagcctattc caaactatca cctaaattgt aagttacatg cataacacga    240
tgacctcatc tatacgttgt gccaaataaa ggtatgaccg ttcaaactaa agaatcaacg    300
agctccaacg catcttttgc tgtgaggatt ctcacggcta acattcatga ccgattacct    360
cctaccaaca aggctttaac tgaacaatcc aaacaattac agctaacaat caacgggcgc    420
caacggatca ttttgtcagc ctcgaagcag cattgttata tgtatatgaa tagaatagat    480
caatgtaact tggagatgct aatttgaagc ccttctctga aggtggacaa ttccagcacc    540
agtggtctaa agcctcaata tggctataga aattcttctg ggggttgcac ctatggaaga    600
gggtcggaga ggacgaagct gtggatcgct cttaccatct                          640
```

<210> SEQ ID NO 334

<211> LENGTH: 1028
<212> TYPE: DNA
<213> ORGANISM: Pinus taeda
<220> FEATURE:
<221> NAME/KEY: modified_base
<222> LOCATION: (953)
<223> OTHER INFORMATION: a, t, c, g, other or unknown
<221> NAME/KEY: modified_base
<222> LOCATION: (973)
<223> OTHER INFORMATION: a, t, c, g, other or unknown
<221> NAME/KEY: modified_base
<222> LOCATION: (981)
<223> OTHER INFORMATION: a, t, c, g, other or unknown
<221> NAME/KEY: modified_base
<222> LOCATION: (1002)
<223> OTHER INFORMATION: a, t, c, g, other or unknown
<221> NAME/KEY: modified_base
<222> LOCATION: (1004)
<223> OTHER INFORMATION: a, t, c, g, other or unknown

<400> SEQUENCE: 334
atactcaagc tatgcatcca acgcgttggg agctctccct atggtcgacc tgcaggcggc 60
cgcgaattca ctagtgatta gatggtaaga gcgatccaca gcttcgtcct ctccgaccct 120
cttccatagg tgcaaccccc agaagaattt ctatagccat attgaggctt tagaccactg 180
gtgctggaat tgtccacctt cagagaaggg cttcaaatta gcatctccaa gttacattga 240
tctattctat tcatatacat ataacaatgc tgcttcgaga ctgacaaaat gatccgttgg 300
cgctcgttga ttgttagctg taattgtttg gattgttcag ttaaggcctt gttggtagga 360
ggtaatcggt catgaatgtt agccgtgaga atcctcacag caaaagatgc gttggagctc 420
gttgactctt tagtttgaac ggtcatacct ttatttggca caacgtatag atgaggtcat 480
cgtgttatgc atgtaactta cagtttaggt gatagtttgg aataggctgt cactatccac 540
atcatcaaag atgggtattt ttttatctag ttgtttttag cgtgattttg gggaagtttt 600
tttcgtgagt ttttatggtc taaaattttt ttcgtgagtt tttatggtct aatttctcta 660
aaatccgaga ggaatttatt gaaaccagcc cgggccgtcg accacgcgtg ccctatagta 720
atcgaattcc cgcggccgcc atggcggccg ggagcatgcg acgtcgggcc caattcgccc 780
tatagtgagt cgtattacaa ttcactggcc gtcgttttac aacgtcgtga ctgggaaaac 840
cctgcgtacc cacttaatcg ccttggagca catcccccctt tcgccagctg gcgtaatagc 900
gaagaggccc ggacccgatc ggccctttcc aacaaattgc gcaaccctga atngggaaat 960
gggccccccc ctnttaccgg ngcaattaaa ccccgggggg gngngggggt tccccccccc 1020
gtggacct 1028

<210> SEQ ID NO 335
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 335
aagctttttt tttttg 16

<210> SEQ ID NO 336
<211> LENGTH: 13
<212> TYPE: DNA
<213> ORGANISM: Artificial Sequence
<220> FEATURE:
<223> OTHER INFORMATION: Description of Artificial Sequence: Primer

<400> SEQUENCE: 336

-continued

```
aagcttgatt gcc                                                  13


<210> SEQ ID NO 337
<211> LENGTH: 13
<212> TYPE: DNA
<213> ORGANISM: Artificial Sequence
<220> FEATURE:
<223> OTHER INFORMATION: Description of Artificial Sequence: Primer

<400> SEQUENCE: 337

aagcttcgac tgt                                                  13


<210> SEQ ID NO 338
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 338

ctcttaatta agtacgcggg                                           20


<210> SEQ ID NO 339
<211> LENGTH: 507
<212> TYPE: DNA
<213> ORGANISM: Artificial Sequence
<220> FEATURE:
<223> OTHER INFORMATION: Description of Artificial Sequence:
      Clone LPS-097

<400> SEQUENCE: 339

gggcacaaag ctccgcagcc tgagcgagcg tcattagctt gtcagtcgga accattaccc     60

ctttcctctt cgctggctag cgaatgatag ggaatgctag ccagcgaaca agattagagc    120

acagaaagta tagccagcga atcaacagca taacaactta gagatttctt gcattcccca    180

gacggtatca agtcatagtg gagaataatc ataataagat ttgtgaaaat gtttgtgtag    240

attaatgtgt aaaattcaat ccatcaacca tgaagtgaag tgcattccgt ttttaaatgt    300

ttattgtatt tgaatgaata aacagtttac acgcgaaaat ccctacttta tgtgcgtaca    360

aactatgatt tttttgcagt atataaaagt ttccactatc gtaattattt tccagatccg    420

tcttcttaac aacccgattt cctagcatcc atctgcgtgg aataaatcta ttgaattatt    480

aacccttgtg attggctaaa aaaaaaa                                        507
```

DIFFERENTIALLY-EXPRESSED CONIFER CDNAS, AND THEIR USE IN IMPROVING SOMATIC EMBRYOGENESIS

CROSS-REFERENCE TO RELATED APPLICATIONS

This patent application claims benefit of priority of provisional application U.S. Ser. No. 60/239,250, filed Oct. 11, 2000, and claims benefit of priority of provisional application U.S. Ser. No. 60/260,882, filed Jan. 12, 2001.

FIELD OF THE INVENTION

The present invention relates to a relational database of cDNA molecules, including those corresponding to Loblolly Pine Major Intrinsic Protein (MIP), which are differentially expressed during plant embryogenesis. The present invention further relates to the use of DNA arrays for evaluating gene expression in somatic and zygotic embryos. The invention encompasses related nucleic acids, proteins, antigens, and antibodies derived from these cDNAs as well as the use of such molecules for the staging, characterization, and manipulation of plant embryogenesis, in particular conifer embryogenesis. The cDNAs and related nucleic acids, proteins, antigens, and antibodies derived from these cDNAs are useful in the design, selection, and cultivation of improved crops, specifically including coniferous trees, which provide raw materials for paper and wood products.

BACKGROUND OF THE INVENTION

The world demand for paper is expected to increase nearly 50% by the year 2010 (McNutt and Rennel, *Pulp Paper Intern* 39: 48 (1997)). The United States' forest products industry faces a great challenge in order to keep pace with the growing demand for paper. This challenge is made greater by the decreasing availability of a forest land-base, resulting from environmental restrictions and urban growth, from which to harvest timber resources. Additionally, valuable wood resources are lost to the environmental stresses and biotic diseases. Consequently, the push to secure a renewable and sustainable source of raw material for paper and other wood related products has become an important priority for the forest products industry.

Current forestry related research and development is focused on creating sustainable fiber farms or tree plantations. Farming trees with elite germplasms will increase growth rates and yields of wood per acre. However, creating improved tree stock requires the ability to identify and generate genetically superior trees and a way to propagate such superior trees without diluting their genetic quotient.

A. Breeding and Selection

Addressing the need to propagate genetically superior trees without genetic diminution demands full research attention. Traditional methods of tree propagation relied on selected breeding programs to achieve genetic gain, i.e., the development of a strain, sub-strain, or line having any heritable and economically valuable characteristic or combination of characteristics not found in the parents. Based on the results of progeny tests, superior maternal trees are selected and used in "seed orchards" for mass production of genetically improved seed. The genetic gain in such an open-pollinated sexual propagation strategy is, however, limited by the breeder's inability to control the paternal parent. Additional gains can also be achieved by control-pollination of the maternal tree with pollen from individual trees whose progeny have demonstrated superior growth characteristics. Nevertheless, even under controlled conditions where both parents of each seed are the same, sexual propagation results in a "family" of seeds, i.e., siblings, comprised of many different genetic combinations. As not all genotype combinations are favorable, the genetic gain in any particular progeny is frequently offset and obscured by the genetic variation among sibling seeds and those seedlings retaining undesirable or previously masked pre-cross traits.

In addition to inherent genetic limitations of a traditional breeding programs, large-scale production of control pollinated seeds is also expensive. Consequently, economic and biological limitations of large-scale seed production has lead the industry to turn towards methods of asexual reproduction, such as grafting, vegetative propagation and micropropagation, as more viable alternatives.

B. Asexual (Clonal) Propagation

Asexual propagation permits the application of very high selection intensity, resulting in the propagation of only those progeny showing a high genetic gain potential. These highly desirable progeny can have unique genetic combinations that result in superior growth and performance characteristics. Thus, with asexual propagation it is possible to genetically select individuals while avoiding a concomitant reduction of genetic gain due to intra-familial variation.

Asexual propagation of trees can be accomplished currently by grafting, vegetative propagation, and micropropagation. Grafting, widely used to propagate select individuals in limited quantities for seed orchard establishment, is not applicable to large-scale production for reforestation. Vegetative propagation, achieved by the rooting of cuttings, and micropropagation by somatic embryogenesis, currently hold the most potential for reforestation of conifers. Although vegetative propagation by rooted cuttings can be achieved in many coniferous species, large-scale production via this method is extremely costly due to difficulties in automating and mechanizing the process, not to mention the need for tremendous quantities of stock tissue. This propagation method is still further limited by the fact that the rooting potential of stock plants decrease with time, making it difficult to serially propagate from select genotypes over extended periods of time.

Micropropagation is the most promising method of asexual propagation for mass plantings. This process involves the production of somatic embryos in vitro from minute pieces of plant tissue or individual cells. The embryos are referred to as somatic because they are derived from the somatic (vegetative) tissue, rather than from the sexual process. Both vegetative propagation and micropropagation have the potential to capture all genetic gain of highly desirable genotypes. However, unlike conventional vegetative propagation methods, somatic embryogenesis is amenable to automation and mechanization, making it highly desirable for large-scale production of planting stock for reforestation. Moreover, somatic embryogenesis is particularly amenable to high intensity selection of a large number of clones. These advantages are compounded by the ability to safely preserve somatic embryogenic cultures in liquid nitrogen for long-term storage. Consequently, long-term cryogenic preservation offers immense advantages over other vegetative propagation systems that attempt to maintain the juvenility of stock plants. Techniques for somatic embryogenesis in a wide variety of plant species are well known in the art; exemplary methods for performing somatic embryogenesis in conifers are taught in U.S. Pat. Nos. 5,036,007; 5,236,841; 5,294,549; 5,413,930; 5,491,090; 5,506,136; 5,563,061; 5,677,185; 5,731,203; 5,731,204; and 5,856,191, herein incorporated by reference in their entirety.

Thus, somatic embryogenesis has great potential for clonal production of conifer embryos to meet the increased demands of the pulp and paper industry. Assessment of embryo quality, however, needs improvement. The process of creating better tree stock begins with understanding the process of tree development from embryogenesis through full maturation.

In general, plant tissue culture is the broad science of growing plant tissues on or in a nutrient medium containing minerals, sugars, vitamins and plant hormones. By adjusting the composition of the media, cultured tissues can be induced to grow or differentiate into specific cell types or organs. "Somatic embryogenesis" is a type of plant tissue culture where a piece of a donor plant is excised, cultured and induced to form multiple embryos. An embryo is a discrete mass of cells with a well-defined structure that is capable of growing into a whole plant.

The methods generally in use for somatic embryogenesis today involve several steps. Prior to the tissue culture process, a suitable "explant" is harvested. A typical explant in conifer somatic embryogenesis is the "megagametophyte", a haploid nutritive tissue of the conifer seed, which is extracted from the ovule of a pollinated female cone. This ovule contains single or multiple zygotic seed embryos. In the seeds of many coniferous species, one or more genetically unique embryos naturally undergo a process called cleavage polyembryony, where a zygotic embryo grows and divides to form a small clones of embryos.

The first step in somatic embryogenesis is the initiation step. The explant is placed on a suitable media. When the explant is an ovule, a process called extrusion occurs. Extrusion involves the emergence or expulsion of a zygotic embryo or multiple embryos and embryogenic tissue out of the megagametophyte. If culture conditions are suitable, initiation proceeds and the extruded embryo or embryos undergo the process of cleavage polyembryony. This results in the formation of early stage somatic embryos in a glossy, mucilaginous mass.

After embryogenic cultures are initiated, the somatic embryos are transferred to a second medium with an appropriate composition of plant hormones and other factors to induce the somatic embryos to multiply. In the multiplication stage, cultures can double up to 2–6 times in one week. Once large numbers of embryos are obtained in the multiplication stage, the embryos are moved to a development and maturation medium. Here, the correct balance of plant hormones and other factors will induce the early-stage embryos to mature into late stage embryos. Following the maturation and development stage, embryos are germinated to form small seedlings. These seedlings are then acclimated for survival outside of the culture vessel. After acclimation, the seedlings are ready for planting.

The relative ability to propagate plants by somatic embryogenesis can vary greatly between species. Among conifers, for example, spruce (*Picea*) species and Douglas fir are easily propagated, while *Pinus* species are much more difficult. Many *Pinus* species, including Loblolly pine (*Pinus taeda*), do not readily initiate embryonic cultures. Typical initiation frequencies between 1% and 12% are reported for various *Pinus* species (Becwar et al., *For. Sci*. p1–18 (1988), Jain et al., *Plant Sci*. 65:233–241 (1989), Becwar et al., *Can. J. For. Res*. 20:810 (1990), Li and Huang, *J. Tissue Cult. Assoc*. 32:129 (1996)). Laine and David, (*Plant Sci*. 69:215 (1990)), however, were able to obtain high frequencies of initiation (up to 59%) in *Pinus caribaea*, suggesting that not all *Pinus* species are recalcitrant. Also, one earlier report described initiation frequencies of 54% in White pine (*Pinus strobus*). Finer et al., *Plant Cell Rep*. 8:203 (1989). However, other workers were not able to duplicate this success. Michler et al., *Plant Sci*. 77:111 (1991). The results in the literature demonstrate the recalcitrance of *Pinus* species, especially Loblolly pine, in regeneration by somatic embryogenesis.

Nevertheless, once this process is understood from the standpoint of developmental genetics, breeders will then have the appropriate tools to monitor, intervene, and improve both the regeneration frequency and the overall quality of tree stock through genetic engineering. For example, both environmental requirements and responsiveness of a developing embryo change as the embryo passes various developmental milestones. Consequently, accurate and timely knowledge of the developmental stage of an embryonic culture would allow the skilled practitioner to beneficially adjust the growth media components and other environmental factors to achieve optimal embryo survival, growth, and maturation. In addition, an understanding of developmentally regulated genes would allow for early selection of advantageous clones and provide tools for developmentally regulated transgenic expression systems.

Currently, a reasonable determination of the precise developmental stage of an embryo requires a practiced, physical familiarity with the morphological appearance of embryos at different stages, which is further complicated by the presence of morphological variations between species. Consequently, visual determination is performed best by experts in the field. Thus, there is a need in the art for a staging method which can be reliably practiced by the ordinary practitioner. The current invention will allow one to stage embryos based on a relational database system profiling gene expression patterns instead of physical morphological differences, thereby permitting one less skilled in the art of visual staging to biologically determine the stages of embryogenesis.

The traditional morphological staging method provides only a crude indication of the underlying biochemical condition or state of an embryo. This level of information is insufficient for refining culture conditions, including media formulations, or for selecting potentially advantageous embryo clones for further development. Thus, there is a need in the art for a more sensitive staging method that precisely defines the physiological age, health, growth requirements, and potential fitness of a particular embryo. The current invention will allow definitive staging significantly beyond that currently practiced in the art, and provides a detailed analysis of the biochemical state and potential fitness of an embryo by comparison to developed relational database profiles.

Visual staging methods depend on morphological markers to assign a numerical stage of 1–9 to an embryo. Nevertheless, it is well accepted that visually undetectable developmental changes occur in an embryo after it reaches stage 9. The current invention is particularly useful in providing means for monitoring and evaluating the developmental state of these older embryos, as genetic responses occur and are detectable up to and through an adult tree's life.

There further exists in the art a need for information regarding the proteins, genes, and gene expression patterns in plant embryo development, as well as a more thorough understanding of how this information relates to the physiology, developmental potential, and genetic quotient of a plant embryo. The relational database system provides a platform for which to monitor individual gene expression levels during embryo development while directly correlating expression with, for example, environmental conditions, age, and embryo fitness, as well as the protein identification achieved by BLAST searches of publicly available databases (i.e., GenBank) for desirable genes. Accordingly, the present invention therefore provides the additional ability to correlate the direct, global gene expression response within the embryo system to a typically non-expressing gene driven by a stage-specific promoter.

SUMMARY OF THE INVENTION

The present invention addresses these needs by providing in a relational database format nucleic acid and protein sequences that are differentially expressed during various stages of plant embryogenesis. The invention encompasses a set of isolated nucleic acid molecules comprising the DNA sequence of any one of SEQ ID NOS: 1–334 and nucleic acid molecules related or complementary to any one of SEQ ID NOS: 1–334. (See Table I) As such, the invention includes both single-stranded and double-stranded RNA and DNA nucleic acids, including variants thereof. The nucleic acids of the invention can be used as an expression template in the form of DNA arrays, including for example, gene arrays, DNA chips, and dot array Southerns, for which to compare and evaluate expression in test samples. (See Table II) The nucleic acids of the invention can be further used as probes to detect the presence or level of both single-stranded and double-stranded RNA and DNA encoding variants of polypeptides or fragments of polypeptides encompassed by the invention. The nucleic acids of the invention can be further used as promoters for the expression of sense and antisense molecules at specific stages of embryo development. Data acquired through the use of the present invention can in turn be provided to the relational database for further development.

Isolated nucleic acid molecules that hybridize to a denatured, double-stranded DNA comprising the DNA sequence of any one of SEQ ID NOS: 1–334 under conditions of moderate or high stringency are also encompassed by the invention. The invention further encompasses synthetic and naturally-occurring variants of the nucleic acids described in SEQ ID NOS: 1–334, for example, isolated nucleic acid molecules derived by in vitro mutagenesis from SEQ ID NOS: 1–334. In vitro mutagenesis would include numerous techniques known in the art including, but not limited to, site-directed mutagenesis, random mutagenesis, and in vitro nucleic acid synthesis.

The invention also encompasses related molecules (variants) including isolated nucleic acid molecules degenerate from SEQ ID NOS: 1–334 as a result of the genetic code, for example, naturally-occurring or synthetic allelic variants of the genes encoding SEQ ID NOS: 1–334. Such related molecules also encompass both smaller and larger nucleic acids that contain sufficient sequence to support hybridization to any of SEQ ID NOS: 1–334 under conditions of moderate or high stringency. Consequently, recombinant vectors, including those that direct the expression of these nucleic acid molecules and host cells transformed or transfected with these vectors are herein defined as variants and are encompassed by the invention.

Another embodiment of this invention is the production of transgenic vectors and transgenic plants comprising vectors or other nucleic acids comprising any one of SEQ ID NOS: 1–334 and related molecules. Particularly preferred are those capable of expressing polypeptides or peptides encoded by any of SEQ ID NOS: 1–327. In a preferred embodiment, the transgene comprises SEQ ID NO: 327, or a variant thereof.

SEQ ID NO: 327 encodes a protein which corresponds to a novel Loblolly pine homolog of the plant Major Intrinsic Protein (MIP) family. MIPs comprise a large family of related proteins that function as membrane channels for the transport of water and possibly ions across cellular membranes. Henceforth, the encoded protein of SEQ ID NO: 327 may be referred to as Loblolly MIP. Variants, including naturally-occurring and artifactually-programmed allelic variants, vectors, and other nucleic acids which hybridize to SEQ ID NO: 327 under conditions of moderate or high stringency are encompassed by the invention. Also encompassed are plant cells, seeds, embryos and trees, transgenic for loblolly pine MIP, and variants thereof.

The invention also encompasses isolated polypeptides, or fragments thereof, encoded by any one of the nucleic acid molecules of SEQ ID NOS: 1–327, including variants thereof. The invention further encompasses the use of these peptide sequences as markers for staging, monitoring, and selecting embryos and embryo cultures. The invention also encompasses methods for the production of these polypeptides or fragments thereof including culturing a host cell under conditions promoting expression and recovering the polypeptide or peptide from the culture medium. In particular, the expression of polypeptides or peptides encoded by SEQ ID NOS: 1–327 in viral vectors, bacteria, yeast, plant, and animal cells is encompassed by the invention. Isolated polyclonal or monoclonal antibodies that bind to peptides encoded by SEQ ID NOS: 1–327 are also encompassed by the invention.

Further encompassed by this invention are methods for using the nucleic acid molecules of any one of SEQ ID NOS: 1–327 to obtain full length cDNA and genomic sequences of the corresponding genes, including cognate, homologous, or otherwise related genetic sequences, which hybridize to any of SEQ ID NOS: 1–327 under conditions of moderate or high stringency. Also provided by this invention are oligonucleotides derived from any one of SEQ ID NOS: 1–334 that can be used as probes and/or as primers in PCR, RT-PCR, and other assays to detect the presence or level of the nucleic acids of SEQ ID NOS: 1–334 and related molecules.

The primers and other probes of the invention may be used to monitor and characterize the development of plant embryos, in particular, pine tree embryos. Characterization of embryonic gene expression provides means for correlating gene expression with current and potential plant phenotypes. Consequently, the present invention encompasses means for monitoring and adjusting growth conditions (see FIG. 6), as well as means for selecting genetically superior embryonic clones for further propagation and expansion (see FIG. 8). Thus, the present invention encompasses the use of DNA or RNA probes derived from the nucleic acid molecules of SEQ ID NOS: 1–334 in any form, e.g., in DNA arrays, and antibodies raised against polypeptides or peptide fragments encoded by SEQ ID NOS: 1–327, to determine relative or absolute levels of expression of the genes or proteins encoded by SEQ ID NOS: 1–327. In addition, these nucleic acid and antibody probes may be used for staging, monitoring, characterizing, or selecting plant embryos or embryo cultures, particularly pine tree embryos.

The relational database of the present invention allows expression information pertaining to embryo stages to be viewed as sequence data generated in accordance with the present invention. The invention includes a database for storing a plurality of sequence records for which to correlate embryo stages to sequence records. The method further involves providing an interface which allows a user to select one or more expression categories contained within the database.

The relational database is designed to include separate parts or cells for information storage. One cell or part may contain a gene expression database which contains nucleic acid molecules of SEQ ID NOS: 1–327. Other cells or parts may contain descriptive information pertaining to each nucleic acid molecules of SEQ ID NOS: 1–327, additional sequence data related to the gene expression database, protein encoded by nucleic acids disclosed herein, similarity values to known proteins of other systems, and to conditions under which expression data was obtained.

The database system described in the present invention will allow identification or selection of particular genes of interest for further use with DNA arrays. Identification or selection of particular genes may include, for example, those related to patterns of expression, those identified with homology to known genes from other studies, and those sequences considered novel.

BRIEF DESCRIPTION OF THE DRAWINGS

FIG. 1 depicts differential display of loblolly pine zygotic and somatic embryos at different stages of development.

FIG. 2 displays embryo gene expression observed by high-density array Southern hybridization.

FIG. 4 depicts graphical representation of hybridization of 'dehydrin' and LPZ216 cDNA probes to total RNA isolated from zygotic embryos of loblolly pine.

FIG. 7 shows detection of gene expression by high-density array Southern hybridization for loblolly pine genotype 333 after 12 weeks on two maturation media.

FIG. 9 displays slot blots and expression levels for three embryogenesis-related genes.

FIG. 10 depicts clone LPS-097 sequence (SEQ ID NO: 339) (LP2-3 differential display fragment.)

FIG. 12 displays a slot blot of total RNA from somatic embryo tissue probed with an LP2-3-specific probe. Panel A depicts an image of the slot blot and panel B depicts quantitation of the image.

FIG. 13 displays a slot blot of total RNA from zygotic embryo tissue probed with an LP2-3-specific probe. Panel A depicts an image of the slot blot and panel B depicts quantitation of the image.

DETAILED DESCRIPTION OF THE INVENTION

Figure 3:
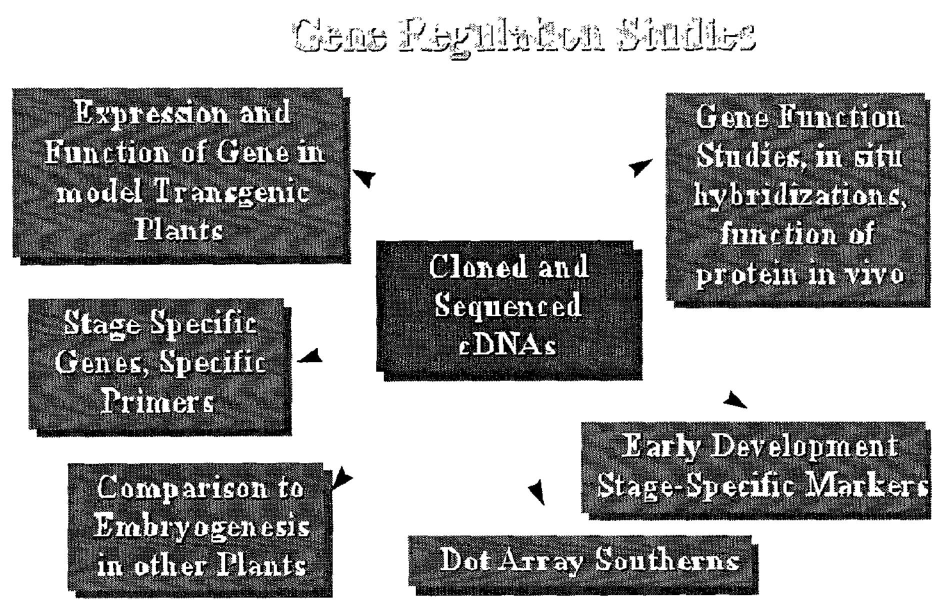
FIG. 3 provides a general schematic for gene regulation studies arising from the cDNA cloning of genes expressed in embryos.

The three hundred and twenty-seven differentially expressed cDNAs isolated from plant specimens of known developmental ages are disclosed in SEQ ID NOS: 1–327. The seven stage-specific promoters isolated from plant specimens are disclosed in SEQ ID NOS: 328–334. The discovery of these cDNAs and promoters enables the design, isolation, and construction of related nucleic acids, proteins, antigens, antibodies other heterologous genes. Both the cDNAs and promoters facilitate the staging, characterization, and manipulation of plant embyrogenesis, in particular, conifer embryogenesis. These molecules, and related nucleic acids, peptides, proteins, antigens, and antibodies are particularly useful when compiled into a relational database for the monitoring, design, selection, and cultivation of improved crop plants.

The cDNAs of SEQ ID NOS: 1–327, in addition to the promoters of SEQ ID NOS: 328–334, were originally derived from *Pinus taeda* embryos, commonly known as the Loblolly Pine. Nevertheless, it is understood that the invention is applicable to and encompasses all plants, including all dicotyledonous plants, including all conifers, including all species of *Pinus, Picea*, and *Pseudotsuga*. Exemplary conifers may include *Picea abies*, and *Psedotsuga menziesii*, and *Pinus taeda.*

Nucleic Acid Molecules

In a particular embodiment, the invention relates to certain isolated nucleotide sequences including those that are substantially free from contaminating endogenous material. The terms "nucleic acid" or "nucleic acid molecule" refer to a deoxyribonucleotide or ribonucleotide polymer in either single-or double-stranded form, and unless otherwise limited, would encompass known analogs of natural nucleotides that can function in a similar manner as naturally occurring nucleotides. A "nucleotide sequence" also refers to a polynucleotide molecule or oligonucleotide molecule in the form of a separate fragment or as a component of a larger nucleic acid. The nucleotide sequence or molecule may also be referred to as a "nucleotide probe." The nucleic acid molecules of the invention are derived from DNA or RNA isolated at least once in substantially pure form and in a quantity or concentration enabling identification, manipulation, and recovery of its component nucleotide sequence by standard biochemical methods. Examples of such methods, including methods for PCR protocols that may be used herein, are disclosed in Sambrook et al., *Molecular Cloning: A Laboratory Manual,* 2nd ed., Cold Spring Harbor Laboratory, Cold Spring Harbor, N.Y. (1989), *Current Protocols in Molecular Biology* edited by F. A. Ausubel et al., John Wiley and Sons, Inc. (1987), and Innis, M. et al., eds., *PCR Protocols: A Guide to Methods and Applications*, Academic Press (1990), each of which are herein incorporated by reference in their entirety.

As used herein a "nucleotide probe" is defined as an oligonucleotide capable of binding to a target nucleic acid of complementary sequence through one or more types of chemical bonds, through complementary base pairing, or through hydrogen bond formation. As described above, the oligonucleotide probe may include natural (ie. A, G, C, or T) or modified bases (7-deazaguanosine, inosine, etc.). In addition, bases in a oligonucleotide probe may be joined by a linkage other than a phosphodiester bond, so long as it does not prevent hybridization. Thus, oligonucleotide probes may have constituent bases joined by peptide bonds rather than phosphodiester linkages.

A "target nucleic acid" herein refers to a nucleic acid to which the nucleotide probe or molecule can specifically hybridize. The probe is designed to determine the presence or absence of the target nucleic acid, and the amount of target nucleic acid. The target nucleic acid has a sequence that is complementary to the nucleic acid sequence of the corresponding probe directed to the target. As recognized by one of skill in the art, the probe may also contain additional nucleic acids or other moieties, such as labels, which may not specifically hybridize to the target. The term target nucleic acid may refer to the specific nucleotide sequence of a larger nucleic acid to which the probe is directed or to the overall sequence (e.g., gene or mRNA) whose expression level it is desired to detect. One skilled in the art will recognize the full utility under various conditions.

As described herein, the nucleic acid molecules of the invention include DNA in both single-stranded and double-stranded form, as well as the RNA complement thereof. DNA includes, for example, cDNA, genomic DNA, chemically synthesized DNA, DNA amplified by PCR, and combinations thereof. Genomic DNA, including translated, non-translated and control regions, may be isolated by conventional techniques, e.g., using any one of the cDNAs of SEQ ID NO: 1 through SEQ ID NO: 327, or suitable fragments thereof, as a probe, to identify a piece of genomic DNA which can then be cloned using methods commonly known in the art. In general, nucleic acid molecules within the scope of the invention include sequences that hybridize to sequences of SEQ ID NOS: 1–334 under hybridization and wash conditions of 5°, 10°, 15°, 20°, 25°, or 30° below the melting temperature of the DNA duplex of sequences of SEQ ID NOS: 1–334, including any range of conditions subsumed within these ranges.

DNA Arrays

In a further embodiment, DNA arrays are used to identify hybridizing sequences from test samples. The term "DNA array" refers to "gene arrays," "DNA chips," "dot array Southerns," etc. One of skill in the art will appreciate that an enormous number of array designs are suitable for the practice of this invention. The DNA array will typically include one or a multiplicity of nucleic acid molecules derived from SEQ ID NO: 1 through SEQ ID NO: 327 that specifically hybridize to the nucleic acid expression of which is to be detected. In addition, the array may include one or more control probes to monitor the expression system. Control probes refer to known expression products present at each stage of expression, e.g., ribosomal gene products or the transcripts of other housekeeping genes. The organization of the DNA array will be known to facilitate interpretation of results. Examples in the art describing the uses and composition of DNA arrays can be found in U.S. Pat. Nos. 5,700,637, 5,837,832, 5,843,655, 5,874,219, 6,040,138, 6,045,996, and are incorporated by reference.

Molecules that Hybridize to Identified Sequences

Thus, in a particular embodiment, this invention provides an isolated nucleic acid molecule selected from the group consisting of:

(1) a DNA sequence comprising any one of the sequences presented in SEQ ID NO: 1 through SEQ ID NO: 334;

(2) an isolated nucleic acid molecule that hybridizes to either strand of a denatured, double-stranded DNA comprising the nucleic acid sequence of (a) under conditions of moderate stringency; and (3) an isolated nucleic acid molecule that hybridizes to either strand of a denatured, double-stranded DNA comprising the nucleic acid sequence of (a) under conditions of high stringency.

As used herein, stringency conditions in nucleic acid hybridizations can be readily determined by those having ordinary skill in the art based on, for example, the length and composition of the nucleic acid. In one embodiment, moderate stringency is herein defined as a nucleic acid having 10, 11, 12, 13, 14, 15, 16, or 17, contiguous nucleotides identical to any of the sequences of SEQ ID NOS: 1–334, or a complement thereof. Similarly, high stringency is hereby defined as a nucleic acid having 18, 19, 20, 21, 22, or more contiguous identical nucleotides, or a longer nucleic acid having at least 80, 85, 90, 95, or 99 percent identity with any of the sequences of SEQ ID NOS: 1–334; for sequences of at least 50, 100, 150, 200, or 250 nucleotides, high stringency may comprise an overall identity of at least 60, 65, 70 or 75 percent.

Generally, nucleic acid hybridization simply involves providing a denatured nucleotide molecule or probe and target nucleic acid under conditions where the probe and its complementary target can form stable hybrid duplexes through complementary base pairing. The nucleic acids that do not substantially form hybrid duplexes are then washed away leaving the hybridized nucleic acids to be detected, typically through detection of an attached detectable label. It is further generally recognized that nucleic acids are denatured by increasing the temperature or decreasing the salt concentration of the buffer containing the nucleic acids. Under lower stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches. One of skill in the art will appreciate that hybridization conditions may be selected to provide any degree of stringency.

As used herein, the percent identity between an amino acid sequence encoded by any of SEQ ID NOS: 1–334 and a potential hybridizing variant can be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess (*Nucl. Acids Res.* 14:6745, 1986), as described by Schwartz and Dayhoff (eds., *Atlas of Protein Sequence and Structure*, National Biomedical Research Foundation, pp. 353–358, 1979); (2) a penalty of 3.0 for each gap and an additional 0.10 penalty for each symbol in each gap; and (3) no penalty for end gaps.

Alternatively, basic protocols for empirically determining hybridization stringency are set forth in section 2.10 of *Current Protocols in Molecular Biology* edited by F. A. Ausubel et al., John Wiley and Sons, Inc. (1987). Stringency conditions can be determined readily by the skilled artisan. An example of moderate stringency hybridization conditions would be hybridization in 5×SSC, 5× Denhardt's Solution, 50% (w/v) formamide, and 1% SDS at 42° C. with washing conditions of 0.2×SSC and 0.1% SDS at 42° C. An example of high stringency conditions can be defined as hybridization conditions as above, and with washing at approximately 68° C., in 0.1×SSC, and 0.1% SDS. The skilled artisan will recognize that the temperature and wash solution salt concentration can be adjusted as necessary according to factors such as the length of the probe.

Due to the degeneracy of the genetic code wherein more than one codon can encode the same amino acid, multiple DNA sequences can code for the same polypeptide. Such variant DNA sequences can result from genetic drift or artificial manipulation (e.g., occurring during PCR amplification or as the product of deliberate mutagenesis of a native sequence). The present invention thus encompasses any nucleic acid capable of encoding a protein derived from SEQ ID NOS: 1–327, or variants thereof.

Deliberate mutagenesis of a native sequence can be carried out using numerous techniques well known in the art. For example, oligonucleotide-directed site-specific mutagenesis procedures can be employed, particularly where it is desired to mutate a gene such that predetermined restriction nucleotides or codons are altered by substitution, deletion or insertion. Exemplary methods of making such alterations are disclosed by Walder et al. (*Gene* 42:133, 1986); Bauer et al. (Gene 37:73, 1985); Craik (*BioTechniques*, Jan. 12–19, 1985); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462, all of which are incorporated by reference.

Thus, the invention further provides an isolated nucleic acid molecule selected from the group comprising of (1), (2), and (3) above and further consisting of:

(4) an isolated nucleic acid molecule degenerate from SEQ ID NOS: 1–334 as a result of the genetic code; and (5) an isolated nucleic acid molecule selected from the group consisting of an allelic variants and species homologs of SEQ ID NOS: 1–334.

Obtaining Full Length cDNAs

The cDNAs isolated and cloned through the differential display procedure will often only represent a partial sequence (generally the 3' end) of the mRNA from which it was derived due to the nature of the arbitrary primer used in the differential display PCR reaction. Consequently, the cDNA sequences of SEQ ID NOS: 1–327 provide powerful tools for obtaining the sequences of full-length cDNAs. This can be accomplished by using a partial cDNA as a probe to identify and isolate the full length cDNA from a population of full length cDNAs or from a full length cDNA library. As is well known in the art, similar procedures can be used to identify corresponding genomic DNA sequences.

Alternatively, one can obtain the 5' sequence of a partial cDNA by performing Rapid Amplification of cDNA Ends (RACE) procedures such as those disclosed in Frohman, *Methods in Enzymology,* 218:340–356 (1993) and Bertling et al., *PCR Methods and Applications* 3:95–99 (1993) which are hereby incorporated by reference. For example, Clonetech Laboratories, Inc. (Palo Alto, Calif.) offers a SMART™ cDNA product line that allows one to generate high quality full length cDNAs and cDNA libraries. SMART™ technology can also be used to perform RACE. One skilled in the art will readily recognize that there are other equivalent products and procedures for obtaining full length cDNAs. Full length cDNAs may be sequenced and their sequences compared to sequences in public databases to assess their identities and/or homologies to other known sequences.

Cloned full length cDNAs can be used in the construction of expression vectors for the production and purification of pine tree polypeptides which contain the pine tree peptides encoded by the cDNAs of any one of SEQ ID NOS: 1–327.

Oligonucleotide Primers for PCR Assays

In another embodiment, the present invention encompasses oligonucleotide fragments derived from any one of SEQ ID NO: 1 through SEQ ID NO: 327 or from the reverse complement sequence of any one of SEQ ID NO: 1 through SEQ ID NO: 327. Such oligonucleotides would be useful as primers in the performance of RT-PCR assays to detect, or even quantify, pine embryo stage-specific transcripts. Such oligonucleotide primers will generally comprise from 10 to 25 nucleotides substantially complementary to the ends of the target sequence and may contain additional non-complementary nucleotides, for example, nucleotides that generate a restriction endonuclease site or cloning junction. Programs useful in selecting PCR primers may be used to design the oligonucleotides of this invention, but use of such programs is not necessary. By way of example, the Wisconsin Package™ software available from the Genetic Computer Group (Madison, Wis.) includes a program called Prime that can aid in selecting primers from a given template sequence. Protocols for the design and optimization of PCR reactions are commonly known in the art and are described in Saiki et al., *Science* 239:487 (1988); *Recombinant DNA Methodology*, Wu et al., eds., Academic Press, Inc., San Diego (1989), pp. 189–196; and PCR Protocols: *A Guide to Methods and Applications*, Innis et al., eds., Academic Press, Inc. (1990).

Antisense Nucleic Acid Molecules

Other useful fragments of the nucleic acids include antisense or sense oligonucleotides comprising a single-stranded nucleic acid sequence (either RNA or DNA) capable of binding to target mRNA (sense) or DNA (antisense) sequences. Antisense or sense oligonucleotides, according to the present invention, comprise a fragment of DNA from any one of SEQ ID NO: 1 through SEQ ID NO: 327. Such a fragment generally comprises at least about 14 nucleotides, preferably from about 14 to about 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*Bio/Techniques* 6:958, 1988).

Binding of antisense or sense oligonucleotides to target nucleic acid sequences results in the formation of duplexes or other nucleic acid complexes inimical to efficient production of gene products. The antisense oligonucleotides thus may be used to block expression of proteins or the function of RNA. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sufficient sequence specificity to be able to bind to target nucleotide sequences.

Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides. Such modifications may modify binding specificities of the antisense or sense oligonucleotide for the target nucleotide sequence.

Antisense or sense oligonucleotides may be introduced into a cell containing the target nucleic acid sequence by any gene transfer method, including, for example, lipofection, $CaPO^4$-mediated DNA transfection, electroporation, or by using gene transfer vectors such as Epstein-Barr virus or adenovirus.

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. In one embodiment, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Polypeptides Encoded by Differentially-Expressed cDNAs

The cDNAs of SEQ ID NOS: 1–327 can be translated into amino acid sequences potentially corresponding to portions of developmentally-regulated plant proteins. These amino acid sequences can be identified from sequences listed in Table I, below. The cDNAs encoding these predicted polypeptides are grouped into early, middle, and late transcripts according to the staged embryo population from which they were derived.

(See Table I)

Although the term "peptide" is generally understood to reference synthetic sequences, or fragments of larger proteins, and includes short amino acid sequences of between 2 and 10 amino acids, whereas "polypeptide" refers to larger sequences and full-length proteins, the terms are used interchangeably herein to indicate that the invention applies to peptides and polypeptides of any length and variants thereof. Moreover, the discovery of presumptive open reading frames in SEQ ID NOS: 1–327, and the ability to isolate additional cDNA sequence, enables the construction of expression vectors comprising nucleic acid sequences encoding those polypeptides. The cDNAs of the invention also enable cells transfected or transformed with expression vectors driving the expression of the encoded polypeptides and antibodies reactive with the polypeptides.

In one embodiment, the invention provides for isolated polypeptides, preferably, pine tree polypeptides. As used herein, the term "polypeptides" refers to a genus of polypeptide or peptide fragments that encompass the amino acid sequences identified from Table I, as well as smaller fragments. Consequently, the invention encompasses any polypeptide fragment comprising at least 5, 6, 7, 8, 9, 10, 11, 12, 13, 14, or 15 contiguous amino acids encoded by the cDNAs of any of SEQ ID NOS: 1–327, or comprising at least 5, 6, 7, 8, 9, 10, 11, 12, 13, 14, or 15 contiguous amino acids of any of amino acid sequence derived from Table I.

Alternatively, a polypeptide may be defined in terms of its antigenic relatedness to any peptide encoded by SEQ ID NOS: 1–327. Thus, in one embodiment, a polypeptide within the scope of the invention is defined as an amino acid sequence comprising a linear or 3-dimensional epitope shared with any peptide encoded by the cDNAs of SEQ ID NOS: 1–327. Alternatively, a polypeptide within the scope of the invention is recognized by an antibody that specifically recognizes any peptide encoded by SEQ ID NOS: 1–327. Antibodies are defined to be specifically binding if they bind pine tree polypeptides with a $K_a$ of greater than or equal to about $10^7$ $M^{-1}$, and preferably greater than or equal to $10^8$ $M^{-1}$.

A polypeptide "variant" as referred to herein means a polypeptide substantially homologous to a native polypeptide, but which has an amino acid sequence different from that encoded by any of SEQ ID NOS: 1–327 because of one or more deletions, insertions or substitutions. The variant amino acid sequence preferably is at least 80% identical to a native polypeptide amino acid sequence, preferably at least 90%, more preferably, at least 95% identical over at least 6, 7, 8, 9, 10, 11, 12, 13, 14, 15, 16, 17, 18, 19, 20, 21–25, or 26–30 contiguous amino acids. The percent identity between an amino acid sequence encoded by any of SEQ ID NOS: 1–327 and a potential variant can be determined manually, or, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program, described above, utilizes the alignment method of Needleman and Wunsch (*J. Mol. Biol.* 48:443, 1970), as revised by Smith and Waterman (*Adv. Appl. Math* 2:482, 1981).

Variants can comprise conservatively substituted sequences, meaning that a given amino acid residue is replaced by a residue having similar physiochemical characteristics. Examples of conservative substitutions include substitution of one aliphatic residue for another, such as lie, Val, Leu, or Ala for one another, or substitutions of one polar residue for another, such as between Lys and Arg; Glu and Asp; or Gin and Asn. See Zubay, Biochemistry, Addison-Wesley Pub. Co., (1983) incorporated by reference in its entirety. The effects of such substitutions can be calculated using substitution score matrices such a PAM-120, PAM-200, and PAM-250 as discussed in Altschul, (*J. Mol. Biol.* 219:555–65, 1991). Other such conservative substitutions, for example, substitutions of entire regions having similar hydrophobicity characteristics, are well known.

Naturally-occurring peptide variants are also encompassed by the invention. Examples of such variants are proteins that result from alternate mRNA splicing events or from proteolytic cleavage of the polypeptides of Table I. Variations attributable to proteolysis include, for example, differences in the N- or C-termini upon expression in different types of host cells, due to proteolytic removal of one or more terminal amino acids from the polypeptides encoded by the sequences of Table I (generally from 1–5 terminal amino acids).

As stated above, the invention provides recombinant and non-recombinant, isolated and purified polypeptides, preferably pine tree polypeptides. Variants and derivatives of native polypeptides can be obtained by isolating naturally-occurring variants, or the nucleotide sequence of variants, of other plant lines or species, or by artificially programming mutations of nucleotide sequences coding for native pine tree polypeptides. Alterations of the native amino acid sequence can be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered gene wherein predetermined codons can be altered by substitution, deletion or insertion. Exemplary methods of making such alterations are discussed supra.

The following sections are examples of the various expression vectors, host cells, and protein purification methods that are known in the art. These examples are provided merely as illustrative and should not be construed as the only means to express and purify the polypeptides and polypeptide variants of the invention.

Expression Vectors and Purified Proteins

Recombinant expression vectors containing a nucleic acid sequence encoding the polypeptides of the invention can be prepared using well known methods. In one embodiment, the expression vectors include a cDNA sequence encoding the polypeptide operably linked to suitable transcriptional or translational regulatory nucleotide sequences, such as those derived from a mammalian, microbial, viral, or insect gene. Examples of regulatory sequences include transcriptional promoters, operators, or enhancers, mRNA ribosomal binding sites, and appropriate sequences which control transcription and translation initiation and termination. Nucleotide sequences are "operably linked" when the regulatory sequence functionally relates to the cDNA sequence of the invention. Thus, a promoter nucleotide sequence is operably linked to a cDNA sequence if the promoter nucleotide sequence controls the transcription of the cDNA sequence. The ability to replicate in the desired host cells, usually conferred by an origin of replication, and a selection gene by which transformants are identified can additionally be incorporated into the expression vector.

In addition, sequences encoding appropriate signal peptides that are not naturally associated with the polypeptides of the invention can be incorporated into expression vectors. For example, a DNA sequence for a signal peptide (secretory leader) can be fused in-frame to the pine tree nucleotide sequence so that the polypeptides of the invention is initially translated as a fusion protein comprising the signal peptide. A signal peptide that is functional in the intended host cells enhances extracellular secretion of the expressed polypeptide. The signal peptide can be cleaved from the polypeptide upon secretion from the cell.

Fusions of additional peptide sequences at the amino and carboxyl terminal ends of the polypeptides of the invention can be used to enhance expression of the polypeptides or aid in the purification of the protein. Such peptides include, for example, poly-His or the antigenic identification peptides described in U.S. Pat. No. 5,011,912 and in Hopp et al., (*Bio/Technology* 6:1204, 1988).

Suitable host cells for expression of polypeptides of the invention include prokaryotes, yeast or higher eukaryotic cells. Appropriate cloning and expression vectors for use with bacterial, fungal, yeast, and mammalian cellular hosts are described, for example, in Pouwels et al., *Cloning Vectors: A Laboratory Manual*, Elsevier, N.Y., (1985). Cell-free translation systems could also be employed to the disclosed polypeptides using RNAs derived from DNA constructs disclosed herein.

Prokaryotic Expression Systems

Prokaryotes include gram negative or gram positive organisms, for example, *E. coli* or *Bacilli*. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, the disclosed polypeptides can include an N-terminal methionine residue to facilitate expression of the recombinant polypeptide in the prokaryotic host cell. The N-terminal methionine can be cleaved from the expressed recombinant polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and a DNA sequence encoding one or more of the polypeptides of the invention are inserted into the pBR322 vector. Other commercially available vectors include, for example, pKK223-3 (Pharmacia Fine Chemicals, Uppsala, Sweden) and pGEM-1 (Promega Biotec, Madison, Wis., USA). Other commercially available vectors include those that are specifically designed for the expression of proteins; these would include pMAL-p2 and pMAL-c2 vectors that are used for the expression of proteins fused to maltose binding protein (New England Biolabs, Beverly, Mass., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776), and tac promoter (Maniatis, *MoLecular Cloning: A Laboratory Manual*, Cold Spring Harbor Laboratory, p. 412, 1982). A particularly useful prokaryotic host cell expression system employs a phage $\lambda$ $P_L$ promoter and a cI857ts thermolabile repressor sequence. Plasmid vectors available from the American Type Culture Collection ("ATCC"), which incorporate derivatives of the PL promoter, include plasmid pHUB2 (resident in *E. coli* strain JMB9 (ATCC 37092)) and pPLc28 (resident in *E. coli* RR1 (ATCC 53082)).

DNA encoding one or more of the polypeptides of the invention may be cloned in-frame into the multiple cloning site of an ordinary bacterial expression vector. Ideally the vector would contain an inducible promoter upstream of the cloning site, such that addition of an inducer leads to high-level production of the recombinant protein at a time of the investigator's choosing. For some proteins, expression levels may be boosted by incorporation of codons encoding a fusion partner (such as hexahistidine) between the promoter and the gene of interest. The resulting "expression plasmid" may be propagated in a variety of strains of *E. coli.*

For expression of the recombinant protein, the bacterial cells are propagated in growth medium until reaching a pre-determined optical density. Expression of the recombinant protein is then induced, e.g., by addition of IPTG (isopropyl-b-D-thiogalactopyranoside), which activates expression of proteins from plasmids containing a lac operator/promoter. After induction (typically for 1–4 hours), the cells are harvested by pelleting in a centrifuge, e.g., at 5,000×G for 20 minutes at 4° C.

For recovery of the expressed protein, the pelleted cells may be resuspended in ten volumes of 50 mM Tris-HCl (pH 8)/1 M NaCl and then passed two or three times through a French press. Most highly expressed recombinant proteins forms insoluble aggregates known as inclusion bodies. Inclusion bodies can be purified away from the soluble proteins by pelleting in a centrifuge at 5,000×G for 20 minutes, 4° C. The inclusion body pellet is washed with 50 mM Tris-HCl (pH 8)/1% Triton X-100 and then dissolved in 50 mM Tris-HCl (pH 8)/8 M urea/0.1 M DTT. Any material that cannot be dissolved in 50 mM Tris-HCl (pH 8)/8 M urea/0.1 M DTT may be removed by centrifugation (10, 000×G for 20 minutes, 20° C.). The protein of interest will, in most cases, be the most abundant protein in the resulting clarified supernatant. This protein may be "refolded" into the active conformation by dialysis against 50 mM Tris-HCl (pH 8)/5 mM $CaCl_2$/5 mM $Zn(OAc)_2$/1 mM GSSG/0.1 mM GSH. After refolding, purification can be carried out by a variety of chromatographic methods such as ion exchange or gel filtration. In some protocols, initial purification may be carried out before refolding. As an example, hexahistidine-tagged fusion proteins may be partially purified on immobilized Nickel.

While the preceding purification and refolding procedure assumes that the protein is best recovered from inclusion bodies, those skilled in the art of protein purification will appreciate that many recombinant proteins are best purified out of the soluble fraction of cell lysates. In these cases, refolding is often not required, and purification by standard chromatographic methods can be carried out directly.

Yeast Expression Systems

Polypeptides of the invention can also be expressed in yeast host cells, preferably from the *Saccharomyces* genus (e.g., *S. cerevisiae*). Other genera of yeast, such as *Pichia* or *Kluyveromyces* (e.g. *K. lactis*), can also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionine, 3-phosphoglycerate kinase (Hitzeman et al., *J. Biol. Chem.* 255:2073, 1980), or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657 or in Fleer et. al., *Gene,* 107:285–195 (1991); and van den Berg et. al., *Bio/Technology,* 8:135–139 (1990). Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* can be constructed by inserting DNA sequences from pBR322 for selection and replication in *E. coli* ($Amp^r$ gene and origin of replication) into the above-described yeast vectors.

The yeast α-factor leader sequence can be employed to direct secretion of one or more of the disclosed polypeptides. The α-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U.S. Pat. No. 4,546,082; and EP 324,274. Other leader sequences suitable for facilitating secretion of recombinant polypeptides from yeast hosts are known to those of skill in the art. A leader sequence can be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp+ transformants in a selective medium, wherein the selective medium consists of 0.67% yeast nitrogen base, 0.5% casamino acids, 2% glucose, 10 μg/ml adenine, and 20 μg/ml uracil.

Yeast host cells transformed by vectors containing ADH2 promoter sequence can be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian Expression Systems

Mammalian or insect host cell culture systems could also be employed to express recombinant polypeptides of the invention. Baculovirus systems for production of heterologous proteins in insect cells are reviewed by Luckow and Summers, *Bio/Technology* 6:47 (1988). Established cell lines of mammalian origin also can be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line (ATCC CRL 10478) derived from the African green monkey kidney cell line CVI (ATCC CCL 70) as described by McMahan et al. (*EMBO J.* 10: 2821, 1991).

Established methods for introducing DNA into mammalian cells have been described (Kaufman, R. J., *Large Scale Mammalian Cell Culture,* 1990, pp. 15–69). Additional protocols using commercially available reagents, such as Lipofectamine (Gibco/BRL) or Lipofectamine-Plus, can be used to transfect cells (Felgner et al., *Proc. Natl. Acad. Sci. USA* 84:7413–7417, 1987). In addition, electroporation can be used to transfect mammalian cells using conventional procedures, such as those in Sambrook et al. Molecular Cloning: A Laboratory Manual, 2 ed. Vol. 1–3, Cold Spring Harbor Laboratory Press, 1989). Selection of stable transformants can be performed using resistance to cytotoxic drugs as a selection method. Kaufman et al., *Meth. in Enzymology* 185:487–511, 1990, describes several selection schemes, such as dihydrofolate reductase (DHFR) resistance. A suitable host strain for DHFR selection can be CHO strain DX-B11, which is deficient in DHFR (Urlaub and Chasin, *Proc. Natl. Acad. Sci.* USA 77:4216–4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotcs, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and later promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology,* 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology,* 1997, pp. 529–534) and the tripartite leader (TPL) and VA gene RNAs from Adenovirus 2 (Gingeras et al., *J. Biol. Chem.* 257:13475–13491, 1982). The internal ribosome entry site (IRES) sequences of viral origin allows dicistronic mRNAs to be translated efficiently (Oh and Sarnow, *Current Opinion in Genetics and Development* 3:295–300, 1993; Ramesh et al., *Nucleic Acids Research* 24:2697–2700, 1996). Expression of a heterologous cDNA as part of a dicistronic mRNA followed by the gene for a selectable marker (eg. DHFR) has been shown to improve transfectability of the host and expression of the heterologous cDNA (Kaufman, *Meth. in Enzymology,* 1990). Exemplary expression vectors that employ dicistronic mRNAs are pTR-DC/GFP described by Mosser et al., *Biotechniques* 22:150–161, 1997, and p2A5I described by Morris et al., *Animal Cell Technology,* 1997, pp. 529–534.

A useful high expression vector, pCAVNOT, has been described by Mosley et al., Cell 59:335–348, 1989. Other expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984, has been deposited as ATCC 39890. Additional useful mammalian expression vectors are described in EP-A-0367566, and in U.S. patent application Ser. No. 07/701,415, filed May 16, 1991, incorporated by reference herein. The vectors can be derived from retroviruses. In place of the native signal sequence, a heterologous signal sequence can be added, such as the signal sequence for IL-7 described in U.S. Pat. No. 4,965,195; the signal sequence for IL-2 receptor described in Cosman et al., Nature 312:768 (1984); the IL-4 signal peptide described in EP 367,566; the type I IL-1 receptor signal peptide described in U.S. Pat. No. 4,968,607; and the type H IL-1 receptor signal peptide described in EP 460,846.

The polypeptides of the invention and the nucleic acid molecules encoding them can also be used as reagents to identify (a) proteins that the disclosed polypeptides or their constituent proteins regulate, and (b) other proteins with which it might interact. The disclosed polypeptides can be coupled to a recombinant protein, to an affinity matrix, or by using them as a bait in the yeast two-hybrid system. The use of the yeast two-hybrid system developed by Stanley Fields and coworkers is well known in the art and described in Golemis, E., et al Section 20.1 in: Current Protocols in Molecular Biology, ed. Ausubel, F. M., et al., John Wiley & Sons, NY, 1997 and in *The Yeast Two-Hybrid System*., ed. P. L. Bartel and S. Fields, Oxford University Press, 1997.

Antibodies and Peptide Binding Proteins

Purified polypeptides of the invention can be used to generate antibodies that bind to one or more epitopes of the disclosed polypeptide. Such anti-polypeptide antibodies includes polyclonal antibodies, monoclonal antibodies, fragments thereof such as F(ab')2, and Fab fragments, as well as any recombinantly produced binding partners. Antibodies are defined to be specifically binding if they bind pine tree polypeptides with a $K_a$ of greater than or equal to about $10^7$ $M^{-1}$. Affinities of binding partners or antibodies can be readily determined using conventional techniques, for example, those described by Scatchard et al., *Ann. N.Y. Acad. Sci.,* 51:660 (1949).

Polyclonal antibodies can be readily generated from a variety of sources, for example, horses, cows, goats, sheep, dogs, chickens, rabbits, mice, hamsters, guinea pigs, or rats, using procedures that are well-known in the art, for example, as described for example, in U.S. Pat. No. 5,585,100, incorporated by reference herein. In general, a composition comprising at least one of the polypeptides of the invention is administered to the host animal, typically through intraperitoneal or subcutaneous injection. In the case where a peptide is used as the immunogen, it is preferable to conjugated it to a suitable carrier molecule, such as a T-dependent antigen (Bovine Serum Albumin, cholera toxin, and the like). The immunogenicity of the disclosed polypeptides can also be enhanced through the use of an adjuvant, for example, Freund's complete or incomplete adjuvant or alum. Following booster immunizations, small samples of serum are collected and tested for reactivity to the disclosed polypeptides or their constituent epitopes. Examples of various assays useful for such determination include those described in: *Antibodies: A Laboratory Manual*, Harlow and Lane (eds.), Cold Spring Harbor Laboratory Press, 1988; as well as procedures such as countercurrent immuno-electrophoresis (CIEP), radioimmunoassay, radio-immunoprecipitation, enzyme-linked immuno-sorbent assays (ELISA), dot blot assays, and sandwich assays, see U.S. Pat. Nos. 4,376,110 and 4,486,530, each of which is incorporated by reference in their entirety.

Monoclonal antibodies (or fragments thereof), directed against epitopes of the disclosed polypeptides can also be readily prepared using well-known procedures, such as, for example, the procedures described in U.S. Pat. Nos. RE 32,011, 4,902,614, 4,543,439, and 4,411,993; *Monoclonal Antibodies, Hybridomas: A New Dimension in Biological Analyses,* Plenum Press, Kennett, McKearn, and Bechtol (eds.), 1980, each of which is incorporated by reference. Briefly, the host animals, such as mice, are injected intraperitoneally at least once, and preferably at least twice at about 3 week intervals with isolated and purified polypeptides optionally in the presence of adjuvant. Again, if peptide fragments are used they may need to be conjugated to a suitable carrier protein. Mouse sera are then assayed by conventional dot blot technique or antibody capture (ABC) to determine which animal is best to fuse. Approximately two to three weeks later, the mice are given an intravenous boost of pine tree polypeptides. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG). Fusion is plated out into plates containing media that allows for the selective growth of the fused cells. The fused cells can then be allowed to grow for approximately eight days. Supernatants from resultant hybridomas are collected and added to a plate that is first coated with goat anti-mouse Ig. Following washes, a label, such as, $^{125}$I-pine tree polypeptides is added to each well followed by incubation. Positive wells can be subsequently detected by autoradiography. Positive clones can be grown in bulk culture and supernatants are subsequently purified over a Protein A column (Pharmacia).

Monoclonal antibodies and specific-binding fragments of the invention can be produced using alternative techniques, such as those described by Alting-Mees et al., "Monoclonal Antibody Expression Libraries: A Rapid Alternative to Hybridomas", *Strategies in Molecular Biology* 3:1–9 (1990), which is incorporated herein by reference. Similarly, binding partners can be constructed using recombinant DNA techniques to incorporate the variable regions of a gene that encodes a specific binding antibody. Such a technique is described in Larrick et al., *Biotechnology,* 7:394 (1989).

It is understood of course that many techniques could be used to generate (antibodies against the polypeptides of the invention and that the above embodiments in no way limits the scope of the invention.

Nucleotides, Proteins, Antibodies, and Binding Proteins as Probes and Reagents

The disclosed nucleic acids, polypeptides, and antibodies directed against the disclosed polypeptides can be used in a variety of research protocols, such as in DNA arrays or as reagents. A sample of such research protocols are given in Sambrook et al. *Molecular Cloning: A Laboratory Manual,* 2 ed. Vol. 1–3, Cold Spring Harbor Laboratory Press, (1989), incorporated by reference. For example, the compiled sequences, polypeptides, etc., can serve as markers for cell specific or tissue specific expression of RNA or proteins. Similarly, this system can be used to investigate constitutive and transient expression of the genes encoding the cDNAs of SEQ ID NOS: 1–327 and the proteins encoded by these genes.

Further, the disclosed cDNA sequences can be used to determine the chromosomal location of the genomic DNA and to map genes in relation to this chromosomal location. The disclosed nucleotide sequence can be further used to identify additional genes related to the nucleotides of SEQ ID NOS: 1–334 and to establish evolutionary relatedness among species based on the comparison of sequences. The disclosed nucleotide and polypeptide sequences can be used to select for those genes or proteins that are homologous to the disclosed cDNAs or polypeptides, using well-established positive screening procedures such as Southern blotting and immunoblotting and negative screening procedures such as subtractive hybridization.

Method for Using Nucleic Acid Probes or Antibodies to Stage Embryos

Accurate staging of tree embryos is critical. It is known that different stages of tree embryos have different capacities as subjects for genetic transformation and genetic engineering. In addition, environmental requirements exhibited by embryos vary due to increasing physiologic age. Currently, the staging of tree embryogenesis is most accurately performed by an expert in the field who is very familiar with the morphological appearance of embryos at different stages. The cDNAs and related molecules of this invention can be used as markers for different stages of tree embryogenesis, thereby eliminating the need for a subjective eye to assess maturity and potentially allowing for more accurate staging of tree embryos. Moreover, by monitoring the expression of the underlying genes, it is possible to determine when an embryo has reached a certain level of development even if that level does not correspond to a visible difference in embryo morphology. The relational database of this invention aids the ability to monitor expression levels and tailor research approaches, such as the use of DNA arrays, to the specific needs of the objective, i.e., staging.

The information provided in this invention can be used in whole or in part to stage embryos. For example, one or a multiplicity of nucleic acid molecules from SEQ ID NOS: 1–327 having an expression profile consistent with a particular embryo stage can be used in this invention. A researcher may find it beneficial to use oligonucleotide probes or antibodies, for example, that specifically recognize proteins derived from genes expressed during middle embryonic stages, or that specifically monitor expression levels for embryos that have reached maturity associated with late developmental stages. A researcher can quickly determine that an embryo subset has progressed to or through an embryonic stage with the use of this invention and make appropriate changes in conditions if necessary, e.g. alter growth media or other environmental conditions.

Method for Monitoring Enhancing, or Determining Expression of Stage-Specific Genes Expression patterns of SEQ ID NOS: 1–327 indicate that gene activation can be classified as stage-specific, such as in the case of SEQ ID NO: 327, otherwise known as "LP2-3." The promoter that drives such a gene can perform valuable functions. For example, a promoter from LP2-3 operatively linked to a reporter gene presented within an embryo system is expected to produce the reporter product under the conditions for expression of gene LP2-3. Thus, the system allows a rapid determination of stage specific embryos by a simple phenotypic reporter screen, perhaps by visualization of green fluorescent protein (GFP) or by loss of fluorescent protein product. Similarly, a set of promoters from known, differently staged genes operatively linked to reporter genes will be effective for monitoring developmental changes within the system as the embryos mature. The LP2-3 promoter is identified as SEQ ID NOS: 328–334 in Table I. The promoter expression pattern is that of the natively linked gene, LP2-3.

Virtually any indicator or reporter gene can be used for this approach or for other methods associated with this invention provided they are compatible with the system studied. Generally, reporter genes are genes typically not present in the recipient organism or tissue and which encode for proteins resulting in some phenotypic change or enzymatic property. Examples of such genes and assays are provided by Schenborn, E. and Groskreutz, D., Mol. Biotechnol., 13:29, 1999; Helfand, S. L. and Rogina, B., Results Probl. Cell Differ., 29:67, 2000; Kricka, L. J., Methods Enzymol., 305:333, 2000; Himes, S. R. and Shannon, M. F., Methods Mol. Biol., 130:165, 2000; and Leffel, S. M. et al., Biotechniques, 23:912, 1997, which are incorporated in their entirety by reference. In one embodiment of this invention, the reporter used is GFP, or any ariant of the fluorescent protein.

Additionally, one skilled in the art would recognize that a promoter, like that from LP2-3, has potential to stimulate production of products not ordinarily observed at a particular stage. A promoter derived from a gene that expresses during a known stage, for example an early stage, can be operatively linked to a gene that does not normally express during that stage, yielding controlled expression of any targeted gene. It may be shown that earlier or later expression, or prolonged expression of a particular gene may give a desirable genotype or phenotype in a mature plant, may result in increased vigor in culture, or may be sufficient to alter the normal maturation process of the embryo. Prolonged expression of any desired gene also may be achieved from linking a constitutively expressed promoter to the targeted gene. Further, the ability to manipulate gene expression during embryogenesis allows for a detailed study of the effects of an individual gene or multiple genes on embryogenesis, leading to a better understanding of the developmental processes involved in embryogenesis.

Method of Correlating Gene Expression with Improved Tree Stock or Culture Conditions Importantly, the cDNAs and related molecules of the invention can also be used as markers to examine genetic heterogeneity and heredity through the use of techniques such as genetic fingerprinting. These markers can also be correlated with improved agronomic traits including good initiation frequency, embryonic maturation, high frequency of germination, rapid growth rates, herbicide tolerance, insect resistance, pathogen resistance, climate and environmental adaptability wood quality, and wood fiber quality and content, to name a few. Additionally, the expression of these developmentally regulated genes can be compared among genetically identical clones grown under different culture conditions to determine the best protocols and media for somatic embryogenesis.

Cryogenic storage of pine embryos is effective for maintaining stocks of embryos determined by this invention to have the desired fitness traits or exist at the appropriate developmental stage. With such storage, one can specifically target desirable embryos for expansion many years after they are frozen. For example, a culture of somatic embryos can be divided into at least three portions, one of which is cryogenically stored, one which is used to study gene embryonic gene (and protein) expression, and one that is used to produce seedlings for field testing. Clones producing valuable mature plants could be selected and expanded from frozen stocks. Additional clones exhibiting similar expression patterns could be selected for future expansion and cultivation.

As will be evident to the ordinary practitioner, there are numerous ways in which the nucleic acids, polypeptides and antibodies of this invention might be used to characterize the gene expression of embryos. Ideally the stage-specific gene expression of embryos of several different genotypes and at several different stages of embryogenesis are characterized. For example, sets of oligonucleotide primers designed using any one of SEQ ID NOS: 1–327 may be used in RT-PCR assays to characterize expression of a gene product. In situ hybridization assays or antibody staining protocols may also be used to characterize RNA and/or protein expression and localization.

Embryos of the same genotype in which gene expression has been characterized may also used be to generate plantlets that are used in field testing. Once the embryos have developed into mature trees, the various genotype trees can be evaluated for important traits such as growth rates, herbicide tolerance, insect resistance, pathogen resistance, climate and environmental adaptability, wood quality, and wood fiber quality and content, among others. Finally the phenotypic data collected from the field testing can be correlated with gene expression during early embryogenesis to further enhance the database of the present invention. This will allow further identification of gene products which whose expression is correlated, either positively or negatively, with commercially valuable tree characteristics.

It will be clear to those skilled in the art that identification of such gene products can have several uses. Determining the correlation between a desirable phenotype and a genotype would allow for the "pre-selection" of tree embryos for field testing. It would also be useful in evaluating experimental tissue culture conditions for somatic embryogenesis; in other words, the expression level of a gene known to correlate with the development of trees with desirable characteristics could serve as the criterion on which culture media is evaluated, as opposed to assessing the phenotype of fully matured trees. The ability to evaluate culture conditions without having to develop fully mature trees and do field testing would save a great deal of research time and expense. And of course, the knowledge of the correlation between gene expression and desirable tree phenotypes would serve to identify target genes for genetic engineering.

Genetically Engineering Trees and Other Plants

There are several methods known in the art for the creation of transgenic plants. These include, but are not limited to: electroporation of plant protoplasts, liposome-mediated transformation, polyethylene-glycol-mediated transformation, microinjection of plant cells, and transformation using viruses. Because the invention is especially concerned with the transformation of woody species, the two prevalent methods for transforming forest trees, namely *Agrobacterium*-mediated transfer and direct gene transfer by particle bombardment, will be discussed in more detail, though it is understood that the present invention encompasses generation of transgenic plants via standard methods commonly known in the art.

*Agrobacterium* Mediated Transfer

*A. tumefaciens* and *A. rhizogenes* are two soil microorganisms that naturally infect a wide variety of plants including dicotyledonous plants, gymnosperms and some monocotyledonous plants. Infection by these organisms results in the growth of crown gall tumors or in hairy root disease, respectively. Each of these organisms carries a large plasmid, the tumor inducing (Ti) plasmid, in the case of *A. tumefaciens* and the root-inducing (Ri) plasmid in the case of *A. rhizogenes*. These plasmids have two critical features, a set of virulence genes and a segment of DNA called T-DNA that is delimited by conserved regions of approximately 25 base pairs known as the left and right borders. During infection, the T-DNA is transferred to the plant cell where it is able to stably integrate in single copy in the plant genome. Transfer of T-DNA requires the function of the virulence genes.

In its natural state, T-DNA contains genes that mediate progression of disease such as growth hormones or genes controlling root morphogenesis. Using recombinant DNA technology, however, T-DNA may be modified to contain an expression cassette encoding a foreign gene of interest. There are several T-DNA vector systems commonly in use for the transformation of plants. Several of these vector systems are reviewed in Hansen et al., *Current Topics in Microbiology and Immunology* 240: 21–57 (1999) which is hereby incorporated by reference. T-DNA vectors must include the left and right borders. In addition they must either be capable of replication in *Agrobacterium* or be designed so as to recombine with a plasmid that does so. The latter type of vector is known as a co-integrate vector. For transformation to proceed, there must also be a source of virulence (vir) genes. The vir genes may be on the same plasmid with the T-DNA or more likely supplied by a helper plasmid. For example, binary T-DNA vector systems are comprised of two plasmids, one containing the vir genes and the other containing T-DNA. Some plants known to be recalcitrant to *Agrobacterium*-mediated transformation may be transformed if additional copies of some or all virulence genes are provided. Extra copies of VirG and VirE can be particularly useful.

Additionally, it is convenient to include in the T-DNA a selectable marker that will allow identification and selection of transformed plant cells. The selectable marker should be one that works in both *Agrobacterium* and the target plant. For example, the genes encoding chloramphenicol acetyltransferase and neomycin phosphotransferase are suitable marker genes that confer resistance to chloramphenicol and kanamycin, respectively. Additionally, a selectable marker may be provided on a separate T-DNA from the T-DNA encoding the gene of interest. Co-transformed T-DNAs can integrate at separate sites in the plant genome. This can be useful because it will later allow segregation of the marker gene in progeny enabling the generation of transgenic trees expressing the gene of interest but not the marker gene.

The gene of interest and the selectable marker genes must also be under the control of promoters that function in the transformed plant cell. Examples of suitable promoters include, but are not limited to: the abscisic acid (ABA)-inducible promoter from the early methionine (Em) gene from wheat (Marcotte et al., *Plant Cell* 1:976–979 (1989); the cauliflower mosaic virus (CaMV) 35S promoter (Odell et al., *Nature* 313:810–812 (1985); and the nopaline synthase (nos) promoter (Sanders et al., *Nucl. Acids Res.* 15(4):1543–58 (1987). Tissue-specific plant promoters or plant promoters responsive to chemical, hormone, heat or light treatments may be used. Additionally, the gene of interest may be expressed under the control of its endogenous promoter to ensure proper regulation.

The process of transformation requires plant cells that are competent and that are either embryogenic or organogenic. The plant cells to be transformed are then co-cultivated with *Agrobacterium* containing an engineered T-DNA vector system for 1–5 days. Following the co-cultivation period, the cells are incubated with the antibiotic against which the selectable marker confers resistance, and transformed lines are selected for further cultivation. The use of *Agrobacterium* mediated transfer in woody trees is described in Loopstra et al., *Plant Molecular Biology* 15:1–9 (1990), Gallardo et al., *Planta* 210:19–26 (1999) and Wenck et al., *Plant Molecular Biology* 39:407–419 (1999), each of which is hereby incorporated by reference.

Direct Gene Transfer by Particle Bombardment

Direct gene transfer by particle bombardment provides another method for transforming plant tissue. This method can be especially useful when plant species are recalcitrant to transformation by other means. In this technique a particle, or microprojectile, coated with DNA is shot through the physical barriers of the cell. Particle bombardment can be used to introduce DNA into any target tissue that is penetrable by DNA coated particles, but for stable transformation, it is imperative that regenerable cells be used. Typically, the particles are made of gold or tungsten. The particles are coated with DNA using either $CaCl^2$ or ethanol precipitation methods which are commonly known in the art.

DNA coated particles are shot out of a particle gun. A suitable particle gun can be purchased from Bio-Rad Laboratories (Hercules, Calif.). Particle penetration is controlled by varying parameters such as the intensity of the explosive burst, the size of the particles, or the distance particles must travel to reach the target tissue.

The DNA used for coating the particles should comprise an expression cassette suitable for driving the expression of the gene of interest. Minimally this will comprise a promoter operably linked to the gene of interest. As with *Agrobacterium* mediated transformation. Suitable promoters include, but are not limted to, the the abscisic acid (ABA)-inducible Em promoter from wheat (Marcotte et al., *Plant Cell* 1:976–979 (1989), the CaMV35S promoter (Odell et al., *Nature* 313:810–812 (1985), and the NOS:promoter (Sanders et., *Nucl. Acids Res.* 15(4):1543–58 (1987).

Methods for performing direct gene transfer by particle bombardment are disclosed in U.S. Pat. No. 5,990,387 to Tomes et al. Additionally, Ellis et al. describe the successful use of direct gene transfer to white spruce and larch trees in *Bio/Technology* 11, 84–89 (1993).

Researchers skilled in the area of DNA or gene transformation will recognize that additional procedures, or combination of procedures, may be useful for the successful tranformation of genetic stock.

Antisense Expression

The cDNAs of the invention may be expressed in such a way as to produce either sense or antisense RNA. Antisense RNA is RNA that has a sequence which is the reverse complement of the mRNA (sense RNA) encoded by a gene. A vector that will drive the expression of antisense RNA is one in which the cDNA is placed in "reverse orientation" with respect to the promoter such that the non-coding strand (rather than the coding strand) is transcribed. The expression of antisense RNA can be used to down-modulate the expression of the protein encoded by the mRNA to which the antisense RNA is complementary. This phenomenon is also known as "antisense suppression." It is believed that down-regulation of protein expression following antisense RNA is caused by the binding of the antisense RNA to the endogenous mRNA molecule to which it is complementary, thereby inhibiting or preventing translation of the endogenous mRNA.

The antisense RNA expressed need not be the full-length cDNA and need not be exactly homologous to the target mRNA. Generally, however, where the introduced sequence is of shorter length, a higher degree of homology to the endogenous mRNA will be needed for effective antisense suppression. Preferably, the introduced antisense sequence in the vector will be at least 30 nucleotides in length, and improved antisense suppression will typically be observed as the length of the antisense sequence increases. The length of the antisense sequence in the vector may be greater than 100 nucleotides. Vectors producing antisense RNA's could be used to make transgenic plants, as described above, in situations when desirable tree characteristics are produced when the expression of a particular gene is reduced or inhibited.

Methods

Tissue Samples

The cDNAs of the current invention can be derived from any sets of plant tissue. The cDNAs of SEQ ID NOS: 1–334, for example, were originally derived from embryonic tissues of pine tree embryos staged 1–9.9 as classified in Pullman and Webb TAPPI R&D Division 1994 Biological Sciences Symposium, pages 31–34, which is hereby incorporated by reference. LPS and LPZ clones are derived from somatic and zygotic embryos, respectively. As noted, embryos may be of either somatic or zygotic derivation, and the embryos may be grown in either semi-solid or liquid tissue culture systems. Applicable methods for growing embryos in semi-solid or liquid tissue culture systems are disclosed in U.S. Pat. Nos. 5,036,007; 5,236,841; 5,294,549; 5,413,930; 5,491,090; 5,506,136; 5,563,061; 5,677,185; 5,731,203; 5,731,204; and U.S. Patent Application 60/212,651 filed Jun. 19, 2000, which are hereby incorporated by reference.

RNA Isolation

In one embodiment, RNA isolated from staged cell populations provides the starting material for reverse transcription, differential display, and cloning of amplified cDNA. Methods and kits for isolating total RNA from cellular populations, or for generating poly(A)+ RNA, are commonly known in the art. For example, several procedures for isolating RNA are disclosed in Chapter 4 of *Current Protocols in Molecular Biology* edited by F. A. Ausubel et al., John Wiley and Sons, Inc. (1987) (incorporated herein by reference). As an example, the TRI Reagent7 available from Molecular Research Center, Inc. (Cincinnati, Ohio) is a suitable reagent (used according to the manufacturer's instructions) for isolation of RNA from plant tissues.

Differential Display

Differential display provides a method to identify individual messenger RNAs that are differentially expressed among two or more cell populations. In the practice of the present invention, these cell populations may be provided by pine tree or other plant embryos of different developmental stages. The differential display procedure is taught in Liang et al., *Science,* 257:967–71 (1992) and in U.S. Pat. No. 5,262,311, which are hereby incorporated by reference. Briefly, mRNA sequences are PCR-amplified using two types of oligonucleotide primers known as "anchor" and "arbitrary" primers. Anchor primers are designed to recognize the polyadenylate tail of messenger RNAs. Arbitrary primers are short and arbitrary in sequence and anneal to complementary sequences in various mRNAs. Products amplified with these primers will vary in size and can be differentiated on an agarose or sequencing gel based on their size. If different cell populations are amplified with the same anchor and arbitrary primers, one can compare the amplification products to identify differentially expressed RNA sequences.

Cloning

PCR-amplified bands representing differentially expressed RNA samples are excised from the gel, transferred to tubes and reamplified using the same primer pairs and PCR conditions as used in the differential display procedure. Methods for the cloning of PCR products are commonly known in the art and there are several commercially available reagents and kits for cloning PCR products. For instance, the pCR-Scipt™ Cloning kit from Stratagene, La Jolla, Calif.) is suitable for this purpose. Using this kit, *E. coli* transformants containing plasmids with PCR fragment inserts can rapidly be identified using blue/white color selection followed by plasmid purification and restriction digests. The pCR-Script vector contains T3 and T7 polymerase recognition sites allowing for in vitro transcription of the inserted fragment.

Sequence Determination

Methods for sequencing DNA, including cloned PCR products, are commonly known in the art. The selection of cloning vectors having M13, T7 or T3 primer annealing sites flanking the PCR-amplified insert can be used in sequencing reactions directly. Most sequencing procedures in use today are modifications of Sanger's dideoxy chain termination sequencing reaction as disclosed in and Sanger et al., *Proceedings of the National Academy of Sciences,* 74:5463–5467 (1977), which is hereby incorporated by reference.

Homology Searching and Identification of Protein Coding Sequences

As understood by one of ordinary skill in the art, the sequence of a cloned cDNA insert obtained, may be compared against public databases such as Genbank to discern any identity or homology to known sequences. Programs, such BLAST, for performing such a search are available on the National Center for Biotechnology Information's web page. The results from Genbank search may reveal the potential function of a polypeptide or RNA molecule encoded by the cDNA. In addition to searching gene sequence database, the use of commercially available analysis software is well known in the art. For example, software packages such as the Wisconsin Package™ (Genetic Computer Group, Madison, Wis.) include programs such as FRAMES and CodonPreference that help to identify protein coding sequences in a query nucleotide sequence. FRAMES displays open reading frames for the six DNA translation frames, allowing one to quickly assess the presence or absence of stretches of open-reading frames that are likely to be protein encoding regions. CodonPreference is a more sophisticated program that identifies and displays possible protein coding regions based on similarity of the codon usage in the sequence to a codon frequency table (Gribskov et al., 1984).

EXAMPLE 1

Differential Gene Expression Analysis in Pine Tree Embryogenesis cDNA libraries were prepared from staged pine tree embryos, as described above. The differential display technique was used to identify 327 novel cDNAs that were preferentially-expressed during early, middle, or late stages of pine tree embryogenesis, as set forth below. Clone nomenclature is divided into subsets based on tissue type; a clone is designated LPS to indicate somatic origins and LPZ for zygotic origins.

Plant Materials

Somatic embryos were collected at different stages of development. Cultures of somatic embryos of were initiated from Loblolly pine immature zygotic embryos as described by Becwar et al., *Forestry Science* 44:287–301 (1994) (incorporated by reference) or with minor modifications in media mineral composition. Somatic embryos were grown in cell suspension culture medium 16 (Pullman and Webb, Tappi R&D Division 1994 Biological Sciences Symposium) and a maturation medium similar to that of a standard maturation media. Resulting somatic embryos were selected and classified as stages 1–9 according to morphological development following the teachings of Pullman and Webb, Tappi R&D Division 1994 Biological Sciences Symposium pp. 31–34. Somatic embryos were sorted into tubes containing the same stages and stored at −70° C.

RNA Isolation

Total RNA was isolated from all stages of somatic embryos of loblolly pine and grouped into early, middle, and late phases of development. The early phase is represented by a liquid suspension culture containing embryos of stages 1 through stage 3. Middle phase contains embryos of stages 4 through stage 6, while stages 7 through 9 formed the late phase. 60–100 mg aliquots of staged frozen embryos were ground in 1.0 ml of TRI Reagent® Isolation Reagent (Molecular Research Center, Inc.), a commercial product that includes phenol and guideline thiocyanate in a monophase solution and extracted according to the manufacturer's instructions.

Reverse Transcription of mRNA (RT-PCR)

The total RNA was used as a template to synthesize single stranded DNA mediated by MMLV reverse transcriptase (100 U/μl). The method involves the reverse transcription by PCR of the mRNA with an oligo-dT primer (H-$T_{11}$G: 5' B AAGCTTTTTTTTTTTG 3') anchored to the beginning of the poly(A) tail, followed by a PCR reaction in the presence of a second short (13-mer) primer which is arbitrary in sequence [$AP_1$ (5' B MGCTTGATTGCC-3') or $AP_2$ (5' B MGCTTCGACTGT-3')]. Reverse transcription and Differential Display were conducted using the GenHunter RNAimage Kit I.

A 19 μl reverse transcription reaction (10 μl sterile water, 2.0 μl 5× RT buffer, 1.6 μl dNTP (250 μM), 2.0 μl anchored primer (2.0 μM), 2.0 μl RNA template at 100 ng/μl) was prepared for each embryo phase sample. The reaction mixture was heated to 65° C. for 5 minutes in a thermocycler, cooled to 37° C. and paused after 10 minutes while 1.0 μl MMLV was added. The program was allowed to resume at 37° C. for 50 minutes. The reaction was then heated to 75° C. for 5 minutes, cooled to 4° C. and stored at −20° C.

Incorporation of Radiolabeled Nucleotides by PCR

Differential Display PCR was performed in a 20 μl reaction containing 2 μl of the reverse-transcribed cDNA template; 10 μl sterile water 2.0 μl 10× PCR buffer, 1.6 μl dNTP (25 μM), 2.0 μl anchored primer H-T11 G, (2.0 μM), 2.0 μl 13 mer arbitrary primer ($AP_1$ or $AP_2$ (2.0 μM), 0.2 μl Taq DNA polymerase, and 0.2 μl $\alpha^{32}$P-dATP (2000 Ci/mmole). The cDNA was amplified by PCR: 94° C. for 3 minutes, 40 cycles of 94° C. for 30 seconds, 40° C. for 2 minutes, and 72° C. for 30 seconds, followed by 72° C. for 5 minutes. The reaction was cooled to 4° C. and stored at −20° C.

Differential Display

The PCR products were separated on a Stratagene (La Jolla, Calif.) pre-cast 6% polyacrylamide sequencing gel at 30 watts constant power for approximately 2.5 to 3 hours. 3.5 μl of sample was mixed with 2.0 μl of loading dye and incubated at 80° C. for 2 minutes immediately before loading onto the gel. The gel was rinsed in water and dried. Dilute $^{33}$P-dATP with loading dye was spotted at the corners as alignment markers and the gels were exposed to Kodak BioMax™ autoradiography film. An exemplary gel is shown in FIG. 1.

Bands that appeared to be possible markers for phase specific gene expression were marked on the film and aligned over the gel. The bands were excised by cutting through the film. The gel pieces were scraped from the gel and transferred to tubes and re-amplified using the same primer pairs and PCR conditions as used for incorporation of radiolabeled nucleotides.

Cloning of DNA Fragments from Differential Display

The PCR products from the gel fragments were purified, polished, ligated and cloned into XL 10-Gold Kan ultracompetent cells by heat shock with the Stratagene pCR-Script Amp SK(+) Supercompetent Cell Cloning Kit according to manufacturer's instructions. The transformed cells were spread on LB agar plates containing ampicillin, IPTG, and X-Gal each at 50 μg/ml. The plates were incubated overnight at 37° C. Plasmids containing PCR inserts were identified using blue-white colony screening. The presence of inserts was confirmed by digesting the clones with restriction endonucleases, Msc I and Nla III, followed by standard DNA gel electrophoresis. Transformants representing early, middle, and late phase embryos were sequenced using standard dideoxy protocols known in the art with the T3 primer.

Sequence Analysis

All sequences were analyzed using a program-database pair search of the NCBI BLAST 2.0 server, blastn-nr, blastn-others ests, and blastx-nr. In each case, the query sequence was filtered for low complexity regions by default and entered in FASTA format. Other formatting options were set by default; alignment view-pairwise, descriptions-100, and alignments-50. Using these parameter settings, significant similarity to known DNA, RNA, or protein sequences was found for several of the nucleic acid molecules of SEQ ID NOS: 1–334, for example, those described herein. (Alignment data not shown).

EXAMPLE 2

Characterization of Full Length LP2-3 cDNA Sequence

SEQ ID NO: 327, designated LP2-3, was first identified through differential display with $T_{12}$MG and $AP_1$ primers (GeneHunter). The differential display band appeared to be present only in liquid suspension cultures of Loblolly Pine somatic embryos. The conditions for mRNA isolation, reverse-transcription, differential display-PCR, and gel separation/visualization for producing this band were all as described in Example 1. Likewise, the band containing the original LP2-3 fragment was excised from the differential display gel, amplified, and cloned into pCR-Script AMP SK(+) according to standard protocols known in the art.

Northern Hybridizations Demonstrating Early-Specific Expression

Figure 11:
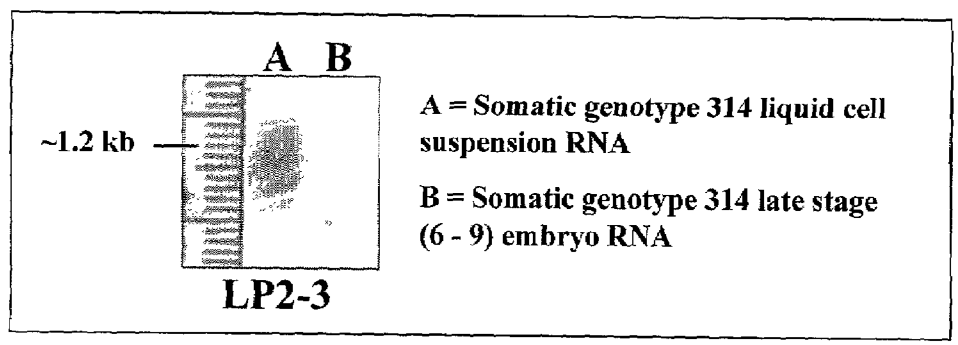
FIG. 11 displays a northern blot for the LP2-3 gene during stages 1–3.
Figure 14:
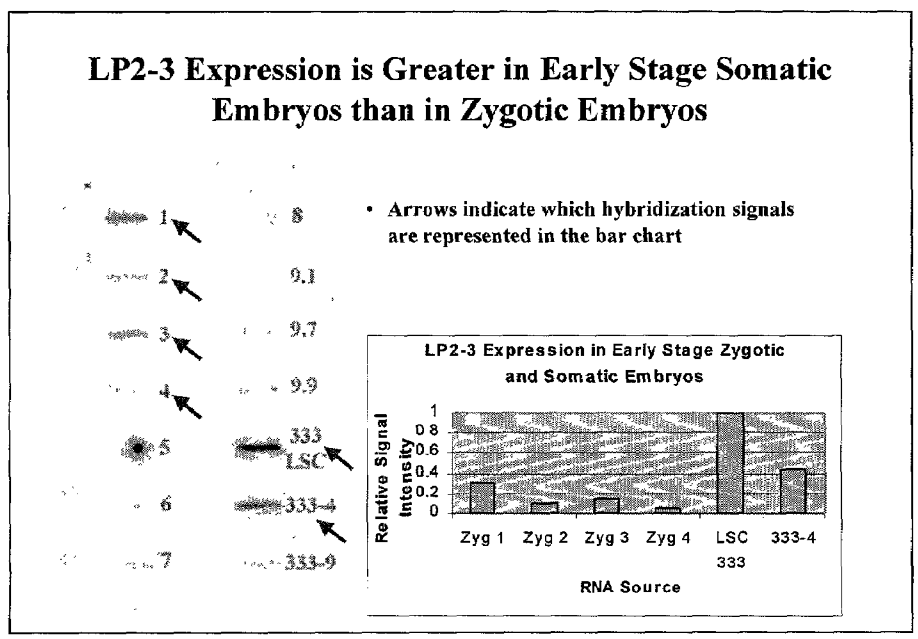
FIG. 14 depicts the quantified expression of early zygotic embryos compared to early somatic embryos. Panel A depicts an image of the slot blot and panel B depicts quantitation of the image.

Northern analysis demonstrated that the LP2-3 differential display clone hybridized to an approximately 1.2 Kb mRNA from liquid suspension culture embryos but was undetectable in late (6–9) stage embryo RNA. (FIG. 11) In general, LP2-3 is most highly expressed in early stage embryos in liquid culture. LP2-3 mRNA is found most abundantly in early stage somatic embryos, especially for embryos grown in liquid multiplication medium. (FIG. 12) Further, transcription decreases rapidly as embryos are transferred to maturation medium (stage 3 and stage 4) and begin to mature. LP2-3 transcripts are virtually undetectable at stage 6–9 somatic embryos grown on maturation medium. (See FIG. 12) Additional studies indicate that LP2-3 mRNA is expressed zygotically, particularly in early stage zygotic embryos, but is undetectable in mature vegetative tissues. (FIGS. 13 and 14) Specifically, the signal intensity from liquid suspension somatic embryo RNA was about 3 times greater than the signal from the analogous stage 1 zygotic embryo RNA. (FIGS. 13 and 14) LP2-3 transcripts were not detectable in total RNA from needles, stems, or roots of one year old seedlings, including those exposed to cold, ozone, wound stresses, or the hormone jasmonic acid (not shown).

LP2-3 Differential Display and 'Full-Length' cDNA Sequences

A 'full-length' cDNA was captured from SMART™ cDNA made from somatic embryo liquid suspension by using a biotinylated LP2-3 differential display fragment as a capture probe. The "full-length" cDNA was cloned and sequenced according to standard protocols known in the art. This sequence was designated at LP2-3$^+$.

GenBank blastx searches conducted with the above sequence translated in all 6 reading frames indicated that LP2-3$^+$ likely encodes a member of the major intrinsic protein family. This family of proteins encodes membrane channels for the transport of water and/or ions across cell membranes. They may play a significant role in osmoregulation and may play a role in the cellular responses to water and salt stresses. As is known in the art, the MIPs are induced by dessication, flooding, and high levels of the plant hormone ABA. In contrast, the LP2-3 sequence was not detected in desiccated late-stage embryos which have high levels of ABA and, thus, appears to be regulated by some embryo-specific signal.

EXAMPLE 3

Hypothesis Development for Improved Protocols

Figure 6:
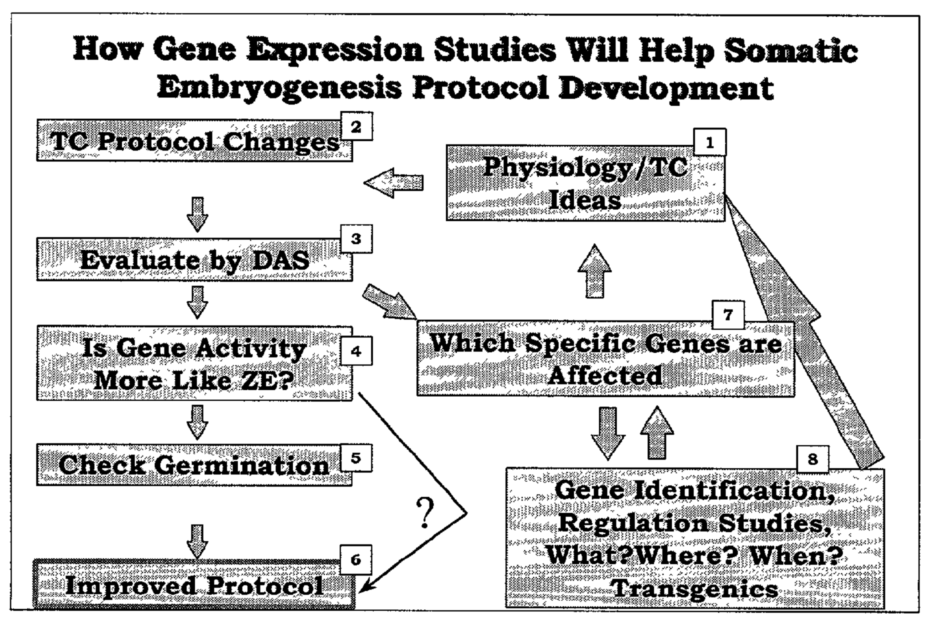
FIG. 6 shows schematic of gene study for improved somatic embryogenesis.

Currently the improvement of tissue culture practices arises via hypothesis, evaluation and adoption. Hypotheses arise from observation of size, shape, weight, etc. and physiological measurement of ion or sugar content (FIG. 6, box 1). These observations are limited in scope and this limits the improvements that can be made to the tissue culture process. Gene expression is closely linked to metabolic condition, thus the observation of which genes are induced or repressed under a given growth condition, naturally, on the tree, or in a culture vessel, provides insight into the metabolic state of the embryo. This information can be used to create new hypotheses that can be evaluated by modifying tissue culture.

To this end, mRNA levels of two cDNAs (LPZ-202 and LPZ-216), similar to "Late Embryogenesis Abundant" (LEA) proteins, identified in other plants, were monitored. These genes are induced by the plant hormone ABA. Two peaks of mRNA were observed in these clones rather than the typical single peak in most plants. (See FIG. 4 for clone LPZ-216; clone LPZ-202 is similar but data is not shown.) It was subsequently confirmed that two peaks in ABA activity are observed during development and that these correspond in timing to the elevation in mRNA for LPZ-202 and LPZ-216. Thus mRNA abundance profiles are providing insight into embryo physiology. (See FIG. 7) The effect of giving two pulses of ABA to our somatic embryos is assessed; a tissue culture modification that we might not have considered as important had the gene expression data been unavailable. Internal data shows fluctuations in the abundance of mRNA for cDNAs listed in this collection (data not shown.)

Zygotic and Somatic Loblolly Pine Embryos

Loblolly pine cones were collected weekly from a breeding orchard near Lake Charles, La., and shipped on ice for experimentation. Embryos were excised and evaluated for developmental stage (Pullman et al. 1994). Stage 9 embryos were separated by the week they were collected—9.1 (week 1), 9.2 (week 2), etc. Staged zygotic embryos were sorted into vials partially immersed in liquid nitrogen and stored at −70° C. Somatic embryos for loblolly pine were initiated as described by Becwar et al. (1995) or with minor modifications. Somatic embryos were grown, selected, and staged as described by Pullman et al. (1994) and stored at −70° C.

cDNA Probe Preparation and Hybridization 30 ng of purified Lea protein cDNA fragments was labeled with $^{32}$P dCTP using the Ready-To-Go cDNA Random Labeling kit (Pharmacia). The labeled cDNAs were purified using NICK Column (Pharmacia) and heat denatured for hybridization. The RNA slot blot was pre-hybridized in hybridization buffer (0.5 M sodium-phosphate, pH 7.2, 5% SDS, and 10 mM EDTA) at 65° C. for 2 hours in a hybridization oven (Model 400, Robbins Scientific, Sunnyvale, Calif.) and the hybridized in the same conditions with the cDNA probes. After hybridization, the membranes were washed at 65° C. in 0.2×SSC and 0.1% SDS. Each wash was 15 min. The membranes were then exposed to Image Plate.

The probes can be stripped from the RNA slot blot by pouring boiling 0.5% SDS onto the membrane twice and incubating without heating for 30 min. The stripped blot was then exposed to Image Plate for overnight to check the completeness of the de-probing before next round of hybridization.

To ensure the equal loading of the each RNA sample, the same membranes were stripped and hybridized with a $^{32}$P-dCTP labeled 26S ribosomal rDNA fragment. These results were used as controls to normalize the Lea protein gene expression levels.

As a means of evaluating the usefulness of these arrays, we followed the expression of three cDNAs that have strong sequence similarity to late embryo-abundant proteins, (Lea) proteins from cotton (Baker et al 1988). Lea proteins and mRNAs appear in embryos at a stage when ABA is high and the genes can be induced in vegetative tissue by application of ABA. The transcript level of Lea genes LPZ-202 and LPZ-216 showed two peaks, rising from stage 5 and returning to a base line about stage 9.2 then rising again around stage 9.5. (See FIG. 4 for clone LPZ-216).

To confirm the fluctuation in lea transcript levels by Northern analysis. RNA was extracted from zygotic embryos at different stages of development. A pine 'dehydrin' cDNA from the North Carolina State University cDNA collection was used as probe for some experiments. Dehydrins are a class of lea protein, originally identified as water deficit inducible proteins. Since the expression of this class of protein is well characterized, in contrast to our lea genes, the dehydrin expression profile could act as a reference point. After probing with dehydrin, blots were stripped and probed with a 26S rDNA probe from *Arabidopsis* to check the loading of the original gel. The normalized expression pattern of dehydrin in the zygotic embryogenesis is illustrated in the top panel of FIG. 4. The expression of the dehydrin gene was induced at stage 5 and reached a peak at stage 6. It declined at stage 7–8, just prior to the onset of the desiccation. Then the mRNAs level remained low from stage 9.1 through 9.5. The dehydrin mRNA levels rose again late in development, from stage 9.6 on, apparently dropping in very late development. A similar pattern of expression was observed in a parallel experiment when our lea-like clone, LPZ-216, was used as a probe.

Figure 5:
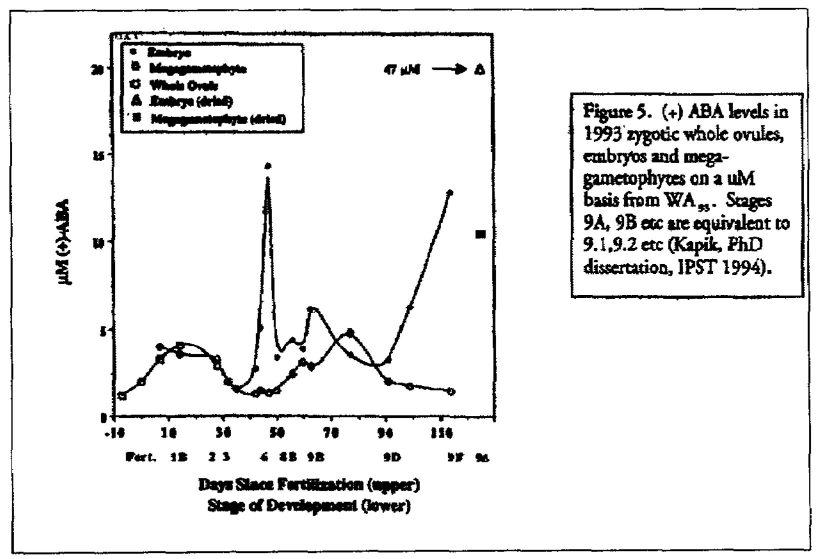
FIG. 5 displays ABA concentration of loblolly pine embryos.

This pattern reveals two significant peaks at the early development of the embryos and high expression levels for the stage 9.6 and beyond. The expression pattern of these two lea genes in loblolly pine embryos is consistent with the changes in ABA concentration observed in pine during embryogenesis. (See FIG. 5)

EXAMPLE 4

Evaluation of Metabolic State of Somatic

Embryos as Compared to Zygotic Embryos for Fitness Determination

The model and goal for somatic embryogenesis is to produce an embryo that in vigor, germinatability, etc., resembles a zygotic embryo. Standard measurements reveal relatively little about the embryos; thus the metabolic state of somatic and zygotic embryos is unknown. The metabolic state of zygotic (natural) embryos can be evaluated by DNA arrays containing the cDNA clones described in this application. A database of mRNA levels for the genes represented on the DNA arrays can then be established. Embryos growing under a new tissue culture protocol (FIG. 6, box #2) can be evaluated by DNA array southerns (FIG. 6, box #3). The array elucidates patterns of gene activity and reveals whether those patterns are similar to the natural state (FIG. 6, box #4). The germination, or further development can be checked (FIG. 6, box #5) to confirm the conclusion. Where a link between specific gene activity and embryo performance has been demonstrated, protocols can be modified with efficiency as seen in FIG. 6, box 6.

To illustrate this process, elevation of plant hormone ABA in maturation medium was evaluated as a protocol modification, as described below. This modification proved beneficial, elevating the number and quality of the embryos produced. The mRNA abundance for cDNAs was assessed by DNA array using RNA isolated from control and elevated ABA conditions; several differences were observed in the mRNA levels of specific genes. Further, abundance of mRNA in the elevated ABA condition, more closely resembled the mRNA abundance observed for the these same genes in zygotic embryos. Thus a protocol which produces higher quality embryos produces, in these embryos, a mRNA profile that more closely resembles that observed in natural embryos.

Zygotic and Somatic Loblolly Pine Embryos

Loblolly pine cones were collected weekly from a breeding orchard near Lake Charles, La., and shipped on ice for experimentation. Embryos were excised and evaluated for developmental stage (Pullman et al. 1994). Stage 9 embryos were separated by the week they were collected—9.1 (week 1), 9.2 (week 2), etc. Staged zygotic embryos were sorted into vials partially immersed in liquid nitrogen and stored at −70° C. Somatic embryos for loblolly pine were initiated as described by Becwar et al. (1995) or with minor modifications. Somatic embryos were grown, selected, and staged as described by Pullman et al. (1994) and stored at −70° C.

Mass Isolation of Genes Differentially Expressed in Loblolly Pine Zygotic Embryos The following RNA differential display method is sensitive enough to produce banding patterns from one mid- to late-stage embryo or 10–20 early stage embryos. This technique, which extracts mRNA directly from tissue using oligo(dT) beads, avoids losses inherent in conventional RNA extraction methods, is fast, reliable, and inexpensive. Differences in gene expression during development, as well as between somatic and zygotic embryos, can be easily detected.

To achieve these results, 50–100 μl lysis buffer containing 100 mM Tris-HCl, pH 8.0, 500 mM LiCl, 10 mM EDTA, 1% SDS and 5 mM DTT was added to 10–100 mg of staged embryos in a 1.5 ml tube. The mixture was ground thoroughly with an electric drill containing a plastic pestle bit (VWR, Cat# KT95050-99) that had been sterilized by autoclaving. An additional 50–100 μl lysis buffer was added and ground briefly. The grinder and vortex was washed with 100 μl lysis buffer. If multiple samples were processed, each is stored on ice until ready for the next step. The grinding tip was washed with sterile water and dried for the next sample.

After all the samples were ground, they were spun at 4° C. for 15 minutes in a bench top centrifuge at 14,000 rpm. 8 μl oligo(dT) coated Dynal beads (mRNA DIRECT Kit, Dynal, N.Y.) was placed in a 1.5 ml tube. The Dynal beads were washed twice with a 100 μl of the above mentioned lysis buffer and suspended in an equal volume of the lysis buffer used in tissue grinding. If more than one sample is handled, the beads for all the samples can be washed together and dispensed in several 1.5-ml tubes. The cleared embryo lysate (after centrifugation) was added to the beads and mixed well.

The mixture was then incubated on ice for 5 min., placed on a magnetic stand (Promega) for 5 min., and partially dried by careful removal of the liquid. To this, 100 μl of washing buffer with LiDS containing 100 mM Tris-HCl, pH 8.0, 0.15 mM LiCl, 1.0 mM EDTA, and 0.1% SDS was added. (mRNA DIRECT kit.) The mix was transferred to a 200 μl PCR tube. The beads were washed once with 100 μl washing buffer with LiDS and once with 50 μl washing buffer containing 100 mM Tris-HCl, pH 8.0, 0.15 mM LiCl, and 1.0 mM EDTA. (mRNA DIRECT kit.) The beads were then washed quickly with 20 μl 1× RT Buffer (25 mM Tris-HCl, pH 8.3, 37.6 mM KCl, 2.5 mM MgCl2, and 5 mM DTT) and 20 μl RT Mix containing 1× RT Buffer and 20 μM dNTP was added. The tube was heated at 65° C. for 5 min. and cooled to 37° C. 1 μl MMLV reverse transcriptase (Promega) was added and the mixture was incubated at 37° C. for 1 h. with occasional shaking. Next, 20 μl of water was added to the RT reaction, mixed and a 1.0 μl to 20 μl aliquot of the PCR mix containing 1× Perkin-Elmer PCR buffer, 2.0 μM dNTP, 1.0 μM T12VN, 0.2 μM arbitrary 10-mer, 1 unit AmpliTaq (Perkin-Elmer), 50 μCi $\alpha^{35}$S-dATP (Amersham) was taken. PCR using temperature settings of 94° C. 30", 40° C. 1', 72° C. 2', 40 cycles, and 72° C. 10' extension was performed with the Perkin Elmer 9600 Thermal Cycler. All PCR product was run on appropriate gels for band visualization.

cDNA cloning of Differential Display Bands

All dried gels were marked with radioactive ink prior to film exposure for proper alignment between the X-ray film and the dried gel plate. Appropriate bands were marked by puncturing. A scalpel blade was used to score the gel around each band to be excised. The excised gel pieces were placed into a PCR tube containing 2 μl water. PCR was performed using a 50 μl PCR mix (same as for differential display with the following modifications: the primer concentration was 1 μM, and the dNTP concentration was 200 μM; no $\alpha^{35}$S-dATP is added.) The cycle settings were the same as above.

A portion of the PCR products was run on a gel to determine amount and size of PCR products; DNA that did not correspond to the size of the original differential display band was discarded. The remaining PCR fractions were purified using CHROMA SPIN-100 columns (Clontech, Palo Alto, Calif.) according to the manufacturer's instructions. The purified PCR fragments were cloned into the pCR2.1 TA cloning vector (Invitrogen) according to Invitrogen cloning protocols supplied with the vector. The only variation from the standard protocol was an increase in the molar concentration of PCR product to vector (over 100-fold); multiple insertions were not found to be a problem. All ligations were performed at 16° C. overnight, transformed into *E. coli* strain DH5α, and plated onto LB with X-gal/IPTG.

Five colonies were chosen for PCR verification; PCR products of expected size were selected. About 10 μl of the 30 μl PCR reaction was simultaneously digested with Nla III and Mse I overnight at 37° C. (a 5 h digestion was used as well.) cDNA clones were selected according to the colony PCR and the restriction enzyme digestion pattern.

The differential display protocol for finely staged zygotic embryos of loblolly pine as described above, has produced more than 600 differential display patterns and more than 60,000 bands. Within that set of bands, we have identified bands that increased and/or decreased during embryo development. From those bands, cDNA clones of this invention were isolated and sequenced.

Detection of Gene Expression by Micro-Array Assay

In order to verify expression patterns of the cloned DNA in loblolly pine embryos a micro-array assay was developed. The cloned cDNAs were amplified by PCR and adjusted to equal concentrations (0.1 μg/μl). The cDNAs were then dispensed in the wells of a 384-well plate, denatured in 0.3 M NaOH at 65° C. for 30 min. and neutralized with 2 volumes of 20× SSPE mixed with 0.00125% bromophenol blue and 0.0125% xylene cyanol FF (5% gel loading dye). The denatured DNAs were then blotted on to Hybond N+ membranes (Amersham) as arrays using a VP 386 pin blotter (V&P Scientific, Inc., San Diego, Calif.). Each DNA was dot-blotted four times as a quartet on the membrane. An example of quartet spotting is seen in FIG. 7. Each dot is about 1.2 mm in diameter and contains about 3 ng of DNA. DNA was then cross-linked to the membrane at 120,000 mJ/cm2 in a CL-1000 UV-linker. (Strategene, Inc., Upland, Calif.) The dot image of each membrane was scanned, numbered and saved in computer for later use in data digitizing.

The cDNA array membranes were pre-hybridized in hybridization buffer (0.5 M Na-phosphate, pH 7.2, 5% SDS, and 10 mM EDTA) at 65° C. for 30' in a hybridization oven (Model 400, Robbins Scientific, Sunnyvale, Calif.) and then hybridized under the same conditions with total cDNA probes made from mRNA. The membranes were washed twice at room temperature in 2× SSPE and 0.1% SDS, twice in 0.5× SSPE and 0.1% SDS, and twice in 0.1× hybridization buffer. Each wash was roughly 20 min. Each membrane was then exposed to Kodak Biomax MR films.

The total cDNA probes referred to above were made by initially creating the first strand cDNA. This was accomplished by mixing loblolly pine embryos (0.05–0.1 gm fresh weight) with 100 μl lysis buffer (containing 100 mM Tris-HCl, pH 8.0, 500 mM LiCl, 10 mM EDTA, 1% SDS and 5 mM DTT) in a 1.5 ml Eppendorf tube. The mix was then ground with an electric drill as described above. Another 100 μl lysis buffer was added and the lysate was ground again briefly. The drill pestle was washed with 100 μl lysis buffer that was pooled with the lysate. After centrifugation at 14K at 4° C. for 15 min. in a Beckman bench top centrifuge, the clear embryo lysate was mixed with 10 μl Dynal beads washed twice with lysis buffer. The suspension was incubated on ice for 5 min., with occasional mixing to allow binding of Poly (A) RNA to the oligo (dT) on the beads, and then left on a magnetic stand at room temperature for another 5 min. The liquid was removed and the beads were moved to a 0.2 ml PCR tube by suspending in 100 μl lysis buffer.

The beads were washed twice with 100 μl of washing buffer with LiDS and once with 50 μl of washing buffer. The mRNA was eluted from the beads in 6 μl water at 65° C. for 2'. One μl T21VN primer (10 μM) and 1 μl SCSP oligo (cap switch primer, 5'-ctcttaattaagtacgcggg-3', 10 μM) were added to the mRNA eluate. The mixture was incubated at 70° C. for 2' and cooled on ice. Three μl 5× First Strand Buffer, 1.5 μl DTT (20 mM), 1.5 μl dNTP (10 mM each) and 1 μl MMLV Superscript II (Gibco BRL) were added to the mRNA-primer mixture followed by incubation at 42° C. for 1 h to synthesis first strand cDNAs. The cDNA was heated to 72° C. for 1 min. to degrade RNA and then diluted to 100 μl with water. The lysis buffer, washing buffer and Dynal beads are components of the mRNA DIRECT kit (Dynal, N.Y.). The first strand buffer (5×), 20 mM DTT and 10 mM dNTP are components of the SMART PCR cDNA synthesis kit (Clontech, Palo Alto, Calif.).

The first strand cDNAs synthesized as described above contains a T21VN sequence at their 5' ends and the SCSP sequence (see "SMART™ cDNA, Clontech, Palo Alto, Calif.) at their 3' terminals. Total cDNA probes were made by PCR amplifying the first strand cDNAs using SMART cDNA PCR (Clontech, Palo Alto, Calif.) in the presence of labeling agent. Five 5 μl first strand cDNA solution was mixed with 5 μl 10× KlenTaq PCR buffer (Clonetech), 5 μl dATP+dGTP+dTTP (5 μM each), 1 μl T21VN primer, 1 μl SCSP oligo, 1 μl KlenTaq Mix, 5 μl 32P-dCTP (10 mCi/ml, Amersham) and 27 μl water. The PCR was performed using the setting of 94° C. 2', 15 cycles of 95° C. 15", 52° C. 30", 68° C. 6'. The PCR products were purified using NICK column (Pharmacia) according to the manufacture's instructions.

Currently, high-density array Southerns for both somatic and zygotic embryos at all the developmental stages have been performed. The dot array Southern data indicate that gene expression of late stage somatic embryos resembles middle stage zygotic embryos; many transcripts present during late zygotic embryogenesis (ZE) are absent in somatic embryos and late stage somatic embryo gene expression patterns resemble the patterns of middle stage zygotic embryos.

Cairney et al. (*In Vitro Cell. & Devel. Biol.—Plant.* 36:155–162 (2000); *Appl. Biochem. Biotech.* 77–79:5–17 (1999)) have discussed how this gene expression information may be used to improve the process of somatic embryogenesis; the references are incorporated in their entirety. As shown in FIG. 2, the high-density array Southerns allows rapid evaluation of embryos subjected to protocol changes. Following the expression of a known gene permits inferences about metabolism and is very valuable in developing media-improvement hypotheses. Further, detailed gene expression studies may help by providing an understanding of the timing and location of gene expression (e.g., in situ hybridization). The isolation of key genes also provides the ability to monitor the expression of these genes as stage specific markers and allows protocol variations to be quickly evaluated.

EXAMPLE 5

Identification of Markers for Superior Performance in Tissue Culture

Figure 8:
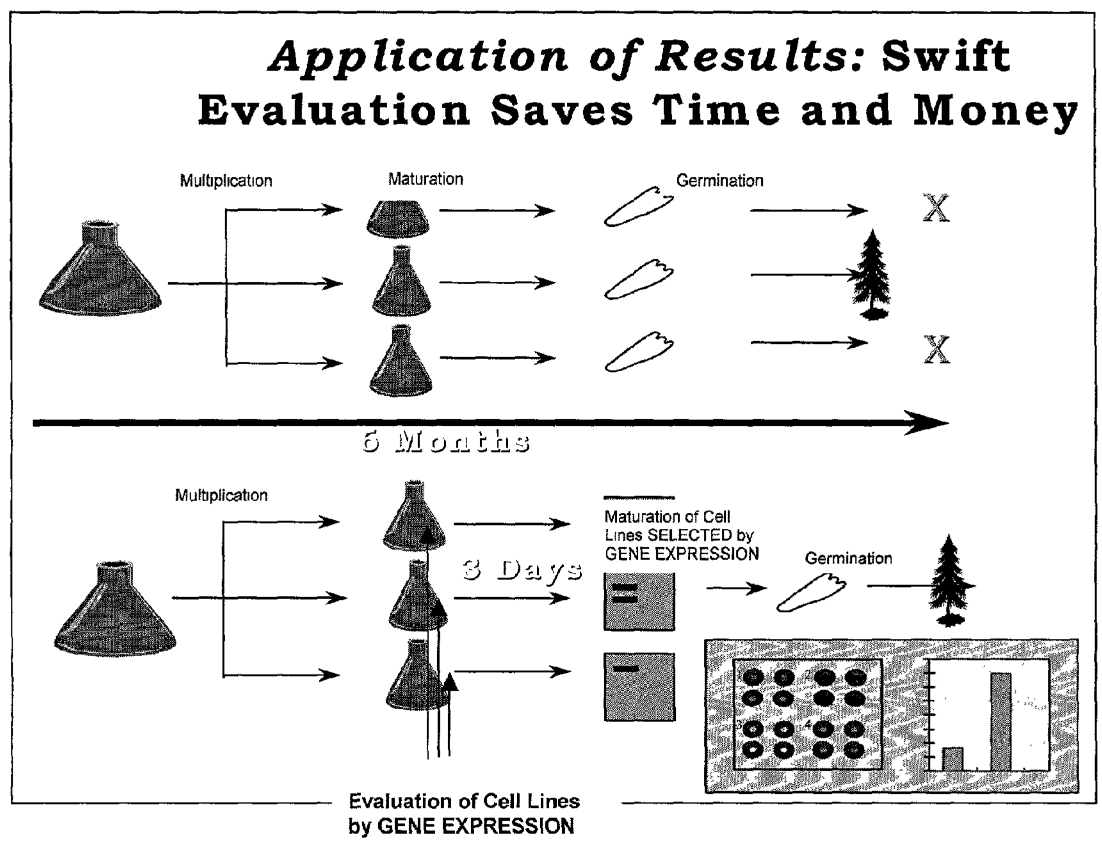
FIG. 8 depicts the application of embryogenic gene expression studies.

The evaluation of tissue culture modifications for pine somatic embryogenesis, depicted in FIG. 8, is typically a lengthy process. However, where molecular tools are available, potentially improved media or genotypes can be discerned more rapidly, thereby avoiding the months of costly evaluation. (See FIG. 8) Table 5 illustrates this proposition.

Table 4 describes several publicly available clones, Lec, Fie, and Pkl, used to provide a representative model for this example. Any clone within Table 1, SEQ ID NOS: 1–327, can be substituted for those in Table 4 to assay increased performance in tissue culture. Any promoter within Table 1, SEQ ID NOS: 328–334, can be incorporated with those in Table 4 or SEQ ID NOS: 1–327 to assay increased performance in tissue culture. In this scenario, Table 5, a representation of the information contained in FIG. 9, shows performance of selected genotypes (260, 480, 499, and 500) in various media (1133 or 16) determined by the total number of embryos produced per medium as described by Pullman and Webb (1994), incorporated herein. Embryo maturation was determined by the presence of recognized morphology according to methods previously mentioned above. (Pullman and Webb, (1994)) Genotypes that produced high, medium, and low numbers of embryos were selected for RNA extraction. Gene expression assays, such as DNA arrays, Northern blots, slot blots, etc., were used in attempt to correlate embryo performance with mRNA abundance for selected genes. In the example shown in FIG. 9 and Table 5, expression of loblolly pine genes, designated as Lec, Fie, and Pkl, obtained from the Pine Gene Discovery Project, was evaluated. The preliminary correlation appears to be that the high levels of the Lec gene's mRNA correlates with greater number of pine embryos. (See table 5.) These experiments can be further expanded to incorporate additional or alternative genotypes with the prospect of identifying a large collection of gene indicators of good or poor performance in tissue culture based on high or low mRNA levels. It is clear from the above that this approach, using the sequences disclosed in this application, can evaluate a genotype entering tissue culture, saving both time and expense.

Somatic Embryos

Immature zygotic seeds were collected from loblolly pine genotype 260 (mother tree BC-3, Boise Cascade). Somatic embryos were initiated as described by Becwar et al. (1990) or with modifications in media mineral composition. The early stage somatic embryos were grown in cell suspension culture medium 16 and sub-cultured every week (Pullman and Webb, 1994). The embryos collected from the suspension, which include stage 1 and stage 2 somatic embryos, are referred to as stage S embryos. At the end of the subculture week, the somatic embryos in the suspension were settled in a cylinder and transferred to maturation medium 240 (Pullman and Webb, 1994). Resulting somatic embryos were selected, staged, sorted into vials containing the same stage, and stored at −70° C. until analyses were performed.

Probes

For the following example analysis RNA was isolated from embryos at different stages in development, early stage somatic embryos and late-stage somatic embryos. The cDNA probes used in this example are not contained in the SEQ ID NOS: 1–327, but rather, are generic, publicly available pine sequences obtained from the Pine Gene Discovery project. These clones are homologs to the well-studied *Arabidopsis* genes that have been shown to have significant influence on embryo development in this plant. The pine clone names (first column) and corresponding references for the *Arabidopsis* homologs are shown in Table 4. The three clones listed, Lec, Lie, and Pkl, are for representative purposes within this example and it will be clear to one skilled in the art that any of the SEQ ID NOS: 1–327 could be substituted for those here as all will help identify conditions for improved performance in culture.

Probes were made by preparation of DNA using Wizard Minipreps (Promega, Madison, Wis.) and cDNA inserts isolated by restriction enzyme digestion. For the cDNA probes, 50 ng of the isolated cDNA insert DNA was used to make $^{32}$P-labeled probes with Ready-To-Go DNA labeling beads (Amersham Pharmacia Biotech) according to manufacturer's instructions. Blots were prehybridized (7% SDS, 1% BSA, 0.25 M $NaPO_4$ (pH 7.2), 1.0 mM EDTA) for 3 hours at 65° C. and hybridized in fresh buffer at 65° C. for 12 to 18 hours (4). Each blot was washed 6 times with the following conditions: 1) RT, 2×SSC, 0.1% SDS, 15 min; 2) RT, 2×SSC, 0.1% SDS, 30 min; 3) 42° C., 0.2×SSC, 0.1% SDS, 15 min; 4) 42° C., 0.2×SSC, 0.1% SDS, 30 min; 5) 60° C., 0.2×SSC, 0.1% SDS, 30 min; 6) 60° C., 0.2×SSC, 0.1% SDS, 30 min. Blots were exposed to a phosphorimaging plate for 10 minutes. Screens were read with a BAS1800 (software v1.0) and images were manipulated with Image-Gauge (v2.54) (Fuji Photo Film Co., Ltd., Kanagawa, Japan).

The hypothesis tested within this example is that genotypes that produce large numbers of embryos have high Lec expression and low Pkl expression, poor genotypes have the opposite pattern, and that Lec and Pkl expression act as indicators of embryogenic potential. FIG. 9 shows that Lec is not expressed in late stages of embryogenesis in somatic embryos. The Lec gene is expressed throughout embryogenesis in *Arabidopsis*. The blot reveals that the Lec gene is a useful early expression marker for embryogenesis. One interpretation of these results is that the somatic embryos do not express Lec in the manner that Lec is expressed in zygotic embryos, i.e. the use of Lec expression has highlighted a defect in gene expression in somatic embryos. This defect could be used to identify desirable genotypes, i.e. those likely to progress through development and produce a large number of healthy plantlets compared to undesirable genotypes that will cease development prematurely or produce low numbers of plantlets. This is an example of the principle described pictorially in FIG. 8.

The results described in the previous section of Example 5 reveal ways in which gene expression analyses can be used to improve somatic embryogenesis based on several genes. However, this principle applies as well when the assay is expanded to determine the expression of hundreds or thousands of genes simultaneously (e.g. by DNA arrays). We can create hypotheses which state that expression of a single specific gene can be used to determine the potential of a culture, or hypotheses that state that the expression of a group of genes (e.g., hypothetical genes A, B, C, D, E, F) acts as an indicator of high embryogenic potential. For example, all these genes may be expressed at a high level in cell lines that produce large numbers of embryos, thus we would select cell lines which exhibited this characteristic. Alternatively specific levels of expression for genes A, B, C, D, E and F may be required and a combination of high and low expression of particular genes will identify desirable cultures. Alternatively, experience will determine that certain exceptions can be tolerated.

While the previous paragraphs discuss numbers of embryos produced, the principle applies to ANY desired characteristic: by establishing a correlation of gene expression with e.g., germination potential, embryo size, growth of plantlets in their first year, disease resistance of mature plants, environmental hardiness or wood quality. Any trait where could be evaluated by these gene expression assays and correlations with gene expression established, resulting in a molecular tool which could be used to predict desirable characteristics. Explicitly, we could use these gene expression tools to select cell lines which will produce high quality plantlets months before they grow into plantlets, or cell lines or juvenile plantlets which will produce hardy trees with desirable wood quality, years before these traits are expressed.

TABLE I

| cDNA | Embryo Phase | Clone | Nucleotide Sequence |
|---|---|---|---|
| SEQ ID NO:1 | Late | LPS-001 | GGTACTCCACCGTAATAACCCTTGGGAAATAGCCTATGATCCAGGGGAGGCAACC |
| | | | ACCTATATCATTGACAACAGCGAAAAATGTGGCGCAAGAAGTTTCACATACAATTCA |
| | | | TGGTTACAAAGATCACATACCAGGTGTTGGAGCAGATTCGATAGATATTGAAGATAT |
| | | | GAAGCCAAGGAGTGGAGCAGTTATTGAAAAGGGCACAAAAAAATTTGCCATTTACA |
| | | | AAGATGAAAATGGGCTGATTCACAAATACTCGGCAATATGCCCACACATGAACTGT |
| | | | ATTGTGAAATGGAATCCTATAGACTCAACTTTCGATTGCCCCTGCCATGGTTCAATG |
| | | | TTTGATAATCTGGGTCGATGCATCAATGGACCTGCCAAGGCGGACCTATTTCCCGA |
| | | | AGATTAACGATAGTTGTTTGTACATGTAATTATCTTGATATTGTATATATATGTATTTA |
| | | | AATTATACAGTACAATAAATCCATGTTTGCAGGCTATTTCTGCTTGATAATTTAGCTC |
| | | | CAGATTTATACATAACCAGTTTATTTGGCTGTTTTTCCCCTGGCAAAAAAAAAAA |
| SEQ ID NO:2 | Late | LPS-003 | 003GGTACTCCACAGAAAGAAATGATTTGACAGAAAAAGAGAGCTGTAGGATTGGGT |
| | | | AAACCCTGCAGTGGATATATACAATGTATATGTACTCTGTCTGTTTTTCTGTTATTTG |
| | | | ACGGAAATAAAAACGCCATAGCGACGGATGACTGTAAATCCTTAGGGACGGATGAC |
| | | | TGTAAATCCTTAGGTTGGAAGATTACAAACGACATATGGGTCTTTCAATTTTCAGAT |
| | | | TTCTGTAAGACTTACATTTCAAAGACTGTTTGGATGGGCAAAAAAAAAAAA |
| SEQ ID NO:3 | Middle | LPS-004 | GGTACTCCACCAGAATGCCGCAGTTTAGTTCTCTAAAGCAAGCAGTAAATTAATTTT |
| | | | GTCAAAATCTAAAGAGTGTATAGTATCAGTGGGTTTGTATTTCCTAGTTTGCCTACA |
| | | | ATAACGATGGGGATTCACCAGTTTTTGTAGAATTTGCAATCATCGGATGACAATTTC |
| | | | AAAGTTTTCTCTAAGTCACCCGCATTGATATCGAGAAGCCTTCCATTTTCAATTATTT |
| | | | AATATCAGAAAATCTTTTCAGTTGGCAAAAAAAAAAAA |
| SEQ ID NO:4 | Middle | LPS-006 | AGCCCAGCTGCGAAGGGGATGTGCTGCAAGCGATAAGTGGTAACGCCAGGTTTCC |
| | | | AGTCAGACGTGTAAACGACGCCAGTGATGTATACGAATCACTATAGGCGATGGCCT |
| | | | TCTAGATGCATGCTCGAGCGCCGCAGTGTGATGAATTGCAGAATCGGCTGGTACT |
| | | | CACGGGCTAGAGAAAGGCACAAGCACTTTTTGTCATTTTAGGATCAGAGGCATTCA |
| | | | GGTATAGGAAGGGTGGCTCAGATAGGCAGATGGATCGGCATTTTGCCCAGTCATG |
| | | | AAACATTTTATGCATGTTATTGCCTCCCAAGGACGAAATCAGTTCTTTGTGCCTTCT |
| | | | GGTGATATCACTTCAAACAAAAGGCAACAGTTCTGTGATTTCATATGGTTTGTCACT |
| | | | GAATATTTTGTTGCAGATGTTCTCTACTATTTTTTATCTGCTTTCAAGTGATTATTTG |
| | | | TTGATTCCCCATGGATAGTTATGCTAATCAGTTGCATTTCTCTTGTACCAGTCAACA |
| | | | AACAAAAATGCTTGTAGGAATCCATTACTATTTATTTTCAGACAGGTAAACGTGTAG |
| | | | CTAATTGTTCTGGCAAAAAAAAAAAA |
| SEQ ID NO:5 | Middle | LPS-007 | TCCAAAATACAAAGGCTTTATTTGCATCATGATATAATACAAAGTAAGAAATTTACCC |
| | | | AACTGTTTAACCTAATAATAATACAAAGGAAGCATTTTACCCAACTCTTTAACGTAAT |
| | | | AATACCAAAGAGTGGAATGCTTTATTGACCAGCAAGACCTTGAAATTTTTATAACCA |
| | | | ATGCCCATCAACAGAGCCTTTCTTAAAAAACGCAAAGCCCAGCTCTGTCACCTTATT |
| | | | AGTTAGTATAAACTGACATTCTTCCAAGCTTGTGTGCGCAGAAACAATAAAGAACTT |
| | | | CACCTTGGTTTAAAGAACGTGCCATGAAGAAAACGTCCCAAGAAAAATGAAATGGC |
| | | | TCCTTCGACCATTCAGTCCTCCCTAGAAAAATCAAAAGACTCCTTCGACCATTAGGT |
| | | | CCTCCAATTGGGCATCTAACTACAAGCGGTC |
| SEQ ID NO:6 | Middle | LPS-008 | GGTACTCCACGGGCTAGAGAAAAGGCACAAGCACTTCTTCGTCATTTTAGGGATCA |
| | | | GAGGCATTCAGGTATAGGAAGGGGTGGCTCAGATAGGCAGATGGATCGGCATTTT |
| | | | GCCCAGTCATGAAACATTTTATGCATGTTATTGCCTCCCAAGGACGAAATCAGTTCT |
| | | | TTGTGCCTTCTGGTGATATCACTTCAAACAAAAGGCAACAGTTCTGTGATTTCATAT |
| | | | GGTTTGTCACTGAATATTTTGTTGCAGATGTTCTCTACTATTTTTTATCTGCTTTCAA |
| | | | GTGATTATTTGTTGATTCCCCATGGATAGTTATGCTAATCAGTTGCATTTCTCTTGTA |
| | | | CCAGTCAACAAACAAAAATGCTTGTAGGAATCCATTACTATTTATTTTCAGACAGGT |
| | | | AAACGTGTAGCTAATTGTTCTGGCAAAAAAAAAAAA |
| SEQ ID NO:7 | Middle | LPS-010 | ACGACGTGTAAACGACGGCCAGTGATTGTATACGACTCACTATAGGGCGATTGGC |
| | | | CTTCTAGATGCATGCTCGAGCGGCCGCAGGTGATGGATATCTGCAGAATTCGCTT |
| | | | GGTACTCCACGGCTAGAGAAAAGGCACAAGCACTTCTTCGTCATTTTAGGATCAGA |
| | | | GGCATTCAGGTATAGGAAGGGTGGTCAGATAGGCAGATGGATCGGCATTTTGCCC |
| | | | AGTCATGAAACATTTTATGCATGTTATTGCCTCCCAAGGACGAAATCAGTTCTTTGT |
| | | | GCCTTCTGGTGATATCACTTCAAACAAAAGGCAACAGTTCTGTGATTTCATATGGTT |
| | | | TGTCACTGAATATTTTGTTGCAGATGTTCTCTACTATTTTTTATCTGCTTTCAAGTGA |
| | | | TTATTTGTTGATTCCCCATGGATAGTTATGCTAATCAGTTGCATTTCTCTTGTACCAG |
| | | | TCAACAAACAAAAATGCTTGTAGGAATCCATTACTATTTATTTTCAGACAGGTAAAC |
| | | | GTGTAGCTAATTGTTCTGGCAAAAAAAAAAAA |
| SEQ ID NO:8 | Middle | LPS-011 | GGTACTCCACGAAGCAAAAAGAGTCAGGGGAATGAAGATGGGGGGCTCCGACAAG |
| | | | AAGCGGATCAGAGAAGAGCAGGAAATGAGTCCACCTGAGGAATCCTGGAGACAGA |
| | | | AACAGGGGCGTTTAATGGAGTTTGAGGCAGGGATGGCCTATGATAAACCTGAAAAT |
| | | | GCCGGTGCAGGTAATGAGAATTTGCCAGAGTTTTGCTCTCTTTCAAATGAGTACTC |
| | | | GATGTTATTGAAAGATCCATGGAGTTGGGAGGATAGCACTGGTTTCGGAATCCGAA |
| | | | GCTTAGCTGCTGTCAGGAAGCAGTCTTGTATATTGGACTATCTCCATGATTCTGCT |
| | | | GTAGATAATCGCTGTGAAAAGGATTTTGCCGAGCAGCACAAGGTACAGGAAGAGG |
| | | | AGGATTGTTTGAGAAGGTCTCTTTTTGAAGCCACAGATGATCAGCTCTGGAGGCTT |
| | | | CAGAGTCTTTGCAGGATACAGAAGGTCTGTTTCCTCTGGATTCCGTGGGTAGCCAT |
| | | | GATTGCACGACCTTGTTGCAGGATGAGAGCATTGTTCAGGGCGCTGCTTCTTACTT |
| | | | CAGAATTTGGGAACAGGATGATGGTCACAAGGATGCCAAAATTCATGAAGATGGCA |
| | | | TTGGTTTTGTGTATGGGAGTGGGATCTCGGATTGGATTCGGAGGGCTCCCTCGAA |
| | | | TCAATCTGAGTTTTCTGAATCTGTTGAATTTGAAAGCTCTATGTTTTCACTGTAATTT |
| | | | GGGTCTTTTTAATTTCTTCCTATGTAATTTGGGTGTTTCTAATTTCTTCCTTCAGCAA |
| | | | AAAAAAAAAA |
| SEQ ID NO:9 | Middle | LPS-012 | GGTACTCCACCATATCCAGGTAAACAAGGGAAAACAGAGTCAGCTTCTAGTATGTT |
| | | | GTATGCCTTGCTCTGTCTGTTTTCTTTGATCTTTGATGCCAAGCAAGTTGAATGTGA |
| | | | TCACTAAATGTTGCTGGCAGTAGAGCTGGAGATGTGCTGTCTCTTTGGTGTCATTA |
| | | | GCACAGAAGCTATTGGAGAAATGATTATTATCTGTTTGATAACTTCTAGAGCATTTT |

TABLE I-continued

| cDNA | Embryo Phase | Clone | Nucleotide Sequence |
|---|---|---|---|
| | | | TCTGCTTCCAATTCCACAAGGTGGAAAGTGCAAGGATGTTTACTTTCTTAAACTGTA<br>CTTGCCTTGTATTTGATGATGTAAGGTTGTGTGGCAAAAAAAAAAAA |
| SEQ ID NO 10 | Middle | LPS-013 | GGTACTCACCATATCCGGTAACAAGGGAACAAGTCAGTTTTAGAAAGTGGACCCCC<br>GGTTCCGTCGTTTTCTTGATCTCGGAGCCAAGCAAGTGGATGTGATCACTAAATGT<br>TGCTGGCAGTAGAGCTGGAGATGTGCTGTCTCTTTGGGTCATTAGCACAGAAGCTA<br>TTGGAGAAATGATTATGGTATTCCACCATATCCAGGTAAACAAGGGAAAACAGAGC<br>TCAGCTTCTAGTATGTTGTATGCCCTGCTCTGTCTGTTTTCTTTGATCTTTGATGCC<br>AAGCAAGTTGAATGTGATCACTAAATGTTGCTGGCAGTAGAGCTGGAGATGTGCTG<br>TCTCTTTGGTGTCATTAGCACAGAAGCTATTGGAGAAATGATTATTATCTGTTTGAT<br>AACTTCTAGAGCATTTTTCTGCTTCCAATTCCACAAGGTGGAAAGTGCAAGGATGTT<br>TACTTTCTTAAACTGTACTTGCCTTGTATTTGATGATGTAAGGTTGTGTGGCAAAAA<br>AAAAAAA |
| SEQ ID NO:11 | Middle | LPS-014 | GGTACTCCACCATATCCATGTAAACAAGGGAAAACAGAGCTCAGCTTCTAGTATGT<br>AGTATGCCCTGCTCTGTCTGTTTTCTTTGATCTTTGATGCCAAGCAAGTTGAATGTG<br>ATCACTAAATGTTGCTGGCAGTAGAGCTGGAGATGTGCTGTCTCTTTGGTGTCATT<br>AGCACAGAAGCTATTGGAGAAATGATTATTATCTGTTACATAACTTATAGAGCATTTT<br>TCTGCTTCCAATTCCACAAGGTGGAAAGTGCAAGGATGTTTACTTTCTTAAACTGTA<br>CTTGCCTTGTATTTGATGATGTAAGGTTGTGTGGCAAAAAAAAAAAA |
| SEQ ID NO:12 | Late | LPS-015 | GGTACTCCACTAGACCGGGTAGGGTCTCTCCATGGTTTTGCGACTTAGGTTAGGTG<br>TCCTGTTCTGTTAATGATTTTGAGGTTTTGTAATTGTGAGTATGTTTCCAGGGTTTT<br>GAACCTGGGTACTCGGCCTTTGTTGGAATGTAGTCTGGTTAATTTATATGTATATGT<br>AACCTTGGGGTTTCGAGCCCAGTTCTCTGTTCTTCTTGAAATGAAATGCGATTTGTT<br>CTAAAAAAAAAAAA |
| SEQ ID NO:13 | Late | LPS-019 | ATATATACGTATGGTATTCCACAGCATGAACTCTTCGACATTATATGCTTGTTATAGT<br>TTTTAAGAGAGGAGACTTACCTCACACATGTACAGCTTTTTATTGTCGTGCTTTCAG<br>TTGATGGATGATTGTTGTAGTCCTGTCATTGGTTGGACAATTTTCATCATCCTAAAG<br>ATCCAAGAATTCATGTGGCAAGAAACTTTAATAAAGTCAAATATAATCCGATGACGT<br>AACCCTAAAAAAAAAAAA |
| SEQ ID NO:14 | Late | LPS-020 | GGTACTCCACTAGTGATCGATTCTCTGTATGTGACGCTGCGCGGCGGCTTATAGC<br>GCTTCACTGAGAATGTACGGTATATTATGATTGATGTGATGGATTTGCTCCGCAGC<br>TTCGGCTGTTGTATCTGCTCACTTCGGCGTATATATGTAATATGTTGCTTCTTCAGA<br>GAGATGAACTTCCCCCTAAAAAAAAAAAA |
| SEQ ID NO:15 | Middle | LPS-023 | ATAGATCATTTTAAAGTTTCAGTGATTTGAATCTAATTCCACTGCATTTCCTCGCAAA<br>CTGGCAGTCAAATAGTATTCCCTCTTTCAGTGACAGGCTGGCAGGTGTTTCATTCT<br>TATACAAACATGATTATCATAATTCCATTAATTCATGGCGTTTTCTTTGCCAAAAAAA<br>AAAAA |
| SEQ ID NO:16 | Late | LPS-024 | TTTTTTTTTTTTAGGGAGAAAGGTAACTTCAGCCAGCTTTCAAAGGCAACACCTACA<br>AAAGGGGTGACTGAGAACTCAGACACAGACGACAAGTGATCATTCGGGCCAGATT<br>TTTGTTGAGAGAGTTGTAGTGTGTAATTGATTCATTTCATACATTTGATATGCAAGC<br>CTGTACAATAGCCTGTGACTGTTAAGGGCATTCTTTTGTCTCCCTGTTGCTATTTGG<br>GTTTCCGGTGTGTTCATTTTCACTTATTTTTGTGTTTTAGCTGGAAGAATTTGAGAG<br>GGTAGAATTGTGTCATCGCTATGGCTTGTGCATGACTCATGAGCCAGCAGTTGAAA<br>CTTTTATTTATTAAGTTATAATACTATGTCTTGTCAATTCTCAATAAAAGATATTTTAT<br>GCTGTTGGGCAGCATCTAAAATGTTTTGTATGTTAGCATAAAATCCCATTTTCTATA<br>AGTTTTTGCCAAAAAAAAAA |
| SEQ ID NO:17 | All | LPS-025 | AGCAGGTTCAGTCAGACGTGTAAACGACGCCATGATGTATACGAACTCATATAGGG<br>CGATTGGCCTTTAGATGCATGTTGACGGCCCGCAGTGTGATATTCGCAGATCGCTT<br>TTTTTTTTTTTTAGGCATGGTGCGCGATGAGCTGATAGCGATGATGAAGACCAAGA<br>CCACCAAAGGAAGATTCTTCAGAGCAAAAGCTACGGAGACAGAACCAGAGGACTC<br>AAAGCCGGAATCCATTGGTGAGGTACCTGCAAATGTGTGATGGACTAACTAAGAAG<br>GCTCCTTGAGAGGACCCATTAAGCACAGTGTTTTTAAGTCCCAAATTCTGTTGCAAT<br>TCCGTTGAAAATCATTTTTACGATTTTAGGTATGATGTGTGCAATTTTAAAGTTGGAA<br>TTATTGTGGGCAAAGGCTATAAGTGATTGTCTAATCCATTTAATTTATTATCTTTTGA<br>CTAAGAGCATATCTAGGCTGGAAGAAATTAGGGCACATTAATGTAAGTTTTGAATTT<br>GAACATTCTGGGTTTTGCAATGCAAAACACCACAAATATTTTATAATGTTAGAGGTG<br>TACTTTTTCTGGCCAAAAAAAAAAAA |
| SEQ ID NO:18 | Middle | LPS-026 | GGTACTCCACCAATAATACTTGTCTGTTCTTGCTTCCCTGCTGATCCACTAAGCAGA<br>TTATTTCTGTCCACCCCACTTTAGAGTCTCAGTTTGTAAAGCACTCCCTAGGAGCTA<br>AACTCATTTCCAATGGATTAAAGCACTCCATAGGAGCTAAACTCATTTCCAAGGGAT<br>TTTTGTCCATTTCTCTGTGCTAAAAAAAAAAAA |
| SEQ ID NO:19 | Early | LPS-027 | ATGTATACATATATGTGGTACTCCACACACTCAAATAACAGCATCACAATCAAAACA<br>AGAAGGCGGCCAGAAAGCTTTAAAATGCTAAGCCTACAGGTAATATTCACAACTGC<br>ATTAAGCACCCCGCTTCCTAGTTCTGAAGAAGCCAGAAAGCTTTAAAATGCTAAGC<br>CTACAGGTAATATTCACAACTGCATTAAGCACCCCGCTTCCTAGTAGGCTAGTACTA<br>GGACTAGGACCGCATTACCAGTTCCCTTATCTTCTACTCATCCTCTACAGGAAAAAC<br>TATGACTAAAACTGCATTACCAGTTCCCTTATCTTCTCAACTCGTCCTCTACAAAAAA<br>AAAAAA |
| SEQ ID NO:20 | Early | LPS-028 | GGTAATTTCCACCCACCACGGGCTTTTTCAATTAACCCATTTCTACCACTCCACATT<br>AGGGTTCTAAGTTTTGTGACTCACCCCCAATTTCGCTGATATTTTGCATTGCAGCTT<br>GTTTATCTACAGGAAATGGCTAATCAGTACTTTCAGAATTTGGTTGCTTCTGTACAG<br>GAAATGGATAATCAATCAGTACTTCTATACTTAAGTTGCTTACGCGGGGATCAGAG<br>CCTTACTTCAGAAAATTGAATACATTTTCTTCTTTGTGTATGTATCAGGCATGGAATT<br>ATATGTAGCATGCCATGGAATGCGTATTTACTAGATTATCTTTTAATTTAATACATAT<br>GTTGCTTACTAATTTGTCCACAAAAAAAAAAAA |
| SEQ ID NO:21 | Early | LPS-029 | GGTACTCCACACACTCAAACAACAGCATCACAATCAAAACAAGAAGGCGGCCAGAA<br>AGCTTTAAAATGCTAAGCCTACAGGTAATATTCACAACTGCATTAAGCACCCCGCTT |

TABLE I-continued

| cDNA | Embryo Phase | Clone | Nucleotide Sequence |
|---|---|---|---|
| | | | CCTAGTTCTGAAGAAGGCCAGAAAGCTTTAAAATGCTAAGCCTACAGGTAATATTCA<br>CAACTGCATTAAGCACCCCGCTTCCTAGTAGGCTAGTACTAGGACTAGGACCGCAT<br>TACCAGTTCCCTTATCTTCTACTCATCCTCTACAGGAAAAACTAGGACTAAAACTGC<br>ATTACCAGTTCCCTTATCTTCTCAACTCGTCCTCTACAAAAAAAAAAAA |
| SEQ ID NO:22 | Middle | LPS-030 | GGTACTCCACTATTAGATTGATGCAAGACCAACTGATCATGGCTAGGGTGTATTCA<br>AGCATTTCCCAGGCTAGGAATAATCTTGATTTATACCATGAATTGATGCTTCGTATT<br>AAAGAATGTCAACGTACATTGGGTGAGACTAATGCCGATTCTGATCTACCTCAAAG<br>GTAATAATTTTTGCATTAGCTGCTTCTAAATCAAGAGTAGTAAGTGCTTCCATTTGC<br>AAAAAAAAAAAA |
| SEQ ID NO:23 | Middle | LPS-031 | GGTACTCCACAAGGCATATATGGGCAATTGATTTTGCCTAGCCCAAATTCCTATTCA<br>AGCTTGCGTATTTCTAAAAGATGCACTATTTTTTGTCCGAGTGTAGGTTTTGAATTC<br>ATTGTAACATTCAGCAATATTAATTCAGGGGTAGCATTTCTGGCAAAAAAAAAAAA |
| SEQ ID NO:24 | Middle | LPS-032 | TTTTTTTTTTTTAGGGTAGAAAACCATGCTTCACTAACAAGGTATAAAATTACAATAT<br>AATTCTGGGTGTAAACGACCTGATAGATGATCTGCAAGTGCCAGGAGGCAATATCT<br>AGCAGAATACGTACAAATTAAATTGCCAAAAAAAAAAA |
| SEQ ID NO:25 | Late | LPS-036 | GGTACTCCACCAATGATCACCCATGTCCATTTGGTTAATTCAATGTCAAGATTTAGT<br>AGTTCCGTATTCCCTTGGGTAAGCTGTAATGGTCCATTTGGGAACAGTCCATGTTT<br>GGGACACAAGTTCAATAGAGATGTCATCCATAAATATGGGTATGAATCTCTTCCTTC<br>CCTCTCCGCCCAATAATAAAAAAAAAA |
| SEQ ID NO:26 | Late | LPS-037 | TTTTTTTTTTTTAGTAGCAATAGCAATCCATTTTAGGGATCTGCAGATCAGTGACTAA<br>GTGACCCCTACCCCCAAAGGATTAATTGTACTTTGGCTTAACCACAAAACCTGATTC<br>AAAAAATGTGAAGTTTTTACCCATTAAATTAATTCCCAAAAGTAACTACAAATTCCAG<br>AGTACATTTTTACCCAAAAAAAAAAA |
| SEQ ID NO:27 | Middle | LPS-038 | GGTACTCCACTATACAATATCAAGGCATATCTGCCGGTTGTTGAATCATTCGGATTC<br>TCAAGCACTCTCCGTGCCGCAACTTCTGGCCAGGCTTTCCCTCAATGTGTGTTTGA<br>CCACTGGGATATGATGGGATCTGATCCATTGGAACCTGGTTCCCAAGCTGGGCAG<br>CTTGTGACTGATATCCGTAAGAGGAAGGGTCTTAAGGAGAGTATGACTCCCTTGTC<br>AGAGTTCGAAGACAAGCTGTAGAGCTTTGCTATGTTTGCATGTCGGATGCTGTCAA<br>GATTGAGGAACCTCCGAGTATTAAAACACAGTTTTGTGTGCTAGGACTATTTAAATT<br>TATGCTATTCACGTATTTTTGTGATCTGTTATTTATGTTATTCACGTATTTTTGATTG<br>GAAAATACTTTTTACAAGTCATCCATTAATCTTTTAAATGTTACATAATTCTCTCTTGT<br>C |
| SEQ ID NO:28 | Late | LPS-040 | AAGCTTGGTACCGAGCTCGGATCCACTAGTAACGGCCGCCAGTGTGCTGGAATTC<br>GGCTTGGTACTCCACTATACAACATCAAGGCATATCTG |
| SEQ ID NO 29 | M,L | LPS-041 | CTTTTCTTCGTGCTTTTCGTGGAGTACC |
| SEQ ID NO:30 | Middle | LPS-042 | GGTACTCCACAAAGTGAGATGAGTGATATGAGGTCAAACACGTAAATGACAATAGC<br>TATTATTTCCCCACTTGTTTGTGGCTGTGTATATTATACTTCATTGTCAGGACTTTTG<br>TATGGTTGAAGTTGCAAGGTTTTGGCAAAAAAAAAAAAAAAA |
| SEQ ID NO:31 | Middle | LPS-043 | GGTACTCCACCTCCAGCTGCTTATCCAAGTACTACGGATAGTTCATACTCCTATTAT<br>GCTTCTGCCAAGTGAACCAGAAGGCTTCTGTTTCTACACTAGCAAACTGATAGCTC<br>GAGCATTCTGATTTACTAAGGATGATAATTCAAAATTGTAACATTGCAAACATCAGC<br>AAACATCAGCATCAACTCTGTTACTATTACAAGCAATGGATGCGTCGCTGATGCTG<br>CGGGAGAGTAAATTTTTAGTTTACTGCGGTTGGTAATTGAGTAGGTTGACTTACATT<br>TCTGTTGTAAAGCCGTTGTCGGGCATTGTTTATCTGGCCGAGTTAGCGCCAGGAAG<br>CTAAATGTACCAAATATTTATTTTTATTTTATTAAGAATATAAAATTTAGTCGTCTTCT<br>GCTGCCCAAAAAAAAAAAAAAAA |
| SEQ ID NO:32 | Late | LPS-044 | ATGGCCATGGACTTATGACTTTCAAAACCCTAAAACCTATCTACAACTTTCCACGCT<br>GAGATTTTCCGAGGAAGGCATTCTAAGCCATTCCCACCGTACTTTAATAAAATAAAA<br>ACAAGAAGATAGTAAAGCTAAGCTACAACCTTCCGCCAAAAAAAAAAAA |
| SEQ ID NO:33 | Late | LPS-045 | GACCGCTTGTAGGAACACTAGCAGATTCCGGAACATAGGTACTTTGAACATCTTTC<br>ACTCCTCACCATATGAATAGTGAGTCGATGGCGGCCTTAACAGTCGAGCATGCTTT<br>GATTTCGTCTCTCTCTCTAGTGACCGAAATCAATCTCATTATATATGTCATTATGCAT<br>TCATTCCCACTTCCTAACTTTCATTATTGTTCAAAACTTCGCCTTCCTGAAAATGCTA<br>TAATAGTAGGGGAATATTGAAAAACTTCCGCCAAGCTAAAAAGGCACTTAAAGCAC<br>CTGGATTTGAACCAGGATTTCCCACCCCGATGAGGGGGGGTGTCTTTCCATTGAG<br>ACGATGCCTTACTCGGCAGACCCTGTGGGGGTCTTTATAGGTGACTTAATACTTAA<br>GTATAGGACTTAAGAGAGAGGAAGCGACCGCCTCTCTGATCAAGCCTTTACGTGC<br>GACGTGCCCAGGTAAAGGCTGATCTCACCAAATAATTCAGAGAAAGAAGATGACTC<br>CACAGTAGCGAAACTCCTACATTGTCTTACATATCGTAACAAGCGGTC |
| SEQ ID NO:34 | Middle | LPS-046 | GACCGCTTGTGCCTGGTGTCCAAACTAGGACGCCTTAGTTTTCCTAAGAAGGAAAC<br>CCAGGCGTTGACTTGAGGCAGACTTGTGCTTCTGGGTACTCTCATTCACTGCGTGA<br>CCTTGAGAAAGGGACTTTACCTCCAGGATCCTCAAACTTCTTCTCTGTAAAATGAGC<br>ATTGTAATAATTATATCCCAGGCTTATGTTGGGAATATTCAATAAATGCTCCCTTCAT<br>TCTTTAAAAAATAAGTAAAGACAGCCTGAATGGGAGCCACGTTCTCATTCTTCTTTC<br>TCTATGCAAAATGTATTGTGTAATGTTTGTGTACTAGTAGTTCAAGAGCAAATAAGT<br>AGTTGGTTAATGGCTAACATATTTCTTAAATTTGTAACTGTTAAGATAAACATTGAAC<br>AAGGAAAAAGATTCGTAACTGAAATGTAAAGTCATTTGACCCTGGATAGTCAATGAC<br>AATCTTATTCACAGTGTAATAAGTAATTCATAACGAGATGATTATTATGAAATTATCA<br>ATAGCCTGCTATATCACTTTATGTTTATGATCCACAAGCGGTC |
| SEQ ID NO:35 | All | LPS-047 | GACCGCTTGTGGAAGAAAAGAAAGAATCTCTTTCGGATTCAATAGGCGGTATGGGA<br>GAGTCTGCTACTGCCTCTTGGATTCCAGGAATCCTAGAGCTGGGAGTATGAGTTGG<br>AGATGATGAAGGTGTCTCTTACCTATTTCTTGAAGTGGATGGAGTTGTGAAAATCGA<br>ACTTCTAGCTTCAGCTAAAAACCTTCCCCTAGAATCTCTTGCTCTATGCATATCATTT<br>TTATTTTTTCTTTCAAGATAGGGTAATAATTCTCTTTCTGATCTTCCAGGTCACTCTA<br>GGTGCAAGAAGAGAGCATAGTCAAGGAACTATTAAACCAATAACTTTCTCTTTTCTG<br>ATCCTCCAGTTCACTCTAGGTACAAGCGGTC |

TABLE I-continued

| cDNA | Embryo Phase | Clone | Nucleotide Sequence |
|---|---|---|---|
| SEQ ID NO:36 | All | LPS-050 | GACCGCTTGTGCAAAGTAGATACCGTCCTGTTCCGGTGAATTGAAGTACATTTTCA<br>AAATGCGCTACTATGACATTTTATAGGATGTCTGAGTGTAAAATAATGGTACTGGTT<br>GTTGCAAAGAATCTGATGTTTGGATGTATGGAACTATAAATAGATGTTATTTTCTGA<br>TCCAGAAGGCTTTCCTTACCAACTGATTTCATCTTCAGAAACTAAAAGCTCTTGAAC<br>TTGTGTAGATGGGGCTTGGTCATTGTAGTTTAAATGCATTATGTAGTGGCAAAAAAA<br>AAAAGTTATAGCCTACGTTTCAAATGGATTTGCTCGACAATCAAATGAATTACAATT<br>GAATATTCATGTATACCCAAATTTTAAATGTAGAATGACATCATCAATGTAGACAAAC<br>ACCACTGTGCTTGTCCTTGATATCCTCTTTCACCATATAATTGGTGGCTTACTCAAA<br>GTCACTATCTGATGCAACTACAAGCGGTC |
| SEQ ID NO:37 | Late | LPS-051 | GACCGCTTGTTCAATGCAGAATCTCGAAGAGATGTCTTGGACAAATACTGAACTGG<br>CACGATTGGTGTAGTGCGGTTCAAAAGGCGCTCCAGATTCGTCTGGAACGAATCTT<br>CATACGCTGAACAATTAGACATCTTGTACGCAAGAGAATTACGATCGGCCATATAAA<br>AACCCCAAAGAGAAGAAAGTGTTTCGAAATTCTCCCAGAAAACAGTCTTATGCCAC<br>CGATTTGTCTTTTCAACATGCATTTGCAATGAAGTCTTTGGATTCTTACTGTGAGTG<br>CTGATCAGCAACGGATTTTCGATCTGTATAGCTCTGCCGATTCCTGGTTAAAGCAG<br>CTAAGAGTTAGGCATCCAGATTTTGAGTTTTTTGCATCTCACAATGTTTGAATACATT<br>TCAAATCCATTGTTGGAGTAACCTAACAACAACTGTACTCTTCTTCCTATTTCTGAA<br>GCCCTCTGCCAGTTTAAGGCAGAGAACTGAGTTATCTACAAGCGGTC |
| SEQ ID NO:38 | Late | LPS-052 | GACCGCTTGTATAATAAAGTGGTACCGCGTCCTGCAAACAGGGTTCTCTTGCCATC<br>CTGCTACAACCCTGCAGTGGTCGCAGTAGAGAGAATCGGAGCAACGAACGTTTTC<br>CCGAATATATGGAGCGGGAGGAAGAGTTTTCTTGCTGATGATCCAATCGGAGTCGA<br>ACTGCCACCGCTGGATGAAGGGCGGCGAGGAAATCTTGGGGGGCAGAGGCCCGT<br>CGGCGTAGGAAATAAGAAACGATTTGATATGGAACGAAAGGGCCCGTCCAGGGTT<br>CGATCCCCGGCAGGGCAGCCAGCCCCGAACTAAACAAAACAATAAGAACAAACAG<br>CAAAGTAAAAGAAAGCACCAGAAGAAACAGCAGCAGACGAAGAGTAAGGAGCTGC<br>CCACAAGCGGTC |
| SEQ ID NO:39 | All | LPS-053 | GACCGCTTGTAATCCACAGCATTTTCAATAACTTCCTGAGGTGACATCCACCTCCAC<br>TCAGAAAACTCGGCTGCATCTGTCCCATCACCAGCTAGATTGATCTCACTCTCGTC<br>TCCTCTAAATTTTAGGAGGAACCATTTCTGTGCTTGACCTTTCCATTCGCCTCCCCA<br>CAAGCGGTC |
| SEQ ID NO:40 | Middle | LPS-054 | GACCGCTTGTATATAATGTGAAGACACAATAAAATTTTGTCCAACAAAGCAACCAAA<br>CGACCAAAAATTTAGCTGTGACATCAAAAAGCTCAACCCCTACAATGAATGTAACCT<br>TAATCTAGAAAATTGATCCATGATCTCCACTGAATTTTCTCGTTCATCCTGAAGAAT<br>GAGAAACTTAAATGTACCCGATTCCCTCAACCAAGCCCCCACAAGCGGTC |
| SEQ ID NO:41 | Early | LPS-055 | GACCGCTTGTAATCCACAGCATTTTCAATAACTTCCTGAGGTGACATCCACCTCCAC<br>TCAGAAAACTCGGCTGCATCTGTCCCATCACCAGCTAGATTGATCTCACTCTCGTC<br>TCCTCTAAATTTTAGGAGGAACCTGTAATTGGTAGGGGCTTGTCATAAATGATCAAG<br>ACGACCCGCATCGTGATGCCAAGCTTAGTCTTTCTACTTACTGTCTATGTAATGGTC<br>ACGGGCCCTTCTTATGTTTATGTCTCTTTGAAATGGACGATTTTTTTGTTTTAGGTAT<br>TCAGTTTCTGAAGCTGTTTTGGTAGTAAACTGGGCTCAATCATTTCTGTTGCTTGAA<br>CTTTCCATTCGCCTCCCCCACAAGCGTCAGCCGAATTCTGCAGATATCCATCACCT<br>GGGGGGGCCGCTCGAACATGCATCTAGAAGGCCAATCCCCTATATGAATTCTATTA<br>AATCCCTGGCCTCGTTTTA |
| SEQ ID NO:42 | Early | LPS-056 | GGTGCGATCCAGAAAACTATCATCTCTCACTGCTCGTGAACAAAATGCTGGTTCAT<br>AGCCATCACTAAGGCTAAGGTACTATCCAGCCAAACTGATCTCAAATAATAATTTCA<br>TAAGCTTAAATAAATAGTCCAGCCAGTAGATGGAGCCAAAAAGCCATAGAAGCTTC<br>AAATACTTGTGGTATCAATCTCTCCTCTGTTAAGGGAGGTATCAGATCAGAAGCACT<br>AATCAAATGCATACATAAATGCAGTAGACTGCAATAAAACAAAATCTGCAGATAGCA<br>ACAGAGCGCTTAACGAACGGAAAAGAGTTTAACTTGATCTATCACAGGATCGCACC |
| SEQ ID NO:43 | All | LPS-057 | GGTGCGATCCACAATAGTTCGTACGAGCGACGTCTATCTGGTTAATCAGAACACAT<br>ATCTAATTTGGAAATTTGTGGGCATAAAGCTCCACAGTGTAGGTGGGCTAATCCCA<br>TGAAACATTACTCTTCAAAACATCATACAACTGAGGTGGAAATTGCAAAAGATTATT<br>ACTGGATGCTGATCTGGGACTAAGGTGGTGGCCATTGGTAATGTTGTGTTTCAGAA<br>ATATATCTTCATGATGATCAGTAGTTGCATCTGGTTGGAAGAATGATAAATTCTGGT<br>AATTTGTCTTGGGATCGCACC |
| SEQ ID NO:44 | Late | LPS-058 | GGTGCGATCCAACTAGAAGAATATAAAGAAAAATTACGGACTACCAGAAAACATCA<br>CATCACAGTGTATTGCATTCTCAATAATCAGAACTGTACTGGCTAATATCGCTGTGC<br>CTGTCGTTTCATTTTCCTGTCATCCGCATAGGGCCCCTCATTTTCCCTATCTTGCAG<br>AAATCCAAGAAATGCAAGAAAACCAAAAAGGAAGAAACCCCCAGAGGAAGAGTCCG<br>AAGAGGATATGGGTGTCAGTCTTTTTGACTAGATTGGAGGATCGCACC |
| SEQ ID NO:45 | Early | LPS-059 | GGTGCGATCCCAGAACATTTCAGACAGATTAAAACAAGATCTAGTCAATTCCTACAA<br>GGGAAACTTTTGTCAAGATCCGGATCCAGATTTTCCTCAAGTAAAACTAATCTCATT<br>AAATCCAAGCCAATCTCTAGCAAAATTCAAACACTTTTTATTAAATCCAAGCCATATA<br>TCTGGCAAATTCACCGAAATATGTACAATCGCAGCGCATTGCTTGGCTTGCGACAG<br>AAACCATATTCGCACGTCTTCATAAGGCTTTGGATCGCACC |
| SEQ ID NO:46 | All | LPS-060 | GGTGCGATCCAACAACACAGCTTCACACTTACTCCATCCTCTGGAACTCTCATCAG<br>ATTGTGTTCTTCGTAGACCAAGTTCCTGTGAGAGTCCACAGGCACACTGAGGCTAC<br>AAGCGATGTGTTCCCTAAAGAACAGGGGATGTACATGTTTTCCAGCATTTGGAATG<br>CAGACGACTGGGCAACCAGGGGTGGGCTTGGGAAGACAAACTGGACTGCCGCTC<br>CATTCAGCGGATCGCACC |
| SEQ ID NO:47 | All | LPS-061 | GGTGCGATCCCAACACCAAGTGAGAATGAAGCAATATAAATCAGCAGACTCACTAA<br>AGCCAAAACAGTGAAAAATGTTTCATATTGGGAATCTGCTCCAGAATGAGCCTTCAA<br>GTAAAATGACAAACTAACGAGGAAGAGACATACGGCCATGCCCCCAGATGAGACC<br>ATGAGGAGGAGACGTCGTCCGGCTTTATCCATGAGCCATACAGCAACTGCAGTCAT<br>GATGACCTGGATCGCACC |

TABLE I-continued

| cDNA | Embryo Phase | Clone | Nucleotide Sequence |
|---|---|---|---|
| ksSEQ ID NO:48 | Late | LPS-062 | GGTGCGATCCAGGAAATCATCAAAGGGGAGCACATCCAATGTGCAAAATAAGATCA<br>TCATGCAGCAAGATCTCTGAAATATAAGCTCTGTAAGACCAATCTGAAGTGCTGATG<br>ATCAATATGAACTGAAACATCATGCCACAATGGGCTGGTACTTGTGCAAAATTCTCT<br>GGCATGTGATGAGAATCACATGGTTACCTCTTTGGATCGCACC |
| SEQ ID NO:49 | Early | LPS-063 | GGTGCGATCCAAAGAGCCTTCTTGCAGACAATCCGTGAAAACATGGCTATACAATA<br>AATTCCCAGTTTGGAATTCTAAATAAAACTGTTCAATATTTGAAGGCCTCTGATATCA<br>CAGAGACTGATATTAGAATGGAAGCATGTAGCAACCCTAGAAGCTTTCGCATAAAG<br>ATACCAGATTAATTCATAAGAAGGATCTCTCGTTCACCAGTCACATATCACAGTCGG<br>ATCGCACC |
| SEQ ID NO:50 | Late | LPS-064 | GGTGCGATCCGTTAGATGAGCTGCCAAGTATGGAATTATTGACATTTTTGGACGGG<br>TTATGGGCAGAGGGATGTGCCAAGCTGAAGAAGATACCGGGGTTGGAGCAAGCCA<br>CAAAACTTCGAGAGTTAGATGTTAGTGGGTGCCCTCAGTTAGATGAGCTGCCAAGT<br>ATGGAATTATTGACATCTTTGGACGGCTTGTGGGCAAAGGGATCGCACC |
| SEQ ID NO:51 | Middle | LPS-065 | GGTGCGATCCACATAGTTTGAATGCAAGGAAATTGCACATACTTCGTGGGGAATTT<br>CGATGGCAAATCAGTCCAGGTAAATGACTTCTCAACATAGGTCCAAAACTCTTTCAT<br>AGACCAGATCTTGACCGTGTTGTCCATGCCACAGCTTGCAATACGATATACATCTG<br>AAGGATGAAAATCTACACTGAGAACTTCATTGCGATGTCCCCCAGCTCCAGCAAAT<br>ATCAAAATGCATATTCCAGTTTGAACATTCCAGAGTCGTACAGATTCATCTTTGCTA<br>GCAGATAAAATAAGGGAAGGTTTCAGTTGCTTGGGTCCTTATTTCATTCACAGAACT<br>CCATGGCCAACGAAACTCTTATGGACTTTTCATTTGCACATCCATTCTCGAATTATA<br>CATTGTGACCGCAGCCACTAATAATGGGGAACATCACTCGCCTGCCCACTTATGTG<br>TTAAAGAATC |
| SEQ ID NO:52 | Late | LPS-066 | GGTGCGATCCCCTCCATTTACCATGGTATACTGTTCCAAAGGTTCCAGAGCCTAGC<br>TCTTTCAATTCTTCAAGGTCAGCATTCTTTATTATCTGGAAACTTCGCTAGCTGTGT<br>CTATAATCACGAAACCCAGACGGGGAACTAATAGGCGATGAAGTTTCTCTTATCCA<br>TAACCGTTGCAAAGATCTTACACGGAGTTTTCTCTTCTTCTGCGTGGCTTTTCTTTC<br>CCGTATTCTCGGATCGCACC |
| SEQ ID NO:53 | Late | LPS-067 | GGTGCGATCCATACATGCGAGGGCGCATGAGAGACTACCACAAATCCTACATACCT<br>CCATTCACCCCTGGATCGGTTATACAAGGATTTGGGGTGGCTAAAGTGATACTCTC<br>AAATCACCCAGACTTCAGAGAGGGTGACTTTGTATCTGGTACTATAGGATGGGAAG<br>AGTACAGCATAATACCAAAAGGGAGTAACTTAAGAAAGATCAAATATACGGACGTAC<br>CACTTTCATATTTTGTGGGTGTTTTAAGAATGCCCGGGTTTACTGCTTATGCTGGAT<br>TCTTTGAAGTTTGCTCTCCTAAAAAGGGGGAGCATGTTTTTGTCTCTGCCGCTTCA<br>GGAGCTGTTGGCCAGCTTGTTGGGCACTTTGCAAAGTTGATGGGTTGCTATGTTGT<br>TAGGGAGCGCGGGTAACAAACAGAAGGCTGATCTGCTGAAACATAAAATGGGCTTT<br>GATGATGATCTCCACCATAACGAGGAGCATGACTTCGATGTGGCTTTAAAAAGGCA<br>TTTTCCAGATGGGATTGCACC |
| SEQ ID NO:54 | Late | LPS-069 | GGTGCGATCGAACTGAATGAATGACGTTGCCAAGCTATGTTTGGGAATTAAAACTT<br>GAATGCCGTTATTCTCTCCTTTTTCCAAAAGGGCCTTTTCTGCCAGAAAACCTTAAA<br>TTTCTGACTGGTTTCCAAGTCCAATTTTTAAAATATGGATTGGTTTACCATTGAAGG<br>CACCACCATGCTCTGAAAGTTATGGACTGCACTTGCCCCAGTGCTATATTTAGTCC<br>AGATAGCGCTTGTGTCTCTAAATGCATCTCCCTGCTCGGATATCACC |
| SEQ ID NO:55 | Late | LPS-070 | GGTGCGATCCGAACAGAGGGAGCAGATTTTGCCCTTGCAAGTATTCACAACATTAG<br>AGAAGCCCTGCCAGAGATATGGGAGGAAGAAGATGCAGAGAACACCAAAAATGTT<br>GTGGGATCAAGAGGAGCGGATGCAACTATAGAAACTGTTGTCACGGCATAAGCCA<br>TCGCCTCATTGAATGAGGGAATGGAGGACTAGACAAATCCCTTTGGATCGCACC |
| SEQ ID NO:56 | Middle | LPS-071 | GGTGCGATCCGATTGGGCAGCTGCAGCCTTGGGAAGCTTTAGAATCAAATTGCAC<br>TCATCCTCCAGGAGGTATTGAGAAGTCAATTTCTCAAGGTCTACAGTGACAGAAGG<br>AACCATCTTGACAATCTTATCAGGTTTCCTGCTCTGGTTAAACACTTCAACTTTGAC<br>AGGACGAGAGAATGTGACTAATTCATCTTCTTCATCAGACTCTACATCTTCCTGTTT<br>CAAGAAACAAAGATACTGATCATCACTAGGGCAAGAATTGATGATTTTGATATCTCT<br>GGAGAAGCCAGTGTTTACATTGGTTTGCTTCATGGCCACCAGTCTATGGCATAAAG<br>CTTTCCCGAAAGGGTACTTGGCAGATTTAACAGAGCCCAACGTTATATTTAAGGCC<br>CATCTCTTTGCTCTCAAAATTTTTCTTGCATCCTCTGGAGAATATAAAACCCCTTGG<br>TGTCTCTTTCCACAAACACCTTCTCATTGATC |
| SEQ ID NO:57 | Late | LPS-072 | GGTGCGATCCAACTGAGAAGGGTGTTTGGTGGAAAGATGACACCAAGTGGGTTCT<br>ATATTCTCCAGAGGATGCAAGAAAAATTTTGAGAGAAAGAAGATGGGCCCTTAAATA<br>TAACGTGGGGTTCTGTTAAATCTGCCAAGTACCCTTCAGGAAAGTTTATGCCATAG<br>ACTTGGTGGCCATGAAGCAAACCAATGTAAACACTGGTTCTCCAGAGATATCAAAA<br>TCATCAATTCTTGCCCTAGTGATGATCAGGAAGATGTAGAGTCTGATGAAGAAGAT<br>GAATTAGTCACATTCTCTCGTCCTGTCAAAGTTGAAGTGCTTAACCAGAGCAGGAA<br>ACCTGATAAGATTGTCAAGATGGTTCCTTCTGTCACTGTAGACCTTGAGAAATTGAC<br>TTCTCAATACCTCCTGGAGGATGAGTGCAATTTGATTCTAAAGCTTCCCAAGGCTG<br>CAGCTGCCCAATCGGATCGCACC |
| SEQ ID NO:58 | Late | LPS-073 | GGTGCGATCCATGTAGTGCCAACTTACGAGATCACTAACTTTAAAACTATCATGCAA<br>TTGGCCAATAGAAGCGACACTTGCTGTGCCAAAGTATCGATAGGCTACTCCCGATG<br>GCTCAATCATATATAGTTGGGGCCCATCTCTATCATAACCTCCAAGGATAACTCCAG<br>ATCCAAAAGGCCTTAACCACCAATATAGTGTGCACAAATGCACATAACTGGCAACA<br>CGTTCACAAAGTTCCTTAAT |
| SEQ ID NO:59 | All | LPS-074 | GGTGCGATCCCATGGGATAGTTGCAAGACACACAAATTTGTTGTGAAAGAAGAGAG<br>ACACGCACAGACAACCATATGATCTTTTTTTTTTTTTTTTTTTTTTTTTTTTTTTTTTTT<br>TTAGCAAAATTCAAACACTTTTTATTAAATCCAAGCCATATATCTGGCAAATTCACCG<br>AAATATGTACAATCGCAGCGCATTGCTTGGCTTGCGACAGAAACCATATTCGCACG<br>TCTTCATAAGGCTTTGGATCGCACC |

TABLE I-continued

| cDNA | Embryo Phase | Clone | Nucleotide Sequence |
|---|---|---|---|
| SEQ ID NO:60 | Early | LPS-075 | GGTGCGATCCCACTGTAGTTGTCCTTGTTGAGCATAGTTCAAGCTGTTCTGATTCC ACCAGTTAGTGGCCCAACACTGCGAGGTGCTGCCATTTCCATTCCATTCACAGACG TCAGTGTTGAAATTCATATAGGAAGCCACAAAGGGTGAGGAAGACCAATCTATTTTC ACTCGCCCCCCTTGAGTTGCCCACTGGTCTCCGCTCCATATGCTAGAGAATACTCT CATTGCCTGCTCATTCGGATAGGGAACGCCTATGTTTTCATTGTTTGCAAATACTCT GATTGGCAAACCATCAACGAAAATCGCAATTTGCTGGGGGTTCCAGAGAATAGAGT AATTGTGGAAATCTGCTGTAGGATCGCACC |
| SEQ ID NO:61 | Early | LPS-076 | GGTGCGATCCCACACTCCTAACCCTATTATATGTCTCCCGTCCATGGAGTCATAGA AGGAGTACGATAATATGCCCTTCAGCCAAGCGAAGTATGACTTTAGTATGGCCAGG CAGCAGTATGAAAGCACATCTTGTTTCTTCCAGGTCGGCATGTATAGTCTCCGGAG GCTAACAATGTCACCCAAAGCTAATTGCGCAAACGGAACTCCTCTGCTGATCTCCC GGGAACTTAGGCGGAACCACCCTGAATCCACTATTCTCACCGCGCATTTCATCCCT TTGGTGAACGCCGCTGCCTCTGGTAGATACAGAGCTGGCTTGTCTCCACTGGAAC CCCCTTTCCGGATCGCACC |
| SEQ ID NO:62 | All | LPS-077 | GGTGCGATCCAAACTGTGGTTATCGGTGGAGAGATTAAGCAATTTATTGGAGTAGC AAGTACGCTGAATTAAGGGGGTCCATCTTCAAGCAAAGGTTCCTTTGGATGACTAT GTGTTCTGGAAGTGTTTATGGATCAATCATCTCATAAATTTTGGTAATATATAACAGA AGATTATGGCATCCAGTTAGGATGGTAGTTTCATTGAGGTATAGTAAAAACTACACT AGTCTTGTGTTGCCACCCACTTTTCAGAGAAGTCAGGAGGTCTCTTTGTGAATCATT GATAACTTTATGAGTGGGTACCTAAATGAAATATTTGCATCTTGAGTATATACTCAAT TGATCTTACTTGTGGATCGCAC |
| SEQ ID NO:63 | Middle | LPS-078 | CTTGGTACCGAGCTCGGATCCACTAGTAACGGCCGCCAGTGTGCTGGAATTTACG GCTGCGAGAAGACGACAGAACACCTATCATAACTTGAATTCTGATGCAAATCGGAA TTTGCCAAAAACTTGGACGGAAATATAATAGGCAATATCATCCCCGCAAGTAACAAA AAAATTGCATGAAAGCTCAAATCCTATGTGCTTTACACCTTGACTGCATACTTTCTC ATTGGAAAATACATCTCTTTCTTTTTCTGTCTCTCAGTCTTCAATGACGCCTGATGCT TGGTAAGGCGTCGCCTGATAGCACGAGTCTTCTTGGGACGCAAATCAAGAGGCAG GTACTTCTTTTTTTTGTATGCTTCTCTTAATGCGGATCGCACC |
| SEQ ID NO:64 | Late | LPS-079 | GGTGCGATCCAAGATTGTACGGCACAGGCAAATGCTGTTCTTTTTCTTAATCACGA TGTGCTTGAAGAATATGAGCGCCGATGTGAACAGATCCACAACCTGGAGTTAAAAT TGGAGGAAGACAGAGCAGTGCTGAATAGGAGCTTGGCAGAAATAAATAGTCTTAAG GAATCCTGGCTTCCCACATTGAGGAGTTTGGTTACCAGAATTAATGAAACTTTCAGC CACAACTTTCAAGGGATGGCTGTTGCTGGAGAAGTTACACTAGATGAACATGGCAT GGATTTTGACAAGTTATGGTATTCTAATAAAAGTCAAGTTCAGGCAAACTGGACAGT TGCAGGTATTGAATTGCTCATCATCAGTCTGGAGGGATCGCACC |
| SEQ ID NO:65 | All | LPS-080 | GGTGCGATCCGAGGGAAGCGATGTAGTCTTGCCCCAAGCGACGACCATGATCCCT TATTCTTGGGCAATATGTGCAAGACGTGGACAAATGAAGCGGTTAAAGGGAAGCTT ATGGACTATGGAATAGAGGGTCTTGAAGAGCTAACTCTAGTGGGTGATACTCAAAA TGAAGGAATAAGCCGTGGTTTTGCATTTATAGCATTTTCTACGCACATGGATGCGAT GAATGCATACAAACGCCTTCAGAGGCCAGATGTTATTTTTGGTGCTGATCGAACTG CGAATGTGGCATTTGCAGAGCCACTGCGTGAGCCTGACGAAGAGATCATGGCCCA GGTTAAGTCAGTGTTGTTGATGGGATCGCACC |
| SEQ ID NO:66 | Late | LPS-081 | GGTGCGATCCAGTCCTGAAAATGTACTTTACCATTTGTATAATGATGTAAAAATCTT GGCCATAGTCTGGTCAAACCAGACTGTATTGTTGCTAAAGTTATGGAAATTCTGGC CATATTTTTGTCTAACCAGACTGTATTGTTGCCAAAGTTATGGGAATTCCGGCTATA TTTTTGTCTTCGAAAAAAAAAAAAAAAAAAAAAAAAAAAAAAAAAAAAAAGATCATAGGG TTGTCTGTGCGTGTCTCTCTTCTTACACAACAAATTTGTGTGTTTTGCAACTATCCC ATGGGATCGCACC |
| SEQ ID NO:67 | Early | LPS-083 | GGTGCGATCCGCTGGAAGGTGGGCAGCTGGACATCTGGGAATTATAAGTCGAATG TCAATTGCTGGGCCATCTGGGGGATGAGCAATAGCATCGGAGGCCAAGTTCTTCT GCAGCCGGGCACCAAATGCCATGTGGAGGTCTGAATCTTAGTTTGGAGGTCGAAG TTTCAATCCCCTTGTGTTTACTCTGTTTCTGGTTTTATTTGAATAATTTGAGCAATTT AATGTGGGTCCTTAGTGCTTCTGTGGATCAGATTCTAGGGAACGCCATCCTGATAA GTAAAGATCCGAGTTTTAATGGAGATTCAATTCTATCAGAATTCCATGGTGGTTTAA ATTCCCTTGTACTGTTGATCTACGTCGCTTTGTATATCAGTGTGTGTTAAGATTTTCT CAGAATCCACAGCTTTGTTATGGATCGCACC |
| SEQ ID NO:68 | Middle | LPS-084 | GGTGCGATCCAAGCACTTACGACTCCCAACAAGGACGGGAAACTCTAAAATCGGAA AAATATCATATACTGAGGCATCAACTTTGTTGATAAAACTTTAAACAAGAACAATATT TGCAGCATATTAGCCCACATGCCATAATGACAAACAAATATGAGAACACTGCCTACA GGTTTGCCAAAAGCATGGCCCTCACTTTTGCCCTGAGGTCATCAGGAGCTTCTGAG GCTCGAGAAGGAGAAAAAGATTGTGTCACTTCAGGAGCTGAGGCCTCCACATCTTT TAATGATTTCGCAGCAGGCCTCTCTTTAATGTTTTCTTTAGAGGATCGCACC |
| SEQ ID NO:69 | Early | LPS-086 | GGTGCGATCCAAGGTACGAGCGAACAAGTTTCTTCAGCAAGCCACCTGGAACTTTC CATGAGTCCAAAACAAGTTGAAGAAGGCTTCTTTGGCTACTTTTAAGATGCTGAAGT GATTGTGCTCGCCTCTTGCACAGTTCAACCGCAATAACATTGGGTTTTACAAAACC GATTACCTGTTTAACCTGCTGTGCACTCTTTTTCGAAACATGACAAGTTCCAACAAG ATAAACTTCGGCCCCATTCTCGCCATTCCGCAAATAAACCACGCTCTCATCTTCTGT TATCGAACTCGAGTGCATGCCACGACGCTCAATTGCAGGATTCCAACCCCGGACTT GCGAATGGTGCAAAGCGATGCCCGTTCGTCTCAGCGATACTGCTAAAGATCGGCA GACCCGAACCAGTTTGATGCTTCCATTGCCTTAAACATCCAGAGTTTTCCTTCGACC TTAAACCCTAACAAGATTACTGATTTCTGGTCCGGATGTTCACTGTCTGTTATACTT CTCACAAATCTGTCACACTCCTGATAATCTTCGGTATTGAACTTCATTGAATTGAATT TTCCTTCTCATTGGAATTCAATTGTACCTTGTAAATGTCTGGATCCTACACTATACCA ATATTTACAGGTCTGAGTATTTTGCCTGTAGTATAATTATCTTTCCTTCGGTCTCGT GTTTCCGTATTATTCGTGTAGGATCGCACC |

TABLE I-continued

| cDNA | Embryo Phase | Clone | Nucleotide Sequence |
|---|---|---|---|
| SEQ ID NO:70 | Late | LPS-087 | GGTGCGATCCCGGGGGGAGGTTGATGTTCTGAGAGAATCAATGAAGGGATTTCAG<br>CTGAGCTTGCCTTTTTGAAGACGGAATGCGAACAACCAGTCATTTGCAATAGCGAG<br>AATTCTCTTAAGCCACTGCCTGCTGGGGAGGCGAGTTCTGATTCCGGTGATTGCAT<br>CACTCAACGGCAGCAGCAGCGGCAGAACCTTTAGTTTCCCATGACAGGTCTCTCTG<br>TACAAGTATCTTCCTGTTATGATCTAATTCCGGGTTGTTCGATTATCGTGATGTCTC<br>CTGTATTGACATATTAGCAGAATATTACCATGATACGATGTTAAGTGGCATGGTTTA<br>TGCCCTGCATGTTATGTTATGGAGGAGGTGAGGCATGTGGCGCTCATGGGAGGGC<br>CCACATGGTCCATGGACGTCTTATTAAACGCATAGTCGTGAATGAAAATAGTTCAAT<br>ACATTCAAAATTCCAACACAATTTCATTACAATGGAAGTGACTTCGACTTGAATGTT<br>CATTGAAGCATTTGCATGCACAAACAAAGTATACTAGATTAGAAGAAAATTGCAAAA<br>AAGGACATTGTGCCCTTCTTAGTGAATATATAAAGATGTTCTTCATGCTGGATCGCA<br>CC |
| SEQ ID NO:71 | Middle | LPS-088 | GGTGCGATCCCAATAGCCAATATTGCCTCCAAGATAGCCTAGACTGCCTTTTGCAT<br>AGTTCTAGAAGCCAGTCACCCAACCTCCCAAAAGAAATTGCGCAATCTTTCCCATC<br>AGTTTCCCGGGTATGTGTTCTGTCATTCCCCGAATTTTCTTTGGTTTTCACTAATAG<br>ATTTCTTTCCATGCACATTGCTTGTCTCCAGATCTTTTAGGTGTTCATCCATCTCTTA<br>GTAGTACTAGATCGATGGCTTCCAAGAGAACAGGATCATATGACACTGTTGGAAAT<br>GTAGCTGGAGCAGCAGTTGAGCAAGTGTCCTCTAGTCTATCTATCTATGAAAGATA<br>CACATTGTTTCTAGACATGGATATCAAATTGAAATTGCGAGAAGTCCATGAAACATT<br>TGCCGCCTTTTGAAGAAAGGCTCCAAACTGTCAGGGTTCGTTGAACATCACATGTT<br>CTCGCTGTCTGATCCCCCC |
| SEQ ID NO:72 | Middle | LPS-089 | GGTGCGATCCTCAGGGTAATGGCCTGGCTGAATCAAGTAACAAGAATCTTATAACC<br>ATTATCTAAGAAGATAGTAGGAGATAACAAGCGGTCTTGGGACAACAAAATCAAGT<br>GCGCTTTGTGGGCAGATAGGATAACTAAAAAGAAAGCCACTGGTAAAAGTCCCTTT<br>GAACTTGTCTATGGCATGGATTTGACATTACATGCCCATCTTAAATTACTAGCTTAC<br>CAACTCCTTCAACATTTTTCTAGTGATAAAGGTGTTGTCCAAAACATGGTTGATCAA<br>ATTGTGCAGTTGGATGAAATCCGCAGGAAAGATTTTGATAGTGCAAAAATCAGTCTA<br>CCATTAAGAAAATCTTTGACAAATCTTCTCGGTCTAGATATTTACAGGTTGGAGATA<br>TGGTTTTACTATGGATTCCACC |
| SEQ ID NO:73 | Late | LPS-090 | GGTGCGATCCTGCAGGCTTAGATAGTTTCGGCGCTCCTCTGAAAGAAGCACGAGT<br>AGGTGTCTCCACATTAGGTTGGCCTGATCCCTTGCCTGCACTTGCAGCTTGTCTTA<br>CAACATCTCCTATGCTTTGATCCAGGCTTTTCACTGACATAACTTCAGGGGCTTCCT<br>TCTCCCAGGGCCGTGCTGCCATCCAGCGTTCTAGCCAGCTCCATCCCCAATTTGG<br>CTTGTTTGGGTCAATTTCCATCAGCATAGGATGAGCTGCTCCTCGTGTGCTTTTCAA<br>TGACTGATGAGAATATGCGTTATGCCAATGCCCTTTCTCGCTTCATGGCTGCTTCTT<br>GCTTGCTTTGCAAACTAGCCTCAATTTCCTCTTTGGATTGCAACTGTCATCCAATCC<br>TTTGCTTCCATACTGGATCCAC |
| SEQ ID NO.74 | Late | LPS-091 | GGTGCGATCCCAAATGAACATTCAACATTCGATCATGTCAAGCGCTAAATGCCTTG<br>GCAGCTTAAAAGCTAGACTCCGCAAGTGACCCTTCTGACTTAGTACACATATTAAGA<br>CTCATCAAGGGTCCAATTCCATGAAAAGAAATTTTAAAACGGTTACATATTCACAAG<br>AACAGCACGAGATTTCCCAGATAGTCAACCACCAACTTGCCCTATCAGCCCAAATA<br>TTACTCATTCCATGTTAAAAATAGCAAATTTCCAGATAGAATGTCGAAAGAGATCTT<br>CATGCACCATATATGGACTCTTAAAACCAGCCAAAATCTATACTGCCATGCTTGGAT<br>GGCACC |
| SEQ ID NO:75 | Late | LPS-092 | GGTGCGATCCTGGAGAGAGAAGCAAAAAGCCTACCATCTAAATCTACATTCTAAAT<br>CAGATATCTTTACTGTGAAAGGAATTGAATGCTGCTTCAGATATCCTACAAGAATTA<br>AGAAGAAAAGAATGATCAACTCCAAATCAGGCAGATGGCTCAGAATTTCCCGCAGC<br>TTCATTTTCGACGGCCTCCACAACACCAACCTCGGCAGGACGTATTACTCTGCCAT<br>GAAGTGTATAGCCAGGCTTCAAAACCACAGCCACACTGCCAGGCTGCTTACTAGCA<br>TCTTGAACTTGAGATACTGCCATGTTGCATATGAGGATCAAACTCTTCATTTATTGG<br>ATCGCACC |
| SEQ ID NO:76 | Late | LPS-093 | GGTGCGATCCCCAGAGGTTATTTTGGGTTCAAAGTATTCTACACCAGTTGACATGT<br>GGTCATTTGCTTGCATAATTTTTGAACTGGCTACAGGTGATATGTTATTTGATCCTC<br>AGAGTGCAGAAGGTTATGACCGCGATGAGGACCACCTTGCCCTGATGATGGAGCT<br>TCTTGGAAAAATACCTCGTAAGATCGCCTTAGGTGGGAGCTATTCACGGGAACTTT<br>TTGACAGGCATGGGGATTTAAAGCACATTAGACGGCTTCGGTATTGGCCCTTGGAT<br>CGCACC |
| SEQ ID NO:77 | Late | LPS-094 | GGTGCGATGCTAAACTGTATGTCTCCACAATTGTCTTCAATATAGAAGCAGCTACG<br>CCCCTCCTAAGTCATCATAAGTTAAAAACTTCATCTTTCCAATACAATTAAACTATCT<br>AGCTTATCAGTTTGGAATAGAGATACAAAATTACAGATAGATTAGCGAAACTGTGCC<br>ACAAAACCTCTTCAAAATTAGAAGCATGATTGTCTACAACTCCACTTCAAAAAGGAG<br>CTGAACCAGTCCTTCGAAGGGTGTGCTTTGGTTGTGGTGGAGGTACAGAAGGCAG<br>CAATTTCTCCAAGAACTGCTGTTTTTTTAGCCTCTCATTCTCCTCTTTAAGCTGCATC<br>ACTTCATTCTCTAGCTCATTTGTGTATGCCTGCTTTCTTGCCCTGGATCGCACC |
| SEQ ID NO:78 | Middle | LPS-095 | GGTGCGATCCGAGTGATGGCACAAAGAAAAGCAATGATAGAAAACAAAGAACAGGT<br>AGCTCAGAAGGTTCAGCAACTTAGAGAGTCAACTTCGAGTTAAGGAGGGCGGGAG<br>CAATTGGCAGATTCTTCCAAATTTGTCAAGATCTCTTGGCATGAGATGACCTTATAG<br>GATGTTAAGGAGCAAGAGGATTCTAGGAATAATGCCAAGGATAATAAGACTAAAAG<br>GATGCTTCAAGACCAGGTGGCAAGGAAGGCTTCTAATTCAAAGGGAGTTAGCAAC<br>GGCAACAGATGCAATTCTAGGATCGGACC |
| SEQ ID NO:79 | Middle | LPS-096 | GGTGCGATCCTAGAATTGCATCTGTTGCCGTTGCTACTCCCTTTGAATTAGAAGCC<br>TTCCTTGCCACCTGGTCTTGAAGCATCCTTTTAGTCTTATTATCCTTGGCATTATTC<br>CTAGAATCCTCTTGCTCCTTAACATCCTATAAGGTCATCTCATGCCAAGAGATCTTG<br>ACAAATTTGGAAGAATCTGCCAATTGCTCCCGCCCTCCTTAACTCGAAGTTGACTCT<br>CTAAGTTGCTGAACCTTCTGAGCTACCTGTTCTTTGTTTTCTATCATTGCTTTTCTTT<br>GTGGCATCACTCGGATCGCACC |

TABLE I-continued

| cDNA | Embryo Phase | Clone | Nucleotide Sequence |
|---|---|---|---|
| SEQ ID NO:80 | Middle | LPZ-001 | ATCTAGATCATCGATCTTGTCCAAATTTTAACTAGTGAATAGTTTTAAAAAAAAGCAA<br>CTAGCAGAAGAGAACCTAACCACTGACAAATTGCAAATACTCTAGAACACTATTCAT<br>CATTTTTTGCGATTCACGCTGGACCCACAAGAACCCCTTGAGCTGAACTTTCTTTTC<br>GTTCTCCCTCCTTTTGGATCGCACCATCTAGACCATCGATCTTGTCCAAATTTTAAC<br>TAGTGAATAGTTTTAAAAAAAAGCAACTAGCAGAAGAGAACTAACCACTGACAAATT<br>GCAAATACTCTAGAACACTATTCATCATTTTTTGCGATTCACGCTGGACCACAAGAA<br>CTCTTGAGCTGAATTTCTTTTCGTCTCCTCCTTTTGGATTGGACATCNAATCCTGCA<br>GCCGGGGATTCATATTCTTAACGGCGCNCGCGNGGACTCCATNCCCCATATGATC<br>TTTTCATCCTGGCGCNTTTAACTCTGAAGGGAAACCGGNTTNCCCTTATCCCTGGA<br>NATCCCTTCC |
| SEQ ID NO:81 | Middle | LPZ-002 | GTGGAGTGTAAAGGTCAACGTGCCATCCGGGTACAAACTATTGTAGAAAAAATGGC<br>AAAGTTAGGTCTGAAAATATCCATTTGGCCTGCTCTAGTTGTACAGTACATGATTTT<br>GCACTCGCACAACAATGGACTATAATTATTTTCCTGGCAAAAAAAAAAAA |
| SEQ ID NO:82 | Late | LPZ-003 | GGTGCGATCCAGGACATGAGGCCGAGTTTGCCATTGTGATATGATTGAGGAAGTC<br>CAGTCCTAAAATTAGGTTTATCTTGATGTTTGACAAGAGATATAGAGGGGCATGATG<br>ATTCATTGATCTGTTTGCAGATCTGTAACTGCAACCATTCTAATGACATAATAGCGC<br>TATTGTTTGGGTTCGTGTGATGACATAATAAATTGATTTAATTTAATAACATCTGTTA<br>ATGCAATGGCTGTAGCTGCATCATCACCGTATCCATCGAATGTTCCATTTTTCCAAA<br>TGTTTGTTTCCAAAACCAGAACACCAAAATGTCCCCTGCGTTTGTNTTGAAAAATAT<br>TGGGCCCNTACTATACTATAATNTTTNGGCATACTATACTATAATGTTTCTCCCATTC<br>CCCCCAAATGANTCCTATACAATCCTGGCCGNCTTTACACTCCTGACNGGAAACCC<br>GGCTTNCCACTAATCCCTGGNCNANCCCTTC |
| SEQ ID NO:83 | Late | LPZ-004 | GGTGCGATCCGACTGTGATATGTGACTGGTGAACGAGAGATCCTTCTTATGAATTA<br>ATCTGGTATCTTTATGCGAAAGCTTTTAGGGTTGCTACATGCTCTCCTCTTTTGTAT<br>GAATTTCCATTCTAATATCAGTCTCTGTGAT |
| SEQ ID NO:84 | M,L | LPZ-005 | GGGGAGTGTCAAGGGATAAGTGGTAAGCCAGGTTTCCAGTCAGAAGTGTAAAGGC<br>GGCCAGTGATGTAATAGATTCATATAGGGGAATGGAGTCACCGGGGTGCGCCGTT<br>TTAGAATAGTGGATCCCCGGCTGCAGGATTTGATGGTGCGATCCTGCCCCTGATAA<br>TTTGGTTGCAATGGAAAATGCAGTATTAGGTGCGAGATGTAAAGCCCGCCCGGAG<br>CGGTGCATGAAGTACTGCAATATTTGTTGTAGTAAATGTGCTGGTTGTGTTCCCAG<br>CGGTCACTATGGCAACAAGGACGAGTGCCCCTGCTACAGAGATATGAAGTCCGCA<br>GCCGGCAAGCCCAAGTGTCCCTGATCTTAGCACTTCAGTCCAGTCGCTCACTTCTT<br>TTATTCTTTTTTTTTATAAAAGTGACGAGGCCGTTTTTCTTGTACTTGGTGGCCATAT<br>GTAGAGCGGTGGCTACTTCTCCTGTGTTAGGAAATGTTGCAGTACTAATAATAAGA<br>ACTTCTTTGGCAAAAAAAAAAAA |
| SEQ ID NO:85 | M,L | LPZ-006 | GGGTTTCCTTAAGAGTTAAAGGCGCATGATGTATAGAATCATATAGGGGATGGATT<br>CCCCCCGGGGGGCCTTTCAGAATAGGGATTCCCGGCTGCAGGATTGATAGTGCGA<br>TCCAAGACACAGTGGAGTACCACAATGGGGATCTGGCCAGTGCTTTGTGGCTATTC<br>ACTGCAGCTGTATTAAAACAGGAAGCCGCAAATGGCCAGAAGGCCATTGAACTTGC<br>TGAGAGCAGACTATCTAAGGATGGCTGGCCTGAATATTATGATGGGAAGCTTGGAC<br>GATATATTGGAAAGCAGTCTCGAAAGTGGCAAACCTGGTCAGTTGCTGGATATCTT<br>GTAGCCAAGATGATGCTTGAAGATCCATCCCATTTAGGTATGATAGCATTGGAAGA<br>GGACAAAAAGATGAAGCCGTCCCTCACTCGATCAGCTTCTTGGATAATGTAAAATG<br>GGGAAATCCTAAACTTTCAGGCCACTCTTGAATGTTTTGTCACTTCTGTATGACAAA<br>TGAGGCAATTCATAGTACATGTTGTGCAAAAAAAAAAAA |
| SEQ ID NO:86 | M,L | LPZ-007 | GGTGCGATCCCAGAGAATATTAGTTCATGTGTTGCTCTCATTTTCTTCAATATGCAG<br>GGCAACCATTTGAATGAAATTATTCCTTTCGAATTTCAAAAACTTAATAGGCTAACTT<br>ATCTATCTGGAGCCGATTTTCATTGACGAGTAACCTGTAAGCTGGCCAGCAAAAGC<br>CAACAGATGTTCAGCTCGTTGGAACCAGTTGAAGATTGTAATAGAGATGGTGAATA<br>ATCGCGGACGGCTCGGCCAATGGAATATTTGTTGCATCATCATCAAGGGGGTATGA<br>ATTCCAAAGAACTTGTTGATTGAAATTCCCAAGCAAAATTCTGTGAAATGAAAAATTT<br>ATTGAGACCATTGGGCAAAAAAAAAAAAA |
| SEQ ID NO:87 | Late | LPZ-008 | GGTGCGATCCAAAGAACACAAGATGGAGTTACCACAATGGAGGATGTTGGCCAGT<br>GCTTTTGTGGCTATTCACTGCAGCCTGTATTAAAACAGGAAGGCCGCAAATGGCCA<br>GAAGGGCCATTGAACTTGCTGAGAGCAGACTATCTAAGGATGGCTGGCCTGAATAT<br>TATGATGGGAAGCTTGGACGATATATTGGAAAGCAGTCTCGAAAGTGGCAAACCTG<br>GTCAGTTGCTGGAT |
| SEQ ID NO:88 | Late | LPZ-009 | GGTGCGATCTGTGTGGCTCTGAAACATCCCGGCTCCCCTCTGCACTATAATAATCC<br>CAAAATTAAGTGAACCCAACAGAATTTGCTCATATCTCTACAGTTATTGCAGACTGA<br>GCAAAACCCTCAAACTCATGTGACCTCTCAATAGGAGCCCACGCCCAAGATTTGTC<br>CAGCATGTAACACACCTGATCGCCGCCACTGCAAGCACAACCGCTCACAAATATCT<br>TGTCACACCACACTGTTGCGCAAGTTAACAATATTCATGTCTCCAGGAAAGAAATGC<br>CACACTTCCCAACATTCTCTTTACTATTATAGAACTTCCTTGTTGCTATGGAAAAAAT<br>ACATTCCCAACGCAGAACCCCAACGGGGGTTCCCAATANCCCATTTCCCCCCTNTC<br>CAAANCCNNTNTGAATGCNCCCCATNCCCTATTGNATNNTTTAAATCCNGGCGCNTT<br>ANCTGGAAGGNAACCCGNTTGCCN |
| SEQ ID NO:89 | M,L | LPZ-010 | GTTTTCCCAGTCAGGACGTGTAAAACGACGGCCAGGGATTGTAATACGATTCACTA<br>TAGGCGAATTGGAGGTCGATCCGTATAGGTAGTTGGATGATGAACGGGCAAAGAA<br>GGCAAAGGAGTACAGTGATGGATCCTGTAATTCCTGTTTCAGAAAACAGAAAATCT<br>GCAATATAAGGATGGCTAAGCTTTTCAGCTATGAAAATATATGGTGCAGTGGCACT<br>CATATCAGTTGCAGAGTTGTCAATATAACTTTTGTGAATAGGAAAGTTGTCCTCTTT<br>TAGAGTGCAGAATCCTGCAATATAAGGATGGCTAAGTTTTTCAGCTATATGAAAAT<br>ATATGGTGCAGTGGCAAAAAAAAAAAA |

TABLE I-continued

| cDNA | Embryo Phase | Clone | Nucleotide Sequence |
|---|---|---|---|
| SEQ ID NO:90 | All | LPZ-011 | GGTGCGATCCTACAGAGAGCAGCTTGACGAGGGCCAAGGTTAAGGATGAAGAA<br>TGACCTCAGCTAGTAAGGTTTACAGAAGCAGCAGAGGCATCTTAACTGTTTTTATGT<br>TTTGGCAAAAGTTGTTGCGTCGGTTGTTTAATCCAGGATTTCAGATGTATTTTGTAG<br>A |
| SEQ ID NO:91 | Late | LPZ-012 | ATTGTAATACGACTCACTATAGGGCGAATTGGAGGGTCCGATCCTGCGAGACCGA<br>GGGTTCATTTTCCTTTAGACAACGACGTTCAGTGGCGACCAGAGTTTCCCAATCAC<br>TTCAGCGATTCTATTCCTTCGTTGTAATAAAGCTTAAGGAATGCATGCTTTATTCCTT<br>GGAAGGTTTGAATATTTATATTTATTGGCAAAAAAAAAAAA |
| SEQ ID NO:92 | Late | LPZ-013 | AGGTGACCGTCAAAATGATTGCAGAGGACTTAGAGAGGGAAAACCGTTCCGATCT<br>GGTGAAGCAATTGGATGAAGCAGCTCTGGAATTGATTCCCGTTTCTGATGATATCG<br>TACGGCTAAGCTCAGCTCTTCAGGCAATTGGCAGAGAATACGATTCTTCAAATGAG<br>ATGACAGATTTTAAGAAACTTATAGATGAACATATTTCCAAGCTTGAAGCGGATTCC<br>CCTACGGTCACCT |
| SEQ ID NO:93 | Late | LPZ-015 | AGGTGACCGTAAAATACTATGAGAAATGCTTTCATCAGGCACCGCTGGTAGGTTTT<br>CTTCAAGCTTTTCATTAGGCAAAAGAGGCTCCGTGAGTTGATCGTTAATTCTCTCCT<br>TGAATGGCCATATTGACCAGACACTCTGATTAGAAACTGGAATACAACTGCACATAT<br>AGTCATTCTTATATGATTCATCCTTCTGCACTTCAGCATCCTGCGGCAACTCTTCAT<br>CCCGCCATACTGCAGAAAAATTATTTGACTCTTGATCATGTTGTAGATGAATCTTCA<br>TGAATCTTCTCATCTTGCATTCTTGTCTTTATATCTTTAGGAAATTGCATCTGGTAAA<br>AGTATAAATGCATCTTCACTGGTTGCTTCAGTTTTTGCATGCTCCTGTTCTTCTTGTT<br>TACATGTGATCTACCAAATCATCTAATGTATTCTCTCAATGTCTTGTGGACATTCTCC<br>TTCATTCCGAGATTACCAATCATCTACCCGAATAAATGTTGCCCCGTCAGCAATGCC<br>GTTTTGGTCC |
| SEQ ID NO:94 | Late | LPZ-016 | AGGTGACCGTAGTAGGCGTCCAGAGGCTGACAAAATCCCAGGCCTGTGCAAATCT<br>GGAAGCCGCATGCAGGGCCGTGGCACCTTACACTTGCGGCCTTAACAAAGTGGCC<br>CGCGGGACCCACTTCTACCAGTGTGTTTATATTCTTGTGCAGCCAACACCAGAGGT<br>TATGCAGGCGAATGTGCTGGCCAAGCGTTGTTTCGGCTTGTCCGCAAACCCTCTC<br>GAGTCTTACATGCCGCATATGAGTCTTGTGTATGGCGATTTGCCTGACGACGAGAA<br>AGAGAAGGCCAAGGTTAAGGCGCAGCTAAATTCGATGAACTTATCCGCAACACGGA<br>ATTCCAAGTCTCCAGCTTGTGCTTGTACTCGACAGATCTGAAAATAATCCTCACTCA<br>TGCATAAGTGCAAAATGTGATCTTAACCTGCTCTGAAAATTACATAA |
| SEQ ID NO:95 | Late | LPZ-017 | AGGTGACCGTCCACGAGAATTTGGCTTCAAAACCGTAGGAGAGGGATATGAACTTG<br>CCAAGGCACAACTGACGCATGAACAAGACGTAAAATGACTCATTAGACACTGACAT<br>GATAATGAAAAACCTATGAATGATGATAGACTCAGCTACTTGATGACATCGCCCGC<br>CATTTGGACATCTTTATAAGGAGTTTAAGCAAACCCTAGACCTACTGCCTAGTGACC<br>AACTTTTGCTTGACGACTCACTGAAATGACAATATTTGACCTTGACACTTCAAAATC<br>ACTTTGTAGGAACTCATTTGATCACTGGAGGACGGCTGGAAAGACTGACACTAACA<br>GGACTTTATATATGCACCTCGTCTATCCGAACTT |
| SEQ ID NO:96 | Late | LPZ-018 | AGGTGACCGTAAGCACAAGTCGTCAAAATTATCTCTATTCCGGCAGTAAAAACCTAT<br>AGCTAATGATGGATCAATAGCACTAAGTGGCAGCTGGCGTACATCACTGCAATGAT<br>AAGAACCAGTATCAACCCCCATATTATCAGGAGATATCTCCACCACCTGCTGCACT<br>ACATGTGGATCTAAGTACAGAGCCTGATCATCCTGAACACCAACAATATACGTTGAA<br>GCTCCAGGCTTTCCACCAGCAATACCAAGACTTTGGGGAAATGTGAACGTTTCACG<br>AAGTGATGGTACATACCTTGGGTTGATCTTCTCTACACCAAGAACAAGCGGCACCA<br>AAATCAGGATAGGCACTTGGTCTTCCCCTTCTCCATTGGACCAGTCTGAACACAGC<br>CTCGCAGCATCATCAATGCAGATAACTGGAGTCCCTCCACGGTCACCT |
| SEQ ID NO:97 | Middle | LPZ-019 | AGGTGACCGTGAATATGGTGGGTATTTGCAGGGCAAGATTCAGGATGCTGCTCCC<br>GGAGCTTAAGTAAGGTCTTGGACCCTAATAAATTCAGGGTATATGCATTATGTATAT<br>GCTCTCATTTAGCTGCTCATCTGATTTCCATTGGGTGAATCAGTTGTTTTGCAGTAC<br>GTGGGGGTCTGTTTATTTTGTGAGTTTATGGTGGAGTTCATTTTGTTGTTGTTGTTT<br>TTTCTTATCTAGGGTTTAGGGTTTTGCCCTGTAATCGGTCTTCCCCTCTCTCCTGCG<br>CTTGAATTTGACCTGAAACCTCTTGAAGTAGGCCCTGGTTTTCTGGGCTTTGACGA<br>AAACCATGGTTGTGGATCTCCTCTCTCCTGCTACGGTCACCT |
| SEQ ID NO:98 | Late | LPZ-020 | AGGTGACCGTCCTACTTCACCGCAGTGACTTCCATCTGGTTTTAGGAAACTATCCC<br>TAAATCCTTCACTAGTTGACGAATTGATTGACTCAAATCAACTGTCGGTCAAACCCA<br>CTCTCTCTGAAAGTGAATTCTATGAGTCTATACCCAACCCAAATCAATAGGTTGAGG<br>TAACAGTTGACCCGATTTCACCTTCAACAAATCATACCTTTCCCGAAGAGAGTGAAC<br>ATGATTCAACACAAGTTCTTTTTGGTTCACCAGATTCAAATGAGCTTGGGGGTAATC<br>CTCCTGTTCCATCAAGACAAGAAGAATCCTCCCACTCTCGTAACTCAAGGGTTAA<br>TCCTCCCATTTCTACGGTCACCT |
| SEQ ID NO:99 | Late | LPZ-022 | AGGTGACCGTCNCGGGATAGNTGGAGCCNAACAAAGTACNGAANAAANTGAANCG<br>CNCTGGGAAGCGNGCNGAAANNTGGNCANACNTGCCCTNCNACTCGGTTACCCAG<br>CCNTTCTCTACCNANAATTATNACNNNANAGCNCCATGCTGGGTTTGTNANAAAAN<br>AACNGCTNTTGATAAAATTACATAGANTNNNGAACACGTTAAGAGGAATATGGTTCC<br>ANATNCATTNTNAATNANNANTTAAAAACTNNNTATGTNCTAGNGTCNCCT |
| SEQ ID NO:100 | Late | LPZ-023 | AGGTGACCGTACAGCACAGGTATACAAATCATAGAAATGGGCTTCTGTCCAACTGT<br>CAGCAGAAGCGATATGAAACCCAGAAGCATCAACTCTGCTTTCAATTTTTCAAGCG<br>CTTCATATAGAGCCTTTTTATTTCTTCTGGAGAGCCAATTGCTAGCATAATGAATAC<br>CATGTTCAAGAAGTAAAGAGATGACCACAAATGCCAAACAAACAACTGCTACTGCC<br>CAAGTTAGGAGTTTGCTCTAGAGAACGGTCATTGCCACGGTCACCT |
| SEQ ID NO:101 | M,L | LPZ-024 | AGGTGACCGTGGATATGGGAGCAGAGCCGTCCGCAGTGGATGCTGCAATTCAACT<br>TGAAGTGGCAGAAGCTGTGAAGACTCTCCAAATGGACAAGGCACGAAGACAAAAC<br>CAAGACAAGGATGAGGGCAAGAGTGGCAACGCTGATTCAGATGACTTGAATGAAAT<br>GGAAGTCAAAGCTAAAGCAGCCGAACAACTGCTTGCTGTGCATGGGGCAGCATTA<br>CTACAGAATGCTCTGAAAGAAAATTTGTCGAGTCATGAAATGCGGGTTGGTTCAAA<br>TACAAGGGAGGAAGGTGAAGTTAGAAAGAACAGAAAGGGCATCAACGCAGACCCC |

TABLE I-continued

| cDNA | Embryo Phase | Clone | Nucleotide Sequence |
|---|---|---|---|
| | | | TCACTGATATCGGCAACACTACGGTCACCTAAGCCAATTCTGCAAATTTCCATCACT<br>GGCGGGGCCCGCTCCAACTTCCTCTAAAAGGCCAATTCCCCTATATGATTCTTATT<br>ACAATCCCTGGCCCTCCTTTTCCACTTCT |
| SEQ ID NO:102 | M,L | LPZ-025 | AGGTGACCGTAGCAGGAGAGAGGAGATCCACAACCATGGTTTTCGTCAAAGCCCA<br>GAAAACCAGGGCCTACTTCAAGAGGTTTCAGGTCAAATTCAAGCGCAGGAGAGAG<br>GGGAAGACCGATTACAGGGCAAGGATCCGCCTGATTAACCAAGATAAGAACAAGTA<br>CAACACACCCTTGCCAAAAAAAAAAAAAAAA |
| SEQ ID NO:103 | Middle | LPZ-026 | AGGTGACCGTATGAGCAAGGAGGGAACAGTATGACAGGCAGTCAAAGCCCACGAG<br>GGGTGCCCCACTGCCTGCAGCAGCGCACTTACTTGGACTAACAAACTTGTATCGTG<br>ATTAAAACGATGAACATCGTATTGTGGAGTGGAGCCACTCGTGACCTGATTCTGTC<br>CTAAGTACTTGGTCCTGGAATACAATATTGCACGGTCACCT |
| SEQ ID NO:104 | All | LPZ-028 | AGGTGACGGTCAAAGTACAATGGAGTCATATATCCACTTGAATTGAAACCTCTAATT<br>TAAAAGTTCTCAAAAAATATTTTATTTACAAAACAGGGAAAATAAAAAATGACTCTAT<br>CAACTATACAATCCTAACATCCATCTCCCGACAGACCTCCAGTATATGTACAAGGC<br>GCTGAAAGAAGGCTGATTATTTTCTATTCCAGCTCGCATAACGTGGTTCTTCTGAG<br>GCTTTGCCTATTCCTTTCTTTAAAATCTTTCGCACGAAAGATTGGCATTGACCTTCG<br>GCTAAATCTCAGACTCCAGGGAACCTTGGACTCCCTTTAAAACCTAGAGCTACTTTT<br>TACGAACGCCTGCTTCTCTTGAACACTTAGGGAACTTATACTTACAAAACTTCGGGA<br>ACTCCACCCCCTAGCTTTGCAGGACTCCAGCAGATTCCCCAAACTGCCAGAAGGCA<br>TATTTCCATGCACTGTTAGGGGTGAATTCCTACTATCAAAACCCCCAAAACATCATA |
| SEQ ID NO:105 | Late | LPZ-029 | AGGTGACCGTATGGGAACAAGTATGGGAACAAGAACGTTATTACATAAAAGATGGA<br>GATGCAACACAGCATAAATTGATGCTAAGTTTGTTACAATGATGCATACAGCTTAAC<br>CAAGCTTGGAAATGACATCATTAAGTGCGGTCACAGCCTCTGCATAGTATTTCTCT<br>GCCTTGGGTGTATCCTTGCTCCTTGCAGCGTAGTCCAGGTTGTCAAGGGTTGTCAA<br>AAAGCTTGGTGGTGAAGGTTTTGAGGGGCTTCTTCTGGTCCTTGGGCTTTGAGGA<br>GATAACGGTGTTTGAAGTCCTTAGCGAAAGTAAGAAACCTTTGGAACCGAAGTCCG<br>TTCTTGACGTTACCGCACGCCTTCCTTATCTATCACTTTTTCACCTCCAGAAATTGC<br>TTCCCGAATCCCTTGCTCTCCCACCCCCTGTTCCCCC |
| SEQ ID NO:106 | Late | LPZ-030 | AGGTGACCGTAGTGTTGCCGATATCAGTGAGGGGTCTGCGTTGATGCCCTTTCTG<br>TTCTTCTACTTCACCCTCCTCTCTTGTATTTGAACCAACCCGCATTTCATGACTCGA<br>CAAATTTTCTTTCAGAGCATTCTGTAGTAATGCTGCCCCATGCACAGCAAGCAGTTG<br>TTCGGCTGCTTTAGCTTTGACTTCCATTTCATTCAAGTCATCTGAATCAGCGTTGCC<br>ACTCTTGCCCTCATCCTTGTCTTGGTTTTGTCTTCCGTGCCTTGTCCATTTGGAGAG<br>TCTTCACAGCTTCTGCCACTTCAATTTGAATTGCAGCATCCACTTGCGGAACGGTCT<br>GCTCCCCATATCACGGCACCTT |
| SEQ ID NO:107 | Late | LPZ-031 | AGGTGACCGTAGTGTTGCCGATATCAGTGAGGGGTCTGCGTTGATGCCCTTTCTG<br>TTCTTCTACTTCACCCTCCTCTCTTGTATTTGAACCAACCCGCATTTCATGACTCGA<br>CAAATTTTCTTTCAGAGCATTCTGTAGTAATGCTGCCCCATGCACAGCAAGCAGTTG<br>TTCGGCTGGTTTAGCTTTGACTTCCATTTCATTCAAGTCATCTGAATCAGTGTTGCC<br>ACTCTTGCCCTCATCCTTGTCTTGGTTTTGTCTTCGTGCCTTGTCCATTTGGAGAGT<br>CTTCACAGCTTCTGCCACTTCAATTTGAATTGCAGCATCCACTGCGGACGGCTCTG<br>CTCCCATATCCACGGTCACCT |
| SEQ ID NO:108 | Late | LPZ-032 | AGGTGACCGTCGTGAAATAGCGAGAACGGCGTGGAACATCGCAACGGCGGGGAG<br>GCTGGCGGACGTTGCACGTTTCTGGAAGGTATGCGGCTCTCTCCTCCGCCTCAGT<br>TTCCATGAAGAGGTCCTCCCTGGTTGAATCATACGATTGCGATTGATCGAGTACTT<br>GCTGTATGGCTCGGCATCGGCATTGTGGAGACATTCTTTCCTATTCCTCGCAGCAT<br>CTCTCCGATGGTTGCTCTCTCCGGAGCTCCATGTTATCCCCGGCACTGAGACAGTC<br>GCTGCCGAATCGCAAGAGCTTCTTTGTTTTTTGCAGGCTTCTCCAAACATAATGCCT<br>CCGGGCCCCTCAACCGAATTCTGCCAAATCCACCCC |
| SEQ ID NO:109 | E,L | LPZ-033 | AGGTGACCGTGGACGACAGTGAGTGCAGTCATCATGCTCTCCAGTGGACTTTAAG<br>CAATCTGCATCTTTATGGAAGTGATGTATCTCTTGTGGTTTTTCATGCTCAACCATT<br>GGCAGTCTTCAACAGTGCTGCAACAATGGGCATAACGTCTCCCGAATTAATTGAAA<br>CTATTGTGAATCAACAGATAGGTTTCTGGTCACATCTAGCAATACAAACACAAATAA<br>CTGTGGAACAGAGCCACAAAACTATGCTTCAGAGCATCTAATTACACATATCTTCTC<br>TAAAACCCTTGCATAAAAAATAAACTGAATCTCGACCTTAGCACTATTGCCACCATC<br>ATCTCAAGCAAACATTCTCTAGAATACCATCTTCACAATGCACTAAAGTTACATAAG<br>CACTGAACTTAAAACATTTCTGTGACGAATGAAGGACCAATTCATCATAGTCAGCCT<br>TTGCATCCAATCTGTTGAATGTGCTGAAAAATGCCCAATAAACGTCCATCCAACACT<br>GTCTTCCTCTCTGAGGTGCACACTGATTTCTGCTGCTGAACCAGTCGGGATTCCCT<br>GCTCAACGTCCC |
| SEQ ID NO:110 | Middle | LPZ-034 | AGGTGCCCGTGGAACTACTGTTAAATCTGGAATCCCTTGTCTAGCTGTAAAAACTC<br>GACAAGTGCATGTTGGTATTAGTAGGGTTAACAGAAGGGTTCTTACCCAGATTTAC<br>CCCTTTGGCGGAGATATTTAAAAAAAAAGAATTGTCATTATGGTAAATAGGTGTGAC<br>AGGTTATCAATAGAATAACTGACGAGAGTAAACTGATAATTATTAAGGTTAAAGTGT<br>TCGTAAAGGAGACTTGGACTCTAGGTTGGATGCCTACACTTAGAGCCGTTCCCGCA<br>CTTGGACGGTCACCT |
| SEQ ID NO:111 | Middle | LPZ-035 | AGGTGACCGTCCAGTGCGGGAACGGCTCTAAGTGTAGGCATGCACCTAGAGTCCA<br>AGTCTCCTTTACGAACACTTTAACCTTAATAATTATCAGTTTACTCTCGTCAGTTATT<br>CTATTGATAACCTGTCACACCTATTTACCATAATGACAATTCTTTTTTTTTAAATATCT<br>CCGCCAAAGGGGTAAATCTGGGTAAGAACCCTTCTGTTAACCCTACTAATACCAAC<br>ATGCACTTGTCGAGTTTTTACAGCTAGACAAGGGATTCCAGATTTAACAGTAGTTCC<br>ACGGTCACCT |
| SEQ ID NO:112 | Late | LPZ-037 | AGGTGACCGTATGGGAACAAGAACGTTATTACATAAAAGATGGAGATGCAACACAG<br>CATAAATTGATGCTAAGTTTGTTACAATGATGCATACAGCTTAACCAAGCTTGGAAA<br>TGACATCATTAAGTGCGGTCACAGCCTCTGCATAGTATTTCTCTGCCTTGGGTGTA<br>TCCTTGCTCCTTGCAGCGTAGTCCAAGTTGTCAAGGGTGTCAAAAAACTTGGTGGT |

TABLE I-continued

| cDNA | Embryo Phase | Clone | Nucleotide Sequence |
| --- | --- | --- | --- |
| | | | GAAGGTTTTGAAGGGCTTCTTCTGGTCCTTGGGCTTTGAAGAAATAACGGTGTTGA AGTCCTTACCAAAGGTTAATAAACCTTTGGAGCCGAAGTCGTTCTGGACGTACGGC CACCCCTTCCTTATCTATCAGCTTTTTCACCTCCAAGAATTTGCTTCCCCGAATTCC TTTGCTCTCCCAGCCGCCTGGTCCCCCGAAAAGGGCTGAATATAAAACCGTCCTCA ACGGCATTCCATTCCTCCCTCGTCTGAAACACTTCCCCGGTGCCCCCGAGGTGAA GGGCCATCAACTTGATGAACGGCTTTTGCAAGGCTCTGACCCCGGCCCCGTCACT AACCAATTCTGCAATC |
| SEQ ID NO:113 | Middle | LPZ-038 | AGGTGACCGTGGGGAACAACTACATGACAAATCATTTCTTTGTGGTGGATGTACTG GACACCAAATAAGTGTTGAGAGTCCACTGGCTCTGTACGCGTGGCAGAATCACAAC GGACTTGAGAAAGTTGAAGATGGAATTTGTATCGCTAGATGGCCAGACCATGTTGC TTCAAGGGATGCACTCGTAACCCCCACAGTCTGTCTCTACCCACTAGATGGAGGCT GACATGAGACATGGAGACATTAATTGGGTTGTGGAGTTAAAGATCTCTCACGTTCG GGGAAAATCCAAGCCATCATACTTATATATCCGTCCCGTGCATGTAACCTCCTCCA CTCTGTCCCTTAGGCCCGTTGTTGCCT |
| SEQ ID NO:114 | E,L | LPZ-039 | AGGTGACCGTATGAGCAAGGAAANNACCGCACTGGCTCCCAGCAGCATGAACANC CAGGTCCCAACCATANACCNCNTGGAGAANGTGATCAAGATATTAGCGACAGTGTN ATTGTACNTCTCNCCAAACACATTATACACGATAAGAGAGCNTAAACTACTCTATTC CTTTGACGNAGTGACTACNTGAGTANAAGCGATCATTATCTTGCNAACTTTGCATGA AAAACAACAAACCCACNTCCAGTTTCTCTATANTCTGGCCCCACNATGAATAANANT CCTGCCATAATAATGANTCTTTGTCCCCANACANAAATTNNATAAGACAGGAGCCC ACTGTTGCTTGCATGACTACCANTCACTTTAAGGCGTTGCGAATCCCGGTCCTAAC CATCTGCATACCATNGGCANNCTTTACTTTCCAACTGCCCAAGACTGTGAACAGGG CGGTTCNNACCCTATAANTTTTAGCCTCTNNTCGAANCNCTTNTTTTCGTTCCCCGG AAANCCGNTTCCCACCCTTTGGAACCTTTTTTTTTTGCCGGGCCCCAGGCNAATTC TNCAATTCCCCNCTGGGGGG |
| SEQ ID NO:115 | Late | LPZ-040 | AGGTGACCGTGGCGGAGGTTAGGGAAGTTTGACTTCTCATTTTCTCACGCACTCCT CTCCCTCGTAACCTCGGTCGAGTCGATGGCGGCTTTTTAGTCGAGTGTGCTAACG CACCCTCCGGGCCTCAAAATTTCCAGCTACTCGTATTTGATCAATGCTGAAATCGC GTAATCACGTAGATAATAAAGCGTAATGAATTCTATAATGAAGCATGTTTCTCTATA GTTCATGTTGCCGAGAAGGAATAATGAAAATGAAGCCTTATATATTATCTGGGGCTC AAGGAGATGTTATCTTTTCTCTTCCTTGGTTAGAGACCGTCACCTTCACTTTGAATT GGATAAAGCTTCATTTGTTTAAGACCTCCCACCCGTAAATACATACGGTAGCCTTCT TATGTTAGAAACATACGTCACCTACGCAGAATTGTTAGAATGAAATGA |
| SEQ ID NO:116 | Late | LPZ-041 | AGGTGACCGTGGAACAAGATGATTAGTTCTCATGCGGGCCAGGATGATTAGTTCTC CTATGGCAACTGTTGGACAGGATGATTCGTTCTCCTGTGGACAGGATGATTAGTTC TCCTATCGAGGCATCCTACCCAAGCAGTTTGGGACTCATGGGAAGTACCTCTCATC TGATCAATGAGTAGGAAATGGGGTTAGGGACCATTAAGTAGTATTATCGATGGATG CATTGTTGTATCTATTGTACTCCCTATGCTAGAATGAACTCCATTGATCTGGGATCA ATGAATACTGTTTCTGGGAATCATTGAAAATTTGTATGAACACACTCTGAACACTGA ATTTCCGGTTCATTGGAAGAGATGGTTTTAAACACTCTCCTCATCTCATTTCTTCCC CTTCCTTATTCCAACCAAATTTGGGCCACCCTGCCAGGAAATTCATTTGATGGTTGG AAAATACCACGGGCCCTAACCAATTCTGCAA |
| SEQ ID NO:117 | Late | LPZ-042 | AGGTGACCGTNCATCTCTACCATNATNCCTCCCTCCCGNCTGTATCANCNGGCNTN NANGTCNTTNNCTANNNNAAGNTTAATCCTATCCCNTTANAGTTGACGGTCTCTAN NCCTAGAAGAGAANCCATAACATCTCCTTGAGCNACACATGGGATATACCGCCANC TTATNTAATACTTTCNCNGCACGGTAACNGACCANAANCATTCTTCACTATAGAATT CATGTCGCTTCATTATCTACCTCATTNCNCCANATCCCCCTTNATCTCATNNATTTAT CTAGAAANTTCTGAAGNTCCNNAAGGGTTCGTTTTGCACCNCCCCAANTAAAAAAN CCCTNCCGNTTACNTCGAACGAAGGTTTTCAAANGAACAGNAATTCCTTTACAAAAA TCAANAATTTTAACTTCCCNAATCCGGCCCCCCNGTNCCCGAAACCCNATTTCTAC GATTGCATCACCCCGGGGGNCCNCTCAANCCNNCTTCTTAAAGGNCCATNCCCNT NNNTGATCCTCTNGCATCCAANGGCNCCTTTCCACTTTTATTGGAAAACCCCCNTT CCCCNTTTTACCCTTNNAAGGCCCCTTCCC |
| SEQ ID NO:118 | Late | LPZ-043 | AGGTGACCGTGGAACTACTGTTAAATCTGGAATCCCTTGTCTAGCTGTAAAAACTC GACAAGTGCATGTTGGTATTAGTAGGGTTAACAGAAGGGTTCTTACCCAGATTTAC CCCTTTGGCGGAGATATTTAAAAAAAAAGAATTGTCATTATGGTAAATAGGTGTGAC AGGTTATCAATAGAATAACTGACGAGAGTAAACTGATAATTATTAAGGTTAAAGTGT TCGTAAAGGANACTTGGACTCTAGGTTGGATGCCTACACTTAGAGCCCGTTCCCGC ACTTGGACGGTCACCT |
| SEQ ID NO:119 | Late | LPZ-045 | AGGTGACCGTGGGGGATGGGGCCGTGGGGAAGACTTGTATGCTCATCTCCTACAC AAGCAACACGTTTCCAACGGATTACGTGCCGACTGTTTTTGACAATTTTAGTGCAAA TGTGGTTGTTGATGGCAATACAGTAAACCTTGGCTTGTGGGACACTGCAGGGCAA GAAGATTACAACAGACTGAGGCCATTGAGTTATAGAGGTGCAGATGCTTTTCTGCT TGCCTTTTCTCTGATCAGCAAGGCTAGTTATGAAAATATATCAAAGAAGTGGATTCC AGAACTTAGACATTATGCACCAAATGTGCCAATCATTCTTGTGGGAACTAAATTAGA TTTGCGTGATGACAAGCAGTTCTTTGCTGATCATCCTGGAGCAGCCCCTATAACAA CAGCTCAAGGTGAAGAGTTGAAGAAGCAGATTGGAGCAGCAGCATATATTGAGTG CAGTTCCAAAACCCAGCAGAATGTCAAGGCTGTTTTTGATGCTGCAATTAAAGTGG TTCTTCAGCCACCAAAGCAGAAAAAGCGGAGAAAAAAGCAGAAAAATTGTTCTATTC TCTAAGAAAAATGTGGATGTTCTGAACGCNCTTCACTGACAATAANGNTGACGTNG GAATATCTTCCTCC |
| SEQ ID NO:120 | Late | LPZ-047 | AGGTGACCGTAAGCACAAGTCGTCAAAATTATCTCTATTCCGGCAGTAAAAACCTAT AGCTAATGATGGATCAATACCACTAAGTGGCAGCTGGCGTACATCTCTGCAATGAT AAGAACCAGTATCAGTCCCCATATAATCAGGAGATATCTCCAGCACCTGCTGCACT ACATGTGGATCTTAGTACAGAGCCTGATCATCCTGAACACCAACAATATACGTTGAA GCTCCGGGCTTTCCACCAGCAATACCAAGACTTTGGGGAAATGTGAACGTTTCACG |

TABLE I-continued

| cDNA | Embryo Phase | Clone | Nucleotide Sequence |
|---|---|---|---|
| | | | AAGTGATGGTACATACCTTGGGTTGATCTTCTCTACACCAAGAACAAGCGGCACCA<br>AAATCAGGATAGGCACTTGGTCTTCCCCTTCTCCATTGGACCACTCTGAACACAAG<br>CCTCGCAGCATCATCAATGCAGATAACTGGGCGCCCTCCACGGTCACTT |
| SEQ ID NO:121 | Late | LPZ-049 | AGGTGACCGTGCCATAGCGCATGGCGTGTAACTGGATGAGACCGCATGGCTCAAA<br>TCTGCTAGGAATCAACATGAAATCAGCTCCAGCTGTTATCATATGAGCAAGTGGCA<br>CGTTAAACTTTGCTACTCCCCTGACGTTGTCTGGATATTTCTCTTCAAGCTCTTCAA<br>GCTGCTTCTCCAAGTACTTTTTACCGGTGCCTAGGATAATTAACTGCACGTTTTCAT<br>CTGCAATTAGAGGGACAGCTTCAGCAAGAATATCTGGACCTTTCTGCTCTTCAAGT<br>CTTCCAATAAATCCTATAACAGGAATATCTGGATCCACGGTCACCT |
| SEQ ID NO:122 | Early | LPZ-051 | ATGTGACCGTCAAAAGGGCATATAAATCGGGGAGCTCAATGGCAAGAATGTACGAT<br>TTCTGGCCTCAAGTCGCCCTGAATTTGGTCAACAACATCTTGATAGAGCGAGAGGA<br>CGCTCCCAATTAAGATCTGGAAACTGTCGAGAGTGATTGAGGTCATTTTTAATCTAA<br>ACTGAATTGTGGGGACAATTTTTCAATTCAGATCCTTCTAGCAAAGCAAAGCAAAGC<br>TTAACAGTATTGTATCCATGAGAATGGATTCTGCACAGGTCAGGCTCCACGGTCAC<br>CT |
| SEQ ID NO:123 | All | LPZ-053 | AGGTGACCGTGGAGAAGAGAACGCTTTGCCGACTCTCTGGGATGCCCTTCCCTCC<br>ATAGCCGTCGTGGGAGGACAGAGCTCCGGGAAATCCTCTGTGCTGGAGAGCATCG<br>TTGGAAGGGATTTTTTACCGCGTGGATCAGGTATTGTTACTAGACGGCCGCTTGTC<br>CTTCAACTTCACAAGACTGATGAAGGCAGCAGGGATTACGCCGAATTCCTTCACCA<br>ACCCAGAAAGAAATACACCGACTTTGCACTGGTAAGGAAGGAAATTGCGGATGAGA<br>CTGATCGAATTACAGGGCGTTCCAAGCAAGTCTCAAGTGTCCCAATTCACCTTAGT<br>ATTTATTCACCCAATGTTTGTAAATTTGACTCTAATTGATCTCCCTGGGTTGACAAAA<br>GTGGCTATTGACGGTCACCT |
| SEQ ID NO:124 | Middle | LPZ-054 | AGGTGACCGTGCAATATTGTATTCCAGGACCAAGTACTTAGGACAGAATCAGGTTA<br>CGAGTGGCTCCACTCCACAATACGATGTTCATCGTTTTGATCACAATACAGGTTTGT<br>TAGTCCAAGTAGGTGCGCTGCTGCAGACAGTGGGGCAGCCCTCGTGGGCTTGGA<br>CTGCCTGTCATACTGTTCTCTCCTTGCTTCAGGCTCTACTGCTGTTGCTGCTGCTG<br>ATACGGTCACCT |
| SEQ ID NO:125 | Middle | LPZ-055 | AGGTGACCGTACATACAAGGTCTTATCACCAGCAGCAAGAATAATCAGTTGGCCAT<br>CTTCTGCAGGCTTCTTGCTGCCTGAGACAGGAGCCTCAAGAAATCTTCCCCCCTTT<br>TCAATGATTGCCTCATTGATCTTTGTTGAAGTGATAGTATCAAGTGTTGACATGTCA<br>ATGTATCCTTTTCCTGTACACATTTGCTCTAGGACACCATCCGAGAGGGCAGCAGG<br>AGGATCAGACAGGATGGCTATGGTATAGTTGCACTTCTTTACAACTTCGGCAGGAG<br>TGCTTCCTATGGAAGCACCTTGCTGAACAAGTTCTTCACACCTAGACATTGTCCTAT<br>TCCACACGGTCACCT |
| SEQ ID NO:126 | Late | LPZ-056 | GGTGACCGTACATACAAGGTCTTATCACCAGCAGCAAGAATAATCAGTTGGCCATC<br>TTCTGCAGGCTTCTGGCTGCCTGAGACAGGAGCCTCATGAAATCTTCCCCCCTTTT<br>CAATGATTGCCTCATTGATCTTTGTTGAAATGATAATATCAACTGTTGACATGTCAAT<br>GTATCCTTTGTCCTGTACACATTTGCTCTAGGACACCATCCGAGAGGGCAGCAGGA<br>GGATCAGACAGGATGGCTATGGTATAGTCGCACTTCTTTACAACTTCGGCAGGAGT<br>GCTTCCTATGGAAGCACCTTGCTGAACAAAGTTCTTCACACCTAGACATTTGTGCTA<br>TTCCGCACGGTCACCT |
| SEQ ID NO:127 | Late | LPZ-057 | AGGTGACCGTGGAGGGGCTCCAGTTATCTGCATTGATGATGCTGCGAGGCTGTGT<br>TCAGAGTGGTCCAATGGAGAAGGGGAAGACCAAGTGCCTATCCTGATTTTGGTGC<br>CGCTTGTTCTTGGTGTAGAGAAGATCAACCCAAGGTATGTACCATCACTTCGTGAA<br>ACGTTCACATTTCCCCAAAGTCTTGGTATTGCTGGTGGAAAGCCTGGAGCTTCAAC<br>GTATATTGTTGGTGTTCAGGATGATCAGGCTCTGTACTTAGATCCACATGTAGTGC<br>AGCAGGTGGTGGAGATATCTCCTGATAATATGGGGGTTGATACTGGTTCTTATCAT<br>TGCAGTGATGTTCGCCACTGCCACTTAATGCTATTGATCCATCATTAGCTATAGGTT<br>TTTACTGCCCGGAATAGAAATAATTTTGACAACTTGTGCTTACGGCACCT |
| SEQ ID NO:128 | Late | LPZ-058 | AGGTGACCGTGGAGGGGCTCCAGTTATCTGCATTGATGATGCTGCGAGGCTGTGT<br>TCAGAGTGGTCCAATGGAGAAGGGGAAGACCAAGTGCCTATCCTGATTTTGGTGC<br>CGCTTGTTCTTGGTGTAGAGAAGATCAACCCAAGGTATGTACCATCACTTCGTGAA<br>ACGTTCACATTTCCCCAAAGTCTTGGTATTGCTGGTGGAAAGCCTGGAGCTTCAAC<br>GTATATTGTTGGTGTTCAGGATGATCAGGCTCTGTACTTAGATCCACATGTAGTGC<br>AGCAGGTGGTGGAGATATCTCCTGATAATATGGGGGTTGATACTGGTTCTTATCAT<br>TGCAGTGATGTACCCACTGCCACTTAGTGCTATTGATCCATCATTAGCTATAGGTTT<br>TACTGCCGGAATAGAAAAATTTTGACAACTTGTGCTTACGGTCCCT |
| SEQ ID NO:129 | Late | LPZ-059 | AGGTGACCGTGCTAGGACACACAATTTCTCAGCAAGGATTACAGGTGGATCCTAAC<br>AAAATTGCTATAATTCAAAAGGTTCCACCTCCTTAAAAGGTAAGAGATGTTTGGAGT<br>TTTCTAGGCTTGGCAGGATATTATAGAAGATTCATCAAAGATTTCATTAAGCTAGCC<br>TCGCCATTGTCTAGCCTCTTAGGGAAAGATGTTGAGTTTCAATGGACTGATGACTG<br>CCAAGGGGCTCTGGATGAGTTGAGAGATAAGCTGGTATCCGCCCCGATCTTGAGA<br>GGTCTAAACTGGGCCCTACCTTTCCACATCCACATTGATGCCTCGAACAAAGCCAT<br>AGGGGCAGCCTTAGGACAAGTTGAAGAGAAAATACCATATGCCATATACTTTGTCA<br>GCAAAAATCTGTCTAAGGCAGAACTGAACTATACGGTCACT |
| SEQ ID NO:130 | Late | LPZ-060 | AGGTGACCGTCATATTCCCCTCTATAGCAGCACTAACAATCCATTTTCTGAGTGCAT<br>CAGAAAATCAACAGACGGTAAATGTCTTGAGACTAACGAGAAATTAATAATCACGTT<br>GTACAAAGAACAGTATGTCCCGTCACGTCACGAGTGCCCTGAGAGATCATCCAACT<br>TTCTCTGAACCCTCGTGTTACACGCACGCAAAATCAAGGATCAGTTGTAGTTATTGC<br>TGGCGTGACAGACGTGACACCTACTGTTCCGCTACAAACGATATAATTGAATCCAT<br>GATCGGATTATGTATTATGATCTTAGCGCAGTGGTTATGAAATTATGATGAATTTGC<br>TTATGATTTTCTCAGCGTTTGTGGAAGAATCTCGCTATTGAAAACTTCCCCGTATAT<br>TTCCAAACTTATTATCATCCCACGGTCCCT |
| SEQ ID NO:131 | Late | LPZ-061 | AGGTGACCGTACAGCATTTATTGATGTTCTATTTTGTTGTTTGCAAGTTTTTCCGATT<br>CGCTGTGAGGCACGGAAAACGAGATAAGTTGTAAAAGTTTGCTCGCTGATTTGAGG |

TABLE I-continued

| cDNA | Embryo Phase | Clone | Nucleotide Sequence |
|---|---|---|---|
| | | | CACGGAAAACGAGATAAGTTGTAAAATTTTGCTCGCTGATTTTTTGCTGAATATTTC<br>TCTCACTATAAAAAGCATTTTCCAGAAATAAGAAGGAGCTTTCGAACTGGTTTTCCC<br>CAAGAGTTGTAGGGGGTTTTTCCACGGTCACCT |
| SEQ ID NO:132 | Late | LPZ-062 | AGGTGACCGTATTTATGGTCGCAGGCACAAATTCTGCTACTGTAGAAGGGTTCTTA<br>CCAACTTTAGGTAGAAGGCGAGGAGGGCTTTATTAGTACAGTTCTGTGTAATCTTA<br>ATGATATTTTTTGCACTATTATTTTATGGTAAAAGGATTGATTTGTCTTTTGCAAAGG<br>CCTTAGGATTGTTTATTTACCTTTGGGCTAAGGGAGGAGGTAAATTTTTCACATTGG<br>GAAAAAAAATGGCTCGGTCGTTGTCACGGTCACCT |
| SEQ ID NO:133 | Late | LPZ-063 | AGGTGACCGTGCCAGTATGACAGATGGAACCATGCAGCTAGCCACCAAATTGTAAA<br>CATCAAATTTTGTCTTCAATATAAGTTGCAAATTCTTAATTAATTATGATCACCATTTC<br>AACGGTCACCT |
| SEQ ID NO:134 | Middle | LPZ-065 | AGGTGACCGTGAATAGAAGCGAACACATCCTTGTTGCTGAATCTAACGACCAATCG<br>GTATTTGGGTGTGTTGTACTTGTTCTTATCTTGGTTAATCAGGCGGATCCTTGCCCT<br>GTAATCGGTCTTCCCCTCTCTCCTGCGCTTGAATTTGACCTGAAACCTCTTGAAGTA<br>GGCCCTGGTTTTCTGGGCTTTGACGAAAACCATGGTTGTGGATCTCCTCTCTCCTG<br>CTACGGTCACCT |
| SEQ ID NO:135 | Middle | LPZ-066 | AGGTGACCGTGGTAGAGGAGGCAGGCACTCATCTAACAGTCGAAAGCCCTTTACA<br>AAGGGGAATGGTACCAGCATAGAGAAGAAACACAGACGGTTTGAAGAGGATGATG<br>TTCCATGCATCCCACTTGGCTCTGTCCCTCAAGTTGAATATACCTGGACGAGAGGT<br>ATTGCATTTCCCAACGGTCACCT |
| SEQ ID NO:136 | Middle | LPZ-067 | AGGTGACCGTACTGATAATAGAAGAGGCAGGGAAAGAGAAATCAATGATAATAGAA<br>GAGGCAGGGAAAGGGAGATCAATGGCATCATGCTACTTCTTGTAGCTGTTTAACCT<br>TAGTGATGTAATCTTCCATGGCAGACTCGGGGGTTTTATCTTTAAGTTGAATTTCCA<br>TGCATCCCCTTGGGCTCTGTCCTCCAGTTGAATATCCTGGAACAAGAGGTTTTGCT<br>TTCCACGGTCCCCT |
| SEQ ID NO:137 | Late | LPZ-069 | AGGTGACCGTGAGAAGGCAACTTTATCCCCTGCTAAACCAAGTCCAGAAATGAGGA<br>AAATATGTGAAAACTGAATTGCTATATATGATGCCTAGTCTTGGCCTCTCAATTACA<br>AGTTCAACGTCTTCAAATGATTGAAATATGGACCTTCTTAACCGTTCTGGAAATCTA<br>TCAATCTTCAAAATTTTGAAACTTTGCCTCGATCTTGGAGTGATCAGACTTGATTTCT<br>AATCCTAGAAATACCCTATCACTGGCTACCTGGTCTGTACGGTCACCT |
| SEQ ID NO:138 | Late | LPZ-070 | GGTGACCGTGGGATAGGCAGAAGCAAGAAACACAGAAGTTCTTCCGGGAATGTAA<br>GCGCTGACAGTGGGGGAGAAAGTAGTGAACAAGGACATGGTCGGTATGAAATACA<br>TGGCAGGCGATGGATTTCAAGGGATTAAGCATCTCAATGGATATTTACTATTGGAC<br>TGTAGTAACTTTCGCCATCGCTTTTTGAACACATCTGTGGCTTAACTGTCATCTGTA<br>ATGGTAAGCGAACCAGGTTTTGTTCTGAACCACTTGTATGTACGGTCACCT |
| SEQ ID NO:139 | Late | LPZ-071 | AGGTGACCGTGGTGGAGCGATTAGTGATTGTGATAAAGGGAGCATCAATATCTATG<br>TAGACGCCGTATAAAGGTGGAAAAGGTATGTTTTGCAGGTATTTCTTTGTAAATGGT<br>TTATAATGGGTTAAGCTCGGATATATGAGGTTTATATATAAGTCCTGTTAGTGTCAG<br>TCTTACCAGCCTTCCTCCAGTGATCAAATGTGCTCTAACAAAGTGATTTTGAAGTGT<br>CAAGGTCAAATTATGTCATTTCAGTGAGTCTTCAAACAAAATTTGGTCACTAGGCAT<br>TAGGTCTAAGGGTTTGCTTGAACTCCCTCTAGAGTTGTCCAAATGGGCGGGCTATG<br>TCATCATTTAAGCTGAATCTATCATCCAATCAATAAGGTTTTTCATTATCATGTCAGT<br>GTCTAAATGAGTCATTTTACCGTCTTGTTCACGGCTTCACTTGTGCCTTTGGCAAAT<br>TCAATTCCCTCCTCCAAGGGTTTGAAACCAATTCTCTTGGACGGCCCCTAAACCAA<br>ATCTGCAAAATCCAC |
| SEQ ID NO:140 | Late | LPZ-072 | AGGTGACCGTGGTGGAGCGATTAGTGATTGTGATAAAGGGAGCATCAATATCTATG<br>TAGACGCCGTATAAAGGTGGAAAAGGTATGTTTTGCAGGTATTTCTTTGTAAATGGT<br>TTATAATGGGTTAAGCTCGGATATATGAGGTTTATATATAAGTCCTGTTAGTGTCAG<br>TCTTTCCAGCCTTCCTCCAGTGATCAAATGTGCTCTTACAAAGTGATTTTGAAGTGT<br>CAAGGTCAAATTTTGTCATTTCAGTGAGTCTTCAAGCAAAATTTGGTCACTAGGCAT<br>TAGGTCTAAGGTTTGCTTTAACTCCTTCTAAAAGTTGTCCAAATGGCGGGCTATGTC<br>ATCATTTAGCTGAGTCTATCATCATCATAGGTTTTCATTATCATGTCAGTGTCTAATG<br>AGTCATTTACGTCTTGTTCAGCTGAGTGTGCCTGGCAATTCATTCCTCTCTAAGGTT<br>TGAACCATTCTCTTGACGGCACTAAGCCAATCCACACTGGGGCCGTCTATTGAATC<br>AACCCGGACACTGGGTTACAGGCAAC |
| SEQ ID NO:141 | Late | LPZ-073 | AGGTGACCGTCCAAGAAGAAATTGGCTTCAAAACCCTAGGAGAGGGAAATGAACTT<br>GCCAAGGCACAACTGAAGCATGAACAAGACGTAAAATGACTCATTAGACACTGACA<br>TGATAATGAAAAACCTATGAATGATGATAGACTCAGCTAAATGATGACATAGCCCGC<br>CATTTGGACAAATTTTAGAAGGAGTTAAAGCAAACCTTAGACTTAATGCTTAGTGAC<br>CAAATTTTGTTTGAAGACTGACTGAAATGACAAAATTTGACCTTGACACTTCAAAATC<br>ACTTTGTAAGAGCACATTTGATCACTGGAGGAAGGCTGGAAAGACTGACACTAACA<br>GGACTTATATATAAACCTCATATATCCGAGCTTAACCCATTATAAACCATTTACAAAG<br>AAATACCTGCAAAACATACCTTTTCCACCTTTATACGGCGTCTACATAGATATTGAT<br>GCTCCCTTTATCACAATCACTAATCGCTCCACCACGGTCACCT |
| SEQ ID NO:142 | Middle | LPZ-074 | AGGTGACCGTGATAGACCCCAAGAAAAATAGATCCAACCCTCAGAGGGACAAAGA<br>CTTATAAAGACTAGAAGAGTGAATCAACCTATTCTATTTAGAATATATATTTTTGGGG<br>TGCTTGCTTATCGTTTTGGGGGTTAATGTATGTCGTACTACGGTCTTATGCCCTAAT<br>TTGCCCATTGAAATCAACTAAATTGACAGTAACCGACTAAAAGTTGGTCCACACTAA<br>GATATCGATGACCAACGATCATAAAGGTGTCCATGATCCTAATAGTATATGTGTCAA<br>TTAATGTAACTTTGGTGCTACAACATAAAACCATTCGTGGGGATCCTCCTTTTTATG<br>CGGTCACCT |
| SEQ ID NO:143 | Middle | LPZ-075 | AGGTGACCGTGGGACCGACCTTGACTACAGGCCAAAATTTTGACTGTTGACCAGC<br>GTTCACTTCTGTATTTTTGGTTGGTATGAGCAACATTGACTTGCTGGAAATTGACCA<br>GGTTTGACTGGTATTTGGACTTGGATTTTGGCACAGATTTCTAGACAATTTGTATTT<br>GTAAACCTTACAGAAGAATAATTTATCGAAGAAGAAAAATGCTAGGTTTCCCCTCAA<br>GTTTGGGTTTCCCAAGGAAAAATTGTTGTCCCAATGGTTGAATTTTCCAAAGGTCT |

TABLE I-continued

| cDNA | Embryo Phase | Clone | Nucleotide Sequence |
|---|---|---|---|
| | | | CCTAACCCGACAATACCTCCTAAGAATTCCTTAATTTAACCTTTCTTGTTTTCACGGT<br>CACCT |
| SEQ ID NO:144 | Middle | LPZ-076 | AGGTGACCGTGAAGGAGCAGCAACAATTTGATTTTGTTTGGGTAGATCGGGGATTT<br>TCTCGTGGAACATACCTGATTGAGTATAAACTAAGTCAAGGTACTGTGCTTGAGAAA<br>TTACTTGCTCCTCAGTAACTACTCTGGCCTTAGCTACATCCTCAGTGATCTTGGGTA<br>GTAAAGATTTTACAAACCATTCAGCTAAGATCTGATCCGGGATATAAACTTTCACTA<br>AACGTCGTCGACGTCTCCATTCATGGATATGATCTGAAATGTAAGTGGACGTTGAC<br>TGCTTTAACGAAGTTAATAATTCTGTGCCATTTTCATATCTGACGGTCACCT |
| SEQ ID NO:145 | Late | LPZ-077 | AGGTGACCGTACCTAATGGGAAGACACTTCAAGGTAAAAACAAATCATGATAGTCT<br>TAAATACCTTTTAGAACAAAGATTATATTCAGAACAACTTGCTGGAAGTGTACCAAG<br>TATGACTGGTATTGAGACTTAGATCTTCGCACAGATTTCAAGACAATTTGTTGTTGT<br>AAGACTCACTCACGAAAAGTGATGTGGATATGAAGAACTTCCCTGTCGCCTCTTGG<br>TTAGGAGTCTCCCACTCATAGGAATTGTGTAACTTATAACTTGGTCCACTAAAGAAG<br>TTAGGTACAGTGTGTTCCTTTACCAGGTTCCCTGTTGTAACTTACAAATCTACGGCT<br>ACCT |
| SEQ ID NO:146 | Late | LPZ-078 | AGGTGACCGTCACTGGAGGTTTGAGATGCTTGATCGGTACTGAAATGAGACATGAT<br>CAGAATAGGACCTTGTTGAGGCCGTGTCTCACCCCCCATCCACAATCTTTTGTAAT<br>TTTGAGTTTCGTTTAGAACATACTTGTAGGATAAAACTTACCTTACTCATGGATCAT<br>GGCTGTATATGTTTATCGACCAGAGACAGATATGCCGAATGAAAGCGAGTCTAGTA<br>TTCTAATGCAATATATTGGTAGTATGGGACATAGTACTGAACACTTGTATAGTACGG<br>TCACCT |
| SEQ ID NO:147 | Late | LPZ-079 | AGGTGACCGTGGTCTCAGTTATGCCATATGTCCGCCCCTCCATATGATGCTCCGCC<br>TCTATGGGGGTCTTTGCGATGTTGATATCTAGTAGTACTTCTTGTCCTATTGCAGCA<br>ACCTGTACTGGTGTTGGTGTTGGTTATGGGTCTCCTACGCGATGGAGATATGAGAC<br>ACCCATAGGTCGAACAGGTCTAATATCTGGAATCCAACGCTATTTGTTGTAGAAG<br>ACGTTGCTCCCGTCCTTTAGCTTTGGCTGGTCACTATCCTTACGCTCCACGTACGG<br>TCACCT |
| SEQ ID NO:148 | Middle | LPZ-080 | AGGTGACCGTTGGGAAATGCAATACCTCTCGTCCAGGTATATTCAACTTGAGGGAC<br>AGAGCCAAGTGGGATGCATGGAATTCACTTAAAGATAAAACCCCCGAGTCTGCCAT<br>GGAAGATTACATCACTAAGGTTAAACAGCTACAAGAAGTAGCATGATGCCATTGAT<br>CTCCCTTTCCCTGCCTCTTCTATTATCAGTACGGTCACCT |
| SEQ ID NO:149 | Late | LPZ-081 | AGGTGACCGTCAAGGCAAAGTGTCATGCCACTCATTGGAATTAGTTAATATAGCTA<br>ATTTGAGATATTACAGTCAACTGTGGGTATATGTATGTGAGATCAAGGTGCAGTTTA<br>GATATTATCAGTGGTGCAGTTTAGATATTATCAGTGTTTGTGAATCTGCATACTGCT<br>TTTGGTTGGTTCTAACTACGGTCACCT |
| SEQ ID NO:150 | Middle | LPZ-082 | AGGTGACCGTAGACATATATCATGGAAAACCCAAGTAACATACAAACACAAAACACA<br>TGGAAACTTCATAAAACCTCCACTCGTCATAAGCTTTATTGCTATGTTATTGTGGTG<br>TTGCATCGTACTTAGTGGAGGTTATTGTTATGTTATGTGTTCTATTTTCCTCCCGAA<br>CGCCCTTCGGAATTGAGCTAACCGTGGTTAACAACATGTGGGCTTTTTTTCTCGAC<br>AGTATATATATAATAAATCTTTATTTTTTTAAAAACTAATGCTATTGCATTTATATACT<br>GGAAAAAATGATTTTTCTTGTATTATCGAAAATAATAATTTAGTTTCTTGATAATCACT<br>TGGAATTAAGAAATTACAAACCCTAACAACATCAAGAAATTTTAAAACACATAAGCTA<br>GAAATTTTAAAACACATAAGCGTGACAACAAGAAGATCAAATCTAATACTTGCTTGG<br>GCCGGAGATTATGGATTCATGAAGCGATTTGACAGCGTCCATTGATCTTCCTCTCC<br>CACGGTCACCT |
| SEQ ID NO:151 | Late | LPZ-083 | GGGGGTAGGGGTGTTTATACTGAGCATACTTCGAAAGTGGTTCACCACCACCATGA<br>TGACTAATTGTTCCTGACTTTGGTAGACCTATAATAAATTCCATAGAAACCTCCGTC<br>CATATTGATGCCGGAATGGGCAACGGTTGTAATGTGCCTGGTACTTTGACGGTCAC<br>CT |
| SEQ ID NO:152 | Middle | LPZ-084 | AGGTGACCGTTGGGAAATGCAATACCTCTCGTCCAGGTATATTCAACTTGAGGGAC<br>AGAGCCAAGTGGGATGCATGGAATTCACTTAAAGATAAAACCCCCGAGTCTGCCAT<br>GGAAGATTACATCACTAAGGTTAAACAGCTACAAGAAGTAGCATGATGCCTAGACA<br>AATAGCTTTGCTCAACACATCCTGATAGTGTACACTAAATCGCACAACTTTACTACT<br>ACAAAGAAAGATCGTTGACACCTTGACAAATAGCTTTGCTCAACACATCCCAACAAT<br>TTGGATTGCGAATACCGACTCCAATTTGTACTTGATCCATATGTCGTTGCGATGTAC<br>TAGTTCCTCTATACATATGTTTCTGCAAGAATCGGAGTTGGACCTCTTCTTCCCTGT<br>TATCAGCACGGTCACT |
| SEQ ID NO:153 | Early | LPZ-085 | AGGTGACCGTGGATAAGAGAACGCTTTGCCGACTCTCTGGGATGCCCTTCCCTCC<br>ATAGCCGTCGTGGGAGGACAGAGCTCCGGGAAATCCTCTGTGCTGGAGAGCATCG<br>TTGGAAGGGATTTTTTACCGCGTGGATCAGGTATTGTTACTAGACGGCCGCTTGTC<br>CTTCAACTTCACAAGACTGATGAAGGCAGCAGGGATTACGCCGAATTCCTTCACCA<br>ACCCAGAAAGACATACACCGACTTTGCACTGGTAAGGAACGAAATTGCGGATGAGA<br>CTGATCGAATTACATGGCGTGCCAAGCANAGTCTCAAGTGTCCCAATTCACCTTAA<br>TATTTATTCACCCAATGTTGTTAATTTGACTCTAATTGATCTCCTGGGTTGACAAAAT<br>TGCTATTGACGGTCACT |
| SEQ ID NO:154 | Middle | LPZ-086 | AGGTGACCGTTGGGAAATGCAATACCTCTCGTCCAGGTATATTCAACTTGAGGGAC<br>AGAGCCAAGTGGGATGCATGGAATTCACTTAAAGATAAAACCCCCGAGTCTGCCAT<br>GGAAGATTACATCACTAAGGTTAAACAGCTACAAGAAGTAGCATGATGCCATTGAT<br>CTCCCTTTCCCTGCCTCTTCTATTATCATTGATCTCTCTTTCCCTGCCTCTTCTATTA<br>TCAGTACGGTCACCT |
| SEQ ID NO:155 | All | LPZ-089 | AGGTGACCGTACATACAAGTGCTCAGTACAATGTCATATACTACCAATACATTTGAT<br>TAGAATACGAGACTCGCTTTCATTCGGCATATCTGTCTCTGGATGATAAACATATAA<br>AGCCTTGATCCATGAGTAAGGTAAGTTTGAAGCTACAAGTATTTTCTAAACGAAGTT<br>CAAAATTACATAAGATTGTGGCTGGGGCGTGAGAAACGGCCTCAACAATGTCCTGT<br>TCTGATCATGTATCATTTCAGTACCGATCATGCCTATCATACCCGCCTGGTGACGG<br>TCACCT |

TABLE I-continued

| cDNA | Embryo Phase | Clone | Nucleotide Sequence |
|---|---|---|---|
| SEQ ID NO:156 | Middle | LPZ-090 | AGGTGACCGTACTGATAATAGAAGAGGCAGGGAAAGGGAGATCAATGGCATCATG CTACTTCTTGTAGCTGTTTAACCTTAGTGATGTAATCTTCCATGGCAGACTCGGGG GTTTTATCTTTAAGTGAATTGCCATGCATCCCACTTGGCTCTGTCCCTCAAGTTGAA TATACCTGGACGAGAGGTATTGCATTTCCCAACGGTCACCT |
| SEQ ID NO:157 | Late | LPZ-091 | AGGTGACCGTATAGTGTCAAGCTTTTCTGGATTGGATAATGGACGGCGGCTTGCGA CATACATCTACACATTCTGTAACAAGTACACTCTACTGCAACAGCAGACCCAATTTC ACCTCTTCAGTCAGCCAGAGATCTCGATGGATTTGGGTTGAGGAGGTTGGGGTTCT GCCTGCTTCGGCACGGTCACCT |
| SEQ ID NO:158 | Early | LPZ-092 | AGGTGACCGTGCTAAGTAATTATCATCTGTACCTGTGCTTGCTGCAGGAAGTAAAC CAACCCGACTAGTCTTTTTAATAATACAGGGAGCCTTGCCACCAATTTCCTCTTGAA GCACCCATATTGGACGGGTTTGTGTCATCCTCTGTATTATCCTTTTTCATCCCAAGC AGGCTGTCTGTTTTTGTAGTAGAAGGATCACAACACAGATCAGGCCCTCCATAGTA CAAAGAAGAACCGAGGAAAGTATCATTAACGTTCTGACTCCTGCCATGAAGGCTTC CACTATGACCTTGACCCTTTTGTGAATTACTGCCATTTAGACCTTGACTGGCTCTTG CAACCAAATGCCCCAGAATGGAACTTCTTTGTGCTCCAGTTCCATTGTGGTTAGTT GAATCCCTACCACGGTCACT |
| SEQ ID NO:159 | Late | LPZ-093 | AGGTGACCGTGCAATATTGTATTCCAGGACCAAGTACTTAGGACAGAATCAGGTCA CGAGTGGCTCCACTCCACAATACGATGTTCATCGTTTTAATCACAATACAAGTTTGT TAGTCCAAGTAAGTGCGCTGCTGCAGACAGTGGGGCACCCCCCGTGGGCTTTGAC TGCCTGTCATACTGTTCCCTCCTTGCTCCTGCTCTTGCTCTCGCTGGGCTGTGGTG AGTTACTAACCTGGTTCGACCCACAAGGGCTTCTCACTAGGGCGTTAGGCTGCATG GATCTGCCAGATATTGTGGTTGCAAGGGACAGAGGCATGAGACACAGGCCTTTGC TTTGCAGAAACTGCATTGCTGACCCCATGTTTTCATCCATCAGTTTTGCTACCTCTC CTTCTGTTATGGACGGTCACCT |
| SEQ ID NO:160 | Late | LPZ-094 | AGGTGACCGTATCCGCAGCAGCAACAGCAGTAGAGCCTGAAGCAGGGGACCTAAT TACAGTCAAAAGTCCAGGGCTACCAATGCCTGCTAACAGCGCACTTACTTGGACTA ACAAACTTGTATTGTGATTAAGACGATGAACATCGTATTGTGGAGTGGAAGCCACT CGTGACCTGATTCTGTCATAAGTACTTGGTCCTGGAATACAATATTGCACGGTCAC CT |
| SEQ ID NO:161 | Late | LPZ-095 | AGGTGACCGTATCCGCAGCAGCAACAGCAGTAGAGCCTGAAGCAGGGGACCTAAT TACAGTCAAAAGTCCAGGGCTACCAATGCCTGCTAACAGCGCACTTACTTGGAACT AACAAAATTTTTATTGTTAATTAAAAACGAATAACATCGTTTTTGTGGGAGTGGAACC ACTCGTGAACTGAATCCTGTCCTAAGTTCTGGGTCCTGGGAATAACATATTGCACG GGTCACCTT |
| SEQ ID NO:162 | Middle | LPZ-096 | AGGTGACCGTTACAGCTAGGGAAGACTTTAAAAGTTTGTAAAACTAAGCATAGCTCT TAAACACTGAAGTTAAAAGACATGATTGGAATGTGCAAGTGGTTCAGTATCCAAATA TTGAAGGTTGCAGAATATGGAGCTACTGTGCAAACGAGTAACTTTATCTATATTTTC ACAAGATCATACAATGGGAAACGTTGAGATAACAACTGCATCGGTGAACCAGAATA GTTATAAAAGTTCTTGCAAGTAAAGGGATGAATAATTGCATGGTTGGAATTAAGAAT GACCATGTAGAGCTGCTATACAGATTCTCCAAGGTTTTATATTTGAGGAGTGCGCG CTATTGATGTTGTGCAAAAATTTCAGAAATTAAGTTCTGCGGCATTTATCAAGGTTG TTTGAGCCATTTAAATAGCAAGTTTTTGTTTCTCCAAGTACTTTCAGGAAAGCAGAT AGCTCTAGTTATAATGCTCCAGTGACAAACACATCTAGTTGGGGCAGTGAATGACG CTTTTGTCATTCTCTTTTGGTTTCAGGCACGGTCACCT |
| SEQ ID NO:163 | Early | LPZ-099 | AGGTGACCGTGGACAAACTCTAGAACAGGCATAGCTTTCATGTTCAGTTGTTTTTAA AGAGCAGTCCTCGCAGCAGATGGTGCAGCTTCCTGCTTCACTTCCGTTGATTTTCC TGATCTGAAATACCCGTAAACTTGCTGAAAGAACCCAAATACTTAATAGCGTCTCTAA ACAAAA |
| SEQ ID NO:164 | Late | LPZ-100 | AGGTGACCGTGCCTGAAACCAAAAGAGAATGACAAAAGCGTCATTCACTGCCCCAA CTAATGTGTTTGTCACTGGAGCATTATAACTAGAGCTATCTACAAGCCAAAACAGTG TTTGGGAGAGATTCCATAACGTCATTGCCTCTGCTACACATCATTCATTGGTTCCAA TAATGAAGCCACGTGCTAAGGACATTGAGAGAATCTTATAAAACAAGAAATATAGTA AATTGGGAAATGCATTTTATCGTCTAACCTGCTTTCCTGAAAGTACTTGGAGAAACA AAAACTTGCTATTAAATGGCTCAAACAACCTTGATAAATGCCGCAGAACTTAATTTC TGAAATTTTTGCAAACATCAATAGCGCGCACTCTTCAAATATAAAACCTTGGAGAAG TCTGTATAGCAGCTCACATGGTCATTCTTAATTCACACCATGCAATTATTCATCCCTT TACTTGCAAGAACTTTATAACTATTCTGGTTCACCGATGCAGTTGTTATCTCAACGT TTCCCATTGTATGATCTTTGAAAATATAGATAAAGTTACTCGTTTGCACAGTAGCTC CATATTCTGCAACCTTCAATTTTGGATACTGAACCACTTGCACATTCCAATCATGTC TTTTAACTTCAGTGTTTAAGAGTATGCTTAGTTTTACAAACTTTTAAAGTCTTCCCTA GCTGTAACGGTCAC |
| SEQ ID NO:165 | Middle | LPZ-101 | AGGTGACCGTAAAATACCATGAGAAATGCTTTCATCAGGCACCGCTGGTAGGTTTT CTTAAGCTTTTCATTAGGCAAAAGAGGCTCCGTGAGTTGATCGTTAATTCTCTCCTT GAATGCCATATTGACCAGACACTCTGATTAGAAACTGGAATACAACTGCACATATAG TCATTCTATATGATTCATCCTTCTGCACTTCAGCATCCTGCGGCAACTCTTCATCCC GCCATACTGAGAAAAATTATTTGACTCTTGATCATGTGTAGATGAATCTTCATGAAT CTTCTCATCTTCATTCTTGTCTTTATATCTTTAGGAAGTGCATCTGGTAAAAGTATAA ATGCATCTTCACGGGTGCTTCAGTTTTTGCATGCTCCCGGTTCTTCTTGTTTAGCAT GTGGATCTAGCAAATCACTAAATGTAGTTCTCTCAATTGGTCTGGTGGAAATTCTCC TCAATTCGAGAATTACGAATCATCATACCTGAGTAATATATGTTGCCCTGTACATGC ATATGCTGGTTTTTGGCTCCACCATTCTCCAAAGGGCTCAAAAACTATGCGACCCC TGGTTGCCGTAGTGGAAGGTTATACATTGCGTTCCCAGTAGCCACGGTCAC |
| SEQ ID NO:166 | Middle | LPZ-102 | AGGTGACCGTGGAGGGGCTCCACTTATATGCATAGATGATGCTGCGAGGCTGTGT TCATCTGGTCCAATGGAGAAGGGGAAGACCAAGTGCCTATCCTGATTTTGGTGCC GCTTGTTCTGGTGTACAGAATATCAACCCAGGGTATGTACCATCACTTCGTGAGAC GTTCACATTTCCCCACTTCTTGGTGGAGCTGGTGGAAAGCCTGGAACTTCATCAAT |

TABLE I-continued

| cDNA | Embryo Phase | Clone | Nucleotide Sequence |
|---|---|---|---|
| | | | CTATCGTTGGTGTGAGGATGATCAGGCTCTGTACTTATATCCACATGTAGTGCAGC<br>AGGTGGTGGAGATGTCTCTGATAAGTTGGGGGTTGATACTGGTTCGTATCATTTGC<br>AGTGATGTTCCCCCGCTGCCCTTAATTGCTATTGATCCATCATTAACTATAGGTTTT<br>TACTCGCCCGGAATAAGACAATCTTTTGACACTTGTTGCTTGGGTCAC |
| SEQ ID NO:167 | Early | LPZ-103 | AGGTGACCGTGGCGCCTGACCTGTGCAGAATCCATTCTCATGGATACAATACTGTT<br>AAGTTTGCTTTGCTTTGCTTGAAGGATCTGAATTGAAAAATTGTCCCCACAATTCTG<br>TTTCGTTAAAAATGACCTCAATCACTCTCGACAGTTTCCAGATCTTGATTGGGAGCG<br>TCCTCTCCTCTCTCAAGATGTTGTTGACCAAATTCAGGGCGACTTGTGGCCAGAAA<br>TCGTACATTCTGCCATCTACCTGTTATTGAGCTCCCCGATTTATATGCGCTTTTGAC<br>GGTCAC |
| SEQ ID NO:168 | Middle | LPZ-106 | AGGTGACCGTCAATACCATTAAACTGGGGATTCGTCTCAACAAGTCAACATGCTAA<br>CCTCACAGCTCCAATCAAACAACGTCCGTCGAAGGGCGCTCACACTCATCCAAATT<br>ACTTCCCTCTGCAAGACTCACAAAATCAGATTCTTCATGAATTGCTCAAACGAGGCT<br>GTTATGGATGATGCAGCTGATTACTCAAGTGACAGCACTCTGAATCCCCGTCCCAT<br>ATATAGCGACGCGGCGTTTCAGCCGTGACTGGTCGCAACAGCCTCAGTGGGACAA<br>AAGGCCAGAAGCCCCCCAAGGTTCTCACGGTCAG |
| SEQ ID NO:169 | E,L | LPZ-107 | AGGTGACCGTGTCGATGTTGTTAGATGTGATTAGGGTTTTATTTCTTGATACAGATG<br>CACTGTTTCTGTGTTTATTCTTTTATTTCTTCAATGTATGTTGTCAAATTATACTTAGT<br>CA1GATCTCCTTTTATCGTTCGTCAAAAAAAAAAAAAAAAAAAAAAAAAAAAAAAAAG<br>TTTAACAATTAAAAGGGGAAATTAGGCCATATCAGCTTGTCGTATGGACCCACATGC<br>ACTGTAGGTCAC |
| SEQ ID NO:170 | Middle | LPZ-108 | AGGTGACCGTATGCAGAGTCAAGGTTTAGTTCCTTCAGAGCCTGCCCGAGTAGCA<br>CTGAGGCAGCTCAAGCCATTTCACGTAGGAAGCCCACAACAAAATAGAAATCAGAG<br>TGAGTCTTTGATCGAGTAACCCATAAGTTCTTAGCTCCCGTTCCATCTTAACATAAG<br>CATTTTTCTTGGTCTTCTCGCAGCCGT |
| SEQ ID NO:171 | Late | LPZ-109 | ATTGCAGAGGACTTAGAGAGGGAAAACCGTTCCGATCTGGTGAAGCAATTGGATGA<br>AGCGCTCTGGAATTGATTCCCGTTTCTGATGATATCGTACGGCTAAGCTCAGCTCT<br>TCAGGCATTGGCAGACAATACGATTCTTCAAATGAGATGACAGATTTTAAGAAACTT<br>ATAGGATGACATATTTCCTAGCTTGAAGCGGATTCCCCCTACGGTCAC |
| SEQ ID NO:172 | All | LPZ-110 | AGGTGACCGTCCGATAAAGGATGAGAATATAGGTAGATCAACCCAAAAACACTCTC<br>AGAAAACGATTAAAGCCTAACCCCAAGATCGTTGAGTAAATTTAACCCGGTAACCTC<br>CACATAAATATACTTAGCAACAATAAACTCAACAACTAAACTATCCCTTTAAAATTA<br>AATTATCCTTATTTATTTAAAAAAACAAATCCTTTATATACTAAGGTCCCCTGCACAT<br>CTATTACTAAGGTAAAGGAAGGGAATTATATGCTATCATTGTAAACTTTGACTTCCG<br>TATTTATGATCAGACCATGAGTTTGATAATTAATTTTACGCTCTTTACTCCCCATTCA<br>AGGCACGTGCCTGGTGATATATGAACGCCAAATTATT |
| SEQ ID NO:173 | Late | LPZ-111 | AGGTGACCGTAGAATACAATCTATGTATCAAAATGCTAACAAAGAGAATTTGTTGTC<br>TAGCTTGTAAATATACAAAAGAAACTCTCACAAGGAGTGAGAAGCACTAAGGCCCT<br>TGGAAAGAATACGTTTCTATTCAGCGGAGTGTATTTTGAGCTACGGCTTGGCACAA<br>CTCATCCTATAAAACAAGACTCTGTGAGAGGGCAGAGACCTTGATCCTGGGCGTG<br>GCAAGCCGGGTGGCTATTGCGGTAAATCGAGAAGGGGGACCCTGGAAAAGAGAG<br>GCTGAAATTTGTTTCATTCTGCAACTGAAACCTAACCGGAGGCCGAATCTGATCATT<br>TCTAAGACCTTTGGGGTCCTGGGCATCCCATTAAAAGAACGCTGCTAACTCTCCCC<br>TCCACAAAGGGCCAATGCGCTCAGGTCGGGCTTCTCATCTTCACATTTCTTGCCGA<br>AATCTATCTGAATTTGTTGTATTGAATAACACTGCCTCCTACACGGTCAC |
| SEQ ID NO:174 | Late | LPZ-112 | AGGTGACCGTGGGCGCCGTGGCTCAAAAGGCCCTCGCAGACGCCCGCTCCATCA<br>AGCTCATGGGCCCCCTCCACCCTCGGGGGGCAAGCCGGGAACGTTGCTGTCAGA<br>CGAGGCGAGGACCTGGAACTGCCGTTGAAGGAACGGTTCTATATTCAGCCCCTCT<br>CGGCGGACCAGGCGCTGCGAGAGCCAAGGAATCCGCGGAAGCAAATCCTGGAGG<br>TGAAAAAGCTGATAGATAAAAGGCGTGGCCGTACGTCCAGAACGACCTCCGCTCC<br>AAGGCTTCTTACCTTCGCTACGACTCAACACCGTTATCTCCTCAAAGCCCAAGGAA<br>CAGAAAAAACCCCTCAAAACCTCACCCCAAAGCTTTTTTGACACCCTTGACAAACCT<br>GGACTACGCTGCAAGGAGCCAAGGATACCCCAAGGGCAGAAAAAATACTTTGCAG<br>AGCTGGTGAACCGCCCTTAATGATGTTCATTCCAAGCTTGGTTAAGCTGTATTGC<br>ACTCATTGTTAACCACACTTAACGCCAATCCAATCTATGCTGTGTTGCATCTCCACT<br>TCTTAGTTAATAACGTTCTGTGTTCCCAAACTCTGTGCCACACACGGTCAC |
| SEQ ID NO:175 | All | LPZ-114 | AGGTGACCGTACAATACAAATAGGTAGTTTATCACATTGTAGCTTATAGAATGTACA<br>ATTGAAATCAAATAAATTCAACCAAACTCAAATAATATGATCATGTGCTCCTCACCTT<br>CTCAGCAAACTCGTAGAGCAGAAAAAAGGATTATGTTAAATCACAGTTCACACATTA<br>GGGTAAATCCCACTAAATGACCTCTCTTCATTATCCAAGTATCTGACACCAACATAT<br>TTCAAACAAATAGTGCAAAAAGGAATGGTGAAGTAAATAGTCAAACTAAAAAATA<br>AGCTTAAAATTTCTCACATGTTTGAATATGTGCACCACAAATTTTGTTAGTGTCATCA<br>AAATGCATGTAATCAACTTGCCGTGTATATAATTTCACAATATCCGTAAAATTTTG<br>CAATTCCTTATGAGCATTTCATGTCTAGAGATTGCAATGACTTGGCTACAAACATGT<br>TTCTCTACACAAGATCACAATATTTAGTCAGGACACGAATTGCAATGGGGATTCTCA<br>CAAGCATCACAAGTCATCTCCCATGTACTAAAAAATTGTTTAAAT |
| SEQ ID NO:176 | Middle | LPZ-115 | AGGTGACCGTATAGTGCATATTCAGATTGCAATTACAGACGTATTAGAACCAGATTT<br>TCGCTTCGATACAGCTCATCGAGAGCAACAGAGATCCAGATCAAAAACCAGACACA<br>GTTTAAGAACATCGAAATACCAAGCCCAGGGACAGTTACCAGCATATAGCTCTACC<br>ACCAACAGATTATTACAGAACCAAAACATAAGACCACTTGCAGACAAAAATAAACCC<br>TAACGCAGAACGTGGCAACTATCTCCTCCAGCTACCACCATCGGAACCACCACCAC<br>CATAGCGAGAACCCCACCACCACCATAGCCGCCACCGCCACCACCATAACCACCA<br>CCACCACCACCACTGTACCGCCACTACCGCCATAACCACGGTCAC |

TABLE I-continued

| cDNA | Embryo Phase | Clone | Nucleotide Sequence |
|---|---|---|---|
| SEQ ID NO:177 | E,L | LPZ-116 | AGGTGACCGTCCTTGGAGATAGCAGCTTCAAAACCTCCAGTGGTGGAGTCGATGAT CAA1ACTGCACAGTCAGCCTGAGATGTTCCAGTAATCATGTTCTTGATAAAATCACG ATGGCGGGGGCATCAATCACAGTGCAGTAGTATTTAGTTGTCTCAAACTTCCAGAG TGCAATATCATTGTGATACCACGGTCAC |
| SEQ ID NO:178 | E,M | LPZ-117 | AGGTGACCGTATAGTAGGAACTTTAGGTGCTTTGGTGGCACTCTCCAATTTTCATG TCCTTACATACCCCACTACGGAGAAGGGTAGCCCAAGATTTGAACCCAAGACTTCC GGTTCGTGAGACTTCATTTCCACGGTCAC |
| SEQ ID NO:179 | All | LPZ-118 | AGGTGACCGTAAGATCAAGAGCACAGAAAGCAGCCATAGCCCCGCCCATTGAATG CCCATAACAATAATCTGTAACCCATCTCTCTGTTTCTGAGCTTTCTGAACTGCTTCT ACAACAGTGGTCGTAAGGTTGTGTTGTGATAAGCAGAGTAAAATCCATAATGTACC ATTGCACCAGCATATTAGGATAGTTGAGATCAAGTGTCTTACAGAATAAATCCTCCA CCCAATTCTGTAGCTCCTTTCTTGAGTACCCCTGAATGCAATTACAATTGCATTGAT ATCTTCTGCCACACCACAAAAGCCTGAAGGCAGTGTTGTACATCAACTATAAGCTCT ACCACCTGAAAACCCCAGTCAAACCATTGCACCTAGAACAAGTCCAAGACATTAGA GCACTCAAATCATCCATA1AGACCGCAGAAGCATATTGCACAAGTATCTCAGCAAGT GTTCGATTATAGACATGGCCA1GGTCAC |
| SEQ ID NO:180 | Middle | LPZ-119 | AGGTGACCGTGGGAGGGGAGATTTTTGATTTATATTTCCAATATAAAAGAAAATCTA NGTTGTAAGGACATGGCAAGAGCTCTTATTTCCGGGGTTTTAGCCGTGGCCCGGA GCGGATGAAAGCAAATGTAAGTCACTCCGTGCTTTCTCGGCATTTGGACGCTTCTA CTCTACCGCACTACAGACGGGATTGAACCTCGCATCTCTGAGTGTTTGGTCGTTTA CATGGCGGACTTGTTCCGCACCTCTGCGGACGTCAAATGCCGCGACGATAATCCC TTTGAGAACAGCGATACGGCAGAAAGATCGCCGTTGACGAAGCGAGAAAACTATTG AGACTTGCAGATGTGGAGCTGAAGAAGAGCTTGAGTCGACGGTCAC |
| SEQ ID NO:181 | Middle | LPZ-120 | AGGTGACCGTCCGTTCGGGGTGTATTGTCGAACACGTAGGATGGTGCTACGTTGA AACCACCGTTACGTTCTTCGATATGTTATAGTTCGAGTTCATACGGAGGGAATACC GTTTGTAGTGTTATTCAGCACAACCCCGTCCTGATTAAACACCCCCGCAACCAAGG ACGTATTCGACGTTCGGTATTGTTTGACACACTCAAGTTATAACCCTGAATAGGCG CTACCCGAAGTAAGCATTGTACCAGTCGTTATTTTTGCCTTCGTATTGCGAAGGATT TTGAAATATATCCGGACAGGCTGCAACCGATCTTCATAAAACTCTTTCTTAAACTGA GCAAACTGAACAGCATTAGCATTTTGACCCGACCTTTCATCGGCACCTGCTGCACA CCCGCATACGTATTAAAGCTATGTTCGTCTGGCCAGGTTTGCCTTTTTTGGTTGTAA TCAGGACAACGCCGTTAGCCGCCCGCGATCCGTAGAGCGACGTAGAAAGCCGCAT CTTTCAGCACGGTCAC |
| SEQ ID NO:182 | Late | LPZ-122 | AGGTGACCGTGAAATATGTGGGAGATGATATGTGGTTTCCTGAATATTCACCTCTT GTGTAGAAAAGTGAGATCCTTAAGATGTTTTGCTAATAAGACTCTTAGGAATGTTGG AGCCCTTTCAGAATGCCATTTGAATAGATTCAAGGTGGTAGCTGTTGCCTGGGGCT GTTTTAGGGTTTTAGGCCATGCTCTGTAATTTCATTGAGTCAAAATTGGATTAACTG GTGTCTTTTACCTCATAATAGCTACTGCAGTATTTGTCGATATAGCTTCCCTATTTAT TGACTCTCCTTAGGTACGGTCAC |
| SEQ ID NO:183 | Late | LPZ-124 | AGGTGACCGTCCGTTCGGGGTGTATTGTCGAACACGTAGGATGGTGCTACGTTGA AACCACCGTTACCTTCTTCGATATGTTATAGTTCGAGTTCATACGGAGGGAATACC GTTTGTAGTGTTATTCAGCACAACCCCGTCCTGATTAAACACCCCCGCAACCAAGG ACGTATTCGACGTTCGGTATTGTTTGACACACTCAAGTTATAACTCTGAATAGGCGC TACCCGAAGTAAGCATTGTACCAAGTCGTTATTTTTGCCTTCGTACTGCGAAGGATT TTGAAATATATCCGCACAGGCTGCAACTGATCTTCGTAAAACTCTTTCTTAAACTGA GCAAACTGAACAGCATCAGCATTTTGACCCGACCTTTCATCGGCACCTGCTGCACA CCCGCATACGTATTAAAGCAATGTTCGTCTGGCCAGGTTTGCCTTTTTTGGTTGTAA CAGGACAACGCCGTTAGCCGCCGCGATCCGTAGAGCGACGTAGAAGCCGCATCTT TCAGCACGGTCAC |
| SEQ ID NO:184 | Middle | LPZ-126 | AGGTGACCGTCGTCAGAAAAAACGTGATTTCCGCAAACTTTGGATCACTCGTATCA ATGGGCAGCTCGTTTGAACGGACTTTCATACTCACAATTGATGCATGGTTTGAAGTT GGCTGAATCGAAGTGAACCGTAAAATGTTGGCTGACTTGGCTGTTAACGATGCAGC AGCTTTCAAACTCTTGCAGACGCAGCTAAAGCTAAGCTTGGGTAAATAATTAAAAAA AGAAGCGAGGTTTCCTTGGTTCTTTTTTATAACTTTTAATGAAAAGTATGAAGAGAG AAACAGCCTGTCTTCTACTTATAGTATAAGATAAAAGCTTGTTACTGATAAGACAGC TTTCATGGTAAAGCAGTTAAAAATAGGGATTTGCGATATAATAGAAAAAACAGACGT TTATGTAAATAAAAAACAGTAGAATGGAGAAATTATGTCAGAGAATCGTTTGGCTTG GGATCAGTATTTTGCGGCCAGGCTCTCTTAATCGCTAATCGCTCAACCTGTAAGCG AGCCAAAGGTGGCTCCGTATTGTCAAGGATAATAAGGGTTATTTCAACTGGGTACA ATGGCTCAGTTTCAGGGACTGGAGACTGTATTGACCAAGGAGTGCCTGGTCATTGA CGGTCAC |
| SEQ ID NO:185 | Late | LPZ-127 | AGGTGACCGTGGCGGAGGTTAGGGAAGTTTGACTTCTCATTTTCTCACGCACTCCT CTCCTCGTAACCTCGGTCGAGTCGATGGCGGCTTTTTAGTCGAGTGTGCTAACGC CCCTCCGGCCTCAAAATTTCCAGCTACTCGTATTTGATCAATGCTGAAATCGCGTAA TTACGTAGTAATAAAGCGTAATGAATTCTATAATGAAGCATGTTTCTCTATAGTTCAT GTGCCGAGAGGAATAATGAAAATGAGGCCTTATATATTATCTGGGGCTCAAGGAGA TGTTATCTTTTCCTTCCTTGGTTAGAGACCGTCAACCTTCACTTGATTGGATAAAGC TTCATTTTGTTAAAACCTCCAAGCCAGTAGATACATACGGTAGGCACGTATTATGGT AGAGACATACGGTCAC |
| SEQ ID NO:186 | Late | LPZ-128 | AGGTGACCGTCCTGTTGCCTAACCGCGAATCCAAATCGACTTGGGCTGCTTCCTTT CGTGCAGATATTTCTGGTTTGGACTCTAGTTCTTGCTCCTGGAAATCATGCTTGAGT GCTGGGTAGCTGCCTCCAAGTTTGGTTGACAGGCCCATTCCTTACAGCTTCTCTCT TCCGCTTATGACAGAGTAATGACAGGAATTCAACCTGACGGATCCGTCTAGCTCTC TGGATGAGCCCTCAGCTCTGTGTACTATTGTTCATGTACTGGATACTTTGTAAATGA TTTTATTCTGGTTTTACCCCGGGGGGGCATTTTGACTCCTGGGTTTAATACGGTC AC |

TABLE I-continued

| cDNA | Embryo Phase | Clone | Nucleotide Sequence |
|---|---|---|---|
| SEQ ID NO:187 | Late | LPZ-131 | AGGTGACCGTGGAACATGATGATTAGTTCTTCTGTGGGCCAGGATGATTAGTTCTC TGTGTGACTGTGGGCCAGGATGATTAGTTCTCCTGTGACGACTGTTGGATAGGATG ATTCGTCTCCTGTGGACAGGATGATTAGTTCTCCTGTCGAGGCACCCTACCCATGC AATTTGGGATCATGGGAAGTACCTCTCATCTGATCAATGAGTAGGGAAATGGGGTT AGGGACCATTAGAGTACTATCGATGGACACATCGTTGTATCTACCGTCCTATGCTA GGACGACCTCCATTGTTTGGGATTAGTGAGAGTGGTATGACACTCTGAGACTGACT TTGGGTCAGTGGAGGATGTATGATACATCCTCGATCATTTCTTCTTCTTCATAGTTC GAGCAGAGCAGAGCACAACAGGCCAAGTAGTGCAGGGTAGTGCATTTGATGGCTG GGATAGTAGCGACGGTCAC |
| SEQ ID NO:188 | Middle | LPZ-133 | AGGTGACCGTAAATAAGATGACCCACATGGAGTTTGGCCCTAGTTTCCAATTTTAA CAC1CGCTCTCAACTAGGGAGAACTCCATTCGCTGATCCATTTGTCCGACTATACTA TCTCTGCATCAGTGCCCTACACTACTCTGCACTGCTCTGCTCTACTAAACCATGAA GAAGAAGAATGACCGAGAATGTCTCATGCCATTCTCTATTGACCTGAAGTTAGTCC TATATGAAGAGA1TGTGTCATATCACTCTTATTGACCCAAAGTCAGTTTTATTGATCC CAGATCAATATCACAGAGAGTGTCTCAAACCACTCATACTGATCCCAGATCAGTTTC ATTGATCCCATATCAAGGAGATCATCCTAGAATAGGGAGTACAGTAGATACAATGAT GCATCCATCAATAGTACT1CTATGGTCCCTAACCCCATTTCCCTGCTCATTGATCAG ATGAGAGGTACTTCCGATGAGCCCACACTGCATGGGTAGGATGCCTCGACATGAG AAATAATCATCCTATCCACAGGAGACGAATCCTCCTGTCCCACGGTCAC |
| SEQ ID NO:189 | Middle | LPZ-136 | CTAGGGAAGACTTTAAAAGTTTGTAAAACTAAGCATAGCTCTTAAACACTGAAGTTA AAGACATGATTGGAATGTGCAAGTGGTTCAGTATCCAAATATTGAAGGTTGCAGAA TATGGGCTACTGTGCAAACGAGTAACTTTATCTATATTTTCACAAGATCATACAATG GGAAACGTGAGATAACAACTGCATCGGTGAACCAGAATAGTTATAAAAGTTCTTGC AAGTAAAGGGTGAATAATTGCATGGTGTGAATTAAGAATGACCATGTAGAGCTGCT ATACAGACTTCTCAAGGTTTTATATTTGAGGAGTGCGCGCTATTGATGTTGTGCAAA AATTTCAGAAATTAATTCTGCGGCATTTATCAAGGTTGTTTGAGCCATTTAAATAGCA AGTTTTTGTTTCTCCAGTACTTTCAGGAAAGCAGGTTAGACGATAAAATGCATCTTC CCAATTTACTATATTTCTGTTTTAAAAGATTCTCTCAATGTCCTTAGCACGTGGCTTT CATTATTGGGACCAATGAAGATGTGTAGCAGAGGCATTACGTTATGGAATCTCTCA CCAAGAACACTGTTTTGGGCTTTAGATAGCTCCTAGTTATAAATGCTCCAGTGACAA ACACATCCTAAGTTTGGGGCAATTAATGACGCCTTTTGGTCATTCTCCTTTGGGTTT CAGGCACGGTCAC |
| SEQ ID NO:190 | Late | LPZ-137 | TCCCTTTAGTGAGGGTTAATAGATCTATAGTGTCACCTAAATCGCGGCCGCTCTAG AACAGTGGATCCGCAAGCAGGATAGACGGCATATGCATTGGATGCTGAGAATTCG ATATCAACTTATCGATACCGTCGACCTCGAGGG |
| SEQ ID NO:191 | Middle | LPZ-138 | GGTGCGATCCTAAACATGCAAGCTTTGAGTTTGTAACTTTGTAGAAGTGGACATTTC TAAGTTGGATGTACAAATCTACTGTTGGTTGTATTGTCATCCCATAAACAACTGTTT GATGAGATGTTTTTTAAAAACCACATCATAATATTTTTAGGCCTTGTAAAAAAAAAA AAAAAAAAAAAA |
| SEQ ID NO:192 | Late | LPZ-140 | ATTCCAAACTTTTCTTTCAAGATGTACACCAACATCATTGTCCCCAACTTAGTAGACT TGACTTTTCACCAGGTCCAAAGAGAGGGGTGGTGGAAGCAGATTTCAGGCTTTCG AATAAGTATCAATGATATAAGCATCATCCCCTTGCCAATTGTTCTGGATCGCAC |
| SEQ ID NO:193 | All | LPZ-141 | GGTGCGATCCCATCAGGGGTTGTGTTTCTAAGAATCACTTCCATGTTTCAAATTCAG CACTTGATCTTGTACATACCCAATTTGTTGCCTGCTACTAGCTAGTATTGTCTTTCA GTTTGAACCATTTTTTGAGTAAATCGTGTTTAGTCTTTGGCAAAAAAAAAAA |
| SEQ ID NO:194 | Middle | LPZ-143 | GGTGCGATCCGCATTAGAGAAGCATACAGGAAAAAGAAGTACCTGCCTCTTGATTT GCGCCCAAGAAGACTCGTGCTATCAGGCGACGCCTTACCAAGCATCAGGCATCAT TGAAGACGAGAGACAGAAAAAGAAAGAGATGTATTTTCCAATGAGAAAGTATGCAG TCAAGGTGTAAGCCACAGGATTTGAGCTTTCATGCAATTTTTTTGTTACTTGCGGGA TGATATTGCCTATATATTTCCGTCCACGTTTTTGGCAAATTCCGATTTGCATCAGAA TTCAAGTTATGATAGTGTTCTTTCGCTTTTGAGCAGTTGATATTGTTTATCTTTTATT TCTCTTGAATTGCAACATATTCTAATGCAATGAGTGGATTATTATATTGTGGTATTTC CATGTTGAACTCATATAAATGAGCGTAATTTGAGTGGTAGCGCTAGGATATTTACAC TTGGCAAAAAAAAAAA |
| SEQ ID NO:195 | Middle | LPZ-144 | GGTGCGATCCGTATAGGTAGTTTGGATGATGAACGGGCAAAGAAGGCAAAGGAGT ACAGGATGGATCCTGTAATTCCTGTTTCAGAAAACAGAAAATCTGCAAATATAAGGAT GGCTAACTTTTCAGCTATGAAAATATATGGTGCAGTGGCACTCATATCAGTTGCAGA GTTGTCAAATAACTTTTGTGAATAGGAAAGTTGTCCTCTTTTAGAGTGCAGAAATCC TGCAATATAAGATGGCTAAGTTTTTCAGCTATATGAAAATATATGGTGCAGCAAAAA AAAAAA |
| SEQ ID NO:196 | Late | LPZ-145 | GGTGCGATCCCATATACAATTACATATATTTCAACAATTCTTTTGTTGTTATGAAAA TCTATTGAAATAAATTGAAATAGTTTGCATCATTTATTTATCGGAATTCGTATTTATAT ATTAAATTTCTGATGTCTCAAATCCTTCGTTACTGTAACGATATCATTAATATAATGT GTCTGCAAGTTTATTGGGCAAAACAAAATTTATTTTTCGGTCACATCATAAGTTTATT TTTGGTCACATCATATGCACCATCACATTAAGCATAAGCATATACAGTAGCGTAAAA ATACAATTATTGTTGTTGACTAGGATCGGAC |
| SEQ ID NO:197 | Late | LPZ-146 | GGTGCGATCCTAGTCAACAACAATAATATGTATTTTTACGCTACTGTATATGCTTAT GCTAATGTGATGGTGCATATGATGTGACCAAAAAATAAACTTATGATGTGACCGAAA AATAATTTTGTTTTGTCCAATTAGACTTGCTGTATATGTCTGGAGTCCTACCCTTGAA AATTGACTTGTTTCCC |
| SEQ ID NO:198 | Late | LPZ-147 | GGTGCGATCCCATATACAATTACTTATATTTCAACAATTCTTTTGTTGTTATGAAAA TCTATTGAAATAAATTGAAATAGTTTGCATCATTTATTTATCGGAATTCGTATTTATAT ATTAAATTTCTGATGTCTCAAATCCTTC |
| SEQ ID NO:199 | Late | LPZ-148 | CCACTGCACCATATATTTTCATATAGCTGAAAAACTTAGCCATCCTTATATTGCAGAT TTCTGTTTTCTGAAACAGGAATTACAGGATCGATCACTGTACTCCTTTGCCTTCTTT GCCGTTCATCATCCAAACTACCTATACGGATCGCAC |

TABLE I-continued

| cDNA | Embryo Phase | Clone | Nucleotide Sequence |
|---|---|---|---|
| SEQ ID NO:200 | All | LPZ-149 | AGAGCCTTCTTGCAGACAATCCGTGAAAACATGGCTATACAATAAAAATTCCCAGTT<br>TGAATTCTAAAGAAAACTGTTCAATATTTGAAGGCCTCTGATATCACAGAGACTGAT<br>ATTAAATGGAAATTCATACAAATGAGGAGAGCATGTAGCAACACTAGAAGCTTTGG<br>CATAAAGCACCAGATAAATTCATAAGAACTAAATCCATAAGAAGGATCTCTCGTTCA<br>CCAGTCACAATCACACTCGGATCGCAC |
| SEQ ID NO:201 | Middle | LPZ-150 | GGTGCGATCCCTGGCCCTGATAACTTTGGTTGCAATGGAAAATGCAGTACTAGGTG<br>CGAAATGCTAAAGGCCGCCCGGAGCGGTGCATGAAGTACTGCAATATTTGTTGTAG<br>TAAATGGCTGGTTGTGTTCCCAGTGGTCACTATGGCAACAAGGACGAGTGCCCCT<br>GCTACAGAGAATGAAGTCCGCAGCCGGCAAGCCCAAGTGTCCCTGATCTTAGCAC<br>TTCAGTGCAGTCGCCACTTCTTTTATTCTCTTTTTTTATAAAAGTGACGAGGCCGTTT<br>TTCTTGTGCTTGGTGCCATATGTAGAGCGGTGGCTACTTCTCCTGTGTTAGGAAAT<br>GTTGCAGTACTAATAATAGAACTTCTT |
| SEQ ID NO:202 | Middle | LPZ-151 | GGTGCGATCCAATAAAGATATACTTTGCAACAATAATCAAAATATCATTATGCAAAG<br>TTTAAGATCAAAATAGAATGCAACAAAAAAATGGTTGTAACATAGGAACCAACAATG<br>TTGCATTCAAGTAAGACTCTTTGCAAAAAAAAAAAATAAAAAAAAAAA |
| SEQ ID NO:203 | Middle | LPZ-152 | GGTGCGATCCACAAGTAAGATAATTGAGTATATATTCAAGATGCAAATATTTCATTA<br>GGACCACTCATAAAGTTATCAATGATTCACAAAGAGACCTCCTGACCTCTCTCAAAA<br>GTGGTGGCAACACAAGACTAGTGTAGTTTTTACTATACCTCAATGAAACTACCATCC<br>TAACTGATGCCATAATCTTCTGTTATATATTACCAAAATTTATGAGATGATTGATCCA<br>TAAACACTCCAGAACACATAGTCATCCAAAGGAACCTTTGCTTGAATATGGACCCC<br>CTTAATTCAGGTACTTGCTACTCCAATAAATTGCTTAATCTCTCCACCGATAACCAC<br>AGTTTGGATCGCC |
| SEQ ID NO:204 | Early | LPZ-153 | GGTGCGATCCAGGACATGAGGCCGAGTTTGCCATTGTGATATGATTGAGGAAGTC<br>CAGTCTCAAAATTAGGTTTATCTTGATGTTTGACAAGAAATATAGAAGGGCATGATG<br>AATCAAGAACCTTTTCCAAATCTGTTACTGCAACCAATCCAATGACATAATAACGCC<br>AATGGTTGGTTCCTGTGATGACATAATAAATTGGATTAAATTAATAACATCCCTAATG<br>CCATGTGGTTAGCTGCATCATCACCGTATCCATCGAGTGTTCAATTTTTGGGATGTA<br>TGTATCAAAAAAA |
| SEQ ID NO:205 | Early | LPZ-154 | AAATATTTTTCAATACAACGCCATGTGACATTTTTGTGCTTCTTGTTTTTGATACATA<br>CTTCCAAAAACTGAACACTCGATGGATACGGTGATGATGCAGCTACAGCCATTGCA<br>TTACGATGTTACTAAATTAAATCAATTTATTATGTCATCACACGAACCCAAACAATAG<br>CGCTATATGTCATTAGAATGGTTGCAGTTACAGATCTGGAAACAGATCAATGAATCA<br>TCATGCCCTCTATATCTCTTGTCAAACATCAAGATAAACCTAATTTTGAGGACTGGA<br>CTTCCTCAACATATCACAATGGCAAACTCGGCCTCATGTCCTGGATCGCAC |
| SEQ ID NO:206 | Middle | LPZ-155 | GGTGCGATCCGTATAGGTAGTTTGGATGATGAACGGGCAAAGAAGGCAAAGGAGT<br>ACAGGATGGATCCTGTAATTCCTGTTTCAGAAAACAGAAAATCTGCAATATAAGGAT<br>GGCTAACTTTTCAGCTATGAAAATATATGGTGCAGTGGCACTCATATCAGTTGCAGA<br>GTTGTGAAATAACTTTTGTGAATAGGAAAGTTTTCCTGTTTTAGAATGCAGAAATCC<br>TGCAATATAAGATGGCTAAGTTTTTCAGCTATATGAAAATATATGGTGCAGCAGAGT<br>TGTCAATATAAACTTGTGAATAGGGAAGTTTTGGCAAAAAAAAAAAAAAAGAAAAAAA |
| SEQ ID NO:207 | Late | LPZ-157 | GGTGCGATCCTCGTTGTGAAGACGTAGTGATGGAAAGGTCATGTTTGTAGGAGAC<br>ATAATTATAGGAGTTTCTTTATTATAATAACCAAGAAGTCCGATCCTGGGGGCGTTG<br>AGTATATAGTCAGTCTTTGGTAATTTGGTGTGGTGCTGTTTGACCTGCCTTTCCTTT<br>GGAGCAATGATCCTTGAGGATGGAAGAGGTTATGTTGAGGCTCAAGAGATGATTGT<br>TTGAGTTGTGGAAAGCAAAAGGTTTCGAGATGTAGTCAGATAGTAACTTCTATGCTT<br>TTAATAAAATTTAGTCTGTGGGGCATGCCCCTTTTTGCTGGCAAAAAAAAAAAAGAA<br>AAAAAAAAAA |
| SEQ ID NO:208 | Late | LPZ-158 | GGTGCGATCCGTATAGGTAGTTTGGATGATGAACGGGCAAAGAAGGCAAAGGAGT<br>ACAGTGATGGATCCTGTAATTCCTGTTTCAGAAACAGAAAATCTGCAATATAAGGA<br>TGGCTAAGCTTTTCAGCTATGAAAATATATGGTGCAGTGGCACTCATATCAGTTGCA<br>GAGTTGTGAATATAACTTTTGTGAATAGGAAAGTTTTCCTGTTTTAGAATGCAGAAA<br>TCCTGCAATATAAGGATGGCTAAGTTTTTCAGCTATATGAAAATATATGGTGCAGCA<br>GAGTTGGAAAAAAAAAAAAAAAAAAAAAAAAAAA |
| SEQ ID NO:209 | Middle | LPZ-162 | GGTGCGATCCCAGGAGAATATTAGTTTCATGTGTTGCTATCATTTTCTTCAATATGC<br>AGGGCAACCATTTGAATGAACTATTCCTTTCGAATTTCAAAAACTTAATAGGCTAA<br>CTTATCTATCTGGAGCCGATTTTCATTGACGAGTAACCTGTAAGCTGGCCAGCAAA<br>AGCCAACAGATGTTCAGCTTGTTGGAACCAGTTGAAGATTGTAATAGAGATGGTGA<br>ATAATCGCGGACGGCTCGGCCAATGGAATATTTGTTGCATCATCATCAAGGGGGTA<br>TGAATTCCAAAGAACTTGTTGATTGAAATTCCCAAGCAAAATTCTGTGAAATGAAAA<br>ATTTATTGAGACCATTGGGCAAAAAAAAAAAAAAAATAAAAAAAAAAAAAA |
| SEQ ID NO:210 | All | LPZ-165 | GGTGCGATCCGACTGTGATATGTGACTGGTGAACGAGAGATCCTTCTTATGAATTA<br>ATCTGGTATCTTTATGCGAAAGCTTCTAGGGTTGCTACATGCTTCCATTCTAATATC<br>AGTCTCTGTGATATCAGAGGCCTTCAAATATTGAACAGTTTTCTTTAGAATTCCAAA<br>CTGGGAATTTTTATTGTATAGCCATGTTTTCACGGATTGTCTGCAAGAAGGCTCTTT<br>GGCAAAAAAAAAAAA |
| SEQ ID NO:211 | M,L | LPZ-166 | TTTTTTATTTTTTTTTTTCCAACGAGATCACTGTCATTGTTCAATAACTATATGCCA<br>AAGAGCCTTCTTGCAGACAATCCGTGAAAACATGGCTATACAATAAAAATTCCCAGT<br>TTGGAATTCTAAAGAAAACTGTTCAATATTTGAAGGCCTCTGATATCCCAGAGACTG<br>ATATTAGATGGAAATTCATACAATGAGGAGAGCATGTAGCAACACTAGAAGCTTT<br>GGCATAAAGACACCAGATAAATTCATAAGAACTAAATCCATAAGAAGGATCTCTCGT<br>TCACCAGTCACATATCATACTCGGATCGCACC |
| SEQ ID NO:212 | Middle | LPZ-167 | GGTGCGATCCGACTGTGATATGTGGCTGGTGAACGAGAGATCCTTCTTATGAATTA<br>ATCTGGTATCTTTATGCGAAAGCTTTTAGGGTTGCTACATGCTCTCCTCTTTTGTAT<br>GAATTTCCATTCTAATATCAGTCTCTGTGATATCAGAGGCCTTCAAATATTGAACAG<br>TTTTATTTAGAATTCCAAACTGGGAATTTATTGTATAGCAATGTTTTCACGGATTGTC<br>TGCAAGAAGGCTCTTTGGAAAAAAAAAAAAATAAAAAAAAAAA |

TABLE I-continued

| cDNA | Embryo Phase | Clone | Nucleotide Sequence |
|---|---|---|---|
| SEQ ID NO:213 | Middle | LPZ-169 | TCCCAAAGGCAATTATACATGGATCGCACC |
| SEQ ID NO:214 | All | LPZ-170 | GGTGCGATCCCCACTGCAGAAAGATGAGCCAGTACCCTGAAATTTTGCTGTTGTCCATGCCTGGGTCACGGAGGAAAGAACGGCACGGTGCAATATGATTTTGCTACATACAAGTTCCAAGAGTGGATGCAGACAGTGCTGGCCATGGCTGATTATTTGCAGGTGACTAATGCTCTTTTGGTTATCCTTACCATCATCATCTTCCTGCCATTCTTTTGTACCTCGGTATGGAGACGAACACCCACTTTTCAAAGTTTGCAGAGGAAGCATGTATTCATAACAGGAGGATCAAGCGGCATTGGCCTTGAGATTGCCAAAGAGGCTCTTTCACAGGGTTCTTACGTGACACTGGCGTCAAGAAATCTTTCTAAACTTCGTAGGGCTGTTGAAGAAATCATCCAAGAAGTGGAGTGCGACGGAGACAAGATTAATATCAAGGTAATATACCCTGCAAAATGTTGTCTGGAATACAATCCAAAACCAATTTAGCAATTAACCCATTGGCAAAAAAAAAAAA |
| SEQ ID NO:215 | All | LPZ-171 | GGTGCGATCCAAGTGCGGTATTCTTCCTTTGGCAGTTCTCTGAACTGTTGAGAGAATTTGAGTAGGATAACGACAATAATTACTATGCTCAGAAGCCCAGACAACACGAATAGACTCCCTTCCGTGCGTCGCCTTCCAGAGGACGCAGCAGCTAAAATCTCGGCCTGACTCACCACATATATATTTAATAGCTTGTATATGCCATATGAACTGTTAGCATGATCTCCCTCTAACTGCGAATTGTGTTGCTGTAAACTAATCCCAAAGGATGTTTACTCTGTTGCTTTTCCAACTGCTGATGGATTTCGCTCATACAATGACCCGAGAGCACCATAAACCTACCCAGCGTTGTGGCCTATGACCCATAGCTTTTTGTTCGCACAGCAATTGAAGACCGGCTACAGGAGATGACTAATGCACTTCCGAGAAGGTTTCACCGCGAATGACAGGGAAGGACAAGGCAGAGCAGCAGGCCAAGACAGCTTTAGTCGCAGAAGTTCAAGCAGATCTAGATTCATAGTAAATGGAAGTTCTACACTAGTTACAAATTTAAAAACGTACCTGCATGGACTACACGGTTTATTTACGAGTGCCACTTGTCTCATTGTTTTCCATCAGATGTCTGCTGGATTGTGGTAGTGTGTTCTACCGTATCGGTGCGGGTTTTGTATATTGTGCGTCGACAGAGTGACAGGTGGTGATTTTACTGGCAAAAAAAAAAAACAAAAAAAAAA |
| SEQ ID NO:216 | Late | LPZ-172 | GGTGCGATCCTAGTACAGGCGTTTGGAACAGAGTGGAGAATATGTGGAGTATTGGGGGATGCGCCCGGTCGTGTGTTGCTGCGTTTGGGAATTTGTATTTCTTCCATAGGCAACAAGTGATGTCTTATAATAGTAAAGAGAATGTTTGGGAAGTGGTGGCATCTCTTCCTGGAGACATGAATATTGTTACTTTGCGCAACAGTGTGGTGTGACAAGATATTTGTGAGCGGTTGTGCTTGCAGTGGCGGCGATCAGGTGTGTTACATGCTGGACAAATCTTGGGCGTGGGCTCCTATTGAGAGGTCACATGAGTTTGAGGGTTTTGCTCAGTCTGCAATAACTGTAGAGATATGAGCAAATTCTGTTGGGTTCACTTAATTTTGGGATTATTATAGTGCAGAGGGGAGCCGGGAAGTTTCAGTGTACAGTGATGGGCACCACATGTTGCCAGCATTGGGGGTGCCCTGTGAATATGATTTCTATAAGTCCGGATTTTAAATATCTAGGCCATCTATCTCATCCAGCCTCTGATTGTGTCTGTACTAAATATATCCTGTATATTCGTGATCCCTGGTTTTGAAGTGAGCAAGTTTTAGTGGAAGAGGATTTTTATTAAATATATATAAAGTTTCTGTATTCAGGGTTTTGGCAAAAAAAAAAAAAA |
| SEQ ID NO:217 | Middle | LPZ-173 | GGTGCAATCCGCCATAAGAGAGGCATACAGGAAAAAGAAGTACCTGCCTCTTGATTTGCGTCCCAAGAAGACTCGTGCTATCAGGTGACGCCTTACCAAGCATCAGGCATCATTGAAGACTGAGAGACAGAAAAAGAAAGAGATGTATTTTCCAATGAGAAAGTATGCAGTCAAGGTGTAAAGCCATAGGATTTGAGCTTTCATGCAATTTTTTTGTTACTTGCGGGATGATATTGCCTATTATATTTCCGTCCACGTTTTTGGCAAATTCCGATTTGCATCAGAATTCAAGTTATGATAGGTGTTCTTTCGCTTTTGAGCAGTTGATATTGTTTATCTTTATTTCTCTTGAATTGCGAACATATTCTAATGCAATGAGTGGATTATTATATTGTGGCAAAAAAAAAAAAAAAAAAAAAAAA |
| SEQ ID NO:218 | Middle | LPZ-174 | GCGGACGCCTCAGGATAGCGTTAGGGTTGCCTTAGGATAGCGTTAGCTCTGCCTTCTAAGGTTGCCGTCTTATCCTCCAGCGTCTAGGGCTTCCACTCCTAGGATTTCTCTTCCACTAAAACCCAAGACAAGTGGAGAGAAATCAAGATAGAAGTGTGTGTGAAATGACTCTTAAGTCATCTCCTTTTAGACTAAAACATTGAGCACATGTGGGGTTTATTTGGTTGCTGGCCGTCGTT |
| SEQ ID NO:219 | Middle | LPZ-175 | GGTGCGATCCTGAAACAACATATTCCCGATGGCTCTTCCGAAGGAACCATTGCTCTACTGTGTGGCCCTCCCCCCATGATCCAAGATGCCTGCCTACCTAACCTGGCCAAAATGAATTATGACATTCAGAATTCGTGTTTTCAGTTCTAATTACACCCTTCTGGTTAATCAAATTGGGACATCCCCTCCCACATCCTGTTATTAATTAAGCCATAGTCTAGTGTATAAAATCTGTTGATGTGTACAGCATCAAGTTAATTTCCTCCTTTTCTGTCAAAAAAAAAAAAAAATAAAAAAAAAAAA |
| SEQ ID NO:220 | Late | LPZ-177 | GGTGCGATCCGATCCTAAGCGGGTGCATATATATAATGACAAGCTGTAGTAACTAACTCTTGTCATGAGGCCATTGCTAACATAGCCTGTCCAATGCACATAGCAGTCAAAAAAAGCAAATAGCCGCCATGTTCCCATACACGAAGTAAGTACCCTCCCTATTGAGTCACCTTACCCGCCGAGAGAGATCCCAATTCCATGTATTCGGTTAAGTAAGCCCTGCCAGCTATGTCCCACCCATGAAAGAAAGTACTGATCCGAGTGGATCGCACC |
| SEQ ID NO:221 | Late | LPZ-179 | GGTGCGATCCAAACTGTGGTTATCGGTGGAGAGATTAAGCAATTTATTGGAGTAGCAAGTACGCTGAATTAAGGGGGTCCATATTCAAGCAAAGGTTCCTTTGGATGACTATGTGTTCTGGAAGTGTTTATGGATCAATCATCTCATAAATTTTGGTAATATATAACAGAAGATTATGGCATCCAGTTAGGATGGTAGTTTCATTGAGGTATAGTAAAAACTACACTAAGTCTTGTGTTGCCACCCACTTTTGAGAGAGGTCAGGAGGTCTCTTTGTGAATCATTGATAACTTTATGAGTGGTACCTAATGAAATATTTGCATCTTGAATATATACTCAATTGATCTTACTTGTGGATCGCACC |
| SEQ ID NO:222 | Late | LPZ-181 | CAATCTGTCTGCAATTGATATTATTGCATCCAGTAAACCAGATACACATTCACCACAACATTAGAGACTCTAGAAGTTCCTTTGGCGACAGGCAAAACTCATGATTACAGATAATTGGAGTTTCCTCTAACCAGAGTCAAACGATCTAAAGGGATTTGTCTAGTCCTCCATTCCCTCATTCAATGAGGCGATGGCTTATGCCGTGACAACAGTTTCTATAGTTGCATGCGCTCCTCTTGATCCCACAACATTTTTGGTGTTCTCTGCATCTTCTTCCTCCCATATCTCTGGCAGGGCTTCTCTAATGTTGTGAATACTTGCAAGGGCAAAATCTGCTCCCTCTGTTCGGATCGCACC |

TABLE I-continued

| cDNA | Embryo Phase | Clone | Nucleotide Sequence |
|---|---|---|---|
| SEQ ID NO:223 | Late | LPZ-182 | GGTGCGATCCTCTCAGTTACGAGCTCAATTTCGACCAGGGGTCTCGGCAAATTGAGGATCATGAGAAGCAGGGTATGCCCTTGAATGCCCTGAAGCCAGGGGAGTCTCAGGGCAATCACGAATGAAACCTGACAAACCCTAAGAAAACCCCTAGAGCGTGCCCTGCAGAAAGGGAATTCTTTTTGAGGCCGGCGGTCTTTCTGTCGTCTTCTCGCAGCCGTA |
| SEQ ID NO:224 | Late | LPZ-186 | GGTGCGATCCAGCAAGAGAACGAAAAAGGTATGAGAATCTATGAAATATTTGTACATCACTGTATTCATATGAGGGCCTTTTTTTACAATGCGGTAGGGTTGTTTGGAGAATTAGAACCTGATTAAAATGTAGATGGATTCAAGCTTTTAGTGAAATGAGGCTCGGAACGCAAGTATGCTGTCCACTTTGAGACTCATTCTTCTATAGTATCTGAAGCCAAAGCC |
| SEQ ID NO:225 | Middle | LPZ-189 | GGTGCGATCCCATGGGATAGTTGCAAAACACACAAATTTGTTGTGAAAGAAGAGAGACACGCACAGACAACCATATGATCTTTTTTTTTTTTTTTTTTTTTTTTTTTTTTTTTTTTTTTTTTTTTTCACAACTCTGCTGCACCATATATTTCATATAGCTGAAAAACTTAGCCATCCTTATATTGGAGGATTTCCGCATTCTAAAACAGGAAAACTTTCCTATTCACAAAAGTTATATTCACAACTCTGCAACTGATATGAGTGCCACTGCACCATATATTTTCATAGCTGAAAAGCTTAGCCAGCCTTATATTGCAGATTTTGTGTTTTCTGAAACAGGAATTACAGGATCCATCACTGTACTCCTTTGCCTTCCTTGCCCGTTCATCATCCAAACTACTATACGGATCGCACCA |
| SEQ ID NO:226 | Late | LPZ-194 | GGTGCGATCCTGCGAGAGCCGAGGGTTCATTTTCCTTTCGACAACGACGTTCAGTGGCGACCAGAGTTTCCCAATCACTTCAGCGATTCTATTCCTTCGTTGTAATAAAGCTTAAGGAATCCATGCTTTATTCCTTGGAAGGTTTGAATATTTATATTTGTTGGCATTAATGCTATATACATCTATACTAATTTTGGGTTGTTCTAAACTTGTTTTGAATAACTTAAAT |
| SEQ ID NO:227 | All | LPZ-195 | GGTGCGATCCATGGCAAAGAGCTCGTTCAAGCACGATCATCCTCCAGAGAGAAGACAAGCTGAAGCTTCTCGGATTCGAGAAAAGTATCCGGACAGGATTCCGGTTATTGTGGAGAAGGCTGAGAGAAGTGAGATACCTGATATTGATAAAAAGAAATATTTAGTCCCAGCAGATTTGACTGTTGGGCAATTTGTTTATGTTGTCCGAAAAAAAAAAAA |
| SEQ ID NO:228 | Middle | LPZ-196 | GGTGCGATCCCCTGTATTCTTGAAAGGGTTATAACGGAAGATAGCATTTTGCTCAGATTGTAGACAGTCTGCATGATTTGTCAATACTACTATTTCGCATTATTTGTTAATACTACTAATCCTTGTACTCATCTAGACTATTTAATTATTAAATTCTACAGTTTCTTTCTCCTAGATGGCAAACAATATGAATAAAATGCCAATAGTTTTGGAACTACTCCATTAAGAGCTTTAGATGATTATCATTCATCATTTGCCTGTTTTGAATCGTAAATGAATGTGTCACGGTCTTCTTTTCTGTTAGTCTCTATGCTTTCATCAGAAGAGTCTAAGCCAGTTACTGGAAGCTATTTGTCATCTCTTTAAACATTGTTTCCGTGCCAAAAAAAAAAAAAAAAAAAAAA |
| SEQ ID NO:229 | Late | LPZ-197 | GGCAGAACTTCCAAAGTCTAGTATTTGATTAACTAATATGATGAAGACACTCAGTCTATAACATGACGCCAGAAATCAGACCATATGCATGATAACTAGCACGATTAAAATACAATTCGCAACCTTTAATACACTAAAAACGTTTACTGTATAGTCCACTCAGAACATTTCGATAGTATTGTCAGATCGACTTATTTAGCTCATATTCAGCAATCTGAACTGTACGATGCGGCTCATTCAAGGGCATTTGGGTTTGCCCTTGGCATTCTTCATATCCCGATAGCAAGGACACGCGTTCTTGTTGCCATATGTCCCTGGGGGATCGCACC |
| SEQ ID NO:230 | Early | LPZ-198 | GGTGCGATCCAGATTGGCCAGGCCGGTATTCAGGTCGGCAATGCCTGTTGGGAGCTTTACTGTCTCGAGCACGACATTCAGCCTGATGGACAAATGCCAAGTGACAAGACCGTTGGCGGTGGAGATGATGCATTCAACACATTTTTCAGTGAGACAGGTGCCGGTAAGCATGTTCCTCGT181GCCGTGTTTCTGGATCTGGAGCCAACTGTCATTGATGAAGTTCGAACCGGCACATATCGGCAGCTTTTTCACCCAGAGCAGCTGATCAGTGGCAAAGAAGATGCCGCCAACAACTTTGCTCGTGGCCATTATACCATTGGTAAGGAAATTGTGGATCTGTGCTTGGATCGCACC |
| SEQ ID NO:231 | Late | LPZ-199 | GGTGCGATCCCAGCATTGGATGCATTTCTAGCACAAAGCCATCTTGACTAAAATAGCACTGCGGGCAACTGCAGTCCATAACTTTCAGAGCATTGTTGCTGCCTCAATTGTATACCAATCCATATTCTAAAAATTAGACCTGGAAACCAGTCAGAAATTTAATGTTTTCTTGCAGAAAATGCCCTTTTAGAAAAAGGAGAGAATAACTGCATTCAAGTTCTAACTCCCAGACATAGCCTGGCAACGTCATTCATTCAGTTCGGATCGCACC |
| SEQ ID NO:232 | E,L | LPZ-201 | GGTGCGATCCAGAAAACAGCACAAGCAATCTGTAAGACCAATATTATTATCATCTCTCACTGCTCGTGAACAAAATGCTGGTTCATAGCCATCACGAAGGCTAAGGCTACTATCCAGCCAAACTGATCTGCAACAATAATTTCATAAGCTTAAATAAATAGTCCATCCAGTGGATGGAGCCAGAAAGCCATAGAAACTTCAAATACTTGTGGTATCAATCTCTCCTCTGTTAAGGGAGGTATCAGATCAGAAGCACTAATCAAATGCATACATAAATGCAGTAGACTGCAATAAAACAAAATCTGCAGATAGCAACTGAGCGCTTAACGAACGGAAAAGAGTTTAACTTGATCTATCACAGGATCGCACC |
| SEQ ID NO:233 | Late | LPZ-202 | GAAAATGGGAGCCTCAAATATTCAAAGCCTCATCTCAAGAGTCTCAGATTCGGATTCATTTCATTTGGTTCGTAATAAAATAATGCATCAAATAGTTATTATCCACAAAAATGGGAGAATTATTACAATCTGTCTTCTCAACATAAAGTCATAGCATAGCATAGAACCACACCACAGTCGTCATCATTTGTTTTGTTCACCACCGAAGGGGCTCTTTACAGCGTCCATGAAGCCCTGTGTAGCACCCTTCGCCTTGTCCCCCGCCTGTTGGAAGAAAGAGCCAGTTTGTTCTTTCCCCTCTTGGGCTTTTCCCGTGATGGATCGCACC |
| SEQ ID NO:234 | Late | LPZ-203 | GGTGCGATCCTATTATAGAACCATGACTCTTGTCGATGGGGCATAAACTTCTCATTCTTAGGCGTGCCTACTGTGACTCTTGCCGATGTGGCATAAACTGCTTATTCTTAGTTGTGCCTTCTGTGCAGAACTTGTTGAGTCGGTGGATTACACTGAC |
| SEQ ID NO:235 | Late | LPZ-204 | GGTGCGATCCATTAACTAGATTAACGATAACATTCCTCTGCATCCAATCCAATGCTCATCTAAATCTACTTCTACTTAGATCTCTGCCTCATCTTTCTCCACCTCCTCATCCATTCTGAAATATTAATTTCTGCATAGATTTTGTTAGGGTCTAGTAATCATTTTCATGAATTTAAATCTGTTCTAGTCTCTTATTATTATGCTGCTTATGCTAGCATCAGAACCTGTGTATAATTCATTCATGTATATATTGGATTACACAAATTATACGGATGCCAGAAAAAAAAAAAAAAAAAAAAAAAAAAAAAAAAAAAAAAAAAAAAAAAAAAAAAAAA |
| SEQ ID NO:236 | Late | LPZ-205 | CTTGAAGCTGATATGTTTGAACCCGAAATTTTGTTACCCAACTCCAGTGTACATTGTGTCACTGTCAAAGAGAACATGAGAGCTGCATGCAAGCTTTTGCATGATAGATAGATTACTGATCACCGAACATTTCTTACTCTACTTTCCTCTCCTATCCCCAGTGATTTTTGGGCATTTTCTATACCCTTCGGATCGCACC |

TABLE I-continued

| cDNA | Embryo Phase | Clone | Nucleotide Sequence |
|---|---|---|---|
| SEQ ID NO:237 | Late | LPZ-206 | CTCATGAACAGCAATATGATGCATTCCTCTTATACACATTTCATATATGTTCACCCTT<br>GCCGTCATGGCTACTCTAAGAAGAGCAAAACAGACCCATTGAATCTTTACACGCGC<br>TTGTTTATATGAATACAAATAATTTAGGCGTTTCTTTACACGCCCTTGTTTACATTAA<br>TACAAGTGATTTAGGCGTTGTTACCAGAATAGTGCCACGGATCGCACC |
| SEQ ID NO:238 | All | LPZ-207 | GGTGCGATCCCAAGATAGAAAAGGGAACTATGGTCTCGAGGAGTGTCAGGTGCTA<br>CAGATCACAATATACATAAGGGTCTGATAGTAGTACTCGGCCCAATGTTTGAGGGC<br>TCTAACTAAGGAGGATCAACCGTACCCTTAGCCGTAAAACCCGACTACCCTATCGT<br>ACGGGCGAGTAATCTCTCTGAGTGTTGTTCTCGGTGTATCGTAGCAGCAACACGG<br>CTGACGGTTTATCTATGGTGAGGTTTCAAAGGAGCTAGGGGGCTTCCAATATACCC<br>AGAGGGTACTTGGAAGACAGTTTATACGCGGTTCTGTCTAATGCGCTACTACTCGA<br>AGGGGTACCCACAGGGGTTACAAGAGAGTGCAACAAGCATGACCACCCCTTGTAT<br>TTCTTGCATGTATGCCTCCCCAAATCCGCAGGTTTATGCGCTCATTGACAGATTCC<br>GTGGTTTAAAGATGCCGGAACATGTCTCTAGCCAAAAAAAAAAAAAAAAAAAAAAAA<br>AAAAAAAAAAAAAAAAAAAAAAAAAAAAAAAAAAAAAAAAAAAAAAAAAAAAAA |
| SEQ ID NO:239 | E,L | LPZ-208 | GGTGCGATCCTCCTAACCTGCAATGTCCTTCCTGCAACCTGCAATTATTCAACAGA<br>AATTAGGTT-<br>TATTTTTCTTTTTGTCTTTTCTTCTTTTTTTTTTTTTTTTTTTTTTTTTTTT<br>TTTTTTTTTAAGTAAACGACCATTTCAAACGCCATTTCAAATGCTATGAATTAATGTT<br>GAATTAATGTTAGCATTAAGTCTTAAACATTTTATGTTAAGGCATATATATCGTTCCA<br>ACTACTCTTACAATACACCTGCGGTGTACTCCTGCCACCGCATGTACCACCGTTAC<br>ATGTACGCCTGCCAGCACATCTAAGAGGTGCCAACTCCTTTGAACTCATCGTCGCC<br>ATTTTTGTATGCATATTTGAACTCATCGTCGCCATTTTTGGTATCTTCACATATGGCC<br>AGTGCAGGATCGCACC |
| SEQ ID NO:240 | Late | LPZ-210 | GGTGCGATCCAAGGAGTGGGCGTGCAATGCGTCGAAGATAGCCACCACTGCAGG<br>GGCGTGGCATGCTGCCGTGCTTCCCACAGGGAGATCAACACCTGCACCTCCGCCT<br>CCTTCCGCGGTTACCACGAG |
| SEQ ID NO:241 | Middle | LPZ-211 | GGTGCGATCCAGCCACAGAAAGATTGGTTTACTCGATAATTGAACGGTAGACTTTG<br>TGCAGGTTTAGATTGTGTACATGCTGATCAGTATTGTCTACACCATTTTCAATCTTG<br>TTTAGTTCTATGGTAATTTATGTAACAAATTCAGCGATGTTGGGGAAATTGGTCACA<br>TCAGCTTTGTGCCTATATATTTCAAGTAAATCAGGGGATCCATTAATACTGCTTTTAA<br>AATAATTGGGGCAAAGTTGTGGGATGACTGCTTCAGCGGAATACGTGCTTTTCATA<br>GTGCTGTATGACATTTTGTTGAATATGAATTTTCTTTGTGATACAGTTGCGCGAAAA<br>AAAAAAAA |
| SEQ ID NO:242 | Middle | LPZ-212 | GGTGCGATCCATGCCAAGAGGGTGACCATCATGCCCAAGGACATTCAGCTCGCTC<br>GCCGCATCCGTGGAGAGAGGGCATAAACAGTCAGTCAGATCCAATGGTGTGTTTT<br>CACACCACCATATGTTTCTTTTACTAAATTTGTTAGGTCCCTTCGGTGGGTCTTTTC<br>TTTCGCCCGATTTTAGTATTTTGTTGTTCTTCTGAGTTTCATCATTGCAAGTACAAGA<br>TGCAGAATTGATGGTTATTGGGACTTGGAGACTGGTTATTGCTATGTAGAGTATTTA<br>TATTAGACAGGTTTCACTTGAAGATATAAAATTG |
| SEQ ID NO:243 | Late | LPZ-213 | GGTGCGATCCTCATGTGTTATAACCGAAGTTTGCGGGATTCAGATGGTCAGTATCT<br>TAAATGTCCAACTTTCGGTACGAATGGGGTGCGTTCTGAAACGTGCCACGAAAGAG<br>GTGTTCAGGATCTGTCTGAGGCATCTTTCCGGTATTTTCCACTTCCATGGTATGAG<br>AAACTTTCGTCTTGTTGCAG |
| SEQ ID NO:244 | Late | LPZ-214 | AGGAGACACAACTTTACGAAAAAGTTCAATCTGGAGTCTTCTAAGTTTTTCAGACTC<br>TCTAAATATGAAAAGCGCCGAGTTTCTCCTATACTGGACTCGTTAAAATTTTACAGT<br>AAAGGACCTGTTCTATTACAAACAGGAACGGACCGCTCCTCCTTAGGGATCGCACC |
| SEQ ID NO:245 | Late | LPZ-215 | GGTGCGATCCAGCAAGAGAACGAAAAAGATATGAAGAATCTATGAAATATTTGTAC<br>ATCACTGTATTCATATGAGGGCCTTTTTTTACAATGCGGTAGGGTTGTTTGGAGAAT<br>TAGAACCTGATTAAAATGTAGATGGATTCAAGCTTTTAGTGAAATGAGGCT |
| SEQ ID NO:246 | Late | LPZ-216 | CTCAACATAAAGTCATAGCATAGCACCACACCACAGTCGTCATCATTTGTTTTGTTC<br>ACCACCGAAGGGGCTCTTTACAGCGTCCTTGAAGCCCTGTATAGCACCCTTCGCCT<br>TGTCCCCCGCCTGTTGGAAGAAAGAGCCAGTTTGTTCTTTCCCCTCTTGGGCTTTT<br>CCCGTGATGGATCGCACC |
| SEQ ID NO:247 | Middle | LPZ-217 | GGTGCGATCCGATGGGATAGTTGCAAAACACACAAATTTGTTGTGAAAGAAGAGAG<br>ACACGCACAGACAACCATATGATCTTTTTTTTTTTTTTTTTTTTTTTTTTTTTTTTTT<br>TTTTTCGGGACCAAATATTTTTCAATACAACGCCATGTGACATTTTTGTGCTTCTTGT<br>TTTTGATACATACATTCCAAAAACTGAACACTCGATGGATACGGTGATGATGCAGCT<br>ACAGCCATTGCATTACAGATGTTATTAAATTAAATCAATTTATTATGTCATCACACCA<br>ACCCAAACAATAGCGCTATTATGTCATTAGAATGGTTGCAGTTACAAGATCTGCAAA<br>CAGATCAATGAATCATCATGCCCCTCTATATCTCTTGTCAAACATCAAGATAAACCT<br>AATTTTAGGACTGGACTTCCTCAATCATATCACAATGGCAAACTCAGCCTCATGTCC |
| SEQ ID NO:248 | Late | LPZ-219 | GGTGCGATCCTGGACTGGCCATATGTGAAGATAACAAAAATGGCGACGATGAGTTC<br>AAATATGCATAGAATAAGCGTTCTGTAATTGGAACGGCCATAGGAGTTGGCACCTG<br>TTAGATGTGCTGGCAGGCGTACATGTAACGGTGGTACATGCGGTGGCAGGAGTAC<br>ACCGCAGGTGTATTGTAAGAGTAGTTGGAACGATATATATGCCTTAACATAAAATGT<br>TTAAGACTTAATGCTAACATTAATTCAACATTAATTCATAG |
| SEQ ID NO:249 | E,L | LPZ-220 | GGTGCGATCCCATGGGATAGTTGCAAAACACACAAATTTGTTGTGAAAGAAGAGAG<br>ACACGCACAGACAACCATATGATCTTTTTTTTTTTTTTTTTTTTTTTTTTTTTTTTTT<br>TTTTTTTTTTTTTTTTTTTTTTTTTTTTGTTTTTTTTTTTTTGTGAAGTGACAAAATCTA<br>AACCAAAGATTAAAAGGCTTTGGCTTCAGATACTATAGAAGAATGAGTCTCAAAGTG<br>GACAGCATACTTGCGTTCCGAGCCTCATTTCACTAAAAGCTTGAATCCATCTACATT<br>TTAATCAGGTTCTAATTCTCCAAACAACCCTACCGCATTGTAAAAAAAGGCCCTCAT<br>ATGAATACAGTGATGTACAAATATTTCATAGATTCTCATATCTTTTTCGTTCTCTTGC<br>TGGATCGCACC |

TABLE I-continued

| cDNA | Embryo Phase | Clone | Nucleotide Sequence |
|---|---|---|---|
| SEQ ID NO:250 | Late | LPZ-221 | GGTGCGATCCCAACCAGGTGTCCATGCAATATATGGTGAGCATCAAGTTTGAGGTG GTTGATTGAAAGTTACAAATTGGTGACATCTGAAGTCTCATTCAGTTATGTTTTTGT TATAAAAACCATAACCAATTTTGTATATAAGATCCATAATCAATTTTGGCCAA |
| SEQ ID NO:251 | Late | LPZ-222 | GTTTTCAAGAAGAGCCTGACGGTTTCCTCGGCGGGATGACGGAAACAGGAAGCGG CCGGCCGGTTCCGGACCCTCCGCAGGCGGAGCATAGCATTTTGCCGGAACCACC GCATGTCCTGCACCCAACATCCGCGTCTGACCAGCGGAGGCACATGCACCCAACC CTCCCGGTTCCATTGCACCTCGGGCAGCGCGGCCACCCGCCGGGCATCGGCTTAT CCATCATGGATGGCACC |
| SEQ ID NO:252 | Late | LPZ-223 | TGGGCGAATCATATGGCTTGCATTTTCATTGTAACATGTATACGTTAAGGATTATCA TAATGCCTCCAAAACCTTGTATCTTCGTCCTTGCCACAATACATCCAGGATAACTAA TGGAAGCTTGACATGTCTTCACCAGTAATAATATATCAACTATAATACATGCCATTCT TTTATCAGTTTTGAACAAAATAATCGATTTGCATTCTTGACAAAGAACCTCGCGCAT AAAAACAAATAAATTCTCATAATGCCTCCCAAACCTTGTAGTCTGGGCCCTCAGTCG CCACAATCCATTTAAGAGGAATTTGGGGGTTGATAGTGCCCAGGTCCAATCTTCAT GAAAATTCGTTCATCAATCTTTGCTGCATACACATCTCTCTCTGCTTTCACTATCTG GGATCGCACC |
| SEQ ID NO:253 | Late | LPZ-224 | CCACTATAATGAACATTGATATTACAAATATAATATACATTAATATTACAATTCAAATC ATTGACAATGAGCAGGCACTACTTGCAGTGCTTTGGAATTCAGACTTCTGATTTGCA ATTAATTCTTGTAGACGCTTTTCTGGGAGGGCAGGTTTTCCGCTTCAGAGAAAACC ACGTACAAAACGATATTAAATAAAAATAGACACATACAAAAAATACTTCATTTTTTGC TCTTTCCATTTGGTTTCTTCCTCTATCTCCATTTTGGAGGGCTTAAATGACTTCAAAT TTAAAAGTCAACAACAGAGTGCAGCACATTCTATTAGCTTTGCTGTAAATATCTGAT TGGATCGCACC |
| SEQ ID NO:254 | Middle | LPZ-225 | GGTGCGATCCGCATTAAGAGAAGCATACAAGAAAAAGAAGTACCTGCCTCTTGATT TGCGTCCCAAGAAGACTCGTGCTATCAGGCGACGCCTTACCAAGCATCAGGCATC ATTGAAGACTGAGAGACAGAAAAAGAAAGAGATGTATTTTCCAATGAGAAAGTATG CAGCCAAGGTGTAAAGCACAGGATTTGAGCTTTCATGCAATTTTTTTGTTACTCGCG GGATGATATTGCCTATTATATTTCCGTCCAAGTTTTTGGCAAATTCCTATTTGCATCA GAATTCAAGTTATGATAGGTGTTCTTTCGTTTTTGAGCAGTTGATATTGTTTATCTTT TATTTCTATTATTAATCTTCTAAGTTGGATCGCAC |
| SEQ ID NO:255 | Late | LPZ-226 | AAACAGACAAATATAGAAATATGCATACATAAGTCCCTGCAGAATTGTTTTCCGCAA TGAATTCTGGTTTATGGCAACATTACCTACTTAGTACTAACCCTAAGATTATTTTCAG GTCTGATAAGTGGCATACGTGTATCAATCTTGCATGAGTCTATCCCTGTTTTAATCT TTTGTTGGGATCGCACC |
| SEQ ID NO:256 | Late | LPZ-227 | GTGGAAGCTTCATTGTAAAACACTACTGGTTTTGAGAGAACAAAATATATACGCTAG CCGAGTGGATTATAACAAAATATAGGCTTTATTCTATTGGATCGCACC |
| SEQ ID NO:257 | Late | LPZ-228 | GGTGCGATCCCATACATTAACATAGCCATCACAGCCCCCAGTGGCAAAAGTACCAT AGCTGCAAAAACATTATAAAACTAACATTCCTACAAGGAAATAAAATACAACTAAAAA AGCAAGCAATAGGCATTAGGGGAGGGAGAAGCTAAAACTATTAAGCAACTTACATG GGATGAAAGGCAATTGCGTTTACTGGATAAACAGTATCTCTGCCAGCCTCTGACTT GCGATGACATTTAAAGGCATATTTTTTAAGCTTGACCAGCTTCAGATACATCATAAT ACTCCATAGCCATGCGAGCTTCCACAGAACTAAGGGGCAAAACCTGTTCCATTTGG ATCGCATCA |
| SEQ ID NO:258 | Late | LPZ-231 | GGTGCGATCCAACTGAGAAGGGTGTTTGGTGGAAAGATGACACCAAGTGGGTTCT CTATTCTCCAGAGGATGCAAGAAAAATTCTGAGAGCAAAGAAGAATGGGGACTCAA ATATTACGTTGGGTTCTGTTAAATCTGCCAAGTACCCTTCAGGAAAGCTTTATGCCA TAGACCTGGTGGCCATGAAGCAAACCAATGTAAACACTGGCTTCTCCAGAGATATC AAAATCATCAATTCTTGCCCTACTGATGATCAGGAAGATGTAGAGTCTGATGAAGAA GATGAATTATTCACATTCTCTCGTCCTGTCAAAGTTGAAGTGATTAACCAGAGCAGG AAACCTGATAAGATTGTCAAGATGGTTCCTTCTGTCACTGTAGACCTTGAGAAATTG ACTTCTCAATACCTCCTGGAGGATGAGTGCAATTTGGTTCTAAAGCTTCCCAGGGC TGCAGCTGCCCAATCGGATCGCACC |
| SEQ ID NO:259 | Middle | LPZ-233 | GGTGCGATCCAGCTAATCAAACTTAATGGAGAGCCCTTCCCAGGAAGAGTAAATGG TAGTCACTTGAAGCCCTACACGGGTGGGCTGGCGGTCTGACTAACTGACCAAAAC ATAGTCTTCGCGACCCAACAAGCCAGACAGAGGTGTGGGACTATAAGCACAAGTAC TAGAAGCTAGCATCAAAGTAGAGAATTAAGTTAGATACAGATGATTCAGAAGCAGAA ATGGAGCAGATCCAGACCACGGTAGCATGGTGAGTTACGAACCTTCACGCCACAC CAACGCAATTGGTTAAGACTTCGCACTAGGATCGCACC |
| SEQ ID NO:260 | Late | LPZ-234 | GGTGCATCCATAGTTCCTTTTGCTAAGCGACTACTCTATCTCTTTTGACATTTCTCC AAATATTGGGTCTTTCAGTTCCTTCAAATGCTAGAATCATATCAACATGGGATTTAG TGAGGCCGCAATACTAACCAGGGCATTAAAATAATACATTTCATTGATCCTATTCCC AAAACATTTCCCGCTATCGTACGTTGACTCAGCATATTTAGAGCAATTCTTCTTACA AACCTTAAGAAGGTTGTTCATGATAGTCTTTCCGTCTGCAATATTGGATCGCACC |
| SEQ ID NO:261 | Late | LPZ-235 | GGTGCGATCCCACCCAAGAGTTAAATTCACTTCTCCGCCTTTCTGAGGAAGAGCAC TCTTTGGATGATGAAAAGTGGTCCACTCTTAAAAACCGTATTCGGAACCCTGTTC CGCGGACGGTCGTATGGCGTAACCGGCGCAGACATTTTATCTCCTCACACAATATC AACATTCAAGTCCCCGCTGTTCCCCGTTGCCTTTCTCTGCTCCCGACCGTTAAACA AGAACGACCACAAGAATGAACAACACCGCAACCGAAACCTGACCCTGCACGTTGTC TTCGGTTCGGATCGCACC |
| SEQ ID NO:262 | Late | LPZ-237 | GCGGACGCCTGGCAAAAACAGAGGGTATGCTCAAGCCTTACAGAAATTGAAAAATA AGAGAACGTATGACCATCAATCTCAATCTCAAGAAAAGAAGTTGCAATACGACTCCA ACACTTTTGAAAGTTGGAGGTTTGCTCTTTCTAGCGTTGCAGACATGGTTGGTTTTG AGCTGGAAGCGTGTAACGGGCACTTTACAGTTGCGGGAATTGGAGATTGAGGACC CCCTCTCAAACGTCGATAGGGAGGCTAAGCATCTATAGAGGATTGTGATTGGTCCT TTTCCGCTACATGGAAAGAAAGTCAAACTCAGAAAATTACCAGAAGAATTCTGTCGT CTTCTCGCAGCCGT |

TABLE I-continued

| cDNA | Embryo Phase | Clone | Nucleotide Sequence |
|---|---|---|---|
| SEQ ID NO:263 | Late | LPZ-239 | GACGTTGTAAAACGACGGCCAGTGTAAAGAGCAGCCCCGATGCGCCGAAGCTCGC GAGGGAAAAGCTGCAGAAGATGGGACCGATGACCAAGAATGAGATCATCATGAGC GGCACGCTACTGGTCACGGTGGGTCTTTGGATATTTGGGGGAATGCTGAACGTGG ATGCTGTTACTGCAGCGATCCTTGGTTTGTCTGTCCTACTCTGCACAGGCGTCCGC |
| SEQ ID NO:264 | Late | LPZ-240 | TACGGCTGCGAGAAGACGACAGAAGCAGAACCTGCCAATATAGGATCAATTGAATG TTGTGGGATTGCTGCATGCCCACCTTTCCCAGTTATTACTGCCTTGAAGAACCCAC AGCCAGCGAGTAAGGGCCCGGGTTTCGAACCAATCACAGATGTAGGATAATCGCT TGAAACATGCATAGCGAATATGCCTTCCACATTTTCCAGTGCTCCCTCGTCTATCAT TCTTTTTGATCCTGCACCTGATTCCTCTGCAGGCTGGAAGAGTAATATGACAGTTCC CTGTAACAAATGCTGACGTTGTTGCAAAATCTTTGCACCACCAAGAAGCATGGTAA CATGTGCATCATGTCCACAGGCGTCCGC |
| SEQ ID NO:265 | Middle | LPZ-241 | TACGGCTGCGAGAAGACGACAGAAAAGAGGCAAACCGAGCTCGACACCTCCACTC AGAGCATTTGCAAAAATCCACAACAAATCTGGAGCCAAGGTCTTTCCCTCATTGAAA ACATTTATCGGACACATCAATGTCTGTAGTCTTTCCCATGGTCCATCCAGAGTAATC ACGGGAAGAACAATGCACTTCAGTTCAGAATTTTTGATGACAGCTATCAGCTCCTG ATCCTTTGAACCAGGTATATAATAATCTTGACCTGACTCCTGTTTCAACAGTGTAGA GGTTCTGTCAACCTCAAGCAATGAATCGGCAGAACTTCCATTTGCTGTTTTGTCAAT ACAGGCATTGTTTTTACCAAGACTGTGACGCATCTTCTGTCCTTGTCTATACAGTGC AGTTTGTTCAAGCATAGACTTATGTGCTAGAACATGTCTTCCTTTTAAATTGTAAGA GAAATGTAGGGGTTGACTGCTTTTACTGAGGCGTCCGC |
| SEQ ID NO:266 | Middle | LPZ-242 | ACGGCTGCAGAAGACGACAGAACCCTGGCTGACTACAACATTCAAAAGGAGTCTAC CCTGCATCTGGTGCTCCGTCTAAGAGGAGGCATGCAGATTTTTGTTAAAACCCTTA CAGGCAAAACAATTACTCTGGAAGTGGAAAGCTCGGACACTATTGACAATGTAAAA GCTAAGATCCAGGACAAGGAGGGAATCCCACCTGACCAGGAGAGGTTGATCTTTG CCGGAAAGCAGCTAGAAGATGGTCGTACTCTGGCCGATTACAACATTCAGAAGGA GTCGACCCTTCACCTGGTGCTCCGTCTCCGTGGTGGCTTTTAGGTTGGCTGTTGT GTGTCAATGTAGTCTGGTGATGTTCAGTGGTTTTCCTGCTTAATCCTTTTTATGTAT GCATGTGTTTGTTGTGTTTGTGTTTTGTCTCTATGTTTTTTCTACTTGGTTTGTCGGT CGGTTGAAGCCCGGCTGGTGTCCTGGTAGGCGTCCGC |
| SEQ ID NO:267 | Middle | LPZ-243 | GCGGACGCCTGGACAAACACAGAAGGCGAAGTAAAAGCCAGTCTTACTTTTCATGT AAATACTATCAAACTGCATGGCCGTTCCGCTGGTTGGCAATACCACACCTGCGCCG GTAGTGCCAATGAACACTGCACCGGCAGCTCTTTCAGAAGTTGCAGAGGACTTACC ATTTTAATTTTCACGGCATCCCGTCAAACGGCGGGATGCTTTTAATTTTTTAATCAA AAAAAATATTAATTATGGCACACAATATTGTTTTCAACGAACAGACAGGCAAACACA GTTTCTTTAGTGTAAAAGAAAAAGCATGGCATGGTTTGGGGCAAATTGTACAGGAC TATCCCAACAGTAAAGAAGCATTGCAATTTGCAGGGCTTGATTTTGAAGTTTGCAAA AGGCCCAATATTCACAGGCTTGATAATGGTAATGAGATTATTTCTACCAGTTCATTC TATACTTAGCGTCCTGATACCAACGCCATATTAGGCGTCCGC |
| SEQ ID NO:268 | Late | LPZ-244 | GCGGACGCCTGAACATAGGAGCATTCTTAAGCATATCAGGTATAACCATAAACCTG ACTTTGCTGCCCCGAATAAAGACATGCTCCAATTGGGATACTTTTCCATCCTTGGCA GTGTAAGTGATGCCCTCGAGCTGGCAATTCCAGTTATCTTCGCATTCGATCATGCT ACCCCTGTACAGCTCGCCACTTTTGAGTTCAACTGTCACAACATGCCCGGCTGCTT CATGGAGCAACTTCACAGGAATCCCCAAACTTCTGCTCATTTTTTTGTCACTGCTCA AAAACCCTAAACCCCAGATAAAACCCTCGGTTCTGTGCCTTTTATCCCCGGGTGGC TTATTGTTGCAGTAGTTGGCAACGGCTAGACTTACTCACATTTTGATTTCAATCTTT CTAAGTTTGCCCTTTTGGGTTTTCCTCACAGTAGATCCTATTTTATGTATTTTCTCGT CTTCTCGGCAGCCGTA |
| SEQ ID NO:269 | Late | LPZ-246 | GCGGACGCCTGCAGGAATCGGCCGATTTGCAGTTCGAGGCATAAGCGCATCGAG GTCGCGTTCGATGTAGCAATTAAGCGCGCATGAACCGCCGCTAAGCAAGCCAGTC CCAATCAAAGCACATGCAAAGCGGATGCAATCAAATCTTCCGTTGTAAGCAAGCAC AAATCCAACTGCACATGAGATCACCACCATGAATGCAATTCGAGTGCGAGCTAAAT CCCAAAACGCTGCGAGTGTCCCCTGAAGGCGATTCGTATGTAATATTTGACCGCTG CTCAACACAAGCAGTACTCCAAACACCAGTGCTTCCGCCGTCAATTCTGTCGTCTT CTCGCAGCCGTA |
| SEQ ID NO:270 | Late | LPZ-247 | CTGCGAGAAGACGACAGAACACAGACACAAAATTTGGAAACTACAGAAAAGACCAT GTCATGAAATCTTCATAATTGGGCTTCAGATGCAGAGGGGGTCGGTTTTGGATTAA GCAATGGCTGAAGTGCTTTGACAACAATACTCATGTTAGGACGAAAATCTGCTTCAT ACTGCACACACAATGCCGCAACAGCAGCCATCTTTGCAACAGCCTTTGGAGGATAT TCACTCTTCAACTTGGGATCAACACACTGCTTTACTTTGTCTTCACTCAATCTTGGA GTTGCCCAAGTAACAAGGCTTTGTTGTCCCCTAGGCATTGTATGGTCCACAGGCGT CCGC |
| SEQ ID NO:271 | Late | LPZ-248 | TACGGCTGCGAGAAGACGACAGAAAGAGACAGGCTTGGACTTCGTGGCCTTCTTC CACCACGCATTATTTCTTTTCAGCAGCAATGTGATCGTTTCATGGTTTCTTTTAGAT CCCTGGAGCATAACACTCGAGATGGTTCAGCTGACTTAACAGCTCTGGCAAAATGG CGTATTCTTAACAGATTGCATGACAGAAATGAAACACTATACTACAAGGTTCTTATA GATCACATTGAAGAGTTTGCTCCAATAATCTACACTCCAACTGTAGGATTGGTTTGT CAGAATTATGGTGGGCTGTTCAGGCGTCCGC |
| SEQ ID NO:272 | Early | LPZ-249 | GCGGACGCCTCAATAGTTATGGAAGGGCAGCTGCACTACTTCAGCATGAGTGGAG GCCTAAAAGTTTTGTTAATCTTTCTGGTGAGGTGGACACCAAAGCCCTTCACAACA GTGCAAAGGTGGGGCTATCTCTGGTTTTGAAGCCTTGAAGGATATGCACTATTTGG TACAGATTTAAGCGAAGGTCTGTGCCAAATTTTTATTGGAATTTTTGAGTTTTTCCTT TCAGAATAATTATTTCAATGCCTGTGTTTTCTGTCGTCTTCTCGCAGCCGTA |

TABLE I-continued

| cDNA | Embryo Phase | Clone | Nucleotide Sequence |
|---|---|---|---|
| SEQ ID NO:273 | Late | LPZ-250 | GCGGACGCCTTTTGCCCAATTAACATCCCTGCATCTGCGCATTAAAAATTGATTGCAGACCTGAGGTTTAAGTGGAAGCTTCTTCCACCATCTCTCCCCTGTTTAAGGAAGACCCGAAACCCTAGCCACTGTCTCCTCTGTGACTTAAAATTCCAGTTCACCAACCTTAACTCTGCGTCCGTTAAAATTCTGGGCAAACTGCACTGCCAATTGGTCATCATATCCTCTGAATTTGGCAAAGAAAACATAGGTCATTCTGTCGTCTTCTCGCAGCCGTA |
| SEQ ID NO:274 | ND | LPZ-251 | GCGGACGCCTCGTCAATCCATGGTTGTAAACATGCCTTCAAAACTGTTTCCTTATGTCGCACAATGTCTACATGTTCCTTGAGCGATTTTTCCTGCTGCATTGCGAGCCTCTGTGTAAGTCCCACTATCTGCGCTGTCCCTTTTACTTCATAATACTTCTGTCGTCTTCTCGCAGCCGTA |
| SEQ ID NO:275 | Late | LPZ-255 | TACGGCTGCGAGAAGACGACAGAAAAAACTGTATACGAGTAGGCAGCGAGTCCTGGCAGTATGGGAGATTGAACTCCAATTACATTTAGTTACAAGTAGCATCAACAGTGACTGAGCCAAGAGCTCTACACAGAAAAATAAAATAAAAACTGTATATATTTACAGGAGAAACCCCAATGGCCTCAGGGCCTGAATAAATCAATCGCAGCGGTGGTCGATGTGGCCTTTTCAGGGCTGCAAATCTTGCAAGGGGAAGCCATCATCCTTGTTCCGTATCCTTTTTGAGGGATAGCGAGCCACGCAGCCAAGATTTGAAGCGATTGAATACTTTGGGGTGTCGAGAACGCACCAGAACAATGCCACTCGAGAAATACTACTGTGATTACTGTGACAAACAATTCCAGGATACTCCCTCCGCTAGAAAGCGACATCTACAAGGCGTCCGC |
| SEQ ID NO:276 | Late | LPZ-256 | GCGGACGCCTGTACCGTATTGGAATTCTAAACCCTTCCTTGGTATAGGGTTTTCGCCACCCTTGCGTTCATTTGGTTTTGTATTACGTCCGATTCCTCCGTCTGCGAGCTCTCTGCAACTTGGCAATTTCATTGTGATTTTATCCTATGATGCTTCGTATTTGTTTGAAGCTCGTCCTCCTAGTTCTCTGTGATACCAGTTGGTAGTCTGCAAGTTTCGATGTGGGTTCTTTTAGCTGGTCTGGGGTTTTGTTGCTCTGAGTATGTTGAGCTGCATGCTCGTGGCGGTCTTCACGGCTCCATTTGTTCGGAATCTGTTGTGGAAGTGTCTCGGTCATCTGTGGAACTGTGGAAACCTGGTAAGATTTGTTTATCTGCTTGTGTCTAAACTGTTCTTGAGTTTTCTGTCGTCTTCTCGCAGCCGTA |
| SEQ ID NO:277 | Late | LPZ-257 | GCGGACGCCTGCTGTTGAAGAAGGATGAAGTCATTGTCTGCGGCCCTGTTCAGCATGATTTCGGCATTCTTAATCTGGTCAACCAGTCAGAAGGTGGCGCTGAAGGTGACGAAGAGGCAACCTGGGTAGCTGCACTGGAAACTCAAGCTGCAAGGGGCACCGACCCTCAGACTTCGCGCGATTAACTTCTCCCTCTGGCTAAGTCGATGCCAAGGTCCTTGTTCTGGGTTCTTCTCTCTGTTTCGCATGTTGTTCTTCTCTCTGTTTCATTTGTTTTTCTTCTGTCGTCTCTCGC |
| SEQ ID NO:278 | Late | LPZ-258 | GCGGACGCCTGCACATACAAAGAACGACAAAAACAAAAGCATAAAATCCAATAGATGCAACTATATATCAAGTCAGAAATGATATAACTCATCATTATTACAAAGAACAATAAGAGTGGAACCATAATAATAGTCGTCTATTATTGATAAATAAAGAAGAATACAACCATAGTTCTGTCGTCTTCTCGCAGCCGTA |
| SEQ ID NO:279 | Late | LPZ-260 | GCGGACGCCTGTATAACATGCACCAAGAGACCCAATCAAAGCACATGCAATCTGTATATATAGCAGAATAACAGCCAGGGATTGCACTCTATCGTAATCGCGAAACCACGCACTAATATGTGCCCATGCTGATGATGCACACAGCATGTTCTGTCGTCTTCTCGCAGCCGTA |
| SEQ ID NO:280 | Late | LPZ-261 | GCGGACGCCTGAACTGTATAGAGTTGAAACTTGAGGGAAGGCTTGCTGCCACCAAAGCCTCCCTCCTCTTTCCTTGGCGGTTCGTCACCTCCTTTCGCGTCAGAGCCCCAATTCCCCTCCTGCGCACACCAGCAAACTGCATCGAATGTTTTTTCCACCATTCTGTAAATTCCCTCGGAGTTACCTTGGGGCAGAAGCCGCATTGAAGAGCATTGAATGCTATTCATTATCCCACCGTAAACTACCATTGCAACCTGCCTGTGTATCGACCCGCTGTCCTCTACGCGTGGCTGGCACATGGCGTCGTTAATTGCATGTTGACACCCGTATCCGGGTGTGCTTGTGTGCTCGTCTGCATATCATGTTTTAGGATCTCATAGAAGGTGGACCATTCTGTCGTCTTCT |
| SEQ ID NO:281 | Late | LPZ-264 | GCGGACGCCTCTTACAATGTCTCTTAAAGATTGGAAAGATTGTCTTGTCTGCAACCATAACTTCCGCGTGCTTTCTTATTAATGCAACCCACTGTGATCCTTTCCGCCATTTATCCTTTCGAATGGTTGGAGCCATTTTTGGGTTGTACCGACTAGCTTTTGGGTCTACAAAGCTGTCTACAAAACTCTTTGGAGATGACATTACATAATCATATGTATAGCTGAAGTTGTACAAAGGTACACAACTATCTGAAACCAAAATGAATCTCTCGTTAGCTGGATCCTCGAGTGCTTTCCTAAGTAGAATACGCTCCGCTTCTATCATACTGGCTTCTCCCCAAAGTACCTGTATGCTATCACTAAGCTGCCAGCCGTAACAAAATGTACATTCTGTCGTCTTCTCGCAGCCGTA |
| SEQ ID NO:282 | E,M | LPZ-265 | GCGGACGCCTTGCTAGGAGAGCTCTACGCCATTATTTGAACGATTGAGCCGAAGTTTCACCGTTTAAGGCATTTGTGTCCCAGAGGTTATTGGAGATTAGCAGCTTGGATTTGGCTGCTTCGCTCAGCGCCGTGATTCAGCTTTTGATTGATTCTCTCCAGTTTCATAACCTGTAACGACAATGGCAATGAAGACCTACACATTTGCAGTGGCAGCTGCGTACGCTGTAGTCCTGATGTTCGCTCTCTTTGGCATCGCAAAGGCTGCTGATGCACCGTCTCCCAGCCCCGTTACTGGCGCGGGTTCCATGGACTTCGTTCCTTCTGTCGTCTTCTCGCAGCGGTA |
| SEQ ID NO:283 | Middle | LPZ-266 | GCGGACGCCTTATCAGCTGGGGGCATTCATAGGTATGGAAATTCAGATCAACTTCAGTGGACAGTATGTGGATTTAGGCGACCTGTGACAGTTCACGATATCTATTCATTTCTATCCAGAGACAGATTCCCATACTCACCTCCGTCCTTCCCATATATTTTCTGGAAGGCATCATGTCCTCCCAAATTTACTCATTTTGCCTGGCCGTCGTTTTACAA |
| SEQ ID NO:284 | Late | LPZ-268 | GCGGACGCCTGTTGCCACAGAAGAATGAATAATGCTTCAAATTTTGAGACCTCTTCGGAGGAAAATCCTTGTTCTTACTGCCTAACCACTCATGATGATCTGCGTCACGCTGATTATGAGCTGCAATTTAAATTATTTCAGATGAAACATTCCCATATTGAGCTTGCAGACAAGTTGCAGACCCTTCAATTTCAGTTCTGTCGTCTTCTCGCAGCCGTA |
| SEQ ID NO:285 | Middle | LPZ-269 | GACGTTGTAAAACGACGGCCAGGATTAAGGTTCATGAGCTCCGCAACAAGAGCTCAG |
| SEQ ID NO:286 | Late | LPZ-270 | GCGGACGCCTCTAGGAGCCGGCGGAATTCCTGTGAGCTCGAATTTGCCGAGCAGGTTATTGTCCTTCGTCCGCGCTCGCTCACCTTCATATACTTGAATTAGAACCCCAGGCTGATTATCTGAGTAAGTTGAGAAAATCTGCTCCTTCTTGGTTGGAATGGTGGTGTTCCTCGGTATTAATACTGTCATTACACCTCCCGCTGTCTCCAACCCCAGACTTAAT |

TABLE I-continued

| cDNA | Embryo Phase | Clone | Nucleotide Sequence |
|---|---|---|---|
| | | | GGCGTGACATCTAGCAACAGCAGGTCCTGCACCTTCTCGTTGCCTTCGCCGCTGA<br>GAATGGCAGCCTGCACAGCTGCACCATATGCCACGGCTTCGTCTGGGTTAATGCT<br>CTTACAAAGCTCTTTGCCATTGAAGAAATCTTGGAGCAATTGTTGTACTTTGGGGAT<br>ACGAGTCGAACCCCCGACCAAGACGACATCATCTATTTGGCTCTTGTCCATCTTAG<br>CATGTTCGCATACATTTCTCGACAGGCTCCATACTTCTCCTGAAAAGATCCATGTTG<br>AGTTCCTCGAAGCGAGCTCGCGTAATTGTGGCGTAAAAATCAATTCCTTCATATAG<br>AGAATCAATCTCAATCGTTGTCTGTGTAGTAGAAGACAGCGTTCTTTTTGCCCTCTC<br>ACATGCTGTTCTCAGCCTGCGAAGAGCTCTGGCATTCCCGCTGATGTCTTTTCTGT<br>GCTTTCTTTTGAATTCCTGCACAAAGTGATTCACCATTCTGTCGTCTTCTCGCAGCC<br>GTA |
| SEQ ID NO:287 | Late | LPZ-271 | TAGCCATCGCCATTTCTATAATCTTAGGATCCTTGCTGAACGATAAGCCCATAAAAT<br>TGATGCACTGCCTCGCTATCCCTGGCCGTCGTTTTACAACGTC |
| SEQ ID NO:288 | Middle | LPZ-272 | GACGTTGTAAAACGACGGCCAGGAAATTACAGCTACCTCTAACTGGTTTGACGGCG<br>TTGCATCTTATGAGCCCGCAAGGGTTCGAATCCTCTGCGGGCCAGATCTGCGATGG<br>AACCCTGGGCGAGTGCAATGATGATGAAGAAGAGTTTGCGATGGATTCTGAAGCG<br>CACGGGAGGCTTCTGAGGAGGATCCGTTACTATATCAGCTACGGAGCATTGGCTG<br>CTAATCGCGTTCCTTGCCGACCTCGGTCTGGGAGGTCTTATTACACTCGGAATTGT<br>TACGGCGCAACAGGCCCCGTCAGACCTTACCACAGAAGCTGCACTGCTATCACTC<br>GTTGCAGGCGTCCGC |
| SEQ ID NO:289 | Middle | LPZ-273 | GCGGACGCCTGGGAAGCAATGGATGGGTGGCTAGACGCCATCCGTCTTGTGTATA<br>CTATTTTTGCACGCGGAAAGAGTGATGTCCTGGCCGTCGTTTTACAACGTC |
| SEQ ID NO:290 | Late | LPZ-274 | GACGTTGTAAAACGACGGCCAGATTCAAAAGAAAAAATCCTCACTTCTTGGCTCCG<br>TTTGCGGTCCCGCCGAAGCTCCTCTGCAACCCCTCTGCAGCGTACACTGCATCCC<br>GCTCGCGGTGCTGGCTCACCTCGCAGGTCCGCTGACGGTAAATGGTTTCCAATAA<br>AGCTATTTGTCCTCTACCCAAAATCCATCTAGCATTCGTTGTGGATTGACATTCTGC<br>CATTTCTCTGCTTTTCTGGTTGATATGCAAAGATTGAAAGCCCAATTGCAAGCAGTG<br>GTCGTGGATTCACTATAAGGCGTCCGC |
| SEQ ID NO:291 | Late | LPZ-275 | GACGTTGTAAAACGACGGCCAGGAATAAAACAAAGCATCACTGCAAAATTTCAAAC<br>GTGGTAATAACGGCTAGCGAGCTCGACGTGAAGGCAGTGGGGGCCTTGAGGTTGC<br>CTTTTGGCGTTCAAAATTGGCTAGACTACCATAACATAAATATTGATTTCTCAGTGA<br>CATCACTGGTTTGGAGTCATCCACAGCCTGTGCACCAGTACGGCAATTGCCTTTTA<br>CATGAAGCCATCCTTTCACTTTTACTTTTGAGATTCTCAGAACTGAGGGGCTAGGC<br>GTCCGC |
| SEQ ID NO:292 | Middle | LPZ-276 | GACGTTGTAAAACGACGGCCAGCACCTTCCTAGTCCCCTGTTCCATTCTCCTGAAA<br>TAGGAGCAGTTTGACCCAGTCCAGTTTTCAGAATTGAGAATATGAAACAAAGAACCT<br>AAGCATATGAGAGAACATACAAAGACTTTGTATAAACTACTTTTCACAGGATCTCAA<br>CAGCCCTCTGCTGAGATCCATTTGATACAAGGCCCCTTGCATCTCCACCCTCTCCC<br>TTATCACCTCCACTAGAAAGATGATGGAAAGCAGACACATGGAAATGTTGCTGCAG<br>GCGTCCGC |
| SEQ ID NO:293 | Middle | LPZ-277 | GACGTTGTAAAACGACGGCCAGTTAGGTTGTATATTGATTGATGACTCTTTGACTCC<br>ATTTATGAAAACATCTTTGTTCTCGAGATTTAATCAGTATTAAGCTTTCAGAGTGAAG<br>TTCAGTTTGATCTGCATAAACCTGATCCACCATATCTACATCACATCTAAAATTACTA<br>AAATGTGAGGAGATGGAATTTGTTTCTTGAGAATCCCTATTCCTCATCGACACTGTT<br>TACTGGATCAGATCCAATCAAACTCTTGAGAAGTAATCTCTGGAAAGAAATTAAAAA<br>GTCTTTACCTGAATTATCTCGATATCAGAAGCAGAAATTATGATACATAGACTTCTTA<br>ATAATGAAGAGTCATTTTGCCAACGTTGTCTTTGCCACCCCACCAATCCCCATGATC<br>CCAAAGATCTGAGGTTTCCATCTCTATGTGGCTGTGATAACACTGGATTTTTCAAAA<br>ATCTTCTACTTTCGCATCCAAACCTTTTTGGGATATTT |
| SEQ ID NO:294 | Late | LPZ-278 | GACGTTGTAAAACGACGGCCAGGGGATGGGAGATACAGAAAGATTCCGGATAAA<br>AGGGAGCAATGAACGGCTGGTTAAAGCGTAGTCCACCACACTAGCCCCACCTCCA<br>TGAGGCCTACACGTGAAGAAGCAGGATTCTGGGAAGCGCGAGAGGCCGTTCAAGA<br>TTATCAGCTCATGTGATTCGCCCAACTGCAAAAGATGTCTACCGTAGGCTGTGATG<br>GGGCCCAAGGCGTCCGC |
| SEQ ID NO:295 | Late | LPZ-279 | GCGGACGCCTATCAGATGGGTGAGTTGACCGACATTTATCGTCCGATAAATGTTTG<br>AGGCTGATGTCATGGCAATCCACGTGTCTGCACCATATTTCATCGGAGCCCCTCGT<br>CGGAATATTCCATCGCCGGAGAGCTGGCGCGATAGGTTTCAGGCGGCCGGTTTCT<br>GGTTTGCAGCTGTGGCTTCCCGCGCGCCTTAACTGTTGGCCCGCGCGCACAGGG<br>GAAATTACAAATTTCAACATATCCAATACCATCATATAACCCAACAACACTAGCAACA<br>GATCCTGTTCTGTGCCATCGTCCAACTCTTGA |
| SEQ ID NO:296 | Late | LPZ-280 | GCGGACGCCTTAATTCGACTACAAAGATACTGAAGCCAATGATGACAGGTTGTGCC<br>ACTTTCCCAGCTGATAAAGACAGCTCTGAAATTGATAGAGCCAGAACTCCAGCTGC<br>AATGCTCCCCAGAGCCTGGTTGAAGCGCTTGCTAAAGGTGGCACTTTATAGACCGA<br>CCCAAAACCTCCCTGGCCGTCGTTTTACAACGTC |
| SEQ ID NO:297 | Early | LPZ-281 | GCGGACGCCTACTGGAAACCCGGTCCACCGAAGGCTGAAATTGTCCTGCTTTGTA<br>TACCGAATGGCAGGAAGGTTGTCGAGCATCAGGTTCACCTGGTAAAGATTATCGAT<br>CCTATGCTTCAATACCTTCAGCTGCTCTGCCCCAAGGACAGTAGTATTGCACAGGT<br>AAATTTCAGATTCATTGACATTCATCCGGAAGCGATATGGTGAGTTCTCGATCCTGT<br>CCCCCATGAGGAGCTCCCCAAGATTTTCTGCCATGTCCTTCACACCATCCAAGGGC<br>TTGCAGAAGGGCAGGCTGTAATAGCTGTAGGGAAGCTCTGTCTCGACTGAGGTAA<br>GGGAATTGACGTTCACCCATAAATCTGACCCCTGGGAGAATATGATGTGAGGAATA<br>CAGTGCCCAGTAAATATAACTCCGCATTATACGTTTGTGTGTGCCTTCCCCAATATT<br>GCCCCAACATAATCAAAACCCACAATCCCAAATCCTGGACCGTCGTTTTTACAACTG<br>TC |
| SEQ ID NO:298 | Early | LPZ-282 | GCGGACGCCTTGTCAGGACCAAATGTGTAAGAAACACCTCTGTCATTCGAGCCCCA<br>TCCTTGAATTGCATTGCAGGGGTCTGACCAAAGAAGATCACATAACAACCCTGTAT<br>CTGGCACATCTGTAGGTCGAGGTATATTCTTTATTTGTTCCAAATTGGTCAGTTCAG |

TABLE I-continued

| cDNA | Embryo Phase | Clone | Nucleotide Sequence |
|---|---|---|---|
| | | | GCGAAAGACCACCATGCATGCATAGGATCTTTTCATCTATAAGTGCAGCAACAGGCAGGCAGTTGAAACAGTCTGTAAAAAGTTTCCATAGTCTTACATTGAATCTGCGCTTGCACTCATCATAGAAACCATATATGCGATTTATTGAGGCACATTCATGATTTCCCCTCAGAAGGAAAAAGTTCTCTGGGTATTTAATTTTGTAAGCAAGGAGGAGGCATATTGTCTCTAGGCTTTGTTTGCCCCGGTCCACATAATCTCCCAAGAAATAAGTAATTTGATTCTGGTGGGAAGCCACCATATTCAAAAAGCCTTAGACAGATCAGAATACCGGCCTGTCGTTTTACAACGTC |
| SEQ ID NO:299 | Early | LPZ-283 | GACGTTGTAAAACGACGGCCAGGAGACGGGAATACCTATTTTTGGGAGGATTATTGGGCTCGGGAATCAGCATATTGATGTGGCTGCAACTCGCATCCTCGATCTTTGGTGGTTCTTCGGCGATTTACACATTTGAGATCTACTTCGGTCTGCTAGTTTTCCTTGGGTATATTATATTTGACACACAGATGATCATCGAGAAAGCGGACCATGGAGACTATGATTATTTAAAACATTCACTGGACCTCTTTATTGACTTCGTTGCTGTATTTGTTCGCCTGATGGTCATAATGGCAAAGAATGCAGACAGTAAATCCAGGGAAGGGAAAAAGAAGAGAAGGGCTTGAACTATGTGAGATACAAAAATATCGAGAATAGAAGGGCTTGAACTAGGGCTTGAAAGCGTCCGC |
| SEQ ID NO:300 | Middle | LPZ-284 | GCGGACGCCTATCAGACAAGGGTTGTTGACCGAACTTTATCGTCTGAAAAGTGCTTGAAGCTGATGTCATGGCAATCCACGTGTCTGCACCATATTTCATCGGAGCCCCTCACACGGAAACAACCTTAAGCCAAAAGGTGGTGCGATGACTTACCGGCCGTTTATGGTTTGCTTCGGTGGTTTTCTGTTGGGTGGTTTCCCGCGCGCGTTAACTGCTGGCCGTCGTTTTACAACGTC |
| SEQ ID NO:301 | Late | LPZ-286 | GACGTTGTAAAACGACGGCCAAGAGGGGGAAACTCCCAAAACACTTTTCCATTTTTCTTCTTTTATTAAACTTCAAAGTATTTTCCAACAGAGTTACAAGGGGCCAACCATGTCCAAATCCATGCATTTACCAAGTACAAAGAATGGTAGTCCTTGGCTTGACCTATCGCACTAGCCAAAAGTGCCAAGTCCACAACTAGGGTGTGCCCAACCTAAGGTTGACACCTTGCCTAGAAAAAACCCCAAACTTGGCACCACAAATAACACAGAAACACAACTCTTGACCTCTGCCAGAAACCAGGCTCTCTTGGGAAAGCCACACCTCTCTCTGTGATATGTCTTATCTCCAATTTCCCTTTTTGTGATGCACTCCCTTGCTTGTGGTTCTGCGATATCACACAAACTTACATTTCTGCGATTTTTGTTTCTTGCTTCTCCAAATCATGCGATCTTATTTTTAACCCTTGAGACCCTTCACACTTTCCATCCATGACGTCACTTCATCGTTTTAGCCAATTCGTCATTTGGGCATGTTGGGCGTTGGGTCTACCCGTATTCCGGTCGTACAGGCCAAATTGAGCATTTTGGTCCAGGTGGGTGCACCCATTCCTGGAGGGCGTTCGGC |
| SEQ ID NO:302 | Late | LPZ-287 | GCGGACGCCTCCACAGAGCTCACACATACAATATACTATGATGCCTCCAGAACTATGGCACTCTGTATGCCGCTTCAATATGGATTAGCCCACACTGCGCCATCCAATTAGGCGAATCAACCTTATAGCACCATCCACAACCTCCAGCGCTCTCTTTTTCACGCTAGATTGGCCAACTACAGGGTTTACAACACTACTCATATACAACTCAACTCGGCTCCTCTGCTCACCACTAAATGACACAGGCTCCAATCGCTAGACAGAGCCACTACACAGGCAGTAATAGCCACTACACAGGCACTAATCTTGGCGTCCTCCACCAGGTTCCAACAACAACCCCAAATTGCATATGCACTCCACAGTGAGCACCAACTAGGTCCACACAATAGGCCACACCAACAACACTCCAAGGACCCTAGATCCTGCCTCACCCAGACACCACTAGGCCTTCCTCACAGCTCACCTAAGTGAGCCAACAACTGGCTGGGCACACAGCTCCCAACTATATGAGCACACAGCCCAACTACAGCTCCACCACACGCACAGCTACACGCACAATGCCTTCTCAAGTTCACAGCCACACCATAACGCAGCACAGTTCTTACAAACATATCTCTCCAGGCGTCCGC |
| SEQ ID NO:303 | Middle | LPZ-288 | GACGTTGTAAAACGACGGCCAGGATAATGGACACGAGAAACCTTTGGATGTGCCTGTAAAGTGCGGGCAATCCTTAAAGCTGTTGAATTTTGTTGCTGTACACGAAGGTGCAGGGTCTTTATGCCACGAAGAATCAAGTACGCTGCATTTGGACTTAATACACCTCCCAAGACATTGTGCAAAGCACGTACTGTGCCAATAACCTTGTTTGAACCACTCAAACTGCCTGCAAGAACATCATTATGACCTGCAATATATTTAGTTACCGAATGCAATACAATATCTGCGCCGAGTGCTAACGCTTTCTGGTTAACAGGCGTCCGC |
| SEQ ID NO:304 | Middle | LPZ-289 | GACGTTGTAAAACGACGGCCAGTCATTATTGACAATAATCCTTTCAGCTTTTTACTGCAACCTTTAAACGGTATACCTTGCGTTTCTTTCACTGGAGCACACTCAGATGATAATCAGCTTTTACAGGTGCTCTTACCTCTGTTGAAGCATCTTGCCACTCAGGAGGACGTGCGCCCTGTGTTGTATGAAAGATTTTACATGCCCGCATGGTTTGAAAAGCGTGGCATTCCAGCATCTGAGTGGCCCTTGTGACTTGGTTTTGATTTTGGATACTCTTTGTCATTTTGGGTCAAGGTAAAGGTGTACGTATCCAAGTGATGCAAGCGTCCGC |
| SEQ ID NO:305 | Middle | LPZ-290 | GCGGACGCCTGATAGCACGAGTCTTCTTGGGACGCAAATCAAGAGGCAGGTACTTCTTTTTCTTGTATGCTTCTCTTAATGCGGATCGCTGGCTCTGAGAAATCACAGTCAGAACCTGAGCTATTGATAGCCTCACGACCTTGATTTTAGAGAGTTTGTTGGGCGCTCCTCCAGTGACCTTTGCAACTCTGAGCAAGGCAAGCTCAGCCTTGAGCTCCTTGACCTGGCTTAACAGCTCGGATTTGCCCTTGTGGCGGACTCAAGGACCTTTAACCTGGGCGTTCGT |
| SEQ ID NO:306 | Late | LPZ-293 | GCGGACGCCTGGTGTCGCTGGGCCAGTTCAAGTATTTTAGCAACAGTGTTCACACTTATTCCCTGTGATATTCTTGACTCACACAACCACCTTAACTGACGCAGACCATATCGATCTGCTGCTGTAAGCAAATGTTCGATCATTGTCTCAGGTGTCAAAAAGCAAGGGGATGGATCAGAAAGCTCTTCTAAATCTGCATGCTCCTCTAAATCTGGAAGGGTATCTTTGTAAATAAAGTGTAACATAGCCTTAAACACCTCTGGCCGTCGTT |
| SEQ ID NO:307 | Late | LPZ-294 | GACGTTGTAAAACGACGGCCAGAGGTGTTTAAGGCTATGTTACACTTTATTTACAAAGATACCCTTCCAGATTTAAAGGAGCATGCAAATTTAAGAAAAACTTTCCTGATTCAACCCCCTGCCTTTTGGCACCCTGAAGATGGTTCAACAATTTGCTAACGGAACCAATTCAAAAGGGCCGCCTCCATTTAAGGTGTTGTGTTAGTCCAGAATATCACAAGGAATAAGTGTTAACACCGGTGCCAAAATACCTGAACTGGACCAACGACACCAAGCGTTCGCC |
| SEQ ID NO:308 | Middle | LPZ-295 | GCGGACGCCTTGTAATCCAGGGCCTTGAATATTGTAAGAGAAGATCGAGAAATAATAGTTTTCTTATTATCAGGAATCACAGCTTGAAGAAGGCAGACCATGGACTCCCACTGGCTTCGTGATATTGAGTCCCCAACAAACATTAGTCGTTTTCCCCTCAATCTCCACA |

TABLE I-continued

| cDNA | Embryo Phase | Clone | Nucleotide Sequence |
|---|---|---|---|
| | | | GCAAGTCTCTGGCATTGAATCTGCGAAAGGAACACCCGAGTGGCTTCCACCTCCATTTCTCGTAATCAGAATCTGGCCGTCGTTTAACAA |
| SEQ ID NO:309 | Late | LPZ-297 | GACGTTGTAAAACGACGGCCAGCAGAAGACCAGTGCAGTATGCTGCAGCATAGTTTGTAAGCCCTACTTCGAGTCCATAACGAGGCAACTCCCTAGAATAAGCAGCCGACATAACAACATCTCCCGCAAGAGTTGCATAAATGATCTGTGCCACCACATCCTTGTTGCTGAATCTAACGACCAATCGGTATTTGGGTGTGTTGTACTTGTTCTTATCTTGGTTAATCAGGCGTCCGC |
| SEQ ID NO:310 | Late | LPZ-299 | GACGTTGTAAAACGACGGCCAGCATCCATTGCAGAAATTTTGGGGGCTATATTTAGCAACAGATATCACAGCTGTAAGTTCAAAGTTGGACCCTTCTTCTTCGACATCTTTTCCAGCTGTGCAATAAACTGAACACTGTCCTTTTGGATAAGCTTCCTCAACATATTTAGAAAGTTCAACATCCAAGACATTGCGGTACTCCTCAACATATATGGATGCAAGTTCATCATCTGCAGCTGGTCTCACCGCTGTACAAACTTGTTTAACATGGTTGACAGTTGCAACTTGAGCAGTCCGTGGATCCAAATAATGAGTTCCGTCAAGCTCACTGAACTCAGTCACAATCACCTGGCCACTTTGATTGGGCATCTCGAGGGATATCATGTGAGACTTGTTGTGGATGGGGAAAGCGTCCGC |
| SEQ ID NO:311 | Early | LPZ-300 | GCGGACGCCTGCATAAACATCGCTACCCTGGGGATGATTAATAATAGTACCAGGGTTAGGATTTTCTTCATCTTGAGCGATATCATCATACATAAAGACCACAATGTTTTCCTCTTTCAAACCGCCTTTCCTCAGAATTTGGTAGGCATGGCAGATATCAGCCTGATGCCTGTAGTTCCAATAACCGGAAGAACCAGCCAACAGAATAGCCCACTGAGTACCGATCGTATCACTATCATCAACGATATGATCGGTGGGCATTTTCAGTACTGAATCCCAACCCCTTCTGGCCGTCGTTTTACAACGTC |
| SEQ ID NO:312 | Middle | LPZ-301 | GCGGACGCCTAGACTGGGCATACCAACTACCTTCCTCATGCCAGGCCATGGGCCACCTACCTGGTACTTAGGCATAACACCTTACTTACGAGCATGCCAGGCTCAGTCAGATAGGCATGCATCCCACCCACCTAGCTATGACCCAATCCTTATAAACACTAGATATTCTCCCTGGCCGTCGTT |
| SEQ ID NO:313 | Late | LPZ-303 | GCGGACGCCTAGACAATCATTAACTGAAGATCTGTAAGCCATGACAAGACGAATAAAACGAAGCAGGGCGCAACCAGCGTGAATATTGACGCCTTAATTTCATTCAACTGGGTTGCGGATTCTTTATTCCTCAACAAGTGTTCGATAGCTTCACATACGCAAGGCCCCTTTTACTCTCACCTTCATGGTTTAATGCTGTAACCGTCGAAGGTTGATGAAAGGACTTGGATGATGATGTTGCCAAAAAAAAAAAAA |
| SEQ ID NO:314 | Middle | LPZ-304 | GCGGACGCCTGCTCAACACCTGTTATAGTCATTTCTTGTTTCCTTTTCTCAATTTTCTCTTTCGAATGACCGCATTGAAATTCAGGCTGCCCAACGCGTTTTTGTTTTCACAATTAATTTTTGAATCATACGCGAAGATCATGATGAGAATGGTTGTGGAAAAAAACTGTTTGTAAATATTTAG |
| SEQ ID NO:315 | Middle | LPZ-306 | ATATCACATTACCATTCAAAAAATAAACATTTTACAAAATACAATTCCATAACAATTTTCTTCCCTGTTCCAACCTCCACAAAAGTAAATGATCGTATAAGAAATTAACTACCAACAAAAATCCCAAAGTTAAAGGAAGACATCCCCAAAAAAGATGTAACTTTCAAAACCGGATGACTTCACTCCTGCCATTGCACCTAGTCATTTACTTCTCAGAGGAGTTTGGCCCTTTCTTCTTTCCAAAAGTAACCACTGCGGTAACAAACCGGCGGTTGTATTGCATTCGCTTGTAGGCGCGGCCTCTAGGCTTCTTCTTCTGTCTTGTTTGGCCACCTTAGGGTCCGC |
| SEQ ID NO:316 | Middle | LPZ-307 | GCGGACGCCTTGGTACAATGGACTTGCAAAAATAAAATGAGTTCTCATTTGTGGGTGAGATGCGGATATTTTATGCATAGGCACTTCATGGAGATGTGGTTTATAAACGCCATCTTAATATCTGTACCTATTACTTTCAAAATATGAAGGCAAGATGGAAAGCTACTCATCTGTTGTGAAGTCAGAATGTTGGTAGCGGTTGGGCTCTGAAAGTAAGAAACTTTTTGATTGGTTTAATTAAATGAGGGAATTTGCCTGGTTTCCCTCTTCCTTCCGAAAAAAAAAAAAAAAA |
| SEQ ID NO:317 | Late | LPZ-308 | GACGTTGTAAAACGACGGCCAGACAATATTGGAAGGGAGAAAGGCGCCAGCAGGGTTGAGGGGAAGAAATGCATAATGACATATATAATGAGATCTATTTGTATACGATATTACGGGTACGATCGATGATTCGAGCTACGATCCCATACGACGCTAAAGCGTAATTACATATATAATAGATGCATTTCAGAATGACTTATCTATTTCATTACGCGATATTATATACGTAATTACGTATATAATTGCAGAGATCTCACCGACCAACCAAATAGTCTTTCATTTCATCCCAGGCGTCCGC |
| SEQ ID NO:318 | Late | LPZ-309 | GCGGACGCCTGTATCACTAGAGGTGAATACTCAGCAAGCAAAACTGAAGGATATTATTGAAAAAGCTGTCAAGGCTAAATTGGGTGTCAATTCCCCATTGATCATGCATGGTTCTACACTTTTGTTTGAGTCCGGTGATGACATTGAGGAAGATGTTGCTGCACATTATGCACAAAACTTAGAGAAGACGTTAGCAGAATTTCCAGTTCCAATCACAAATGGTGTTATTCTTACAGTAGAGGACTACCAGCAAGAGTTCTTATGCAGTATTAATATTAAGCACAGAGATGACTTTGATGAGGAGTCAGGTGGCATTGTACTGTCTGGAGGCGTCCGC |
| SEQ ID NO:319 | Late | LPZ-310 | GCGGACGCCTCCTTGTAGATACCATACATGAGTCTAAGATCAAAATCATACAAGAAGAGCTTCATTCCGGGCCTCACCTTTTCTACAAGCTCCTTTTTGGCTGGTGGAAAGCCAAACACTCTGTATCGGAAACACTCCTGCCTAGTTTCAGAATTACACATAAAAATCAAGCCGGCAAACCTATCTTTGCCACTGCCATCTTCATTGTTTGCGTCCTGGCCGTCGTTTTACAACGTC |
| SEQ ID NO:320 | Late | LPZ-311 | GCGGACGCCTTACTAAAACGACGGCCAGATGTGTAATGGGGAAAATGTGTCATGATAGTTGGGTACAAATAACGAGCCACCTGCTCTATGTTTTCGAAGTTTTCTGTTGGATTTGTCCGGGTGAGAGAGCGTTCGTTCGTTGCGCGAGAGGGGCAAAATGCTGAGCGTGGGGAATTGCCATTGCCGCCCCTGGAAGTGCCGCACGAACGCGATCACATTTAAATCACCATTTACTTCATCATCACCATGGTTAAATGCAGTCCCTGCTCCTTCAAACAGGAACTTCAGATCCTTCAAGCTCGAAATCTCCGCCTCTGCTTCCTCGAAGACAAGACTCTGTGAGGAGGAAGCGCAGCAGCTGAGCTTAGCGGATCTGCTGAAGCCCGGTGGCCTCGCCCCCGATGGGTTCTCGTACAAGGAGAACTTTACCATACGCTGCTATGAAGTCCGAGTTAAACCGCACTGCCACCATTGAGGCGTCCGC |
| SEQ ID NO:321 | Middle | LPZ-312 | GACGTTGTAAAACGACGGCCAGCAACCAAATAAACCCCACATGTGCTCAATGTTTTAGTATAAAAGGAGATGACTTAAGAGTCATTTCACACACACTTCTATCTTGATTTCTCTCCACTTGTCTTGGGTTTTAGTGGAAGAGAAATCTAGGAGTGGAAGCCCTAGACGTT |

TABLE I-continued

| cDNA | Embryo Phase | Clone | Nucleotide Sequence |
|---|---|---|---|
| | | | GGAGGATAAGAAGGCAACCCTAGAAGGCAGAGCTAACGCTATCCTAAGGCAACCC TAACGCTATCCTAAGGCGTCCGC |
| SEQ ID NO:322 | Late | LPZ-314 | GCGGACGCCTGCTCAGCACCTGTTATAGTCATTTCTTTTTTCCTTTTTCTCATTTTTC TCTTTCGAATGACCGCAATGAAATTCAGGCTGCCCAACGCGTTTTTGTTTTCACAAT TAATTTTTGAATCATACGCGAAGATCATGATGAGAATGGTTGTGGAAAAAAACTGTT TGTAAATATTTAGGTGACCAACAATTTTCATGATTGCAATCTAAAGTTGATAATTGAT TTATCGGGTCGACATTTGTAATTATTAACACGGAAAATCTGAGGCTTACAATTTTTG GATTGTAAATATTTAGGTGACGAACAATTTTCATGATTGCAATCTAAAGTTGACAATT GAGTTATCGTGTCGACATTTGTAATTATTAACACACAAAATCTATGAGGCGTCCGC |
| SEQ ID NO:323 | Late | LPZ-315 | GCGGACGCCTCATCAATCCATGGTTGTACACGCGCCTTCAAAGCGGCTTCCTTATG TCGCGCAGCGTCTACTTGTTCCTTGAGCGCTTTTCCCTGCTACATCCGCGCGAGCC TCTGTGCAAGGGCCACTGTCTGCGCGGTCCCTTTAACTTCGTCGTACTTCTGCTGC AGCTCACGTGTCTCTATTTCTAAGTGCTATATATTTGGGTCCTCCTGCATAGTAGTG AACTTCGAACGACTCCTCAAATAGCCAGGTGTAGTCTTTCATTGCACTATTGATCTC CACTATTCCTGCTATAATGGCGCTAACATGCTGTTCCTTCACCTTTGGCGGAGTTG AAGGCTGCGCCTTCTTGGAGCTCGGTTATTTGAAGCTGAACCTTGGGCATATCTTC CTTCACCTCGTGCATCCCCTGCTTGGAGTTTCTGGATGCACGCCTCCACTGGGTCT TCTGCTGGGATGGGCAACTCTAAGACCAACTGGTATGCGTCGC |
| SEQ ID NO:324 | Middle | LPZ-318 | GCGGACGCCTTCTTCAATCCATCAGGCCTGATTAATGTATTGACCTTCTTTGTCTGA ATGTCATACATTTTTTTCACTGCATCCTTGATCTTCTTCTTGTCTTGCTTTCTATCCT TTCTCTTGCTTTCTATCCTTTCTCTGGC |
| SEQ ID NO:325 | Late | LPZ-320 | GACGTTGTAAAACGACGGCCAGCAAAATTGATATAAAGAATAGACACATCGACTCA AATGAAGTGACTCAACAGTTCATTAATTCATGTCAGCTTGAATGCATGGACATACAC CCATAAATAGGCAGTTGGGGTCACCCAAAAGAACATAGAAACATCTCGCATCTCTC TGAAGAAACTCGGATGGGTACAGGTCTGTGACTTCGCATATTTTGAAGGAGCACTC TCTTGGATAAGTACAATATAGGTACCATCTCGGACTCGCCTGAAATCTCGCAAAGA AGTCTCATTCTCCTCCTTGTTACAGGCGTCCGC |
| SEQ ID NO:326 | Late | LPZ-321 | GACGTTGTAAAACGACGGCCAGAAGCATCAATAAACAAAATGACAGATTAACAAGT TCTCTCTTAATCTTAAGAGAATACATCAACATCCAAGTAAAGTCATAACACATTTACA AAATGGTGCCACGGTATCCATTCTCTGTAACAAGGTTTTTCTGAAAATAGTTTTCCT CTTATCTATGTAACTCTTCATAGGGATGCCTGTGTCAACGTGCCATATTCCCAAATT TGGCCACAATCAAACCTTCCTCATTAGAAGAAACAATCTCTGGTCTAGCTCAAAATT GGCAAAATTTCCAGCATCTCCCTTTAACATCATTAGAAGGCGTCCGC |
| SEQ ID NO:327 | Early | LPS-097 | GGGAGATGCTAATTTGAAGCCCTTCTCTGAAGGTGGACAATTCCAGCAGCAGTGGT CTAAAGCCCCAATATGGCTATAGAAATTCTTCTGGGGGTTGCACCTATGGAAGAGG GTCGGAGAGGACGAAGCTGTGGATCGCTCTTACCATCTGTGCGGAAGGTGGTAGC AGAATTCATTGGAACGTTCTTCCTCATATTTGTAGGATGCGGATCTGTCGTTGTTGA TAAGATAAGCAACGGTTCCATAACTCATCTTGGTGTGTCGCTTGTATGGGGAATGG CGGCCATGATTGTAATTTATTCCATAGGCCATATTTCTGGAGCTCATTTGAATCCTG CAGTGACGTTGGCCCTTGCGGCTGTGAAGAGATTTCCATGGGTTCAGGTTCCAGG CTACATAGTAGCTCAAGTATTTGGATCGATATCTGCTGGGTTTCTCCTACGTTTCAT GTTTGGAGAAGTGGCATTCATGGGAGCCACAGTTCCTTCAGGCTCAGAAATGCAGT CTTTCGCTTTGGAAATTATTACTACGTCATTGTTGGTGTTTGTGGTTTCTGCAGTCG CCACTGATACAAAAGCGGTGGGTGAATTGGGAGGTTCAGCAATTGGAGCGACCAT CGCAATGAATGTAGCCATATCCGGACCAATCTCAGGAGCTTCAATGAATCCAGCAA GGACAATAGGATCCGCAGTGGCTGGCAACAAATATACAAGCATTTGGGTTTACATG GTTGGGCCTGTAATCGGTGCGCTAATGGGTGCAATGAGTTATAACATGATTAGAGA GACAAAAAATGTCCGAAAGGGAGATTATGAAGAGTGGGTCATTTGTTAAGGACATGG GCTCCAGCGAATCAACAGCATAACAACTTAGAGATTTNTTGCATTCCCGAGACGGT ATCCAGTGATAGTGGAGAGTAGTCATAATAAGATTTGTGAAAATGTTTGTGTAGATT AATGTGTAAAATTCAATCCATCAACCATGAAGCGAACTGCATTCCGTTTTTAAATGT TTATTGGATTTGAATTAATAAACAGCTTATACGTGAAAATCCCTACTTTATGTACGGA |
| SEQ ID NO:328 | Early | LPS-098 | ACTATAGGGCACGCGTGGTCGACGGCCCGAGCTGGTATCCGATGAAGCTAGATTC AATGGTTCAAGTCCTATGAAAGCTAGATTGGAGAATTGCAAAGAAATCTAATCTCCG TTAGTTGTCCCAACCACTGACTCGCACCCAATCAGAGTATATTAAAGTTAAAGATTA TATAAAGGTAAATTGAACATTTATAAAATCTTAAATGTATTTTTAGAGTTAAACATTAT ATAGAATATTTAATGTAGTATAGATATAATAAAATATTAAAAATTAATTTCTCTTTACT ATCAAGTGAATAAAAATAAAAAATAAATGTAAGACAATATAATAAAAGACTTGTTTTT AGTGCATTTTTTGGACTCTTCGTTATTGTGTGGTATTGTGTTATTTAAACTGATCTTT TTACTGTATATATGGATGGGTTACCCATCAAACTTGTGATTTCAATAAATTCCTCCC GGATTTTAGAGAAATTAGACCATAAAAACTCACGAAAAAAATTTTAGACCATAAAAAC TCACGAAAAAAACTTCCCCAAAATCACGCTAAAAACAACTAGATAAAAAAATACCCA TCTTTGATGATGTGGATAGTGACAGCCTATTCCAAACTATCACCTAAATTGTAAGTT ACATGCATAACACGATGACCTCATCTATACGTTGTGCCAAATAAAGGTATGACCGTT CAAACTAAAGAATCAACGAGCTCCAACGCATCTTTTGCTGTGGGGGGATTCTCACG GCTTAACATTCATGGANCCGATTACCTTNCTANCCAACCAAGGGTTTTAACCTGG CAAATNCCAAACCAATTACCAGCTTNACAAATCAACCGAGCCGCCCNACCGGGATC ATTTTGGTCAAGTCTCGAAAACNGGCATTGGGTATATGGNATATGGAATTGGAATT GGATCAATGGTAACCTTGGGANAAGCTTAANTTGGAAANCCCTTTTTTTTGANGGG GGCCAANTTCCCGNNCCCCCGG |
| SEQ ID NO:329 | Early | LPS-099 | ATACTCAAGCTATGCATCCAACGCGTTGGGAGCTCTCCCTATGGTCGACCTGCAGG CGGCCGCGAATTCACTAGTGATTAGATGGTAAGAGCGATGCACAGCTTCGTCCTCT CCGACCCTCTTCCATAGGTGCAACCCCCAGAAGAATTTCTATAGCCATATTGAGGC TTTAGACCACTGGTGCTGGAATTGTCCACCTTCAGAGAAGGGCTTCAAATTAGCAT CTCCAAGTTACATTGATCTATTCTATTCATATACATATAACAATGCTGCTTCGAGACT GACAAAATGATCCGTTGGCGCTCGTTGATTGTTAGCTGTAATTGTTTGGATTGTTCA |

TABLE I-continued

| cDNA | Embryo Phase | Clone | Nucleotide Sequence |
|---|---|---|---|
| | | | GTTAAAGCCTTGTTGGTAGGAGGTAATCGGTCATGAATGTTAGCCGTGAGAATCCT |
| | | | CACAGCAAAAGATGCGTTGGAGCTCGTTGATTCTTTAGTTTGAACGGTCATACCTTT |
| | | | ATTTGGCACAACGTATAGATGAGGTCATCGTGTTATGCATGTAACTTACAATTTAGG |
| | | | TGATAGTTTGGAATAGGCTGTCACTATCCACATCATCAAAGATGGGTATTTTTTATC |
| | | | TAGTTGTTTTTAGCGTGATTTTGGGGAAGTTTTTTTCGTGAGTTTTTATGGTCTAAAA |
| | | | TTTTTTTCGTGAGTTTTTATGGTCTAATTTCTCTAAAATCCGGGAGGAATTTATTGAA |
| | | | ATCACAAGTTTGATGGGTAACCCATCCATATATACAGTAAAAAGATCAGTTTACCAG |
| | | | CCCGGGCCGTCGACCACGCGTGCCCTATAGTAATCGAATTCCCGCGGCCGCCATG |
| | | | GCGGCCGGGAGCATGCGACGTCGGGCCCAATTCGCCCTATAGTGAGTCGTATTAC |
| | | | AATTCACTGGCCGCGTTTACACGTCGTGACTGGGAAACCCTGCGTTACCACTTAAT |
| | | | CGCTTGAGCACATCCCCTTTTCCAGTGNGTAAAACGAAAAGGCCCCNCCATCGCCT |
| | | | TTCAAAAATTGGCAACTGAANGGGAAGGACCCCCT |
| SEQ ID NO:330 | Early | LPS-100 | ATACTCAAGCTATGCATCCAACGCGTTGGGAGCTCTCCCATATGGTCGACCTGCAG |
| | | | GCGGCCGCGAATTCACTAGTGATTAGATGGTAAGAGCGATCCACAGCTTCGTCCC |
| | | | CTCCGACCCTCTTCCATAGGTATAAAACCCAGAATTTGGTGAGCAGGAAGAATTTC |
| | | | CATAGCCATATTGAGGCTTTACACCACTGCTGCTCGAATTGTCCACCTTCAGAGAA |
| | | | GGGCTTCAAATTAGCATCTCCAAGTTACATGGATCTATTCTATTCATATATTTATAAC |
| | | | AATGCTGCTTCGAGACTGACAAAATTATTTGTTGGCGCTTGTTCATCGTTAGCTGTA |
| | | | ATGGTTTGGATTGTTCAGTGTAGGACCAGCCCGGGCCGTCGACCACGCGTGCCCT |
| | | | ATAGTAATCGAATTCCCGCGGCCGCCATGGCGGCCGGGAGCATGCGACGTCGGG |
| | | | CCCAATTCGCCCTATAGTGAGTGGTATTACAATTCACTGGCCGTCGTTTTACAACGT |
| | | | CGTGACTGGGAAAACCCTGGCGTTACCCAACTTAATCGCCTTGCAGCACATCCCCC |
| | | | TTTCGCCAGCTGGCGTAATAGCGAAGAGGCCCGCACCGATCGCCCTTCCCAACAG |
| | | | TTGCGCAGCCTGAATGGCGAATGGACGCGCCCTGTAGCGGCGCATTAAGCGCGG |
| | | | CGGGTGTGGTGGTTACGCGCAGCGTGACCGCTACACTTGCCAGCGCCCTAGCGC |
| | | | CCGCTCCTTTCGCTTTCTTCCTTCCTTTCTCGCCACGTTCGCCGGCTTTCCCCGTC |
| | | | AAGCTCTAAATCGGGGGCTTCCTTTAGGGTTCCGATTTATGCTTTACGGCACCCT |
| | | | CGACCCCAAAAAACTTGATTAGGGGTGATGGGTCACGTAGTGGGCCATCGCCCT |
| | | | TGATAGACGGTTTTTCGCCCTTTGACGNTGGAAGTCCACGTTTNTTTAATAGNGGG |
| | | | ACTCTTGGTTCAAAATGGGACAACACTTCAAACCTTTTTTGGGGNTATTTTTTTTGAT |
| | | | TTATNAAGGGATTTTTGCCGNNTTTNGGGCCTTTTGG |
| SEQ ID NO:331 | Early | LPS-101 | ACTATAGGGCACGCGTGGTCGACGGCCCCGGCTGGTTTCAATAAATTCCTCCCGG |
| | | | ATTTTAGAGAAATTAGACCATAAAAACTCACGAAAAAAATTTTAGACCATAAAAACTC |
| | | | ACGAAAAAAACTTCCCCAAAATCACGCTAAAAACAACTAGATAAAAAAATACCCATC |
| | | | TTTGATGATGTGGATAGTGACAGCCTATTCCAAACTATCACCTAAATTGTAAGTTAC |
| | | | ATGCATAACACGATGACCTCATCTATACGTTGTGCCAAATAAAGGTATGACCGTTCA |
| | | | AACTAAAGAATCAACGAGCTCCAACGCATCTTTTGCTGTGAGGATTCTCACGGCTA |
| | | | ACATTCATGACCGATTACCTCCTACCAACAAGGCTTTAACTGAACAATCCAAACAAT |
| | | | TACAGCTAACAATCAACGAGCGCCAACGGATCATTTTGTCAGTCTCGAAGCAGCAT |
| | | | TGTTATATGTATATGAATAGAATAGATCAATGTAACTTGGAGATGCTAATTTGAAGC |
| | | | CCTTCTCTGAAGGTGGACAATTCCAGCACCAGTGGTCTAAAGCCTCAATATGGCTA |
| | | | TAGAAATTCTTCTGGGGGTTGCACCTATGGAAGAGGGTCGGAGAGGACGAAGCTG |
| | | | TGGATGCTCTTACCATCT |
| SEQ ID NO:332 | Early | LPS-102 | ATACTCAAGCTATGCATCCAACGCGTTGGGAGCTCTCCCATATGGTCGACCTGCAG |
| | | | GCGGCCGCGAATTCACTAGTGATTAGATGGTAAGAGCGATCCACAGCTTCGTCCTC |
| | | | TCCGACCCTCTTCCATAGGTGCAACCCCCAGAAGAATTTCTATAGCCATATTGAGG |
| | | | CTTTAGACCACTGGTGCTGGAATTGTCCACCTTCAGAGAAGGGCTTCAAATTAGCA |
| | | | TCTCCAAGTTACATTGATCTATTCTATTCATATACATATAACAATGCTGCTTCGAGAC |
| | | | TGACAAAATGATCCGTTGGCGCTCGTTGATTGTTAGCTGTAATTGTTTGGATTGTTC |
| | | | AGTTAAGGCCTTGTTGGTAGGAGGTAATCGGTCATGAATGTTAGCCGTGAGAATCC |
| | | | TCACAGCAAAAGATGCGTCGGAGCTCGTTGATTCTTTAGTTTGAACGGTCATACCT |
| | | | TTATTTGGCACAACGTATAGATGAGGTCATCGTGTTATGCATGTAACTTACAATTTA |
| | | | GGTGATAGTTTGGAATAGGCTGTCACTATCCACATCATCAAAGATGGGTATTTTTTT |
| | | | ATCTAGTTGTTTTTAGCGTGATTTTGGGGAAGTTTTTTTCGTGAGTTTTTATGGTCTA |
| | | | AAATTTTTTTCGTGAGTTTTTATGGTCTAATTTCTCTAAAATCCGGGAGGAATTTATT |
| | | | GAAATCACAAGTTTGATGGGTAACCCATCCATATATACAGTAAAAAGATCAGTTTAA |
| | | | ATAACACAATACCACACAATAACGAAGAGTCCAAAAAATGCACTAAAAACAAGTCTT |
| | | | TTATTATATTGGCTTACATTTATTTTTTACTTTTATTCACTTGGATAGTAAAAGAGAAA |
| | | | TTAATTTTTAATATTTTATTATATCTATACTACATTAAATATTCTATATAATGTTAACTC |
| | | | TAAAAAACATTTAAGATTTATATATGGTCAATTACCCTTATATAATCTTTAACTTTAAA |
| | | | TCCCTGATGGGGGCCAATAANGGTNGGGAAACTAACGGAAN |
| SEQ ID NO:333 | Early | LPS-103 | ACTATAGGGCACGCGTGGTCGACGGCCCGGGCTGGTTTCAATAAATTCCTCCCGG |
| | | | ATTTTAGAGAAATTAGACCATAAAAACTCACGAAAAAAATTTTAGACCATAAAAACTC |
| | | | ACGAAAAAAACTTCCCCAAAATCACGCTAAAAACAACTAGATAAAAAAATACCCATC |
| | | | TTTGATGATGTGGATAGTGACAGCCTATTCCAAACTATCACCTAAATTGTAAGTTAC |
| | | | ATGCATAACACGATGACCTCATCTATACGTTGTGCGAAATAAAGGTATGACCGTTCA |
| | | | AACTAAAGAATCAACGAGCTCCAACGCATCTTTTGCTGTGAGGATTCTCACGGCTA |
| | | | ACATTCATGACCGATTACCTCCTACCAACAAGGCTTTAACTGAACAATCCAAACAAT |
| | | | TACAGCTAACAATCAACGGGCGCCAACGGATCATTTTGTCAGCCTCGAAGCAGCAT |
| | | | TGTTATATGTATATGAATAGAATAGATCAATGTAACTTGGAGATGCTAATTTGAAGC |
| | | | CCTTCTCTGAAGGTGGACAATTCCAGCACCAGTGGTCTAAAGCCTCAATATGGCTA |
| | | | TAGAAATTCTTCTGGGGGTTGCACCTATGGAAGAGGGTCGGAGAGGACGAAGCTG |
| | | | TGGATCGCTCTTACCATCT |
| SEQ ID NO:334 | Early | LPS-104 | ATACTCAAGCTATGCATCCAACGCGTTGGGAGCTCTCCCTATGGTCGACCTGCAGG |
| | | | CGGCCGCGAATTCACTAGTGATTAGATGGTAAGAGCGATCCACAGCTTCGTCCTCT |
| | | | CCGACCCTCTTCCATAGGTGCAACCCCCAGAAGAATTTCTATAGCCATATTGAGGC |

TABLE I-continued

| cDNA | Embryo Phase | Clone | Nucleotide Sequence |
|---|---|---|---|
| | | | TTTAGACCACTGGTGCTGGAATTGTCCACCTTCAGAGAAGGGCTTCAAATTAGCAT<br>CTCCAAGTTACATTGATCTATTCTATTCATATACATATAACAATGCTGCTTCGAGACT<br>GACAAAATGATCCGTTGGCGCTCGTTGATTGTTAGCTGTAATTGTTTGGATTGTTCA<br>GTTAAGGCCTTGTTGGTAGGAGGTAATCGGTCATGAATGTTAGCCGTGAGAATCCT<br>CACAGCAAAAGATGCGTTGGAGCTCGTTGACTCTTTAGTTTGAACGGTCATACCTT<br>TATTTGGCACAACGTATAGATGAGGTCATCGTGTTATGCATGTAACTTACAGTTTAG<br>GTGATAGTTTGGAATAGGCTGTCACTATCCACATCATCAAAGATGGGTATTTTTTTA<br>TCTAGTTGTTTTTAGCGTGATTTTGGGGAAGTTTTTTTCGTGAGTTTTTATGGTCTAA<br>AATTTTTTTCGTGAGTTTTTATGGTCTAATTTCTCTAAAATCCGAGAGGAATTTATTG<br>AAACCAGCCCGGGCCGTCGACCACGCGTGCCCTATAGTAATCGAATTCCCGCGGC<br>CGCCATGGCGGCCGGGAGCATGCGACGTCGGGCCCAATTCGCCCTATAGTGAGT<br>CGTATTACAATTCACTGGCCGTCGTTTTACAACGTCGTGACTGGGAAAACCCTGCG<br>TACCCACTTAATCGCCTTGGAGCACATCCGCCTTTCGCCAGCTGGCGTAATAGCGA<br>AGAGGCCCGGACCCGATCGGCCCTTTCCAACAAATTGCGCAACCCTGAATNGGGA<br>AATGGGCCCCCCCCTNTTACCGGNGCAATTAAACCCCGGGGGGGNGNGGGGGTT<br>CCCCCCCCCGTGGACCT |

TABLE II

| Clone | SE1–SE2 | SE3 | SE4 | SE5 | SE6 | SE7 | SE8 | SE9 |
|---|---|---|---|---|---|---|---|---|
| LPS001 | 0 | 249.4 | 1400.9 | 827.6 | 1683.8 | 2019.4 | 189.2 | 4303.9 |
| LPS003 | 701.2 | 555.9 | 2815.2 | 2445.1 | 3249.9 | 3094.7 | 227.1 | 3111.6 |
| LPS004 | 466.1 | 335.5 | 2652 | 2701 | 2644 | 2329.6 | 218.5 | 2332.4 |
| LPS006 | 753.1 | 332.7 | 3287.3 | 2964.5 | 2832.2 | 2688.9 | 182.1 | 1591.9 |
| LPS007 | 685.2 | 226 | 2010.2 | 1911.3 | 2600.4 | 1730.1 | 181.5 | 2737.7 |
| LPS008 | 652.8 | 274.8 | 2415 | 2219.3 | 2607.1 | 2294.9 | 155.7 | 1292.1 |
| LPS010 | 558.3 | 356.1 | 2667.6 | 2881.1 | 2584.3 | 1573.4 | 161.7 | 1041 |
| LPS011 | 3536.1 | 424.7 | 4021.5 | 3793.8 | 3590 | 3182 | 160.5 | 1471.7 |
| LPS012 | 809 | 408.4 | 2206.7 | 2187.1 | 2282.2 | 2422.5 | 462.4 | 1483.2 |
| LPS013 | 1211.1 | 391.6 | 2294.7 | 2652.6 | 2005.4 | 2167.8 | 166.8 | 1570.5 |
| LPS014 | 2191.9 | 432.5 | 2651.8 | 3013.5 | 3341.2 | 3586.7 | 178.8 | 3527.1 |
| LPS015 | 1197.9 | 306 | 5651.4 | 14828.6 | 20242.8 | 21558.2 | 1427.2 | 34472.3 |
| LPS019 | 1830.2 | 334.5 | 3329 | 3954.4 | 4347.5 | 4658.2 | 312.1 | 4743.1 |
| LPS020 | 675.2 | 327.8 | 2258.3 | 2284.7 | 2542.7 | 2321.4 | 171.9 | 1609.8 |
| LPS023 | 451.3 | 337.5 | 1401.9 | 1106.8 | 1766.2 | 1842.6 | 109.6 | 1365.2 |
| LPS024 | 4585.8 | 444.5 | 3006.3 | 3431.1 | 3548.8 | 3759 | 157.3 | 4062.3 |
| LPS025 | 5102.3 | 397.1 | 4322.9 | 4699.6 | 5067 | 4973.2 | 262.4 | 5240.4 |
| LPS026 | 1568.7 | 285.9 | 1809.9 | 1830.4 | 2829.9 | 2381.7 | 164.9 | 1404.9 |
| LPS027 | 5499.9 | 458.4 | 4853.9 | 5218.6 | 2598.4 | 1756.6 | 457.9 | 2375.3 |
| LPS028 | 4812.9 | 314.9 | 2368.8 | 2616.5 | 3113.3 | 3292.4 | 557 | 4146 |
| LPS029 | 4464.6 | 251.2 | 2334.4 | 2058.1 | 2930.3 | 3219.3 | 472 | 3814.4 |
| LPS030 | 1142.2 | 352.5 | 2519.8 | 2460.9 | 2499.8 | 2634.5 | 378.3 | 2147.8 |
| LPS031 | 1067.7 | 481.6 | 3510.8 | 2799.2 | 3568.2 | 3257.2 | 287.9 | 2209.7 |
| LPS032 | 1120.2 | 332.3 | 3153.1 | 3032.4 | 1769.2 | 1816.7 | 146.6 | 2689.9 |
| LPS036 | 1498.2 | 1072.9 | 4633.6 | 5524.2 | 5465.1 | 6350.7 | 918 | 14058.5 |
| LPS037 | 1890.3 | 320.9 | 3719.1 | 3618.9 | 4138 | 4518.1 | 513.4 | 5087.5 |
| LPS038 | 2899.5 | 310.3 | 4530 | 4226.1 | 4491.6 | 3969 | 268.4 | 4245.3 |
| LPS040 | 527.4 | 238.1 | 1433.4 | 1611.2 | 1984.5 | 1506.5 | 143.9 | 1988.7 |
| LPS041 | 506.1 | 265.5 | 1958.9 | 2843.2 | 2065.3 | 2016.2 | 147.4 | 2781.7 |
| LPS042 | 1432.1 | 1140.3 | 4379 | 4973.3 | 4525.4 | 4340.8 | 319.6 | 3009.8 |
| LPS043 | 696.9 | 776.2 | 3933.1 | 4894.3 | 3512.2 | 3664.7 | 340.6 | 3098.4 |
| LPS044 | 57.8 | 275.1 | 3365 | 4261.2 | 4773.5 | 4979.9 | 974.4 | 10645.5 |
| LPS045 | 536.1 | 211.1 | 1559.5 | 1415 | 1498.5 | 1584.8 | 562.1 | 1912.3 |
| LPS046 | 796.3 | 231.7 | 1023.9 | 306.4 | 1417.8 | 1328.2 | 83.8 | 946.4 |
| LPS047 | 5029.9 | 518.2 | 3632.5 | 4262.1 | 4755.5 | 4087.9 | 386.3 | 4933.8 |
| LPS050 | 6333.5 | 2620.8 | 5271.4 | 5242.1 | 5586.4 | 5560.1 | 980.1 | 11444 |
| LPS051 | 1378 | 224.4 | 2328.8 | 2221.8 | 2260.5 | 2715.1 | 123.7 | 3670.4 |
| LPS052 | 1526.4 | 267.5 | 2046 | 1856.2 | 2186.5 | 2416.3 | 99.3 | 2010.1 |
| LPS053 | 4438.3 | 361.6 | 4087.6 | 3959.9 | 4786.5 | 3666.8 | 379.6 | 4256.7 |
| LPS054 | 1992.9 | 269.9 | 2734.2 | 2388.1 | 3143.8 | 2337.7 | 177.6 | 2803.9 |
| LPS055 | 4587.8 | 334.4 | 3488.6 | 3474 | 4018.3 | 3101.6 | 196.2 | 4309.4 |
| LPS056 | 5960.7 | 1333.7 | 5338.8 | 5670.3 | 5674.4 | 5533.5 | 446.4 | 5593 |
| LPS057 | 2219.9 | 301.9 | 2397.3 | 2356.1 | 2218.1 | 2085.6 | 184.4 | 2657.8 |
| LPS058 | 4070.4 | 299.9 | 3485.4 | 3721.3 | 4113.8 | 4142.2 | 239.8 | 4945.6 |
| LPS059 | 8729.3 | 279.2 | 3885.7 | 3636 | 2720.4 | 3346.7 | 165.7 | 3734 |
| LPS060 | 4580.2 | 323.7 | 3027.8 | 4713.4 | 4929.1 | 5047.5 | 161 | 4704.8 |
| LPS061 | 2831.9 | 366.8 | 2392 | 2327.7 | 2546.5 | 1991.8 | 177.9 | 3036.7 |
| LPS062 | 1674.1 | 353 | 2711.2 | 2526.1 | 1847 | 1830.3 | 124.5 | 3584.2 |
| LPS063 | 5514.4 | 419.8 | 5238.9 | 5020.3 | 5417.4 | 5041 | 250.1 | 4812.6 |
| LPS064 | 7417 | 3166 | 5229.5 | 7497.4 | 7933.1 | 10261 | 1088.3 | 16829.6 |
| LPS065 | 5634.9 | 343.5 | 5527.8 | 5099.4 | 7833.4 | 5356.6 | 237.5 | 4696.7 |
| LPS066 | 1015.9 | 244.5 | 1702.6 | 1650.5 | 2895.1 | 2437.2 | 128 | 2514.1 |

TABLE II-continued

| | | | | | | | | |
|---|---|---|---|---|---|---|---|---|
| LPS067 | 2796.8 | 240.4 | 3931.5 | 4810.3 | 5407.8 | 5418.3 | 202.5 | 9403.8 |
| LPS069 | 533.4 | 189.9 | 1635.8 | 1816.4 | 2114.2 | 1646.8 | 119.8 | 3208.8 |
| LPS070 | 2516.9 | 240.6 | 1909.5 | 2519.6 | 2156.7 | 1777.4 | 186.4 | 4362.1 |
| LPS071 | 592.8 | 196.4 | 1789.2 | 2189.2 | 1981.1 | 1304.5 | 127.6 | 3430 |
| LPS072 | 444.2 | 217.6 | 1422.9 | 1509 | 2065.3 | 2289.9 | 122.7 | 2678.8 |
| LPS073 | 4362.8 | 273.1 | 3094.9 | 3348.1 | 3771.8 | 4075.3 | 137.7 | 4259.6 |
| LPS074 | 32072.9 | 6816.3 | 33531 | 25258.9 | 38176.4 | 32687.7 | 14607.1 | 37529.6 |
| LPS075 | 7013.9 | 472.7 | 4759.7 | 4933.9 | 5452.2 | 5408.7 | 409.4 | 5397.1 |
| LPS076 | 4236.1 | 362.6 | 3131.9 | 2882 | 3368.5 | 3354.6 | 119.5 | 3141.9 |
| LPS077 | 2958.7 | 276.6 | 4380.4 | 4862.5 | 4475.1 | 4958.7 | 218.9 | 4426 |
| LPS078 | 23685.3 | 2642.5 | 35458.6 | 25869.6 | 42378.9 | 33047.1 | 25402.2 | 37189.8 |
| LPS079 | 4794.3 | 547.8 | 4628.6 | 4821.8 | 5257.2 | 5277 | 829.5 | 5449.7 |
| LPS080 | 30454 | 10527 | 33713.7 | 23785.4 | 32590.9 | 32210.7 | 16224.4 | 37659.2 |
| LPS081 | 30405.9 | 28677 | 35358.3 | 25873 | 22338.1 | 31715.3 | 36436.4 | 36650.5 |
| LPS083 | 5040.1 | 460.8 | 3251.7 | 3487.3 | 2688.9 | 2565.9 | 190.5 | 2979.7 |
| LPS084 | 2031 | 298.9 | 2843.7 | 2718.4 | 2352.2 | 2165.5 | 164.9 | 3398 |
| LPS086 | 3571.7 | 320.1 | 2715.8 | 2648 | 1989 | 2528.4 | 143.9 | 2969.7 |
| LPS087 | 3302.3 | 337.4 | 4873.1 | 5695.8 | 5407.2 | 5450.6 | 670.8 | 18404.9 |
| LPS088 | 826.8 | 302.1 | 2389.2 | 2871.1 | 3180.8 | 2635.2 | 138.6 | 3141.5 |
| LPS089 | 796.4 | 321.2 | 1987.7 | 2640.6 | 3299.1 | 2285.1 | 143.7 | 3176.6 |
| LPS090 | 4031 | 235.9 | 3867.3 | 4064.4 | 4503.3 | 4798.4 | 341.7 | 4697.7 |
| LPS091 | 2423.3 | 196.5 | 2836.8 | 3101.3 | 4049.1 | 4172 | 295.2 | 4612.2 |
| LPS092 | 2914.9 | 208.5 | 4005.3 | 3138.4 | 3911.6 | 4036.1 | 270.4 | 4842.9 |
| LPS093 | 793 | 195.5 | 1619.2 | 1331.6 | 1909.3 | 1843 | 147.1 | 2772 |
| LPS094 | 1374 | 221 | 2205.5 | 2028.5 | 2240.9 | 2632.2 | 163.3 | 2849.1 |
| LPS095 | 728.7 | 174.1 | 2022.6 | 2112.1 | 2335.8 | 1264.6 | 117.5 | 2957 |
| LPS096 | 393.3 | 168.5 | 1531.9 | 1393.4 | 1893.3 | 869.1 | 118.3 | 1691.1 |
| LPZ001 | 2008.6 | 185.4 | 2535.9 | 2937.9 | 3472 | 1981.8 | 118.9 | 2421.7 |
| LPZ002 | 3529.3 | 384.6 | 4579.3 | 4474.6 | 3236.7 | 3855.8 | 313.8 | 3237.5 |
| LPZ003 | 4076.8 | 275.4 | 2651.2 | 2966.7 | 2829.2 | 4177.4 | 378.5 | 4369.7 |
| LPZ004 | 5595 | 687.4 | 5468.2 | 5615.9 | 5243.6 | 5699.6 | 601.6 | 5889.9 |
| LPZ005 | 5680.5 | 3353 | 34994.7 | 26121.9 | 42555.1 | 33144.5 | 16193.7 | 37798.2 |
| LPZ006 | 1199.8 | 299.4 | 3013.7 | 3099.8 | 3517.3 | 3397.1 | 140.6 | 3370.8 |
| LPZ007 | 1159.1 | 462.2 | 3292.7 | 2992.5 | 3121.4 | 2936.7 | 235.5 | 3238.6 |
| LPZ008 | 1874.3 | 237.7 | 3110.8 | 3236.7 | 2516.5 | 3182.2 | 325.3 | 4330.1 |
| LPZ009 | 3331.1 | 296.3 | 2348.5 | 3414 | 2478.2 | 3309.5 | 348 | 5658.1 |
| LPZ010 | 3216.3 | 1186.8 | 4977.3 | 5024.7 | 4564.4 | 4992.4 | 442.6 | 4454.5 |
| LPZ011 | 4613.4 | 910.9 | 4510.7 | 4515.7 | 3729 | 4357.3 | 371.4 | 4695.9 |
| LPZ012 | 1531.5 | 469.5 | 2915.3 | 2611.1 | 2012.3 | 3481.4 | 270.3 | 3804.3 |
| LPZ013 | 3495.1 | 268.8 | 2125.9 | 2584.7 | 3194.7 | 3787.4 | 125.1 | 4929.6 |
| LPZ015 | 2040 | 257.6 | 1971.1 | 2966.7 | 2191.1 | 3056.7 | 227.1 | 4156.6 |
| LPZ016 | 5307 | 2761.1 | 8451.7 | 17219.7 | 22792.7 | 15567.3 | 1073.6 | 35074.1 |
| LPZ017 | 2476.4 | 354.3 | 3175.5 | 4330.8 | 4496.2 | 4061 | 273.2 | 5328.9 |
| LPZ018 | 3929.4 | 417.5 | 12420.2 | 14916.1 | 18116 | 17637.5 | 2541.6 | 31981 |
| LPZ019 | 5404.2 | 427.3 | 32190.3 | 24710.4 | 42102.7 | 32342.6 | 19528 | 36969.5 |
| LPZ020 | 576.9 | 142.9 | 1451.4 | 1505.4 | 3534.8 | 2679.8 | 210.9 | 3046.2 |
| LPZ022 | 1408.2 | 155.2 | 2406.7 | 2845.7 | 3042.5 | 3074.8 | 189.9 | 3829.2 |
| LPZ023 | 562.1 | 152.8 | 2096.7 | 1710 | 2045.5 | 2078.9 | 200.8 | 2874.3 |
| LPZ024 | 496.7 | 158.1 | 1681.3 | 1264.7 | 2102.9 | 1857.1 | 132.1 | 1818.4 |
| LPZ025 | 5431.3 | 464.1 | 13492.2 | 9726.2 | 11911.5 | 13462.8 | 1262.5 | 11780.6 |
| LPZ026 | 1663.2 | 139.7 | 2464.8 | 2760.1 | 3113 | 2219.4 | 159.1 | 3183.5 |
| LPZ028 | 5029 | 190.7 | 5367.2 | 5339.8 | 5483.9 | 5205.5 | 482.3 | 5565.9 |
| LPZ029 | 961.3 | 119.2 | 1805.4 | 1989.6 | 2298.5 | 1998.4 | 126 | 2576.9 |
| LPZ030 | 1457.4 | 177 | 2444.7 | 2687.5 | 1966.4 | 1857.2 | 178.5 | 3312.8 |
| LPZ031 | 3092.8 | 361.7 | 3564 | 3925.3 | 4627.8 | 5171.4 | 506.7 | 5920.5 |
| LPZ032 | 1906.5 | 156.8 | 5542.3 | 24342 | 42917.8 | 33386.1 | 30058 | 37998.6 |
| LPZ033 | 12934.5 | 354.7 | 5280.1 | 7301.2 | 5638.9 | 9238.7 | 375.4 | 15843.5 |
| LPZ034 | 1307.4 | 177.5 | 1737 | 2208.4 | 3213.1 | 1984.1 | 150.2 | 3228.3 |
| LPZ035 | 556.5 | 201.9 | 880.2 | 1280.1 | 1654.5 | 915.1 | 74.1 | 1422.1 |
| LPZ037 | 1356.8 | 269.7 | 2072 | 3110.5 | 2912.8 | 2488.2 | 211 | 4119.3 |
| LPZ038 | 4027.9 | 426.9 | 5639.9 | 5872.3 | 5476.8 | 5614.6 | 796.8 | 5583.3 |
| LPZ039 | 5059.1 | 550.6 | 3807.9 | 4393.8 | 3825.6 | 3889.8 | 342.2 | 5164.2 |
| LPZ040 | 1226.1 | 236.5 | 1566.4 | 1889 | 1679.1 | 2263.6 | 140.6 | 3331.1 |
| LPZ041 | 944.2 | 219.3 | 1629 | 543.1 | 1148.2 | 1416 | 90.2 | 2524.6 |
| LPZ042 | 570.6 | 206.1 | 1129.5 | 806.5 | 1448.8 | 1423.1 | 75.1 | 2013.8 |
| LPZ043 | 1190.2 | 236.7 | 1878.8 | 1024.4 | 2834.6 | 2767.4 | 241.7 | 3236.2 |
| LPZ045 | 5315.3 | 465.7 | 4933.2 | 5580.2 | 5151.1 | 5205.1 | 557.3 | 10754.3 |
| LPZ047 | 859.5 | 285.2 | 1606.2 | 2099.3 | 2059.4 | 1992.6 | 68.3 | 3054.8 |
| LPZ049 | 3232.7 | 108 | 1278.6 | 2834.2 | 3657.8 | 3944 | 244.2 | 5459.6 |
| LPZ051 | 3048.1 | 146.9 | 2373.2 | 2067.3 | 2745 | 2383.2 | 179.1 | 2837.6 |
| LPZ053 | 2580.3 | 135.6 | 2625.8 | 2088.7 | 2468.5 | 2297.2 | 156.8 | 3001.4 |
| LPZ054 | 1838.1 | 159.5 | 2657.8 | 2759.7 | 2658.1 | 2224.7 | 170.4 | 3444.2 |
| LPZ055 | 2181.8 | 151.1 | 2381.2 | 2262.7 | 3228.3 | 2983.9 | 139.3 | 2673.9 |
| LPZ056 | 4028.3 | 219.5 | 2884.6 | 3416.6 | 3779.6 | 3789.9 | 208 | 4518 |
| LPZ057 | 1470 | 121 | 1676.5 | 1629.6 | 1702.7 | 1703 | 112.2 | 2272.1 |
| LPZ058 | 1923.3 | 122.5 | 2453.5 | 2169 | 3127.3 | 2465.4 | 160.6 | 3319.6 |
| LPZ059 | 1760.4 | 113.8 | 2180.6 | 1832.4 | 1997.2 | 1530.8 | 174.4 | 3366.6 |
| LPZ060 | 3296.4 | 139.3 | 2571.1 | 2250.2 | 2721 | 2976.9 | 221.3 | 3898.5 |
| LPZ061 | 2495.6 | 182.8 | 2663.9 | 2235 | 3265.9 | 4227.1 | 498.1 | 4915.1 |

TABLE II-continued

| | | | | | | | | |
|---|---|---|---|---|---|---|---|---|
| LPZ062 | 1992.7 | 194.9 | 3296.7 | 3975.8 | 3861.5 | 5642.6 | 497.6 | 5606.2 |
| LPZ063 | 2167.1 | 145.9 | 2733 | 1843.9 | 3066.6 | 4961 | 305.6 | 4773.2 |
| LPZ065 | 5641.2 | 251.7 | 13690.3 | 9269.2 | 8562.8 | 13254 | 986.3 | 9554 |
| LPZ066 | 6307.3 | 652.4 | 12630.8 | 6968.4 | 4918.9 | 5062.2 | 400.7 | 5456.8 |
| LPZ067 | 10838 | 1548.1 | 16986 | 11776.8 | 5633.2 | 7054 | 1014 | 15262.2 |
| LPZ069 | 1481.9 | 209.6 | 2239.8 | 1480.9 | 2496.7 | 2542.4 | 250.5 | 3717.2 |
| LPZ070 | 1932.5 | 263.8 | 1895.1 | 2221 | 1555.9 | 1570.4 | 145.5 | 3471.3 |
| LPZ071 | 3672.6 | 378.6 | 4185.5 | 3050.5 | 4166.8 | 4246.2 | 553.7 | 5333.4 |
| LPZ072 | 744.5 | 210 | 1210 | 676.7 | 1420.2 | 1393.4 | 95.8 | 1997.1 |
| LPZ073 | 1997.9 | 235.9 | 2275.1 | 2141.7 | 2613.2 | 1989.9 | 170 | 3489.4 |
| LPZ074 | 1375.9 | 237.4 | 1899.1 | 1787.3 | 2472.9 | 1623.7 | 125.6 | 2435 |
| LPZ075 | 831.4 | 247.9 | 1536.4 | 1773.1 | 1886.9 | 920 | 80.6 | 1053.5 |
| LPZ076 | 345.7 | 251.8 | 854.8 | 564.6 | 1747.1 | 526.2 | 55.9 | 1058.3 |
| LPZ077 | 2466.3 | 102.2 | 949.4 | 820.9 | 3093.9 | 3179.6 | 202.9 | 3314.8 |
| LPZ078 | 3102.1 | 197.1 | 3654.2 | 3261 | 4204.3 | 4433.6 | 400.8 | 5559 |
| LPZ079 | 1584.4 | 108.3 | 2389.2 | 2243.3 | 2624.8 | 2677.1 | 208.3 | 3675.6 |
| LPZ080 | 12206.5 | 2043.1 | 25021.4 | 8579.5 | 11707.8 | 8717.6 | 1172 | 18663.9 |
| LPZ081 | 1368.7 | 103.6 | 1902.8 | 1349.9 | 2166.1 | 1597.7 | 103.5 | 2709.6 |
| LPZ082 | 2601.3 | 140.3 | 3264.3 | 2853.9 | 2799.6 | 1742.3 | 251.1 | 4288.2 |
| LPZ083 | 1311.9 | 76.7 | 1622.4 | 1071.1 | 1733.9 | 1878 | 104 | 2007.7 |
| LPZ084 | 9974.7 | 801.3 | 14255.3 | 8399.1 | 5763.9 | 8852.9 | 542.2 | 5714.3 |
| LPZ085 | 4609.8 | 158.4 | 3923.3 | 3729.7 | 4082.8 | 3867.3 | 219.3 | 4075.1 |
| LPZ086 | 10874.1 | 987.4 | 19189.5 | 8284.6 | 5646 | 9109.8 | 1116.4 | 14988 |
| LPZ089 | 3505.8 | 211.6 | 4010 | 3430.6 | 3762.1 | 3770.8 | 224.3 | 5341.2 |
| LPZ090 | 5780.9 | 581.8 | 13217.4 | 6303.4 | 4694.8 | 4779.9 | 425.2 | 5408.9 |
| LPZ091 | 5316.1 | 148.4 | 2263.4 | 2139.8 | 2382.2 | 4067.2 | 256.8 | 14732.6 |
| LPZ092 | 5448.7 | 209.4 | 3631.6 | 4152.7 | 2934.1 | 3403.7 | 174.9 | 4943.6 |
| LPZ093 | 1169 | 159.4 | 2097.9 | 1187.4 | 2050.8 | 2350.7 | 109.4 | 2605 |
| LPZ094 | 1245.5 | 139.7 | 1547.5 | 1650.5 | 1875.2 | 2009.9 | 80.2 | 2376.9 |
| LPZ095 | 711.2 | 177.9 | 900.9 | 1253.3 | 1013.8 | 1395.3 | 48 | 1586.1 |
| LPZ096 | 2122.2 | 249.7 | 2929.3 | 3271.3 | 2132.9 | 2224 | 232.8 | 4443.8 |
| LPZ099 | 4306.4 | 211.2 | 2603.1 | 2144.4 | 3479.2 | 3488.5 | 138.1 | 4085 |
| LPZ100 | 3373.5 | 297 | 3941.3 | 3149.6 | 3790.4 | 3857.5 | 443.8 | 5028.1 |
| LPZ101 | 3007.7 | 272.4 | 3546.9 | 2291.3 | 4299 | 3232.1 | 306.1 | 4819.6 |
| LPZ102 | 2092.7 | 324.7 | 3167.5 | 2109.3 | 3524.3 | 2829.4 | 279 | 4297.4 |
| LPZ103 | 3602.1 | 285.7 | 2923.3 | 3112.9 | 2812.9 | 1318.3 | 87.9 | 1739 |
| LPZ106 | 1359.7 | 305.1 | 2680.3 | 2391.6 | 2838.5 | 2097 | 173.7 | 3009.6 |
| LPZ107 | 28560.8 | 4989.5 | 20821.7 | 17880.4 | 39173.1 | 27035.1 | 11973.3 | 36123.4 |
| LPZ108 | 4136.8 | 179.4 | 4259.8 | 4978.2 | 5553.2 | 4862 | 837.2 | 5597.5 |
| LPZ109 | 3708.3 | 202.4 | 3842 | 3510.4 | 4638.4 | 4453.7 | 469.5 | 5107.4 |
| LPZ110 | 4557.2 | 291.4 | 5020.6 | 4801 | 4487.4 | 4481.1 | 552.3 | 5484.2 |
| LPZ111 | 1625.6 | 130.9 | 2242.1 | 1982.7 | 2740.6 | 2455.4 | 164.6 | 3722.3 |
| LPZ112 | 2887.4 | 195.8 | 3813.2 | 3759.4 | 3984.8 | 4167.1 | 409.7 | 5461.8 |
| LPZ114 | 5029.5 | 213.4 | 5016.7 | 4678.8 | 5036.9 | 5168.1 | 302.1 | 4316 |
| LPZ115 | 24434.4 | 2637.1 | 27958 | 23684.2 | 41104.3 | 30920.9 | 2153.9 | 36902.6 |
| LPZ116 | 8682.9 | 235.7 | 5647.3 | 5316.6 | 5805.6 | 9313.7 | 466.6 | 16018.9 |
| LPZ117 | 30879 | 4843.7 | 36277.1 | 24358 | 24673.1 | 20545.7 | 4669.9 | 5652.6 |
| LPZ118 | 4023.6 | 171.1 | 3743.5 | 4568.2 | 3845.4 | 3783.9 | 254.3 | 4782.5 |
| LPZ119 | 2580.4 | 114.1 | 2507.2 | 3114.1 | 2544.6 | 1963.8 | 127.6 | 3195.4 |
| LPZ120 | 1998.8 | 157 | 1987.2 | 1503.1 | 2331.8 | 1805.1 | 131.5 | 3522.3 |
| LPZ122 | 2041.4 | 119.6 | 2145.6 | 2430.9 | 1998.6 | 2171.8 | 101.3 | 2677 |
| LPZ124 | 2795.6 | 185.4 | 2980.4 | 2672.5 | 2495.2 | 3459.4 | 173.1 | 3081.5 |
| LPZ126 | 2559.7 | 181.8 | 2560.1 | 2349.8 | 3500.6 | 2362.1 | 224.9 | 3646.9 |
| LPZ127 | 1993.5 | 169.1 | 3161 | 3180.8 | 3382.5 | 3321.3 | 180.6 | 4058.4 |
| LPZ128 | 2866.7 | 263.2 | 3556.8 | 3597.4 | 3545.7 | 3813.8 | 306.7 | 4071.3 |
| LPZ131 | 1993.5 | 171.7 | 1983.9 | 2069.6 | 2565 | 2607.2 | 80.3 | 2527.8 |
| LPZ133 | 2446.7 | 290.4 | 3218.6 | 2847.2 | 3830.1 | 2889.5 | 245 | 4252.4 |
| LPZ136 | 1952.3 | 281.1 | 2956.9 | 1870.6 | 3167.6 | 2680.6 | 215.9 | 4291.6 |
| LPZ137 | 2833.8 | 281.9 | 3264.4 | 2350.2 | 3874.4 | 3532.8 | 420.8 | 4935.3 |
| LPZ138 | 2932.9 | 1791 | 5211.5 | 4502.1 | 5409.9 | 4832.8 | 543.1 | 4741.3 |
| LPZ140 | 2284.7 | 337.4 | 3680.2 | 2810.9 | 3196.1 | 3191.2 | 271 | 4613.6 |
| LPZ141 | 4726.2 | 368.5 | 4792.5 | 4412.5 | 5368.1 | 5466.3 | 722.1 | 4956.4 |
| LPZ143 | 25290.6 | 2692.2 | 35967.9 | 25679.9 | 43668.3 | 32612.1 | 25456.9 | 36344.4 |
| LPZ144 | 2620.9 | 286.6 | 3948.7 | 3394.6 | 4505.7 | 4142.8 | 488.7 | 4776.7 |
| LPZ145 | 3472.5 | 171 | 3949 | 3194.2 | 3430.5 | 3539.9 | 327.9 | 4487.2 |
| LPZ146 | 2612.8 | 127.3 | 2482.4 | 2080 | 3000.8 | 2979.1 | 135.1 | 3391.3 |
| LPZ147 | 2447 | 106.3 | 2855.1 | 2237.7 | 3134.2 | 2841.8 | 261.6 | 4388.1 |
| LPZ148 | 2036.8 | 77.7 | 2559 | 1932.3 | 4296.1 | 4699 | 359.6 | 3982.3 |
| LPZ149 | 5720.7 | 267.4 | 5377.3 | 5408.2 | 10999.7 | 5717.7 | 1078.9 | 13033.2 |
| LPZ150 | 5861.7 | 772 | 35541.7 | 26314.8 | 44633 | 33238 | 13126 | 37853.6 |
| LPZ151 | 5550.3 | 3499.3 | 9012.8 | 8380.4 | 11968.1 | 5716.5 | 715.8 | 5536.9 |
| LPZ152 | 4746.6 | 352.8 | 5169.3 | 5647.7 | 5384 | 5394.2 | 408.5 | 5382.1 |
| LPZ153 | 21881.2 | 2773.2 | 14738.2 | 15979.5 | 16996.8 | 15756.8 | 2388.5 | 30812.9 |
| LPZ154 | 4869.8 | 265.9 | 3244.3 | 3497 | 3948.6 | 3703.3 | 303.8 | 4119.1 |
| LPZ155 | 3904.2 | 1596.3 | 5078.5 | 5482 | 4631.7 | 5314.1 | 553.4 | 4112.9 |
| LPZ157 | 4726.5 | 1732.8 | 5427.1 | 5369.5 | 5213.3 | 5705.9 | 756.4 | 5462.2 |
| LPZ158 | 15297.4 | 3817.1 | 17993.9 | 17405.3 | 25168.8 | 22056.6 | 2337.4 | 22375.3 |
| LPZ162 | 5725.8 | 4204.8 | 10380.1 | 11364 | 17948.2 | 14250.8 | 1934.6 | 10535.5 |
| LPZ165 | 5615.2 | 666.7 | 5274.6 | 5486.6 | 5560.3 | 5310.9 | 637.1 | 5405.9 |

TABLE II-continued

| | | | | | | | | |
|---|---|---|---|---|---|---|---|---|
| LPZ166 | 5889.1 | 2603 | 9503.5 | 10943.7 | 13743.3 | 14080.4 | 1772.5 | 5772.8 |
| LPZ167 | 5347.2 | 1948 | 5708.9 | 6769.6 | 5742.3 | 5347.9 | 370 | 5279.7 |
| LPZ169 | 3043.8 | 267.4 | 1976.6 | 2851 | 3451 | 2451.2 | 189.8 | 3420 |
| LPZ170 | 3507.3 | 301.5 | 3532.3 | 3391.4 | 4481.4 | 3398.7 | 130.2 | 5604.2 |
| LPZ171 | 3762.3 | 780.7 | 4554.8 | 4311.7 | 4936.4 | 4511.3 | 398.6 | 5030.5 |
| LPZ172 | 5098.2 | 947.4 | 5550 | 6287.9 | 5135.4 | 5323.9 | 1242.5 | 8539 |
| LPZ173 | 22580.5 | 3313.9 | 35486.9 | 24974.9 | 42874 | 31828.8 | 26531.8 | 36066.9 |
| LPZ174 | 4115.7 | 221 | 5241.5 | 4262.4 | 5765.8 | 5554.9 | 872.5 | 4815.2 |
| LPZ175 | 4388.3 | 1360.6 | 5563.7 | 5504.9 | 5165.3 | 5182.9 | 583.2 | 4602.3 |
| LPZ177 | 1371.6 | 94.5 | 2119.4 | 2218.6 | 2730.7 | 2431.7 | 143.2 | 2893.2 |
| LPZ179 | 3643 | 195.1 | 4409.9 | 4898 | 5458.3 | 5319.8 | 797.9 | 5677.7 |
| LPZ181 | 5573.3 | 215.9 | 4799.6 | 5272.2 | 5825.3 | 5554.4 | 1573.5 | 13689.7 |
| LPZ182 | 4118.9 | 107.6 | 3491.5 | 3182.1 | 4617.5 | 4543.6 | 478.1 | 5527.8 |
| LPZ186 | 5792.2 | 325.5 | 4965.1 | 5182.6 | 12373.6 | 11191.4 | 1804.9 | 37336.4 |
| LPZ189 | 33820.3 | 5188.5 | 30941.4 | 24955 | 43453.2 | 33115.2 | 17929.3 | 38055.6 |
| LPZ194 | 2807 | 151.1 | 2915.9 | 2955.1 | 3306.8 | 3120.2 | 142.9 | 4101.6 |
| LPZ195 | 5345.7 | 532.7 | 5597 | 5628.7 | 5540.4 | 5491 | 545.7 | 5756.7 |
| LPZ196 | 4805.1 | 3512.9 | 5183.2 | 6968.6 | 5465.4 | 5052.4 | 786.4 | 5694.5 |
| LPZ197 | 7268.6 | 159.8 | 5398.9 | 5673.5 | 13582.6 | 15111.9 | 3499.6 | 34684.8 |
| LPZ198 | 7208.3 | 210.6 | 5800.8 | 8043 | 5439.2 | 5183.6 | 409.3 | 5042.7 |
| LPZ199 | 3058.3 | 186.1 | 2749.6 | 2667 | 3713.6 | 3704.3 | 243.4 | 3917 |
| LPZ201 | 7175.3 | 236.7 | 4827.6 | 5029.9 | 5523.4 | 5802.2 | 1981.9 | 14614.5 |
| LPZ202 | 3603.3 | 1113.9 | 35531.5 | 26035.1 | 44762.8 | 33837.3 | 63521.8 | 38225.4 |
| LPZ203 | 4325.4 | 424.4 | 5517 | 5387.3 | 9934.8 | 5662.1 | 2104.8 | 9370.7 |
| LPZ204 | 32355.9 | 34690 | 36443.6 | 26004.3 | 44546.1 | 33680.5 | 55702.6 | 37890.3 |
| LPZ205 | 4904.1 | 519.6 | 5162.4 | 5398.7 | 5427.6 | 5325.6 | 281.4 | 5770.2 |
| LPZ206 | 3504.4 | 319.8 | 3124.8 | 4561.7 | 4192.2 | 3899.9 | 255.7 | 5489.9 |
| LPZ207 | 32035 | 24978.7 | 34825 | 23371.8 | 42639.9 | 32686.4 | 30672.2 | 37674.8 |
| LPZ208 | 25174.6 | 3118.6 | 14244.4 | 13906.3 | 16694.7 | 21111.9 | 2190.1 | 34542.4 |
| LPZ210 | 3885.1 | 422.3 | 3895.8 | 4551.5 | 4205.7 | 5108.7 | 258.6 | 5514.3 |
| LPZ211 | 2569 | 176.7 | 3689.2 | 2943.5 | 4001.9 | 3860.9 | 250.2 | 3113.1 |
| LPZ212 | 5988.8 | 1244.3 | 32684.4 | 11154.1 | 19853.4 | 13654 | 618.3 | 10736 |
| LPZ213 | 3406.9 | 106.8 | 3964.1 | 3876.6 | 4236.4 | 4294.4 | 274.2 | 4874.6 |
| LPZ214 | 1668.3 | 55.3 | 2136.3 | 2394.8 | 2390 | 2269.3 | 105.8 | 3436.2 |
| LPZ215 | 5019.8 | 139.3 | 5020.1 | 5024.8 | 11013.9 | 13747.1 | 1991.7 | 36930.6 |
| LPZ216 | 3336.8 | 1085.4 | 35895.6 | 26245.3 | 44980.1 | 33834.4 | 64482.7 | 38238.1 |
| LPZ217 | 23512.1 | 26363.3 | 36065.8 | 24685.4 | 43193.4 | 31422.4 | 21462.1 | 35990.6 |
| LPZ219 | 4011 | 256.9 | 3193.5 | 3326.3 | 4509.5 | 5258.5 | 455.2 | 5841.9 |
| LPZ220 | 8696.5 | 2383.3 | 5064.7 | 5171.3 | 4923.7 | 5340 | 951.7 | 17530.6 |
| LPZ221 | 1221.4 | 83.1 | 1201.8 | 707.6 | 1556.5 | 2083.9 | 182.1 | 3948.8 |
| LPZ222 | 1885 | 146.1 | 2834.7 | 2253.2 | 2557.7 | 3382 | 196.7 | 4225.1 |
| LPZ223 | 1048.5 | 121.2 | 2339.6 | 2642.1 | 2663.8 | 3573.5 | 383.5 | 4579.2 |
| LPZ224 | 3190.6 | 118.8 | 3049.8 | 2833.2 | 4373.8 | 5139.9 | 858.6 | 5285.7 |
| LPZ225 | 25428.2 | 4079.7 | 35724.5 | 25423.6 | 43300.5 | 32574.8 | 38888.3 | 37219.9 |
| LPZ226 | 1044.9 | 130.4 | 1776.9 | 1210.8 | 2757.7 | 3388.5 | 326.6 | 3520.3 |
| LPZ227 | 1078.3 | 133 | 1461.7 | 973.5 | 7032.1 | 9452.8 | 2043.5 | 4705.3 |
| LPZ228 | 3961.6 | 213.5 | 3373 | 4050.7 | 5575.6 | 10714.4 | 2428.6 | 5928.9 |
| LPZ231 | 3475.2 | 230 | 4096.3 | 3841.1 | 5009.3 | 5690.3 | 959.9 | 5514.3 |
| LPZ233 | 2404 | 218.2 | 2170.9 | 1531.4 | 4362.7 | 4198.1 | 673.7 | 3350.1 |
| LPZ234 | 1688.3 | 312.3 | 1887.6 | 1486.5 | 4228.6 | 4715.6 | 724.8 | 3170.1 |
| LPZ235 | 2661.6 | 199.9 | 2422.2 | 1852.6 | 3078.9 | 2886.6 | 98.2 | 3143.5 |
| LPZ237 | 3174.5 | 324.2 | 3032.5 | 2988.2 | 3931.1 | 4587.9 | 314.4 | 4588.3 |
| LPZ239 | 4061.3 | 309.3 | 3175.1 | 2932.1 | 4131.7 | 3892.6 | 122.3 | 5083.5 |
| LPZ240 | 3799 | 316 | 3730.6 | 3314.6 | 3379.8 | 3538.8 | 212.4 | 4784.5 |
| LPZ241 | 2559.2 | 62.1 | 2610.4 | 1794.5 | 4165.6 | 3754.4 | 134.8 | 2915.1 |
| LPZ242 | 29360.5 | 3262.9 | 35254.6 | 25196.9 | 43028.8 | 31468.2 | 7308.4 | 36768.4 |
| LPZ243 | 3405.3 | 88.8 | 3015.7 | 2683.4 | 3678.7 | 2990.6 | 121 | 4001.4 |
| LPZ244 | 4856.9 | 483.6 | 4842.2 | 5235.3 | 5317.6 | 5432.1 | 205.4 | 5712.9 |
| LPZ246 | 1274.8 | 65.9 | 2301.7 | 1922.8 | 4332.2 | 4628.8 | 672.1 | 4232.4 |
| LPZ247 | 3894 | 69.8 | 2522.8 | 3389.9 | 4451.4 | 4937.1 | 939.3 | 5522.8 |
| LPZ248 | 3016.7 | 268.6 | 2883.2 | 3805.2 | 3791.7 | 3777.6 | 487.1 | 4585.6 |
| LPZ249 | 5224.1 | 138.3 | 3524.5 | 4091.2 | 3022.4 | 3393.2 | 149.9 | 4101 |
| LPZ250 | 1060.6 | 46.5 | 1400.9 | 1246.9 | 1419.5 | 1411.2 | 118.8 | 2908.4 |
| LPZ251 | 1336.8 | 248.5 | 1354.6 | 1049.3 | 657.6 | 924.3 | 70.3 | 2064 |
| LPZ255 | 3787.8 | 171.8 | 4801.8 | 5076.3 | 4608.1 | 4965 | 340 | 5636.6 |
| LPZ256 | 536.6 | 61.6 | 865.5 | 971.6 | 1130.8 | 1327.7 | 82.7 | 936.9 |
| LPZ257 | 844.5 | 112.6 | 1507.4 | 1537.8 | 2337.9 | 2745.8 | 341.5 | 1610.7 |
| LPZ258 | 2588.5 | 142.3 | 3443.1 | 2902.2 | 4576 | 4976.4 | 1182.9 | 3619.6 |
| LPZ260 | 897.7 | 113.7 | 1677.9 | 944.3 | 1217.6 | 1286.6 | 170 | 2928.2 |
| LPZ261 | 981.3 | 132.1 | 1499.6 | 743.4 | 1590.8 | 1953 | 67.2 | 1652.1 |
| LPZ264 | 4559.3 | 231.3 | 4348.5 | 2856.3 | 4869.2 | 5179.7 | 412.3 | 4698.3 |
| LPZ265 | 21063 | 2793.9 | 26928.5 | 12365.5 | 13816.5 | 12134.4 | 691.6 | 17954.8 |
| LPZ266 | 1642.4 | 130 | 1767.5 | 1463 | 1633.8 | 1410.5 | 59.4 | 1444.5 |
| LPZ268 | 2451 | 114.2 | 2803.3 | 2495.4 | 3126.5 | 3433.7 | 79 | 4261.3 |
| LPZ269 | 15670.7 | 3660.5 | 35782.4 | 21720 | 40375.2 | 31597.3 | 2024 | 35213.6 |
| LPZ270 | 3541.2 | 240.8 | 3803 | 3132.4 | 4827.8 | 5213.6 | 79.9 | 5473 |
| LPZ271 | 5590.7 | 677.2 | 5465.4 | 5197.1 | 5703.4 | 5615.2 | 309.2 | 5732.7 |
| LPZ272 | 27369.6 | 3445.9 | 35824.6 | 22832.6 | 40684.8 | 27398.4 | 1732.9 | 37016 |
| LPZ273 | 1107.3 | 46.1 | 456.7 | 336.3 | 1879.3 | 1654.1 | 65.4 | 971.9 |

TABLE II-continued

| | | | | | | | | | |
|---|---|---|---|---|---|---|---|---|---|
| LPZ274 | 3936.2 | 114.5 | 3192.3 | 3024.1 | 4983.3 | 4907 | 293.9 | | 4933.5 |
| LPZ275 | 2567.2 | 42.9 | 1760.4 | 2091.8 | 3656.5 | 3800.5 | 77 | | 2585.4 |
| LPZ276 | 560.9 | 32.9 | 1075.4 | 1878.9 | 1889.9 | 1766.2 | 66.8 | | 1294 |
| LPZ277 | 423.7 | 34.6 | 1199.1 | 1169.8 | 1376.8 | 1383.9 | 91.9 | | 1123.7 |
| LPZ278 | 323 | 39.7 | 937 | 382.9 | 770.1 | 935.2 | 66 | | 1403.4 |
| LPZ279 | 965.9 | 70.7 | 1907.5 | 1368.2 | 1783.7 | 1603.9 | 133.2 | | 2438.8 |
| LPZ280 | 390.7 | 19.6 | 175.4 | 42.3 | 464.9 | 631.5 | 29.9 | | 2074.9 |
| LPZ281 | 84.3 | 8.2 | 0 | 0 | 0 | 0 | 9.7 | | 0 |
| LPZ282 | 1849.7 | 28.4 | 315.1 | 34.2 | 664.3 | 1097.3 | 21.5 | | 1229.5 |
| LPZ283 | 10678.6 | 329.2 | 5134.7 | 5311.1 | 4772.3 | 8591.1 | 226 | | 9633.6 |
| LPZ284 | 996.1 | 39.8 | 236 | 147.2 | 2349.5 | 981.1 | 26 | | 719.7 |
| LPZ286 | 563.8 | 77.1 | 1031.1 | 945.9 | 1347.4 | 1601 | 81.2 | | 1303.6 |
| LPZ287 | 1045.7 | 123 | 2057 | 1475 | 1730.9 | 3003.6 | 149.9 | | 2493.5 |
| LPZ288 | 1201.7 | 116.2 | 1797 | 1448.8 | 1648.3 | 670.4 | 80.6 | | 3700.4 |
| LPZ289 | 1922.3 | 113.3 | 2515.4 | 3395.3 | 3460.7 | 3369.4 | 70.8 | | 2183.8 |
| LPZ290 | 14629.5 | 3945.8 | 34659 | 24047.3 | 40474.8 | 27786.2 | 1348.2 | | 27566.4 |
| LPZ293 | 4364.8 | 385.4 | 4664.2 | 3170.9 | 4321.6 | 4789.8 | 74.6 | | 5095.8 |
| LPZ294 | 564.7 | 171.4 | 1257.5 | 705.2 | 1357.7 | 1610.2 | 18.6 | | 2027.6 |
| LPZ295 | 823.1 | 97.3 | 2102.7 | 1056.2 | 2899.7 | 2698.3 | 39.4 | | 2448.2 |
| LPZ297 | 5273.4 | 169.1 | 5229 | 5074.4 | 5727.8 | 11512.9 | 423.2 | | 10966.8 |
| LPZ299 | 1564 | 161.1 | 1743.9 | 1752.3 | 2764.1 | 2660.5 | 63.5 | | 2791.9 |
| LPZ300 | 3068.3 | 205.4 | 2406.8 | 1881.8 | 2898.6 | 2758.4 | 0.2 | | 2007.2 |
| LPZ301 | 1979.7 | 233.1 | 3207.1 | 2109.3 | 4343.5 | 3713.8 | 40.4 | | 2690.6 |
| LPZ303 | 509 | 32.7 | 281.3 | 877.7 | 893.1 | 751.5 | 30.1 | | 1373.8 |
| LPZ304 | 2531.1 | 289.3 | 3809.4 | 3406.7 | 3674.8 | 3517.4 | 158 | | 2652.7 |
| LPZ306 | 22632.7 | 2861.2 | 34933.8 | 25435.6 | 40453.9 | 30906.9 | 1505.9 | | 34032.8 |
| LPZ307 | 2604.4 | 1395.2 | 4780.6 | 6945.3 | 4419.2 | 4416.9 | 232.6 | | 4299.8 |
| LPZ308 | 1093.9 | 60.5 | 2028.1 | 1751.6 | 1770.8 | 1891.9 | 92.4 | | 3245.8 |
| LPZ309 | 286.1 | 26 | 480.4 | 378.4 | 589.6 | 731.4 | 38.4 | | 1062.4 |
| LPZ310 | 2284.1 | 129.5 | 1622.7 | 1091.7 | 1207.1 | 3089.4 | 101.2 | | 3624.9 |
| LPZ311 | 3309.9 | 43.6 | 2782.6 | 2956.3 | 2828.8 | 4446.7 | 95.8 | | 5593.4 |
| LPZ312 | 446.3 | 52.7 | 1577.7 | 1221.4 | 542.2 | 518 | 56.1 | | 1952.6 |
| LPZ314 | 378.6 | 26.9 | 333.9 | 355.8 | 682.2 | 701.2 | 61.7 | | 732 |
| LPZ315 | 3897.5 | 115.2 | 2611.9 | 3145.8 | 4296 | 5240.2 | 151.3 | | 4499.3 |
| LPZ318 | 9709.6 | 767.1 | 19964.9 | 15678.3 | 20611.8 | 19600.2 | 475 | | 18079.9 |
| LPZ320 | 1126.7 | 82.8 | 1215 | 1002.7 | 1502.5 | 1555.3 | 67.5 | | 2964.4 |
| LPZ321 | 2944.7 | 85.4 | 2590.7 | 2597.6 | 2550.3 | 2962.7 | 72.1 | | 5481.4 |

| Clone | ZE1 | ZE2 | ZE3 | ZE4 | ZE5 | ZE6 | ZE7 | ZE8 | ZE9.1 |
|---|---|---|---|---|---|---|---|---|---|
| LPS001 | 369.9 | 369.9 | 369.9 | 369.9 | 369.9 | 369.9 | 369.9 | 369.9 | 369.9 |
| LPS003 | 600.3 | 363.9 | 0 | 243.7 | 1565.3 | 2624.5 | 1942.7 | 242 | 1892.5 |
| LPS004 | 522.3 | 254 | 0 | 74.6 | 907 | 2638.8 | 1933.6 | 274.9 | 4209.2 |
| LPS006 | 444.6 | 161.2 | 0 | 174.6 | 793.6 | 2651.4 | 1991.5 | 206.5 | 598.8 |
| LPS007 | 528.9 | 136.3 | 0 | 244.9 | 1623.3 | 1202.1 | 2044.7 | 245.1 | 213.9 |
| LPS008 | 534.5 | 215 | 0 | 281 | 1231.2 | 783.4 | 1760.3 | 178.5 | 832.4 |
| LPS010 | 469 | 183.6 | 1.3 | 240.1 | 947.7 | 591.6 | 2208.3 | 161.2 | 482.6 |
| LPS011 | 468.7 | 93.3 | 0 | 142.3 | 1544 | 1021.5 | 2334 | 254.6 | 1223.7 |
| LPS012 | 511 | 278 | 17.7 | 197.2 | 2129.6 | 68.9 | 1362.7 | 478.9 | 960.4 |
| LPS013 | 478.2 | 407.1 | 192.1 | 235.6 | 2470.6 | 9 | 1163.9 | 885.7 | 1109.4 |
| LPS014 | 579.7 | 369.1 | 0 | 272.7 | 2799.6 | 1525.7 | 2222.4 | 606.9 | 2638.6 |
| LPS015 | 419.7 | 254 | 0 | 2380.7 | 7188.1 | 4998.4 | 16519.6 | 5245.1 | 15550.4 |
| LPS019 | 1068.4 | 279.6 | 0 | 396.2 | 3848.5 | 3074 | 3866.9 | 959.1 | 3664.7 |
| LPS020 | 314.2 | 109.1 | 0 | 102.7 | 2036 | 234.4 | 1504.2 | 319.6 | 1053.2 |
| LPS023 | 364.9 | 104.2 | 0 | 100.7 | 1151.8 | 0 | 1253 | 175.5 | 570.5 |
| LPS024 | 804.7 | 213.8 | 0 | 346.3 | 3248.5 | 2523 | 2722.6 | 915 | 1987.4 |
| LPS025 | 1374.7 | 407.8 | 0 | 857.1 | 4731.2 | 2584.2 | 4119 | 1138.4 | 2458.4 |
| LPS026 | 337.6 | 86.1 | 0 | 100.2 | 1242 | 0 | 1052.9 | 242.9 | 988.9 |
| LPS027 | 440.5 | 182.5 | 0 | 118.5 | 1318 | 691.2 | 1274.1 | 226.1 | 385 |
| LPS028 | 369.5 | 166.2 | 0 | 168.7 | 2587.7 | 2597.8 | 4035.5 | 565.9 | 1883.1 |
| LPS029 | 323.4 | 141.9 | 0 | 165.3 | 2524.3 | 2147.2 | 3031.3 | 567 | 2263.9 |
| LPS030 | 362.3 | 226.5 | 0 | 169.6 | 1528.2 | 422.9 | 1236.7 | 239.2 | 1049.1 |
| LPS031 | 591 | 536.7 | 4.9 | 383.6 | 1768.3 | 850.4 | 1013.3 | 399.8 | 781.4 |
| LPS032 | 443.9 | 327.3 | 0 | 328.1 | 3200.9 | 1880.1 | 1832.8 | 265.6 | 1391.6 |
| LPS036 | 1093 | 781.8 | 24.5 | 680.8 | 3911.3 | 3750.9 | 3746.7 | 661.8 | 3856.4 |
| LPS037 | 501.6 | 180.4 | 0 | 200.9 | 2664 | 2369.8 | 1960.5 | 339.9 | 2892.9 |
| LPS038 | 1180.1 | 471 | 155.9 | 1679.7 | 4392.3 | 2103.5 | 3019.9 | 800.3 | 2819 |
| LPS040 | 398.8 | 108.6 | 0 | 103.9 | 1030.7 | 195.9 | 1566.1 | 144.4 | 682.1 |
| LPS041 | 384 | 153.8 | 0 | 149.7 | 989.2 | 1257.5 | 2235.4 | 143.3 | 1228.4 |
| LPS042 | 1381.9 | 951.7 | 44.9 | 716.1 | 3682.1 | 2755.7 | 4011.7 | 508.5 | 2963.4 |
| LPS043 | 1211.6 | 704.8 | 74 | 613.6 | 3494.4 | 2435.3 | 3362.1 | 391.4 | 1544.7 |
| LPS044 | 361.3 | 100.2 | 0 | 142.1 | 2244.4 | 3031.8 | 2653.5 | 393.4 | 1620.1 |
| LPS045 | 285.7 | 75.2 | 0 | 64.4 | 856.5 | 223.5 | 1616.1 | 216.8 | 609.7 |
| LPS046 | 325.8 | 217.2 | 0 | 70.2 | 1758.6 | 0 | 1280.9 | 284.9 | 1115.5 |
| LPS047 | 2041.3 | 1347.8 | 768.4 | 1080.5 | 4169.9 | 3927.9 | 4263.5 | 1831.6 | 4804.9 |
| LPS050 | 3226.4 | 3356.4 | 6064.5 | 3347.5 | 9841.4 | 3046 | 5362.2 | 2924.8 | 5821.2 |
| LPS051 | 377.1 | 96.4 | 0 | 156.8 | 2452.6 | 2286.5 | 3035 | 396 | 2238.1 |
| LPS052 | 330.1 | 80.1 | 0 | 162.6 | 2418.1 | 0 | 2097 | 352.5 | 1677.3 |
| LPS053 | 402.6 | 160.1 | 0 | 146.3 | 2249.5 | 56.9 | 1986.1 | 464.3 | 1349.6 |

TABLE II-continued

| | | | | | | | | | |
|---|---|---|---|---|---|---|---|---|---|
| LPS054 | 497.4 | 147.5 | 0 | 184 | 2188.4 | 379.1 | 1976.1 | 308.6 | 1558.9 |
| LPS055 | 1168.2 | 645.7 | 0 | 354.9 | 3901.1 | 1476.5 | 2607.5 | 774.8 | 3026.1 |
| LPS056 | 1549.5 | 1243.3 | 37.9 | 752.6 | 4770.9 | 3403.7 | 4086.8 | 1204.2 | 4958.4 |
| LPS057 | 387.5 | 154.3 | 0 | 262.7 | 2612.2 | 502.6 | 2317.5 | 365.1 | 1418.8 |
| LPS058 | 671.2 | 198.9 | 0 | 434.8 | 4189.9 | 2258.6 | 3366.3 | 586.3 | 2190.5 |
| LPS059 | 726.2 | 207.5 | 0 | 304.6 | 2974.8 | 2054.3 | 2712.8 | 395.1 | 1331.6 |
| LPS060 | 534.2 | 215.8 | 0 | 221.7 | 2896.9 | 718.3 | 2693.3 | 477 | 2474.9 |
| LPS061 | 530.8 | 369.4 | 0 | 204.3 | 1801.1 | 1286.4 | 1533.6 | 298.7 | 1327.2 |
| LPS062 | 407.4 | 305.2 | 0 | 226.4 | 1509 | 0 | 1413.1 | 212.5 | 954.6 |
| LPS063 | 619.4 | 280.8 | 0 | 282 | 3987.4 | 1805 | 2589.9 | 642.1 | 1650.4 |
| LPS064 | 3689.2 | 4982.4 | 10201 | 3080.3 | 8359.8 | 3622.3 | 8304.6 | 2997 | 13781.1 |
| LPS065 | 466.4 | 189.7 | 117.3 | 817.1 | 4336.3 | 2332.6 | 4393.4 | 1092 | 3866.8 |
| LPS066 | 269.5 | 104.6 | 0 | 131.4 | 1006.2 | 76.7 | 1834.6 | 185.9 | 668.5 |
| LPS067 | 426.4 | 179.7 | 49.3 | 341.3 | 4153 | 4077.7 | 5101.3 | 1195.9 | 3894.1 |
| LPS069 | 367.8 | 136.7 | 0 | 128 | 1456.6 | 0 | 2685.6 | 308.7 | 1234.3 |
| LPS070 | 438.5 | 137.3 | 0.4 | 111.6 | 1932.5 | 25 | 3005.3 | 210.4 | 721.5 |
| LPS071 | 283.9 | 83.2 | 8.5 | 109.2 | 1831.5 | 0 | 3634.2 | 302.8 | 708.3 |
| LPS072 | 301 | 147.2 | 5.7 | 132.9 | 1600.8 | 592.3 | 3051.5 | 331.5 | 1173.5 |
| LPS073 | 692.1 | 485 | 251.5 | 497.9 | 4205.3 | 2827.4 | 3777.9 | 740.1 | 3882 |
| LPS074 | 36280.3 | 66359.2 | 63362.2 | 44047.1 | 47176.9 | 20938.9 | 64534.5 | 33666.4 | 78457.8 |
| LPS075 | 3204.8 | 1250.6 | 650.9 | 1033.7 | 4976.3 | 4377.1 | 4632.6 | 1617.1 | 5570.9 |
| LPS076 | 434.7 | 127.9 | 0 | 204.7 | 1731.3 | 419.1 | 2737.8 | 298.8 | 2175.1 |
| LPS077 | 416.6 | 107.6 | 0 | 327.2 | 3360.7 | 1950.5 | 4020.1 | 609.1 | 3713.9 |
| LPS078 | 5164.5 | 1194.3 | 906.3 | 6556.7 | 20779.8 | 7364.3 | 28847 | 8680 | 22339.1 |
| LPS079 | 1317 | 501.9 | 304.2 | 893.4 | 5047.6 | 3196.6 | 4887.5 | 1058.8 | 4992.1 |
| LPS080 | 27721.4 | 56038.2 | 70896.6 | 26826.4 | 43426.4 | 20557.3 | 47819.2 | 16935.5 | 68145.5 |
| LPS081 | 36397.3 | 66337.3 | 48195.9 | 41685.3 | 46187.5 | 20628 | 66138.1 | 31620 | 78253.7 |
| LPS083 | 844.6 | 534.2 | 123.6 | 305.3 | 3724.2 | 1699.7 | 2524.6 | 583.8 | 3266.4 |
| LPS084 | 665 | 249.4 | 0 | 334.5 | 2570.6 | 1491.7 | 2893.2 | 342.8 | 2061.7 |
| LPS086 | 456.6 | 155.8 | 0 | 165.1 | 1962.7 | 754.5 | 1931 | 130.2 | 2176.5 |
| LPS087 | 967.5 | 450.7 | 17.2 | 633 | 4238 | 3720.3 | 5373.9 | 1754.7 | 19094.1 |
| LPS088 | 468.4 | 276.1 | 0 | 151.1 | 1109.4 | 0 | 1779.7 | 302.8 | 2497.2 |
| LPS089 | 329.2 | 316.9 | 0 | 133.6 | 988.7 | 0 | 1619.6 | 320.7 | 1616.9 |
| LPS090 | 478.9 | 272.3 | 0 | 218 | 4486.4 | 2182.3 | 2923.1 | 584.6 | 2640.7 |
| LPS091 | 385.7 | 177.9 | 0 | 290.7 | 2923.3 | 2008.6 | 2453.2 | 441.5 | 2246.6 |
| LPS092 | 396.3 | 164 | 0 | 345.2 | 2249.1 | 1219.1 | 2906.7 | 413.9 | 1589.3 |
| LPS093 | 308.3 | 164.5 | 24 | 98.7 | 262.3 | 427.8 | 2140 | 175.4 | 661.4 |
| LPS094 | 331.6 | 179 | 54.2 | 146.4 | 773.3 | 948.2 | 1729.1 | 116 | 1030.7 |
| LPS095 | 363.7 | 157.7 | 46.3 | 142.5 | 967.7 | 341.4 | 2639.7 | 199.3 | 1055.4 |
| LPS096 | 266.9 | 90.6 | 0 | 59.3 | 676.5 | 0 | 2616.2 | 136.5 | 215.6 |
| LPZ001 | 270.9 | 49.7 | 21.1 | 121.2 | 1958.2 | 496.8 | 4495.7 | 325.6 | 557.7 |
| LPZ002 | 491.7 | 231.8 | 157.9 | 345.8 | 1929.4 | 1183.4 | 3243.9 | 305.5 | 932.6 |
| LPZ003 | 632.6 | 407.2 | 342.3 | 343.5 | 2630.6 | 2108.3 | 3212.8 | 423 | 4663 |
| LPZ004 | 2034.4 | 2260.7 | 1487.4 | 1442.5 | 5730.7 | 2135.4 | 5424.1 | 1804.4 | 5786.1 |
| LPZ005 | 6301.3 | 4683.6 | 2801 | 10127.5 | 31972.9 | 7747.5 | 51335.5 | 17767 | 52067.8 |
| LPZ006 | 471.7 | 131.2 | 0 | 179.4 | 1964.1 | 1552.2 | 2977.9 | 333.5 | 2954.9 |
| LPZ007 | 584.6 | 383.7 | 69.3 | 294.3 | 1424.1 | 531 | 2664.9 | 265 | 3021.7 |
| LPZ008 | 325.4 | 87.5 | 14.4 | 176.8 | 1966.6 | 1588.5 | 2420.1 | 199.5 | 3481.2 |
| LPZ009 | 451.3 | 281.6 | 143.4 | 362.3 | 3149.2 | 4280.4 | 3006.5 | 357.5 | 4395.9 |
| LPZ010 | 1324.5 | 1442.8 | 621.8 | 931.8 | 4310.4 | 3238.7 | 3926.9 | 617.4 | 4912.5 |
| LPZ011 | 1740.9 | 2073.5 | 1436.2 | 1075.8 | 4631.4 | 5232.7 | 4563.3 | 1080.6 | 5456.6 |
| LPZ012 | 424.4 | 217.8 | 50.1 | 271.8 | 2286.7 | 713.5 | 1791.4 | 390.6 | 3209.9 |
| LPZ013 | 395.4 | 123.8 | 33.1 | 181.1 | 3456.8 | 2121 | 2898.4 | 428.9 | 2673.3 |
| LPZ015 | 490.7 | 210.7 | 60.8 | 130.8 | 2889.2 | 330.5 | 2123.4 | 230.2 | 2680.6 |
| LPZ016 | 2411.9 | 710.9 | 346.5 | 1201.2 | 6897.9 | 4057.6 | 13340.1 | 3246.1 | 16664.2 |
| LPZ017 | 635 | 257.4 | 36.2 | 247.2 | 2797.3 | 1219.1 | 3508 | 558.7 | 3953.8 |
| LPZ018 | 1405.4 | 474.9 | 214.9 | 3188.7 | 8143.7 | 4992.8 | 12908.9 | 4208.2 | 14318.9 |
| LPZ019 | 3487 | 975.9 | 698.4 | 8916.5 | 23680.5 | 15131 | 31656.3 | 14191 | 45343.3 |
| LPZ020 | 251.9 | 195.6 | 0 | 40.9 | 1448.5 | 860.4 | 1113 | 305.5 | 971.2 |
| LPZ022 | 250.1 | 112.4 | 0 | 133 | 2085.9 | 1282.5 | 2538.5 | 532 | 613.2 |
| LPZ023 | 355.5 | 122.6 | 22.9 | 47.8 | 224 | 879.4 | 1419.1 | 132.3 | 605.4 |
| LPZ024 | 366.5 | 108.9 | 45.7 | 94.8 | 225.3 | 723.1 | 1276.8 | 81 | 319.5 |
| LPZ025 | 705.4 | 278.6 | 202.1 | 716.7 | 5145.5 | 4563.4 | 7215.5 | 1581.9 | 4195.8 |
| LPZ026 | 268 | 100.6 | 9 | 92.1 | 1164.5 | 750.4 | 3973.6 | 275.5 | 642.3 |
| LPZ028 | 386 | 174.2 | 96.8 | 374.9 | 4188.4 | 2733.8 | 7024.6 | 1186.8 | 2375.6 |
| LPZ029 | 221.9 | 86.8 | 0 | 47.8 | 225.3 | 264.4 | 2172 | 162.4 | 957 |
| LPZ030 | 319 | 166 | 67.6 | 146.9 | 801.6 | 1385.4 | 2283.4 | 145.8 | 1189.4 |
| LPZ031 | 2010.6 | 881.7 | 538.1 | 754.3 | 4625.8 | 3395 | 4051.7 | 1327.9 | 5202.1 |
| LPZ032 | 36097.5 | 35972.1 | 13659.1 | 19975.4 | 45544.5 | 20035.8 | 63759.8 | 31117.4 | 78268 |
| LPZ033 | 1813.8 | 433.6 | 243.7 | 1171 | 7402.4 | 2278.7 | 10670.5 | 2204 | 5643.8 |
| LPZ034 | 332.6 | 97 | 34.6 | 181 | 1097.2 | 0 | 2704.1 | 262.6 | 3481.4 |
| LPZ035 | 248 | 60 | 0 | 71.4 | 1188.8 | 0 | 1332.5 | 153.6 | 3028.4 |
| LPZ037 | 375.8 | 133.8 | 0 | 114.6 | 3024.3 | 909.1 | 2350.6 | 248.2 | 3546.8 |
| LPZ038 | 577.7 | 237 | 44.3 | 370.7 | 4484.6 | 3572.5 | 4266 | 907.9 | 4571.4 |
| LPZ039 | 965.6 | 406.7 | 361.2 | 537.9 | 4020 | 2304.1 | 4269.9 | 816 | 3717.5 |
| LPZ040 | 399.9 | 127.4 | 0 | 88.3 | 1200.5 | 365 | 2123.2 | 244.3 | 1955.4 |
| LPZ041 | 318.4 | 105.1 | 0 | 136.6 | 856.3 | 716.6 | 1528.5 | 245.6 | 1538.5 |
| LPZ042 | 289.3 | 77.6 | 0.9 | 189.5 | 441.5 | 365.4 | 1007.7 | 239.2 | 1212 |
| LPZ043 | 417.3 | 166.7 | 57.4 | 158.2 | 1197.2 | 1617.9 | 793.5 | 569.1 | 2018.7 |

TABLE II-continued

| | | | | | | | | | |
|---|---|---|---|---|---|---|---|---|---|
| LPZ045 | 754.8 | 310.3 | 152 | 691.5 | 4810.4 | 3305.3 | 4043.7 | 1476.3 | 3925.7 |
| LPZ047 | 270.5 | 155.4 | 53.1 | 39.1 | 2165.6 | 579.6 | 980.9 | 361.7 | 1036.3 |
| LPZ049 | 809.6 | 381.9 | 0 | 461.4 | 4406.4 | 2277.4 | 4764.6 | 2257.8 | 5528 |
| LPZ051 | 333.1 | 121.5 | 0 | 56.6 | 1597.8 | 1677.8 | 891 | 270.7 | 1134.6 |
| LPZ053 | 271 | 119.7 | 0 | 16 | 1662.4 | 2447.8 | 1202.4 | 201.1 | 827.1 |
| LPZ054 | 345.4 | 131 | 61.7 | 79 | 1181.1 | 2238.5 | 1426.5 | 156.5 | 627.5 |
| LPZ055 | 291 | 78.1 | 102.9 | 63.5 | 551.3 | 2343.8 | 1433.5 | 193.6 | 814.2 |
| LPZ056 | 364.6 | 167.9 | 83.6 | 130.3 | 1816.9 | 2580.4 | 2589.4 | 343 | 1579.8 |
| LPZ057 | 250 | 76 | 0 | 11.9 | 426 | 457.6 | 2589.6 | 113.4 | 709.8 |
| LPZ058 | 231.1 | 40.8 | 6.2 | 44.4 | 454.7 | 163.4 | 3403.4 | 208.5 | 1300.4 |
| LPZ059 | 239.2 | 78.6 | 0 | 15.7 | 189.7 | 267 | 3272.7 | 141 | 1439.2 |
| LPZ060 | 235.1 | 26.7 | 29.4 | 35.6 | 524.8 | 1238.2 | 2231.2 | 182.5 | 1908.8 |
| LPZ061 | 402.1 | 268.4 | 141.6 | 254.6 | 1694.1 | 3088 | 2343.5 | 557.3 | 4157.7 |
| LPZ062 | 727.7 | 146.8 | 0 | 203.3 | 2873.3 | 2418.9 | 3109.6 | 926.6 | 5812 |
| LPZ063 | 316.7 | 108.2 | 25 | 190 | 1837.3 | 1025.1 | 2727.2 | 421.8 | 4195.9 |
| LPZ065 | 512.5 | 59.9 | 94.9 | 583.5 | 5694.4 | 3741.6 | 5366 | 1221.6 | 3911 |
| LPZ066 | 622.2 | 66.8 | 23.8 | 405.6 | 6932.1 | 3089.5 | 4804.9 | 642.2 | 4079.9 |
| LPZ067 | 883.7 | 218.7 | 0 | 358.7 | 4518.2 | 2342.9 | 5200.8 | 1318.4 | 5539.6 |
| LPZ069 | 335.6 | 100.2 | 0 | 46.8 | 0 | 0.7 | 1736.5 | 255.4 | 2910.4 |
| LPZ070 | 422.6 | 143.3 | 49.6 | 168.8 | 1231.5 | 1170.6 | 2432.2 | 262.7 | 2122.5 |
| LPZ071 | 356 | 71.9 | 0 | 299.7 | 2303.6 | 1909.8 | 2575.9 | 447 | 2827.6 |
| LPZ072 | 206.5 | 32.6 | 0 | 71.7 | 0 | 0 | 1362 | 189.6 | 907 |
| LPZ073 | 374.2 | 129.6 | 32.1 | 125.8 | 307.4 | 691.8 | 1617.6 | 282.4 | 1306.9 |
| LPZ074 | 434.7 | 86.5 | 0 | 76.6 | 1671.1 | 0 | 1112.5 | 232.7 | 663.5 |
| LPZ075 | 298.5 | 173.5 | 0 | 53.5 | 4083.2 | 0 | 1143.9 | 113.7 | 335.1 |
| LPZ076 | 209.9 | 83.1 | 7.2 | 7.4 | 2185.9 | 0 | 490.5 | 226.6 | 362.9 |
| LPZ077 | 813.4 | 558.3 | 0 | 339.1 | 3733.4 | 4279.8 | 1115.9 | 671.7 | 4136.8 |
| LPZ078 | 532 | 349.8 | 0 | 265.8 | 4460.1 | 3290.7 | 2776.8 | 686.3 | 3283.3 |
| LPZ079 | 347.8 | 183.6 | 11.6 | 53.3 | 2115.4 | 1191.7 | 1451.2 | 160.5 | 1233.2 |
| LPZ080 | 948.1 | 264.9 | 178 | 455.1 | 4633.9 | 2869.1 | 4230.5 | 1378.5 | 5566.5 |
| LPZ081 | 313.7 | 96.1 | 100.2 | 59.7 | 1161.6 | 1470.2 | 1119.7 | 98.5 | 710.9 |
| LPZ082 | 260.9 | 120.3 | 18.4 | 68.3 | 1734.5 | 1430.6 | 1581.6 | 160.1 | 379.4 |
| LPZ083 | 284.9 | 134.6 | 12.6 | 7.8 | 1067 | 906.1 | 1482.7 | 107.2 | 790.5 |
| LPZ084 | 1493.3 | 437.1 | 0 | 788 | 4497.3 | 4608.3 | 5078.9 | 2267.8 | 5087.7 |
| LPZ085 | 468.1 | 139.4 | 0 | 62.1 | 1618.8 | 1355.9 | 4314.9 | 340.5 | 2421.5 |
| LPZ086 | 601.3 | 91.6 | 11.9 | 332.9 | 3540.3 | 3354.6 | 6675.2 | 781.2 | 5545 |
| LPZ089 | 457.1 | 124.1 | 26.2 | 267.7 | 2378.1 | 3364.6 | 3390.2 | 448.7 | 2930.7 |
| LPZ090 | 436.6 | 50.7 | 0 | 149.1 | 3135.3 | 2087.8 | 3090.4 | 483.8 | 3408.1 |
| LPZ091 | 350.2 | 91 | 96.2 | 99.2 | 1524.3 | 1976.3 | 3215 | 315.9 | 4532.8 |
| LPZ092 | 387.6 | 33.6 | 0 | 114.4 | 2386.7 | 2600.9 | 2845.7 | 274.6 | 2036.7 |
| LPZ093 | 195.6 | 25.8 | 0 | 27.1 | 2343.1 | 321.7 | 2875.2 | 252.7 | 1428.2 |
| LPZ094 | 274.8 | 42.8 | 0 | 35.2 | 886.9 | 0 | 2502 | 152.6 | 1571 |
| LPZ095 | 288.6 | 91.5 | 0 | 14.1 | 3.5 | 0 | 2317.2 | 144.4 | 1427.4 |
| LPZ096 | 475.4 | 138.7 | 13.1 | 199.2 | 1690.8 | 1415.2 | 3939.2 | 207.2 | 1889.7 |
| LPZ099 | 428.1 | 73.8 | 0 | 185 | 2531.8 | 2596.6 | 3925.9 | 399.8 | 1967.5 |
| LPZ100 | 474.3 | 131.1 | 24.6 | 266.6 | 2710.6 | 2276.7 | 3358.6 | 503.5 | 2245.1 |
| LPZ101 | 492.1 | 101 | 81.9 | 233 | 2341.4 | 2076.1 | 2199.9 | 423.1 | 2022.4 |
| LPZ102 | 477.3 | 133.2 | 0 | 167 | 3722.9 | 1604.4 | 2432.1 | 386.5 | 1199.8 |
| LPZ103 | 353.5 | 90.7 | 0 | 108.9 | 4756.8 | 214.4 | 1447.5 | 203.9 | 760.7 |
| LPZ106 | 534 | 199.4 | 58.6 | 117.6 | 3052.4 | 1259.2 | 1610 | 277.6 | 1224.3 |
| LPZ107 | 29718.3 | 56194.4 | 31132.5 | 35651.5 | 44972.5 | 20589.6 | 38396.3 | 32828.7 | 75965.1 |
| LPZ108 | 852.4 | 433.1 | 161.4 | 417.4 | 4354.8 | 2259.1 | 3536.9 | 1168.5 | 3161.8 |
| LPZ109 | 554.2 | 248.6 | 83.8 | 254.6 | 3303.4 | 2521.1 | 1972.8 | 608.5 | 2858.5 |
| LPZ110 | 614 | 203.3 | 166.1 | 182.1 | 3236.7 | 2792.6 | 2764.1 | 455.5 | 3139.2 |
| LPZ111 | 349.5 | 167.7 | 77.4 | 82.9 | 1407 | 1386.1 | 1469 | 200.9 | 1397.5 |
| LPZ112 | 497.3 | 279.2 | 65.3 | 242.6 | 3553.5 | 2504.1 | 2454.6 | 328.3 | 2182.2 |
| LPZ114 | 890.2 | 346.7 | 0 | 399.3 | 4520 | 3367.9 | 2902.7 | 1229.6 | 3474.1 |
| LPZ115 | 24782.8 | 12016.1 | 1401.9 | 12188 | 32718.2 | 17087 | 38203.9 | 17191.1 | 25318.5 |
| LPZ116 | 1388.1 | 392.7 | 0 | 884.6 | 8895.4 | 3131.2 | 15554.1 | 2195.7 | 5401.6 |
| LPZ117 | 6228.4 | 4810.2 | 389.7 | 1298.8 | 4199 | 2671 | 5473.5 | 1488.2 | 3911 |
| LPZ118 | 424.5 | 267.3 | 39.9 | 196.2 | 2507.4 | 2210.1 | 2856.3 | 370.3 | 2640.4 |
| LPZ119 | 295.1 | 183.4 | 0 | 59.8 | 2443.3 | 1153.2 | 2040 | 158.7 | 1132.1 |
| LPZ120 | 213.5 | 88.4 | 49.2 | 185.9 | 1336.6 | 1390.4 | 1604.5 | 186.7 | 1360.8 |
| LPZ122 | 317.6 | 120.3 | 0 | 92.1 | 1390.2 | 2045.1 | 1701.2 | 112.5 | 1307.5 |
| LPZ124 | 346.6 | 173.2 | 38.9 | 119.4 | 2097.9 | 543.9 | 2679.2 | 221 | 1941.7 |
| LPZ126 | 436.1 | 185.4 | 0 | 142 | 1762.2 | 0 | 2164 | 283.2 | 2343.6 |
| LPZ127 | 455.7 | 208.6 | 0.1 | 109.8 | 1091.7 | 1925.5 | 3143.4 | 345.4 | 2565.8 |
| LPZ128 | 421 | 602.3 | 25.1 | 651.1 | 4496.3 | 2712.3 | 5456.8 | 1177.7 | 3875.7 |
| LPZ131 | 287.1 | 401.2 | 0 | 58 | 1931.2 | 422.4 | 3510.2 | 232.2 | 1275.8 |
| LPZ133 | 377.8 | 399.9 | 141.9 | 139.5 | 2396.5 | 1989.9 | 4287.5 | 388.9 | 1119.6 |
| LPZ136 | 455.2 | 191.7 | 103.3 | 239.9 | 2289.7 | 1775 | 2586.1 | 322.4 | 1429.8 |
| LPZ137 | 398.1 | 123.1 | 0 | 214.7 | 2480.2 | 1118.7 | 2138.5 | 411.3 | 1935.9 |
| LPZ138 | 1987.8 | 1102.2 | 11.9 | 1112.7 | 4785.6 | 4242.8 | 3044.7 | 1298.3 | 2786.7 |
| LPZ140 | 401.4 | 205.9 | 115 | 316.7 | 2737.2 | 1950.6 | 1491.6 | 414.2 | 2031.4 |
| LPZ141 | 917 | 621.2 | 0 | 726 | 4938.4 | 3889.9 | 3237.4 | 1109 | 4165.8 |
| LPZ143 | 4702.9 | 1483.9 | 774.8 | 6791.2 | 20187.4 | 6913.4 | 23175.5 | 10795.1 | 26322.7 |
| LPZ144 | 529.7 | 392.6 | 25.7 | 303.5 | 2644.9 | 1902.4 | 2380.9 | 486 | 2422.7 |
| LPZ145 | 410.2 | 206.5 | 25.4 | 152.3 | 1618 | 2219.1 | 2012.8 | 357.8 | 2494.3 |
| LPZ146 | 294.2 | 152.3 | 0 | 125.3 | 1063.5 | 1142.1 | 1129 | 215.1 | 1927.1 |

TABLE II-continued

| | | | | | | | | | |
|---|---|---|---|---|---|---|---|---|---|
| LPZ147 | 366.5 | 238 | 0 | 246.5 | 2120.4 | 956.1 | 1343.4 | 260.2 | 1539.3 |
| LPZ148 | 390.6 | 212.9 | 0 | 170 | 2107.1 | 2195.4 | 1832.6 | 1240.9 | 3839.8 |
| LPZ149 | 1872.8 | 1139.7 | 218.5 | 1748 | 6204.2 | 1641.3 | 5144.7 | 3526.5 | 5193.6 |
| LPZ150 | 1958.1 | 1284.1 | 645.6 | 10615.2 | 29419.9 | 2976.7 | 52052.2 | 21478.7 | 41125.9 |
| LPZ151 | 3477.3 | 1936.4 | 155.4 | 1423.9 | 5253.1 | 1925.1 | 5434.9 | 2248.3 | 5180.5 |
| LPZ152 | 963.2 | 481.9 | 42.2 | 658.9 | 4770.8 | 3607.7 | 4661.8 | 1003 | 4661.9 |
| LPZ153 | 13685.9 | 27883.7 | 11205.9 | 13827.1 | 24872.9 | 15412 | 26204.7 | 12163.3 | 41713.9 |
| LPZ154 | 621.9 | 470.5 | 45.6 | 381.1 | 2965 | 2584.3 | 2802.2 | 416.8 | 2738.4 |
| LPZ155 | 2004.5 | 1513.1 | 388.4 | 1358.9 | 4265.3 | 4159.3 | 4386.4 | 1022.6 | 4543.9 |
| LPZ157 | 2978.4 | 1332.8 | 407.8 | 1400.6 | 4650.6 | 3692.3 | 4760.8 | 1195.9 | 5002.5 |
| LPZ158 | 12352.4 | 18933.2 | 12155.7 | 9376.4 | 23120 | 15280.6 | 18384 | 10293.8 | 50995.4 |
| LPZ162 | 3778.2 | 4069.3 | 426.4 | 2285.5 | 6458.4 | 3004.6 | 5794.3 | 4161.4 | 13171.9 |
| LPZ165 | 1181 | 805.1 | 0 | 756.4 | 4641.9 | 2702.4 | 5464.6 | 1470 | 4822.6 |
| LPZ166 | 4624.9 | 5016.4 | 0 | 2508.8 | 9907.8 | 1939.3 | 5655.3 | 2999.9 | 5667.6 |
| LPZ167 | 3339 | 1655.9 | 319.8 | 1101.8 | 4807 | 4980 | 4678.8 | 1968.2 | 4248.1 |
| LPZ169 | 787.5 | 556.1 | 226.4 | 461.9 | 2830.2 | 2225.4 | 3549.7 | 684.4 | 3249 |
| LPZ170 | 851.1 | 501.5 | 0 | 589.6 | 4405.2 | 4440.6 | 4652.4 | 1622.7 | 4556.9 |
| LPZ171 | 1325.6 | 612.2 | 0 | 697.6 | 3647.5 | 3148.7 | 3446.8 | 1053.8 | 4043.4 |
| LPZ172 | 748.6 | 490.4 | 0 | 802.4 | 3953.2 | 2939.1 | 3550.9 | 848.3 | 3809.5 |
| LPZ173 | 4460.6 | 3415.7 | 1050.1 | 5769.8 | 16078.4 | 6658.8 | 16861.6 | 8623.4 | 21007.1 |
| LPZ174 | 501.9 | 308.6 | 36.2 | 358.6 | 3054.1 | 1731.2 | 1954.9 | 862.9 | 2773.9 |
| LPZ175 | 1476.5 | 1057.1 | 181.6 | 836.9 | 3731.4 | 3120.9 | 3879.4 | 755.9 | 3687.2 |
| LPZ177 | 302.3 | 228.3 | 18.6 | 107.1 | 753.6 | 1430.4 | 941 | 165.4 | 1411.2 |
| LPZ179 | 616.8 | 314.9 | 8 | 379.4 | 4544.7 | 2954.4 | 3425.3 | 1361.5 | 5310.3 |
| LPZ181 | 1103 | 430.7 | 0 | 671.3 | 4917.1 | 3821.3 | 4976.3 | 2646.1 | 5785.8 |
| LPZ182 | 992.8 | 435.1 | 0 | 468.1 | 3930.1 | 4177.6 | 3287.5 | 909.9 | 4820.2 |
| LPZ186 | 2455.7 | 1428.7 | 760 | 2414.4 | 9679 | 4431.1 | 5537.9 | 3859.3 | 5921.7 |
| LPZ189 | 40770.3 | 68311.4 | 75133.7 | 45673 | 47303.1 | 21072.6 | 66542.7 | 34849.1 | 78485.4 |
| LPZ194 | 612.8 | 572.1 | 155.6 | 376.3 | 3673.5 | 2240.2 | 3365.2 | 469.5 | 3608.6 |
| LPZ195 | 676.9 | 346.6 | 32.5 | 459.9 | 4278.1 | 4622.4 | 4442 | 1006.8 | 4754.3 |
| LPZ196 | 2923.1 | 1787.1 | 448.6 | 1537.1 | 4490.3 | 3684 | 4875.6 | 1426.9 | 4447.8 |
| LPZ197 | 592.3 | 177.5 | 343.1 | 629.4 | 5825.4 | 3639.7 | 4308.7 | 649.9 | 2838.2 |
| LPZ198 | 801.7 | 295 | 8.2 | 511.1 | 4384 | 3156.4 | 4823.8 | 1125.6 | 3947.2 |
| LPZ199 | 402.5 | 165.1 | 62.7 | 265.9 | 2158.3 | 2363.7 | 3531.7 | 423 | 2360.1 |
| LPZ201 | 1338.5 | 361.2 | 209.6 | 1053.7 | 4997.8 | 4565.6 | 5107.6 | 2350.9 | 5882.2 |
| LPZ202 | 8178.9 | 2795.3 | 2359.9 | 12950.9 | 39890.9 | 20247.9 | 62085.4 | 31826.4 | 78541.6 |
| LPZ203 | 1983.5 | 1083.8 | 1146.8 | 2044.1 | 9173.9 | 2174.8 | 11135.5 | 4073.8 | 19571.3 |
| LPZ204 | 38154.8 | 66241.1 | 88440.7 | 45372.1 | 47166 | 21054.3 | 65826.6 | 33875.6 | 78581.7 |
| LPZ205 | 1079.5 | 521.7 | 589.1 | 758.4 | 4742.5 | 3837.7 | 5220.2 | 1453.2 | 4888.6 |
| LPZ206 | 947.6 | 700.1 | 505.1 | 697.8 | 4089.6 | 2774.1 | 5242.9 | 1190.3 | 4578.7 |
| LPZ207 | 39899.6 | 60813.3 | 95637.5 | 45997 | 47123.6 | 21073.2 | 63996.4 | 35149.4 | 73080.5 |
| LPZ208 | 27268.6 | 27230.4 | 39428.3 | 29579 | 40216.5 | 20480.2 | 42465.8 | 26526.9 | 76872.4 |
| LPZ210 | 683.8 | 538 | 429.6 | 439.8 | 2402.5 | 3285.4 | 2419.1 | 636 | 3965.6 |
| LPZ211 | 603.1 | 530.3 | 87.2 | 434.6 | 3653.3 | 2234.5 | 1744.1 | 359.8 | 1644.7 |
| LPZ212 | 1018.4 | 580.7 | 155.2 | 1734.1 | 9212.3 | 2338.9 | 5061.9 | 2257.3 | 4303.3 |
| LPZ213 | 465.6 | 327.1 | 33.1 | 296.6 | 3012.3 | 2419.4 | 2198.4 | 570.9 | 2013.9 |
| LPZ214 | 245.6 | 267.4 | 0 | 160.5 | 912.5 | 756.5 | 880.7 | 133.9 | 936.8 |
| LPZ215 | 981.1 | 492.8 | 52.3 | 828.3 | 5390.6 | 4771.4 | 4868.1 | 2893.1 | 15622.6 |
| LPZ216 | 9410.5 | 3834.8 | 1843.2 | 14492.9 | 43137.1 | 21097.9 | 63778.6 | 34830.7 | 78538.8 |
| LPZ217 | 31119.9 | 47126.3 | 30689.1 | 28515.4 | 38695.3 | 19884.5 | 37913.9 | 21282.9 | 69590.2 |
| LPZ219 | 1300.2 | 886.5 | 475.3 | 946.3 | 4898.3 | 4361.6 | 3705.4 | 1784.6 | 5810 |
| LPZ220 | 5695.5 | 7233.6 | 9375 | 4579.9 | 6540.8 | 4340.1 | 5612.6 | 2993.6 | 5852.3 |
| LPZ221 | 242.6 | 209.5 | 0 | 186.3 | 2553.4 | 2132.5 | 1632.9 | 258.2 | 3202.9 |
| LPZ222 | 186.9 | 130.5 | 0 | 163.4 | 2138.4 | 1386.3 | 1855.4 | 223.3 | 2407.6 |
| LPZ223 | 289.9 | 168.4 | 0 | 164 | 2019 | 1582.7 | 2374.4 | 250.3 | 2309.2 |
| LPZ224 | 308.3 | 114.3 | 20.5 | 333.9 | 2467.7 | 2535.2 | 2722.9 | 518.9 | 3054.9 |
| LPZ225 | 5540.8 | 1287.2 | 919.3 | 7087.6 | 18926.6 | 9277.7 | 20292.9 | 8705.5 | 19974.7 |
| LPZ226 | 179.1 | 111 | 9 | 136.8 | 1049.8 | 2071.1 | 3332.8 | 463.4 | 2517.8 |
| LPZ227 | 243.5 | 136.2 | 0 | 341.4 | 2502.5 | 2597.6 | 4869.5 | 3226.2 | 16356.7 |
| LPZ228 | 470 | 249.6 | 0 | 349.2 | 4062.6 | 3388.6 | 5688.3 | 2586.2 | 15112.1 |
| LPZ231 | 480.4 | 296.3 | 87.4 | 326.6 | 3832.4 | 2343.1 | 5557.3 | 1542.5 | 5679.2 |
| LPZ233 | 468.6 | 332.9 | 161.7 | 350.3 | 2519.3 | 1967.1 | 5201.8 | 996.1 | 4833.8 |
| LPZ234 | 525.8 | 368.6 | 287.8 | 380.3 | 1626.6 | 1285.8 | 4231.8 | 1235 | 5329.5 |
| LPZ235 | 310.7 | 233.3 | 0 | 370.2 | 1746.3 | 1474.1 | 4135.8 | 541.1 | 3382.9 |
| LPZ237 | 683.5 | 468.8 | 487.2 | 506.9 | 3683.2 | 2108.7 | 3966.8 | 1369 | 5254.5 |
| LPZ239 | 546 | 192.6 | 339.2 | 331.5 | 2584.8 | 2384.8 | 3215.7 | 754.4 | 4041.1 |
| LPZ240 | 353.7 | 280.8 | 163.9 | 274.8 | 2281.8 | 1696.4 | 2345.8 | 319.2 | 2180.8 |
| LPZ241 | 283.3 | 260.2 | 0 | 206.4 | 2481.1 | 1787.8 | 775.1 | 426 | 1729.3 |
| LPZ242 | 7478.4 | 2664.4 | 1039.1 | 7024.1 | 22393.3 | 11120.5 | 20928.9 | 8581.6 | 22951.9 |
| LPZ243 | 242.4 | 167.1 | 0 | 157.2 | 2175.8 | 182.4 | 806.9 | 237.7 | 977.2 |
| LPZ244 | 350.3 | 206.1 | 0 | 409.4 | 4522.7 | 3997.1 | 4486.3 | 1022.8 | 3387.1 |
| LPZ246 | 260.9 | 200.9 | 0 | 251.8 | 1930.9 | 1335.1 | 995.1 | 1033.7 | 4712.9 |
| LPZ247 | 438.3 | 274.4 | 0 | 341.4 | 2994 | 2325.3 | 2926.7 | 1508.7 | 5494.3 |
| LPZ248 | 748.4 | 714.1 | 291.3 | 878.4 | 3814.2 | 2737.7 | 3489 | 1155.1 | 4689.5 |
| LPZ249 | 373.3 | 375.6 | 0 | 613.1 | 4798.1 | 2088 | 3560.8 | 433.5 | 2486.3 |
| LPZ250 | 159.5 | 201.7 | 0 | 317.6 | 2037.8 | 2085.9 | 1721.8 | 220.5 | 2051.7 |
| LPZ251 | 141.7 | 157.9 | 0 | 178.9 | 1377.4 | 1723.8 | 1136.8 | 91 | 1271.1 |
| LPZ255 | 220.8 | 176.1 | 0 | 646.5 | 4160.8 | 2725.5 | 5110.3 | 1217.2 | 5217.7 |
| LPZ256 | 94.6 | 101.7 | 0 | 149.5 | 821 | 812.6 | 1989.5 | 65.4 | 432.2 |

TABLE II-continued

| | | | | | | | | | |
|---|---|---|---|---|---|---|---|---|---|
| LPZ257 | 147.9 | 118.4 | 0 | 135.1 | 1206.9 | 1208.1 | 2197.2 | 207.9 | 745.8 |
| LPZ258 | 168.3 | 124 | 0 | 174.7 | 2264 | 2172.4 | 2672.8 | 532.8 | 2245.2 |
| LPZ260 | 213.5 | 172.9 | 0 | 141.3 | 1172 | 2974.6 | 4118.3 | 232.4 | 1057.4 |
| LPZ261 | 147.2 | 78.5 | 0 | 126.6 | 1212.5 | 2349.9 | 4604.9 | 139.4 | 741.8 |
| LPZ264 | 318.3 | 174.1 | 0 | 201.7 | 3104.4 | 2387.6 | 5505.8 | 582.7 | 3775.1 |
| LPZ265 | 1566.8 | 449.9 | 129.7 | 646 | 4992.3 | 3477.7 | 5635.5 | 988.7 | 4307.2 |
| LPZ266 | 92.8 | 287.2 | 0 | 132.5 | 931.4 | 0 | 4689 | 190 | 726.3 |
| LPZ268 | 171.3 | 217.2 | 0 | 206.8 | 2142 | 2135.8 | 5156.3 | 296.8 | 1912 |
| LPZ269 | 1530.1 | 571.5 | 419.3 | 2333.1 | 11130.7 | 4947.4 | 13881.5 | 5155.2 | 5755.6 |
| LPZ270 | 162.3 | 291.4 | 0 | 450.4 | 3822 | 3736.4 | 4342.8 | 978.4 | 2987 |
| LPZ271 | 454.6 | 266.6 | 45.9 | 381.8 | 3194.7 | 2859.7 | 3598.7 | 1277.5 | 4054 |
| LPZ272 | 2943.2 | 763.9 | 613.2 | 1451.3 | 7894.9 | 2900.8 | 5222.6 | 3222.4 | 16317.5 |
| LPZ273 | 215.5 | 178.7 | 0 | 112.2 | 1288.3 | 908.3 | 145.5 | 182.5 | 544.8 |
| LPZ274 | 271.5 | 189.3 | 0 | 322.8 | 3311.7 | 1141.5 | 1301.4 | 620.8 | 3182.2 |
| LPZ275 | 174.5 | 152.8 | 0 | 99.6 | 1052.3 | 0 | 0 | 109.3 | 887.1 |
| LPZ276 | 146.8 | 139 | 0 | 129.4 | 1165.3 | 123.5 | 505.4 | 82.6 | 461.9 |
| LPZ277 | 201.8 | 137.5 | 1.8 | 57.1 | 761.5 | 931.9 | 497.5 | 106.1 | 1427.3 |
| LPZ278 | 177.9 | 152 | 0 | 76.6 | 588.2 | 1424 | 311.2 | 107.3 | 1178.8 |
| LPZ279 | 183.3 | 179.3 | 0 | 304.9 | 2458 | 1032 | 524.7 | 276 | 1530.9 |
| LPZ280 | 142.1 | 125.5 | 0 | 125.6 | 1116.5 | 623.5 | 1147.9 | 125.4 | 770.5 |
| LPZ281 | 18 | 109.8 | 0 | 58.9 | 563.4 | 850.5 | 564.6 | 11.5 | 317.8 |
| LPZ282 | 54.3 | 164.1 | 48 | 95.5 | 1493.6 | 1874.9 | 1033.3 | 54.7 | 844 |
| LPZ283 | 1607.8 | 392.6 | 48.4 | 1220 | 6358.1 | 2922.6 | 5552.8 | 1970.3 | 5032.3 |
| LPZ284 | 42.5 | 119.4 | 0.3 | 48 | 804 | 748.4 | 1365.8 | 66.6 | 0 |
| LPZ286 | 34.3 | 164.5 | 0 | 74.8 | 973.6 | 1463.4 | 1205.7 | 81.2 | 329.3 |
| LPZ287 | 118.8 | 186.4 | 0 | 116.4 | 1573.7 | 1568.6 | 2124 | 252.9 | 884.4 |
| LPZ288 | 103.4 | 162.8 | 0 | 78.3 | 1328.1 | 2890.4 | 4192.3 | 196.9 | 598.1 |
| LPZ289 | 137.1 | 87 | 0 | 113.6 | 2096 | 2101 | 5147.9 | 332.3 | 913.7 |
| LPZ290 | 1598 | 425.5 | 186 | 1782.8 | 10543.9 | 4598.5 | 16706.4 | 3923.8 | 5648.6 |
| LPZ293 | 155.8 | 225.7 | 0 | 129.9 | 3228.2 | 2291.5 | 4891.2 | 316.9 | 2001 |
| LPZ294 | 65.5 | 180.6 | 0 | 66.6 | 2237.5 | 527.7 | 4397.4 | 127.5 | 688.2 |
| LPZ295 | 119.9 | 258.8 | 0 | 149.7 | 1964.6 | 560.6 | 5062.1 | 141.5 | 897.3 |
| LPZ297 | 333.9 | 277.6 | 59.4 | 830 | 5667.2 | 3950.7 | 5680.5 | 1452.6 | 3614 |
| LPZ299 | 102.6 | 225 | 12.2 | 268.1 | 734.7 | 898.2 | 4025.5 | 371.2 | 913 |
| LPZ300 | 231 | 271.7 | 97.1 | 42.6 | 113.2 | 1713.7 | 3264.5 | 4295.2 | 631.1 |
| LPZ301 | 272.7 | 378.2 | 155.6 | 97.2 | 77.2 | 2110.4 | 1733.8 | 485.6 | 1392.8 |
| LPZ303 | 145.6 | 184.3 | 641.8 | 52.8 | 1562.5 | 1072.8 | 365 | 55.5 | 358.3 |
| LPZ304 | 422.5 | 346.5 | 108.2 | 350.8 | 3262.7 | 2215 | 1102.8 | 264.1 | 1534.7 |
| LPZ306 | 2207.6 | 484.7 | 609 | 3182.2 | 9671.4 | 3639.8 | 17157.3 | 3556.4 | 15015.7 |
| LPZ307 | 1761.1 | 1119.4 | 454.7 | 846.1 | 4114.9 | 2673.3 | 4082.5 | 554.8 | 2983.5 |
| LPZ308 | 153.5 | 213.5 | 85.5 | 113.3 | 1369.9 | 1433.3 | 133.8 | 123.2 | 1146 |
| LPZ309 | 132 | 192 | 14.3 | 49.2 | 1137.6 | 1626.7 | 126.9 | 85.1 | 805.1 |
| LPZ310 | 325.9 | 353.6 | 311.3 | 253.1 | 4210.4 | 2703.3 | 1846.5 | 513.3 | 3102.9 |
| LPZ311 | 176.9 | 217.7 | 72.3 | 245 | 3652.2 | 4352.6 | 4175.7 | 734.7 | 4625.7 |
| LPZ312 | 70.4 | 177.2 | 139.4 | 53.2 | 2094.2 | 1461.1 | 945.5 | 57 | 274 |
| LPZ314 | 247.5 | 221.2 | 217.2 | 66.9 | 1767 | 753.8 | 872.4 | 93.1 | 751.2 |
| LPZ315 | 167.6 | 220.4 | 322.5 | 172.9 | 3442.4 | 1985.7 | 2505.1 | 698.5 | 3667.7 |
| LPZ318 | 912.5 | 297.8 | 441.9 | 957.6 | 7473.1 | 2682.6 | 6826.4 | 2471.8 | 5148.9 |
| LPZ320 | 7.3 | 212.8 | 154.8 | 55.8 | 1682.1 | 1548.5 | 1038.5 | 111.1 | 822.5 |
| LPZ321 | 199 | 259.6 | 157.2 | 96.8 | 2588.8 | 2465.4 | 3436.8 | 409.2 | 3989 |

| Clone | ZE9.2 | ZE9.3 | ZE9.4 | ZE9.5 | ZE9.6 | ZE9.7 | ZE9.8 | ZE9.9 | ZE9.10 |
|---|---|---|---|---|---|---|---|---|---|
| LPS001 | 369.9 | 656.8 | 1322 | 4095.5 | 4733.4 | 7892.2 | 3248.2 | 5064.2 | 6260.9 |
| LPS003 | 442.5 | 392.9 | 262.1 | 648.7 | 2035.7 | 570.6 | 4524.4 | 1332.8 | 543.9 |
| LPS004 | 811.4 | 552.2 | 515.2 | 1694.9 | 2438.2 | 425.1 | 1218.8 | 714.3 | 86.8 |
| LPS006 | 271 | 141.2 | 200.2 | 0 | 662.1 | 1245.1 | 261.5 | 1282.6 | 405.7 |
| LPS007 | 212.1 | 91.8 | 139 | 47.7 | 243.4 | 0 | 929.2 | 568 | 267.1 |
| LPS008 | 197.6 | 196.8 | 224.7 | 0 | 235.1 | 2144.5 | 1034.5 | 985.2 | 307.3 |
| LPS010 | 152.7 | 133.4 | 253.8 | 241 | 299.5 | 1667.7 | 242.1 | 1218.8 | 1170 |
| LPS011 | 186 | 136.1 | 257.9 | 816.5 | 257.4 | 2372.2 | 77.7 | 1377.7 | 1346.8 |
| LPS012 | 317.2 | 238.4 | 236.4 | 817.5 | 1316.7 | 1626.1 | 0 | 1324.1 | 564.7 |
| LPS013 | 349.5 | 403.6 | 412.9 | 1840 | 1582.6 | 2769.8 | 215.4 | 1196 | 1328.8 |
| LPS014 | 511.4 | 1574.1 | 257.3 | 4169.4 | 5035.7 | 4543.5 | 1016.4 | 3744.8 | 3779.2 |
| LPS015 | 2495.9 | 3076.7 | 1720.8 | 7899.3 | 3640.5 | 7103 | 1228.1 | 5376.7 | 11989 |
| LPS019 | 1028.2 | 604.5 | 239.7 | 3074 | 2189.3 | 2161.1 | 1239.9 | 2955 | 2426.7 |
| LPS020 | 324.1 | 222.9 | 120.5 | 1214.3 | 1056.8 | 676.2 | 872.7 | 916.8 | 1058.1 |
| LPS023 | 160.9 | 116.3 | 50.3 | 623.9 | 1984.1 | 0 | 640.7 | 349.7 | 694.3 |
| LPS024 | 359.3 | 324.3 | 198.9 | 1596 | 2789.8 | 1253.1 | 1212.2 | 2644.1 | 3158.3 |
| LPS025 | 614.7 | 616.8 | 493.6 | 3452.4 | 3736.3 | 3726.5 | 1796.1 | 4133.4 | 5569.5 |
| LPS026 | 153.7 | 494.7 | 0 | 3053.4 | 3077.5 | 2157.2 | 806.2 | 3886.5 | 2133.1 |
| LPS027 | 132.2 | 267.1 | 0 | 1309.2 | 2323.4 | 1330.2 | 1501.6 | 1931.3 | 1355.1 |
| LPS028 | 214.3 | 446.5 | 155.7 | 2472.5 | 3336.1 | 2467.9 | 2987.9 | 4507.5 | 3530.8 |
| LPS029 | 202.7 | 384.3 | 223 | 2040.4 | 2060.5 | 2600.8 | 7214.8 | 4150 | 3867.7 |
| LPS030 | 113.5 | 132.5 | 0 | 515.6 | 2793.9 | 110 | 2158.7 | 2684.7 | 1237 |
| LPS031 | 168.7 | 123.5 | 11 | 557.6 | 3086 | 812.5 | 6212.6 | 2534.1 | 3290.9 |
| LPS032 | 145.2 | 160.9 | 1.7 | 650.5 | 2144.2 | 1070.8 | 1474.2 | 2819 | 3561.4 |
| LPS036 | 582.6 | 616.4 | 200.9 | 2224.2 | 2656.4 | 1723.6 | 3073.1 | 1866.1 | 2955.4 |
| LPS037 | 502.6 | 620.4 | 219 | 1626.6 | 3359.2 | 2705.7 | 2125.3 | 2456.9 | 2004.1 |

TABLE II-continued

| | | | | | | | | | |
|---|---|---|---|---|---|---|---|---|---|
| LPS038 | 962.6 | 216.5 | 375.7 | 0 | 1256.5 | 930.9 | 1492.9 | 1578.3 | 1406.9 |
| LPS040 | 228.9 | 86.1 | 158.6 | 0 | 256.8 | 0 | 245.1 | 758.3 | 1.7 |
| LPS041 | 222.7 | 149.2 | 123.3 | 0 | 252.4 | 0 | 965.1 | 1065.9 | 553.4 |
| LPS042 | 447 | 661.1 | 489.9 | 1672.8 | 2520.7 | 492 | 1046.8 | 2834.7 | 1940 |
| LPS043 | 333.7 | 264.6 | 407.3 | 656.8 | 1046.4 | 546.5 | 1412.3 | 1097.9 | 948.4 |
| LPS044 | 249.8 | 277.8 | 652 | 1327.3 | 907.5 | 1110.5 | 1892.3 | 1353.4 | 1674.8 |
| LPS045 | 250.7 | 107.2 | 177.9 | 302.6 | 231.9 | 944.7 | 1881.7 | 0 | 485.4 |
| LPS046 | 232.4 | 285.6 | 224.5 | 1302.1 | 1872.6 | 1104.6 | 2610.7 | 1128 | 1744.2 |
| LPS047 | 2649.2 | 6969.7 | 2792.6 | 14436.1 | 10141 | 5428.8 | 4057.3 | 2999.2 | 13647.7 |
| LPS050 | 2428 | 7502 | 3442.1 | 12204.8 | 7385.4 | 9850.6 | 3395 | 8052.4 | 14726 |
| LPS051 | 478.2 | 219.7 | 175.1 | 1861 | 2222.1 | 1876.9 | 1922.5 | 800.9 | 2052.9 |
| LPS052 | 328.2 | 196.2 | 138.3 | 984.6 | 1458.3 | 1324.4 | 1585 | 1112.9 | 1726 |
| LPS053 | 264.2 | 111 | 0 | 1370.2 | 1524.9 | 1548 | 2692.1 | 2941.5 | 3096.1 |
| LPS054 | 285.4 | 231.1 | 8.5 | 1370.4 | 2138 | 1273.8 | 2930.8 | 2762.2 | 2604.2 |
| LPS055 | 1192.2 | 1118.8 | 180.5 | 5840.8 | 4203.1 | 3690.8 | 1865.1 | 3205.9 | 4824.3 |
| LPS056 | 1541.6 | 2959.9 | 1354 | 9519.2 | 8084 | 6331.3 | 1820.6 | 5902.8 | 11668.9 |
| LPS057 | 214.5 | 406.9 | 0 | 2028.8 | 2744.4 | 756.5 | 2136.1 | 1844.8 | 2454.6 |
| LPS058 | 277.4 | 244.5 | 70.8 | 1623.9 | 1826.1 | 1626.5 | 2708 | 2514.4 | 4077 |
| LPS059 | 115.3 | 135.2 | 1.5 | 996.9 | 1194.7 | 1022.8 | 1723.1 | 1265.3 | 2390.7 |
| LPS060 | 163.3 | 268.5 | 0 | 1866.5 | 1707.3 | 1953.7 | 2184.7 | 2422.6 | 2990 |
| LPS061 | 222.7 | 255.6 | 53.4 | 1448.5 | 2146.6 | 1600.7 | 1956.2 | 2511.7 | 3332.5 |
| LPS062 | 136 | 228.5 | 99.1 | 627.1 | 863.2 | 467.7 | 1610.3 | 2304.9 | 2842.2 |
| LPS063 | 299.7 | 251.8 | 226.3 | 796.8 | 1427 | 1771.5 | 1174.1 | 930 | 1433.9 |
| LPS064 | 3079.8 | 4014.9 | 3039.3 | 7349.2 | 10807.8 | 7372.1 | 10515.8 | 4426.8 | 13038.7 |
| LPS065 | 434.1 | 644.6 | 313.7 | 1147 | 1456.3 | 3097.5 | 2632.9 | 3695.2 | 1575.1 |
| LPS066 | 214.7 | 171.7 | 134.2 | 0 | 69.3 | 249.7 | 726.1 | 871.9 | 586.6 |
| LPS067 | 706.6 | 686.2 | 488.8 | 3013.5 | 2498.9 | 4522.1 | 4844.3 | 4782.1 | 5775 |
| LPS069 | 199.6 | 172.1 | 123.9 | 75.4 | 19.4 | 269 | 874.1 | 854.6 | 0 |
| LPS070 | 143.6 | 186.9 | 117.9 | 289.4 | 685.5 | 222.6 | 528.3 | 582.6 | 322.6 |
| LPS071 | 180.4 | 170.2 | 187.2 | 157.2 | 183 | 882.3 | 326.7 | 508.4 | 310.2 |
| LPS072 | 235.9 | 170.8 | 169.6 | 449.9 | 290.5 | 777.5 | 456.3 | 283.3 | 479.2 |
| LPS073 | 900.4 | 1318.7 | 629.3 | 3416.1 | 4420.4 | 3894 | 4010.1 | 3367.3 | 4106.8 |
| LPS074 | 27858.2 | 33812.3 | 32162.2 | 44513.2 | 111430.2 | 87262.8 | 47575.8 | 18233.4 | 66903.6 |
| LPS075 | 2119.6 | 3296.9 | 1347.3 | 9540.3 | 5518.1 | 6367.8 | 10437.2 | 4054.1 | 9821.4 |
| LPS076 | 347.6 | 336.3 | 218.5 | 2343.7 | 2326.5 | 1569 | 2415.2 | 1580.7 | 1990.4 |
| LPS077 | 568.1 | 612.4 | 550.1 | 2908.9 | 1727.9 | 1660.2 | 2164.5 | 1798.6 | 2588.1 |
| LPS078 | 3174.9 | 3137.6 | 3222.6 | 7616.1 | 6945.1 | 9024.5 | 11397.6 | 7995.6 | 26362.3 |
| LPS079 | 1049 | 1066.4 | 302.2 | 4400.8 | 4126.8 | 4404.7 | 8203.7 | 4645.6 | 9377 |
| LPS080 | 21208.7 | 28180.7 | 9065.4 | 39068.1 | 63741.1 | 37523.8 | 35948.5 | 11444.8 | 57266.6 |
| LPS081 | 27381 | 33419.5 | 10292.3 | 43529.2 | 63629.5 | 28119 | 42128.9 | 15984.6 | 62043.4 |
| LPS083 | 711.4 | 825 | 64.8 | 3306.9 | 3733.1 | 1898.2 | 3688.2 | 3407.5 | 3959.9 |
| LPS084 | 216.4 | 211.2 | 21 | 1350.5 | 1724.2 | 1394.5 | 1965.6 | 2089.4 | 3604.5 |
| LPS086 | 185.6 | 214.1 | 0 | 1808.2 | 1476 | 2915.6 | 2342.5 | 932.2 | 3339.1 |
| LPS087 | 3404.7 | 5840.3 | 4144.1 | 12101.2 | 12860.9 | 14601.5 | 24953 | 5018.8 | 19643.5 |
| LPS088 | 165.2 | 224.6 | 62.5 | 1497.7 | 2813.8 | 1593.8 | 3740.9 | 4017.3 | 3934.9 |
| LPS089 | 223.8 | 213.7 | 0 | 1318.9 | 1574.5 | 2141.4 | 2443.5 | 3799.4 | 4185.6 |
| LPS090 | 398.7 | 693.2 | 142.2 | 2593.7 | 2695.2 | 3465 | 3755.9 | 3638.7 | 3587.8 |
| LPS091 | 391.2 | 700.6 | 270.7 | 1469.2 | 2092.2 | 3047.2 | 3754.2 | 3524.1 | 3149.7 |
| LPS092 | 286.1 | 376.1 | 254.9 | 235.2 | 433.1 | 1353.8 | 1747.8 | 2658.1 | 3246.6 |
| LPS093 | 185.6 | 273.7 | 126.3 | 114.7 | 296.8 | 254.7 | 412.1 | 1076.9 | 483.7 |
| LPS094 | 232.8 | 261.8 | 151.7 | 274.3 | 249.9 | 641.1 | 891 | 577 | 1102.1 |
| LPS095 | 199.3 | 191.7 | 91.4 | 25.7 | 169.9 | 433.7 | 813.4 | 1394.3 | 807.7 |
| LPS096 | 97.9 | 139.2 | 63.2 | 0 | 162.4 | 159.2 | 504.6 | 752.3 | 150.6 |
| LPZ001 | 150.8 | 207.8 | 257.7 | 202.6 | 485.5 | 704.2 | 555.2 | 1924.3 | 528.5 |
| LPZ002 | 154.6 | 167.7 | 323.6 | 937.4 | 717.4 | 755.6 | 1068.8 | 1089.8 | 1107.7 |
| LPZ003 | 1348.1 | 1781.1 | 609.3 | 5019 | 4261.6 | 6148.5 | 5600.4 | 3419.6 | 4858.4 |
| LPZ004 | 2798.4 | 5533.1 | 2921.8 | 10703.8 | 8020.5 | 9958.4 | 10424.8 | 4135.9 | 14742.8 |
| LPZ005 | 8403.4 | 19547.7 | 8589.6 | 32699.4 | 31426.9 | 21580.2 | 19437.9 | 8059.6 | 14660.3 |
| LPZ006 | 360.6 | 2106.1 | 1173.8 | 7812.9 | 7966 | 11310.2 | 10516.8 | 4661.6 | 4618.2 |
| LPZ007 | 272.5 | 409.9 | 454.7 | 2038.3 | 1107.6 | 2043.7 | 2073.5 | 2249.9 | 2751.3 |
| LPZ008 | 207.7 | 258.2 | 212 | 1939.1 | 1482.6 | 1926.1 | 2243.5 | 1036 | 3324.9 |
| LPZ009 | 745.1 | 496.5 | 633.9 | 4276.8 | 7474.5 | 9130.4 | 9814 | 5721.3 | 14116.8 |
| LPZ010 | 893.7 | 1464.1 | 326.6 | 3759.5 | 4034 | 4261 | 4672.2 | 4388.6 | 9625.3 |
| LPZ011 | 1829.5 | 2488.7 | 350.4 | 5922.7 | 4285.4 | 2984.2 | 5579.8 | 4236 | 9972.7 |
| LPZ012 | 227.8 | 289.9 | 28.6 | 1885.9 | 1660.5 | 843.6 | 1913 | 1434.5 | 2785.5 |
| LPZ013 | 247.7 | 213.8 | 84 | 1553 | 2015.3 | 1547.3 | 2567.6 | 3196.5 | 4347.7 |
| LPZ015 | 261.7 | 315.8 | 55.6 | 2254.3 | 2409.8 | 2190.1 | 2562.4 | 1291.2 | 3237.3 |
| LPZ016 | 2750.3 | 2151.8 | 3003.8 | 8316.2 | 6689.1 | 9147.4 | 9444.8 | 3349.6 | 8167.8 |
| LPZ017 | 582.2 | 701.3 | 227.4 | 3830.1 | 3650.3 | 3828.2 | 4552.3 | 4574.5 | 4476.8 |
| LPZ018 | 2867.6 | 6184.2 | 2746.8 | 10513.4 | 9443.1 | 10880.7 | 12748.3 | 5491.2 | 19422 |
| LPZ019 | 7551.3 | 15875.3 | 9232.8 | 20440.4 | 22870.4 | 31026.1 | 33842 | 12823.6 | 38075.4 |
| LPZ020 | 293.1 | 896.2 | 143.1 | 1661.8 | 2519.9 | 2987.1 | 4132.4 | 4022 | 3145.1 |
| LPZ022 | 213.3 | 493.5 | 173.5 | 82.5 | 467.8 | 1355.1 | 1041.1 | 1481.9 | 1035.5 |
| LPZ023 | 191.2 | 616.7 | 118.1 | 78.4 | 184 | 955.2 | 516.3 | 1254.6 | 574.4 |
| LPZ024 | 142.6 | 321.7 | 118 | 0 | 81.9 | 826.8 | 195.8 | 763.9 | 491.7 |
| LPZ025 | 661.9 | 764.4 | 536.9 | 1885.6 | 1791.8 | 3200.6 | 3017.8 | 4028.4 | 3897.8 |
| LPZ026 | 194.7 | 221 | 150.4 | 1102 | 513.6 | 1714.4 | 1291.2 | 1625.6 | 980.7 |
| LPZ028 | 301.3 | 424.2 | 210.9 | 1467.7 | 1654.3 | 2848.4 | 1937.1 | 4092.7 | 3086.2 |
| LPZ029 | 132 | 151 | 124.8 | 319.5 | 644.1 | 478.7 | 452.4 | 564.8 | 709.3 |

TABLE II-continued

| | | | | | | | | | |
|---|---|---|---|---|---|---|---|---|---|
| LPZ030 | 305.3 | 616.6 | 170.6 | 2800.7 | 2572 | 2485.4 | 1960.4 | 1425.4 | 2381.1 |
| LPZ031 | 1945 | 3098.6 | 3636.7 | 12422.3 | 7673.2 | 8643.5 | 11552.7 | 4295.4 | 4600 |
| LPZ032 | 26761.5 | 33518.4 | 33623.2 | 45482.1 | 106536.1 | 114284.5 | 46968.1 | 16371.6 | 42282.1 |
| LPZ033 | 2068.3 | 1779.5 | 6651.8 | 7887.8 | 5249.8 | 9848.7 | 7632.1 | 4500.7 | 7710 |
| LPZ034 | 221.4 | 363.3 | 216.3 | 2503 | 1949.2 | 1674 | 2078.9 | 1428.3 | 1774.9 |
| LPZ035 | 110.7 | 156.8 | 85.2 | 836.6 | 512.1 | 1355.7 | 1217.4 | 294 | 1525.3 |
| LPZ037 | 229.5 | 206.2 | 186.5 | 1422.1 | 1962.7 | 2742.9 | 3023 | 614.1 | 2895.5 |
| LPZ038 | 605.7 | 722.8 | 352.5 | 3551.8 | 3072.2 | 3614.2 | 3266 | 2494.6 | 4039.7 |
| LPZ039 | 366.4 | 964.6 | 177.1 | 3755.2 | 2744.9 | 4599.4 | 3589.7 | 2407.8 | 3925.2 |
| LPZ040 | 185.6 | 278.3 | 100.8 | 2131.2 | 1321 | 1479.7 | 1654.6 | 773.7 | 2087 |
| LPZ041 | 119.9 | 120.8 | 5 | 1199.8 | 1220.8 | 1090 | 1431.2 | 630 | 2206.1 |
| LPZ042 | 61.9 | 121.9 | 2.6 | 731.4 | 1897.5 | 986.4 | 1366.1 | 458.4 | 2625 |
| LPZ043 | 357.9 | 355.1 | 0 | 3236.5 | 2746.8 | 2960.1 | 3138.2 | 911.1 | 3345.6 |
| LPZ045 | 738.6 | 1003.7 | 565.3 | 3866 | 3168.1 | 6406.2 | 4028.7 | 4526.2 | 4573.4 |
| LPZ047 | 139.7 | 133.1 | 0 | 481.3 | 857.9 | 831.8 | 954.1 | 1926.3 | 3129.6 |
| LPZ049 | 1396.5 | 2125.5 | 1496.9 | 4514.4 | 3629.8 | 5942.4 | 6898.6 | 3610.7 | 9214.2 |
| LPZ051 | 264.6 | 610.7 | 205.1 | 826.3 | 1819.9 | 2243.8 | 3000.9 | 3400.7 | 2810.3 |
| LPZ053 | 174.9 | 827.9 | 152 | 161.2 | 563.8 | 1149.7 | 1277.9 | 1243 | 1383.5 |
| LPZ054 | 205.7 | 951 | 128.4 | 976.1 | 1901.4 | 1626.6 | 1265.8 | 1437.6 | 1328.8 |
| LPZ055 | 135.2 | 389 | 168.5 | 420.2 | 524.3 | 1650.6 | 848.4 | 1200.6 | 914.2 |
| LPZ056 | 190.2 | 323.3 | 229.5 | 439.9 | 664.2 | 1613.1 | 1014.2 | 1727.3 | 1126.2 |
| LPZ057 | 87 | 199.9 | 180.1 | 2154 | 863.7 | 3059.1 | 2994.9 | 2696.3 | 2990 |
| LPZ058 | 139.3 | 227.5 | 55.3 | 1695.1 | 902.5 | 2426.6 | 2195.6 | 1925.4 | 1598.2 |
| LPZ059 | 173.4 | 289.6 | 189.4 | 891.7 | 759.7 | 1835.3 | 1332.9 | 962.5 | 1286.6 |
| LPZ060 | 301 | 464.8 | 114.1 | 2296.5 | 2860.4 | 2786.6 | 2974.4 | 1629.6 | 2301.9 |
| LPZ061 | 1212.2 | 1711.1 | 794.4 | 7468.5 | 5190.1 | 7957.5 | 5857.5 | 2819.8 | 3922.3 |
| LPZ062 | 2078.9 | 3648.3 | 2499.3 | 14932.7 | 7691.9 | 9294.1 | 9213.3 | 3077.8 | 4850.3 |
| LPZ063 | 641.6 | 984 | 2114.2 | 5547.2 | 3688.6 | 6191.3 | 4844.5 | 4058.7 | 4162.4 |
| LPZ065 | 520.2 | 443.3 | 332.3 | 2720.4 | 1816 | 2848.5 | 3320.4 | 4501 | 3948.4 |
| LPZ066 | 663.7 | 357 | 356.6 | 3458.6 | 2196.3 | 3567.6 | 3081.4 | 1325 | 2388 |
| LPZ067 | 1469.5 | 2582.6 | 3152.4 | 8674.9 | 8080.1 | 9367.6 | 8556.2 | 4135 | 7240 |
| LPZ069 | 211.4 | 283.6 | 0 | 1921.6 | 913.1 | 1567.5 | 1866.5 | 1043.3 | 2269.1 |
| LPZ070 | 229.6 | 334.9 | 2.8 | 1659.3 | 1254.6 | 1681.6 | 1883.6 | 1360.7 | 2442 |
| LPZ071 | 332.3 | 633 | 15.7 | 3126 | 2729.9 | 3290.2 | 2998 | 2011.7 | 2744.8 |
| LPZ072 | 39 | 38.9 | 0 | 581.2 | 1401.7 | 1307.1 | 1089.7 | 710.4 | 1866.3 |
| LPZ073 | 131.3 | 250.9 | 4.4 | 1176.4 | 2903.2 | 2356.7 | 1718.3 | 985.9 | 2700 |
| LPZ074 | 92 | 116.5 | 0 | 355.6 | 1643 | 1041.3 | 1027.4 | 1042 | 2553.6 |
| LPZ075 | 195.9 | 0 | 0 | 0 | 474.7 | 488.1 | 847.6 | 1488.4 | 2755 |
| LPZ076 | 232.4 | 134.5 | 730.7 | 0 | 268.9 | 0 | 568.3 | 1007.4 | 2624.4 |
| LPZ077 | 1143.1 | 2350.7 | 187.5 | 6551.1 | 5960.9 | 5520.2 | 7189.6 | 3483.6 | 7931.5 |
| LPZ078 | 851.5 | 1021 | 873.3 | 3011.7 | 4619.7 | 5273.6 | 6408.3 | 3950.1 | 8831 |
| LPZ079 | 281.6 | 779.7 | 315.9 | 1296.6 | 2065 | 2090.8 | 2287 | 2271.9 | 1824.5 |
| LPZ080 | 1653.5 | 3124.5 | 3778.7 | 8321.1 | 7987.7 | 10470.3 | 8085.7 | 4454.9 | 8067.4 |
| LPZ081 | 92.6 | 292.7 | 161.8 | 746.8 | 903 | 1558.5 | 1410.8 | 746.1 | 1230 |
| LPZ082 | 123.2 | 430.5 | 240.1 | 1907.9 | 1283.9 | 2707.5 | 1801.7 | 948.9 | 1634 |
| LPZ083 | 77.8 | 183.2 | 120.2 | 4010 | 2437.2 | 4390.6 | 3649.7 | 3983.1 | 7032.5 |
| LPZ084 | 1272.3 | 956.1 | 1297.2 | 5881 | 4505.3 | 10642.2 | 9798.6 | 3938.5 | 8446.3 |
| LPZ085 | 321 | 466.2 | 457.6 | 4324.8 | 4008.4 | 6890.5 | 4599.7 | 5672 | 10082.2 |
| LPZ086 | 1529.6 | 3587.2 | 3236.8 | 10729.4 | 10010.2 | 10739.2 | 10634.9 | 4674.2 | 11980.7 |
| LPZ089 | 614.3 | 500.4 | 601.9 | 4196.2 | 3890.5 | 4405.8 | 4331.9 | 3066.9 | 3960.3 |
| LPZ090 | 643.8 | 1177.5 | 1315 | 4017.8 | 4456.2 | 6394.5 | 4824.4 | 3000.1 | 3538.3 |
| LPZ091 | 1006.7 | 1754.2 | 4090 | 11615.8 | 11728.5 | 16837.8 | 14461.9 | 5005.1 | 14726.4 |
| LPZ092 | 419 | 528.6 | 1336.8 | 4158.4 | 3568.1 | 8393.4 | 8192 | 4638.4 | 3939.4 |
| LPZ093 | 162.2 | 453 | 90.9 | 1436.5 | 899.2 | 2218.6 | 1798 | 741.8 | 1789.8 |
| LPZ094 | 123.1 | 197.1 | 0 | 1355.7 | 779.4 | 1360.5 | 1713.8 | 794.4 | 1597.8 |
| LPZ095 | 94 | 130.6 | 3.5 | 1099.9 | 737.4 | 558.3 | 1473.4 | 871.4 | 1809.3 |
| LPZ096 | 314.3 | 327.5 | 22.1 | 2574.2 | 1620.9 | 2748.1 | 2533.9 | 1858.4 | 2979.9 |
| LPZ099 | 231.7 | 359.8 | 6.2 | 1456.9 | 1335.7 | 1672.4 | 2170.8 | 2160.8 | 2755.8 |
| LPZ100 | 375.6 | 650.4 | 136.7 | 2834 | 2518.6 | 3053.2 | 3159.8 | 2841.2 | 3453.7 |
| LPZ101 | 217.1 | 425.7 | 11.8 | 2769.3 | 3312.6 | 2556.3 | 5262.5 | 1501.2 | 2947.3 |
| LPZ102 | 294.3 | 289.2 | 55 | 1803.6 | 2764.5 | 2532.5 | 2613.4 | 2447.6 | 3377.6 |
| LPZ103 | 224.2 | 92.8 | 17 | 989 | 1850.6 | 1643.7 | 2303.4 | 3729.5 | 4029.5 |
| LPZ106 | 328.4 | 158 | 57.5 | 912.5 | 1239.6 | 1214.5 | 1669.6 | 2062.3 | 4720 |
| LPZ107 | 25137.4 | 28865.6 | 19438.9 | 43316.7 | 75674.1 | 58296.4 | 45927 | 3332.1 | 64391.6 |
| LPZ108 | 1132.8 | 2084.1 | 330.6 | 4299.2 | 3629.8 | 4480 | 6406.5 | 3235.2 | 9993.6 |
| LPZ109 | 548.8 | 1356.1 | 417.7 | 3237.9 | 2581.9 | 3177.5 | 3977.1 | 1874.2 | 4107.7 |
| LPZ110 | 379.7 | 1132.3 | 220 | 3941.9 | 2720.7 | 4103.6 | 3563 | 2245.7 | 3031 |
| LPZ111 | 157.5 | 383.2 | 200.3 | 1188.3 | 749.8 | 1675.7 | 1926.1 | 1685.1 | 1655.3 |
| LPZ112 | 332.1 | 522.9 | 220.7 | 2950.9 | 2223.9 | 2257.5 | 2856.4 | 2632.8 | 2711.8 |
| LPZ114 | 590 | 151.8 | 217 | 4659.6 | 3824.5 | 6848.2 | 7228.9 | 2831.3 | 9446.9 |
| LPZ115 | 6268.6 | 3368.3 | 8724.6 | 25695 | 19481.5 | 33011.8 | 32267.9 | 2903.4 | 52760.4 |
| LPZ116 | 891.2 | 766.7 | 1481 | 6455.1 | 3684.7 | 5597.5 | 8456.7 | 1682.9 | 10139.2 |
| LPZ117 | 529.8 | 826.6 | 126.5 | 3706.8 | 2663 | 2897.5 | 3996.1 | 1807.3 | 2635.2 |
| LPZ118 | 437.8 | 628.1 | 122.1 | 3903.5 | 3245.2 | 3529.9 | 3500.1 | 3506.1 | 2867.9 |
| LPZ119 | 331.3 | 755.1 | 83.1 | 3781.2 | 4072.6 | 4024.9 | 3449.9 | 3742.2 | 2533.9 |
| LPZ120 | 196.5 | 796 | 181.4 | 4219.4 | 3297.7 | 4322 | 4539.3 | 2622.7 | 3763.6 |
| LPZ122 | 154.4 | 208.4 | 158 | 2332.3 | 1468 | 3044 | 2838.8 | 2112.5 | 2323.6 |
| LPZ124 | 172.9 | 420.1 | 136.6 | 2319.5 | 1539.3 | 1722.7 | 2453.6 | 3109.1 | 2297 |
| LPZ126 | 446.5 | 604.2 | 187.3 | 3859.4 | 3120.8 | 2816.9 | 3324 | 2181.4 | 3237.7 |

TABLE II-continued

| | | | | | | | | | |
|---|---|---|---|---|---|---|---|---|---|
| LPZ127 | 439.3 | 499.4 | 53.5 | 3781.8 | 3083.3 | 3769.8 | 3848.4 | 1729.6 | 2902.2 |
| LPZ128 | 1022.3 | 1063.8 | 447.9 | 3904.9 | 3753.5 | 5579.6 | 4534.2 | 2133.1 | 5843.6 |
| LPZ131 | 249.6 | 373.8 | 27.3 | 2170.1 | 1551.6 | 1611.4 | 3077.3 | 2946 | 2409.5 |
| LPZ133 | 325.3 | 328.7 | 42 | 2706.9 | 2358.1 | 2131.3 | 3257.2 | 2598.7 | 2144.3 |
| LPZ136 | 263.6 | 384.1 | 0.9 | 2377.3 | 3386.4 | 2044.7 | 2726.4 | 2398.2 | 2570.6 |
| LPZ137 | 351.6 | 402.6 | 91.9 | 3435.9 | 3122.8 | 2406.9 | 3054.7 | 3392.1 | 3216.6 |
| LPZ138 | 1047.7 | 936 | 530.3 | 3920 | 3091.2 | 2507.9 | 4249.5 | 3109.9 | 4758.4 |
| LPZ140 | 379.9 | 456.6 | 105.6 | 1936.7 | 3674 | 2908.4 | 3678.1 | 3663.2 | 4481.7 |
| LPZ141 | 715.4 | 1341.8 | 536.4 | 4712.8 | 3615.6 | 3746 | 4815.5 | 4533 | 8229.3 |
| LPZ143 | 3251.1 | 4810.8 | 2848.5 | 9675.1 | 8289.6 | 9486.6 | 12270.6 | 4424.9 | 28251.9 |
| LPZ144 | 386.2 | 1338.3 | 294.1 | 3433.8 | 3015.7 | 3333.7 | 4618.9 | 3699.7 | 6825.1 |
| LPZ145 | 277.5 | 1064 | 536.5 | 3072.3 | 1155.6 | 2977.7 | 3188.2 | 7388.2 | 3013.6 |
| LPZ146 | 128.5 | 362.8 | 139.5 | 2224.4 | 1364 | 2125.6 | 2428.3 | 3465.8 | 2351.1 |
| LPZ147 | 266.5 | 544.2 | 241.3 | 3318.1 | 2241.9 | 2162.6 | 2908.8 | 3252.6 | 2525.6 |
| LPZ148 | 725.8 | 725.5 | 290.2 | 5002.2 | 3682.1 | 6542.3 | 6927.9 | 2903.1 | 10410.9 |
| LPZ149 | 2492.7 | 3102.7 | 1052.7 | 8980.9 | 7669.2 | 7185.3 | 9921 | 7375.4 | 12848.8 |
| LPZ150 | 5257.3 | 7586.3 | 3221.3 | 15156.2 | 12776.8 | 7401.2 | 14686.5 | 1570 | 20635.9 |
| LPZ151 | 1384 | 2049.2 | 1128.3 | 5576.7 | 3853.7 | 3780.3 | 7227.3 | 3206.7 | 7702.7 |
| LPZ152 | 975.8 | 1300.2 | 546.4 | 5096.1 | 4344.9 | 4302.5 | 4960.3 | 1566.2 | 4223.4 |
| LPZ153 | 13378.6 | 22235.1 | 10073.1 | 33495.1 | 50802.7 | 28291.5 | 29602.5 | 3224.1 | 40232.7 |
| LPZ154 | 663.3 | 738 | 430.3 | 3847.3 | 3880.2 | 6253.9 | 4707.7 | 5341.9 | 3393.8 |
| LPZ155 | 1121.7 | 612.7 | 748 | 3902.3 | 4289 | 4676 | 5328 | 6964.2 | 5353.5 |
| LPZ157 | 1157 | 957.9 | 762.2 | 4218.8 | 4266.6 | 3777.2 | 4583.7 | 5017.5 | 4396.6 |
| LPZ158 | 13278.5 | 17582.9 | 9898.7 | 32456.5 | 42805.1 | 24534.6 | 31442.6 | 4152.5 | 36015.3 |
| LPZ162 | 3407.5 | 5943.1 | 5126.6 | 10324 | 11710.9 | 7727.6 | 7572.2 | 2312.6 | 9394.1 |
| LPZ165 | 1419.4 | 1550 | 693 | 4519.9 | 3692.9 | 6102.1 | 5617.1 | 3061.3 | 4706.4 |
| LPZ166 | 2642.1 | 3504.9 | 1288.6 | 7134.8 | 6994.5 | 5170.5 | 10453.3 | 4932.9 | 15993.7 |
| LPZ167 | 980.4 | 1518.1 | 564.7 | 4902.6 | 4803.7 | 3343.6 | 4869.5 | 4421.2 | 6582.2 |
| LPZ169 | 621.8 | 792.7 | 93.4 | 3562 | 4266.3 | 1794.9 | 3496.3 | 4238 | 3143.7 |
| LPZ170 | 1009.3 | 1405.3 | 695.2 | 5793.7 | 4469.2 | 4952.7 | 6239.7 | 3914.1 | 6782.3 |
| LPZ171 | 1064.6 | 968.6 | 1050.7 | 4110.8 | 3903.7 | 5467.2 | 5659 | 3164.1 | 6795.3 |
| LPZ172 | 1233.3 | 1113.3 | 401.8 | 4207.9 | 7922 | 8417.5 | 10419.2 | 7983.5 | 15065.2 |
| LPZ173 | 3333.8 | 5236.8 | 6072 | 9552 | 8880 | 8653.2 | 13461.6 | 2408.7 | 25719.1 |
| LPZ174 | 486.7 | 1263.6 | 143.3 | 3318.2 | 2027 | 3632.3 | 4245.3 | 6086.4 | 8781.2 |
| LPZ175 | 594.7 | 1487 | 520.8 | 3051.5 | 3610.8 | 1846.4 | 3642.9 | 4048.5 | 4329.5 |
| LPZ177 | 167.3 | 481.7 | 234.5 | 1955.9 | 1139.2 | 907.8 | 1452.9 | 4462.5 | 1762 |
| LPZ179 | 1231.4 | 1583.2 | 835.8 | 5029.7 | 3654 | 3871.7 | 3248.8 | 2741.9 | 2853.2 |
| LPZ181 | 2259.5 | 4282.9 | 774.8 | 8911.6 | 8788.6 | 6833.3 | 5825.5 | 3398 | 3922.8 |
| LPZ182 | 1194.7 | 2289.6 | 673.8 | 8220.3 | 5601.2 | 5869.3 | 5572 | 1808.4 | 7607.9 |
| LPZ186 | 6255.6 | 6866.5 | 6841.1 | 24861.8 | 16742.4 | 23502.2 | 17304.6 | 1750.4 | 27328.9 |
| LPZ189 | 27581.8 | 34787.4 | 31889 | 45673.7 | 106688 | 95043.9 | 46998.5 | 3548.1 | 67943.9 |
| LPZ194 | 673.9 | 904.9 | 528.7 | 4064.5 | 3530.2 | 3160.6 | 5095.2 | 4531.1 | 3492.1 |
| LPZ195 | 898.9 | 889.6 | 675.7 | 5606.3 | 4004.3 | 5230.5 | 5721.4 | 4908.1 | 4940.9 |
| LPZ196 | 1073.7 | 1935.1 | 558.2 | 3941.1 | 3672.6 | 3681.6 | 5977.8 | 3059.7 | 5050.3 |
| LPZ197 | 488.4 | 522.5 | 386.6 | 2613.4 | 1684.4 | 3541.4 | 3507.4 | 4980.8 | 2763.1 |
| LPZ198 | 575.6 | 733.1 | 299.6 | 4152.3 | 2411 | 2916.8 | 3872.4 | 6530.7 | 2931.8 |
| LPZ199 | 390.7 | 442.5 | 222.4 | 2704 | 2176.2 | 3159.7 | 2957.1 | 5357.6 | 2983.4 |
| LPZ201 | 2255.7 | 3876.6 | 347.6 | 10222.9 | 6897.7 | 6294.3 | 7324.7 | 3549 | 3857 |
| LPZ202 | 25939.2 | 34864.8 | 28937 | 43395.9 | 85136 | 71116.8 | 38688.5 | 2676.2 | 14449.1 |
| LPZ203 | 4917.3 | 4458.1 | 2603.2 | 10348.3 | 6571.1 | 8325.7 | 11034 | 5453.1 | 6598 |
| LPZ204 | 27637.2 | 31853.9 | 22475.7 | 43983.9 | 89520.6 | 46504.2 | 44333.5 | 7963.6 | 58054.1 |
| LPZ205 | 1184 | 1084.2 | 327.7 | 3901.8 | 4402 | 3125 | 4598.2 | 4501.5 | 4714.2 |
| LPZ206 | 1309.8 | 1509.5 | 367.3 | 3961.5 | 3983.3 | 3079.6 | 4196.2 | 3641.4 | 3247.6 |
| LPZ207 | 27569.1 | 30446.2 | 27094.6 | 45211.6 | 90196.1 | 58153.8 | 46488.1 | 9879.3 | 64709.2 |
| LPZ208 | 22722 | 28208.9 | 30019.5 | 40314 | 74354.1 | 37339 | 33919.6 | 3989.8 | 56683.6 |
| LPZ210 | 1015.1 | 1789.8 | 196.8 | 5006.3 | 6159.7 | 3067.8 | 4944 | 4347.5 | 6846.4 |
| LPZ211 | 277 | 327.3 | 519.4 | 2540.7 | 1788.5 | 3048.6 | 1110.8 | 2577.4 | 3506.6 |
| LPZ212 | 1095.5 | 865.5 | 930.6 | 4051.6 | 4491.6 | 2857.6 | 6348.1 | 4078.7 | 16174.9 |
| LPZ213 | 376.6 | 539.3 | 339.6 | 2503.1 | 1540.8 | 1333.7 | 3082.2 | 6024.3 | 4163.1 |
| LPZ214 | 137.5 | 306.1 | 190.1 | 1915.6 | 866.1 | 1280.9 | 1240.8 | 6372.4 | 2111.8 |
| LPZ215 | 3519.4 | 3120.9 | 3300.9 | 16939.5 | 15489.1 | 10948.6 | 12502 | 3515.1 | 16236.4 |
| LPZ216 | 26761.3 | 34226.4 | 28477.9 | 42274.8 | 67630.3 | 41420.3 | 36331.4 | 1433.8 | 17109.4 |
| LPZ217 | 15563.1 | 21739.4 | 12259 | 26824.9 | 34266.3 | 9429.4 | 28156.7 | 1339.2 | 41568.4 |
| LPZ219 | 2404.9 | 3704.5 | 2084 | 8575.1 | 8573.2 | 6237 | 11757 | 3255.4 | 13484.9 |
| LPZ220 | 3617.2 | 6998.6 | 7957.2 | 13960 | 9400.8 | 3432.3 | 10805.5 | 3551.7 | 12867.4 |
| LPZ221 | 482.6 | 478 | 1405.6 | 3296.5 | 3079.8 | 3312.5 | 4143 | 4429.4 | 3267.3 |
| LPZ222 | 318.3 | 524.5 | 406.6 | 3011.7 | 2309 | 3811.8 | 4199.4 | 5319.9 | 3292.3 |
| LPZ223 | 367.7 | 633.2 | 437.7 | 2752 | 1970.3 | 3767.4 | 2514.2 | 3672.3 | 2163.1 |
| LPZ224 | 337.9 | 1030.2 | 317.2 | 2701.2 | 1798.7 | 7393.6 | 2962.5 | 7876 | 3353.7 |
| LPZ225 | 3288.1 | 3590.3 | 2912 | 8781.8 | 7400.7 | 2317.1 | 11370.2 | 3186.6 | 22244.6 |
| LPZ226 | 325.6 | 361.4 | 128 | 2467 | 1263.7 | 10190.1 | 1636.3 | 3808.8 | 1166.9 |
| LPZ227 | 2175.5 | 6375.8 | 458.8 | 6316.2 | 6632.1 | 9013.9 | 6614.3 | 3901.2 | 2588.2 |
| LPZ228 | 2638 | 3701.7 | 500.1 | 5991 | 4819.8 | 5747.8 | 7102.5 | 3182.5 | 4185.4 |
| LPZ231 | 1631.7 | 2090.4 | 260.7 | 5811.5 | 4749 | 2530.8 | 5033.1 | 3191.3 | 3810.5 |
| LPZ233 | 1596.6 | 1223 | 296.6 | 4355.6 | 3818.9 | 2988.8 | 3749 | 3324.7 | 3855.2 |
| LPZ234 | 1734.3 | 1479.2 | 219.6 | 5058.5 | 4614.4 | 2034.9 | 4992.1 | 1979.9 | 5152 |
| LPZ235 | 626 | 635.9 | 185.9 | 4066.8 | 3255.5 | 4035.7 | 3368.7 | 2880.8 | 3643.5 |
| LPZ237 | 1677.8 | 1385.3 | 847.4 | 4536 | 3702.8 | 2943.6 | 4886.5 | 2307.8 | 5136.8 |
| LPZ239 | 673.4 | 407.8 | 245.8 | 2981.9 | 3199.2 | 2781.6 | 4235.6 | 2342.6 | 4863.7 |

TABLE II-continued

| | | | | | | | | | |
|---|---|---|---|---|---|---|---|---|---|
| LPZ240 | 387 | 247.4 | 254.8 | 2075.8 | 2317.4 | 2894 | 2721.7 | 2054.5 | 4317.9 |
| LPZ241 | 258.3 | 337.8 | 110.9 | 3503.1 | 3829.6 | 22593.5 | 1889.5 | 1315.9 | 8842.6 |
| LPZ242 | 4315.9 | 2560.2 | 22.5 | 12510.2 | 12605.3 | 2345.2 | 16197.1 | 1114.8 | 39684.4 |
| LPZ243 | 174.8 | 274.4 | 23.1 | 2193.6 | 346.2 | 2395.7 | 1366.5 | 2568.2 | 3103.8 |
| LPZ244 | 417.5 | 269.1 | 3458.5 | 3545.1 | 1831 | 2834.7 | 1781.1 | 7589.2 | 5662.7 |
| LPZ246 | 889.5 | 918.7 | 2302.7 | 3920.3 | 3228.9 | 4409.3 | 3536 | 1258.8 | 2645.3 |
| LPZ247 | 1203 | 2088.9 | 46.7 | 4956.9 | 4253.2 | 3559.7 | 4570.8 | 1702.6 | 3350.6 |
| LPZ248 | 973.3 | 1338.1 | 86.2 | 3977.4 | 4392.8 | 2033 | 4094.9 | 2062.6 | 4279.9 |
| LPZ249 | 361.3 | 324.3 | 206.7 | 1948.6 | 1764.3 | 2098.7 | 2762.1 | 1643 | 2862.4 |
| LPZ250 | 267.6 | 487.8 | 118.7 | 2690.4 | 1522 | 2989 | 3121 | 1928.9 | 1809.7 |
| LPZ251 | 245 | 279.7 | 168.5 | 1409.9 | 555 | 9932.3 | 2552.5 | 3050.3 | 1371.1 |
| LPZ255 | 2021.3 | 2488.5 | 334.1 | 7289.5 | 7773.7 | 1269.1 | 9020.3 | 4492.4 | 10134.6 |
| LPZ256 | 67.1 | 72.2 | 296.7 | 412.2 | 229.8 | 922.7 | 570.3 | 5040.6 | 1263.9 |
| LPZ257 | 167.3 | 146.9 | 482.6 | 521.8 | 102.5 | 2699.4 | 599.8 | 2362.1 | 1553.4 |
| LPZ258 | 247.5 | 236.5 | 69.7 | 1429.8 | 974.6 | 971.9 | 2668.7 | 2990.8 | 3445.9 |
| LPZ260 | 98.1 | 188.8 | 463.1 | 377.1 | 337.2 | 880 | 808.9 | 1552 | 1084.6 |
| LPZ261 | 73.7 | 20.5 | 386.3 | 1143.6 | 50.3 | 4443.8 | 903.3 | 2309 | 1341.6 |
| LPZ264 | 482.7 | 528.5 | 1151.3 | 3659.7 | 1972.6 | 9892.4 | 2831.4 | 1584.4 | 3208 |
| LPZ265 | 534.6 | 647 | 457.6 | 4473 | 4089.9 | 656 | 5899.6 | 2972.2 | 5649.8 |
| LPZ266 | 16.9 | 61.2 | 1062.3 | 876.1 | 1183.4 | 1624.3 | 663.3 | 622.4 | 1609.7 |
| LPZ268 | 143.7 | 142.9 | 255 | 1983.5 | 810.3 | 9809.8 | 1293.5 | 1757.3 | 2177 |
| LPZ269 | 1747.5 | 1271.8 | 1636.4 | 7364.1 | 5108.7 | 6903.3 | 11401.2 | 3774.1 | 14643.8 |
| LPZ270 | 373.8 | 77.9 | 1901.2 | 5015 | 3872.6 | 3485.9 | 5621.1 | 4284.8 | 5197.8 |
| LPZ271 | 705 | 473.1 | 315.6 | 2863.8 | 2625.4 | 2120.5 | 4048.2 | 1424.9 | 4291.1 |
| LPZ272 | 2809.4 | 2423.8 | 300 | 5056.2 | 2463 | 3534.6 | 3496.9 | 609.7 | 3996.8 |
| LPZ273 | 219.8 | 162.4 | 242.4 | 90.2 | 130.2 | 3251.3 | 166 | 1193.5 | 1836.5 |
| LPZ274 | 489.2 | 367.7 | 284.6 | 991 | 1104.2 | 395.9 | 2282.3 | 747.2 | 4535.7 |
| LPZ275 | 93.5 | 140 | 156.8 | 433.3 | 217.1 | 0 | 837.9 | 1056.2 | 2352.3 |
| LPZ276 | 53 | 109.7 | 106.8 | 0 | 0 | 0 | 369.1 | 1303.6 | 1897.6 |
| LPZ277 | 105.9 | 159.4 | 68.7 | 0 | 0 | 230.1 | 236.2 | 706.1 | 1337.9 |
| LPZ278 | 65.7 | 48.3 | 156.4 | 0 | 0 | 1788.2 | 406.3 | 1442.3 | 1564.1 |
| LPZ279 | 214.7 | 212.2 | 75.3 | 1356.3 | 790.8 | 5213.3 | 1722.4 | 496 | 2426.2 |
| LPZ280 | 156.2 | 247.7 | 1553.6 | 3510.5 | 2515.1 | 289.7 | 3182.1 | 612.7 | 3123.7 |
| LPZ281 | 34.6 | 92.1 | 73 | 0 | 0 | 1648.3 | 565.5 | 522.8 | 543.3 |
| LPZ282 | 200.9 | 187.7 | 218.1 | 536.6 | 205.9 | 7324.8 | 1145.4 | 2977.5 | 957.5 |
| LPZ283 | 1833.5 | 1880 | 775.8 | 3303.2 | 5113.2 | 527.6 | 5281.2 | 324.5 | 3806.8 |
| LPZ284 | 215 | 0.6 | 148.8 | 0 | 29.6 | 848 | 408.4 | 148.8 | 1294.3 |
| LPZ286 | 219.7 | 21.9 | 13.6 | 234.9 | 78.6 | 2703.6 | 198.4 | 947.9 | 1233.2 |
| LPZ287 | 112.6 | 126.2 | 36.5 | 1170.3 | 459.9 | 306.3 | 157.5 | 1173.7 | 1821.3 |
| LPZ288 | 23.6 | 62.2 | 37.5 | 774.1 | 639.3 | 792.6 | 715.8 | 1422.6 | 1169 |
| LPZ289 | 44.1 | 13.1 | 107.4 | 323.4 | 95 | 9975.4 | 889.5 | 2240.6 | 1894.9 |
| LPZ290 | 1324.7 | 1572.4 | 1838 | 6941.6 | 4616.9 | 2995.3 | 11538.8 | 407.1 | 12699.5 |
| LPZ293 | 45.2 | 246.3 | 145.6 | 2785.5 | 1923.1 | 0 | 3185.6 | 0 | 3550.4 |
| LPZ294 | 0 | 19.8 | 0 | 403.3 | 280.4 | 89.1 | 785.9 | 551.6 | 1378.4 |
| LPZ295 | 40 | 24.5 | 0 | 169.9 | 26 | 1324.9 | 1058 | 848.8 | 1406.5 |
| LPZ297 | 385.6 | 127.6 | 17.4 | 1238.5 | 941.5 | 0 | 2680.9 | 2084.3 | 4065.3 |
| LPZ299 | 106.9 | 36.2 | 0 | 0 | 926.2 | 0 | 1060.7 | 1854.9 | 1575.9 |
| LPZ300 | 73.2 | 93.2 | 80.2 | 0 | 1143.6 | 1053.3 | 1034.5 | 2304.9 | 2120.8 |
| LPZ301 | 126.2 | 0 | 5.8 | 161.2 | 1245.7 | 516.3 | 1612 | 761.3 | 2826.1 |
| LPZ303 | 83.1 | 488.8 | 98.6 | 0 | 73.5 | 979.9 | 538.7 | 510.7 | 1214.7 |
| LPZ304 | 213.7 | 498.3 | 137.6 | 1028.6 | 0 | 5405.8 | 860 | 2212.1 | 2201 |
| LPZ306 | 1439.4 | 1735.3 | 2526.4 | 4212.7 | 3140.4 | 2090.1 | 8128.5 | 4874.6 | 14413.9 |
| LPZ307 | 534.1 | 710.5 | 515.5 | 2785.3 | 734 | 0 | 2137.3 | 1692.8 | 3540.3 |
| LPZ308 | 116 | 304.4 | 137.7 | 151.8 | 28.2 | 364.2 | 621.1 | 631.4 | 851.2 |
| LPZ309 | 80.1 | 137.2 | 92.7 | 0 | 0 | 2648.1 | 529.4 | 192.6 | 735 |
| LPZ310 | 430.8 | 584.9 | 799.2 | 1887.2 | 1887.1 | 6161.2 | 2974.3 | 3575 | 2426.6 |
| LPZ311 | 690.5 | 995.7 | 208.4 | 3725.8 | 2843.8 | 0 | 4329.3 | 3620.8 | 4170.1 |
| LPZ312 | 109.8 | 334.2 | 34 | 72.5 | 4.5 | 1489.3 | 140.1 | 431.6 | 744.8 |
| LPZ314 | 26.5 | 200.1 | 3.3 | 181.2 | 0 | 1231.5 | 331.5 | 440.1 | 804.6 |
| LPZ315 | 305.8 | 211.3 | 147.5 | 811.2 | 1008.1 | 3797 | 2231.8 | 1438.8 | 1881.8 |
| LPZ318 | 621.3 | 715 | 337 | 3488.2 | 2480.9 | 781.9 | 4326.1 | 4824.7 | 6969.2 |
| LPZ320 | 214.8 | 92.2 | 9.9 | 1170.9 | 54.5 | 4501.5 | 1122.3 | 1169.4 | 1696.6 |
| LPZ321 | 880.4 | 755.2 | 1899.3 | 6166.2 | 5105.8 | 411.6 | 6096.5 | 4853.6 | 6057.2 |

TABLE III

| LSC Media | Multiplication Media | | Maturation Media |
|---|---|---|---|
| Components (mg/L) | 16 | 1133 | 923 |
| $NH_4NO_3$ | 603.8 | 603.8 | 200.0 |
| $KNO_3$ | 909.9 | 909.9 | 454.95 |
| $KH_2PO_4$ | 136.1 | 136.1 | 136.1 |
| $Ca(NO_3)_2.4H_2O$ | 236.2 | 236.2 | 59.05 |
| $MgSO_4.7H_2O$ | 246.5 | 246.5 | 246.5 |

TABLE III-continued

| LSC Media | Multiplication Media | | Maturation Media |
|---|---|---|---|
| Components (mg/L) | 16 | 1133 | 923 |
| $Mg(NO_3)_2.6H_2O$ | 256.5 | 256.5 | 256.5 |
| $MgCl_2.6H_2O$ | 101.7 | 101.7 | 101.7 |
| KI | 4.15 | 4.15 | 4.15 |
| $H_3BO_3$ | 15.5 | 15.5 | 7.75 |
| $MnSO_4.H_2O$ | 10.5 | 10.5 | 10.5 |

TABLE III-continued

| LSC Media | Multiplication Media | | Maturation Media |
|---|---|---|---|
| Components (mg/L) | 16 | 1133 | 923 |
| $ZnSO_4.7H_2O$ | 14.4 | 14.4 | 14.4 |
| $NaMoO_4.2H_2O$ | 0.125 | 0.125 | 0.125 |
| $CuSO_4.5H_2O$ | 0.125 | 0.125 | 0.125 |
| $CoCl_2.6H_2O$ | 0.125 | 0.125 | 0.125 |
| $FeSo_4.7H_2O$ | 6.95 | 6.95 | 41.7 |
| $Na_2EDTA$ | 9.33 | 9.33 | 55.9 |
| Sucrose | 30,000 | 30,000 | — |
| Maltose | — | — | 20,000 |
| myo-Inositol | 1,000 | 1,000 | 100 |
| Casamino acids | 500 | 500 | 500 |
| L-Glutamine | 450 | 450 | 450 |
| Thiamine.HCl | 1.0 | 1.0 | 1.0 |
| Pyridoxine.HCl | 0.5 | 0.5 | 0.5 |
| Nicotinic acid | 0.5 | 0.5 | 0.5 |
| Glycine | 2.0 | 2.0 | 2.0 |
| 2,4-D | 1.1 | 1.1 | — |
| BAP | 0.45 | 0.45 | — |
| Kinetin | 0.43 | 0.43 | — |
| Polyethylene glycol | — | — | 130,000 |
| ABA | — | 5.2 | 5.2 |
| Gelrite | 2,500* | 2,500* | 2,500 |
| pH | 5.7 | 5.7 | 5.7 |

*For solid media only

TABLE IV

Description of clones used in hybridization study shown in FIG. 9.

| Clone # | Homology | Description | ID with Arabidopsis | Score | E-value |
|---|---|---|---|---|---|
| PC04B12 ('LEC' in figure) | Lotan et al. 1998. Arabidopsis LEAFY COTYLEDON 1 is sufficient to Induce Embryo Development in Vegetative Cells. Cell 93: 1195–1205 | Required for embryo maturation & Cotyledon identity. Ectopic expression induces embryonic differentiation traits in transgenic seedlings. | 79% ID, 93% + ve over 96aa | 171 | 7e−44 |
| ST17B05 ('PLK' in figure) | PICLKE/CDH3, Chromatin remodelling. Ogas et al. 1999. PICKLE is a CHD3 chromatin-remodeling factor that regulates the transition from embryonic to vegetative development in Arabidopsis. PNAS. 96(24): 13839–13844 | The pickle mutants express embryonic traits after germination, Represses lec expression | 50% ID, 74% + ve over 155aa | 166 | 1e−41 |
| PC08C06 ('FIE' in figure.) | FIE, fertilization-independent endosperm protein. Ohad, et al 1999. Mutations in FIE, a WD polycomb group gene, allow endosperm development without fertilization. Plant Cell 11(3), 407–416 | Fie mutants initiate endosperm development w/o fertilization | 61% ID 75% + ve over 67aa | 92 | 8e−20 |

Table 4. Description of clones used in hybridization study shown in FIG. 9.

TABLE V

| Cell Line (Stage of Development) | 488 (Liquid Suspension Culture: Stage 1–3) | 499 (Liquid Suspension Culture: Stage 1–3) | 499 (Liquid Suspension Culture: Stage 1–3) | 500 (Liquid Suspension Culture: Stage 1–3) | 500 (Liquid Suspension Culture: Stage 1–3) | 260 (Stage 7) | 260 (Stage 9) |
|---|---|---|---|---|---|---|---|
| Media | 1133 | 16 | 1133 | 16 | 1133 | Maturation | maturation |
| # | (49.5) | 118.5 | (129.5) | 187.75 | (147) | Na | na |
| Embyros | | | | | | | |
| 'FIE' | ++++ | + | +++ | +++ | +++ | +++ | +++ |
| 'LEC' | (++) | ++ | (+++) | ++ | (++++) | + | + |
| 'PKL' | ++++ | + | +++ | +++ | +++ | +++ | +++ |

Table 5. Table of data from FIGS. 9a & b. Numbers (488, 499, 500, 260) refer to different cell lines. Liquid Suspension Culture contains early-stage embryos (stage 1–3) Embryo number refers to the number of late-stage (stage 8–9) embryos produced by each cell line when matured according to Pullman and Webb (1994). + = low expression, ++ = medium level of mRNA, +++ = high level of mRNA, ++++ = very high level of mRNA. Circles around certain + signs, see text. Na = not applicable. Levels of mRNA are relative and refer to the experiment depicted in FIGS. 9a & b.

The invention claimed is:

1. A method of staging conifer embryos comprising:

a) detecting the expression in a conifer embryo of at least one RNA transcript wherein the RNA transcript is capable of hybridizing to at least one cDNA sequence of SEQ ID NO: 79 or 131; and b) correlating the expression of said transcript to one or more embryonic stages.

2. The method of claim 1 wherein at least two RNA transcripts are detected or determined and correlated to one or more embryonic stages.

3. The method of claim 1 wherein expression of the at least one RNA transcript is analyzed by hybridization with at least one probe of sequence SEQ ID NO: 79 or 131.

4. The method of claim 1 wherein said cDNA sequence hybridizes under conditions of moderate stringency.

5. The method of claim 1 wherein expression of at least one RNA transcript is detected or determined by one or more of PCR, Northern Analysis, or in situ hybridization.

6. The method of claim 1 wherein expression of said at least two RNA transcripts are detected by a DNA array.

7. The method of claim 1 wherein said cDNA sequence hybridizes under conditions of high stringency.

* * * * *